(12) United States Patent
Leo

(10) Patent No.: US 11,938,119 B2
(45) Date of Patent: Mar. 26, 2024

(54) CANNABIS PRODUCTION SYSTEMS AND METHODS

(71) Applicant: INSECTERGY, LLC, Baltimore, MD (US)

(72) Inventor: Daniel Michael Leo, Baltimore, MD (US)

(73) Assignee: INSECTERGY, LLC, Baltimore, MD (US)

( * ) Notice: Subject to any disclaimer, the term of this patent is extended or adjusted under 35 U.S.C. 154(b) by 326 days.

(21) Appl. No.: 17/204,857

(22) Filed: Mar. 17, 2021

(65) Prior Publication Data

US 2021/0251157 A1 Aug. 19, 2021

Related U.S. Application Data

(63) Continuation-in-part of application No. 16/396,134, filed on Apr. 26, 2019, which is a continuation-in-part of application No. 16/029,627, filed on Jul. 8, 2018, now abandoned, which is a continuation-in-part of application No. 15/841,923, filed on Dec. 14, 2017, now Pat. No. 10,694,683, which is a continuation-in-part of application No. 15/784,112, filed on Oct. 14, 2017, now abandoned, which is a continuation-in-part of application No. 15/609,472, filed on May 31, 2017, now Pat. No. 10,595,474.

(51) Int. Cl.
| | |
|---|---|
| *B01D 1/06* | (2006.01) |
| *A01G 22/00* | (2018.01) |
| *A23L 33/105* | (2016.01) |
| *A61K 31/437* | (2006.01) |
| *B01D 3/12* | (2006.01) |
| *B01D 9/00* | (2006.01) |

(52) U.S. Cl.
CPC ............ *A61K 31/437* (2013.01); *A01G 22/00* (2018.02); *A23L 33/105* (2016.08); *B01D 1/065* (2013.01); *B01D 3/12* (2013.01); *B01D 9/0018* (2013.01); *B01D 9/004* (2013.01); *B01D 2009/0086* (2013.01)

(58) Field of Classification Search
None
See application file for complete search history.

(56) References Cited

U.S. PATENT DOCUMENTS

2018/0169172 A1\* 6/2018 Kariman .............. A61K 31/437

OTHER PUBLICATIONS

Jaiswal, et al., 3 Biotech, 5:123. (Year: 2015).\*

\* cited by examiner

*Primary Examiner* — Michael Barker

(57) ABSTRACT

A vertically-integrated *cannabis*-related product production method is described, the method comprises, producing a distilled cannabinoid and/or a crystallized cannabinoid from *cannabis* plants, comprising: in a farming system, growing the *cannabis* plants, the *cannabis* plants comprise a cannabinoid; in an extraction system, extracting the cannabinoid from the *cannabis* plants; in a purification system, purifying the cannabinoid to produce a purified cannabinoid; and in a distillation and/or a crystallization system, distilling and/or crystallizing the purified cannabinoid to produce the distilled cannabinoid and/or the crystallized cannabinoid. Various ways to purify, distill, and process the cannabinoids are described. An insect pest management system may be integrated with the farming system to grow the *cannabis* plants in the presence of predatory mites which feed on insects and/or spider mites.

20 Claims, 51 Drawing Sheets

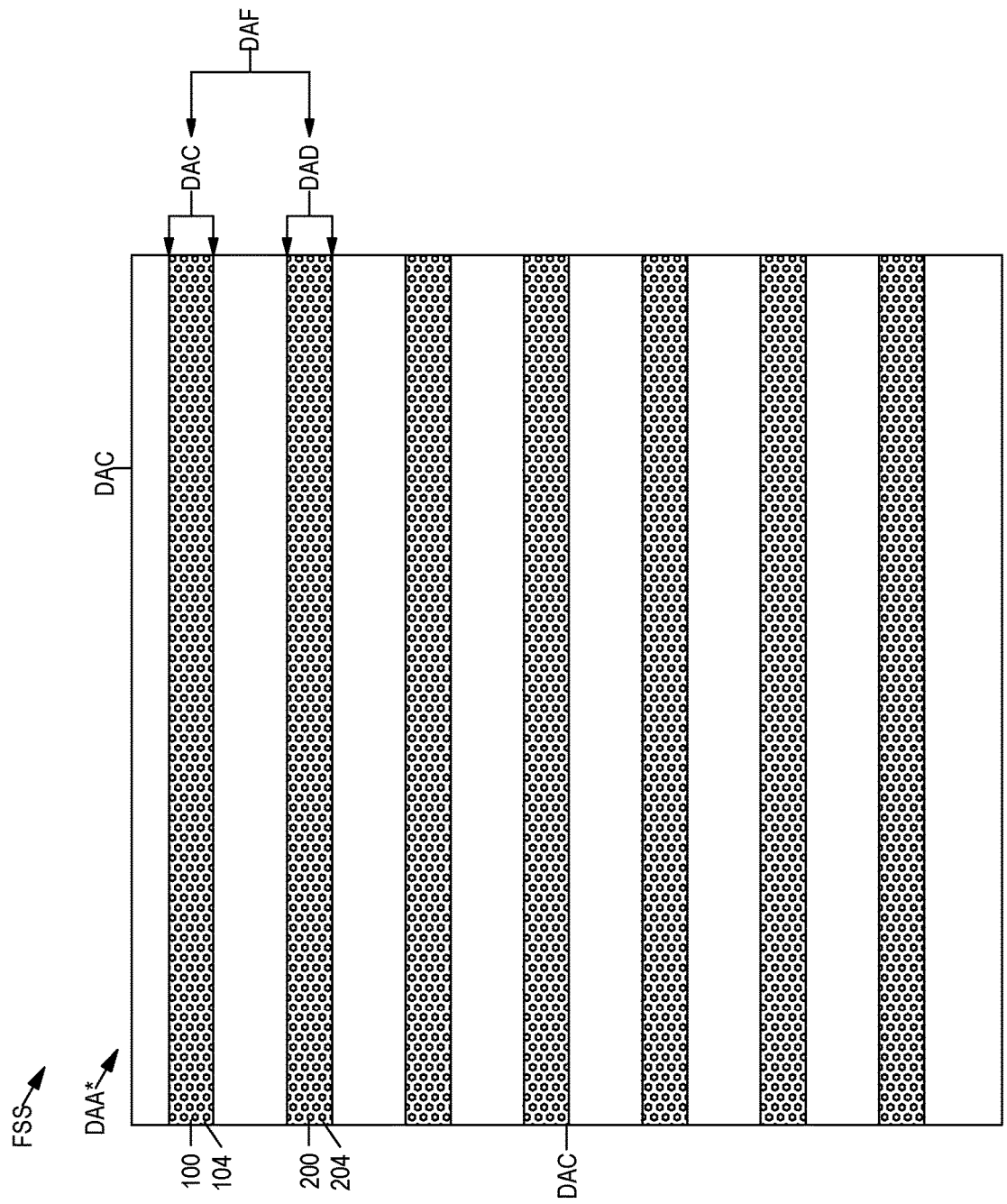

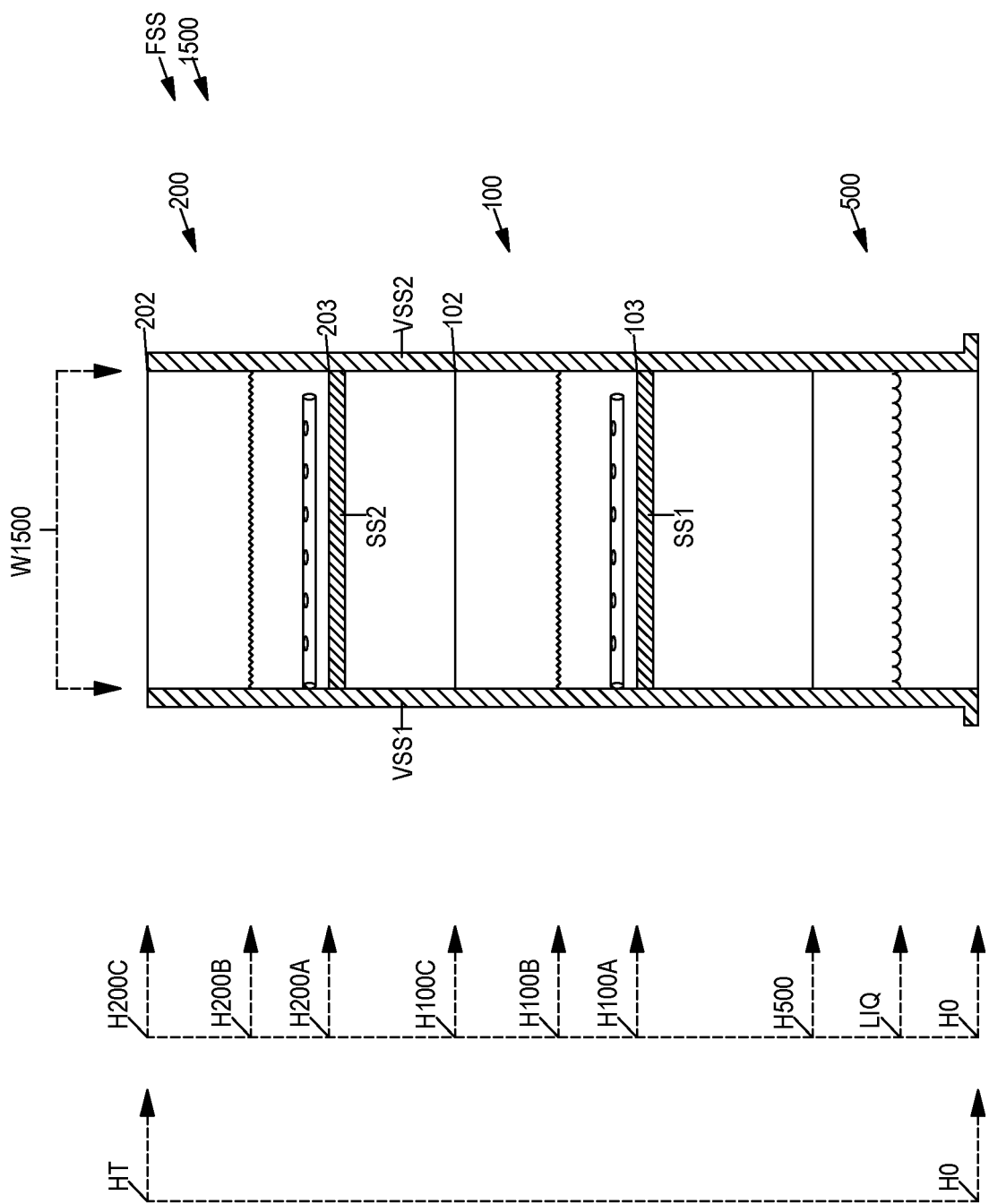

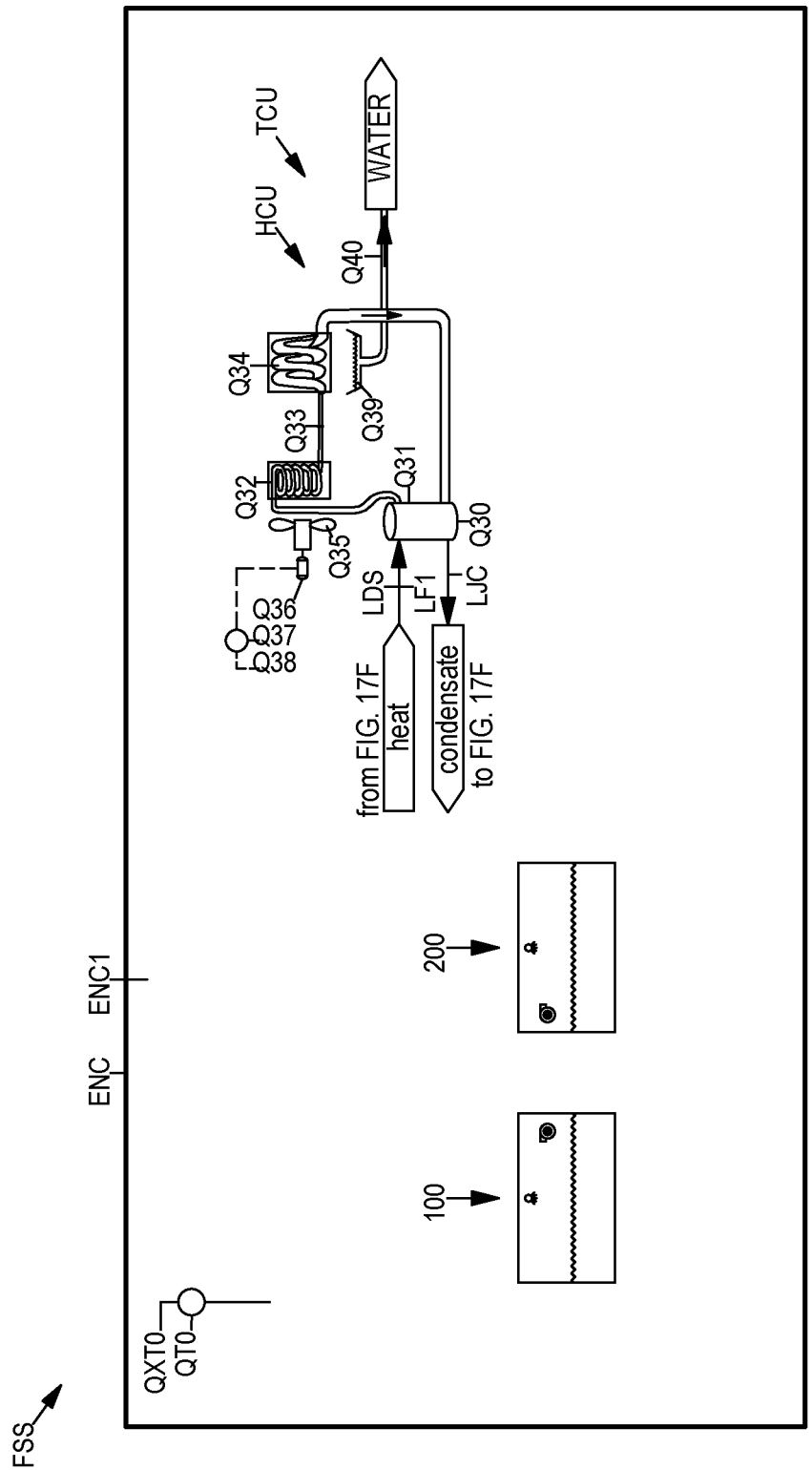

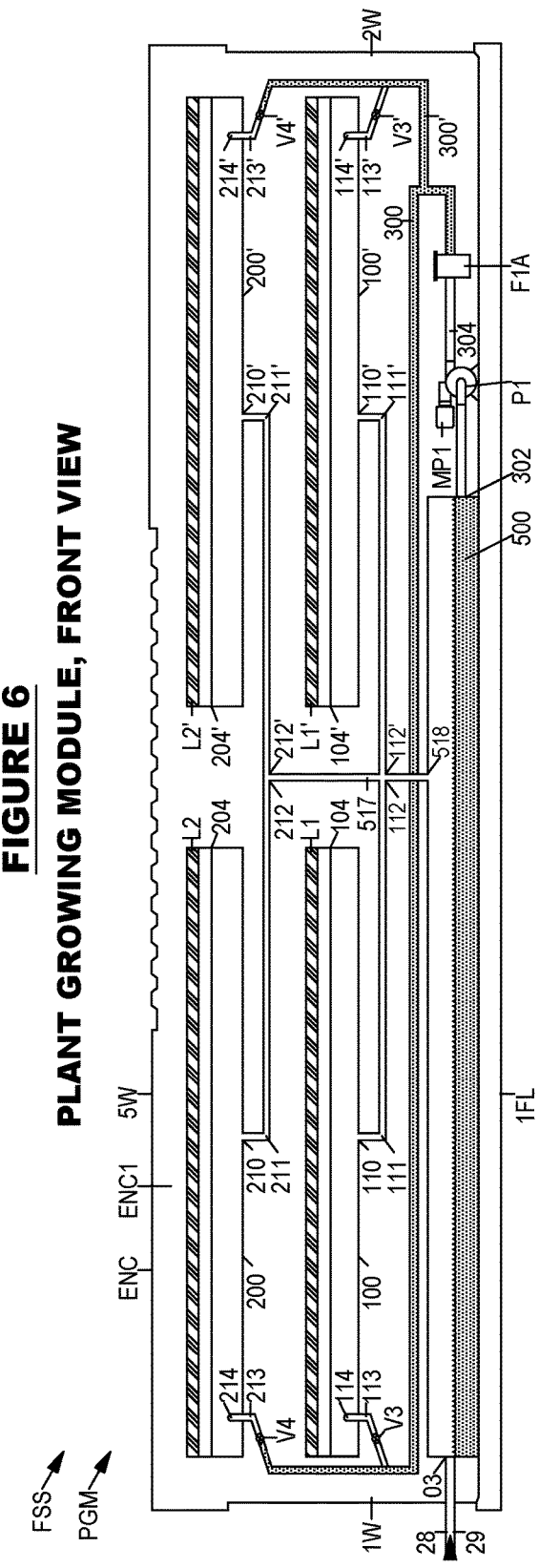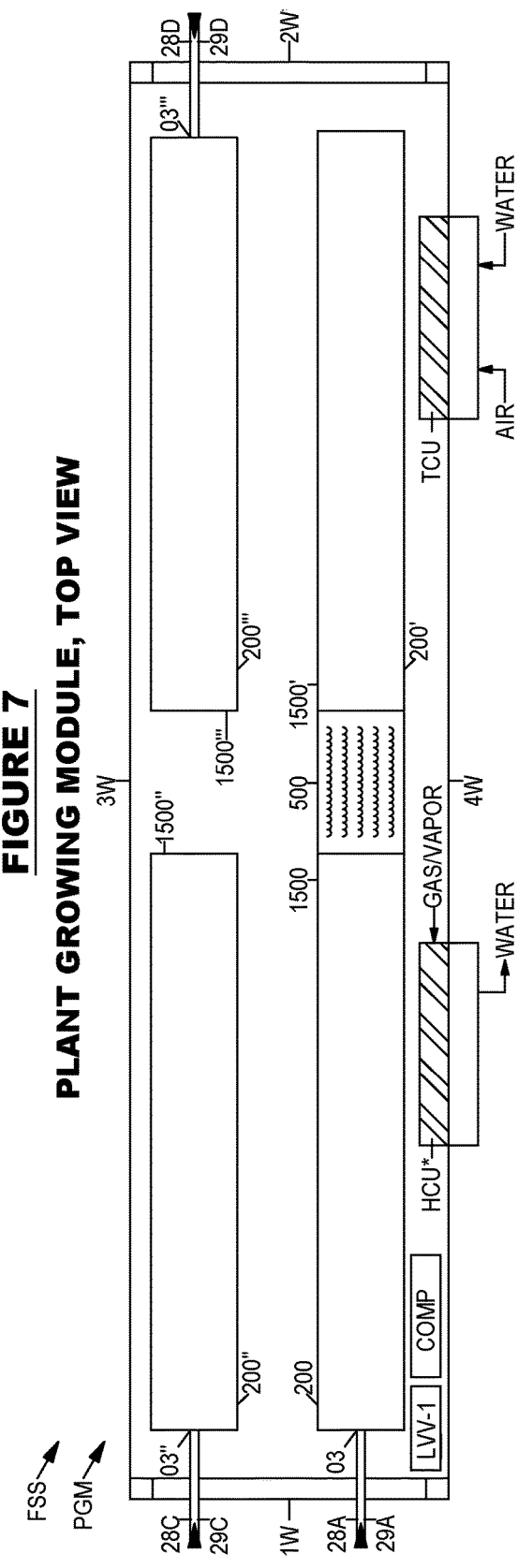

PLANT GROWING MODULE, SIDE VIEW

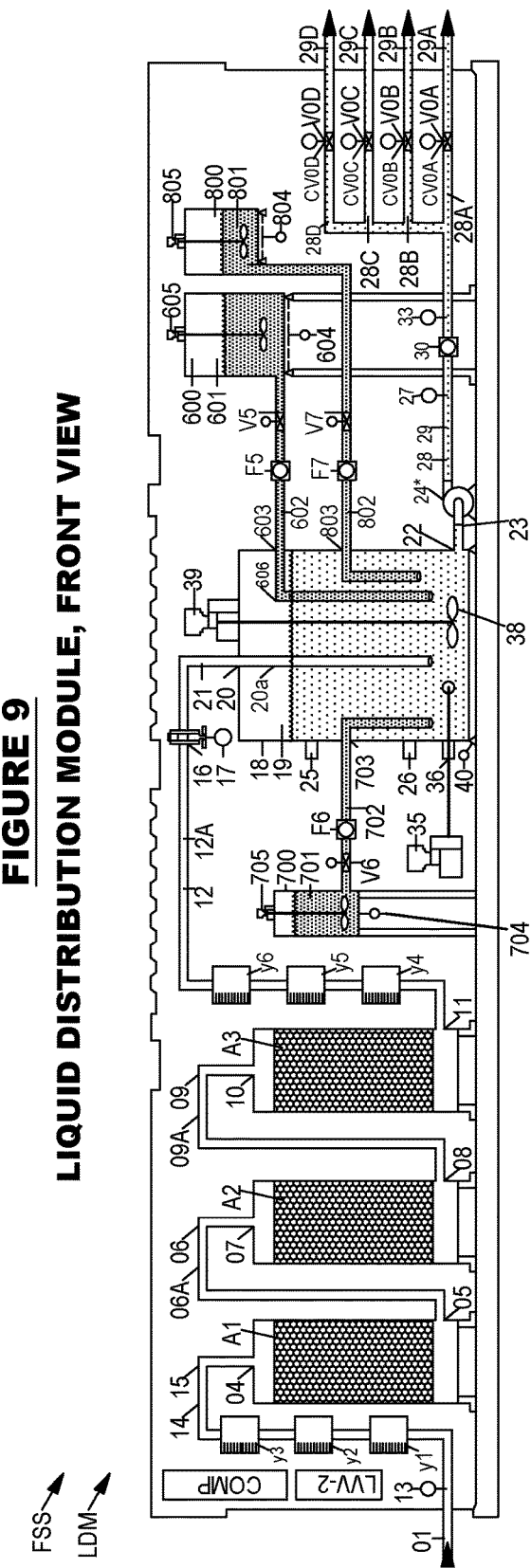

LIQUID DISTRIBUTION MODULE, SIDE VIEW

GRINDING

HEATING

SEPARATION

SEPARATION

SEPARATION

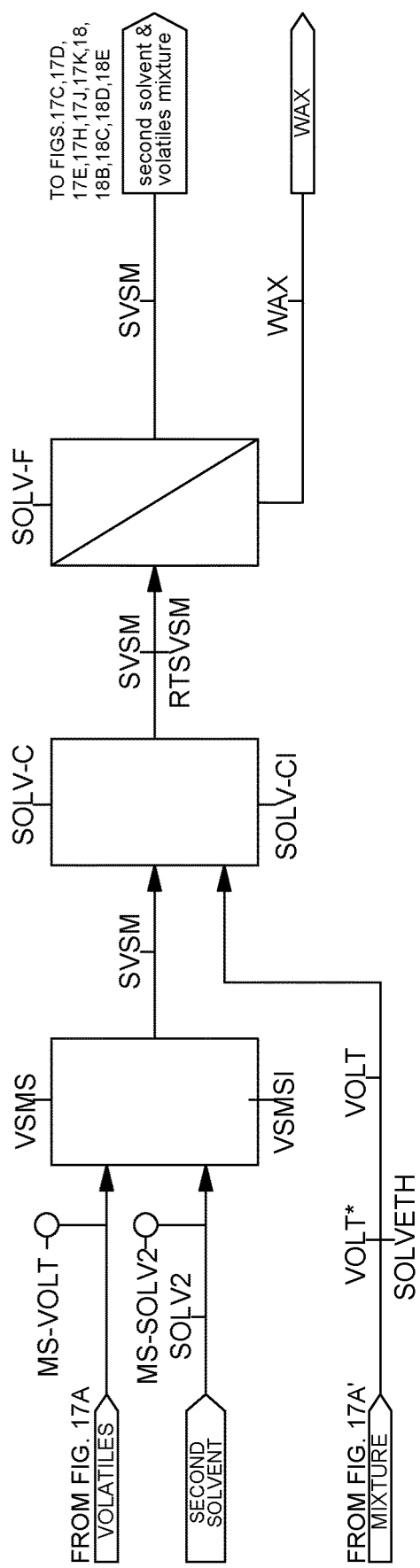

SEPARATION

THREE STAGE SEPARATION SYSTEM

SOLVENT SEPARATION SYSTEM

SPRAY DRYER, CO-CURRENT

SPRAY DRYER, COUNTER-CURRENT

SPRAY DRYER, COUNTER-CURRENT

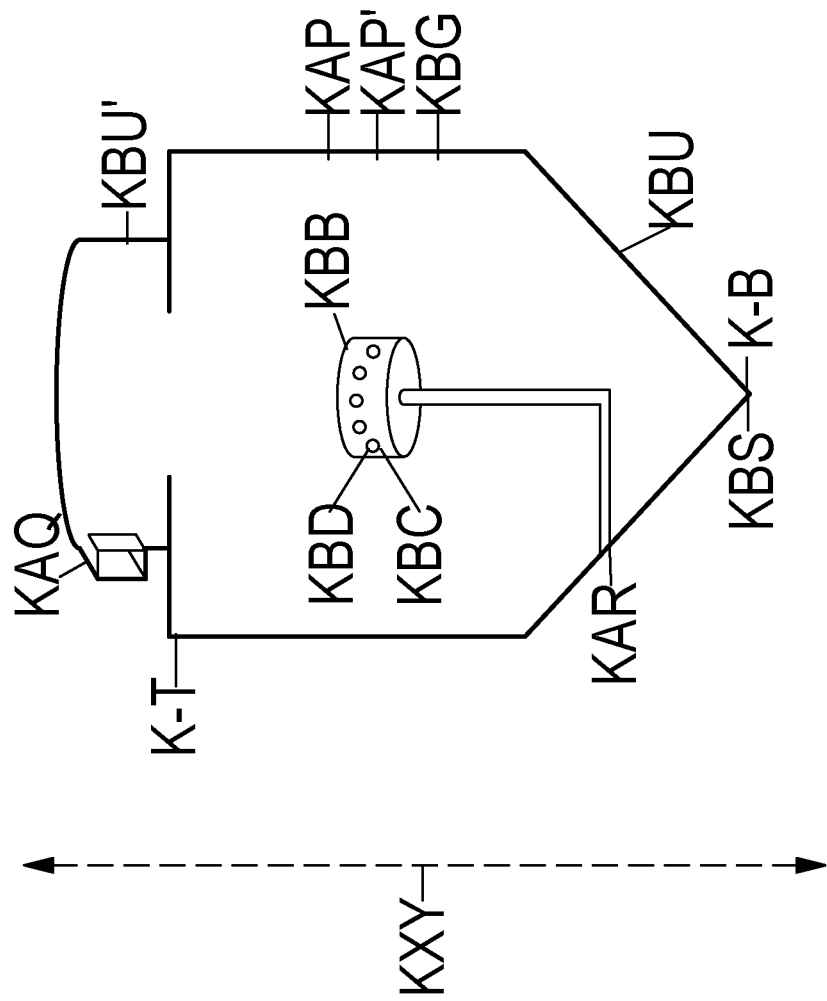

POWER PRODUCTION SYSTEM

CARBON DIOXIDE RECOVERY SYSTEM

CANNABINOID EXTRACTION AND PURIFICATION SYSTEM

EMULSION / COLLOID PRODUCTION SYSTEM

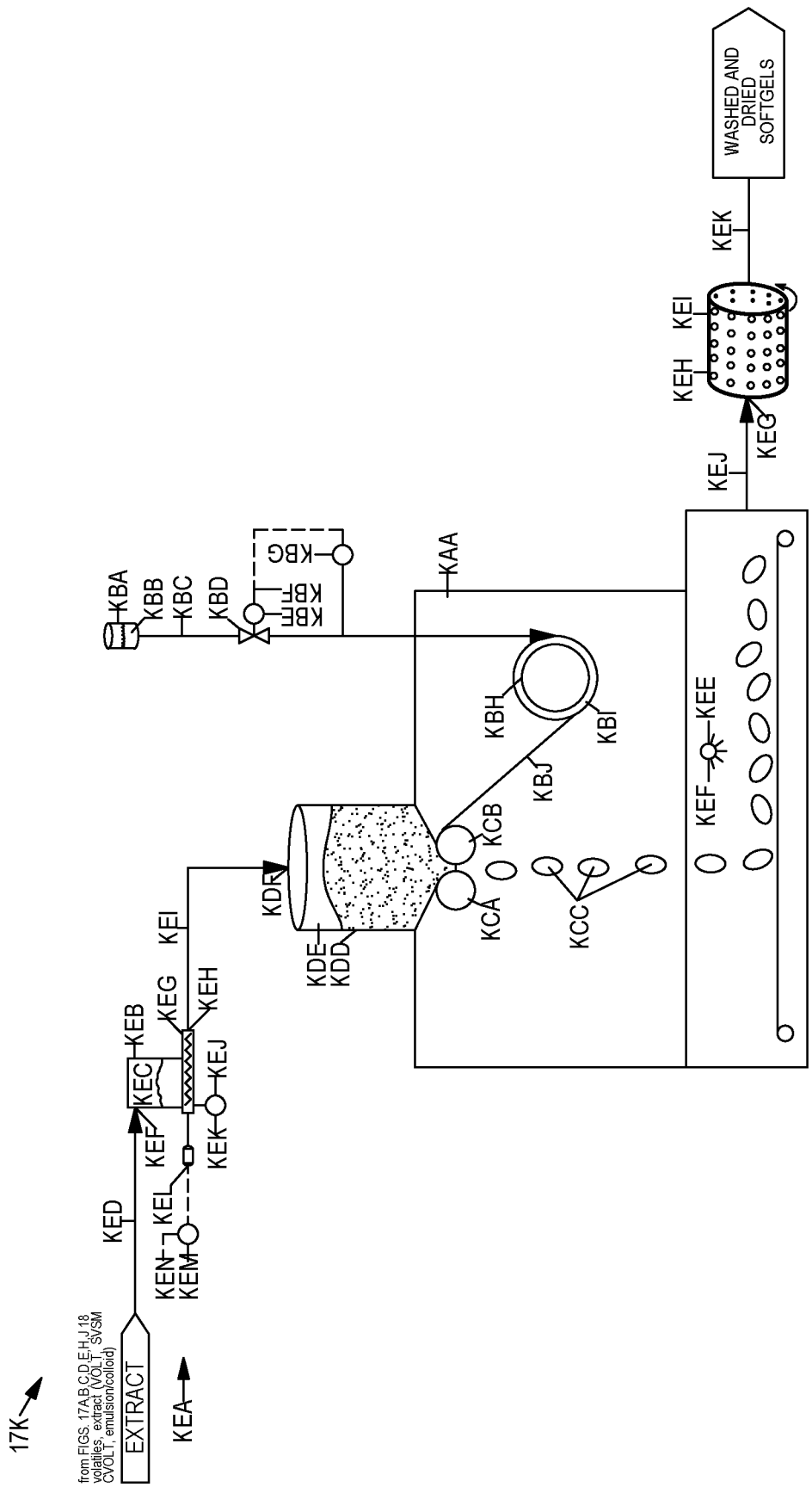

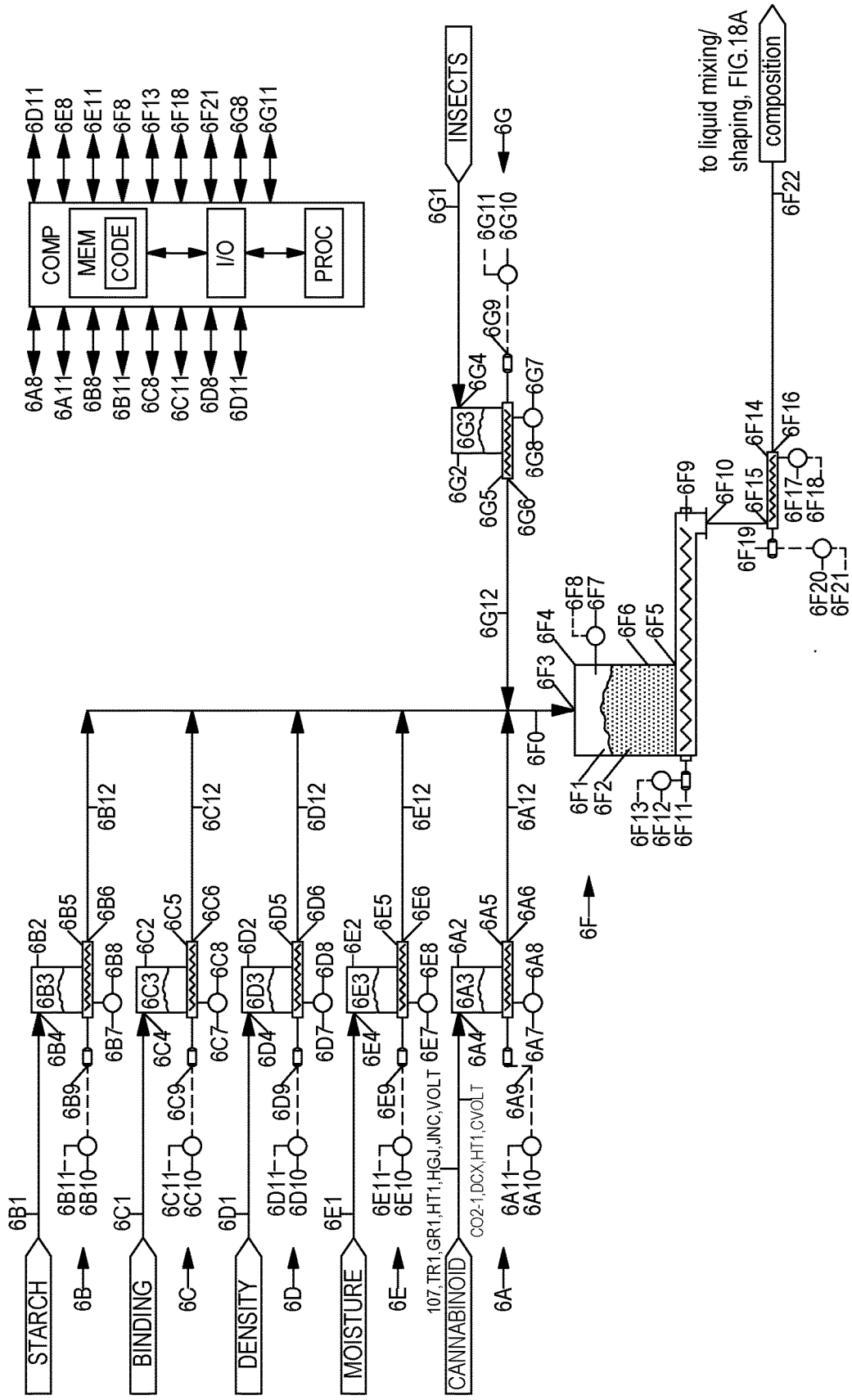

LIQUID MIXING MODULE

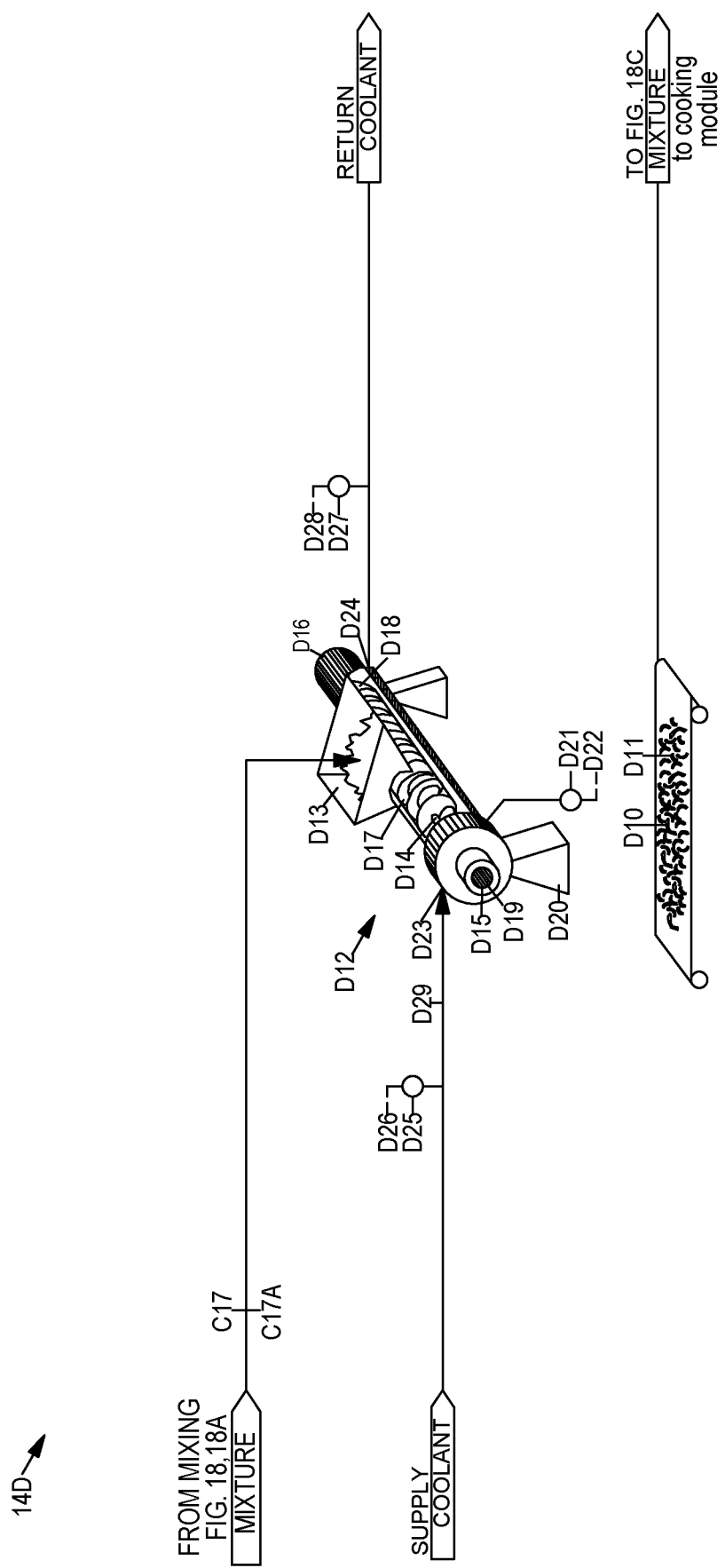

COOKING MODULE

FLAVORING MODULE

BIOCATALYST MIXING MODULE

SEPARATION MODULE

CANNABIS CLONING

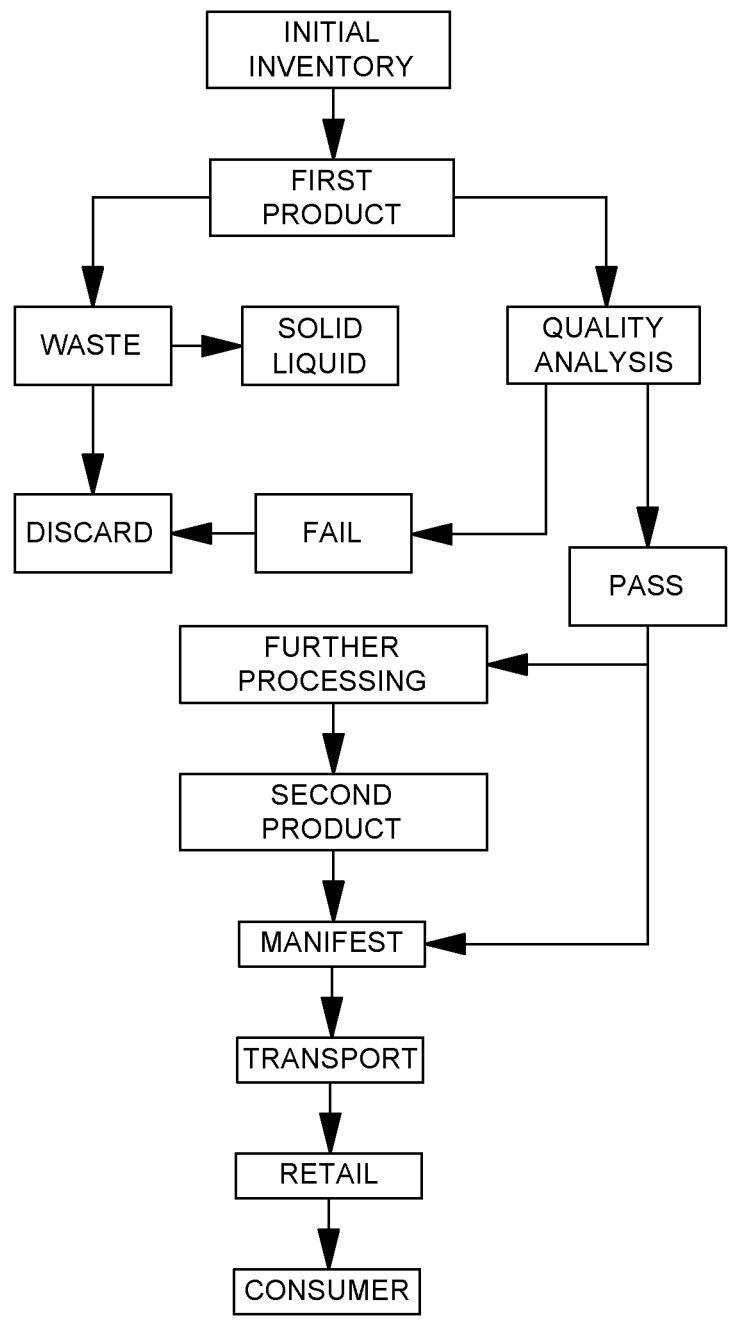

CANNABIS PRODUCTION SYSTEMS AND METHODS

RELATED APPLICATIONS

This application is a Continuation-In-Part of my co-pending patent application Ser. No. 16/396,134, filed on Apr. 26, 2019, which is a Continuation-In-Part of my now abandoned patent application Ser. No. 16/029,627, filed on Jul. 8, 2018, which is a Continuation-In-Part of my now patented patent application Ser. No. 15/841,923, filed on Dec. 14, 2017, U.S. Pat. No. 10,694,483, issued on Jun. 30, 2020, which is a Continuation-In-Part of my now abandoned patent application Ser. No. 15/784,112, filed on Oct. 14, 2017, which is a Continuation-In-Part of my now patented patent application Ser. No. 15/609,472, filed on May 31, 2017, U.S. Pat. No. 10,595,474, issued on Mar. 24, 2020. The contents of the aforementioned applications are incorporated by reference in their entirety.

TECHNICAL FIELD

The present disclosure relates to the field of commercial scale production, extraction, purification, and formulation of *cannabis*-related products derived from plant-derived cannabinoids, insect-derived cannabinoid glycosides, biosynthetic-derived cannabinoids from genetically modified microorganisms, to produce raw crude cannabinoid mixtures, purified cannabinoids, cannabinoid distillates, cannabinoid isolates, spray-dried water-soluble particulates, crystals, powders, emulsions, colloidal dispersions, softgels, beverages, foodstuffs, shaped and cooked compositions, flavored compositions, cosmetics, topicals, pet foods, candies, chocolates, energy bars, consumer products, drugs, pharmaceutical compositions, and insect containing cannabinoid meat replacements, for medicinal or recreational, biotechnology, agrochemical applications.

BACKGROUND

Efficient, reliable, consistent, and profitable *cannabis* farming, production, extraction, purification, and processing systems are needed to meet the cannabinoid-related product demands of society. In recent years, there has been an increasing demand for a wide array of *cannabis*-related products, not only including *cannabis* flower, trimmed *cannabis* buds, *cannabis* trimmings, fresh-frozen *cannabis*, extracted cannabinoids, purified cannabinoids, and *cannabis*-related products not only including extracts, distillates, isolates, emulsions, colloids, softgels, water-soluble powders, beverages, topicals, cosmetics, sleep aids, foodstuffs, for medicinal and recreational use, as well as animal health products (i.e., to reduce anxiety and/or arthritis in dogs) and pet foods.

The complexity of making these individual products can be overcome by vertically-integrating the *cannabis* business to quickly shift from making one product to another: e.g., shifting operations and resources to manufacturing one relatively unpopular product to another relatively more popular product, at that given time, seamlessly using similar or commonly used chemical, bioprocess, or food/beverage technology processing systems or methodologies, or preferably to make them all at once which is the aim of this patent disclosure.

There is also a need to produce cannabinoids from sources other than from a *cannabis* plant. For example, there is a need to produce cannabinoids biosynthetically from genetically modified microorganisms in bioreactors to reduce capital intensity of the *cannabis* plant farming superstructure system, and all of its complexities (such as humidity and temperature control, water treatment, planting, cloning, watering, fertilizing, real estate, etc.). There is a need to supplement *cannabis*-plant derived cannabinoids with biosynthetic-derived cannabinoids to meet to *cannabis*-related product demands of society.

There is also a need to produce water soluble insect-derived cannabinoid glycosides which is yet another way to produce cannabinoids other than from a *cannabis* plant. For example, there is a need to produce cannabinoid glycosides biosynthetically from insects by feeding the insects a first cannabinoid which it then ingests to produce a second cannabinoid, which is a water-soluble cannabinoid glycoside which has many important benefits for drug delivery for humans and animal medicine and nutrition due to its solubility in water. There is a need to supplement *cannabis*-plant derived cannabinoids and/or biosynthetic-derived cannabinoids with insect-derived biosynthetic cannabinoid glycosides to meet to *cannabis*-related product demands of society.

There exists a need to vertically-integrate *cannabis* growth and biosynthetic cannabinoid bioprocessing and extraction, purification, formulation, and sale of cannabinoid-related products to produce foodstuffs, health products, cosmetics, topicals, water-soluble powders, consumer products, chemicals, animal foods, and pharmaceuticals to minimize supply chain disruptions and maximize revenue and predictability and control the entire supply chain of all current and future *cannabis*-related products.

There is a need to combine all aspects of the supply chain within one single organization. There is a need for a business entity to control every aspect of the supply chain (i.e., growing, extraction, purification, formulation, sale), and own and/or operate all aspects of the entire industry. There is a need for a business entity to grow, process, and sell the entire suite of products to produce consistent, high-quality, fun, exciting, new-age, and futuristic products that enhance the happiness, curiosity, intelligence, perception, reduce depression and anxiety, and boost the well-being of all consumers and those who interact with those consumers. There is a need for a repeatable and consistent *cannabis* end-to-end clone- and/or-seed-to-end product that is controlled using a specific and repeatable *cannabis* composition named INSECTERGY III.

There is a need to streamline the clone- and/or seed-to-sale process by maximizing quality and consumer product predictability, familiarity, and enjoyment of the products in the entire product line (i.e., chocolates, insect protein energy bars, gummies, beverages, teas, sports drinks, coffees, candies, specialty milks, fitness supplements, baked goods, frozen treats, cannabinoid-infused meat-replacement insect protein mixtures, etc.) and minimize financial and transactional liabilities related to operating publicly-owned *cannabis*-related businesses in a highly competitive and high risk industry. By owning all sectors of the supply chain, one can maximize profit and also allows a unique opportunity to overcome many challenges related to tracking, accountability, food safety, and state and federal government compliance of the *cannabis* industry, either for food (for humans or animals), drugs, chemicals, and medicine.

There is a need to vertically-integrate multi-state United States *cannabis* operations to minimize capital expenditures on production while increasing yield of the product, better increasing quality control and traceability, all while saving on property costs since one or many facilities within the same business entity can work together to grow, extract, purify, formulate, and sell the products in common facilities and distribute to the public via dispensaries, business-to-business, or home delivery via humans or drones.

Large-scale *cannabis* farming and bioprocessing systems must be designed carefully to minimize environmental impact, reduce manual labor and human interaction, and automate the system as much as possible while maximizing plant and biosynthetic product growth and yield. These systems must be precisely sized and situated to be able to provide systematically timed and controlled computer-operated methods to maintain a sufficient amount of water and nutrients for the cannabinoid to be produced, extracted, purified, formulated, with a precise temperature, humidity level, pH, oxygen and/or carbon dioxide level, air velocity, and light wavelength and schedule, extraction and purification methodology, selected formulation, etc.

Cannabinoids may be extracted from the *cannabis* plants and/or the cannabinoid-containing genetically engineered microorganisms and/or insects by any variety of extraction methodologies not only including with carbon dioxide, ethanol, ethanol and water mixtures, hydrocarbons, chilled water, solvent, oils, lipids, and/or pressure. The extracted cannabinoids may then then be purified and formulated to produce a specific product by a variety of methodologies such as solvent mixing, filtration, heat treating, evaporation, chromatography, adsorption, distillation, crystallization, spray drying, emulsification, softgel production, to produce shaped, cooked, or flavored, foodstuffs, softgels, and packaged products. The purified product may then be used in any number of applications involving emulsions, powders, beverages, topicals, cosmetics, sleep aids, on insect-protein burger patties, or snacks, or for medicinal and recreational use, as well as animal health products and pet foods.

The ability to grow *cannabis*, or to synthesize cannabinoids biologically, and preferably a combination of both in a single facility or cannabinoid production or purification system, with minimal human interaction has been long regarded as desirable and needed to facilitate widespread use for human consumption and for the production of food and beverages. It is of importance that large-scale, standardized, modular, easily manufacturable, energy efficient, reliable, computer-operated *cannabis* farming, bioprocessing, extraction, purification, and processing systems and facilities are extensively deployed to produce cannabinoids for medicinal and recreation use with minimal water and environmental impact.

There is a need to control the entire supply and value chain of all cannabinoid-related businesses and own the entire industry. There is a need to develop a cannabinoid-related business that is defensible in terms of having predictable and stable inputs and outputs and revenue to control pricing, supply, scarcity in certain important ingredients vital to the operation of the business, and intellectual property.

There is a need for *cannabis* farming facilities and biosynthetic cannabinoid manufacturing facilities sufficient to meet the demands of society as well have the ability to clean and decontaminate water from harsh and unpredictable sources and provide a clean water source suitable to feed and grow *cannabis* and produce biosynthetic cannabinoids from genetically engineered organisms. There is a need to re-use old, containerized shipping containers to promote the implementation of widespread commercial production of *cannabis* to promote regional, rural, and urban job opportunities that maximize the quality of living where the *cannabis* is farmed, or the biosynthetic cannabinoid is produced.

There is a need for a superior blend of *Cannabis sativa* L. ssp. *Sativa* and *Cannabis sativa* L. ssp. Indica (Lam.) that provides improved medicinal benefits, and has a high yield to meet industrial, commercial, recreational, and medicinal demand at a low price and minimal economic and environmental impact. There is a need for a new variety of plant that has a repeatable, predictable, and unique chemical composition that is based upon standardized engineered concentrations of: cannabidiol, tetrahydrocannabinol, energy, carbon, oxygen, hydrogen, ash, volatiles, nitrogen, sulfur, chlorine, sodium, potassium, iron, magnesium, phosphorous, calcium, zinc, cellulose, lignin, hemicellulose, fat, fiber, protein, while having preferred specific *Cannabis sativa* L. ssp. *Sativa* and *Cannabis sativa* L. ssp. Indica (Lam.) weight percentages.

A need exists for *cannabis* farming and/or biosynthetic cannabinoid production facilities that maximize cannabinoid production on a small physical outlay while providing adequate space outdoors and/or indoors for high-density plant growth and/or cannabinoid yield all at an economically attractive cost. There is a need for systems and methods that can produce unique and novel foodstuffs, snack foods, and animal foods, and consumer products amongst an array of other futuristic unforeseen optionalities at this time of filing. There is a need for unique and novel products to be created from a cannabinoid and produced from commercially available unit operations, including, multifunctional composition mixing, liquid mixing, shaping, 3D printing, cooking, flavoring, biocatalyst mixing, exoskeleton separation, liquid separation, and lipid extraction.

There is a need for a *cannabis*-related product traceability method that is specifically tailored towards the unique challenges related to tracking, accountability, food safety, and state and federal government compliance of the *cannabis* industry, either for food (for humans or animals), drugs, chemicals, and medicine. There is need for new, sustainable, and safe *cannabis*-related human and animal food products that can be registered with the appropriate State Departments of Agriculture and the Food and Drug Administration. There is a need to adhere to strict compliance and safety protocols for widespread commercialization of *cannabis*-related products. There is a need to improve the lifecycle tracing and tracking of *cannabis*-related products, which are subject to national and international regulations where proof of quality to the end-customer is paramount. There is a need to integrate blockchain technology into production *cannabis*-related products.

A need exists for an insect farm co-located at a *cannabis* farm to purposefully introduce insects and/or arachnids into the *cannabis* plants to protect the plants allowing the insects to feed on other insect eggs, insect larva, and other insects including living organisms which may or may not contain chitin not only including spider mites, rust mites, *thrips*, jumping plant lice, white fly, knats, gnats, aphids, and insects. A need exists for a farming system for growing the *cannabis* plants, the farming system includes an insect pest management system comprising predatory mites configured to feed off of insect eggs, insect larva, insects, spider mites, rust mites, *thrips*, jumping plant lice, white flies, gnats, and/or aphids, within the farming system.

Large scale cannabinoid production systems must be designed carefully to make sure that the genetically engineered microorganisms that produce the biosynthetic cannabinoid, and/or the *cannabis* plants and the insects and arachnids that live on the plants, and make the plants thrive, are freed from hunger and thirst. There is a need to immediately freeze and/or process the *cannabis* plants to euthanize any of the insects and/or the arachnids that live on the plants to be free from discomfort, pain, injury, disease, fear, and distress.

There is a need for a new, sustainable, method to grow *cannabis* to improve soil health and decrease evaporation of water from the growing medium the plants and the additional plants are grown in. There is a need to be able to grow *cannabis* plants indoors or outdoors together with the additional plants to improve soil health and decrease evaporation of water from the growing medium, the additional plants include clover, wildflowers, flowers, shamrock, legumes, nitrogen fixing plants, beans, peas, and/or grass. The additional plants improve insect health for the insect pest management of the *cannabis* farm as well as promoting pollination of *cannabis* plants and/or the additional plants. There is a need to apply a surfactant to the *cannabis* plants and/or the additional plants as non-toxic fungicide, miticide, and/or insecticide in the form of an emulsion of water and the surfactant, or an emulsion of treated water and the surfactant, and may include neem oil, rosemary oil, jojoba oil, insect oil, the bacterium *Bacillus subtilis*, the beneficial fungus *Ulocladium oudemansii*.

A need exists to combine the insect pest management system together with application of a non-toxic fungicide, miticide, and/or insecticide to the *cannabis* plants and/or additional plants to kill and/or deter unwanted pests, reduce mildew, prevent growth of fungi and fungi spores, prevent growth of oomycetes including fungus-like eukaryotic microorganisms.

There exists a need for a vertically-integrated *cannabis* business entity to harness economies of scale to enable consumer price reduction and elevate the quality and predictability and consumer-expectations of products in varying regions of the world to increase production and revenue of that business entity. Modern microeconomics have proved that the average cost of any *cannabis*-related product can decrease while increasing output with vertical integration of the *cannabis* business.

SUMMARY

This Summary is provided merely to introduce certain concepts and not to identify any key or essential features of the claimed subject matter.

Paragraph A. A method for producing a distilled cannabinoid and/or a crystallized cannabinoid from *cannabis* plants, comprising:
  in a farming system, growing the *cannabis* plants, the *cannabis* plants comprise a cannabinoid;
  in an extraction system, extracting the cannabinoid from the *cannabis* plants;
  in a purification system, purifying the cannabinoid to produce a purified cannabinoid; and
  in a distillation and/or a crystallization system, distilling and/or crystallizing the purified cannabinoid to produce the distilled cannabinoid and/or the crystallized cannabinoid;
  wherein:
  the farming system, the extraction system, the purification system, the distillation and/or the crystallization system are owned and/or operated by the same business entity.

Paragraph B. The method according to Paragraph A, wherein:
  in the farming system, growing the *cannabis* plants in the presence of predatory mites, wherein the predatory mites feed off insect eggs, insect larva, insects, spider mites, rust mites, *thrips*, jumping plant lice, white flies, gnats, and/or aphids, within the farming system.

Paragraph C. The method according to Paragraph A, comprising:
  in the purification system, purifying the cannabinoid within an evaporator.

Paragraph D. The method according to Paragraph C, wherein:
  the evaporator comprises one or more selected from the group consisting of a rotary evaporator, a falling film tubular evaporator, a rising/falling film tubular evaporator, a rising film tubular evaporator, a forced circulation evaporator, an internal pump forced circulation evaporator, a plate evaporator, an evaporative cooler, a multiple-effect evaporator, a thermal vapor recompression evaporator, and a mechanical vapor recompression evaporator.

Paragraph E. The method according to Paragraph C, wherein:
  the evaporator comprises a wiped-film evaporator.

Paragraph F. The method according to Paragraph A, comprising:
  in the purification system, purifying the cannabinoid with a simulated moving bed separation process.

Paragraph G. The method according to Paragraph A, comprising:
  in the purification system, purifying the cannabinoid by chromatography.

Paragraph H. The method according to Paragraph A, comprising: in the purification system, purifying the cannabinoid with an adsorbent.

Paragraph I. The method according to Paragraph A, comprising:
  in the purification system, purifying the cannabinoid with an ion exchange resin.

Paragraph J. The method according to Paragraph A, comprising:
  in the purification system, purifying the cannabinoid by microfiltration.

Paragraph K. The method according to Paragraph A, comprising:
  in the distillation system, distilling the purified cannabinoid by short path distillation.

Paragraph L. The method according to Paragraph A, comprising:
  in the distillation system, distilling the purified cannabinoid by molecular distillation.

Paragraph M. The method according to Paragraph A, comprising:
  in the distillation system, distilling the purified cannabinoid by spinning band distillation.

Paragraph N. The method according to Paragraph A, comprising:
  in an emulsification system, emulsifying the distilled cannabinoid and/or the crystallized cannabinoid within a liquid to produce a cannabinoid emulsion; wherein: the emulsification system is owned and/or operated by the business entity.

Paragraph O. The method according to Paragraph A, comprising:
  in a colloid production system, dispersing the distilled cannabinoid and/or the crystallized cannabinoid within a liquid to produce a cannabinoid colloidal dispersion; wherein: the colloid production system is owned and/or operated by the business entity.

Paragraph P. The method according to Paragraph O, comprising:

in a softgel production system, encapsulating the cannabinoid colloidal dispersion within a shell to produce a softgel; wherein: the softgel production system is owned and/or operated by the business entity.

Paragraph Q. The method according to Paragraph A, wherein:
the crystallization system includes a spray-dryer, and spray-drying the purified cannabinoid in the spray-dryer to produce the crystallized cannabinoid.

Paragraph R. The method according to Paragraph A, wherein:
the crystallization system includes one or more selected from the group consisting of a draft tube crystallizer, a draft tube and baffle crystallizer, cooling crystallization, evaporative crystallization, and fractional crystallization.

Paragraph S. The method according to Paragraph A1, comprising:
in a mixing system, producing a multifunctional mixture by mixing the distilled cannabinoid and/or the crystallized cannabinoid, with water, and/or at least one additional ingredient;
in a shaping system, shaping the multifunctional mixture to produce a shaped multifunctional composition; and
in a cooking system, cooking the shaped multifunctional composition to produce a cooked and shaped multifunctional composition;
wherein: the mixing system, the shaping system, and the cooking system are owned and/or operated by the business entity.

Paragraph T. The method according to Paragraph A, comprising:
the business entity produces a topical, a beverage, an animal food, and/or a foodstuff including the distilled cannabinoid and/or the crystallized cannabinoid, the foodstuff comprises one or more selected from the group consisting of ada, bagels, baked goods, biscuits, bitterballen, bonda, breads, cakes, candies, cereals, chips, chocolate bars, chocolate, coffee, cokodok, confectionery, cookies, cooking batter, corn starch mixtures, crackers, crepes, croissants, croquettes, croutons, dolma, dough, doughnuts, energy bars, flapjacks, french fries, frozen custard, frozen desserts, frying cakes, fudge, gelatin mixes, granola bars, gulha, hardtack, ice cream, khandvi, khanom buang, krumpets, meze, mixed flours, muffins, multi-grain snacks, nachos, nian gao, noodles, nougat, onion rings, pakora, pancakes, panforte, pastas, pastries, pie crust, pita chips, pizza, poffertj es, pretzels, protein powders, pudding, rice krispie treats, sesame sticks, smoothies, snacks, specialty milk, tele-bhaj a, tempura, toffee, tortillas, totopo, turkish delights, and waffles.

Paragraph U. The method according to Paragraph A, comprising:
in a bioreactor, growing microorganisms which have been genetically modified to produce a biosynthetic cannabinoid, in a liquid nutrient medium;
in a separation system, separating the grown, genetically modified microorganisms from the liquid nutrient medium; and
after separation, introducing the genetically modified microorganisms to the extraction system together with the *cannabis* plants;
wherein: the bioreactor, and the separation system are owned and/or operated by the business entity.

DESCRIPTION OF THE DRAWINGS

Reference will now be made in detail to various embodiments of the disclosure. Each embodiment is provided by way of explanation of the disclosure, not limitation of the disclosure. In fact, it will be apparent to those skilled in the art that modifications and variations can be made in the disclosure without departing from the teaching and scope thereof. For instance, features illustrated or described as part of one embodiment to yield a still further embodiment derived from the teaching of the disclosure. Thus, it is intended that the disclosure or content of the claims cover such derivative modifications and variations to come within the scope of the disclosure or claimed embodiments described herein and their equivalents.

Additional objects and advantages of the disclosure will be set forth in part in the description which follows, and in part will be obvious from the description, or may be learned by practice of the claims. The objects and advantages of the disclosure will be attained by means of the instrumentalities and combinations and variations particularly pointed out in the appended claims.

Figure 1A:
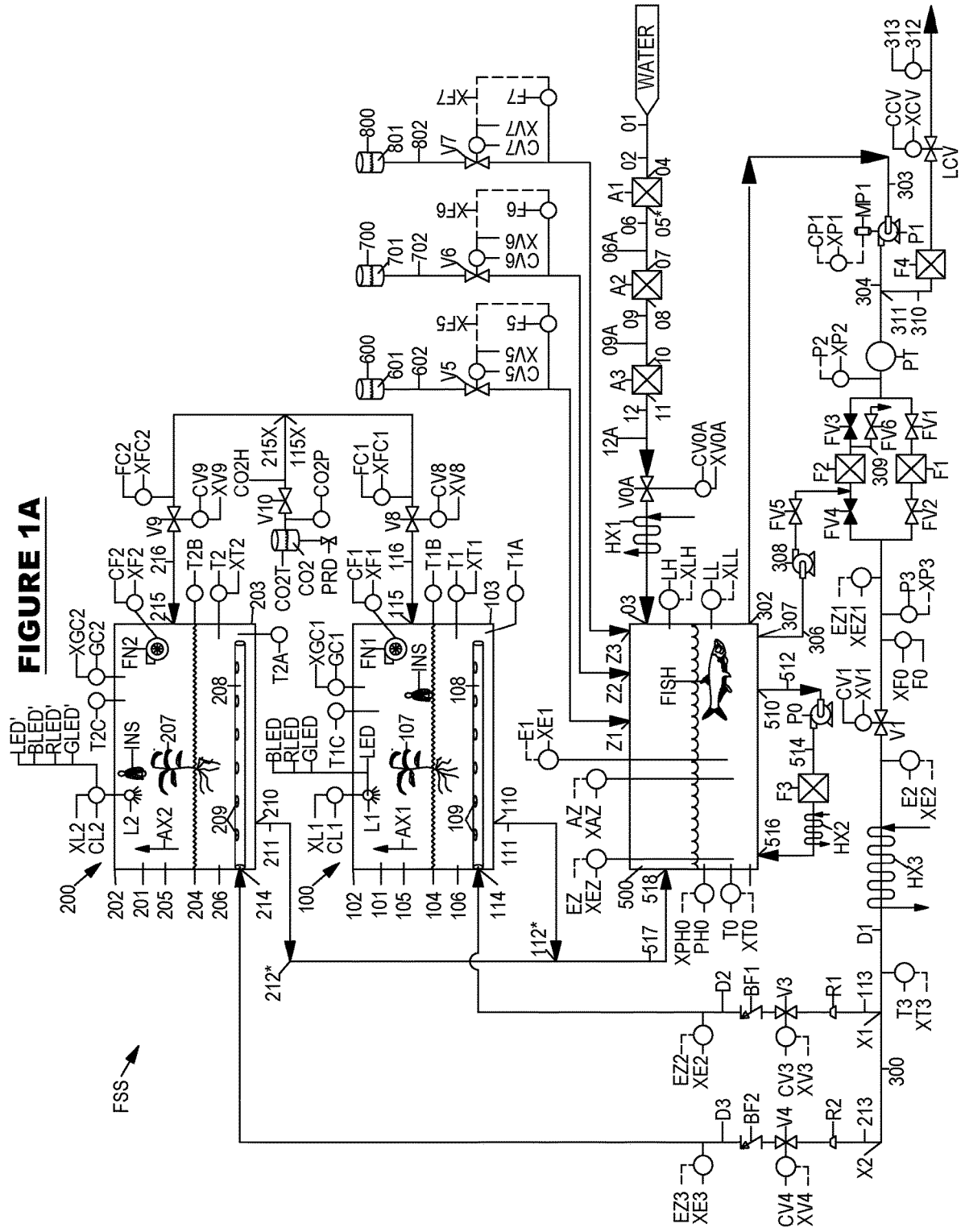

The accompanying figures show schematic process flow-charts of embodiments and variations thereof. A full and enabling disclosure of the content of the accompanying claims, including the best mode thereof to one of ordinary skill in the art, is set forth more particularly in the remainder of the specification, including reference to the accompanying figures showing how the preferred embodiments and other non-limiting variations of other embodiments described herein may be carried out in practice, in which:

FIG. 1A depicts one non-limiting embodiment of a farming superstructure system (FSS) including a first water treatment unit (A1), a second water treatment unit (A2), a third water treatment unit (A3), a common reservoir (500), a pump (P1), a plurality of vertically stacked growing assemblies (100, 200), a fabric (104, 204) that partitions each growing assembly (100, 200) into an upper-section (105, 205) and a lower-section (106, 206), a plurality of lights (L1, L2) positioned within the upper-section (105, 205) of each growing assembly.

Figure 1B:
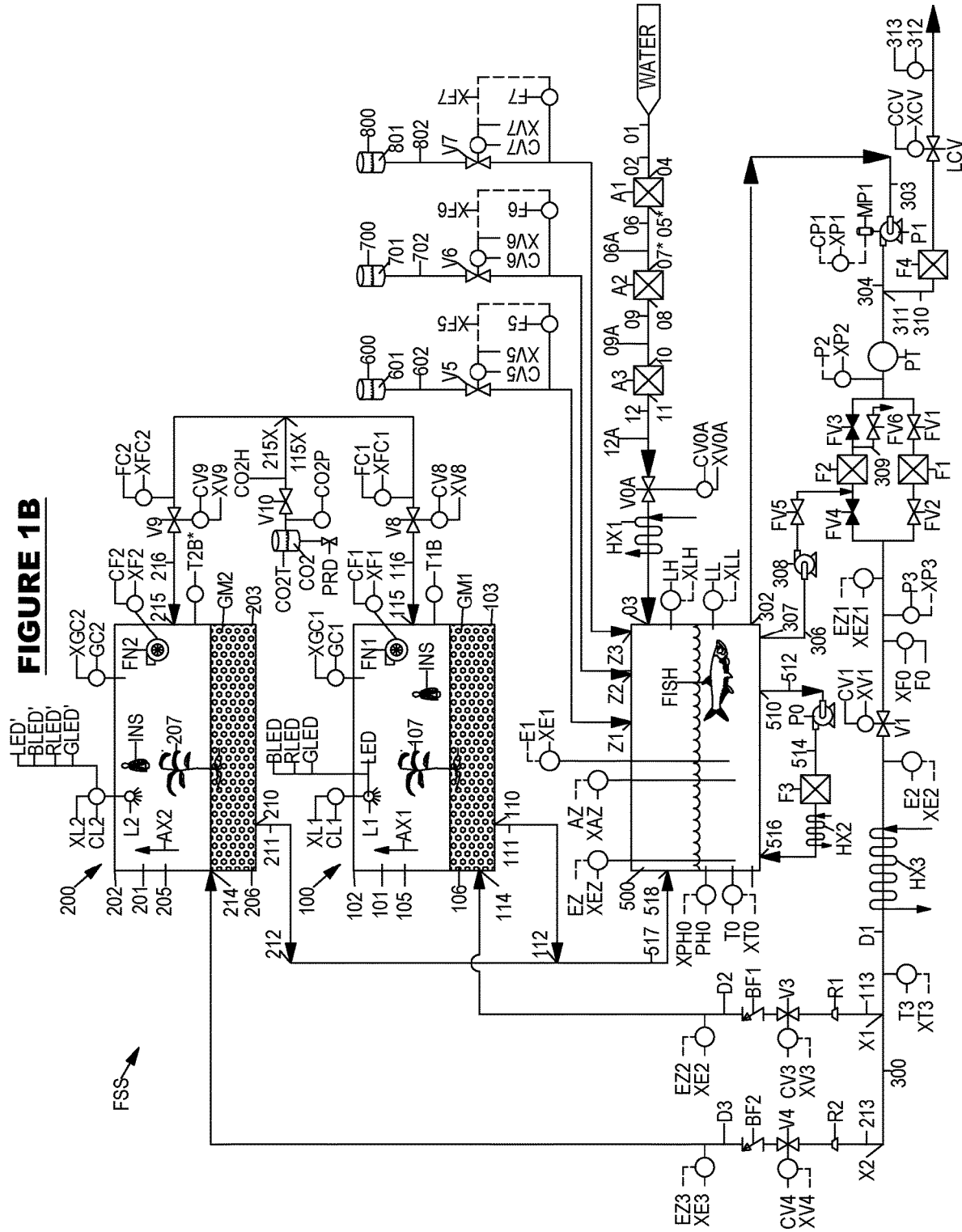

FIG. 1B depicts one non-limiting embodiment of a farming superstructure system (FSS) that includes a first growing assembly (100) having a first growing medium (GM1) and a second growing assembly (200) having a second growing medium (GM2).

Figure 1C:
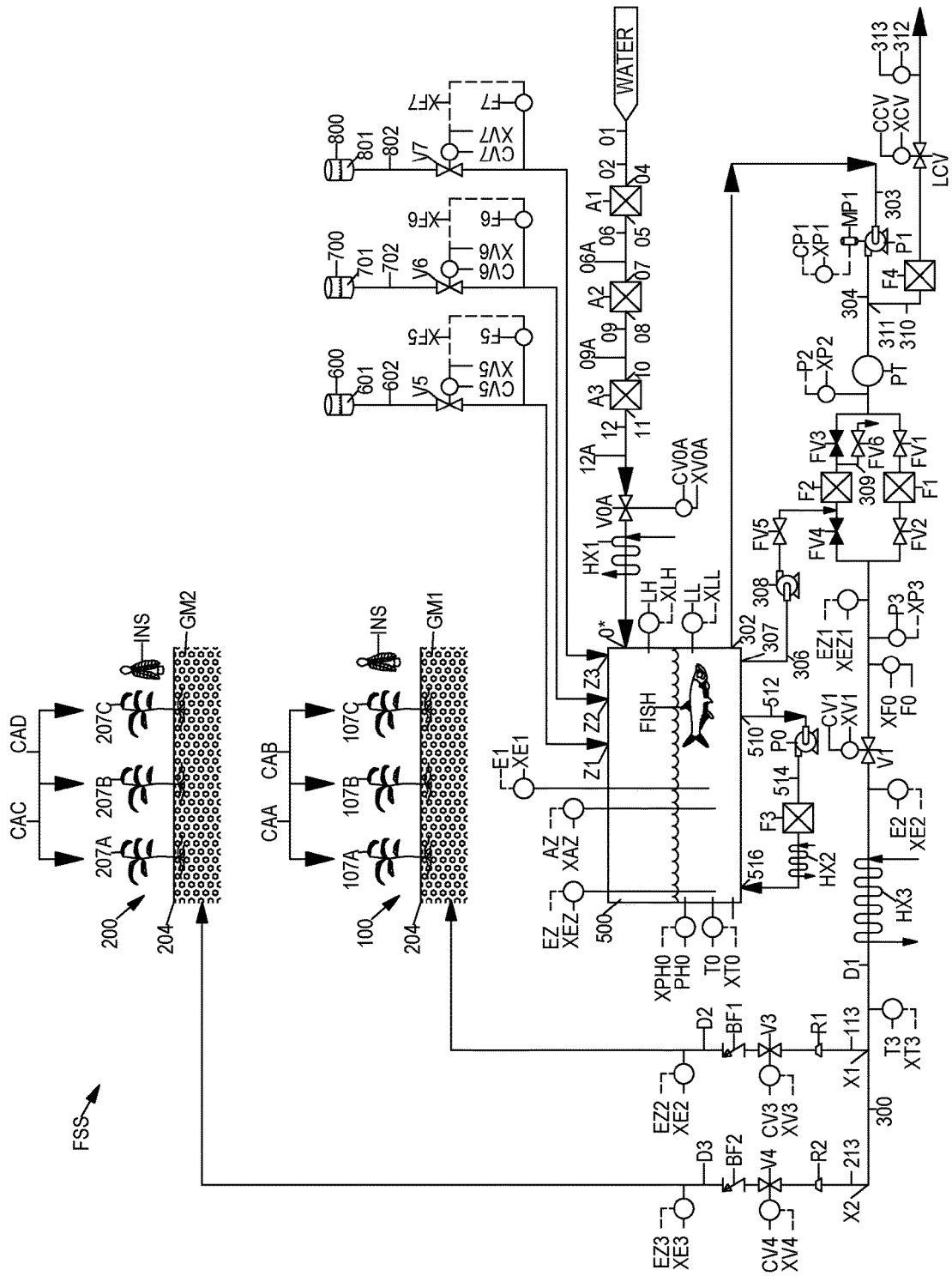

FIG. 1C depicts one non-limiting embodiment of a farming superstructure system (FSS) that includes a first growing assembly (100) having a first growing medium (GM1) and a second growing assembly (200) having a second growing medium (GM2) and the first growing assembly (100) and second growing assembly (200) are grown outdoors.

FIG. 1D depicts one non-limiting embodiment general arrangement of a farming superstructure system (FSS) top-view that includes a first growing assembly (100) and a second growing assembly (200) each configured to grow plants (107, 107A, 107B, 107C, 207, 207A, 207B, 207C).

Figure 17:
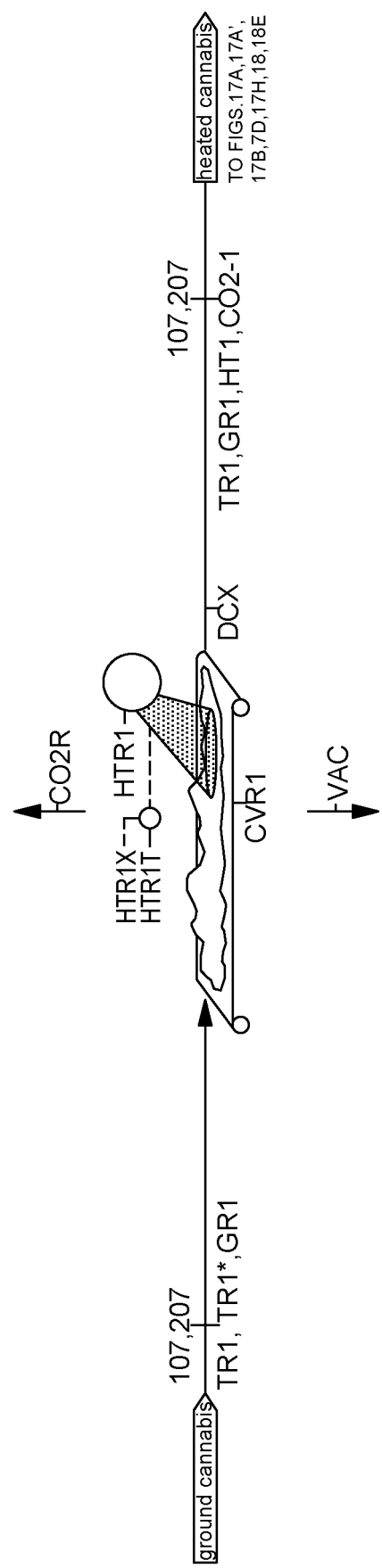
Figure 17A:
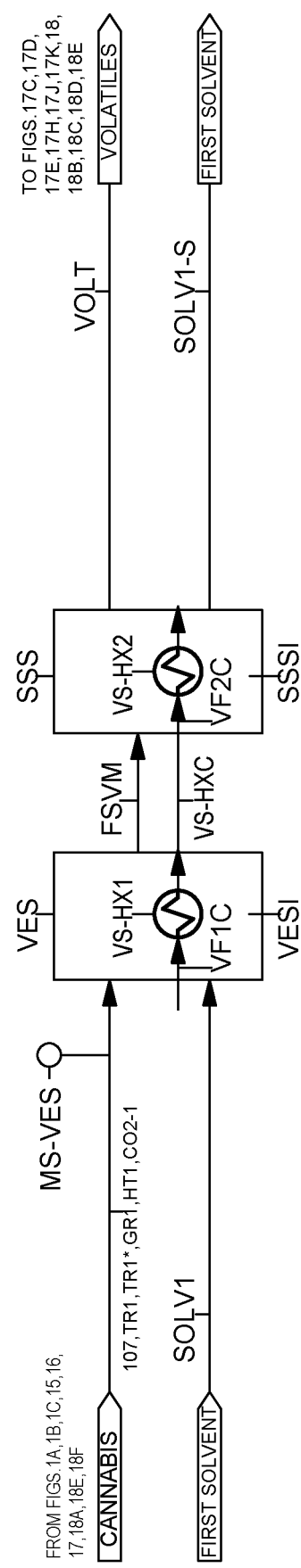
Figure 17A:
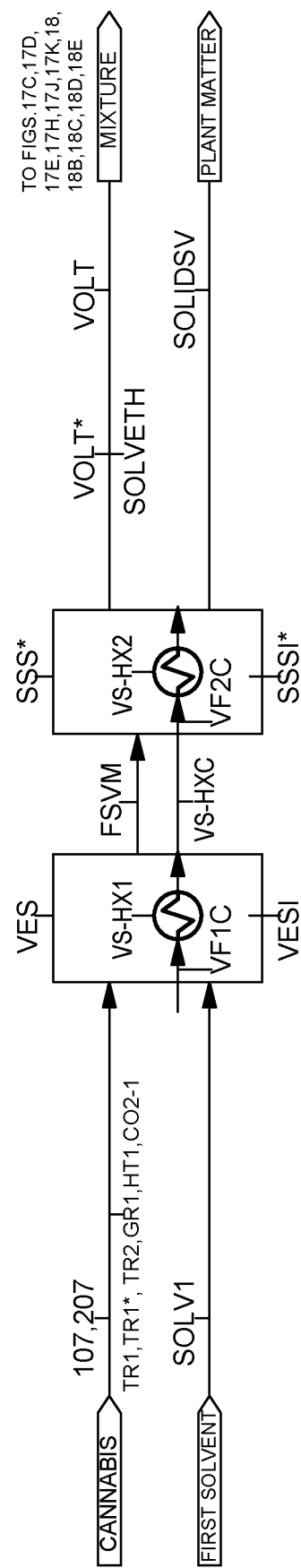
Figure 17B:
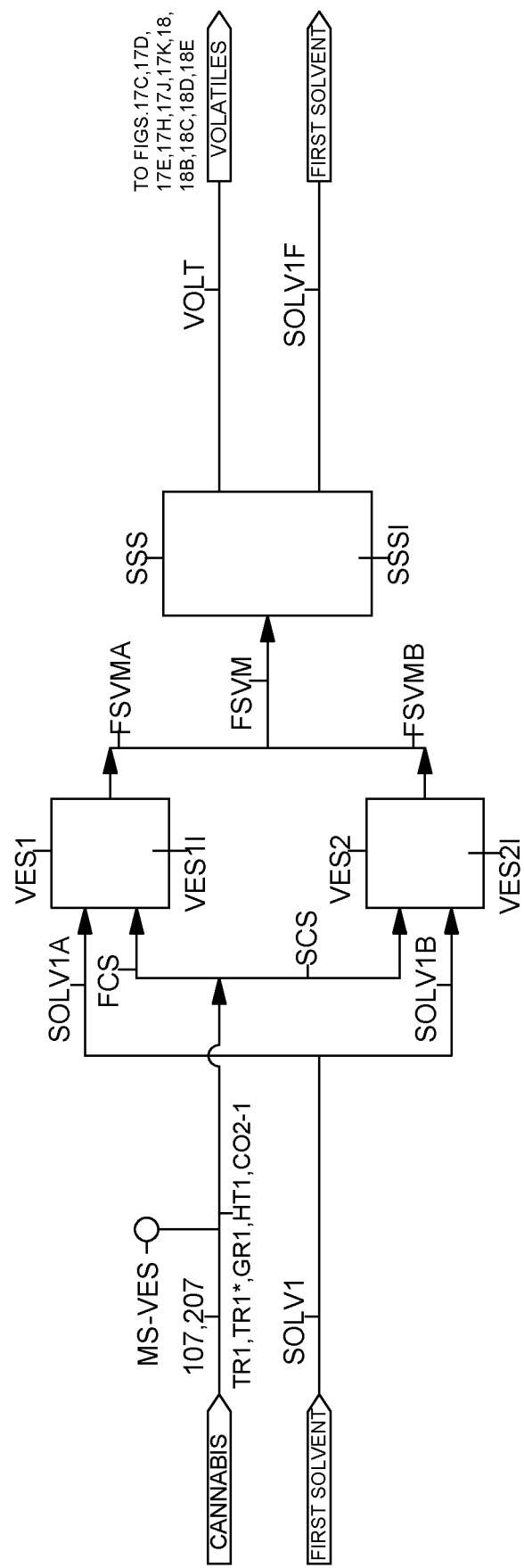
Figure 17D:
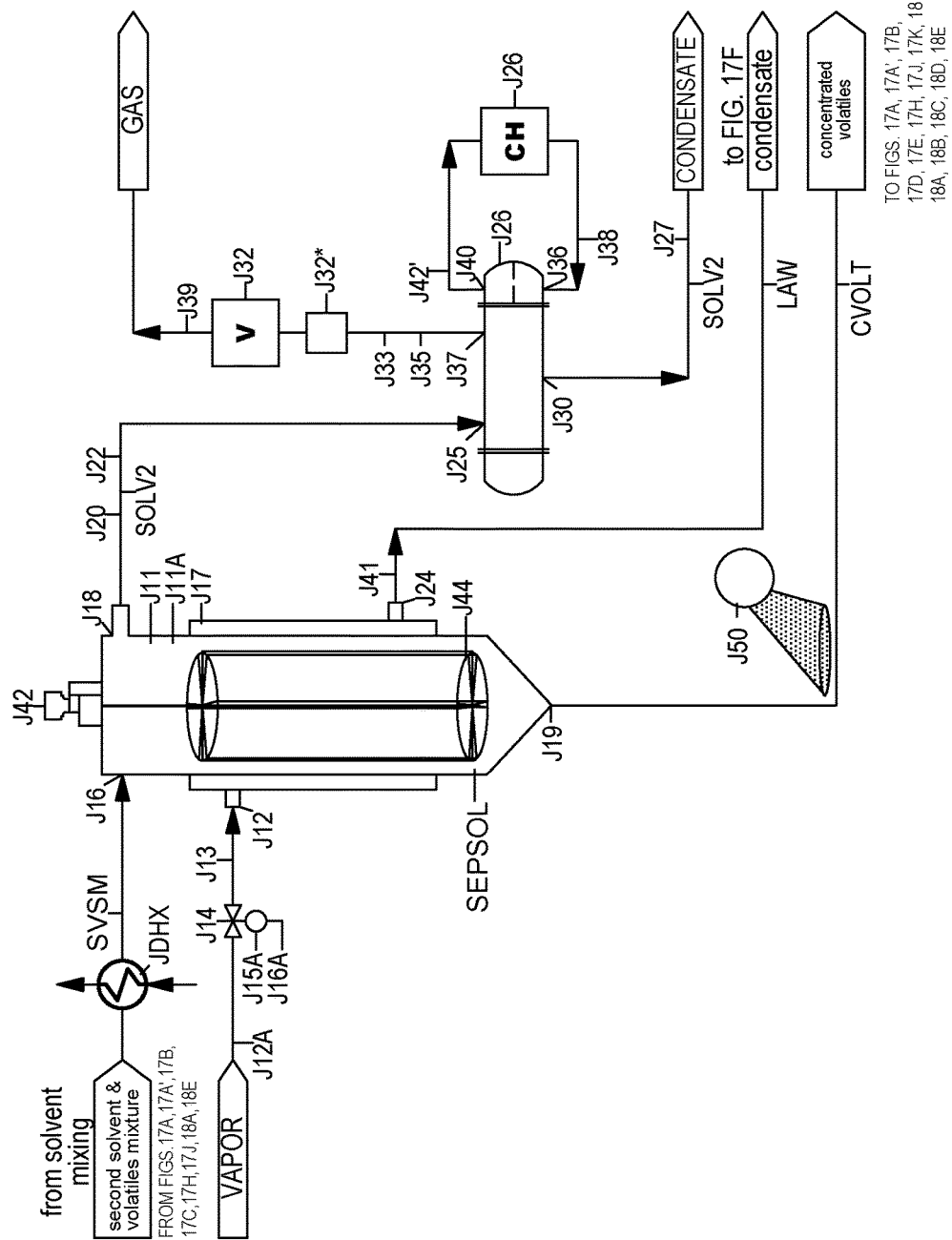
Figure 17D:
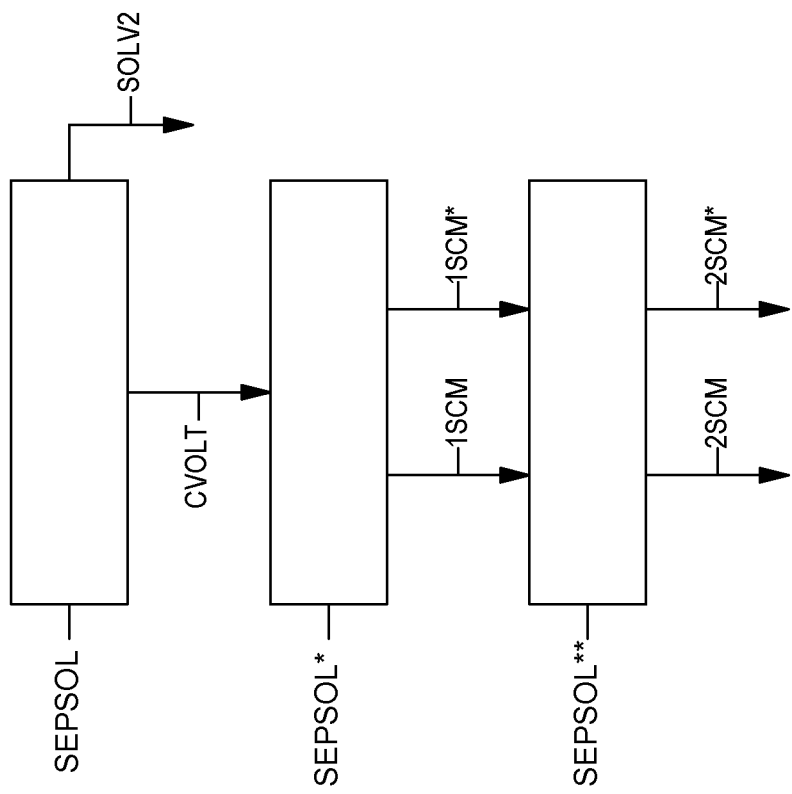
Figure 17E:
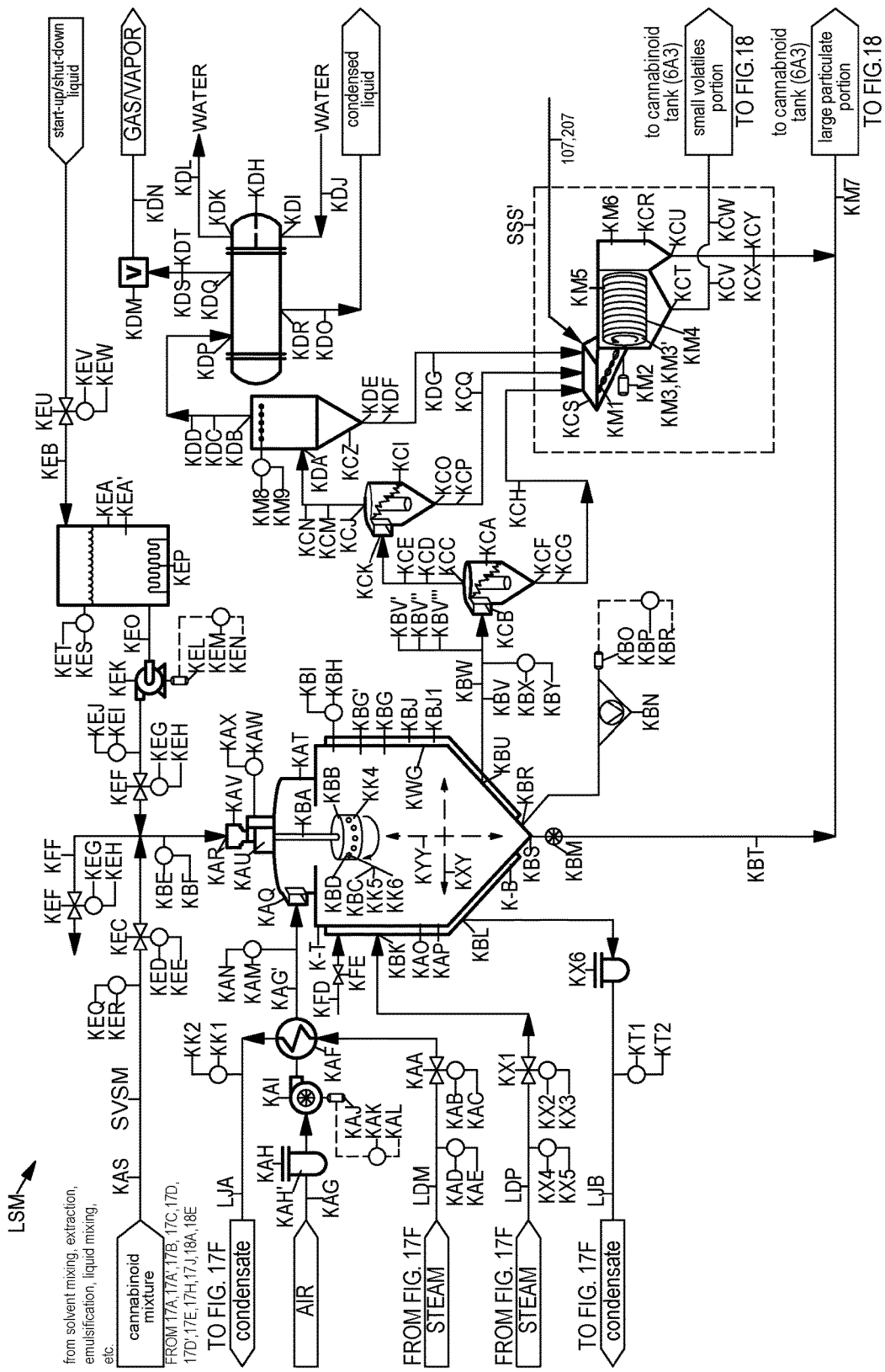
Figures 1, 17E:
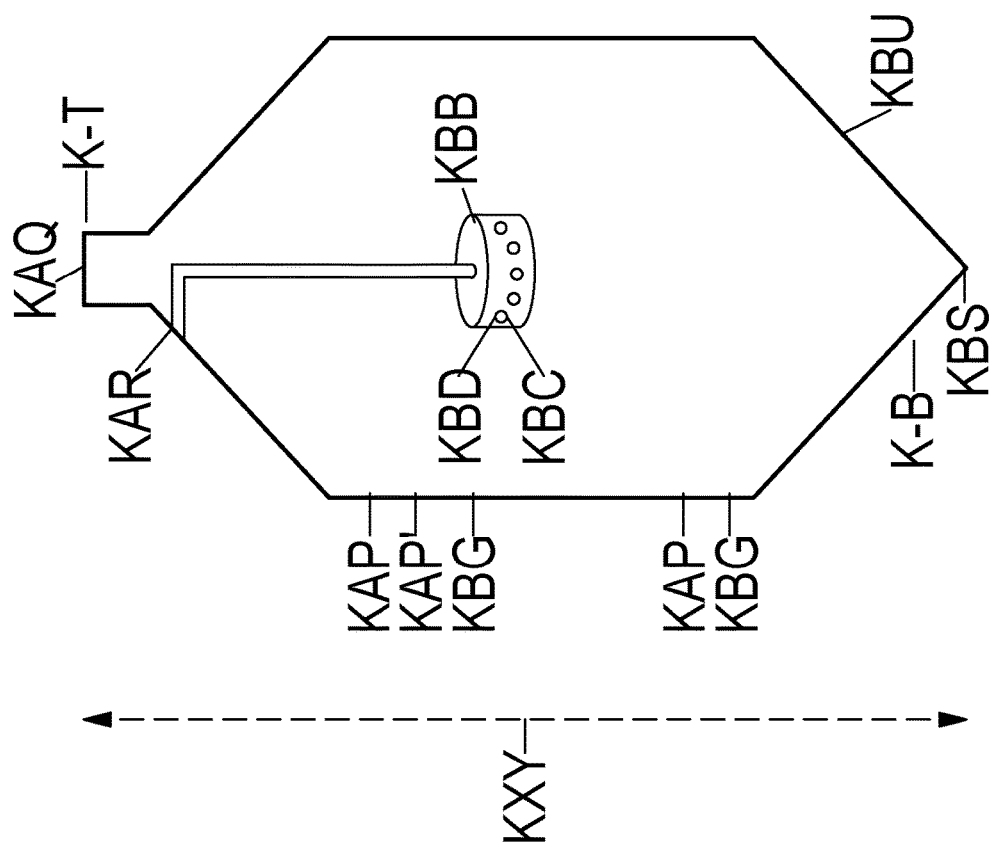
Figures 2, 17E:
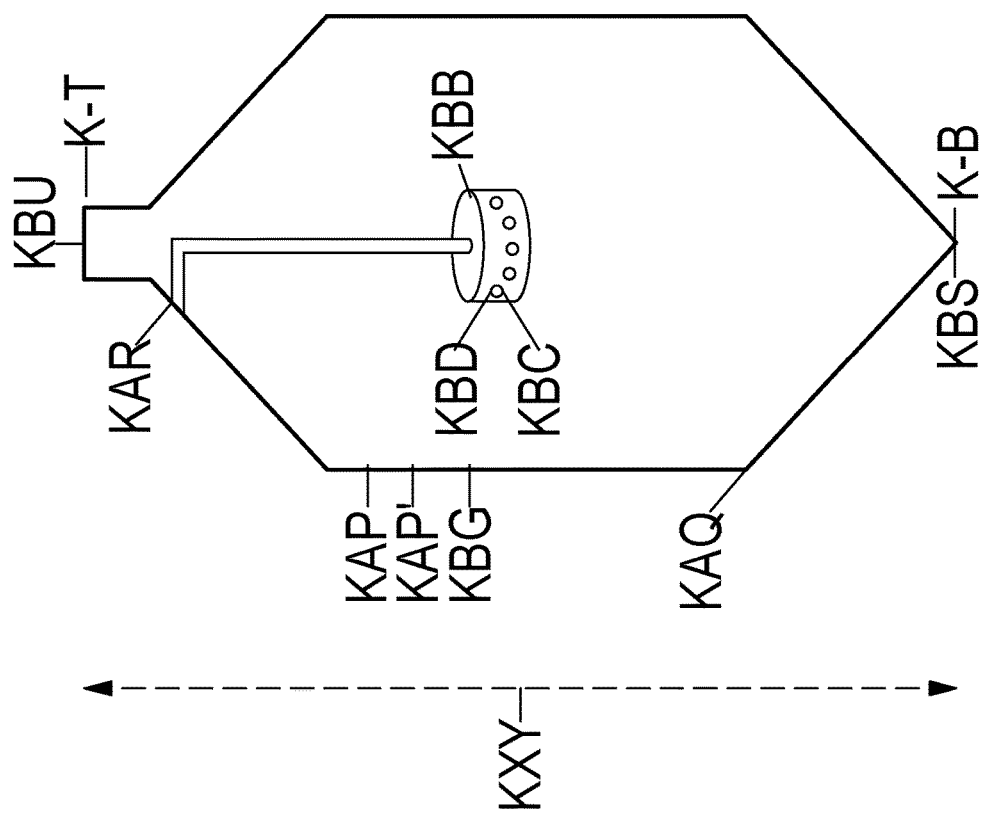
Figures 3, 17E:
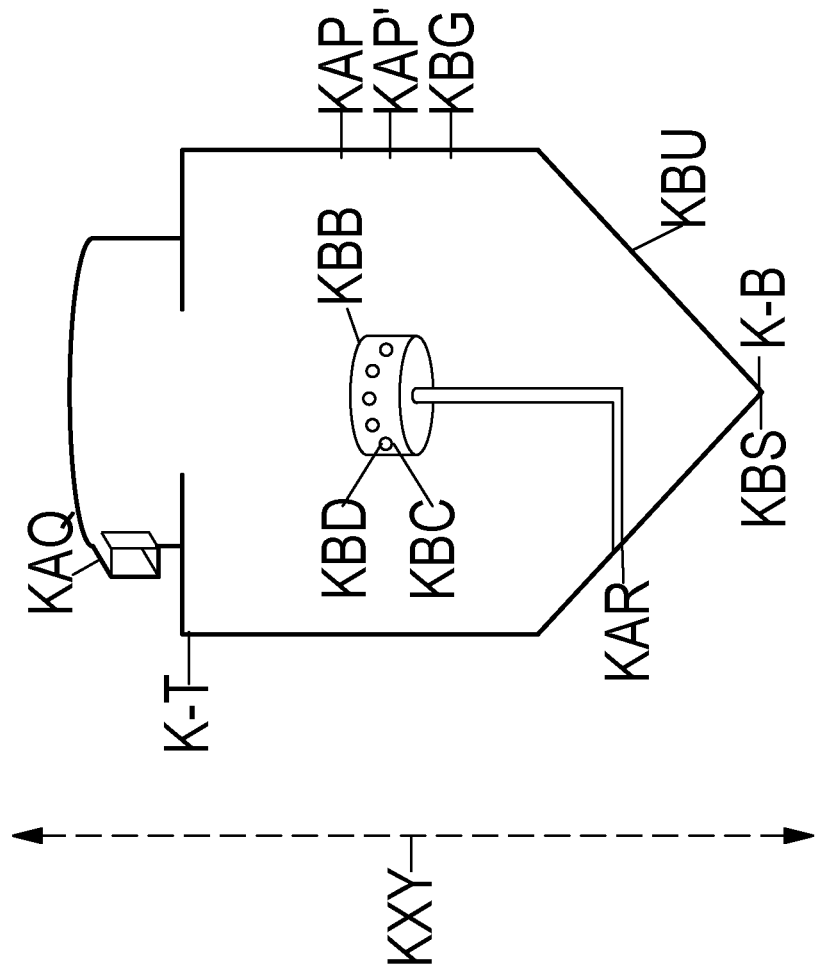

FIG. 2 depicts one non-limiting embodiment of a farming superstructure system (FSS) including a first vertically stacked system (1500) including a plurality of vertically stacked growing assemblies (100, 200) integrated with a first and second vertical support structure (VSS1, VSS2) wherein the first growing assembly (100) is supported by a first horizontal support structure (SS1) and a second growing assembly (200) is supported by a second horizontal support structure (SS2).

Figure 3:
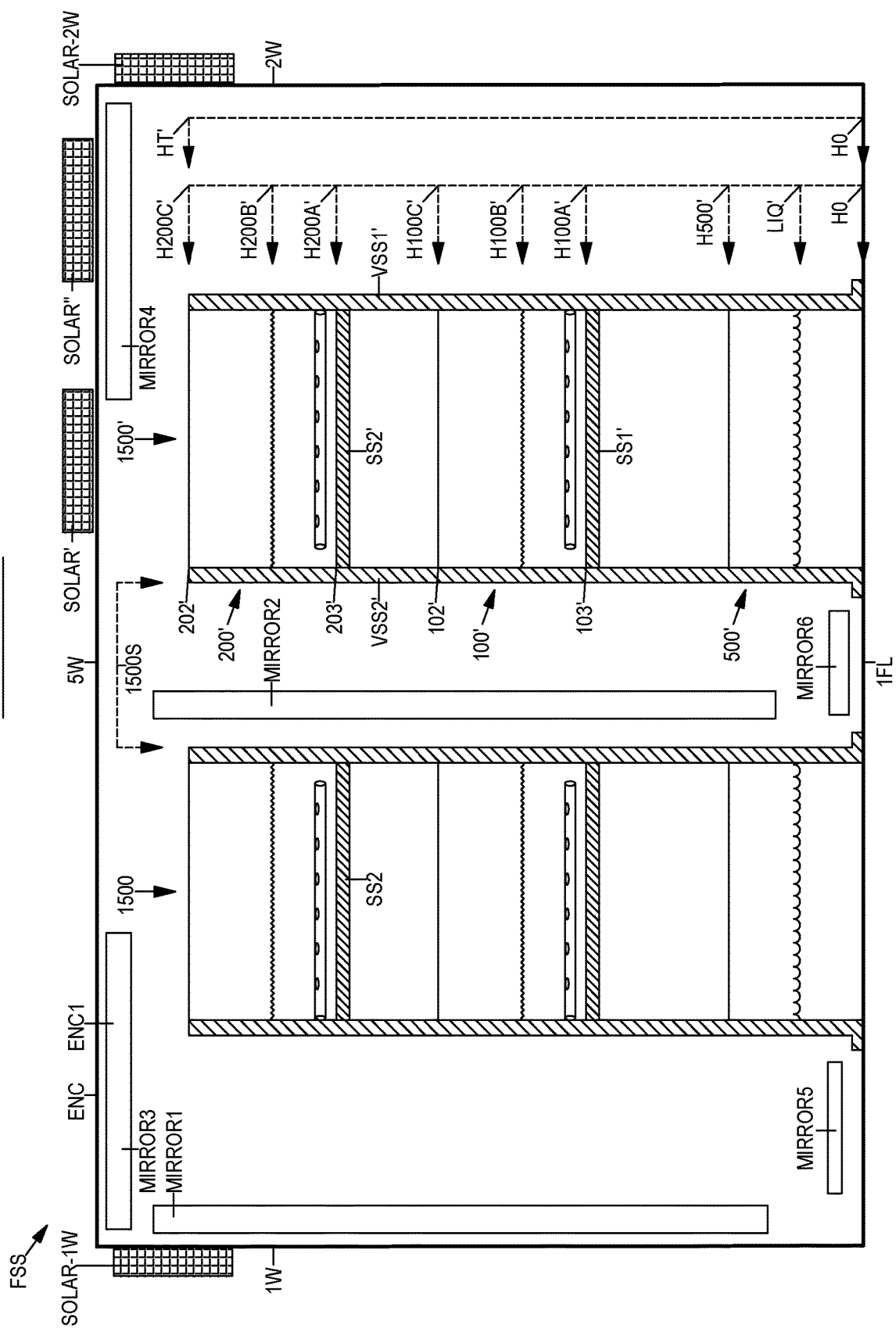

FIG. 3 depicts one non-limiting embodiment of a plurality of vertically stacked systems (1500, 1500) including a first vertically stacked system (1500) and a second vertically stacked system (1500), the first vertically stacked system (1500) as depicted in FIG. 2, also both vertically stacked systems (1500, 1500) are contained within an enclosure (ENC) having an interior (ENC1).

Figure 4A:
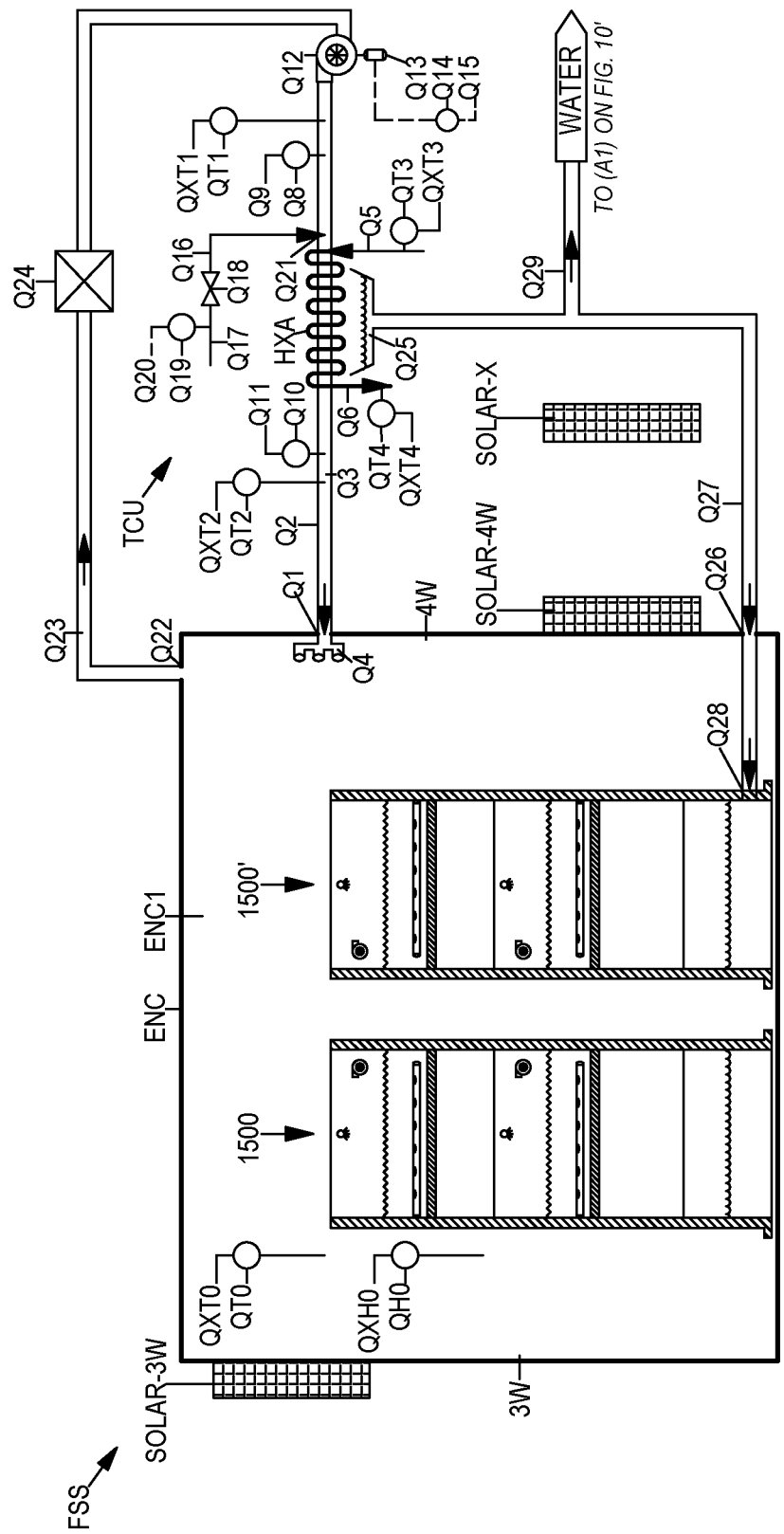

FIG. 4A depicts one non-limiting embodiment of FIG. 3 wherein the enclosure (ENC) is provided with a temperature control unit (TCU) including an air heat exchanger (HXA) that is configured to provide a temperature and/or humidity-controlled air supply (Q3) to the interior (ENC1) of the enclosure (ENC) which contains a plurality of vertically stacked systems (1500, 1500).

Figure 4B:
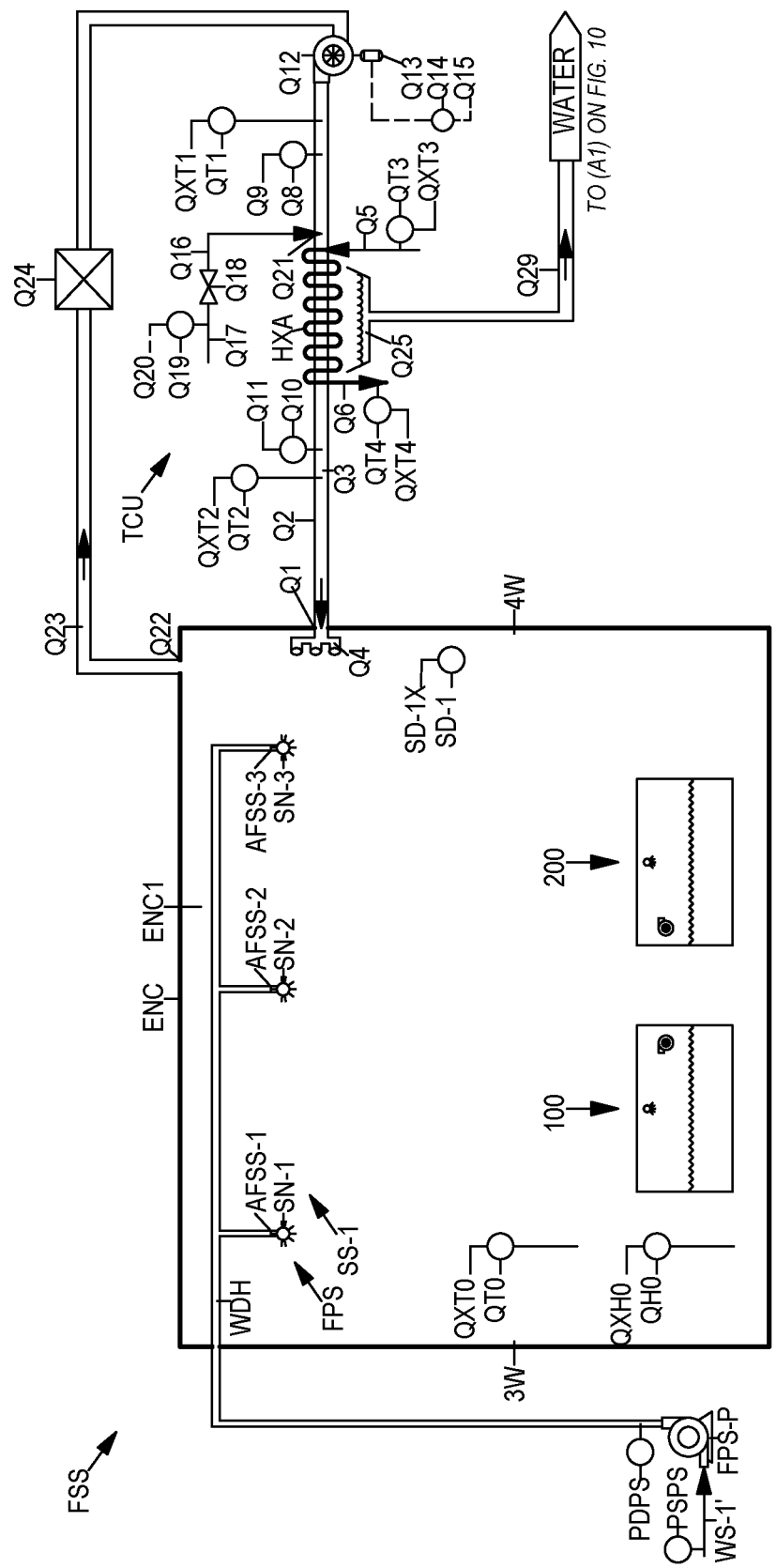

FIG. 4B depicts one non-limiting embodiment of FIG. 1B and FIG. 4A wherein the enclosure (ENC) is provided with a temperature control unit (TCU) including an air heat exchanger (HXA) that is configured to provide a temperature and/or humidity-controlled air supply (Q3) to the interior (ENC1) of the enclosure (ENC) which contains a plurality of growing assemblies (100, 200).

Figure 5A:
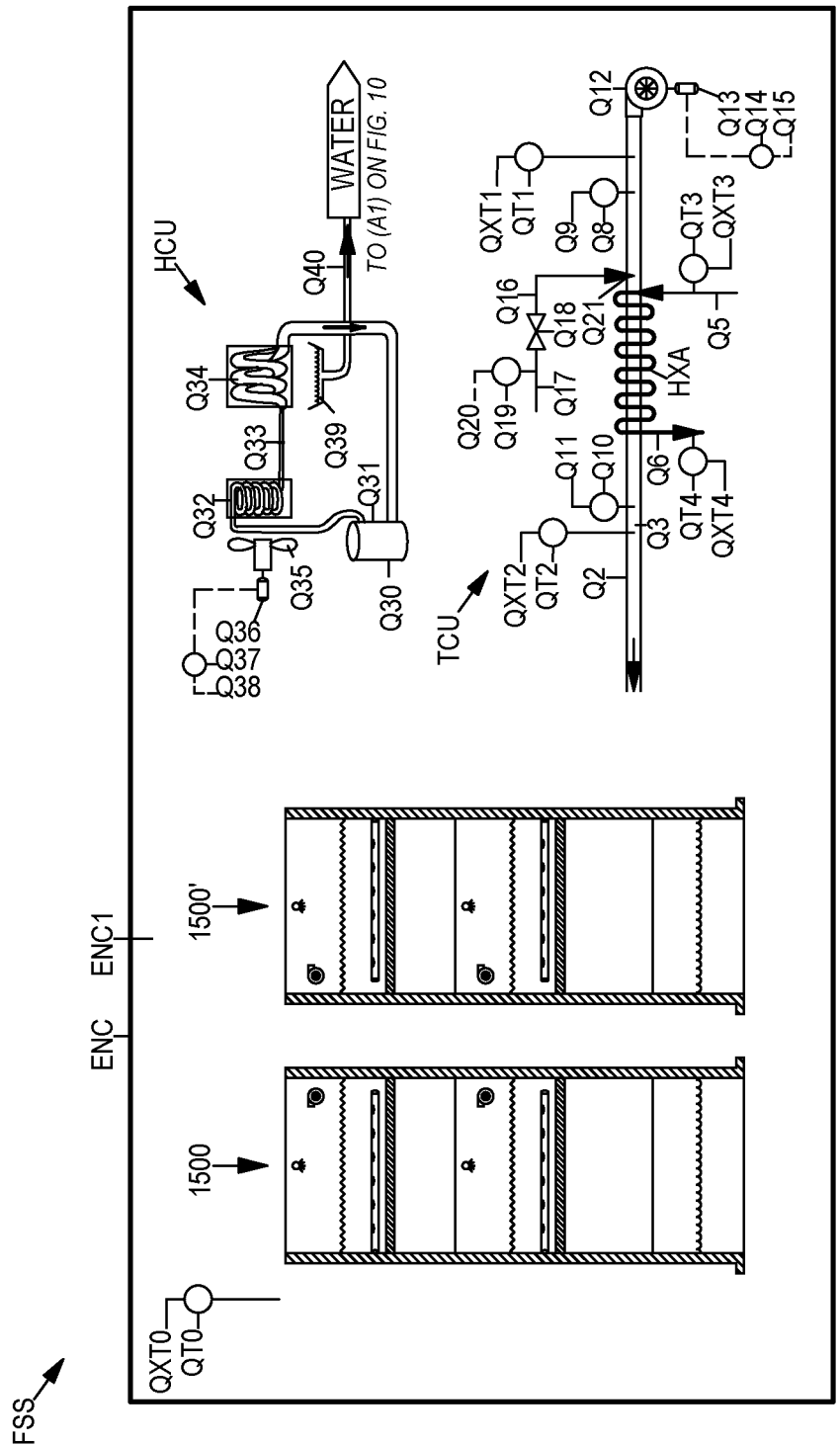

FIG. 5A depicts one non-limiting embodiment of FIG. 4A wherein the temperature control unit (TCU) of FIG. 4A is contained within the interior (ENC1) of the enclosure (ENC) and coupled with a humidity control unit (HCU).

Figure 5B:
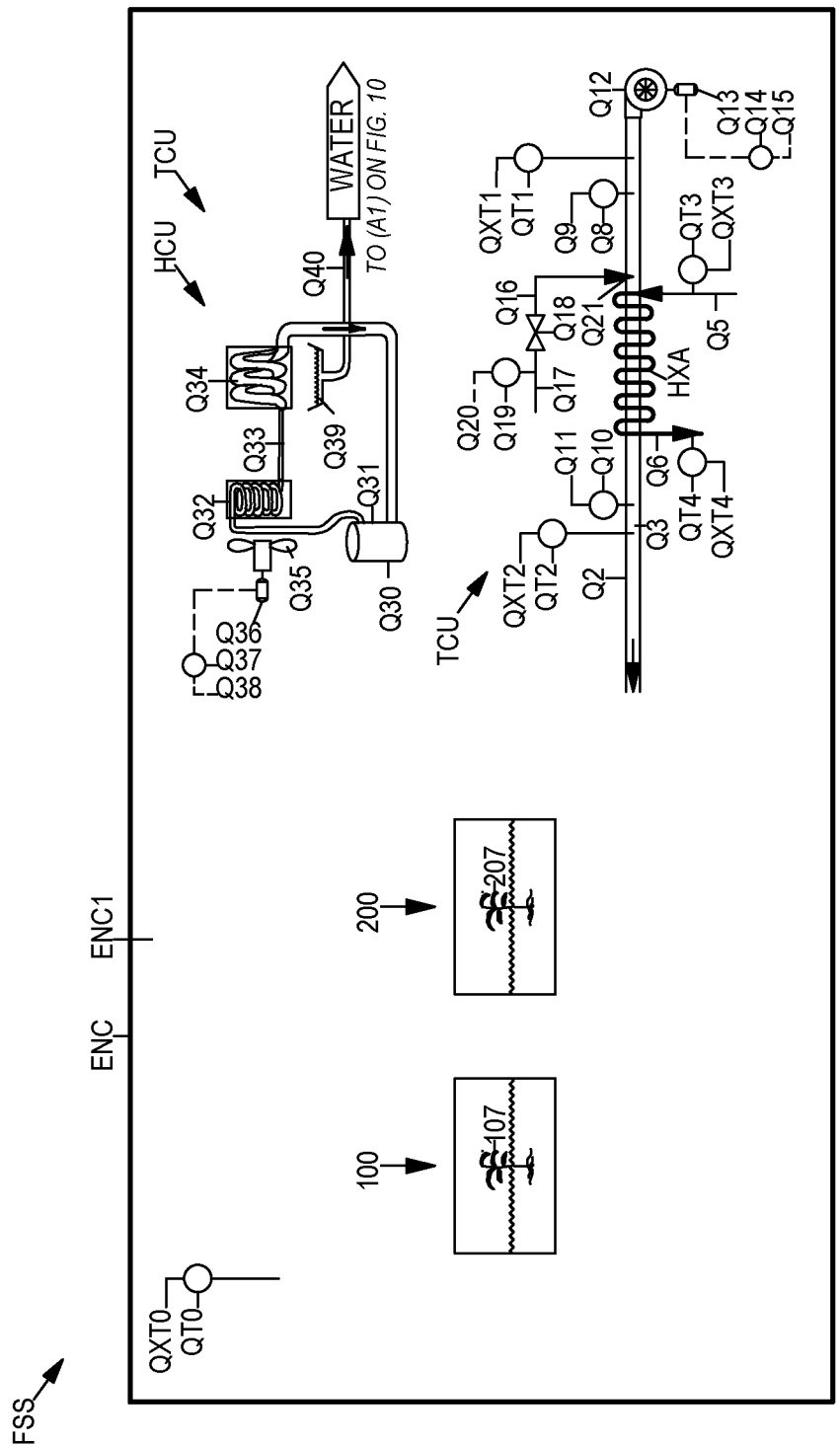

FIG. 5B depicts one non-limiting embodiment of FIG. 4B and FIG. 5A wherein the temperature control unit (TCU) of FIG. 4B is contained within the interior (ENC1) of the enclosure (ENC) and coupled with a humidity control unit (HCU).

FIG. 5C shows one non-limiting embodiment where the compressor (Q30) within the humidity control unit (HCU) is that of a thermal compressor (Q30) that accepts a source of steam.

Figure 5D:
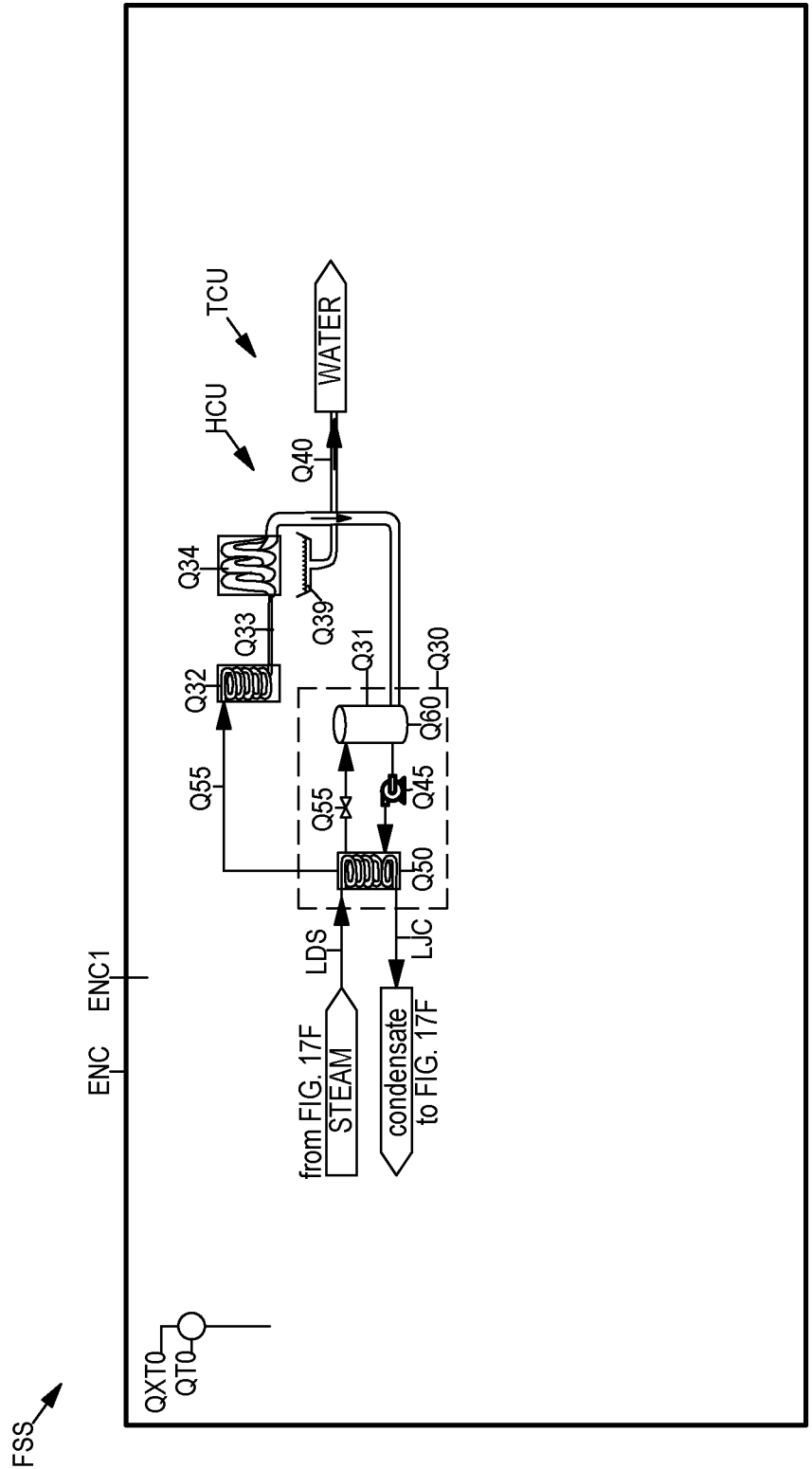

FIG. 5D shows one non-limiting embodiment where the compressor (Q30) within the humidity control unit (HCU) is that of a thermal compressor (Q30) that accepts a source of steam.

Figure 5E:
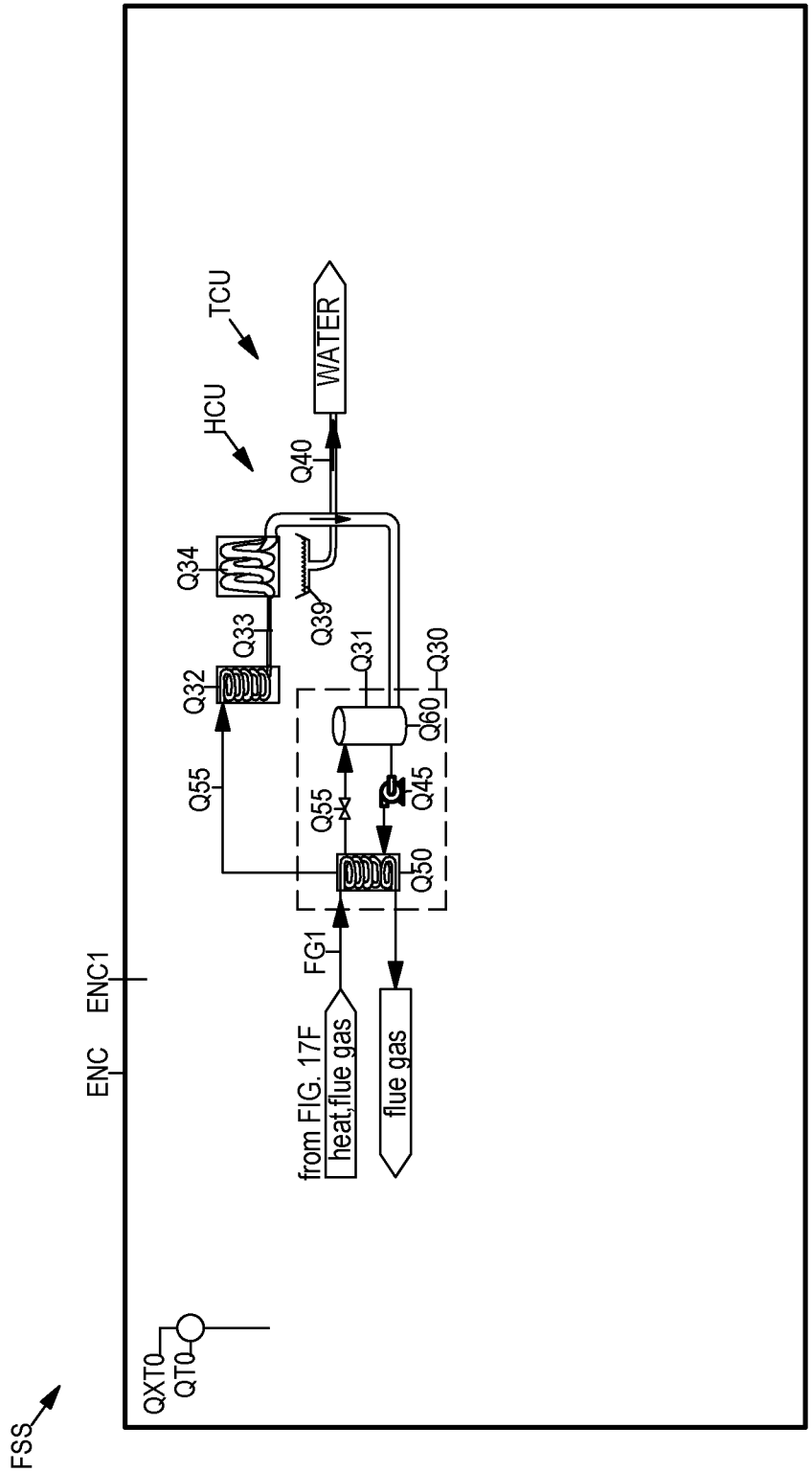

FIG. 5E elaborates upon FIG. 5D and shows one non-limiting embodiment where the compressor (Q30) within the humidity control unit (HCU) is that of a thermal compressor (Q30) that accepts a source of heat, such as flue gas (FG1).

FIG. 6 shows a front view of one embodiment of a plant growing module (PGM) provided inside of a shipping container conforming to the International Organization for Standardization (ISO) specifications.

FIG. 7 shows a top view of one embodiment of a plant growing module (PGM) provided inside of a shipping container conforming to the International Organization for Standardization (ISO) specifications.

Figure 8:
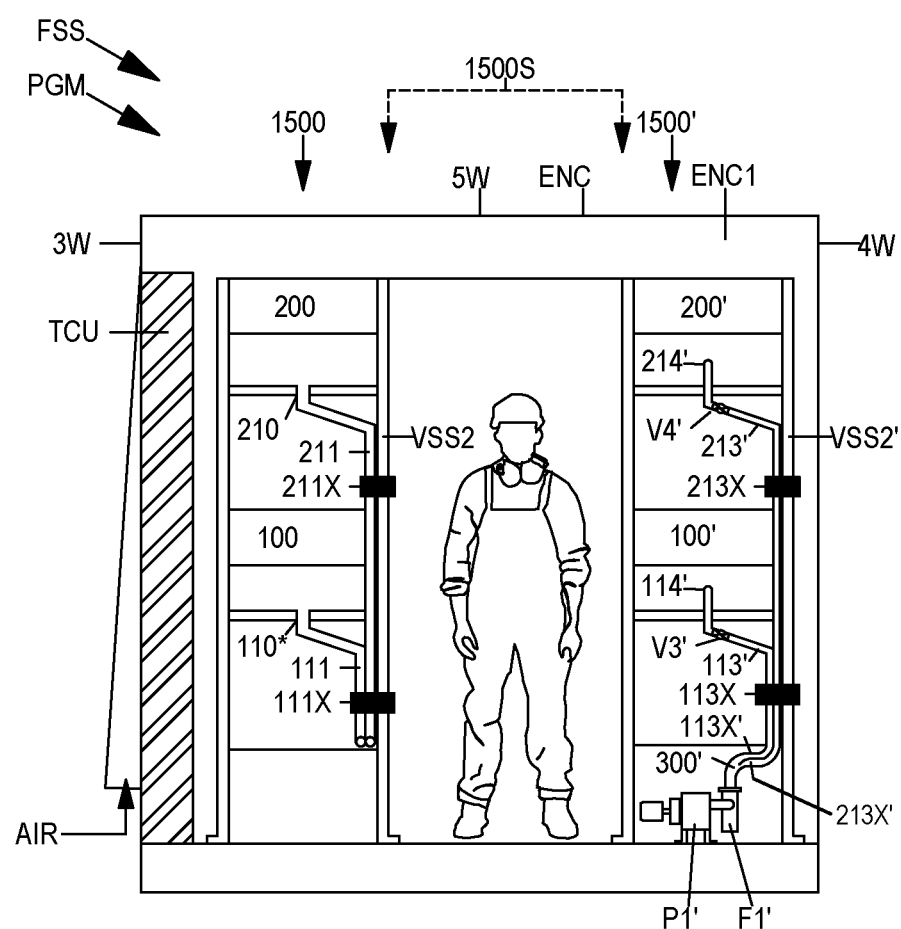

FIG. 8 shows a first side view of one embodiment of a plant growing module (PGM).

FIG. 9 shows a front view of one embodiment of a liquid distribution module (LDM) provided inside of a shipping container conforming to the International Organization for Standardization (ISO) specifications and that is configured to provide a source of liquid to a plurality of plant growing modules (PGM).

FIG. 10 shows a top view of one embodiment of a liquid distribution module (LDM) provided inside of a shipping container conforming to the International Organization for Standardization (ISO) specifications and that is configured to provide a source of liquid to a plurality of plant growing modules (PGM).

Figure 11:
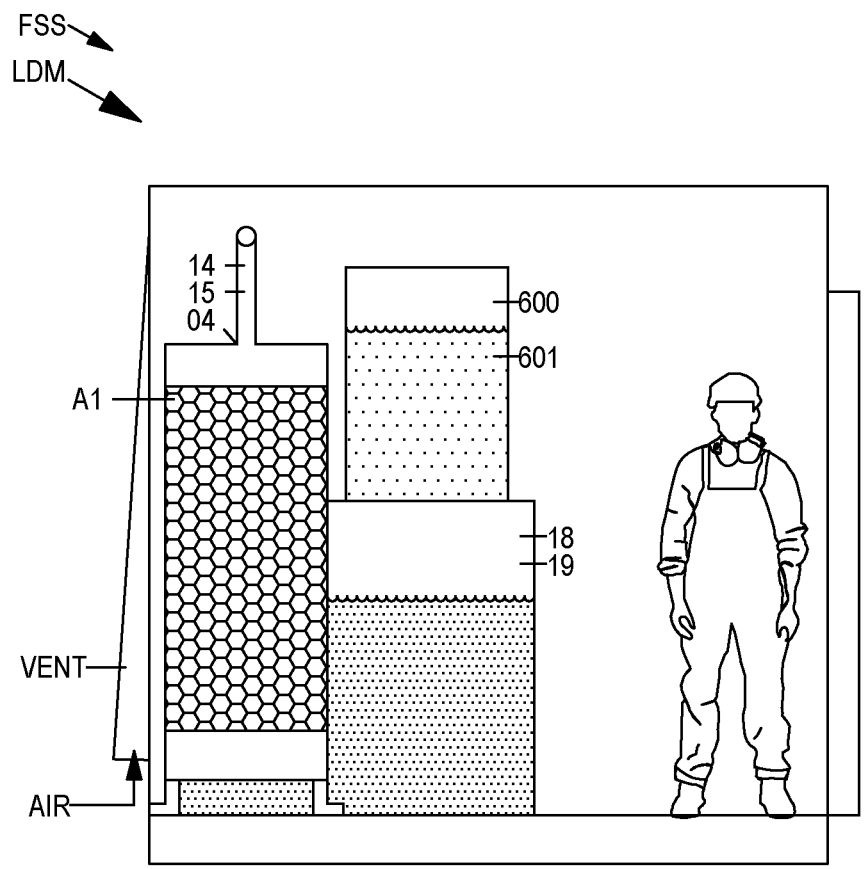

FIG. 11 shows a first side view of one embodiment of a liquid distribution module (LDM).

Figure 12:
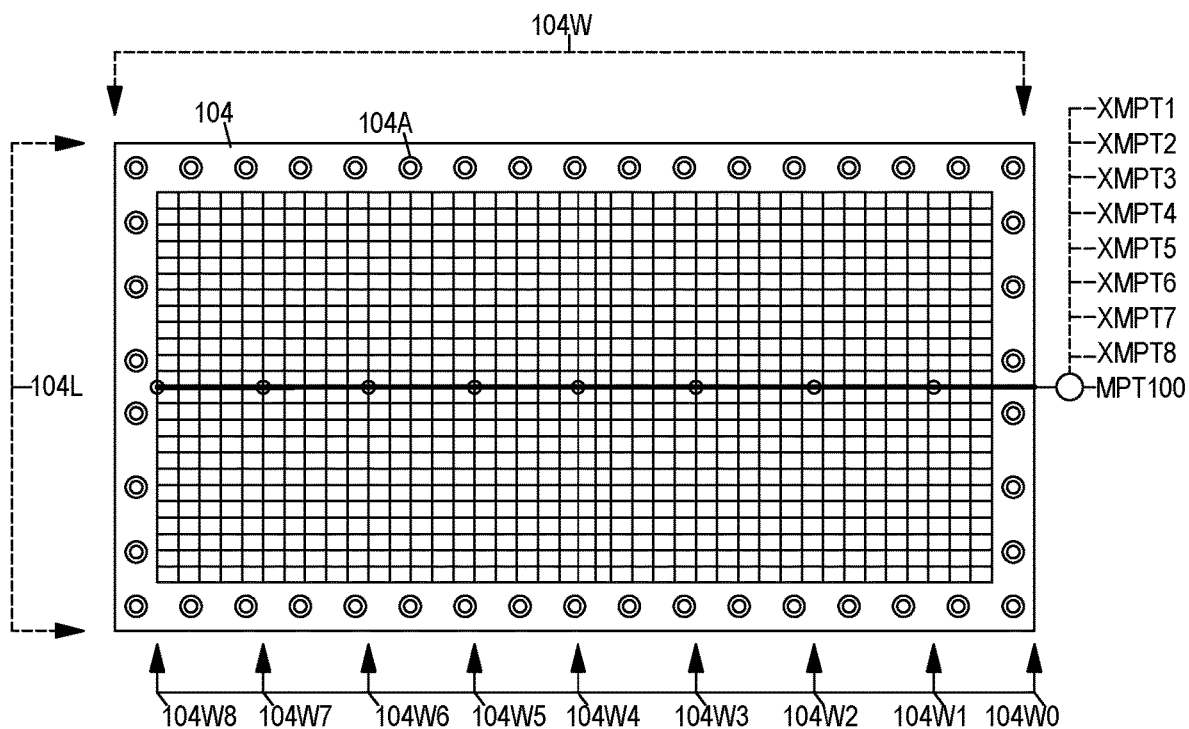

FIG. 12 shows one non-limiting embodiment of a fabric (104) used in a growing assembly (100), the fabric (104) having a multi-point temperature sensor (MPT100) connected thereto for measuring temperatures at various lengths along the sensors length.

Figure 13:
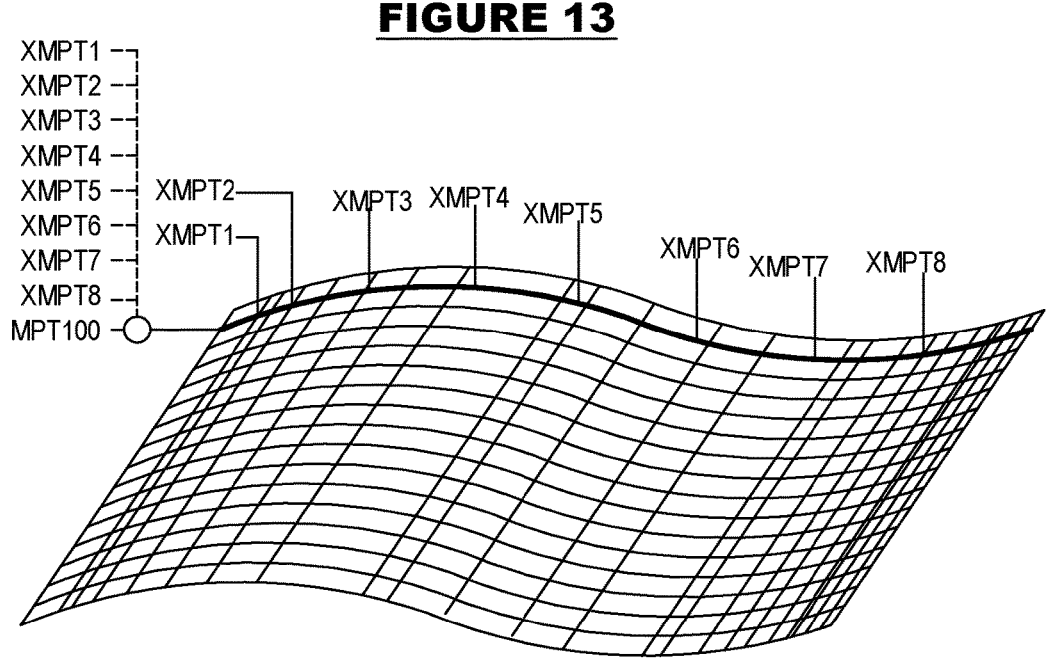

FIG. 13 shows another one non-limiting embodiment of a fabric (104) used in a growing assembly (100).

Figure 14:
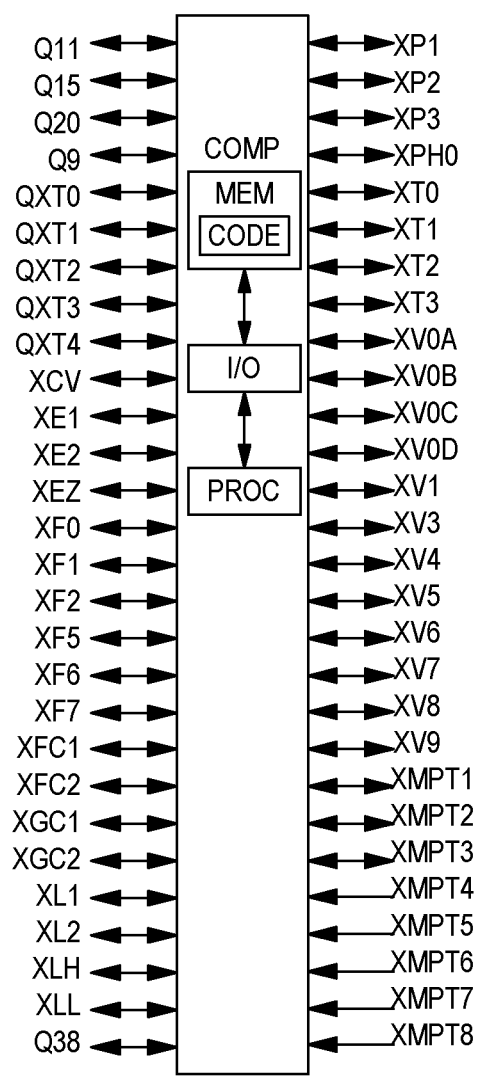

FIG. 14 depicts a computer (COMP) that is configured to input and output signals listed in FIGS. 1-24.

Figure 15:
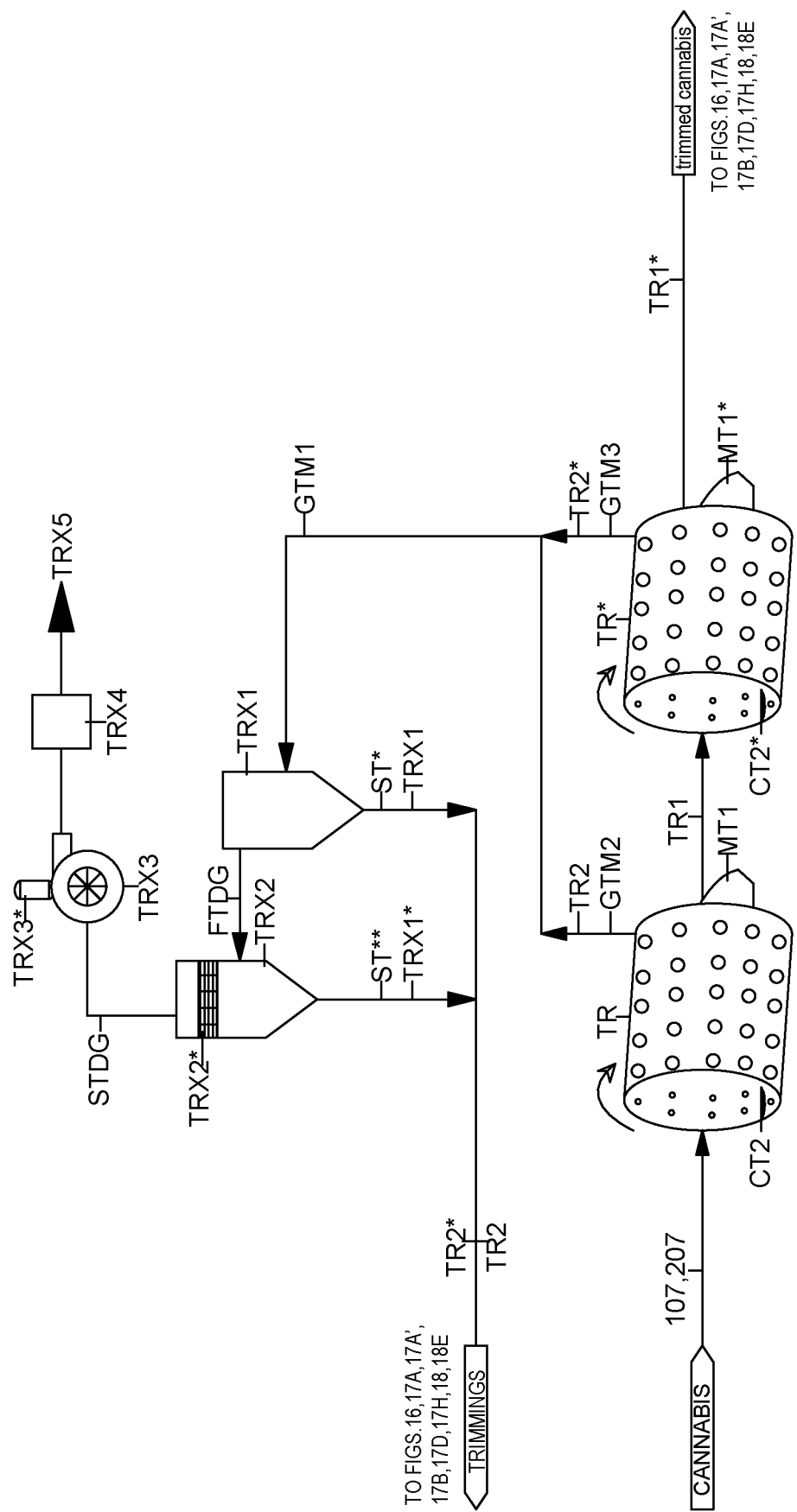

FIG. 15 shows a plurality of *cannabis* trimmers (TR, TR*) that are configured to trim at least a portion of the *cannabis* (107, 207) that was growing in each growing assembly (100, 200).

Figure 16:
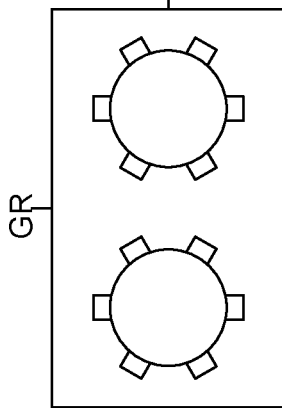

FIG. 16 shows a grinder (GR) that is configured to grind at least a portion of *cannabis* plants (107, 207) that was growing in each growing assembly (100, 200).

FIG. 17 shows a heater (HTR1) that is configured to heat at least a portion of *cannabis* plants (107, 207) that was growing in each growing assembly (100, 200).

FIG. 17A shows one non-limiting embodiment of a volatiles extraction system (VES) that is configured to extract volatiles from *cannabis* (107, 207) with a first solvent (SOLV1).

FIG. 17A' shows one non-limiting embodiment of a volatiles extraction system (VES) that is configured to extract volatiles from *cannabis* (107, 207) with a chilled ethanol separation system (CESS).

FIG. 17B shows a plurality of volatiles extraction systems (VES1, VES2) equipped with one first solvent separation system (SSS).

FIG. 17C shows a volatiles and solvent mixing system (VSMS) that is configured to mix the volatiles (VOLT) with a second solvent (SOLV2).

FIG. 17D shows a separation system (SEPSOL) that is configured to separate at least a portion of the solvent (SOLV2) and/or volatiles and/or cannabinoids from the volatiles and solvent mixture (SVSM) to produce concentrated volatiles (CVOLT).

FIG. 17D' shows a plurality of sequential separation systems (SEPSOL, SEPSOL, SEPSOL) that are configured to separate at least a portion of the solvent, volatiles, and/or cannabinoids from produce concentrated volatiles (CVOLT) and a plurality of different compounds (1SCM, 1SCM, 2SCM, 2SCM)

FIG. 17E shows one non-limiting embodiment of a solvent separation system that is configured to evaporate the second solvent from the volatiles and solvent mixture (SVSM) by use of a spray dryer (KAP).

FIG. 17E-1 shows one non-limiting embodiment of a co-current type of spray dryer (KAP) that may be used with the solvent separation system described in FIG. 17E.

FIG. 17E-2 shows one non-limiting embodiment of a counter-current type of spray dryer (KAP) that may be used with the solvent separation system described in FIG. 17E.

FIG. 17E-3 shows another non-limiting embodiment of a counter-current type of spray dryer (KAP) that may be used with the solvent separation system described in FIG. 17E.

FIG. 17E-4 shows one non-limiting embodiment of a mixed-flow type of spray dryer (KAP) that may be used with the solvent separation system described in FIG. 17E.

Figure 17F:
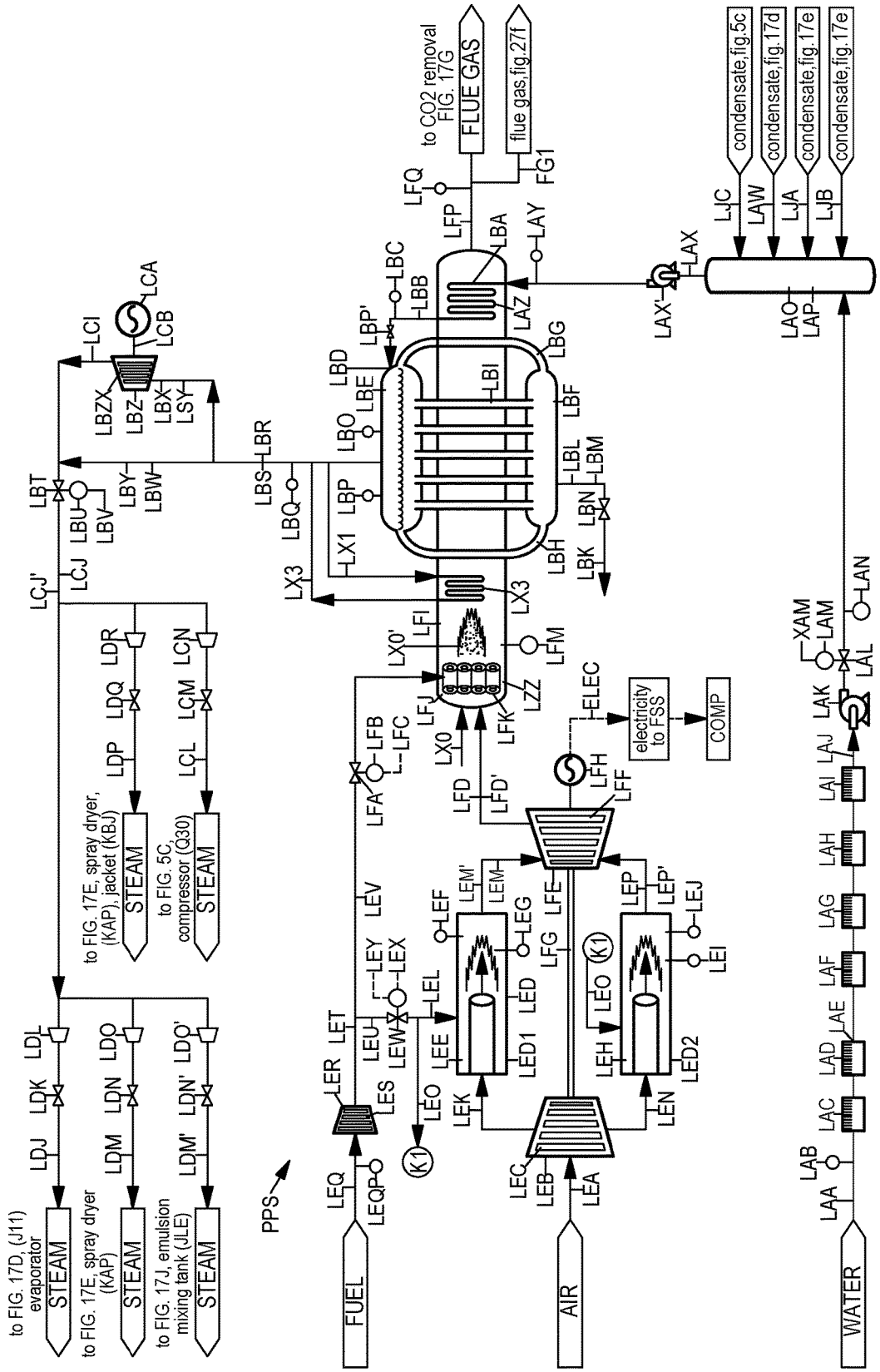

FIG. 17F shows a power production system (PPS) that is configured to generate electricity, heat, or steam for use in the farming superstructure system (FSS).

Figure 17G:
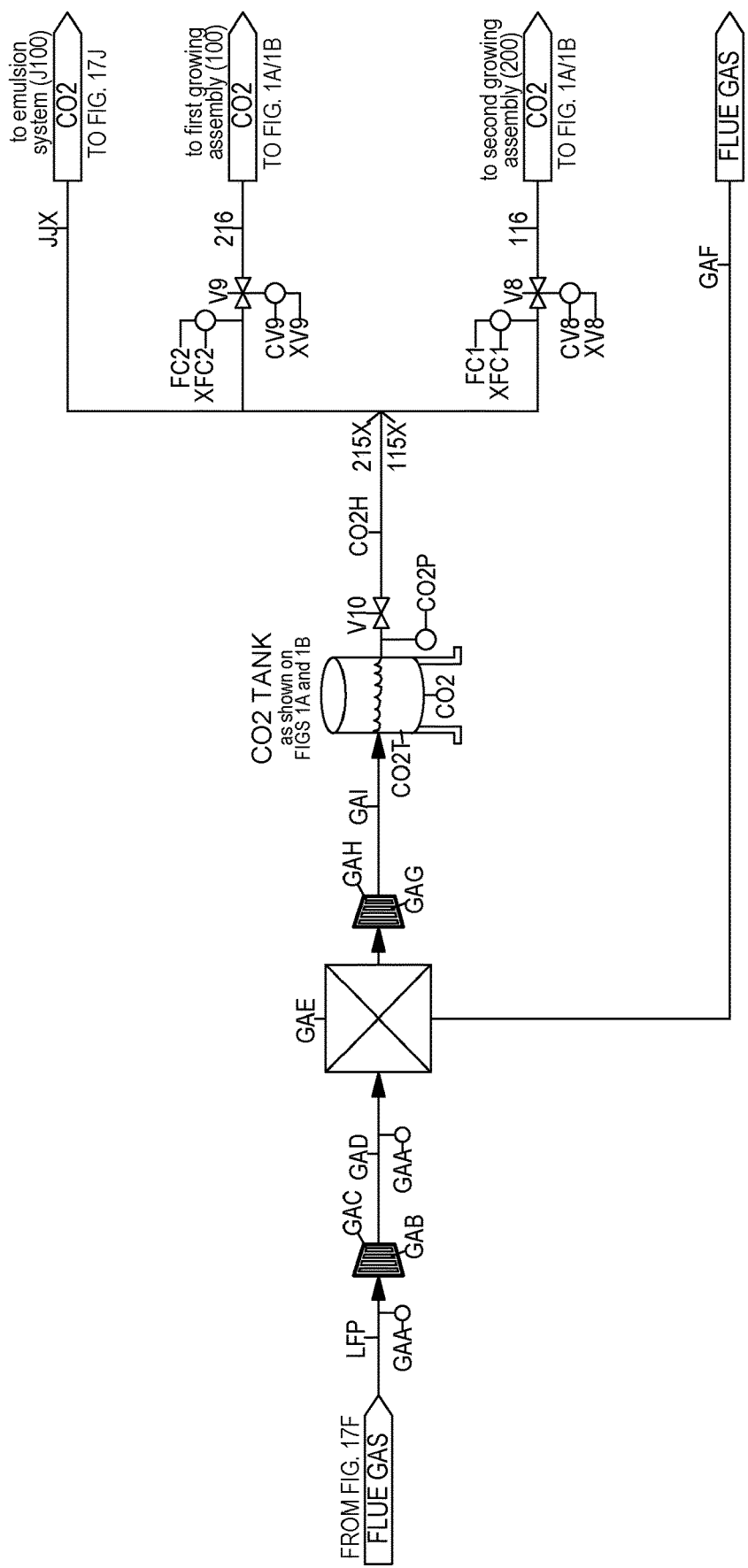

FIG. 17G shows one non-limiting embodiment of a carbon dioxide removal system (GAE) that is configured to remove carbon dioxide from flue gas (LFP) for use as a source of carbon dioxide (CO2) in the farming superstructure system (FSS).

Figure 17H:
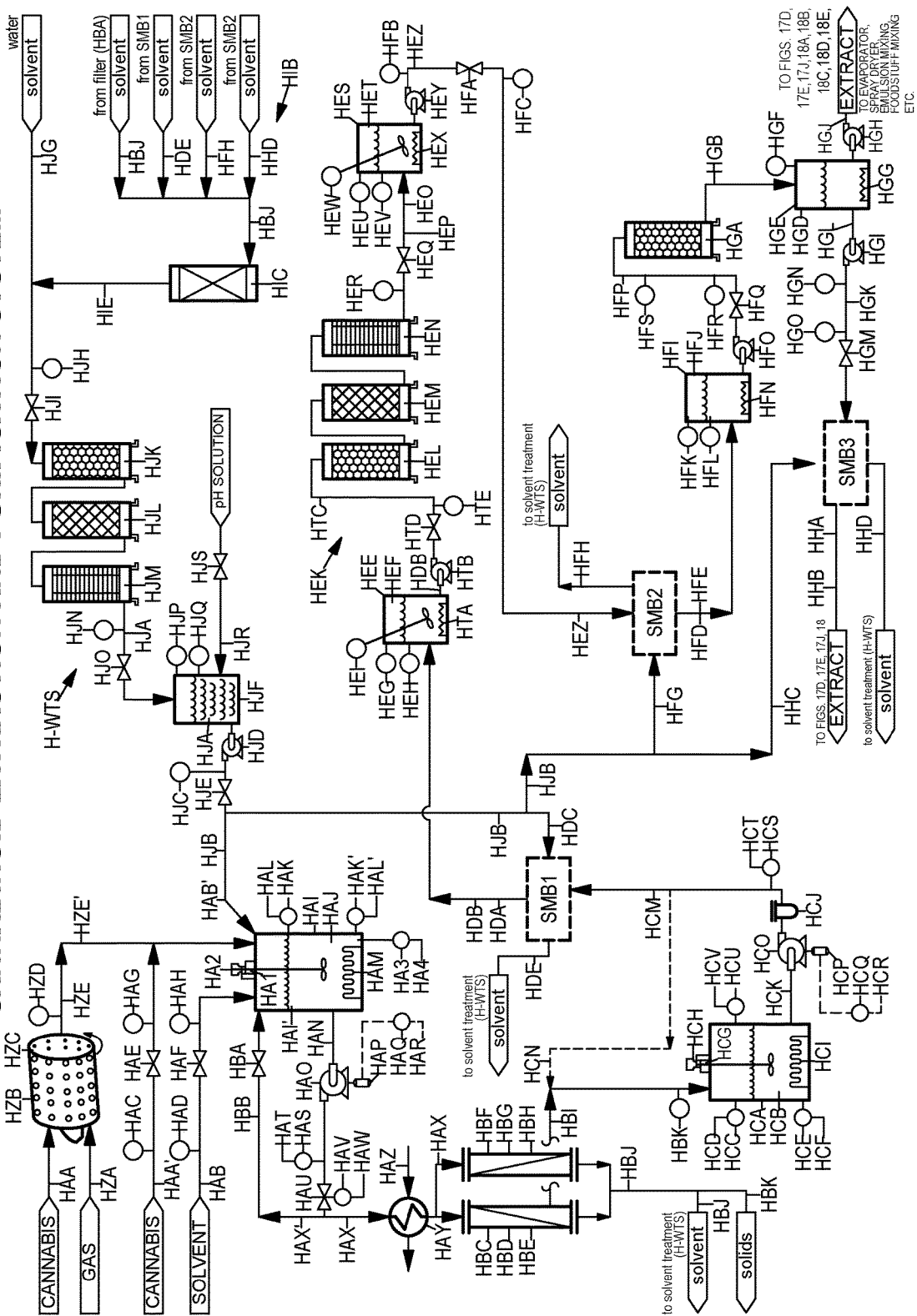

FIG. 17H shows a cannabinoid extraction and purification system including vessels, filters, pumps, and tubing/piping connecting flow between vessels and adsorbers, valving, controllers, pressure regulators, metering equipment, flow control, and microprocessor equipment, their construction, implementation, and functionality.

Figure 17J:
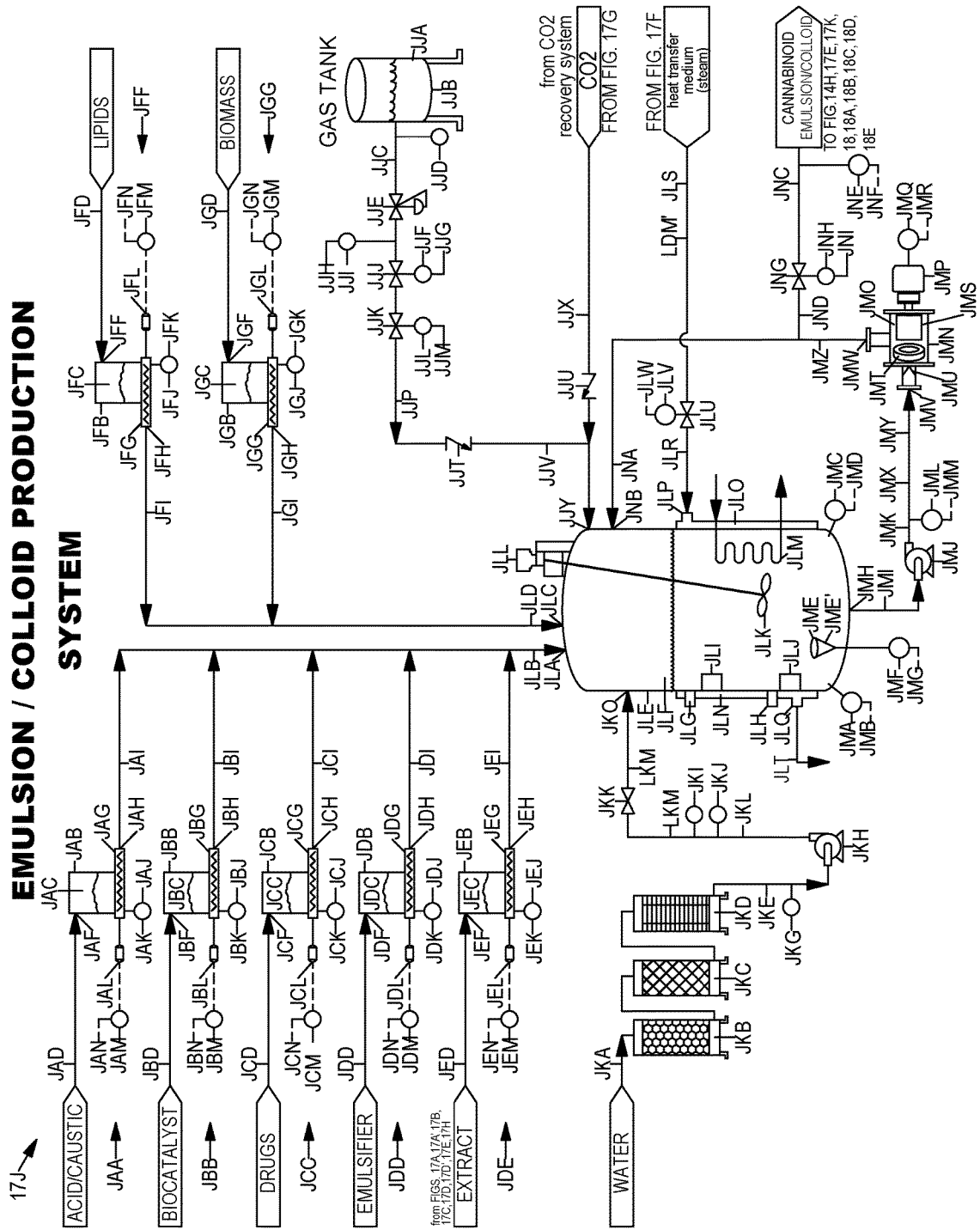

FIG. 17J shows one non-limiting embodiment of a cannabinoid emulsion and/or colloid production system.

FIG. 17K shows one non-limiting embodiment of a cannabinoid softgel encapsulation system (17K).

FIG. 18 shows a simplistic diagram illustrating a multifunctional composition mixing module that is configured to generate a multifunctional composition from at least a portion of Cannabis plants (107, 207) that was harvested from each growing assembly (100, 200), and/or any extracted and/or purified cannabinoid described in this entire specification.

Figure 18A:
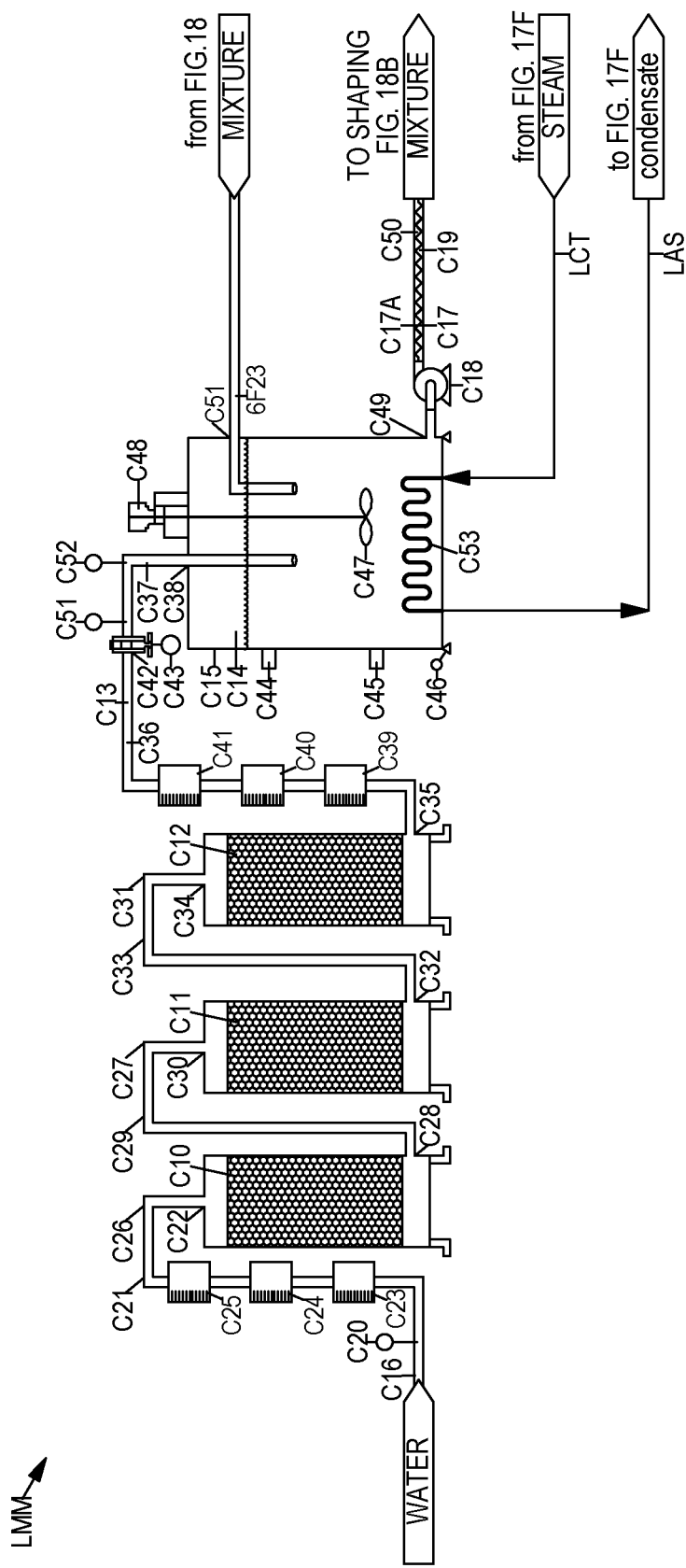

FIG. 18A shows one non-limiting embodiment of a liquid mixing module (LMM) that is configured to mix water with multifunctional composition (6F23) provided from the multifunctional composition mixing module as shown in FIG. 18.

FIG. 18B shows one non-limiting embodiment of a shaping module (14D) configured to shape the multifunctional composition and water mixture (C17) to produce a shaped multifunctional composition (D10).

Figure 18C:
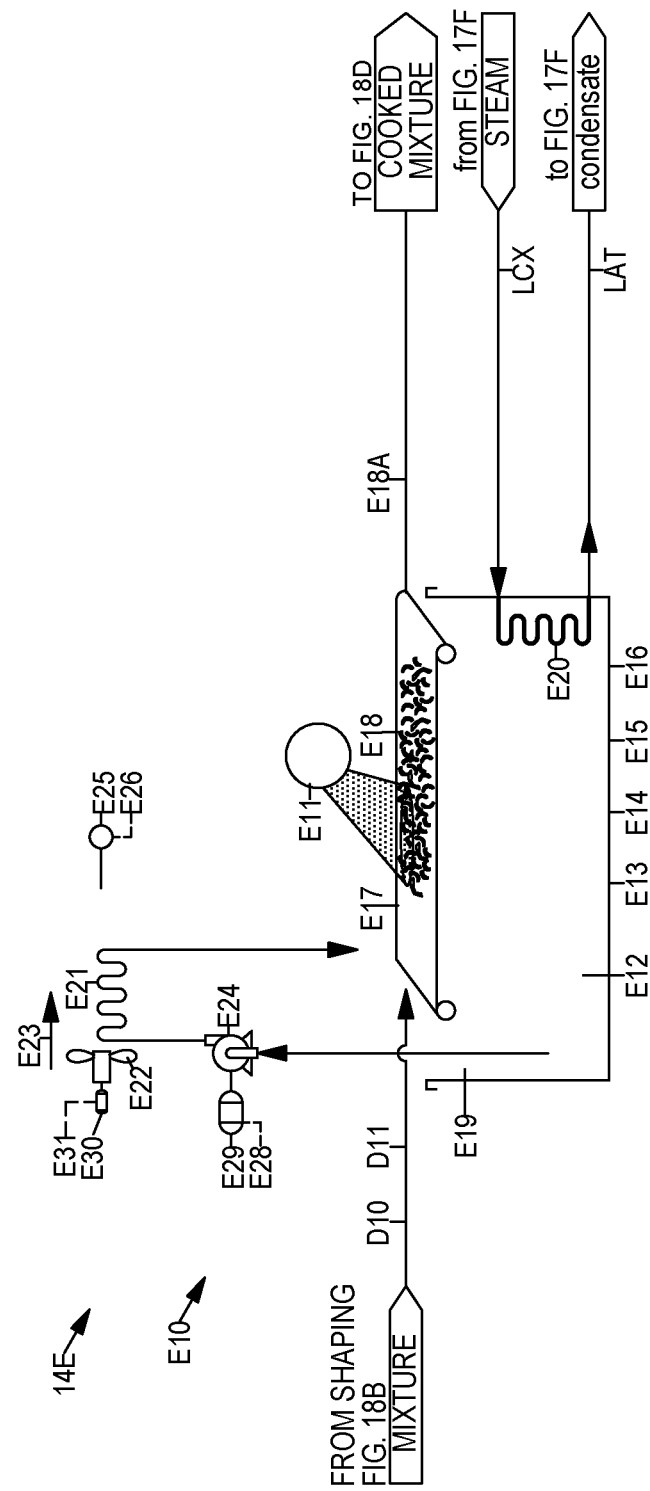

FIG. 18C shows one non-limiting embodiment of a cooking module (14E) configured to cook the shaped multifunctional composition (D10) provided from the shaping module (14D) to form a cooked multifunctional composition (E18A).

Figure 18D:
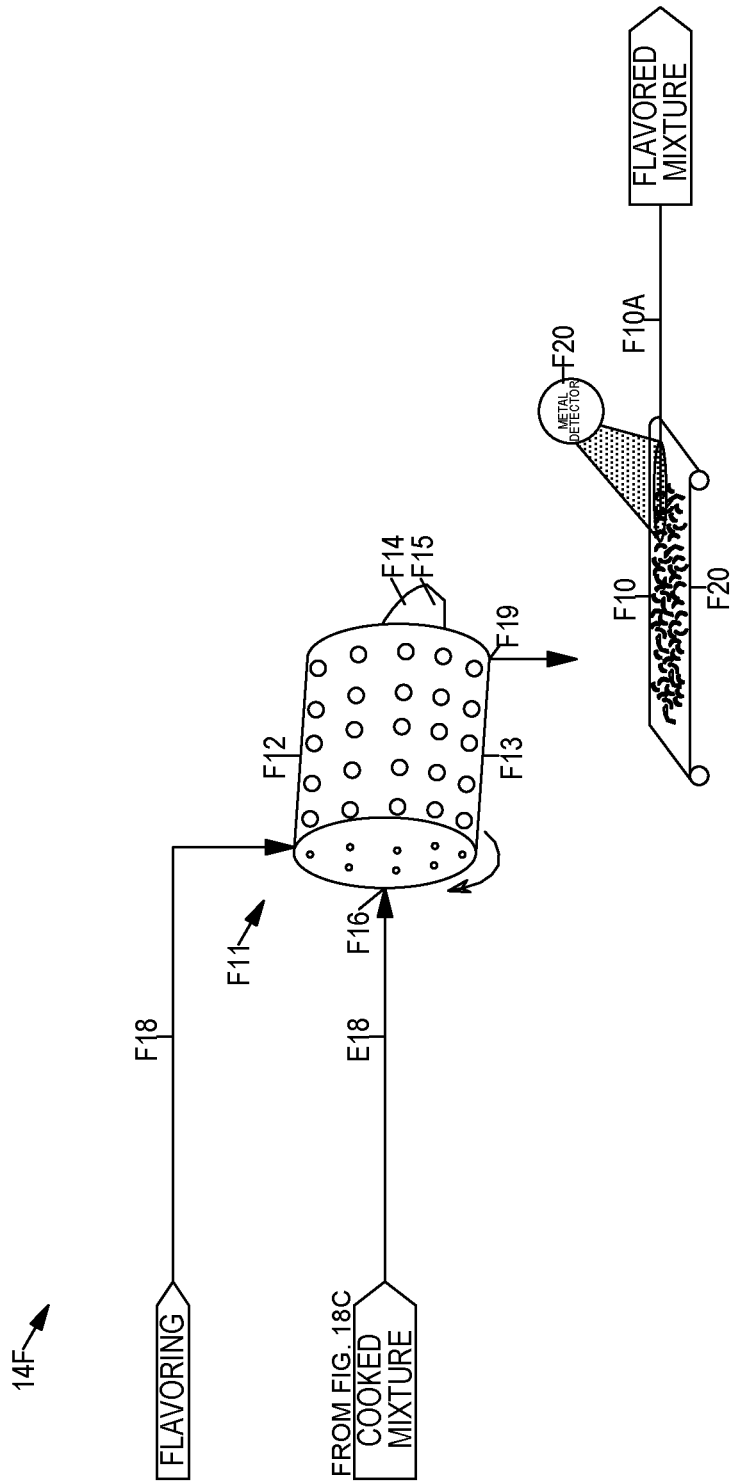

FIG. 18D shows one non-limiting embodiment of a flavoring module (14F) configured to flavor the cooked multifunctional composition (E18A) provided from the cooking module (14E) to form a flavored multifunctional composition (F10).

Figure 18E:
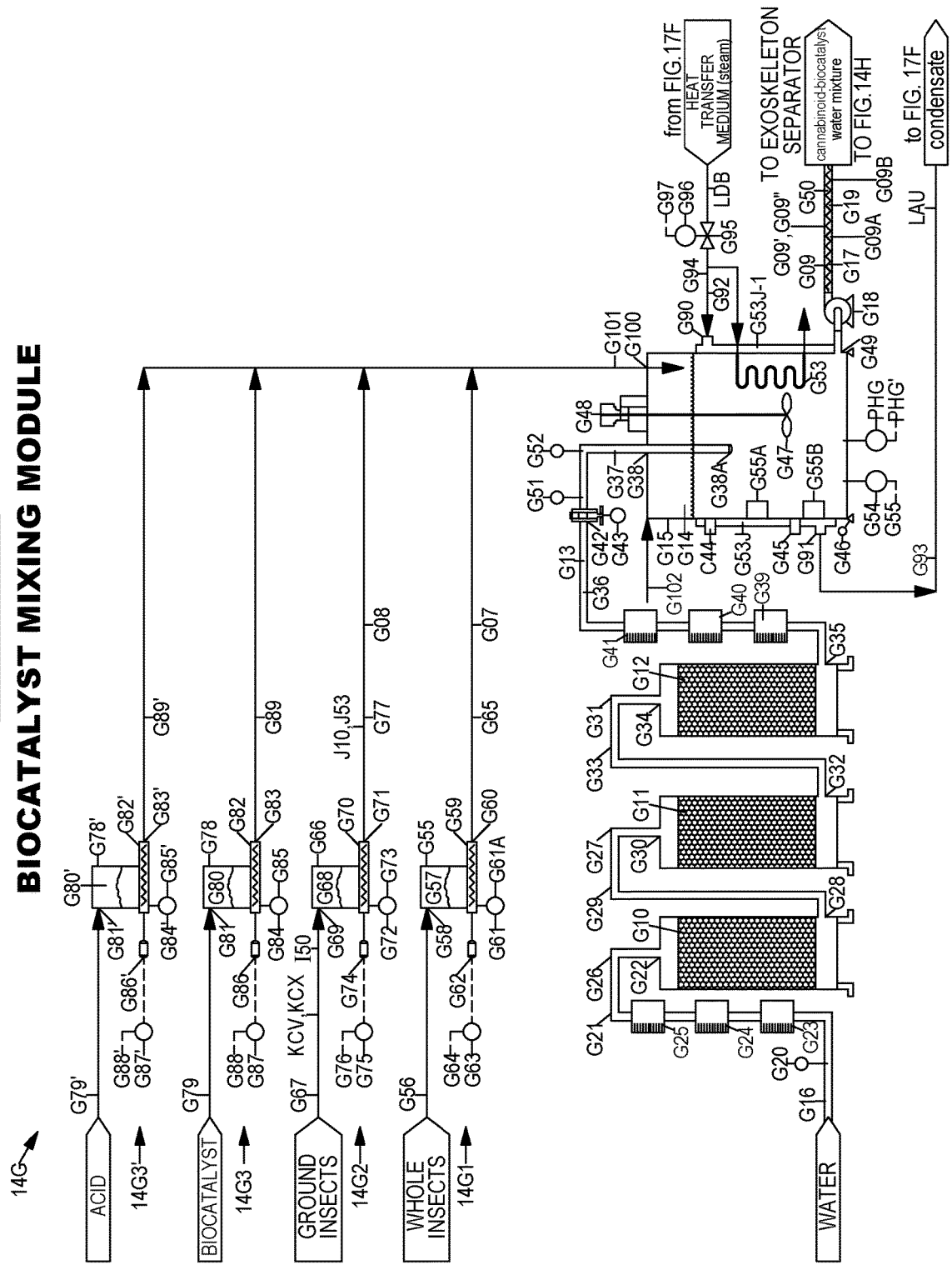

FIG. 18E shows one non-limiting embodiment of a biocatalyst mixing module (14G) that is configured to mix a cannabinoid, with insects, water, biocatalyst, and/or an acid to create an cannabinoid and biocatalyst mixture (G09).

Figure 18F:
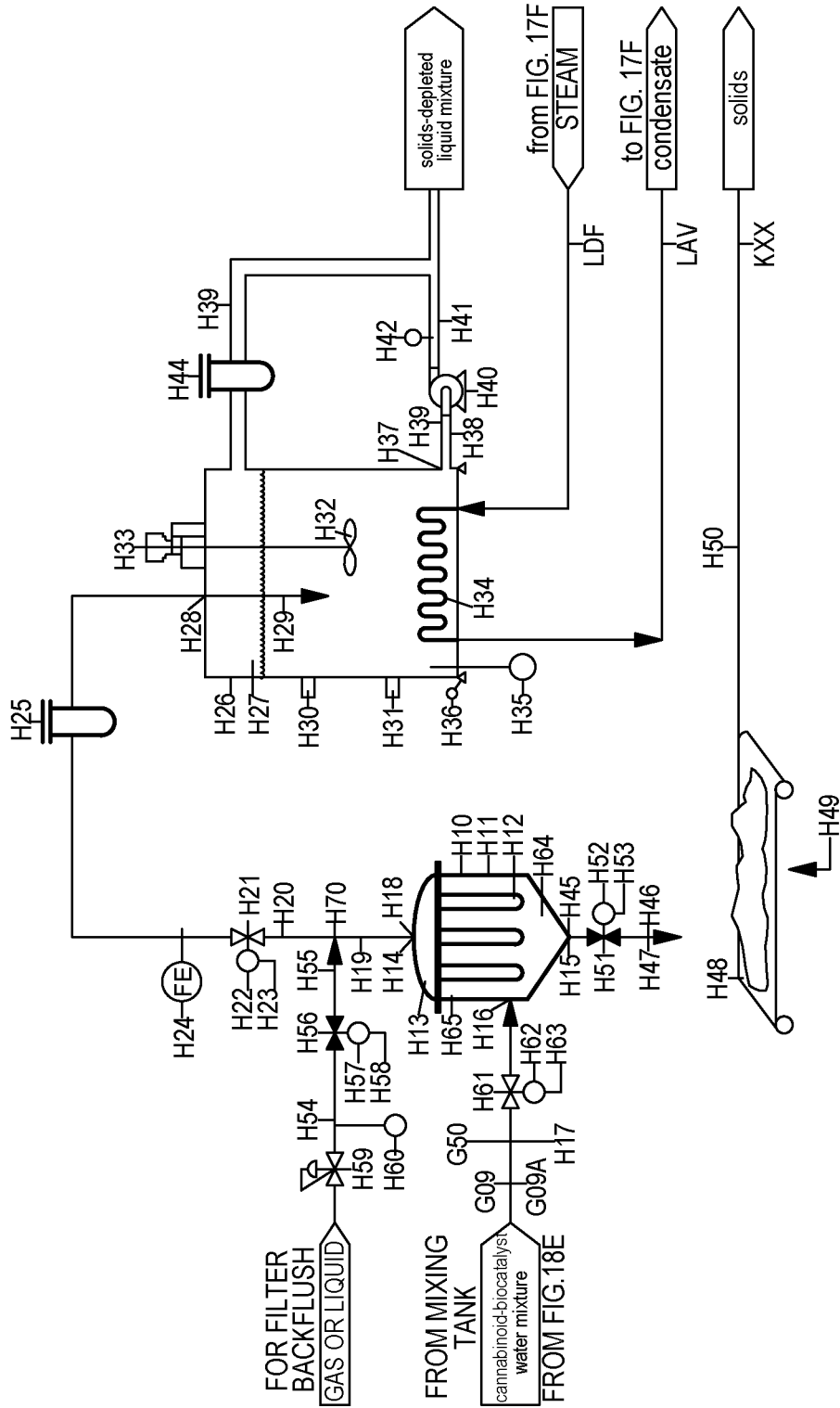

FIG. 18F shows one non-limiting embodiment of a solids separation module (14H) that is configured to remove the solids contained within the cannabinoid and biocatalyst mixture (G09).

Figure 19:

FIG. 19 illustrates a single fully-grown INSECTERGY III plant.

Figure 20:

FIG. 20 illustrates zoomed-in view of a budding or flowering plant.

Figure 21:

FIG. 21 illustrates a single leaf of INSECTERGY III.

Figure 22:
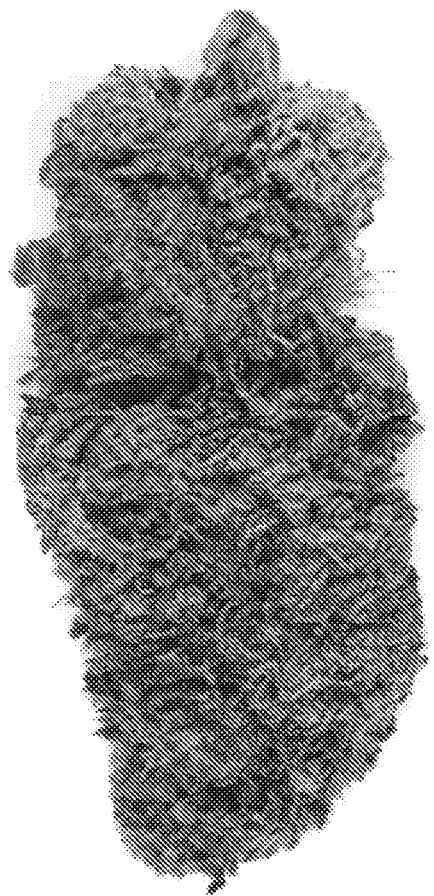

FIG. 22 illustrates a trimmed and dried bud (reproductive structure) of INSECTERGY III.

Figure 23:
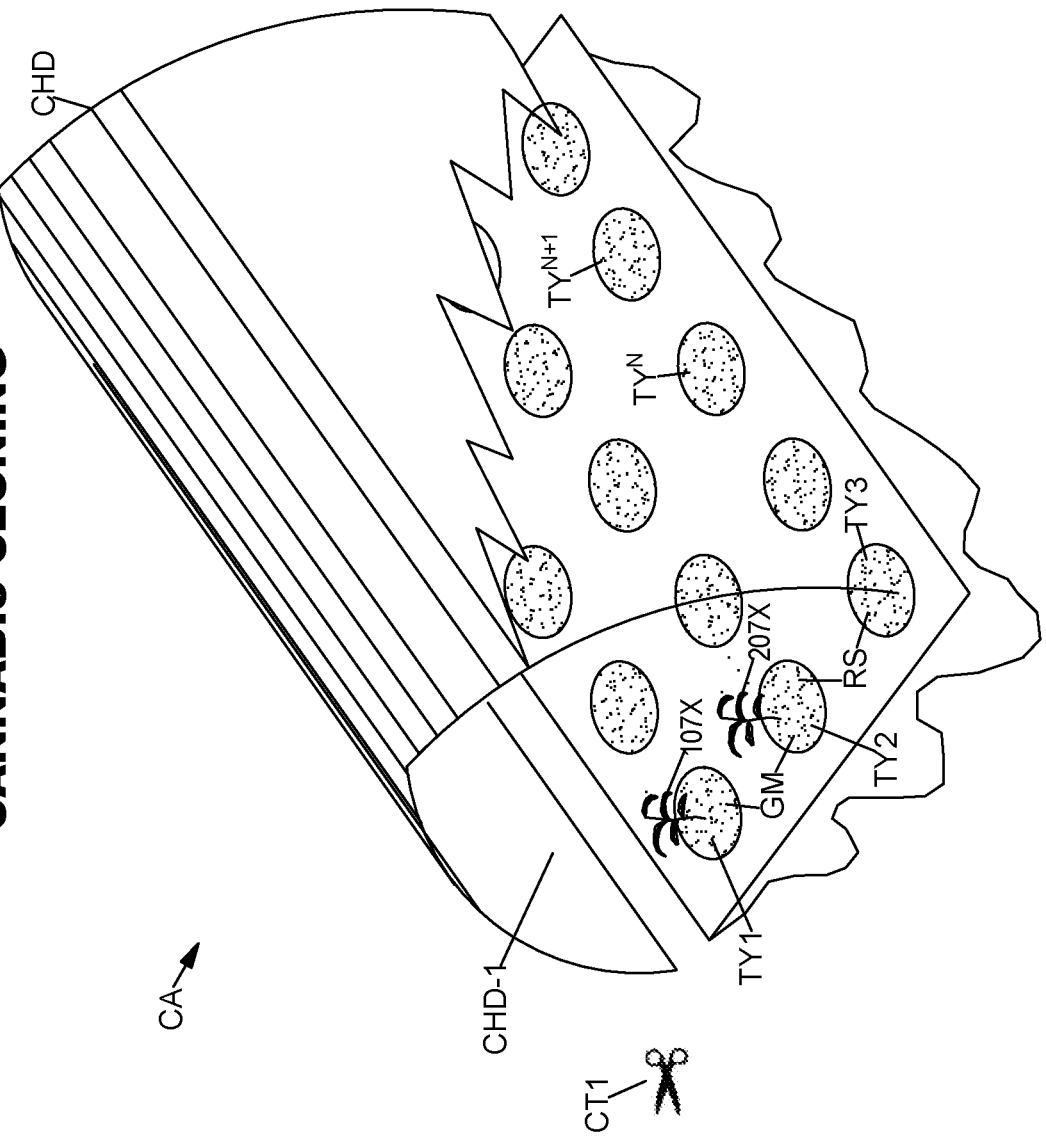

FIG. 23 shows a cannabis cloning assembly (CA) that is configured to clone cannabis plants and/or INSECTERGY III (107, 207) that were growing in each growing assembly (100, 200).

FIG. 24 includes one non-limiting embodiment of a cannabis-related product traceability system flow chart.

DETAILED DESCRIPTION

Reference will now be made in detail to various embodiments of the disclosure. Each embodiment is provided by way of explanation of the disclosure, not limitation of the disclosure. In fact, it will be apparent to those skilled in the art that modifications and variations can be made in the disclosure without departing from the teaching and scope thereof. For instance, features illustrated or described as part of one embodiment to yield a still further embodiment derived from the teaching of the disclosure. Thus, it is intended that the disclosure or content of the claims cover such derivative modifications and variations to come within the scope of the disclosure or claimed embodiments described herein and their equivalents.

Additional objects and advantages of the disclosure will be set forth in part in the description which follows, and in part will be obvious from the description, or may be learned by practice of the claims. The objects and advantages of the disclosure will be attained by means of the instrumentalities and combinations and variations particularly pointed out in the appended claims.

In embodiments, cannabis is grown in the presence of insects. In embodiments, farming superstructure system (FSS) simultaneously includes insects and cannabis plants. In embodiments, insects are used within the farming superstructure system (FSS) to benefit the cannabis plants therein. In embodiments, insects are used within the farming superstructure system (FSS) to benefit the cannabis plants therein because some omnivorous or carnivorous insects eat insects that would otherwise harm the cannabis plants in turn protecting them. In embodiments, insects are used within the farming superstructure system (FSS) to benefit the cannabis plants therein and to avoid use of pesticides.

FIG. 1A

FIG. 1A depicts one non-limiting embodiment of a farming superstructure system (FSS) including a first water treatment unit (A1), a second water treatment unit (A2), a third water treatment unit (A3), a common reservoir (500), a pump (P1), a plurality of vertically stacked growing assemblies (100, 200), a fabric (104, 204) that partitions each growing assembly (100, 200) into an upper-section (105, 205) and a lower-section (106, 206), a plurality of lights (L1, L2) positioned within the upper-section (105, 205) of each growing assembly, a carbon dioxide tank (CO2T), a plurality of fans (FN1, FN2), a plurality of liquid supply conduits (113, 213), a liquid supply header (300), at least one filter (F1, F2), a plurality of valves (V1, V3, V4), a drain port (110, 210), and a computer (COMP).

FIG. 1A discloses a farming superstructure system (FSS). The farming superstructure system (FSS) includes a first growing assembly (100) and a second growing assembly (200) in fluid communication with a common reservoir (500). The common reservoir (500) is provided with a water supply (01) via a water supply conduit (02) and a first water inlet (03). A plurality of water treatment units (A1, A2, A3), along with a contaminant depleted water valve (V0A), and a water heat exchanger (HX1) may be installed on the water supply conduit (02).

A first water treatment unit (A1) may be installed on the water supply conduit (02). The first water treatment unit (A1) has a first input (04) and a first output (05). A water supply (01) may be provided to the first water treatment unit (A1) via a first input (04). Contaminants may be removed by the first water treatment unit (A1) to produce a first contaminant depleted water (06) that is discharged via a first output (05). In embodiments, the first water treatment unit (A1) includes a cation and is configured to remove positively charged ions from water to form a positively charged ion depleted water (06A). The positively charged ions may include of one or more from the group consisting of calcium, magnesium, sodium, and iron. In embodiments, the positively charged ions are comprised of one or more from the group consisting of calcium, magnesium, sodium, and iron. In embodiments, the positively charged ions are comprised of one or more from the group consisting of aluminum, barium, beryllium, calcium, chromium(III), copper(I), copper(II), hydrogen, iron(II), iron(III), lead(II), lead(IV), lithium, magnesium, manganese(II), mercury(II), potassium, silver, sodium, strontium, tin(II), tin(IV), and zinc.

In embodiments, the first contaminant depleted water (06) may be a positively charged ion depleted water (06A). In embodiments, the first water treatment unit (A1) may include a cation, an anion, a membrane, filter, activated carbon, adsorbent, or absorbent. In embodiments, an activated carbon bed may be used to remove chlorine from the water. In embodiments, the water within the common reservoir (500) may be rainwater.

A second water treatment unit (A2) may be installed on the water supply conduit (02) after the first water treatment unit (A1). The second water treatment unit (A2) may include a second input (07) and a second output (08). The first contaminant depleted water (06) may be provided to the second water treatment unit (A2) via a second input (07). The first contaminant depleted water (06) may be provided to the second water treatment unit (A2) from the first output (05) of the first water treatment unit (A1). In embodiments, the positively charged ion depleted water (06A) may be provided to the second water treatment unit (A2) via a second input (07).

Contaminants may be removed by the second water treatment unit (A2) to produce a second contaminant depleted water (09) that is discharged via a second output (08). In embodiments, the second water treatment unit (A2) includes an anion that is configured to remove negatively charged ions from the positively charged ion depleted water (06A) to form a negatively charged ion depleted water (09A). The negatively charged ions may include one or more from the group consisting of iodine, chloride, and sulfate. In embodiments, the negatively charged ions are comprised of one or more from the group consisting of iodine, chloride, and sulfate. In embodiments, the negatively charged ions are comprised of one or more from the group consisting of acetate, aluminum silicate, anions from organic acids, azide, bromide, carbonate, chlorate, chloride, chromate, cyanide, dichromate, dihydrogen phosphate, fluoride, formate, hydride, hydrogen carbonate, hydrogen sulfate, hydrogen sulfite, hydroxide, hypochlorite, iodide, metasilicate, monohydrogen phosphate, nitrate, nitride, nitrite, oxalate, oxide, perchlorate, permanganate, peroxide, phosphate, silicate, sulfate, sulfide, sulfite, superoxide, and thiosulfate.

In embodiments, the second contaminant depleted water (09) may be a negatively charged ion depleted water (09A). In embodiments, the second water treatment unit (A2) may include a cation, an anion, a membrane, filter, activated carbon, adsorbent, or absorbent.

A third water treatment unit (A3) may be installed on the water supply conduit (02) after the second water treatment unit (A2). The third water treatment unit (A3) may include a third input (10) and a third output (11). The second contaminant depleted water (09) may be provided to the third water treatment unit (A3) via a third input (10). The second contaminant depleted water (09) may be provided to the third water treatment unit (A3) from the second output (08) of the second water treatment unit (A2). In embodiments, the negatively charged ion depleted water (09A) may be provided to the third water treatment unit (A3) via a third input (10). Contaminants may be removed by the third water treatment unit (A3) to produce a third contaminant depleted water (12) that is discharged via a third output (11). In embodiments, the third water treatment unit (A3) includes a membrane that is configured to remove undesirable compounds from the negatively charged ion depleted water (09A) to form an undesirable compound depleted water (12A). The "undesirable compounds" may include one or more from the group consisting of dissolved organic chemicals, viruses, bacteria, and particulates. In embodiments, the third contaminant depleted water (12) may be an undesirable compound depleted water (12A). In embodiments, the third water treatment unit (A3) may include a cation, an anion, a membrane, filter, activated carbon, adsorbent, or absorbent. In embodiments, the (10) the undesirable compounds depleted water (12A) has an electrical conductivity ranging from 0.10 microsiemens per centimeter to 100 microsiemens per centimeter.

In embodiments, the first water treatment unit (A1) containing a cation may be a disposable cartridge, portable tank, cylindrical vessel, automatic unit, or a continuous unit. In embodiments, the second water treatment unit (A2) containing an anion may be a disposable cartridge, portable tank, cylindrical vessel, automatic unit, or a continuous unit. In embodiments, the third water treatment unit (A3) containing a membrane may have: a diameter that ranges from 1 inch to 6 inches; and a pore size ranging from 0.0001 microns to 0.5 microns.

The common reservoir (500) is configured to accept a portion of a contaminant depleted water (06A, 09A, 12A) from the at least one water treatment unit (A1, A2, A3). In embodiments, the water treatment units (A1, A2, A3) may be configured to remove solids from the water supply (01). In embodiments, a contaminant depleted water valve (V0A) is installed on the water supply conduit (02) to regulate the amount of water transferred to the common reservoir (500) through the water supply conduit (02) and first water inlet (03). The contaminant depleted water valve (V0A) is equipped with a controller (CV0A) which sends a signal (XV0A) to and from a computer (COMP). In embodiments, a water heat exchanger (HX1) is installed on the water supply conduit (02) to control the temperature of the water transferred to the common reservoir (500) through the water supply conduit (02) and first water inlet (03). In embodiments, the water heat exchanger (HX1) increases the temperature of the water supply (01) introduced to the common reservoir (500). In embodiments, the water heat exchanger (HX1) decreases the temperature of the water supply (01) introduced to the common reservoir (500). In embodiments, the water heat exchanger (HX1) is positioned in between the contaminant depleted water valve (V0A) and the water inlet (03) of the common reservoir (500). So, it is shown that water may be treated with a plurality of water treatment units (A1, A2, A3) before being introduced to the common reservoir (500).

In embodiments, the common reservoir (500) is comprised of metal, plastic, fiberglass, composite materials, or combinations thereof, or any other conceivable material that may contain a liquid within its interior. In embodiments, fish (FISH) are contained within the interior of the common reservoir (500). The fish (FISH) increase the concentration of nitrogen within the liquid contained within the common reservoir (500) which in turn can be provided to the *cannabis* (107, 207).

In embodiments, the fish (FISH) excrete nitrogen. In embodiments, the nitrogen excreted from the fish (FISH) includes ammonia or urea. In embodiments, the nitrogen excreted by the fish (FISH) is consumed by the *cannabis* (107, 207). In embodiments, the nitrogen excreted by the fish (FISH) is mixed with at least a portion of the first contaminant depleted water (06), second contaminant depleted water (09), and/or third contaminant depleted water (12), then pressured and provided to the *cannabis* (107, 207). In embodiments, the fish (FISH) are fed insects. In embodiments, the fish (FISH) are fed insects from the FSS. In embodiments, the fish (FISH) are used as the growing medium for the *cannabis* plants to grow into. In embodiments, the fish (FISH) are used mixed with the insects to provide a source of fish protein, fish scales, and or fish meal used in the enhanced feedstock and/or pet food to feed pets. In embodiments, the fish (FISH) include: bass, carp, catfish, coy, goldfish, perch, salmon, striped bass, tilapia, trout, and combinations thereof.

In embodiments, the fish (FISH) include: *Abramis brama, Acanthopagrus schlegeli, Acipenser baeri, Acipenser ruthenus, Acipenser stellatus, Acipenser transmontanus, Aequidens rivulatus, Anabas testudineus, Anguilla anguilla, Anguilla japonica, Anguilla rostrata, Arapaima gigas,* Aspius aspius, Bidyanus bidyanus, Brycon *moorei,* Carassius auratus, Carassius carassius, Catla catla, Centropomus undecimalis, *Channa argus, Channa micropeltes, Channa punctatus, Channa striata,* Chanos chanos, Chrysichthys nigrodigitatus, Cichlasoma maculicauda, Cichlasoma managuense, Cichlasoma urophthalmus, Cirrhinus molitorella, Cirrhinus mrigala, Clarias anguillaris, Clarias batrachus, Clarias *fuscus,* Clarias gariepinus, Clarias macrocephalus, Colossoma macropomum, *Coregonus albula, Coregonus lavaretus, Ctenopharyngodon* idellus, *Cyprinus carpio,* Dicentrarchus labrax, Diplodus sargus, Dormitator latifrons, Epinephelus akaara, Epinephelus areolatus, Epinephelus tauvina, Esox *lucius,* Etroplus suratensis, Evynnis *japonica,* Gadus morhua, Helostoma temmincki, Heterobranchus bidorsalis, Heterobranchus longifilis, Heterotis *niloticus, Hoplosternum littorale, Huso huso, Hypophthalmichthys molitrix, Hypophthalmichthys nobilis, Ichthyoelephas humeralis,* Ictalurus melas, Ictalurus punctatus, Ictiobus cyprinellus, Labeo calbasu, Labeo rohita, Lates calcarifer, Lates *niloticus,* Leptobarbus hoeveni, Liza *aurata,* Liza macrolepis, Liza parsia, Liza ramada, Liza saliens, Liza tade, Lutjanus argentimaculatus, Maccullochella peeli, Macquaria *ambigua, Megalobrama amblycephala, Micropterus salmoides, Misgurnus anguillicaudatus, Monopterus albus, Morone saxatilis,* Mugil cephalus, Mugil curema, Mugil liza, *Mylopharyngodon piceus,* Notemigonus crysoleucas, Ocyurus chrysurus, Odontesthes *bonariensis,* Oncorhynchus gorbuscha, Oncorhynchus keta, Oncorhynchus kisutch, Oncorhynchus masou, Oncorhynchus mykiss, Oncorhynchus nerka, Oncorhynchus tshawytscha, *Oreochromis andersonii, Oreochromis aureus, Oreochromis macrochir, Oreochromis mossambicus, Oreochromis niloticus, Oreochromis spilurus, Oreochromis* urolepis, Osphronemus goramy, Osteochilus hasselti, Oxyeleotris marmorata, Pagrus major, Pagrus pagrus, Pangasius pangasius, Pangasius sutchi, Parabramis *pekinensis, Paralichthys olivaceus, Perca fluviatilis, Piaractus brachypomus, Piaractus* mesopotamicus, Plecoglossus altivelis, Plectropomus *maculatus,* Pomatomus saltatrix, Prochilodus *reticulatus,* Psetta maxima, Puntius gonionotus, Puntius *javanicus,* Rhabdosargus sarba, Rhamdia sapo, Rutilus rutilus, Salmo salar, Salmo trutta, *Salvelinus alpinus, Salvelinus fontinalis, Salvelinus* namaycush, Sarotherodon melanotheron, Sciaenops *ocellatus,* Seriola dumerili, Seriola quinqueradiata, Siganus *canaliculatus,* Siganus guttatus, Siganus rivulatus, Siluris glanis, Solea vulgaris, Sparus *aurata,* Stizostedion lucioperca, Thunnus maccoyii, Thunnus thynnus, Tilapia *guineensis,* Tilapia rendalli, Tilapia zillii, Tinca tinca, Trachinotus blochii, Trachinotus carolinus, Trachinotus goodei, Trachurus *japonicus,* Trichogaster pectoralis, and combinations thereof.

In embodiments, the fish (FISH) include crustaceans, mollusks, aquatic plants, algae, and other organisms. In embodiments, the fish (FISH) include shrimp, mussels, crawfish, clams, and baitfish. In embodiments, the algae include one or more selected from the group consisting of: microalgae, phytoplankton, microphytes, and planktonic algae. In embodiments, the aquatic plants include seaweed. In embodiments, the algae include one or more selected from the group consisting of: microalgae, phytoplankton, microphytes, and planktonic algae. In embodiments, the seaweed includes kelp, *Saccharina japonica, Undaria pinnatifida,* Pyropia spp., *Porphyra* spp., Pyropia, *Porphyra,* Kappaphycus alvarezii, Eucheuma striatum, carrageenophytes, Gracilaria, Gracilariopsis spp., agarophytes, and combinations thereof. In embodiments, the mollusks include fresh water mollocus. In embodiments, the fish (FISH) include freshwater fish. In embodiments, the fish (FISH) include brackish water fish. In embodiments, the fish (FISH) include saltwater water fish wherein the nitrogen is separated within a separator and provided to the *cannabis* plants, insects, and/or psilocybin mushrooms.

In embodiments, the fish (FISH) include eels. In embodiments, the eels include mollusks attached thereto. In embodiments, the eels include algae attached thereto. In embodiments, mollusks are comprised of an invertebrate of a large phylum which includes snails, slugs, mussels, clams, and octopuses. They have a soft unsegmented body and live in aquatic or damp habitats, and most kinds have an external calcareous shell. In embodiments, the preferred type of mollusks to live within the common reservoir are freshwater mussels. In embodiments, the preferred type of mollusks to live within the common reservoir are freshwater snails. In embodiments, the preferred type of mollusks to live within the common reservoir are freshwater clams. In embodiments, the preferred type of freshwater mussels include freshwater bivalves. In embodiments, the preferred type of freshwater mussels include Order Unionida. In embodiments, the preferred type of freshwater mussels include mussels from the family unionidae, etheriidae, hyriidae, iridinidae, margaritiferidae, mutelidae, mycetopodidae, and combinations thereof. In embodiments, the preferred type of freshwater mussels include mother-of-pearl. In embodiments, the freshwater mussels feed on algae within the common reservoir and filter the water. In embodiments, the freshwater mussels include *Elliptio complanata* (Eastern *elliptio*) or Strophitus *undulatus* (Creeper). In embodiments, the freshwater mussels include etheriidae, hyriidae, iridinidae, margaritiferidae, mutelidae, my cetop odi dae, or unionidae.

In embodiments, the insects grown in the FSS together with the *cannabis* plants are genetically modified. In embodiments, the insects are transgenic animals. In embodiments, the predatory mites are transgenic animals. In embodiments, the bats are transgenic animals. In embodiments, the insects are genetically modified organisms (transgenic organisms). In embodiments, the insects are introduced to the FSS by providing the insects in a satchel. In embodiments, the satchel is positioned on a portion of a *cannabis* plant, such as a stem, a leaf, a bud, a reproductive structure.

In embodiments, the common reservoir (500) is comprised of metal, plastic, fiberglass, composite materials, or combinations thereof, or any other conceivable material that may contain a liquid within its interior. In embodiments, the common reservoir (500) is configured to accept a water supply (01) from the water supply conduit (02). In embodiments, the common reservoir (500) may be configured to accept any permutation or combination of a water supply (01) either a first contaminant depleted water (06), second contaminant depleted water (09), or third contaminant depleted water (12), that is heated or cooled or not heated or cooled. In embodiments, the common reservoir (500) may be configured to accept any permutation or combination of a water supply (01) either a positively charged ion depleted water (06A), negatively charged ion depleted water (09A), or undesirable compounds depleted water (12A) that is heated or cooled or not heated or cooled. In embodiments, the common reservoir (500) may be configured to accept any permutation or combination of a water supply (01) from any number of water treatment units (A1, A2, A3) that includes at least a cation, an anion, a membrane, a filter, activated carbon, adsorbent, or absorbent.

In embodiments, the common reservoir (500) is equipped with an upper-level switch (LH) for detecting a high level and a lower level switch (LL) for detecting a lower level. The upper-level switch (LH) is configured to output a signal (XLH) to the computer (COMP) when the upper-level switch (LH) is triggered by a high level of liquid within the common reservoir (500). The lower-level switch (LL) is configured to output a signal (XLL) to the computer (COMP) when the lower-level switch (LL) is triggered by a low level of liquid within the common reservoir (500). In embodiments, when the lower-level switch (LL) sends a signal (XLL) to the computer (COMP), the contaminant depleted water valve (V0A) is opened and introduces water into the common reservoir (500) until the upper-level switch (LH) is triggered thus sending a signal (XLH) to the computer (COMP) to close the contaminant depleted water valve (V0A). This level control loop including the upper-level switch (LH) for detecting a high level and a lower-level switch (LL) for detecting a lower level may be coupled to the operation of the contaminant depleted water valve (V0A) for introducing a water supply (01) through the water supply conduit (02) and into the common reservoir (500) via the first water inlet (03).

In embodiments, a pump (P1) is configured to accept, pressurize, and transfer liquid within the common reservoir (500) into a plurality of vertically stacked growing assemblies (100, 200). In embodiments, the pump (P1) is configured to accept, pressurize, and transfer at least a portion of the undesirable compounds depleted water (12A) transferred from the common tank (500T) into a plurality of vertically stacked growing assemblies (100, 200). In embodiments, each of the plurality of vertically stacked growing assemblies (100, 200) are positioned above the common reservoir (500).

The first growing assembly (100) has an interior (101), a top (102), a bottom (103), and a longitudinal axis (AX1) extending along a height direction of the first growing assembly (100). The first growing assembly (100) has a fabric (104) that partitions the first growing assembly (100) into an upper-section (105) close to the top (102) and a lower-section (106) close to the bottom (103). The fabric (104) is used to provide structure for cannabis plants (107, 207) to root into. For purposes of simplicity, a cannabis plant named INSECTERGY III (107, 207) may be referred to and is synonymous with the term cannabis (107, 207) for purposes of this disclosure (as described in detail below).

Obviously, the farming systems and methods disclosed herein pertain to any type plant and even any type of cannabis plant (107, 207) and not only limited to growing INSECTERGY III (107, 207). Growing INSECTERGY III (107, 207) within the farming superstructure system (FSS) is merely a non-limiting example of any type of the cannabis plants (107, 207) that may be grown within the farming superstructure system (F S S).

Cannabis plants (107) rooted in the fabric (104) have roots that grow downward and extend into the lower-section (106). The first growing assembly (100) is equipped with a plurality of lights (L1) positioned within the upper-section (105) above the fabric (104). Cannabis (107) rooted in the fabric (104) grow upward extending into the upper-section (105) towards the plurality of lights (L1). The plurality of lights (L1) are configured to be controlled by a computer (COMP) to operate at a wavelength ranging from 400 nm to 700 nm. In embodiments, the lights (L1) have a controller (CLI) that sends a signal (XL1) to and from the computer (COMP). In embodiments, the lights (L1, L2) may be compact fluorescent (CFL), light emitting diode (LED), incandescent lights, fluorescent lights, metal halide lamps, high-intensity discharge (HID) gas discharge lamps, low pressure sodium lamps, sodium lamps, and combinations thereof. In some embodiments, light emitting diodes are preferred. In embodiments, low pressure sodium lamps are preferred. In embodiments, the lights provide heat to the cannabis plants. In embodiments, the lights are turned on and off to provide an illumination on-off ratio. In embodiments, the cannabis plants are not heated with lights when the lights are off. In embodiments, the cannabis plants are heat with heaters when the lights are off.

In embodiments, a first plurality of lights (L1) in the first growing assembly (100) include a first plurality of light emitting diodes (LED). In embodiments, the first plurality of light emitting diodes (LED) include blue LEDs (BLED), red LEDS (RLED), and/or green LEDS (GLED). In embodiments, the first plurality of light emitting diodes (LED) in the first growing assembly (100) include one or two or more from the group consisting of blue LEDs (BLED), red LEDS (RLED), and green LEDS (GLED).

In embodiments, a second plurality of lights (L2) in the second growing assembly (200) include a second plurality of light emitting diodes (LED). In embodiments, the second plurality of light emitting diodes (LED) include blue LEDs (BLED), red LEDS (RLED), and/or green LEDS (GLED). In embodiments, the second plurality of light emitting diodes (LED) in the second growing assembly (200) include one or two or more from the group consisting of blue LEDs (BLED), red LEDS (RLED), and green LEDS (GLED).

In embodiments, the blue LEDs (BLED) operate at a wavelength that ranges from 490 nanometers (nm) to 455 nm. In embodiments, the red LEDs (RLED) operate at a wavelength that ranges from 620 nm to 780 nm. In embodiments, the green LEDs (GLED) operate at a wavelength that ranges from 490 nm to 577 nm. In embodiments, the plurality of light emitting diodes (LED) are configured to be controlled by a computer (COMP) to operate at a wavelength ranging from 490 nm to 780 nm. In embodiments, the plurality of light emitting diodes (LED) are configured to be controlled by a computer (COMP) to operate at a wavelength ranging from 400 nm to 700 nm.

In embodiments, the first plurality of light emitting diodes (LED) and second plurality of light emitting diodes (LED") are configured to operate in the following manner:
(a) illuminating plants with blue LEDs (BLED, BLED') and red LEDs (RLED, RLED'); and
(b) illuminating the plants nanometers with green LEDs (GLED, GLED');

wherein:
the blue LEDs (BLED, BLED') operate at a wavelength that ranges from 490 nanometers to 455 nanometers;
the red LEDs (RLED, RLED') operate at a wavelength that ranges from 620 nanometers to 780 nanometers;
the green LEDs (GLED, GLED') operate at a wavelength that ranges from 490 nanometers to 577 nanometers.

In embodiments, the first plurality of light emitting diodes (LED) and second plurality of light emitting diodes (LED) are configured to operate in the following manner:
(a) providing:
(a1) a first growing assembly (100) having a first plurality of light emitting diodes (LED), the first plurality of light emitting diodes (LED) in the first growing assembly (100) include blue LEDs (BLED), red LEDS (RLED), and green LEDS (GLED);
(a2) a second growing assembly (200) having a second plurality of light emitting diodes (LED), the second plurality of light emitting diodes (LED) in the second growing assembly (200) include blue LEDs (BLED), red LEDS (RLED), and green LEDS (GLED);
(b) illuminating the interiors of the first growing assembly (100) and second growing assembly (200) with green LEDs (GLED, GLED') and optionally with blue LEDs (BLED, BLED') or red LEDs (RLED, RLED'); and
(c) illuminating the interiors of the first growing assembly (100) and second growing assembly (200) with blue LEDs (BLED, BLED') and red LEDs (RLED, RLED'); and
wherein:
the blue LEDs (BLED, BLED') operate at a wavelength that ranges from 490 nanometers to 455 nanometers;
the red LEDs (RLED, RLED') operate at a wavelength that ranges from 620 nanometers to 780 nanometers;
the green LEDs (GLED, GLED') operate at a wavelength that ranges from 490 nanometers to 577 nanometers.

In embodiments, the disclosure provides for a farming method, including:
(a) providing a farming superstructure system (FSS), including:
(a1) a first water treatment unit (A1) including a cation configured to remove positively charged ions from water to form a positively charged ion depleted water (06A), the positively charged ions are comprised of one or more from the group consisting of calcium, magnesium, sodium, and iron;
(a2) a second water treatment unit (A2) including an anion configured to remove negatively charged ions from the positively charged ion depleted water (06A) to form a negatively charged ion depleted water (09A), the negatively charged ions are comprised of one or more from the group consisting of iodine, chloride, and sulfate;
(a3) a first growing assembly (100) having a first plurality of light emitting diodes (LED), the first plurality of light emitting diodes (LED) in the first growing assembly (100) include blue LEDs (BLED) and red LEDS (RLED), and optionally green LEDS (GLED);
(a4) a second growing assembly (200) having a second plurality of light emitting diodes (LED), the second plurality of light emitting diodes (LED) in the second growing assembly (200) include blue LEDs (BLED) and red LEDS (RLED), and optionally green LEDS (GLED);
(b) providing a source of water;
(c) removing positively charged ions from the water of step (b) to form a positively charged ion depleted water;
(d) removing negatively charged ions from the water after step (c) to form a negatively charged ion depleted water;
(e) mixing the negatively charged ion depleted water after step (d) with one or more from the group consisting of macro-nutrients, micro-nutrients, and a pH adjustment to form a liquid mixture;
(f) pressurizing the liquid mixture of step (e) to form a pressurized liquid mixture;
(g) splitting the pressurized liquid mixture into a plurality of pressurized liquid mixtures;
(h) transferring the plurality of pressurized liquid mixtures to each growing assembly;
(i) illuminating the interiors of the first growing assembly (100) and second growing assembly (200) with blue LEDs (BLED, BLED) and red LEDs (RLED, RLED);
and
(j) optionally illuminating the interiors of the first growing assembly (100) and second growing assembly (200) with green LEDs (GLED, GLED);
wherein:
the blue LEDs (BLED, BLED') operate at a wavelength that ranges from 490 nanometers to 455 nanometers;
the red LEDs (RLED, RLED') operate at a wavelength that ranges from 620 nanometers to 780 nanometers;
the green LEDs (GLED, GLED') operate at a wavelength that ranges from 490 nanometers to 577 nanometers;
the positively charged ions are comprised of one or more from the group consisting of calcium, magnesium, sodium, and iron;
the negatively charged ions are comprised of one or more from the group consisting of iodine, chloride, and sulfate;
the macro-nutrients are comprised of one or more from the group consisting of nitrogen, phosphorus, potassium, calcium, magnesium, and sulfur;
the micro-nutrients are comprised of one or more from the group consisting of iron, manganese, boron, molybdenum, copper, zinc, sodium, chlorine, and silicon;
the pH adjustment solution is comprised of one or more from the group consisting acid, nitric acid, phosphoric acid, potassium hydroxide, sulfuric acid, organic acids, citric acid, and acetic acid;
the blue LEDs (BLED, BLED') or red LEDs (RLED, RLED') illuminate the interiors of the first growing assembly (100) and second growing assembly (200) at an illumination on-off ratio ranging from between 0.5 and 5, the illumination on-off ratio is defined as the duration of time when the lights are on and illuminate in hours divided by the subsequent duration of time when the lights are off and are not illuminating in hours before the lights are turned on again.

In embodiments, the disclosure provides for a farming method, including:
(a) providing a farming superstructure system (FSS), including:
(a1) a first growing assembly (100) having a first plurality of light emitting diodes (LED), the first plurality of light emitting diodes (LED) in the first growing assembly (100) blue LEDs (BLED) and red LEDS (RLED), and optionally green LEDS (GLED);
(a2) a second growing assembly (200) having a second plurality of light emitting diodes (LED), the second plurality of light emitting diodes (LED) in the second growing assembly (200) include blue LEDs (BLED) and red LEDS (RLED), and optionally green LEDS (GLED);

(b) illuminating the interiors of the first growing assembly (100) and second growing assembly (200) with blue LEDs (BLED, BLED') and red LEDs (RLED, RLED'); and (c) optionally illuminating the interiors of the first growing assembly (100) and second growing assembly (200) with green LEDs (GLED, GLED');

wherein:
the blue LEDs (BLED, BLED') operate at a wavelength that ranges from 490 nanometers to 455 nanometers;
the red LEDs (RLED, RLED') operate at a wavelength that ranges from 620 nanometers to 780 nanometers;
the green LEDs (GLED, GLED') operate at a wavelength that ranges from 490 nanometers to 577 nanometers;
the blue LEDs (BLED, BLED') or red LEDs (RLED, RLED') illuminate the interiors of the first growing assembly (100) and second growing assembly (200) at an illumination on-off ratio ranging from between 0.5 and 5, the illumination on-off ratio is defined as the duration of time when the lights are on and illuminate in hours divided by the subsequent duration of time when the lights are off and are not illuminating in hours before the lights are turned on again.

In embodiments, the disclosure provides for a farming method, including:

(a) providing a farming superstructure system (FSS), including:

(a1) a first growing assembly (100) having a first plurality of light emitting diodes (LED), the first plurality of light emitting diodes (LED) in the first growing assembly (100) blue LEDs (BLED) and red LEDS (RLED), and optionally green LEDS (GLED);

(a2) a second growing assembly (200) having a second plurality of light emitting diodes (LED), the second plurality of light emitting diodes (LED) in the second growing assembly (200) include blue LEDs (BLED) and red LEDS (RLED), and optionally green LEDS (GLED);

(a3) a carbon dioxide tank (CO2T), at least one carbon dioxide valve (V8, V9, V10), the at least one carbon dioxide valve (V8, V9, V10) is configured to take a pressure drop of greater than 50 pounds per square inch, carbon dioxide is made available to the first growing assembly (100) or second growing assembly (200);

(b) illuminating the interiors of the first growing assembly (100) and second growing assembly (200) with blue LEDs (BLED, BLED') and red LEDs (RLED, RLED'); and (c) optionally illuminating the interiors of the first growing assembly (100) and second growing assembly (200) with green LEDs (GLED, GLED');

(d) adjusting the carbon dioxide concentration within the first growing assembly (100) or second growing assembly (200) to a range between 400 parts per million and parts per million;

wherein:
the blue LEDs (BLED, BLE'D) operate at a wavelength that ranges from 490 nanometers to 455 nanometers;
the red LEDs (RLED, RLED') operate at a wavelength that ranges from 620 nanometers to 780 nanometers;
the green LEDs (GLED, GLED') operate at a wavelength that ranges from 490 nanometers to 577 nanometers;
the blue LEDs (BLED, BLED') or red LEDs (RLED, RLED') illuminate the interiors of the first growing assembly (100) and second growing assembly (200) at an illumination on-off ratio ranging from between 0.5 and 5, the illumination on-off ratio is defined as the duration of time when the lights are on and illuminate in hours divided by the subsequent duration of time when the lights are off and are not illuminating in hours before the lights are turned on again.

The second growing assembly (200) has an interior (201), a top (202), a bottom (203), and a longitudinal axis (AX2) extending along a height direction of the first growing assembly (200). The second growing assembly (200) has a fabric (204) that partitions the second growing assembly (200) into an upper-section (205) close to the top (202) and a lower-section (206) close to the bottom (203). The fabric (204) is used to provide structure for *cannabis* (207) to root into. *Cannabis* (207) rooted in the fabric (204) have roots that grow downward and extend into the lower-section (206). The second growing assembly (200) is equipped with a plurality of lights (L2) positioned within the upper-section (205) above the fabric (204). *Cannabis* (207) rooted in the fabric (204) grow upward extending into the upper-section (205) towards the plurality of lights (L2). The plurality of lights (L2) are configured to be controlled by a computer (COMP) to operate at a wavelength ranging from 400 nm to 700 nm. In embodiments, the lights (L2) have a controller (CL2) that sends a signal (XL2) to and from the computer (COMP).

In embodiments, the farming superstructure system (FSS) is equipped with a carbon dioxide tank (CO2T). The carbon dioxide tank (CO2T) contains pressurized carbon dioxide (CO2) and is equipped with a carbon dioxide pressure sensor (CO2P). A carbon dioxide supply header (CO2H) is connected to the carbon dioxide tank (CO2T). A first carbon dioxide supply valve (V10) is installed on the carbon dioxide supply header (CO2H) and is configured to take a pressure drop of greater than 50 pounds per square inch (PSI). The first growing assembly (100) is equipped with a CO2 input (115) that is connected to a CO2 supply conduit (116). The second growing assembly (200) is also equipped with a CO2 input (215) that is connected to a CO2 supply conduit (216).

The CO2 supply conduit (116) of the first growing assembly (100) is connected to the carbon dioxide supply header (CO2H) via a CO2 header connection (115X). The CO2 supply conduit (116) of the first growing assembly (100) is configured to transfer carbon dioxide into the first interior (101) of the first growing assembly (100). In embodiments, a second carbon dioxide supply valve (V8) is installed on the CO2 supply conduit (116) of the first growing assembly (100). The second carbon dioxide supply valve (V8) is equipped with a controller (CV8) that sends a signal (XV8) to and from a computer (COMP). In embodiments, a CO2 flow sensor (FC1) is installed on the CO2 supply conduit (116) of the first growing assembly (100). The CO2 flow sensor (FC1) sends a signal (XFC1) to the computer (COMP). In embodiments, a gas quality sensor (GC1) is installed on the first growing assembly (100) to monitor the concentration of carbon dioxide within the first interior (101). The gas quality sensor (GC1) is equipped to send a signal (XGC1) to the computer (COMP).

The CO2 supply conduit (216) of the second growing assembly (200) is connected to the carbon dioxide supply header (CO2H) via a CO2 header connection (215X). The CO2 supply conduit (216) of the second growing assembly (200) is configured to transfer carbon dioxide into the second interior (201) of the second growing assembly (100). In embodiments, a third carbon dioxide supply valve (V9) is installed on the CO2 supply conduit (216) of the second growing assembly (200). The third carbon dioxide supply valve (V9) is equipped with a controller (CV9) that sends a signal (XV9) to and from a computer (COMP). In embodiments, a CO2 flow sensor (FC2) is installed on the CO2 supply conduit (216) of the second growing assembly (200). The CO2 flow sensor (FC2) sends a signal (XFC2) to the computer (COMP). In embodiments, a gas quality sensor (GC2) is installed on the second growing assembly (200) to monitor the concentration of carbon dioxide within the second interior (201). The gas quality sensor (GC2) is equipped to send a signal (XGC2) to the computer (COMP).

In embodiments, the carbon dioxide concentration in the upper-section (105, 205) of each growing assembly ranges from between 400 parts per million (ppm) to 500 ppm, 500 ppm to 600 ppm, 600 ppm to 700 ppm, 700 ppm to 800 ppm, 800 ppm to 900 ppm, 900 ppm to 1000 ppm, 1000 ppm to 1500 ppm, 1500 ppm to 2000 ppm, 2000 ppm to 2500 ppm, 2500 ppm to 3000 ppm, 3000 ppm to 3500 ppm, 3500 ppm to 4000 ppm, 4000 ppm to 4500 ppm, 4500 ppm to 5000 ppm, 5000 ppm to 5500 ppm, 5500 ppm to 6000 ppm, 6000 ppm to 6500 ppm, 6500 ppm to 7000 ppm, 7000 ppm to 7500 ppm, 7500 ppm to 8000 ppm, 8000 ppm to 8500 ppm, 8500 ppm to 9000 ppm, 9000 ppm to 9500 ppm, or 9500 ppm to 10000 ppm.

In embodiments, the gas quality sensor (GC2) is equipped to send a signal (XGC2) to the computer (COMP) to operate the first, second, or third carbon dioxide supply valves (V8, V9, V10).

At least one fan (FN1) is positioned in the upper-section (105) of the first growing assembly (100). The fan (FN1) is configured to blow air onto the *cannabis* (107). The fan (FN1) is configured to distribute a mixture of air and CO2 onto the *cannabis* (107). The fan (FN1) is equipped with a controller (CF1) that sends a signal (XF1) to and from a computer (COMP).

A plurality of fans (FN2) are positioned in the upper-section (205) of the second growing assembly (200). The fans (FN2) are configured to blow air onto the *cannabis* (207). In embodiments, the fans blow air and the air is comprised of a gas, vapor, and solid particulates. In embodiments, the gas within air may be oxygen, carbon dioxide, or nitrogen. In embodiments, the vapor within the air may be water vapor. In embodiments, the solid particulates within air may be dust, dirt, or pollen. The fans (FN2) are configured to distribute a mixture of air and CO2 onto the *cannabis* (207). The fans (FN2) are equipped with a controller (CF2) that sends a signal (XF2) to and from a computer (COMP). Each of the fans (FN1, FN2) is configured to operate at a revolutions per minute (RPM) less than 6,000 RPM. In embodiments, it is preferred to operate the fans (FN1, FN2) at a RPM less than 6,000 so that the velocity of air blown onto the *cannabis* ranges from 0.5 feet per second (fps) to 1 fps, 1 fps to 5 fps, 5 fps to 10 fps, 10 fps to 15 fps, 15 fps to 20 fps, 20 fps to 25 fps, 25 fps to 30 fps, 30 fps to 35 fps, 35 fps to 40 fps, 40 fps to 45 fps, or 45 fps to 50 fps.

The first growing assembly (100) is equipped with a temperature sensor (T1) to monitor the temperature within the first interior (101). The temperature sensor (T1) is configured to send a signal (XT1) to the computer (COMP). In embodiments, the temperature sensor (T1) may be a multi-point temperature sensor (MPT100) that is connected to the fabric (104) for measuring temperatures at various lengths along the sensors length and long the length of the fabric (104), as depicted in FIGS. 12 and 13.

The second growing assembly (200) is equipped with a temperature sensor (T2) to monitor the temperature within the second interior (201). The temperature sensor (T2) is configured to send a signal (XT2) to the computer (COMP). In embodiments, the temperature sensor (T2) may be a multi-point temperature sensor (MPT100) that is connected to the fabric (204) for measuring temperatures at various lengths along the sensors length and long the length of the fabric (204), as depicted in FIGS. 12 and 13.

In embodiments, each growing assembly (100, 200) is equipped with an upper temperature sensor (T1C, T2C) positioned within the upper-section (105, 205), a partition temperature sensor (T1B, T2B) positioned at the fabric (104), and a lower temperature sensor (T1A, T2A) positioned within the lower-section (106, 206). Preferably the partition temperature sensor (T1B) is a multi-point temperature sensor (MPT100) that is integrated with the fabric (104) as disclosed in FIGS. 12 and 13.

In embodiments, the upper temperature sensor (T1C, T2C) is configured to input a signal (XT1C, XT2C) (not shown) to the computer (COMP). In embodiments, the partition temperature sensor (T1B, T2B) is configured to input a signal (XT1B, XT2B) (not shown) to the computer (COMP). In embodiments, the lower temperature sensor (T1A, T2B) is configured to input a signal (XT1A, XT2A) (not shown) to the computer (COMP). In embodiments, during the day-time, the upper-section (105, 205) has a temperature that is greater than the temperature within lower-section (106, 206). In embodiments, during the night-time, the upper-section (105, 205) has a temperature that is less than the temperature within the lower-section (106, 206).

A first liquid distributor (108) is positioned in the lower-section (106) of the first growing assembly (100) below the fabric (104) and equipped with a plurality of restrictions (109) installed thereon. In embodiments, the restrictions (109) of the first liquid distributor (108) are spray nozzles, spray balls, or apertures. Each restriction (109) is configured to accept pressurized liquid from the pump (P1) and introduce the liquid into the lower-section (106) of the first growing assembly (100) while reducing the pressure of the liquid that passes through each restriction (109). The first liquid distributor (108) is connected to a first liquid supply conduit (113) via a liquid input (114). The first liquid distributor (108) is configured to receive liquid from a first liquid supply conduit (113).

A second liquid distributor (208) is positioned in the lower-section (206) of the second growing assembly (200) below the fabric (204) and equipped with a plurality of restrictions (209) installed thereon. In embodiments, the restrictions (209) of the second liquid distributor (208) are spray nozzles, spray balls, or apertures. Each restriction (209) is configured to accept pressurized liquid from the pump (P1) and introduce the liquid into the lower-section (206) of the second growing assembly (200) while reducing the pressure of the liquid that passes through each restriction (209). The second liquid distributor (208) is connected to a second liquid supply conduit (213) via a liquid input (214). The second liquid distributor (208) is configured to receive liquid from a second liquid supply conduit (213).

The first liquid supply conduit (113) is connected to a liquid supply header (300) via a first connection (X1). The second liquid supply conduit (213) is connected to a liquid supply header (300) via a second connection (X2). The liquid supply header (300) is connected to the pump discharge conduit (304). In embodiments, the liquid supply header (300) has a diameter (D1) that is greater than both the first smaller diameter (D2) of the first liquid supply conduit (113) and the second smaller diameter (D3) of the second liquid supply conduit (213). A first reducer (R1) may be positioned on the first liquid supply conduit (113) in between the first connection (X1) to the liquid supply header (300) and the liquid input (114) to the first growing assembly (100). A second reducer (R2) may be positioned on the second liquid supply conduit (213) in between the second connection (X2) to the liquid supply header (300) and the liquid input (214) to the second growing assembly (200).

A first growing assembly liquid supply valve (V3) may be positioned on the first liquid supply conduit (113) in between the liquid supply header (300) and the first growing assembly (100). The first growing assembly liquid supply valve (V3) has a controller (CV3) that is configured to input and output a signal (XV3) to or from the computer (COMP). A second growing assembly liquid supply valve (V4) may be positioned on the second liquid supply conduit (213) in between the liquid supply header (300) and the second growing assembly (200). The second growing assembly liquid supply valve (V4) has a controller (CV4) that is configured to input and output a signal (XV4) to or from the computer (COMP).

A back-flow prevention valve (BF1) may be positioned on the first liquid supply conduit (113) in between the liquid supply header (300) and the first growing assembly (100). FIG. 1A shows the back-flow prevention valve (BF1) positioned in between the first growing assembly liquid supply valve (V3) and the first growing assembly (100). A back-flow prevention valve (BF2) may be positioned on the second liquid supply conduit (213) in between the liquid supply header (300) and the second growing assembly (200). FIG. 1A shows the back-flow prevention valve (BF2) positioned in between the second growing assembly liquid supply valve (V4) and the second growing assembly (200).

A second oxygen emitter (EZ2) may be positioned on the first liquid supply conduit (113) in between the liquid supply header (300) and the first growing assembly (200). The second oxygen emitter (EZ2) is configured to oxygenate a portion of the liquid that flows through the first liquid supply conduit (113). The second oxygen emitter (EZ2) inputs signal (XEZ3) from a computer (COMP). A third oxygen emitter (EZ3) may be positioned on the second liquid supply conduit (213) in between the liquid supply header (300) and the second growing assembly (200). The third oxygen emitter (EZ3) is configured to oxygenate a portion of the liquid that flows through the second liquid supply conduit (213). The third oxygen emitter (EZ3) inputs signal (XEZ3) from a computer (COMP).

In embodiments, the oxygen emitter is an electrolytic cell configured to produce oxygenated water. In embodiments, oxygenated water produced by the electrolytic cell may have microbubbles and nanobubbles of oxygen suspended within it. In embodiments, the oxygen emitter is an electrolytic cell which generates microbubbles and nanobubbles of oxygen in a liquid, which bubbles are too small to break the surface tension of the liquid, resulting in a liquid that is supersaturated with oxygen. "Supersaturated" means oxygen at a higher concentration than normal calculated oxygen solubility at a particular temperature and pressure. In embodiments, the very small oxygen bubbles remain suspended in the liquid, forming a solution supersaturated in oxygen. The use of supersaturated or oxygenated water for enhancing the growth of *cannabis* may be incorporated into the FSS. Electrolytic generation of microbubbles or nanobubbles of oxygen for increasing the oxygen content of flowing liquid may be incorporated into the FSS. In embodiments, the production of oxygen and hydrogen by the electrolysis of water may be used to enhance the efficiency of the FSS.

In embodiments, an electrolytic cell is comprised of an anode and a cathode. A current is applied across an anode and a cathode of the electrolytic cell which are immersed in a liquid. Hydrogen gas is produced at the cathode and oxygen gas is produced at the anode. In embodiments, the electrolytic cell tends to deactivate and have a limited life if exposed to the positively charged ions, negatively charged ions, or undesirable compounds. Therefore, a sophisticated water treatment unit is needed for the electrolytic cell to work properly deactivate by unpredictable amounts of positively charged ions, remove negatively charged ions, or undesirable components. The roots of the *cannabis* in the lower section (106, 206) are healthier when contacted with an oxygenated liquid. Further, oxygenated and/or supersaturated water inhibits the growth of deleterious fungi on the fabric (104, 204). In embodiments, the oxygen emitter may be a sparger for increasing the oxygen content of a liquid by sparging with air or oxygen. In embodiments, the oxygen emitter may be a microbubble generator that achieves a bubble size of about 0.10 millimeters to about 3 millimeters in diameter. In embodiments, the oxygen emitter may be a microbubble generator for producing microbubbles, ranging in size from 0.1 to 100 microns in diameter, by forcing air into the fluid at high pressure through an orifice.

The common reservoir (500) is configured to accept a water supply (01). In embodiments, the common reservoir (500) is configured to accept a water supply (01) that has passed through one or more water treatment units (A1, A2, A3). In embodiments, the common reservoir (500) is configured to accept a portion of the undesirable compounds depleted water (12A).

The common reservoir (500) is configured to accept macro-nutrients (601) from a macro-nutrient supply tank (600), micro-nutrients (701) from a micro-nutrient supply tank (700), and a pH adjustment solution (801) from a pH adjustment solution supply tank (800). In embodiments, the macro-nutrients (601) include one or more from the group consisting of nitrogen, phosphorus, potassium, calcium, magnesium, and sulfur. In embodiments, the micro-nutrients (701) include one or more from the group consisting of iron, manganese, boron, molybdenum, copper, zinc, sodium, chlorine, and silicon. In embodiments, the pH adjustment solution (801) includes one or more from the group consisting acid, nitric acid, phosphoric acid, potassium hydroxide, sulfuric acid, organic acids, citric acid, and acetic acid.

In embodiments, the macro-nutrient supply tank (600) is connected to the common reservoir (500) via a macro-nutrient transfer conduit (602) and a macro-nutrient reservoir input (Z1). A macro-nutrient supply valve (V5) is installed on the macro-nutrient transfer conduit (602). The macro-nutrient supply valve (V5) is equipped with a controller (CV5) that inputs and outputs a signal (XV5) to and from the computer (COMP). A macro-nutrient flow sensor (F5) is installed on the macro-nutrient transfer conduit (602) and configured to output a signal (XF5) to or from a computer (COMP). Macro-nutrients (601) may be transferred to the interior of the common reservoir (500) via a macro-nutrient transfer conduit (602) by operation with a macro-nutrient supply tank (600) load cell (604) to measure the loss-in-mass of the macro-nutrients (601) within the macro-nutrient supply tank (600) or the macro-nutrient transfer conduit (602). Macro-nutrients (601) are introduced into the interior of the common reservoir (500) beneath the liquid level via a diptube (606).

In embodiments, the micro-nutrient supply tank (700) is connected to the common reservoir (500) via a micro-nutrient transfer conduit (702) and a micro-nutrient reservoir input (Z2). A micro-nutrient supply valve (V6) is installed on the micro-nutrient transfer conduit (702). The micro-nutrient supply valve (V6) is equipped with a controller (CV6) that inputs and outputs a signal (XV6) to and from the computer (COMP). A micro-nutrient flow sensor (F6) is installed on the micro-nutrient transfer conduit (702) and configured to output a signal (XF6) to or from a computer (COMP). Micro-nutrients (701) may be transferred to the interior of the common reservoir (500) via a micro-nutrient transfer conduit (702) by operation with a micro-nutrient supply tank (700) load cell (704) to measure the loss-in-mass of the micro-nutrients (701) within the micro-nutrient supply tank (700) or the micro-nutrient transfer conduit (702). Macro-nutrients (601) are introduced into the interior of the common reservoir (500) beneath the liquid level via a diptube (606) (not shown).

In embodiments, the pH adjustment solution supply tank (800) is connected to the common reservoir (500) via a pH adjustment solution transfer conduit (802) and a pH adjustment solution reservoir input (Z3). A pH adjustment solution supply valve (V8) is installed on the pH adjustment solution transfer conduit (802). The pH adjustment solution supply valve (V8) is equipped with a controller (CV8) that inputs and outputs a signal (XV8) to and from the computer (COMP). A pH adjustment solution flow sensor (F7) is installed on the pH adjustment solution transfer conduit (802) and configured to output a signal (XF7) to or from a computer (COMP). A pH adjustment solution (801) may be transferred to the interior of the common reservoir (500) via a pH adjustment solution transfer conduit (802) by operation with a pH adjustment solution supply tank (800) load cell (804) to measure the loss-in-mass of the pH adjustment solution (801) within the pH adjustment solution supply tank (800) or the pH adjustment solution transfer conduit (802). The pH adjustment solution (801) are introduced into the interior of the common reservoir (500) beneath the liquid level via a diptube (806) (not shown).

The common reservoir (500) is configured to accept liquid drained from each growing assembly (100, 200). The common reservoir (500) is configured to accept liquid drained from the first growing assembly (100). A drain port (110) is installed on the lower-section (106) of the first growing assembly (100) and is configured to drain liquid into a common reservoir (500) via a drain conduit (111). In embodiments, the first growing assembly (100) is connected to the common reservoir (500) via a drain conduit (111). The common reservoir (500) is configured to accept liquid drained from the second growing assembly (200). A drain port (210) is installed on the lower-section (206) of the second growing assembly (200) and is configured to drain liquid into a common reservoir (500) via a drain conduit (211). In embodiments, the second growing assembly (200) is connected to the common reservoir (500) via a drain conduit (211). It is preferable to drain liquid from each growing assembly at a velocity less than 3 feet per second (fps) or 0.25 fps to 0.50 fps, 0.50 fps to 0.75 fps, 0.75 fps to 1.00 fps, 1.00 fps to 1.25 fps, 1.25 fps to 1.50 fps, 1.50 fps to 1.75 fps, 1.75 fps to 2.00 fps, 2.00 fps to 2.25 fps, 2.25 fps to 2.50 fps, 2.50 fps to 2.75 fps, 2.75 fps to 3.00 fps, 3.00 fps to 3.25 fps, 3.25 fps to 3.50 fps, 3.50 fps to 3.75 fps, 3.75 fps to 4.00 fps, 4.00 fps to 4.25 fps, 4.25 fps to 4.50 fps, 4.50 fps to 4.75 fps, 4.75 fps to 5.00 fps, 5.00 fps to fps, 5.25 fps to 5.50 fps, 5.50 fps to 5.75 fps, 5.75 fps to 6.00 fps, 6.00 fps to 6.25 fps, 6.25 fps to 6.50 fps, 6.50 fps to 6.75 fps, 6.75 fps to 7.00 fps, 7.00 fps to 7.25 fps, 7.25 fps to 7.50 fps, 7.50 fps to 7.75 fps, 7.75 fps to 8.00 fps, 8.00 fps to 8.25 fps, 8.25 fps to 8.50 fps, 8.50 fps to 8.75 fps, 8.75 fps to 9.00 fps, 9.00 fps to 9.25 fps, 9.25 fps to 9.50 fps, 9.50 fps to 9.75 fps, or 9.75 fps to 10.00 fps.

In embodiments, the drain conduit (111) is connected at one end to the first growing assembly (100) via a drain port (110) and connected at another end to the common reservoir (500) via a common drain conduit (517). In embodiments, the drain conduit (211) is connected at one end to the second growing assembly (200) via a drain port (210) and connected at another end to the common reservoir (500) via a common drain conduit (517). The common drain conduit (517) is connected at one end to the common reservoir (500) via a drain input (518) and at another end to the first drain conduit (111) via a first drain connection (112). The common drain conduit (517) is connected at one end to the common reservoir (500) via a drain input (518) and at another end to the second drain conduit (211) via a second drain connection (212). In embodiments, the common drain conduit (517) is connected to both drain conduits (111, 211) from both growing assemblies (100, 200) and is configured to combine the liquid contents of both drain conduits (111, 211) prior to introducing them into the common reservoir (500). In embodiments, as shown in FIG. 8, there is no common drain conduit (517) and each drain conduit (111, 211) of the growing assemblies (100, 200) drains directly into the common reservoir (500).

The interior of the common reservoir (500) is configured to hold water, macro-nutrients (601), micro-nutrients (701) from a micro-nutrient supply tank (700), and a pH adjustment solution (801). In embodiments, the common reservoir (500) is equipped with a reservoir pH sensor (PH0) that is configured to input a signal (XPH0) to a computer (COMP). In embodiments, the acidity of the water is measured by the reservoir pH sensor (PH0) and adjusted to a desirable range from to 6.75. In embodiments, the common reservoir (500) is equipped with a reservoir temperature sensor (T0) that is configured to input a signal (XT0) to a computer (COMP). In embodiments, the common reservoir (500) is equipped with a reservoir oxygen emitter (EZ) that is configured to input a signal (XEZ) to a computer (COMP). In embodiments, the common reservoir (500) is equipped with a reservoir electrical conductivity sensor (E1) that is configured to input a signal (XE1) to a computer (COMP).

In embodiments, the common reservoir (500) is equipped with a reservoir recirculation pump (P0) followed by a reservoir recirculation filter (F3) to remove solids from the common reservoir (500). In embodiments, the common reservoir (500) is equipped with a reservoir heat exchanger (HX2) to maintain a temperature of the liquid contents within the common reservoir (500). In embodiments, the common reservoir (500) is equipped with a reservoir recirculation pump (P0) followed by a reservoir heat exchanger (HX2) to maintain a temperature of the liquid contents within the common reservoir (500). The common reservoir (500) has a reservoir recirculation outlet (510) that is connected to a reservoir recirculation pump suction conduit (512). The reservoir recirculation pump suction conduit (512) is connected to a reservoir recirculation pump (P0). The reservoir recirculation pump (P0) is connected to a reservoir recirculation pump discharge conduit (514) that transfers liquid back to the common reservoir (500) via a reservoir recirculation inlet (516). In embodiments, a reservoir recirculation filter (F3) is installed on the reservoir recirculation pump discharge conduit (514). In embodiments, a reservoir heat exchanger (HX2) is installed on the reservoir recirculation pump discharge conduit (514). In embodiments, a reservoir heat exchanger (HX2) is installed on the reservoir recirculation pump discharge conduit (514) after the reservoir recirculation filter (F3). In embodiments, the reservoir heat exchanger (HX2) may increase the temperature of the liquid passing through it. In embodiments, the reservoir heat exchanger (HX2) may decrease the temperature of the liquid passing through it.

The common reservoir (500) is connected to a pump (P1) via a pump suction conduit (303). The pump suction conduit (303) is connected at one end to the common reservoir (500) via a reservoir transfer outlet (302) and connected at the other end to the pump (P1). The pump (P1) is equipped with a motor (MP1) and a controller (CP1) which is configured to input and output a signal (XP1) to and from a computer (COMP). A pump discharge conduit (304) is connected to the pump (P1). The liquid supply header (300) may be synonymous with the pump discharge conduit (304) in that they both accept a portion of pressurized liquid that was provided by the pump (P1).

In embodiments, a pressure tank (PT) is installed on the pump discharge conduit (304). In embodiments, the pressure tank (PT) may be pressurized by the pump (P1). The pressure tank (PT) serves as a pressure storage reservoir in which a liquid is held under pressure. The pressure tank (PT) enables the system to respond more quickly to a temporary demand, and to smooth out pulsations created by the pump (P1). In embodiments, the pressure tank (PT) serves as accumulator to relieve the pump (P1) from constantly operating. In embodiments, the pressure tank (PT) is a cylindrical tank rated for a maximum pressure of 200 PSI or 600 PSI. In embodiments, the pressure tank (PT) is a cylindrical tank that has a length to diameter ratio ranging from 1.25 to 2.5.

A level control discharge conduit (310) is connected to the pump discharge conduit (304) via a connection (311). The level control discharge conduit (310) is configured to pump the contents of the common reservoir (500) away from the system for any number of reasons. Clean-out, replenishing the liquid within the common reservoir (500) or to bleed off some of the liquid contents within may be some purposes for utilizing the level control discharge conduit (310). A filter (F4) is installed on the level control discharge conduit (310). A level control valve (LCV) is installed on the level control discharge conduit (310) and is equipped with a controller (CCV) that sends a signal (XCV) to or from the computer (COMP). The filter (F4) preferably is installed upstream of the level control valve (LCV) to that solids do not clog the level control valve (LCV). Preferably the connection (311) for the level control discharge conduit (310) is connected as close as possible to the pump (P1) on the pump discharge conduit (304) so that if the filters (F1, F2) on the pump discharge conduit (304) clog, there is still a way to drain liquid from the system. A waste treatment unit (312) may be placed on the level control discharge conduit (310) to destroy any organic molecules, waste, bacteria, protozoa, helminths, or viruses that may be present in the liquid. In embodiments, the waste treatment unit (312) is an ozone unit (313) configured to destroy organic molecules, waste, bacteria, protozoa, helminths, or viruses via oxidation.

A waste treatment unit (312) may be placed on the level control discharge conduit (310) to destroy any organic molecules, waste, bacteria, protozoa, helminths, or viruses that may be present in the liquid. In embodiments, the waste treatment unit (312) includes a filter to remove particulates. In embodiments, the waste treatment unit (312) includes a membrane to treat the liquid waste, and remove contaminants therefrom. In embodiments, the waste treatment unit (312) includes a filter to remove particulates followed by a membrane to treat the liquid waste. The water discharged from the membrane waste treatment unit (312) may be sent back or recycled to the common reservoir (500) for use again to feed the *cannabis* plants (107, 207). In embodiments, the contaminants removed from the membrane may then be sent to an evaporator to concentrate the contaminants by removing residual water therefrom.

At least one filter (F1, F2) may be installed on the pump discharge conduit (304). FIG. 1A shows two filters (F1, F2) configured to operate in a cyclic-batch mode where when one is on-line in a first mode of normal operation, the other is off-line and undergoing a back-flush cycle in a second mode of operation. This is depicted in FIG. 1A wherein the first filter (F1) is on-line and filtering the liquid discharged from the pump (P1) while the second filter (F2) is off-line. The first filter (F1) is shown to have a first filter inlet valve (FV1) and a first filter outlet valve (FV2) both of which are open in FIG. 1. The second filter (F2) is shown to have a second filter inlet valve (FV3) and a second filter outlet valve (FV4) both of which are shown in the closed position as indicted by darkened-in color of the valves (FV3, FV4). The second filter (F2) is shown in the back-flush mode of operation while the first filter (F1) is shown in the normal mode of operation. While in the back-flush mode of operation, the second filter (F2) is shown accepting a source of liquid from the common reservoir (500) via a filter back-flush supply conduit (306).

The common reservoir (500) is equipped with a filter back-flush outlet (307) that is connected to a filter back-flush supply conduit (306). The filter back-flush supply conduit (306) is connected at one end to the common reservoir (500) via a filter back-flush outlet (307) and at another end to the filter back-flush pump (308). The filter back-flush pump (308) is connected to the filter back-flush discharge conduit (309). The filter back-flush discharge conduit (309) has a filter back-flush supply valve (FV5) installed thereon to provide pressurized liquid from the common reservoir (500) to the second filter (F2) operating in the second mode of back-flush operation. The filter back-flush supply valve (FV5) provides liquid to the second filter in between the second filter outlet valve (FV4) and the second filter (F2) to back-flush the second filter (F2). A filter back-flush discharge valve (FV6) is provided in between the second filter and the second filter inlet valve (FV3) to flush solids that have accumulated during the first mode of normal operation.

A filter inlet pressure sensor (P2) is installed on the pump discharge conduit (304) before the filters (F1, F2). The filter inlet pressure sensor (P2) is configured to output a signal (XP2) to the computer (COMP). A filter discharge pressure sensor (P3) is installed on the pump discharge conduit (304) after the filters (F1, F2). The filter discharge pressure sensor (P2) is configured to output a signal (XP3) to the computer (COMP). Then the pressure drop across the filters (F1, F2) reached a threshold predetermined value, the filters (F1, F2) switch modes of operation from first to second and from second to first.

A first oxygen emitter (EZ1) is installed on the pump discharge conduit (304). In embodiments, the first oxygen emitter (EZ1) is installed on the pump discharge conduit (304) after the filters (F1, F2). The first oxygen emitter (EZ1) is configured to output a signal (XEZ1) to the computer (COMP). The first oxygen emitter (EZ1) oxygenates the water passing through the pump discharge conduit (304).

A liquid flow sensor (F0) is installed on the pump discharge conduit (304) after the filters (F1, F2). The liquid flow sensor (F0) is configured to output a signal (XF0) to the computer (COMP). The liquid flow sensor (F0) measures the flow rate of water passing through the pump discharge conduit (304).

In embodiments, the flow rate of water passing through the pump discharge conduit (304) ranges from 0.01 gallons per minute (gpm) to 0.02 gpm, 0.02 gpm to 0.03 gpm, 0.03 gpm to 0.04 gpm, 0.04 gpm to 0.05 gpm, 0.05 gpm to 0.06 gpm, 0.05 gpm to 0.06 gpm, 0.06 gpm to 0.07 gpm, gpm to 0.08 gpm, 0.08 gpm to 0.09 gpm, 0.09 gpm to 0.1 gpm, 0.1 gpm to 0.15 gpm, 0.15 gpm to 0.2 gpm, 0.2 gpm to 0.25 gpm, 0.25 gpm to 0.3 gpm, 0.3 gpm to 0.35 gpm, 0.35 gpm to 0.4 gpm, 0.4 gpm to 0.45 gpm, 0.45 gpm to 0.5 gpm, 0.5 gpm to 0.6 gpm, 0.6 gpm to 0.7 gpm, 0.7 gpm to 0.8 gpm, 0.8 gpm to 0.9 gpm, 0.9 gpm to 1 gpm, 1 gpm to 2 gpm, 2 gpm to 3 gpm, 3 gpm to 4 gpm, 4 gpm to 5 gpm, 5 gpm to 6 gpm, 6 gpm to 7 gpm, 7 gpm to 8 gpm, 8 gpm to 9 gpm, 9 gpm to 10 gpm, 10 gpm to 11 gpm, 11 gpm to 12 gpm, 12 gpm to 13 gpm, 13 gpm to 14 gpm, 14 gpm to 15 gpm, 15 gpm to 16 gpm, 16 gpm to 17 gpm, 17 gpm to 18 gpm, 18 gpm to 19 gpm, 19 gpm to 20 gpm, 20 gpm to 30 gpm, 30 gpm to 40 gpm, 40 gpm to 50 gpm, 50 gpm to 60 gpm, 60 gpm to 70 gpm, 70 gpm to 80 gpm, 80 gpm to 90 gpm, 90 gpm to 100 gpm, 100 gpm to 125 gpm, 125 gpm to 150 gpm, 150 gpm to 175 gpm, 175 gpm to 200 gpm, 200 gpm to 225 gpm, 225 gpm to 250 gpm, 250 gpm to 275 gpm, 275 gpm to 300 gpm, 300 gpm to 350 gpm, 350 gpm to 400 gpm, 400 gpm to 450 gpm, 450 gpm to 500 gpm, 500 gpm to 550 gpm, 550 gpm to 600 gpm, 600 gpm to 650 gpm, 650 gpm to 700 gpm, 700 gpm to 750 gpm, 750 gpm to 800 gpm, 800 gpm to 850 gpm, 850 gpm to 900 gpm, 900 gpm to 950 gpm, 950 gpm to 1000 gpm, 1000 gpm to 1500 gpm, 1500 gpm to 2000 gpm, 2000 gpm to 2500 gpm, 2500 gpm to 3000 gpm, 3000 gpm to 3500 gpm, 3500 gpm to 4000 gpm, 4000 gpm to 4500 gpm, 4500 gpm to 5000 gpm, 5000 gpm to 5500 gpm, 5500 gpm to 6000 gpm, 6000 gpm to 6500 gpm, 6500 gpm to 7000 gpm, 7000 gpm to 7500 gpm, 7500 gpm to 8000 gpm, 8000 gpm to 8500 gpm, 8500 gpm to 9000 gpm, 9000 gpm to 9500 gpm, or 9500 gpm to 10000 gpm.

In embodiments, the velocity of the water passing through the pump discharge conduit (304) ranges from 3.00 fps to 3.25 fps, 3.25 fps to 3.50 fps, 3.50 fps to 3.75 fps, 3.75 fps to 4.00 fps, 4.00 fps to 4.25 fps, 4.25 fps to 4.50 fps, 4.50 fps to 4.75 fps, 4.75 fps to 5.00 fps, 5.00 fps to fps, 5.25 fps to 5.50 fps, 5.50 fps to 5.75 fps, 5.75 fps to 6.00 fps, 6.00 fps to 6.25 fps, 6.25 fps to 6.50 fps, 6.50 fps to 6.75 fps, 6.75 fps to 7.00 fps, 7.00 fps to 7.25 fps, 7.25 fps to 7.50 fps, 7.50 fps to 7.75 fps, 7.75 fps to 8.00 fps, 8.00 fps to 8.25 fps, 8.25 fps to 8.50 fps, 8.50 fps to 8.75 fps, 8.75 fps to 9.00 fps, 9.00 fps to 9.25 fps, 9.25 fps to 9.50 fps, 9.50 fps to 9.75 fps, or 9.75 fps to 10.00 fps.

In embodiments, the velocity of the water passing through the pump suction conduit (303) ranges from 0.25 feet per second (fps) to 0.50 fps, 0.50 fps to 0.75 fps, 0.75 fps to 1.00 fps, 1.00 fps to 1.25 fps, 1.25 fps to 1.50 fps, 1.50 fps to 1.75 fps, 1.75 fps to 2.00 fps, 2.00 fps to 2.25 fps, 2.25 fps to 2.50 fps, 2.50 fps to 2.75 fps, or 2.75 fps to 3.00 fps.

A growing assembly liquid supply valve (V1) is installed on the pump discharge conduit (304). In embodiments, the growing assembly liquid supply valve (V1) is installed on the pump discharge conduit (304) after the filters (F1, F2). The growing assembly liquid supply valve (V1) is equipped with a controller (CV1) that sends a signal (XV1) to or from a computer (COMP).

An electrical conductivity sensor (E2) is installed on the pump discharge conduit (304). In embodiments, the electrical conductivity sensor (E2) is installed on the pump discharge conduit (304) after the filters (F1, F2). The electrical conductivity sensor (E2) is configured to output a signal (XE2) to the computer (COMP). The electrical conductivity sensor (E2) measures the electrical conductivity of the water passing through the pump discharge conduit (304).

A liquid heat exchanger (HX3) is installed on the pump discharge conduit (304). In embodiments, the liquid heat exchanger (HX3) is installed on the pump discharge conduit (304) after the filters (F1, F2). The liquid heat exchanger (HX3) is configured increase or decrease the temperature of the water passing through the pump discharge conduit (304).

A liquid temperature sensor (T3) is installed on the pump discharge conduit (304). In embodiments, the liquid temperature sensor (T3) is installed on the pump discharge conduit (304) after the filters (F1, F2). In embodiments, the liquid temperature sensor (T3) is installed on the pump discharge conduit (304) after the liquid heat exchanger (HX3). The liquid temperature sensor (T3) is configured to input a signal (XT3) to the computer (COMP).

In embodiments, the growing assembly liquid supply valve (V1), first growing assembly liquid supply valve (V3), and/or the second growing assembly liquid supply valve (V4), may continuously be open to permit a continuous flow of liquid into the growing assemblies (100, 200). In embodiments, the growing assembly liquid supply valve (V1), first growing assembly liquid supply valve (V3), and/or second growing assembly liquid supply valve (V4), may be opened and closed by their controllers (CV1, CV3, CV4) and operated by a computer (COMP). In embodiments, the growing assembly liquid supply valve (V1), first growing assembly liquid supply valve (V3), and/or second growing assembly liquid supply valve (V4), may be opened and closed by their controllers (CV1, CV3, CV4) and operated by a computer (COMP) on a timer.

It is preferred to have the valves (V1, V3, V4) operated in a plurality of modes of operation. In embodiments, a first mode of operation includes having the growing assembly liquid supply valve (V1), first growing assembly liquid supply valve (V3), second growing assembly liquid supply valve (V4), all in an open valve position to transfer liquid from the common reservoir (500) into the growing assemblies (100, 200). In embodiments, a second mode of operation includes having the growing assembly liquid supply valve (V1) open, first growing assembly liquid supply valve (V3) closed, and second growing assembly liquid supply valve (V4) closed, to stop the transfer liquid to the growing assemblies (100, 200). In embodiments, a third mode of operation includes having the growing assembly liquid supply valve (V1) open, first growing assembly liquid supply valve (V3) open, second growing assembly liquid supply valve (V4) closed, to transfer liquid to the first growing assembly (100) and not into the second growing assembly (200). In embodiments, a fourth mode of operation includes having the growing assembly liquid supply valve (V1) open, first growing assembly liquid supply valve (V3) closed, second growing assembly liquid supply valve (V4) open, to transfer liquid to the second growing assembly (200) and not into the first growing assembly (100).

In embodiments, the farming superstructure system (FSS) is operated in a manner that switches from one mode of operation to another mode of operation. In embodiments, the farming superstructure system (FSS) is operated in a manner that switches on a cyclical basis from: a first mode of operation to the second mode of operation; a second mode of operation to the first mode of operation. In embodiments, the farming superstructure system (FSS) is operated in a manner that switches on a cyclical basis from: a third mode of operation to the fourth mode of operation; a fourth mode of operation to the third mode of operation. It is preferred to turn on and off at least one of the valves (V1, V3, V4) in a cyclical manner to permit to prevent the roots of the *cannabis* from receiving too much mist or spray.

In embodiments, the first mode of operation lasts for 5 seconds open followed by the second mode of operation lasting for 600 seconds closed. In embodiments, the third mode of operation lasts for 5 seconds open followed by the fourth mode of operation lasting for 600 seconds closed. In embodiments, water is transferred to the first growing assembly (100) for 5 seconds followed by not transferring water to the first growing assembly (100) for 600 seconds. In embodiments, water is transferred to the second growing assembly (200) for 5 seconds followed by not transferring water to the second growing assembly (200) for 600 seconds. In embodiments, water is transferred to both the first and second growing assemblies (100, 200) for 5 seconds followed by not transferring water to both the first and second growing assemblies (100, 200) for 600 seconds. 5 divided by 600 is 0.008.

In embodiments, the first mode of operation lasts for 60 seconds open followed by the second mode of operation lasting for 180 seconds closed. In embodiments, the third mode of operation lasts for 60 seconds open followed by the fourth mode of operation lasting for 180 seconds closed. In embodiments, water is transferred to the first growing assembly (100) for 60 seconds followed by not transferring water to the first growing assembly (100) for 180 seconds. In embodiments, water is transferred to the second growing assembly (200) for 60 seconds followed by not transferring water to the second growing assembly (200) for 180 seconds. 60 divided by 180 is 0.333.

The duration of time when liquid is transferred to at least one growing assembly (100, 200) divided by the duration of time when liquid is not transferred to at least one growing assembly (100, 200) may be considered an open-close ratio. The open-close ratio may be the duration of time when at least one valve (V1, V3, V4) is open in seconds divided by the subsequent duration of time when the same valve is closed in seconds before the same valve opens again. In embodiments, the open-close ratio ranges from between 0.008 to 0.33. In embodiments, the computer (COMP) opens and closes the valve (V1, V3, V4) to periodically introduce the pressurized liquid mixture into to each growing assembly with an open-close ratio ranging from between 0.008 to 0.33, the open-close ratio is defined as the duration of time when the valve (V1, V3, V4) is open in seconds divided by the subsequent duration of time when the same valve is closed in seconds before the same valve opens again. The computer (COMP) opens and closes the valves (V1, V3, V4) to periodically introduce the pressurized liquid mixture into to each growing assembly with an open-close ratio ranging from between 0.008 to 0.33.

In embodiments, the open-close ratio varies. The open-close ratio may vary throughout the life of the *cannabis* contained within the growing assemblies (100, 200). The open-close ratio may vary throughout the stage of development of the *cannabis* contained within the growing assemblies (100, 200). Stages of development of the *cannabis* include flowering, pollination, fertilization. In embodiments, the open-close ratio is greater during flowering and less during pollination. In embodiments, the open-close ratio is greater during pollination and less during fertilization. In embodiments, the open-close ratio is greater during flowering and less during fertilization. In embodiments, the open-close ratio is less during flowering and greater during pollination. In embodiments, the open-close ratio is less during pollination and greater during fertilization. In embodiments, the open-close ratio is less during flowering and greater during fertilization.

In embodiments, the temperature is greater during flowering and less during pollination. In embodiments, the temperature is greater during pollination and less during fertilization. In embodiments, the temperature is greater during flowering and less during fertilization. In embodiments, the temperature is less during flowering and greater during pollination. In embodiments, the temperature is less during pollination and greater during fertilization. In embodiments, the temperature is less during flowering and greater during fertilization.

The open-close ratio may vary throughout a 24-hour duration of time. In embodiments, the open-close ratio is increased during the day-time and decreased during the night-time relative to one another. In embodiments, the open-close ratio varies increased during the night-time and decreased during the day-time relative to one another. Night-time is defined as the time between evening and morning. Day-time is defined as the time between morning and evening.

In embodiments, carbohydrates may be added to the common reservoir (500). The carbohydrates are comprised of one or more from the group consisting of sugar, sucrose, molasses, and plant syrup. In embodiments, enzymes may be added to the common reservoir (500). The enzymes are comprised of one or more from the group consisting of amino acids, orotidine 5-phosphate decarboxylase, OMP decarboxylase, glucanase, beta-glucanase, cellulase, xylanase, HYGROZYME®, CANNAZYME®, MICROZYME®, and SENSIZYME®. In embodiments, vitamins may be added to the common reservoir (500). The vitamins are comprised of one or more from the group consisting of vitamin B, vitamin C, vitamin D, and vitamin E. In embodiments, hormones may be added to the common reservoir (500). The hormones are comprised of one or more from the group consisting of auxins, cytokinins gibberellins, abscic acid, brassinosteroids, salicylic acid, jasmonates, plant peptide hormones, polyamines, nitric oxide, strigolactones, and triacontanol. In embodiments, microorganisms may be added to the common reservoir (500). The microorganisms are comprised of one or more from the group consisting of bacteria, diazotroph bacteria, diazotroph archaea, *Azotobacter vinelandii*, *Clostridium pasteurianum*, fungi, arbuscular mycorrhizal fungi, *Glomus aggregatum, Glomus etunicatum, Glomus intraradices, Rhizophagus irregularis*, and *Glomus mosseae*.

In embodiments, an analyzer (AZ) may be incorporated into the farming superstructure system (FSS). In embodiments, the analyzer analyzes the contents within the common reservoir (500) of analyzes the mixture of water, macro-nutrients, micro-nutrients, and a pH adjustment solution to determine whether any additional treated water, evaporator condensate water, macro-nutrients, micro-nutrients, and a pH adjustment need to be added. A signal (XAZ) from the analyzer may be sent to a computer (COMP). From the signal (XAZ) obtained by the computer (COMP), the computer (COMP) may calculate and automate the introduction of water, macro-nutrients, micro-nutrients, and a pH adjustment solution introduced to the system. In embodiments, the analyzer (AZ) may include a mass spectrometer, Fourier transform infrared spectroscopy, infrared spectroscopy, potentiometric pH meter, pH meter, electrical conductivity meter, or liquid chromatography.

FIG. 1B

FIG. 1B depicts one non-limiting embodiment of a farming superstructure system (FSS) that includes a first growing assembly (100) having a first growing medium (GM1) and a second growing assembly (200) having a second growing medium (GM2).

In embodiments, the first and second growing mediums (GM1, GM2) can be comprised of one or more from the group consisting of rockwool, perlite, amorphous volcanic glass, vermiculite, clay, clay pellets, LECA (lightweight expanded clay aggregate), coco-coir, fibrous coconut husks, soil, dirt, peat, peat moss, sand, soil, compost, manure, fir bark, foam, gel, oasis cubes, lime, gypsum, and quartz.

In embodiments, the first and second growing mediums (GM1, GM2) can be comprised of one or more from the group consisting of: a PH adjuster, amorphous volcanic glass, aged forest materials, aged forest products, aged redwood tree bark, aged redwood tree chips, aged coniferous tree bark, aged coniferous tree chips, alfalfa meal, basalt, bat guano, coco chips, coco fiber, compost, composted chicken manure, composted manure, dolomite, feather meal, fish bone meal, fish scales, gypsum, kelp meal, lava rock, mafic extrusive igneous rock, perlite, protein, rockwool, sphagnum peat moss. In embodiments, psilocybin mushrooms are growing within the growing medium within the Farming Superstructure System (FSS).

In embodiments, a fungus may be added to the growing medium. In embodiment, the fungus may be mycorrhiza. In embodiments, the first and second growing mediums (GM1, GM2) can be comprised of a liquid and includes water. In embodiments, the first and second growing mediums (GM1, GM2) can be comprised of a liquid and includes water and includes a hydroponic system. In embodiments, the first and second growing mediums (GM1, GM2) comprises sphagnum peat moss, perlite, coco coir, calcitic limestone, dolomitic limestone, macronutrients, micronutrients, a wetting agent, and fungi and/or bacteria.

FIG. 1B differs from FIG. 1A since a fabric (104, 204) does not partition the growing assembly (100, 200) into an upper-section (105, 205) and a lower-section (106, 206). Instead, the *cannabis* plants (107, 207) are in contact with the growing medium (GM1, GM2), and the growing medium (GM1, GM2) partitions each growing assembly (100, 200) into an upper-section (105, 205) and a lower-section (106, 206). Liquid from with pump (P1) is introduced into the interior (101, 201) of each growing assembly (100, 200) via a liquid input (114, 214) where the liquid contacts the growing medium (GM1, GM2). In embodiments, liquid from the pump (P1) is the growing medium (GM1, GM2). In embodiments, liquid is transferred to the interior (101, 201) of each growing assembly (100, 200) via the liquid input (114, 214) on a periodic basis.

In embodiments, the computer (COMP) controls the lights (L1, L2). In embodiments, the lights (L1, L2) illuminate each growing assembly (100, 200) with an illumination on-off ratio ranging from between 0.5 to 11. The illumination on-off ratio is defined as the duration of time when the lights (L1, L2) are on and illuminate the *cannabis* (107, 207) in hours divided by the subsequent duration of time when the lights (L1, L2) are off and are not illuminating the *cannabis* (107, 207) in hours before the lights are turned on again.

In embodiments, the lights (L1, L2) are on and illuminate the *cannabis* for 18 hours and then are turned off for 6 hours. 18 divided by 6 is 3. In embodiments, an illumination on-off ratio of 3 is contemplated. In embodiments, the lights (L1, L2) are on and illuminate the *cannabis* for 20 hours and then are turned off for 4 hours. 20 divided by 4 is 5. In embodiments, an illumination on-off ratio of 5 is contemplated. In embodiments, the lights (L1, L2) are on and illuminate the *cannabis* for 24 hours and then are turned off for 0 hours. In embodiments, the lights (L1, L2) are on and illuminate the *cannabis* for 24 hours and then are turned off for 0 hours, wherein the lights include blue lights. 24 divided by 0 is 0. In embodiments, an illumination on-off ratio of 0 is contemplated. In embodiments, the lights (L1, L2) are on and illuminate the *cannabis* for 22 hours and then are turned off for 2 hours. 22 divided by 2 is 11. In embodiments, an illumination on-off ratio of 11 is contemplated. In embodiments, the lights (L1, L2) are on and illuminate the *cannabis* for 8 hours and then are turned off for 16 hours. 8 divided by 16 is 0.5. In embodiments, an illumination on-off ratio of 0.5 is contemplated. In embodiments, the lights (L1, L2) are on and illuminate the *cannabis* for 12 hours and then are turned off for 12 hours. 12 divided by 12 is 1. In embodiments, an illumination on-off ratio of 1 is contemplated. In embodiments, the is desirable to operate the growing assemblies at an illumination on-off ratio that is greater than 1 and less than 11. In embodiments, the is desirable to operate the growing assemblies at an illumination on-off ratio that is greater than 0.5 and equal to or less than 5. In embodiments, the is desirable to operate the growing assemblies at an illumination on-off ratio ranges from 0 to 5.

In embodiments, each growing assembly (100, 200) may include a container that contains a growing medium (GM1, GM2) sufficient to support the roots of the *cannabis* (107, 207). In embodiments, the growing assembly (100, 200) may be a container that contains a growing medium (GM1, GM2).

FIG. 1C

FIG. 1C depicts one non-limiting embodiment of a farming superstructure system (FSS) that includes a first growing assembly (100) having a first growing medium (GM1) and a second growing assembly (200) having a second growing medium (GM2) and the first growing assembly (100) and second growing assembly (200) are grown outdoors.

FIG. 1C shows a fabric (104, 204) that is placed upon the first growing medium (GM1) and the second growing medium (GM2). In embodiments, the fabric (104, 204) is landscape fabric that includes a textile material used to control weeds by inhibiting their exposure to sunlight. In embodiments, the fabric (104, 204) is placed around that *cannabis* plants (107, 207), covering areas where other growth is unwanted. The fabric itself can be made from plastic, rubber, synthetic or organic materials, sometimes from recycled sources. In embodiments, the fabric (104, 204) is woven needle punch polypropylene fabric. In embodiments, the fabric (104, 204) is black.

In embodiments, liquid is transferred to the first growing assembly (100) and second growing assembly (200) on a periodic basic through the plurality of liquid supply conduits (113, 213), the liquid supply header (300), at least one filter (F1, F2), and at least one valve valves (V1, V3, V4). In embodiments, the spacing (CAA, CAB, CAC, CAD) between each *cannabis* plant (107A, 107B, 107C, 207A, 207B, 207C) includes one or more plant spacing ranges selected from the group consisting of 1.00 foot to 1.25 feet, 1.25 feet to 1.50 feet, 1.50 feet to 1.75 feet, 1.75 feet to 2.00 feet, 2.00 feet to 2.25 feet, 2.25 feet to 2.50 feet, 2.50 feet to 2.75 feet, 2.75 feet to 3.00 feet, 3.00 feet to 3.25 feet, 3.25 feet to 3.50 feet, 3.50 feet to 3.75 feet, 3.75 feet to 4.00 feet, 4.00 feet to 4.25 feet, 4.25 feet to 4.50 feet, 4.50 feet to 4.75 feet, 4.75 feet to 5.00 feet, 5.00 feet to 5.25 feet, 5.25 feet to 5.50 feet, 5.50 feet to 5.75 feet, 5.75 feet to 6.00 feet, 6.00 feet to 6.25 feet, 6.25 feet to 6.50 feet, 6.50 feet to 6.75 feet, 6.75 feet to 7.00 feet, 7.00 feet to 7.25 feet, 7.25 feet to 7.50 feet, 7.50 feet to 7.75 feet, and 7.75 feet to 8.00 feet, 8 feet to 10 feet, 10 feet to 12 feet, 12 feet to 15 feet, 15 feet to 30 feet.

In embodiments, the cannabis plants may be grown with additional plants to improve soil health and decrease evaporation of water from the growing medium. The cannabis plants may be indoors within the interior of the enclosure or outdoors for additional plants to improve soil health and decrease evaporation of water from the growing medium. In embodiments, the additional plants include clover, wildflowers, flowers, shamrock, legumes, nitrogen fixing plants, beans, peas. In embodiments, the additional plants also promote insect health. In embodiments, the additional plants also promote pollination of cannabis plants and or the additional plants.

In embodiments, a growing solution is applied to the cannabis plants (107, 207) and/or the first and second growing mediums (GM1, GM2), the growing solution comprises calcium nitrate (CANO3), mono potassium phosphate (KH2PO4), magnesium sulphate (MGSO4), potassium nitrate (KNO3), and/or potassium sulphate (K2SO4), and is used to fertilize the plants during a vegetative and/or flowering stages of the life of the cannabis plants.

FIG. 1D

FIG. 1D depicts one non-limiting embodiment general arrangement of a farming superstructure system (FSS) top-view that includes a first growing assembly (100) and a second growing assembly (200) each configured to grow cannabis plants (107, 107A, 107B, 107C, 207, 207A, 207B, 207C).

FIG. 1D shows a top-down-view of one-acre plot of the farming superstructure system (FSS). In embodiments, the acre (DAA) has a length (DAB) and a width (DAC). The acre is a unit of land area used in the imperial and US customary systems. In embodiments, the acre is a square enclosing one acre is approximately 69.57 yards, or 208 feet 9 inches (63.61 meters) on a side. As a unit of measure, an acre has no prescribed shape; any area of 43,560 square feet is an acre. In embodiments, the acre (DAA) has a length (DAB) of 208 feet 9 inches. In embodiments, the acre (DAA) has a width (DAC) of 208 feet 9 inches.

In embodiments, the width of the fabric (104, 204) includes one or more fabric widths (DAD, DAE) selected from the group consisting of 1.00 foot to 1.25 feet, 1.25 feet to 1.50 feet, 1.50 feet to 1.75 feet, 1.75 feet to 2.00 feet, 2.00 feet to 2.25 feet, 2.25 feet to 2.50 feet, 2.50 feet to 2.75 feet, 2.75 feet to 3.00 feet, 3.00 feet to 3.25 feet, 3.25 feet to 3.50 feet, 3.50 feet to 3.75 feet, 3.75 feet to 4.00 feet, 4.00 feet to 4.25 feet, 4.25 feet to 4.50 feet, 4.50 feet to 4.75 feet, 4.75 feet to 5.00 feet, 5 feet to 6 feet, 6 feet to 8 feet, 8 feet to 10 feet, 10 feet to 12 feet, 12 feet to 14 feet, 14 feet to 16 feet, 16 feet to 20 feet.

In embodiments, the spacing (CAA, CAB, CAC, CAD) between each plant (107A, 107B, 107C, 207A, 207B, 207C) includes one or more plant spacing ranges selected from the group consisting of 1.00 foot to 1.25 feet, 1.25 feet to 1.50 feet, 1.50 feet to 1.75 feet, 1.75 feet to 2.00 feet, 2.00 feet to 2.25 feet, 2.25 feet to 2.50 feet, 2.50 feet to 2.75 feet, 2.75 feet to 3.00 feet, 3.00 feet to 3.25 feet, 3.25 feet to 3.50 feet, 3.50 feet to 3.75 feet, 3.75 feet to 4.00 feet, 4.00 feet to 4.25 feet, 4.25 feet to 4.50 feet, 4.50 feet to 4.75 feet, 4.75 feet to 5.00 feet, 5.00 feet to 5.25 feet, 5.25 feet to 5.50 feet, 5.50 feet to 5.75 feet, 5.75 feet to 6.00 feet, 6.00 feet to 6.25 feet, 6.25 feet to 6.50 feet, 6.50 feet to 6.75 feet, 6.75 feet to 7.00 feet, 7.00 feet to 7.25 feet, 7.25 feet to 7.50 feet, 7.50 feet to 7.75 feet, 7.75 feet to 8.00 feet, 8 feet to 9 feet, 9 feet to 10 feet, 10 feet to 11 feet, 11 feet to 12 feet, 12 feet to 13 feet, 13 feet to 14 feet, and 14 feet to 15 feet.

In embodiments, the spacing (CAA, CAB, CAC, CAD) between each growing assembly (100, 200) includes one or more growing assembly spacing ranges (DAF) selected from the group consisting of 2.00 feet to 3.00 feet, 3.00 feet to 3.25 feet, 3.25 feet to 3.50 feet, 3.50 feet to 3.75 feet, 3.75 feet to 4.00 feet, 4.00 feet to 4.25 feet, 4.25 feet to 4.50 feet, 4.50 feet to 4.75 feet, 4.75 feet to 5.00 feet, 5.00 feet to 5.25 feet, 5.25 feet to 5.50 feet, 5.50 feet to 5.75 feet, 5.75 feet to 6.00 feet, 6.00 feet to 6.25 feet, 6.25 feet to 6.50 feet, 6.50 feet to 6.75 feet, 6.75 feet to 7.00 feet, 7.00 feet to 7.25 feet, 7.25 feet to 7.50 feet, 7.50 feet to 7.75 feet, 7.75 feet to 8.00 feet, 8.00 feet to 8.25 feet, 8.25 feet to 8.50 feet, 8.50 feet to 8.75 feet, 8.75 feet to 9.00 feet, 9.00 feet to 9.25 feet, 9.25 feet to 9.50 feet, 9.50 feet to 9.75 feet, 9.75 feet to 10.00 feet, 10 feet to 11 feet, 11 feet to 12 feet, 12 feet to 13 feet, 13 feet to 14 feet, and 14 feet to 15 feet.

In embodiments, the amount of growing assemblies (102, 207) per acre include one or more ranges of rows of plants per acre selected from the group consisting of 70 rows of plants per acre to 64 rows of plants per acre, 64 rows of plants per acre to 60 rows of plants per acre, 60 rows of plants per acre to 56 rows of plants per acre, 56 rows of plants per acre to 52 rows of plants per acre, 52 rows of plants per acre to 49 rows of plants per acre, 49 rows of plants per acre to 46 rows of plants per acre, 46 rows of plants per acre to 44 rows of plants per acre, 44 rows of plants per acre to 42 rows of plants per acre, 42 rows of plants per acre to 40 rows of plants per acre, 40 rows of plants per acre to 38 rows of plants per acre, 38 rows of plants per acre to 36 rows of plants per acre, 36 rows of plants per acre to 35 rows of plants per acre, 35 rows of plants per acre to 33 rows of plants per acre, 33 rows of plants per acre to 32 rows of plants per acre, 32 rows of plants per acre to 31 rows of plants per acre, 31 rows of plants per acre to 30 rows of plants per acre, 30 rows of plants per acre to 29 rows of plants per acre, 29 rows of plants per acre to 28 rows of plants per acre, 28 rows of plants per acre to 27 rows of plants per acre, 27 rows of plants per acre to 26 rows of plants per acre, 26 rows of plants per acre to 25 rows of plants per acre, 25 rows of plants per acre to 25 rows of plants per acre, 25 rows of plants per acre to 24 rows of plants per acre, 24 rows of plants per acre to 23 rows of plants per acre, 23 rows of plants per acre to 23 rows of plants per acre, 23 rows of plants per acre to 22 rows of plants per acre, 22 rows of plants per acre to 21 rows of plants per acre, 21 rows of plants per acre to 20 rows of plants per acre, and at most 20 rows of plants per acre. FIG. 1D shows only 7 rows of plants per acre for simplicity but many more may be used as described and disclosed herein. For example, in embodiments, the cannabis plants (107, 107A, 107B, 107C, 207, 207A, 207B, 207C) are grown outdoors on 1 to 2 acres, 2 to 3 acres, 3 to 4 acres, 4 to 5 acres, 5 to 10 acres, 10 to 20 acres, 10 to 30 acres, 30 to 60 acres, 60 to 100 acres, 100 to 150 acres, 150 to 300 acres, 300 to 600 acres, 600 to 1000 acres, 1000 to 2000 acres, 2000 to 5000 acres.

FIG. 2

FIG. 2 depicts one non-limiting embodiment of a farming superstructure system (FSS) including a first vertically stacked system (1500) including a plurality of vertically stacked growing assemblies (100, 200) integrated with a first and second vertical support structure (VSS1, VSS2) wherein the first growing assembly (100) is supported by a first horizontal support structure (SS1) and a second growing assembly (200) is supported by a second horizontal support structure (SS2).

The first vertically stacked system (1500) shown in FIG. 2 has a base height (H0) located on a floor or support surface. The first vertically stacked system (1500) shown in FIG. 2 has a total height (HT). In embodiments, the total height (HT) may be dictated by the total height of the first and second vertical support structure (VSS1, VSS2). The common reservoir (500) may be positioned on the base height (H0) located on a floor or support surface. The common reservoir (500) has a liquid level (LIQ) that is located below the reservoir height (H500). The reservoir height (H500) is the height of the common reservoir (500).

The bottom (103) of the first growing assembly (100) is located at a first base height (H100A). The first base height (H100A) is the vertical location on the first vertically stacked system (1500) where the first growing assembly (100) is supported by a first horizontal support structure (SS1). The first partition height (H100B) is the vertical location on the first vertically stacked system (1500) of the partition (104) of the first growing assembly (100). The first growing assembly height (H100C) is the vertical location on the first vertically stacked system (1500) where the top (102) of the first growing assembly (100) is located.

The second base height (H200A) is the vertical location on the first vertically stacked system (1500) where the second growing assembly (200) is supported by a second horizontal support structure (SS2). The second partition height (H200B) is the vertical location on the first vertically stacked system (1500) of the partition (204) of the second growing assembly (200). The second growing assembly height (H100C) is the vertical location on the first vertically stacked system (1500) where the top (202) of the second growing assembly (200) is located.

The first vertically stacked system (1500) has a width (W1500). In embodiments, the width (W1500) is greater than the difference between the first growing assembly height (H100C) and the first base height (H100A). In embodiments, the width (W1500) is greater than the difference between the second growing assembly height (H200C) and the second base height (H200A).

FIG. 3

FIG. 3 depicts one non-limiting embodiment of a plurality of vertically stacked systems (1500, 1500) including a first vertically stacked system (1500) and a second vertically stacked system (1500), the first vertically stacked system (1500) as depicted in FIG. 2, also both vertically stacked systems (1500, 1500) are contained within an enclosure (ENC) having an interior (ENC1).

In embodiments, the interior (ENC1) of the enclosure (ENC) of the farming superstructure system (FSS) grows insects together with the *cannabis* plants. In embodiments, insects (INS) live within the interior (ENC1) of the enclosure (ENC) of the farming superstructure system (FSS) and the insects (INS) include one or more selected from the group consisting of Anthocoridae, minute pirate bugs, pirate bugs, flower bugs, the genus Orius, omnivorous bugs, carnivorous bugs, Orthoptera order of insects, grasshoppers, crickets, katydids, weta, lubber, acrida, locusts, mites, spider mites, predatory mites, *Neoseiulus fallacis*, genus of mites that are in the Phytoseiidae family, arthropods, hexapods, beetles, cicadas, beetles, nematodes, mealworms, bats, mammals of the order Chiroptera, yellow mealworm beetles, *Tenebrio Molitor, Tetranychus Urticae*, carnivorous arthropods, omnivorous arthropods, green lacewings, insects in the family Chrysopidae, insects in the order Neuroptera, mantidflies, antlions, Encarsia *Formosa*, whitefly parasites, ladybugs, spiders, orb-weaving spiders, arachnids, members of the spider family Araneidae, praying mantis, arachnids, eight-legged arthropods, and six-legged arthropods. In embodiments, the insects (INS) are stored in a refrigerator before they are introduced to the interior (ENC1) of the enclosure (ENC).

In embodiments, insects (INS) live within the interior (ENC1) of the enclosure (ENC) of the farming superstructure system (FSS) protect the plants (107, 207) by feeding on other insect eggs, insect larva, and other insects including living organisms which may or may not contain chitin not only including spider mites, rust mites, *thrips*, jumping plant lice, white fly, knats, gnats, aphids, and insects. In embodiments, the insects feed on *thrips* order Thysanoptera. In embodiments, the insects (INS) within the farming superstructure system (FSS) feed on *Tetranychus Urticae*. In embodiments, the insects (INS) within the farming superstructure system (FSS) feed on spider mites. In embodiments, the insects (INS) within the farming superstructure system (FSS) eat other insects that are found on the *cannabis* plants disclosed herein. In embodiments, the bats eat insects that are found on the *cannabis* plants disclosed herein.

The second vertically stacked system (1500) shown in FIG. 3 has a base height (H0) located on a floor or support surface. The second vertically stacked system (1500) shown in FIG. 3 has a total height (HT). In embodiments, the total height (HT) may be dictated by the total height of the first and second vertical support structure (VSS1, VSS2). The common reservoir (500) may be positioned on the base height (H0) located on a floor or support surface. The common reservoir (500) has a liquid level (LIQ) that is located below the reservoir height (H500). The reservoir height (H500) is the height of the common reservoir (500).

The bottom (103) of the first growing assembly (100) is located at a first base height (H100A). The first base height (H100A) is the vertical location on the second vertically stacked system (1500) where the first growing assembly (100) is supported by a first horizontal support structure (SS1). The first partition height (H100B) is the vertical location on the second vertically stacked system (1500) of the partition (104) of the first growing assembly (100). The first growing assembly height (H100C) is the vertical location on the second vertically stacked system (1500) where the top (102) of the first growing assembly (100) is located.

The second base height (H200A) is the vertical location on the second vertically stacked system (1500) where the second growing assembly (200) is supported by a second horizontal support structure (SS2). The second partition height (H200B) is the vertical location on the second vertically stacked system (1500) of the partition (204) of the second growing assembly (200). The second growing assembly height (H100C) is the vertical location on the second vertically stacked system (1500) where the top (202) of the second growing assembly (200) is located.

The second vertically stacked system (1500) has a width (W1500). In embodiments, the width (W1500) is greater than the difference between the first growing assembly height (H100C) and the first base height (H100A). In embodiments, the width (W1500) is greater than the difference between the second growing assembly height (H200) and the second base height (H200A).

A spacing (1500S) exists between the first vertically stacked system (1500) and the second vertically stacked system (1500). In embodiments, the spacing (1500S) between the first vertically stacked system (1500) and second vertically stacked system (1500) is less than the width (W1500, W1500) of either of the first vertically stacked system (1500) and second vertically stacked system (1500). In embodiments, the spacing (1500S) between the first vertically stacked system (1500) and second vertically stacked system (1500) is greater than the width (W1500, W1500) of either of the first vertically stacked system (1500) and second vertically stacked system (1500). In embodiments, the spacing (1500S) between the first vertically stacked system (1500) and second vertically stacked system (1500) ranges between 1 foot to 2 feet, 2 feet to 3 feet, 3 feet to 4 feet, 4 feet to 5 feet, 5 feet to 6 feet, 6 feet to 7 feet, 7 feet to 8 feet, 8 feet to 9 feet, 9 feet to 10 feet, 10 feet to 11 feet, 11 feet to 12 feet, 12 feet to 13 feet, 13 feet to 14 feet, 14 feet to 15 feet, 15 feet to 16 feet, 16 feet to 17 feet, 17 feet to 18 feet, 18 feet to 19 feet, or 19 feet to 20 feet.

FIG. 3 shows the first vertically stacked system (1500) and a second vertically stacked system (1500) contained within an enclosure (ENC) having an interior (ENC1). In embodiments, the enclosure may be an area that is sealed off with an artificial or natural barrier. In embodiments, the enclosure may be a building, or a structure with a roof and walls. In embodiments, the enclosure may be a shipping container conforming to the International Organization for Standardization (ISO) specifications. FIG. 3 shows the enclosure (ENC) having a first side wall (1W), second side wall (2W), top (5W), and a floor (1FL). For completeness, FIG. 4A shows the enclosure (ENC) of FIG. 3 with a third side wall (3W) and a fourth side wall (4W).

In embodiments, the top (5W), may be comprised of one or more from the group consisting of thatch, overlapping layers, shingles, ceramic tiles, membrane, fabric, plastic, metal, concrete, cement, solar panels, wood, a membrane, tar paper, shale, tile, asphalt, polycarbonate, plastic, cement, and composite materials.

In embodiments, one or more solar panels (SOLAR, SOLAR") may be positioned on top (5W) of the enclosure (ENC) may be used to provide electricity for the farming superstructure system (FSS). In embodiments, one or more solar panels (SOLAR-1W, SOLAR-2W, SOLAR-3W, SOLAR-4W) may be positioned on one or more walls (1W, 2W, 3W, 4W) of the enclosure (ENC) may be used to provide electricity for the farming superstructure system (FSS). In embodiments, one or more solar panels (SOLAR-X) not positioned on the top (5W) one or more walls (1W, 2W, 3W, 4W) of the enclosure (ENC) may be used to provide electricity for the farming superstructure system (FSS).

In embodiments, electricity from at least one of the solar panels (SOLAR, SOLAR, (SOLAR-1W, SOLAR-2W, SOLAR-3W, SOLAR-4W, SOLAR-X) may be used to provide electricity for one or more from the group consisting of: anything within the farming superstructure system (FSS) that requires a source of electricity, any motor within the farming superstructure system (FSS); any controller within the farming superstructure system (FSS); any conveyor within the farming superstructure system (FSS); a first plurality of lights (L1) in the first growing assembly (100); a first plurality of light emitting diodes (LED) in the first growing assembly (100); a second plurality of lights (L2) in the second growing assembly (200); a second plurality of light emitting diodes (LED) in the second growing assembly (200); blue LEDs (BLED) within the first growing assembly (100); red LEDS (RLED) within the first growing assembly (100); green LEDS (GLED) within the first growing assembly (100); blue LEDs (BLED) within the second growing assembly (200); red LEDS (RLED) within the second growing assembly (200); and green LEDS (GLED) within the second growing assembly (200).

In embodiment, blue lights are positioned within the first growing assembly (100); red lights are positioned within the first growing assembly (100); green lights are positioned within the first growing assembly (100); blue lights are positioned within the second growing assembly (200); red lights are positioned within the second growing assembly (200); and green lights are positioned within the second growing assembly (200).

In embodiments, the walls (1W, 2W, 3W, 4W) may be comprised of one or more from the group consisting of metal, concrete, cement, wood, plastic, brick, stone, composite materials, insulation, rockwool, mineral wool, fiberglass, clay, and ceramic. In embodiments, the top (5W) and walls (1W, 2W, 3W, 4W) may form one unitary structure such as a dome, semi-spherical shape, semi-cylindrical, or a greenhouse. In embodiments, the top (5W) and walls (1W, 2W, 3W, 4W) may be clear, translucent, transparent, or not clear.

In embodiments, a plurality of mirrors (MIRROR1, MIRROR2, MIRROR3, MIRROR4, MIRROR5, MIRROR6) are positioned within the interior (ENCL) of the enclosure (ENC). In embodiments, the plurality of mirrors (MIRROR1, MIRROR2, MIRROR3, MIRROR4, MIRROR5, MIRROR6) reflect light onto the plurality of plants (107, 207). In embodiments, the plurality of mirrors (MIRROR1, MIRROR2, MIRROR3, MIRROR4, MIRROR5, MIRROR6) reflect light onto the plurality of plants (107, 207) wherein the light is provided by the plurality of lights (L1, L2). In embodiments, the plurality of mirrors (MIRROR1, MIRROR2, MIRROR3, MIRROR4, MIRROR5, MIRROR6) reflect light onto the plurality of plants (107, 207) wherein the light is not provided by the plurality of lights (L1, L2). In embodiments, the plurality of mirrors (MIRROR1, MIRROR2, MIRROR3, MIRROR4, MIRROR5, MIRROR6) reflect light onto the plurality of plants (107, 207) wherein the light includes sunlight that is directed to the interior (ENCL) of the enclosure (ENC) by the plurality of mirrors (MIRROR1, MIRROR2, MIRROR3, MIRROR4, MIRROR5, MIRROR6).

In embodiments, the plurality of mirrors (MIRROR3, MIRROR4) includes a plurality of mirrors (MIRROR3, MIRROR4) located above the plants to reflect light vertically down onto the plants. In embodiments, the plurality of mirrors (MIRROR1, MIRROR2) includes a plurality of mirrors (MIRROR1, MIRROR2) located on the side of the plants to reflect light down horizontally the plants. In embodiments, the plurality of mirrors (MIRROR5, MIRROR6) includes a plurality of mirrors (MIRROR5, MIRROR6) located below the plants to reflect light vertically up onto the plants.

In embodiments, the present disclosure describes methods for applying a new, sustainable, method to grow *cannabis* to improve soil health and decrease evaporation of water from the growing medium the plants and the additional plants are grown in. The *cannabis* plants may be grown indoors or outdoors together with the additional plants to improve soil health and decrease evaporation of water from the growing medium, the additional plants include clover, wildflowers, flowers, shamrock, legumes, nitrogen fixing plants, beans, peas, and/or grass. The additional plants improve insect health for the insect pest management of the *cannabis* farm as well as promoting pollination of *cannabis* plants and/or the additional plants. There is a need to apply a surfactant to the *cannabis* plants and/or the additional plants as non-toxic fungicide, miticide, and/or insecticide in the form of an emulsion of water and the surfactant, or an emulsion of treated water and the surfactant, and may include neem oil, rosemary oil, jojoba oil, the bacterium *Bacillus subtilis*, the beneficial fungus *Ulocladium oudemansii*.

In embodiments, the present disclosure describes methods for applying *cannabis* plants with an insecticide soap (a surfactant) which are sodium or potassium fatty acids salts, produced from the hydrolysis of lipids in a chemical reaction called saponification. In embodiments, the insecticide soap includes an emulsion of water and soap (a surfactant). In embodiments, the insecticide soap includes an emulsion of treated water and soap. In embodiments, the insecticide soap may include neem oil, rosemary oil, jojoba oil, the bacterium *Bacillus subtilis*, the beneficial fungus *Ulocladium oudemansii*. In embodiments, the insecticide soap includes an emulsion, water, soap (a surfactant), and an oil, wherein the oil includes one or more oils selected from the group consisting of neem oil, almond oil, animal-based oils, apricot kernel oil, avocado oil, brazil nut oil, butter, canola oil, cashew oil, cocoa butter, coconut oil, cooking oil, corn oil, cottonseed oil, fish oil, grapeseed oil, hazelnut oil, hemp oil, insect oil, lard, lard oil, macadamia nut oil, mustard oil, olive oil, palm kernel oil, palm oil, peanut oil, rapeseed oil, rice oil, rice bran oil, safflower oil, semi-refined sesame oil, semi-refined sunflower oil, sesame oil, soybean oil, tallow of beef, tallow of mutton, vegetable oil, and walnut oil.

In embodiments, the insecticide soap may be applied to the *cannabis* plants to kill pests not only including mites, spider mites, rust mites, *thrips*, jumping plant lice, white fly, knats, gnats, aphids, and insects, *thrips, thrips* or order Thysanoptera, adult insects, larvae, prepupae, pupae, and nymph stages of pests. In embodiments, the insecticide soap may be applied to plants to kill pets indoors and/or outdoors. In embodiments, the insecticide soap may be applied to plants to kill pensts on plants including flowers, fruit, vegetables, house plants, large-scale agricultural crops. In embodiments, a surfactant may be applied to plants to kill pests on the additional plants including the clover, wildflowers, flowers, shamrock, legumes, nitrogen fixing plants, beans, peas, and/or grass.

In embodiments, the insecticide soap may be applied to plants to reduce mildew. In embodiments, the insecticide soap may be applied to the *cannabis* plants and/or the additional plants as a fungicide, miticide, and/or insecticide. In embodiments, the insecticide soap may be applied to plants as a fungicide to prevent growth of fungi and fungi spores. In embodiments, the insecticide soap is non-toxic to humans, animals, mammals, birds, reptiles, amphibians, and insects. In embodiments, the insecticide soap may be applied to plants to prevent growth of oomycetes. In embodiments, the insecticide soap may be applied to the *cannabis* plants and/or the additional plants to prevent growth of oomycetes, wherein the oomycetes includes a phylogenetic lineage of fungus-like eukaryotic microorganisms.

In embodiments, the FSS is a greenfield site or a brown field site. In embodiments, the greenfield site includes undeveloped land in a city, suburban, industrial, or rural area either which can be used for agriculture and/or landscape design. In embodiments, the brownfield site includes previously developed land that is not currently in use. In embodiments, the greenfield site will be developed to include a FSS, wherein the development of the site includes: earthworks (excavation/backfill), foundations, floor slab, site services, structural steel, building envelope, solar power installation, power installation, building fit-up (mechanical/electrical), and parking, landscaping.

FIG. 4A

FIG. 4A depicts one non-limiting embodiment of FIG. 3 wherein the enclosure (ENC) is provided with a temperature control unit (TCU) including an air heat exchanger (HXA) that is configured to provide a temperature and/or humidity-controlled air supply (Q3) to the interior (ENC1) of the enclosure (ENC) which contains a plurality of vertically stacked systems (1500, 1500).

The interior (ENC1) of the enclosure (ENC) has an enclosure temperature sensor (QT0) that is configured to output a signal (QXT0) to a computer (COMP). The interior (ENC1) of the enclosure (ENC) has an enclosure humidity sensor (QH0) that is configured to output a signal (QXH0) to a computer (COMP). An air input (Q1) is configured to permit an air supply (Q3) to be transferred to the interior (ENC1) of the enclosure (ENC) via an air supply entry conduit (Q2). An optional inlet distributor (Q4) may be positioned to be in fluid communication with the air supply entry conduit (Q2) to distribute the air supply (Q3) within the interior (ENC1) of enclosure (ENC). In embodiments, the air heater (HXA) provides a heated air supply (Q3) to the interior (ENC1) of the enclosure (ENC) via said air supply entry conduit (Q2) and said air input (Q1). In embodiments, the air heater (HXA) provides a cooled air supply (Q3) to the interior (ENC1) of the enclosure (ENC) via said air supply entry conduit (Q2) and said air input (Q1).

FIG. 4A shows a temperature control unit (TCU) including an air supply fan (Q12) and air heater (HXA) integrated with the interior (ENC1) of the enclosure (ENC). The air supply fan (Q12) is connected to the interior (ENC1) of the enclosure (ENC) via the air supply entry conduit (Q2). The air supply fan (Q12) is equipped with an air supply fan motor (Q13) and controller (Q14) is configured to input and output a signal (Q15) to the computer (COMP). An air heater (HXA) may be interposed in the air supply entry conduit (Q2) in between the air supply fan (Q12) and the enclosure (ENC). In embodiments, the air heater (HXA) may be interposed in the air supply entry conduit (Q2) in between the enclosure (ENC) and the air supply fan (Q12) and interposed on the air discharge exit conduit (Q23).

Water (Q16) in the form of liquid or vapor may be introduced to the air supply entry conduit (Q2) via a water transfer conduit (Q17). A water input valve (Q18), and a water flow sensor (Q19) may also be installed on the water transfer conduit (Q17). The water flow sensor (Q19) is configured to input a signal (Q20) to the computer (COMP).

The air supply (Q3) may be mixed with the water (Q16) in a water and gas mixing section (Q21) of the air supply entry conduit (Q2). FIG. 4A shows the water and gas mixing section (Q21) upstream of the air heater (HXA) but it may alternately also be placed downstream. The air heater (HXA) may be electric, operated by natural gas, combustion, solar energy, fuel cell, heat pipes, or it may be a heat transfer device that uses a working heat transfer medium, such as steam, or any other heat transfer medium known to persons having an ordinary skill in the art to which it pertains.

FIG. 4A shows the air heater (HXA) to have a heat transfer medium input (Q5) and a heat transfer medium output (Q6). In embodiments, heat transfer medium input (Q5) of the air heater (HXA) is equipped with a heat exchanger heat transfer medium inlet temperature (QT3) that is configured to input a signal (QXT3) to the computer (COMP). In embodiments, heat transfer medium output (Q6) of the air heater (HXA) is equipped with a heat exchanger heat transfer medium outlet temperature (QT4) that is configured to input a signal (QXT4) to the computer (COMP).

A first humidity sensor (Q8) is positioned on the discharge of the air supply fan (Q12) upstream of the water and gas mixing section (Q21). The first humidity sensor (Q8) is configured to input a signal (Q9) to the computer (COMP). A heat exchanger inlet gas temperature sensor (QT1) may be positioned on the discharge of the air supply fan (Q12) upstream of the air heater (HXA). The heat exchanger inlet gas temperature sensor (QT1) is configured to input a signal (QXT1) to the computer (COMP).

A second humidity sensor (Q10) is positioned on the discharge of the air heater (HXA) upstream of the air input (Q1) to the interior (ENC1) of the enclosure (ENC). The second humidity sensor (Q10) is configured to input a signal (Q11) to the computer (COMP). A heat exchanger outlet gas temperature sensor (QT2) is positioned on the discharge of the air heater (HXA) upstream of the air input (Q1) to the interior (ENC1) of the enclosure (ENC). The heat exchanger outlet gas temperature sensor (QT2) is configured to input a signal (QXT2) to the computer (COMP).

In embodiments, the air supply fan (Q12), air heater (HXA), and air supply (Q2), permit computer automation while integrated with the heat exchanger inlet gas temperature sensor (QT1), heat exchanger outlet gas temperature sensor (QT2), and enclosure temperature sensor (QT0), to operate under a wide variety of automated temperature operating conditions including varying the temperature range in the interior (ENC1) of the enclosure (ENC) from between 30 degrees to 90 degrees Fahrenheit. In embodiments, the interior (ENC1) of the enclosure (ENC) may be maintained within a temperature ranging from between 65 degrees Fahrenheit to 85 degrees Fahrenheit. In embodiments, the interior (ENC1) of the enclosure (ENC) may be maintained within a temperature ranging from between 60 degrees Fahrenheit to 90 degrees Fahrenheit.

In embodiments, the interior (ENC1) of the enclosure (ENC) may be maintained at a pre-determined temperature ranging from between one or more from the group selected from 60 degrees Fahrenheit to 61 degrees Fahrenheit, 61 degrees Fahrenheit to 62 degrees Fahrenheit, 62 degrees Fahrenheit to 63 degrees Fahrenheit, 63 degrees Fahrenheit to 64 degrees Fahrenheit, 64 degrees Fahrenheit to 65 degrees Fahrenheit, 65 degrees Fahrenheit to 66 degrees Fahrenheit, 66 degrees Fahrenheit to 67 degrees Fahrenheit, 67 degrees Fahrenheit to 68 degrees Fahrenheit, 68 degrees Fahrenheit to 69 degrees Fahrenheit, 69 degrees Fahrenheit to 70 degrees Fahrenheit, 70 degrees Fahrenheit to 71 degrees Fahrenheit, 71 degrees Fahrenheit to 72 degrees Fahrenheit, 72 degrees Fahrenheit to 73 degrees Fahrenheit, 73 degrees Fahrenheit to 74 degrees Fahrenheit, 74 degrees Fahrenheit to 75 degrees Fahrenheit, 75 degrees Fahrenheit to 76 degrees Fahrenheit, 76 degrees Fahrenheit to 77 degrees Fahrenheit, 77 degrees Fahrenheit to 78 degrees Fahrenheit, 78 degrees Fahrenheit to 79 degrees Fahrenheit, 79 degrees Fahrenheit to 80 degrees Fahrenheit, 80 degrees Fahrenheit to 81 degrees Fahrenheit, 81 degrees Fahrenheit to 82 degrees Fahrenheit, 82 degrees Fahrenheit to 83 degrees Fahrenheit, 83 degrees Fahrenheit to 84 degrees Fahrenheit, 84 degrees Fahrenheit to 85 degrees Fahrenheit, 85 degrees Fahrenheit to 86 degrees Fahrenheit, 86 degrees Fahrenheit to 87 degrees Fahrenheit, 87 degrees Fahrenheit to 88 degrees Fahrenheit, 88 degrees Fahrenheit to 89 degrees Fahrenheit, 89 degrees Fahrenheit to 90 degrees Fahrenheit, 90 degrees Fahrenheit to 91 degrees Fahrenheit, 91 degrees Fahrenheit to 92 degrees Fahrenheit, 92 degrees Fahrenheit to 93 degrees Fahrenheit, 93 degrees Fahrenheit to 94 degrees Fahrenheit, and 94 degrees Fahrenheit to 95 degrees Fahrenheit.

In embodiments, the air supply fan (Q12), air heater (HXA), air supply (Q2), and water (Q17) permit the computer automation while integrated with the first humidity sensor (Q8), second humidity sensor (Q10), and enclosure humidity sensor (QH0), to operate under a wide variety of automated operating humidity conditions including varying the humidity range in the growing assembly (100, 200) from between 5 percent humidity to 100 percent humidity. In embodiments, it is preferred to operate from between 25 percent humidity to 75 percent humidity. In embodiments, it is preferred to operate from between 40 percent humidity to 60 percent humidity. In embodiments, it is preferred to operate from between 44 percent humidity to 46 percent humidity. In embodiments, it is preferred to operate from between 36 percent humidity to 38 percent humidity, 38 percent humidity to 40 percent humidity, 40 percent humidity to 42 percent humidity, 42 percent humidity to 44 percent humidity, 44 percent humidity to 46 percent humidity, 46 percent humidity to 48 percent humidity, 48 percent humidity to 50 percent humidity, 50 percent humidity to 52 percent humidity, 52 percent humidity to 54 percent humidity, 54 percent humidity to 56 percent humidity, 56 percent humidity to 58 percent humidity, 58 percent humidity to 60 percent humidity, 60 percent humidity to 62 percent humidity, 62 percent humidity to 64 percent humidity, 64 percent humidity to 66 percent humidity, 66 percent humidity to 68 percent humidity, or 68 percent humidity to 70 percent humidity.

In embodiments, the air supply fan (Q12) accepts an air supply (Q3) from the interior (ENC1) of the enclosure (ENC) via an air discharge exit conduit (Q23). The air discharge exit conduit (Q23) is connected at one end to the enclosure (ENC) via an air output (Q22) and at another end to the air supply fan (Q12). An air filter (Q24) may be installed on the air discharge exit conduit (Q23) in between the enclosure (ENC) and the air supply fan (Q12) to remove particles prior to entering the air supply fan (Q12) for recycle back to the enclosure (ENC). In embodiments, the air filter (Q24) filters out particulates from the interior (ENC1) of the enclosure (ENC) and the air supply fan (Q12) recycles the filtered air back to the interior (ENC1) of the enclosure (ENC). The filtered air may be cooled or heated prior to being recycled to the interior (ENC1) of the enclosure (ENC). In embodiments, the air filter (Q24) is configured to remove odor from the interior of the enclosure. In embodiments, the air filter (Q24) is configured to remove odor from the interior of the enclosure by the process of adsorption and/or absorption.

In embodiments, the air heater (HXA) adds heat to the interior (ENC1) of the enclosure (ENC). In embodiments, the air heater (HXA) removes heat from the interior (ENC1) of the enclosure (ENC) and as a result may condense water from the air supply (Q3) provided from the from the interior (ENC1) of the enclosure (ENC). In embodiments, where the air heater (HXA) removes heat from the interior (ENC1) of the enclosure (ENC) water is collected in the form of condensate (Q25). In embodiments, the condensate (Q25) may in turn be provided to the enclosure (ENC) via an enclosure condensate input (Q26) and a condensate conduit (Q27). The condensate (Q25) provided to the enclosure (ENC) via an enclosure condensate input (Q26) may be provided to at least one common reservoir (500, 500) via a common tank condensate input (Q28). In embodiments, the condensate (Q25) may contain undesirable compounds (especially viruses and/or bacteria) and in turn may be provided to the input to the first water treatment unit (A1) as shown in FIG. 10 as a first undesirable compounds-laden condensate (Q29).

FIG. 4B

FIG. 4B depicts one non-limiting embodiment of FIG. 1B and FIG. 4A wherein the enclosure (ENC) is provided with a temperature control unit (TCU) including an air heat exchanger (HXA) that is configured to provide a temperature and/or humidity-controlled air supply (Q3) to the interior (ENC1) of the enclosure (ENC) which contains a plurality of growing assemblies (100, 200).

In embodiments, a fire protection system (FPS) is contained within the interior (ENC1) of the enclosure (ENC). In embodiments, the fire protection system (FPS) includes a sprinkler system (SS-1). In embodiments, the fire protection system (FPS) includes a dry chemical fire suppression system (SS-1) configured to use of a dry chemical powder to extinguish a fire within the interior of the enclosure. In embodiments, the dry chemical powder used within the dry chemical fire suppression system (SS-1) includes monoammonium phosphate, sodium bicarbonate, and/or potassium bicarbonate. In embodiments, the fire protection system (FPS) includes a dry chemical fire suppression system and/or a sprinkler system (SS-1) or combinations thereof.

In embodiments, the sprinkler system (SS-1) includes a water distribution header (WDH) connected to a plurality of spray nozzles (SN-1, SN-2, SN-3). A source of pressurized water (WS-1) is provided to the water distribution header (WDH). In embodiments, at least a portion of the water distribution header (WDH) is a pipe that is made of metal or polyvinyl chloride. In embodiments, at least a portion of the water distribution header (WDH) has a diameter than includes one or more from the group consisting of: 1 inch to 2 inches, 2 inches to 3 inches, 3 inches to 4 inches, 4 inches to 5 inches, 5 inches to 6 inches, 6 inches to 8 inches, and 8 inches to 10 inches.

In embodiments, the dry chemical fire suppression system (SS-1) includes a dry chemical powder distribution header (WDH) connected to a plurality of spray nozzles (SN-1, SN-2, SN-3). A source of a dry chemical powder (WS-1) is provided to the distribution header (WDH). In embodiments, at least a portion of the distribution header (WDH) is a pipe that is made of metal or polyvinyl chloride. In embodiments, at least a portion of the distribution header (WDH) has a diameter than includes one or more from the group consisting of: 1 inch to 2 inches, 2 inches to 3 inches, 3 inches to 4 inches, 4 inches to 5 inches, 5 inches to 6 inches, 6 inches to 8 inches, and 8 inches to 10 inches.

In embodiments, each of the plurality of spray nozzles (SN-1, SN-2, SN-3) is equipped with an automatic fire sprinkler switch (AFSS-1, AFSS-2, AFSS-3) that permits pressurized water and/or a includes a dry chemical powder (WS-1) to pass through the plurality of spray nozzles (SN-1, SN-2, SN-3) when there is a fire detected within the interior (ENC1) of the enclosure (ENC). In embodiments, the pressure drop of the pressurized water and/or the includes a dry chemical powder (WS-1) that passes through the plurality of spray nozzles (SN-1, SN-2, SN-3) ranges from: 15 PSI to 25 PSI, 25 PSI to 35 PSI, 35 PSI to 45 PSI, 45 PSI to 55 PSI, 55 PSI to 65 PSI, 65 PSI to 75 PSI, 75 PSI to 85 PSI, 85 PSI to 95 PSI, 95 PSI to 100 PSI, 100 PSI to 150 PSI, and 150 PSI to 300 PSI. In embodiments, the fire protection system (FPS) includes a smoke detector (SD-1) that is configured to output a signal (SD-1X) to a computer (COMP) in the event of a fire within the interior (ENC1) of the enclosure (ENC).

In embodiments, the fire protection system (FPS) is provided with a pump (FPS-P) that is configured to provide a source of pressurized water and/or a includes a dry chemical powder (WS-1) is provided to the distribution header (WDH). The pump (FPS-P) is configured to accept and pressurize a source of water (WS-1) to form the source of pressurized water (WS-1) that is provided to the water distribution header (WDH) and to the plurality of spray nozzles (SN-1, SN-2, SN-3). In embodiments, the pump (FPS-P) is comprised of one of more from the group consisting of a centrifugal pump or a positive displacement pump. In embodiments, the pump is not needed to provide a source of pressurized water (WS-1) that is provided to the water distribution header (WDH) and to the plurality of spray nozzles (SN-1, SN-2, SN-3). In embodiments, a pump discharge pressure sensor (PDPS) and a pump suction pressure (PSPS) are equipped to measure the pressure at the pump discharge and pump suction, respectively.

In embodiments, a fire protection system (FPS) is contained within the interior (ENC1) of the enclosure (ENC). In embodiments, *cannabis* heating, trimming, grinding, volatiles separation, cooling, filtering, evaporating, purification, distillation, emulsion mixing, softgel production, etc. (and of FIGS. 1-18F) are all positioned within the interior (ENC1) of the enclosure (ENC) (or different regions within) for the fire protection system (FPS) to protect against.

In embodiments, the interior (ENC1) of the enclosure (ENC) is a Class I, Division 1 and 2 classification. In embodiments, the interior (ENC1) of the enclosure (ENC) is a Class I location because of the consist of areas where gases, vapors or liquids may exist that have the potential to become flammable or ignitable, such as first and/or second solvents (SOLV1, SOLV2). In embodiments, the interior (ENC1) of the enclosure (ENC) is two different divisions in Class I, Division 1 and Division 2, along with three Zones; Zone 0, 1 & 2. Division 1 is a subset of Class I and is classified as an area where the explosive or flammable gases, vapors or liquids mentioned above can exist under normal, everyday operating conditions of cannabinoid extraction and evaporation portions of the FSS. Division 2 is also a subset of Class I and is classified as an area where the explosive or flammable gases, vapors or liquids mentioned above are not likely to exist during regular operation of the cannabinoid extraction and evaporation portions of the FSS.

In embodiments, the interior (ENC1) of the enclosure (ENC) is deemed a Zone 0 classification due to the presence of explosive or flammable gases, vapors or liquids for long periods of time during operating conditions or during a large portion of the operating conditions. In embodiments, the interior (ENC1) of the enclosure (ENC) is deemed a Zone 1 classification is described as the presence of explosive or flammable gases, vapors or liquids (e.g.—first and/or second solvents (SOLV1, SOLV2) for some of the time during normal operating conditions of at least the of the cannabinoid extraction and evaporation portions of the FSS. In embodiments, the interior (ENC1) of the enclosure (ENC) is deemed a Zone 2 classification is described as there not being a likelihood of explosive or flammable gases, vapors or liquids (e.g.—first and/or second solvents (SOLV1, SOLV2)) present during normal operating conditions. Since the interior (ENC1) of the enclosure (ENC) since it is a Class I, Division 1 and 2 classification, explosion-proof equipment, valves, controllers, pumps, heaters, chiller, filters, vacuum systems, evaporation equipment, grinders, humidity and temperature control systems, flow meters, mixers, sensors, and all other assets described in this specification.

In embodiments, the fire protection system (FPS) includes one or more fire protection systems selected from the group consisting of a dry chemical fire suppression system, a dry pipe system, a foam fire suppression system, a gaseous fire suppression system, or a wet fire sprinkler system. In embodiments, the fire protection system (FPS) may include more than one fire protection system. In embodiments, the fire protection system (FPS) includes two or more fire protection systems selected from the group consisting of a dry chemical fire suppression system, a dry pipe system, a foam fire suppression system, a gaseous fire suppression system, or a wet fire sprinkler system. In embodiments, the dry chemical fire suppression system includes pressured dry chemicals. In embodiments, the dry pipe system includes automatic sprinklers attached to a piping system containing air or nitrogen under pressure. In embodiments, the foam fire suppression systems includes the use of a foam extinguishing systems are effective for rapidly controlling and extinguishing flammable liquid fires. In embodiments, the gaseous fire suppression systems includes the use of carbon dioxide to as a fire-extinguishing agent. In embodiments, the wet fire sprinkler systems includes automatic sprinklers attached to a piping system connected to a water supply.
FIG. 5A FIG. 5A depicts one non-limiting embodiment of FIG. 4A wherein the temperature control unit (TCU) of FIG. 4A is contained within the interior (ENC1) of the enclosure (ENC) and coupled with a humidity control unit (HCU).

FIG. 5A shows the temperature control unit (TCU) of FIG. 4A but contained within the interior (ENC1) of the enclosure (ENC). FIG. 5A also shows a non-limiting embodiment of a humidity control unit (HCU) positioned within the interior (ENC1) of the enclosure (ENC). A portion of the humidity control unit (HCU) may be positioned exterior to the enclosure (ENC) and not positioned within the interior (ENC1). In embodiments, the humidity control unit (HCU) may also be considered a temperature control unit (TCU). In embodiments, the humidity control unit (HCU) may also be considered a temperature control unit (TCU) since it may be used to regulate the temperature within the interior (ENC1) an enclosure (ENC) wherein a plurality of growing assemblies (100, 200) are positioned within the interior (ENC1) of the enclosure (ENC).

In embodiments, the humidity control unit (HCU) may include a compressor (Q30), a condenser (Q32), a metering device (Q33), an evaporator (Q34), and a fan (Q35). The fan (Q35) may be equipped with a motor (Q36) and a controller (Q37) that is configured to input or output a signal (Q38) to a computer (COMP).

The compressor (Q31) is connected to the condenser (Q32), the condenser (Q32) is connected to the metering device (Q33), the metering device (Q33) is connected to an evaporator (Q34), and the evaporator (Q34) is connected to the compressor (Q31) to form a closed-loop refrigeration circuit configured to contain a refrigerant (Q31). The metering device (Q33) includes one or more from the group consisting of a restriction, orifice, valve, tube, capillary, and capillary tube. The refrigerant (Q31) is conveyed from the compressor to the condenser, from the condenser to the evaporator through the metering device, and from the evaporator to the compressor. The evaporator (Q34) is positioned within the interior (ENC1) of the enclosure (ENC) and is configured to evaporate refrigerant (Q31) within the evaporator (Q34) by removing heat from the interior (ENC1) of the enclosure (ENC). In embodiments, the evaporator (Q34) is contained within the interior (ENC1) of the enclosure (ENC). In embodiments, the condenser (Q32) is not contained within the interior (ENC1) of the enclosure (ENC). The fan (Q35) is configured to blow air from within the interior (ENC1) of the enclosure (ENC) over at least a portion of the humidity control unit (HCU).

The humidity control unit (HCU) is configured to selectively operate the system in a plurality of modes of operation, the modes of operation including at least:
(1) a first mode of operation in which compression of a refrigerant (Q31) takes place within the compressor (Q30), and the refrigerant (Q31) leaves the compressor (Q30) as a superheated vapor at a temperature greater than the condensation temperature of the refrigerant (Q31);
(2) a second mode of operation in which condensation of refrigerant (Q31) takes place within the condenser (Q32), heat is rejected and the refrigerant (Q31) condenses from a superheated vapor into a liquid, and the liquid is cooled to a temperature below the boiling temperature of the refrigerant (Q31); and
(3) a third mode of operation in which evaporation of the refrigerant (Q31) takes place, and the liquid phase refrigerant (Q31) boils in the evaporator (Q34) to form a vapor or a superheated vapor while absorbing heat from the interior (ENC1) of the enclosure (ENC).

The evaporator (Q34) is configured to evaporate the refrigerant (Q31) to absorb heat from the interior (ENC1) of an enclosure (ENC). As a result, the evaporator (Q34) may condense water from the interior (ENC1) of the enclosure (ENC). In embodiments, the water condensed by the evaporator (Q34) contains bacteria. In embodiments, the evaporator (Q34) condenses water vapor from the interior (ENC1) of an enclosure (ENC) and forms condensate (Q39). In embodiments, the condensate (Q39) may contain undesirable compounds (especially viruses and/or bacteria) and in turn may be provided to the input to the first water treatment unit (A1) as shown in FIG. 10 as a second undesirable compounds-laden condensate (Q40).
FIG. 5B FIG. 5B depicts one non-limiting embodiment of FIG. 4B and FIG. 5A wherein the temperature control unit (TCU) of FIG. 4B is contained within the interior (ENC1) of the enclosure (ENC) and coupled with a humidity control unit (HCU).
FIG. 5C FIG. 5C shows one non-limiting embodiment where the compressor (Q30) within the humidity control unit (HCU) is that of a thermal compressor (Q30) that accepts a source of steam. The thermal compressor (Q30) accepts a steam supply (LDS) that is provided from FIG. 17F. Also shown is in the thermal compressor (Q30) discharging condensate (LJC) to the condensate tank (LAP) shown on FIG. 17F.
FIG. 5D FIG. 5D shows one non-limiting embodiment where the compressor (Q30) within the humidity control unit (HCU) is that of a thermal compressor (Q30) that accepts a source of steam. The thermal compressor (Q30) accepts a tenth steam supply (LDS) that is provided from FIG. 17F. Also shown is in the thermal compressor (Q30) discharging a tenth condensate (LJC) to the condensate tank (LAP) shown on FIG. 17F.

In embodiments, the thermal compressor (Q30) includes a generator (Q50) and an absorber (Q60). The first steam supply (LDS), from FIG. 17F, is transferred from the steam distribution header (LCJ) and into the generator (Q50) of the thermal compressor (Q30). In embodiments, a pump (Q45) connects the generator (Q50) to the absorber (Q60). Also, in embodiments, a metering device (Q55) is positioned in between the absorber (Q60) to the generator (Q50). The metering device (Q55) may include one or more from the group consisting of a restriction, orifice, valve, tube, capillary, and capillary tube.

Vapor-phase refrigerant is transferred from the evaporator (Q34) to the absorber (Q60). The refrigerant transferred from the evaporator (Q34) to the absorber (Q60) is then absorbed by an absorbent within the absorber (Q60). In embodiments, the refrigerant includes water or ammonia. In embodiments, the absorbent includes lithium bromine or water.

A mixture of refrigerant and absorbent is transferred from the absorber (Q60) to the generator (Q50) via the pump (Q45). Heat in the form of steam (LDS) is transferred to the mixture of refrigerant and absorbent within the generator (Q50) to vaporize the refrigerant. The vapor-phase, or superheated vapor, refrigerant is transferred from the generator (Q50) to the condenser (Q32). The absorbent is transferred back to the absorber (Q60) from the generator (Q50) through the metering device (Q55). In embodiments, the absorbent that is transferred through the metering device (Q55) takes a pressure drop. In embodiments, the generator (Q50) operates at a pressure that is greater than the pressure within the absorber (Q60).

In embodiments, the thermal compressor (Q30) may also be called an absorption chiller. In embodiments, the thermal compressor may have one stage. In embodiments, the thermal compressor may have two stages. In embodiments, electricity is required to power the pump (Q54). In embodiments, the electricity that is required to power the pump (Q54) comes from the generator (LFH) shown in FIG. 17F.

FIG. 5E

FIG. 5E elaborates upon FIG. 5D and shows one non-limiting embodiment where the compressor (Q30) within the humidity control unit (HCU) is that of a thermal compressor (Q30) that accepts a source of heat, such as flue gas (FG1).

FIG. 6

FIG. 6 shows a front view of one embodiment of a plant growing module (PGM) provided inside of a shipping container conforming to the International Organization for Standardization (ISO) specifications.

FIG. 6 shows a portion of the farming superstructure system (FSS) including a front view of one embodiment of a plant growing module (PGM) provided inside of a shipping container conforming to the International Organization for Standardization (ISO) specifications.

The front view shows four growing assemblies (100, 100, 200, 200) including two first growing assemblies (100, 100) and two second growing assembly (200, 200) contained within an interior (ENC1) of an enclosure (ENC). FIG. 6 shows the two first growing assemblies (100, 100) and two second growing assembly (200, 200) each equipped with drain ports (110, 110) and drain conduits (111, 111) for draining liquid from each growing assembly (100, 100, 200, 200) into a common reservoir (500) via a common drain conduit (517) and drain input (518).

FIG. 6 shows one pump (P1) pulling liquid from one common reservoir (500) and transferring a pressurized liquid through a filter (F1A) into a plurality of liquid supply headers (300, 300) which are in turn then provided to a plurality of first liquid supply conduits (113, 113) and a plurality of second liquid supply conduit (213, 213). Four liquid supply conduits (113, 113, 213, 213) are provided from two liquid supply headers (300, 300) which is provided with pressurized water through one filter (F1A) by one pump (P1) pulling liquid from one common reservoir (500).

The common reservoir (500) of FIG. 6 is provided with a pressurized liquid (29) through a pressurized liquid transfer conduit (28) that enters the common reservoir (500) via a first water inlet (03). FIGS. 9 and 10 describe a liquid distribution module (LDM) that provides the pressurized liquid (29) and transfers it to the plant growing module (PGM) via a pressurized liquid transfer conduit (28).

As depicted in FIG. 6 and FIG. 7, one common reservoir (500) is provided for a first vertically stacked system (1500) and a second vertically stacked system (1500) that contain a total of two first growing assemblies (100, 100) and two second growing assembly (200, 200).

The enclosure (ENC) of FIG. 6 is shown to have a first side wall (1W), second side wall (2W), top (5W), and A floor (1FL). For completeness, the top view of the enclosure (ENC) of FIG. 6 is shown in FIG. 7 and is shown to have a first side wall (1W), second side wall (2W), third side wall (3W), and fourth side wall (4W).

FIG. 7

FIG. 7 shows a top view of one embodiment of a plant growing module (PGM) provided inside of a shipping container conforming to the International Organization for Standardization (ISO) specifications.

The enclosure (ENC) of FIG. 7 is shown to have a low voltage shut-off switch (LVV-1), a humidity control unit (HCU) (as described in FIG. 5), and a temperature control unit (TCU) (as described in FIGS. 4A & 4B). FIG. 7 also shows the first vertically stacked system (1500) and second vertically stacked system (1500) with one common reservoir (500). FIG. 7 also shows a third vertically stacked system (1500) and a fourth vertically stacked system (1500) each equipped with their own source of pressurized liquid (29C, 29D) provided by a plurality of pressurized liquid transfer conduits (28C, 28D) as described in detail in FIGS. 9 and 10.

FIG. 8

FIG. 8 shows a first side view of one embodiment of a plant growing module (PGM). The enclosure (ENC) of FIG. 8 is shown to have a humidity control unit (HCU) (as described in FIG. and a temperature control unit (TCU) (as described in FIGS. 4A& 4B). FIG. 8 shows a first vertically stacked system (1500) on the left-hand-side and a second vertically stacked system (1500) on the right-hand-side.

The first vertically stacked system (1500) is shown to have a second growing assembly (200) located above a first growing assembly (100). The second growing assembly (200) has a drain port (210) and a drain conduit (211) that directly drains into a common reservoir (500) located below both growing assemblies (100, 200). The drain conduit (211) from the second growing assembly (200) is secured to the second vertical support structure (VSS2) via a support connection (211X). In embodiments, the drain conduit (211) from the second growing assembly (200) may be secured to the first vertical support structure (VSS1), or alternately to the first horizontal support structure (SS1), or second horizontal support structure (SS2)

The first growing assembly (100) has a drain port (110) and a drain conduit (111) that directly drains into a common reservoir (500) located below both growing assemblies (100, 200). The drain conduit (111) from the first growing assembly (200) is secured to the second vertical support structure (VSS2) via a support connection (111X). In embodiments, the drain conduit (111) from the first growing assembly (100) may be secured to the first vertical support structure (VSS1), or alternately to the first horizontal support structure (SS1).

The second vertically stacked system (1500) is shown to have a second growing assembly (200) located above a first growing assembly (100). The second growing assembly (200) is configured to receive liquid from the pump (P1) via a second liquid supply conduit (213) and a liquid input (214). The second liquid supply conduit (213) for the second growing assembly (200) is secured to the second vertical support structure (VSS2) via a support connection (213X). In embodiments, the second liquid supply conduit (213) for the second growing assembly (200) may be secured to the first vertical support structure (VSS1), or alternately to the first horizontal support structure (SS1), or second horizontal support structure (SS2).

The first growing assembly (100) is configured to receive liquid from the pump (P1) via a first liquid supply conduit (113) and a liquid input (114). The first liquid supply conduit (113) for the first growing assembly (100) is secured to the second vertical support structure (VSS2) via a support connection (113X). In embodiments, the first liquid supply conduit (113) for the first growing assembly (100) may be secured to the first vertical support structure (VSS1), or alternately to the first horizontal support structure (SS1). In embodiments, the spacing (1500S) between the vertically stacked systems (1500, 1500) in FIG. 8 ranges from 1 foot to 1.5 feet, 1.5 feet to 2 feet, 2 feet to 3 feet, 3 feet to 4 feet, 4 feet to 5 feet, 5 feet to 6 feet, 6 feet to 7 feet, 7 feet to 8 feet, 8 feet to 10 feet, 10 feet to 12 feet, 12 feet to 15 feet, 15 feet to 20 feet In embodiments, the spacing (1500S) between the vertically stacked systems (1500, 1500) in FIG. 8 ranges from 2.5 feet to 4.5 feet.

FIG. 9

FIG. 9 shows a front view of one embodiment of a liquid distribution module (LDM) provided inside of a shipping container conforming to the International Organization for Standardization (ISO) specifications and that is configured to provide a source of liquid to a plurality of plant growing modules (PGM).

FIG. 9 shows one non-limiting embodiment of a liquid distribution module (LDM) to provide a source of liquid to a plurality of plant growing modules (PGM). The liquid distribution module (LDM) of FIGS. 9 and 10 include a first water treatment unit (A1), a second water treatment unit (A2), and a third water treatment unit (A3), that provide a third contaminant depleted water (12) to the interior (19) of a solution tank (18).

The solution tank (18) mixes a water supply (01) with macro-nutrients (601), micro-nutrients (701), and/or a pH adjustment solution (801) to form a mixed solution prior to pumping the mixed solution to at least one common reservoir (500) of at least one plant growing modules (PGM). FIG. 9 depicts the first water treatment unit (A1) to include a cation, a second water treatment unit (A2) to include an anion, and a third water treatment unit (A3) to include a membrane.

A first water pressure sensor (13) is positioned on the water input conduit (14) that is introduced to the first input (04) to the first water treatment unit (A1). In embodiments, a filter (y1), activated carbon (y2), and adsorbent (y3), are positioned on the water input conduit (14) prior to introducing the water supply (01) to the first water treatment unit (A1). The water supply (01) may be considered a contaminant-laden water (15) that includes positively charged ions, negatively charged ions, and undesirable compounds. A first contaminant depleted water (06) is discharged by the first water treatment unit (A1) by a first output (05). The first contaminant depleted water (06) may be a positively charged ion depleted water (06A). The first contaminant depleted water (06) is then transferred to the second water treatment unit (A2) via a second input (07). A second contaminant depleted water (09) is discharged by the second water treatment unit (A2) by a second output (08). The second contaminant depleted water (09) may be a negatively charged ion depleted water (09A). The second contaminant depleted water (09) is then transferred to the third water treatment unit (A3) via a third input (10). A third contaminant depleted water (12) is discharged by the third water treatment unit (A3) by a third output (11). The third contaminant depleted water (12) may be an undesirable compounds depleted water (12A). The third contaminant depleted water (12) is then transferred to the interior (19) of a solution tank (18) via a water supply conduit (21) and water input (20).

Within the interior (19) of the solution tank (18), the third contaminant depleted water (12) may be mixed with macro-nutrients (601) from a macro-nutrient supply tank (600), micro-nutrients (701) from a micro-nutrient supply tank (700), and/or a pH adjustment solution (801) from a micro-nutrient supply tank (700). In embodiments, a cation (y4), an anion (y5), and a polishing unit (y6), are positioned on the water supply conduit (21) in between the third water treatment unit (A3) and the water input (20) of the solution tank (18). The polishing unit (y6) may be any type of conceivable device to improve the water quality such as an ultraviolet unit, ozone unit, microwave unit, a distillation system or the like.

In embodiments, water supply valve (16) is positioned on the water supply conduit (21) in between the third water treatment unit (A3) and the water input (20) of the solution tank (18). The water supply valve (16) is equipped with a controller (17) that inputs or outputs a signal from a computer (COMP). In embodiments, the solution tank (18) is equipped with a high-level sensor (25) and a low-level sensor (26). The high-level sensor (25) is used for detecting a high level and the low-level sensor (26) is used for detecting a low level. The high-level sensor (25) is configured to output a signal to the computer (COMP) when the high-level sensor (25) is triggered by a high level of liquid within the solution tank (18). The low-level sensor (26) is configured to output a signal to the computer (COMP) when the low-level sensor (26) is triggered by a low level of liquid within the solution tank (18). In embodiments, when the low-level sensor (26) sends a signal to the computer (COMP), the water supply valve (16) on the water supply conduit (21) is opened and introduces water into the solution tank (18) until the high-level sensor (25) is triggered thus sending a signal to the computer (COMP) to close the water supply valve (16). This level control loop including the high-level sensor (25) for detecting a high level and a low-level sensor (26) for detecting a lower level may be coupled to the operation of the water supply valve (16) for introducing a water supply (01) through a first water treatment unit (A1), a second water treatment unit (A2), and a third water treatment unit (A3), to provide a third contaminant depleted water (12) to the interior (19) of a solution tank (18). The liquid distribution module (LDM) is equipped with a low voltage shut-off switch (LVV-2).

The interior (19) of the solution tank (18) is equipped with an oxygen emitter (35) for oxygenating the water within. The oxygen emitter (35) is connected to the interior (19) of the solution tank (18) via an oxygen emitter connection (36) which protrudes the solution tank (18). The solution tank (18) may be placed on a load cell (40) for measuring the mass of the tank. The solution tank (18) may be equipped with a mixer (38) for mixing water with macro-nutrients (601), micro-nutrients (701), and/or a pH adjustment solution (801). The mixer (38) may be of an auger or blade type that is equipped with a motor (39).

The solution tank (18) has a water output (22) that is connected to a water discharge conduit (23). The water discharge conduit (23) is connected at one end to the water output (22) of the solution tank (18) and at another end to a water supply pump (24). The water supply pump (24) provides a source of pressurized liquid (29) via a pressurized liquid transfer conduit (28).

A second water pressure sensor (27) is positioned on the pressurized liquid transfer conduit (28). A flow sensor (30) and a water quality sensor (33) may be positioned on the pressurized liquid transfer conduit (28). The water quality sensor (33) can measure electrical conductivity or resistivity. The pressurized liquid transfer conduit (28) can be split into a plurality of streams for providing to a plurality of plant growing modules (PGM) having a plurality of common reservoirs (500, 500, 500, 500).

The pressurized liquid transfer conduit (28) can be split into a plurality of streams including a first pressurized liquid transfer conduit (28A) for sending to a common tank (500) for the first vertically stacked system (1500) and second vertically stacked system (1500) of FIG. 6, a second pressurized liquid transfer conduit (28B) as a back-up water source to the common tank (500) of FIG. 6, a third pressurized liquid transfer conduit (28C) for the common tank (500) for the third vertically stacked system (1500) of FIG. 6, and a fourth pressurized liquid transfer conduit (28D) for the common tank (500) for the fourth vertically stacked system (1500) of FIG. 6.

FIG. 10

FIG. 10 shows a top view of one embodiment of a liquid distribution module (LDM) provided inside of a shipping container conforming to the International Organization for Standardization (ISO) specifications and that is configured to provide a source of liquid to a plurality of plant growing modules (PGM).

FIG. 11

FIG. 11 shows a first side view of one embodiment of a liquid distribution module (LDM).

FIG. 12

FIG. 12 shows one non-limiting embodiment of a fabric (104) used in a growing assembly (100), the fabric (104) having a multi-point temperature sensor (MPT100) connected thereto for measuring temperatures at various lengths along the sensor's length.

FIGS. 12 and 13 disclose a fabric (104) that includes a multi-point temperature sensor (MPT100). The fabric (104) may be used in each of the growing assemblies (100, 200). The fabric has a width (104W) and a length (104L). The multi-point temperature sensor (MPT100) is connected to the fabric (104) and is configured to measure the temperature of the fabric (104) along several points along the width (104W).

FIG. 12 shows the multi-point temperature sensor (MPT100) having 8 temperature sensor elements to measure the temperature across a first distance (104W1), second distance (104W2), third distance (104W), fourth distance (104W4), fifth distance (104W5), sixth distance (104W6), seventh distance (104W7), and eighth distance (104W8). In embodiments, each of the 8 temperature sensor elements is configured to input a signal to the computer (COMP). The temperature element at the first distance (104W1) sends a first signal (XMPT1) to a computer (COMP). The temperature element at the second distance (104W2) sends a second signal (XMPT2) to a computer (COMP). The temperature element at the third distance (104W) sends a third signal (XMPT3) to a computer (COMP). The temperature element at the fourth distance (104W4) sends a fourth signal (XMPT4) to a computer (COMP). The temperature element at the fifth distance (104W5) sends a fifth signal (XMPT5) to a computer (COMP). The temperature element at the sixth distance (104W6) sends a sixth signal (XMPT6) to a computer (COMP). The temperature element at the seventh distance (104W7) sends a seventh signal (XMPT7) to a computer (COMP). The temperature element at the eighth distance (104W8) sends an eighth signal (XMPT8) to a computer (COMP). An average temperature of the fabric (104) may be obtained by averaging at least two of the signals from the multi-point temperature sensor (MPT100).

Each of the distances (104W1, 104W2, 104 W3, 104W4, 104 W5, 104W6, 104 W7, 104W8) is measured relative to the base width (104W0) of the fabric (104). In embodiments, the fabric (104) is comprised of one or more from the group consisting of plastic, polyethylene, high-density polyethylene (HDPE), low-density polyethylene (LDPE), polyethylene terephthalate (PET), polyacrylonitrile, and polypropylene.

In embodiments, the fabric (104) is configured to have a wicking height constant characterized by a wicking height range from 0.4 inches to 1.9 inches. In embodiments, the fabric (104) is configured to have a wicking height constant characterized by a wicking height range from 0.40 inches to 0.45 inches, 0.45 inches to 0.50 inches, 0.50 inches to 0.55 inches, 0.55 inches to inches, 0.60 inches to 0.65 inches, 0.65 inches to 0.70 inches, 0.70 inches to 0.75 inches, 0.75 inches to 0.80 inches, 0.80 inches to 0.85 inches, 0.85 inches to 0.90 inches, 0.90 inches to 0.95 inches, 0.95 inches to 1.00 inches, 1.00 inches to 1.05 inches, 1.05 inches to 1.10 inches, 1.10 inches to 1.15 inches, 1.15 inches to 1.20 inches, 1.20 inches to 1.25 inches, 1.25 inches to 1.30 inches, 1.30 inches to 1.35 inches, 1.35 inches to 1.40 inches, 1.40 inches to 1.45 inches, 1.45 inches to 1.50 inches, 1.50 inches to 1.55 inches, 1.55 inches to 1.60 inches, 1.60 inches to 1.65 inches, 1.65 inches to 1.70 inches, 1.70 inches to 1.75 inches, 1.75 inches to 1.80 inches, 1.80 inches to 1.85 inches, or 1.85 inches to 1.90 inches.

The wicking height constant is a measurement of an ability of the fabric (104) to absorb moisture. In embodiments, the fabric (104) is configured to have an absorbance constant characterized by an absorbance range from 0.001 $lb/in^2$ to 0.005 $lb/in^2$. In embodiments, the fabric (104) is configured to have an absorbance constant characterized by an absorbance range from 0.0010 $lb/in^2$ to 0.0015 $lb/in^2$, 0.0015 $lb/in^2$ to 0.0020 $lb/in^2$, 0.0020 $lb/in^2$ to 0.0025 $lb/in^2$, 0.0025 $lb/in^2$ to 0.0030 $lb/in^2$, 0.0030 $lb/in^2$ to 0.0035 $lb/in^2$, 0.0035 $lb/in^2$ to 0.0040 $lb/in^2$, 0.0040 $lb/in^2$ to 0.0045 $lb/in^2$, or 0.0045 $lb/in^2$ to 0.0050 $lb/in^2$, or 0.0050 $lb/in^2$.

In embodiments, the absorbance constant is a measurement of moisture the fabric retains. In embodiments, the moisture that the fabric (104) retains may be provided by a liquid, mist, spray, water, mixture of water with macro-nutrients, micro-nutrients, pH adjustment solution, carbohydrates, enzymes, vitamins, hormones.

FIG. 13

FIG. 13 shows another one non-limiting embodiment of a fabric (104) used in a growing assembly (100).

FIG. 14

FIG. 14 depicts a computer (COMP) that is configured to input and/or output signals listed in FIGS. 1-22 (not all inputs and/or outputs to the computer are shown in FIG. 14).

FIG. 15

FIG. 15 shows a plurality of *cannabis* trimmers (TR, TR*) that are configured to trim at least a portion of the *cannabis* (107, 207) that was growing in each growing assembly (100, 200). FIG. 15 shows a first trimmer (TR) configured to trim at least a portion of the *cannabis* (107, 207) to produce a first trimmed *cannabis* (TR1) that was growing in each growing assembly (100, 200) followed by a second stage trimmer (TR\*) configured to trim at least a portion of the trimmed cannabis (TR1) from the first stage trimmer (TR) to produce a second trimmed cannabis (TR1\*).

Once the cannabis (107, 207) is harvested from each growing assembly (100, 200), the cannabis (107, 207) may be trimmed by use of at least one trimmer (TR, TR\*). In embodiments, trimming the cannabis (107, 207) is necessary to obtain a final product for medicinal or recreational use. Trimming the cannabis (107, 207) may be done for several reasons including improving appearance, taste, and cannabinoid concentration.

In embodiments, the cannabis (107, 207) consists of the leaves, seeds, stems, roots, or any reproductive structures. In embodiments, the reproductive structures may be flower. In embodiments, a flower may be a reproductive structure. In embodiments, the reproductive structures may be buds. In embodiments, a bud may be a reproductive structure. In embodiments, trimming removes at least a portion of the leaves and stems from the reproductive structures. In embodiments, cannabis (107, 207) is harvested from each growing assembly (100, 200) by severing the plants with a cutting tool. In embodiments, the roots of the cannabis (107, 207) are not introduced to the trimmer (TR) and provided to freezing, grinding, heating, extraction, multifunctional mixing. In embodiments, cannabis (107, 207) comprising leaves, seeds, stems, and reproductive structures (buds) are introduced to the trimmer (TR). In embodiments, cannabis (107, 207) comprising leaves, seeds, stems, roots, and reproductive structures (buds) are introduced to the trimmer (TR).

In embodiments, the first trimmer (TR) separates the leaves and/or stems from the buds. In embodiments, the first trimmer (TR) separates the buds from the leaves and stems. In embodiments, the first trimmer (TR) separates the buds from the leaves and stems by applying using a rotational motion provided by a first motor (MT1). In embodiments, the trimmer (TR) imparts a rotational motion upon the cannabis (107, 207). FIG. 15 displays the trimmer (TR) accepting a source of cannabis (107, 207) and trims leaves and/or stems from the reproductive structures (buds) to produce trimmed cannabis (TR1) and first trimmings (TR2). In embodiment, the first trimmer (TR) rotates at a revolutions per minute (rpm) including one or more selected from the group consisting of 30 rpm to 35 rpm, 35 rpm to 40 rpm, 40 rpm to 45 rpm, 45 rpm to 50 rpm, 50 rpm to 55 rpm, 55 rpm to 60 rpm, 60 rpm to 65 rpm, 65 rpm to 70 rpm, 70 rpm to 75 rpm, rpm to 80 rpm, 80 rpm to 85 rpm, 85 rpm to 90 rpm, 90 rpm to 95 rpm, 95 rpm to 100 rpm, 100 rpm to 105 rpm, 105 rpm to 110 rpm, 110 rpm to 115 rpm, 115 rpm to 120 rpm, 120 rpm to 125 rpm, 125 rpm to 130 rpm, 130 rpm to 135 rpm, 135 rpm to 140 rpm, 140 rpm to 145 rpm, 145 rpm to 150 rpm, 150 rpm to 155 rpm, 155 rpm to 160 rpm, 160 rpm to 165 rpm, 165 rpm to 170 rpm, 170 rpm to 175 rpm, 175 rpm to 180 rpm, 180 rpm to 185 rpm, 185 rpm to 190 rpm, 190 rpm to 195 rpm, 195 rpm to 200 rpm, 200 rpm to 205 rpm, 205 rpm to 210 rpm, 210 rpm to 215 rpm, 215 rpm to 220 rpm, and 220 rpm to 225 rpm.

In embodiments, the first trimmer (TR) moves the cannabis (107, 207) to a second trimmer (TR\*) to produce a second trimmed cannabis (TR1\*). Use of two stages of trimmers (TR, TR\*) increases efficiency of the trimming process and reduces manual labor in quality control by minimizing hand trimming.

In embodiments, a rotational motion cannabis (107, 207) passes the cannabis (107, 207) across a first blade (CT2), the first blade is configured to separate the leaves or stems from the buds, to provide first trimmed cannabis (TR1) that is depleted of leaves or stems. In embodiments, the first trimmer (TR) moves the cannabis (107, 207) across a first blade (CT2), the first blade is configured to separate the leaves or stems from the buds, to provide trimmed cannabis that is depleted of leaves or stems.

In embodiments, the second trimmer (TR\*) separates the leaves and/or stems from the from the first trimmed cannabis (TR1). In embodiments, the second trimmer (TR\*) separates the buds from the leaves and stems of the first trimmed cannabis (TR1) to produce a second trimmed cannabis (TR1\*) that has a reduced amount of leaves and/or stems relative to the first trimmed cannabis (TR1). In embodiments, the second trimmer (TR\*) separates the buds from the leaves from the first trimmed cannabis (TR1) and stems by applying using a rotational motion provided by a second motor (MT1\*). In embodiments, the second motor (MT1\*) is not needed since the first motor (MT1) rotates both the first trimmer (TR) and the second trimmer (TR\*).

In embodiments, the second trimmer (TR\*) imparts a rotational motion upon the first trimmed cannabis (TR1). FIG. 15 displays the second trimmer (TR) accepting the first trimmed cannabis (TR1) and trims at least a portion of the leaves and/or stems therefrom to produce a second trimmed cannabis (TR1\*) and second trimmings (TR2\*). In embodiments, a vacuum is pulled on the first trimmings (TR1) and the second trimmings (TR1\*).

In embodiment, the second trimmer (TR\*) rotates at a revolutions per minute (rpm) including one or more selected from the group consisting of 30 rpm to 35 rpm, 35 rpm to 40 rpm, rpm to 45 rpm, 45 rpm to 50 rpm, 50 rpm to 55 rpm, 55 rpm to 60 rpm, 60 rpm to 65 rpm, 65 rpm to 70 rpm, 70 rpm to 75 rpm, 75 rpm to 80 rpm, 80 rpm to 85 rpm, 85 rpm to 90 rpm, 90 rpm to 95 rpm, 95 rpm to 100 rpm, 100 rpm to 105 rpm, 105 rpm to 110 rpm, 110 rpm to 115 rpm, 115 rpm to 120 rpm, 120 rpm to 125 rpm, 125 rpm to 130 rpm, 130 rpm to 135 rpm, 135 rpm to 140 rpm, 140 rpm to 145 rpm, 145 rpm to 150 rpm, 150 rpm to 155 rpm, 155 rpm to 160 rpm, 160 rpm to 165 rpm, 165 rpm to 170 rpm, 170 rpm to 175 rpm, 175 rpm to 180 rpm, 180 rpm to 185 rpm, 185 rpm to 190 rpm, 190 rpm to 195 rpm, 195 rpm to 200 rpm, 200 rpm to 205 rpm, 205 rpm to 210 rpm, 210 rpm to 215 rpm, 215 rpm to 220 rpm, and 220 rpm to 225 rpm. In embodiment, the second trimmer (TR\*) rotates at a revolutions per minute (rpm) greater than the rpm of the first trimmer (TR). In embodiment, the second trimmer (TR\*) rotates at a revolutions per minute (rpm) lesser than the rpm of the first trimmer (TR). In embodiment, the second trimmer (TR\*) rotates at a revolutions per minute (rpm) equal to rpm of the first trimmer (TR).

In embodiments, the second trimmer (TR\*) moves the cannabis (107, 207) from the first trimmer (TR) to another location. In embodiments, a rotational motion is imparted upon the first trimmed cannabis (TR1) within the second trimmer (TR\*) which passes the first trimmed cannabis (TR1) across a second blade (CT2\*), the second blade is configured to separate at least a portion of the leaves and/or stems from the first trimmed cannabis (TR1) to provide a second trimmed cannabis (TR1\*) that has a reduced amount of leaves and/or stems relative to the first trimmed cannabis (TR1).

In embodiments, the first trimmings (TR2) include a first gas and trimmings mixture (GTM2). In embodiments, the second trimmings (TR2\*) include a second gas and trimmings mixture (GTM3). In embodiments, the first trimmings (TR2) including the first gas and trimmings mixture (GTM2) are mixed with the second trimmings (TR2\*) including the second gas and trimmings mixture (GTM3) to produce a combined gas and trimmings mixture (GTM1). The combined gas and trimmings mixture (GTM1) includes the first trimmings (TR) and the second trimmings (TR*) and a gas. In embodiments, the gas includes air, nitrogen, carbon dioxide.

In embodiments, the combined gas and trimmings mixture (GTM1) is introduced to a cyclone (TRX1). The cyclone (TRX1) is configured to separate the *cannabis* trimmings (TR2, TR2*) from the combined gas and trimmings mixture (GTM1) and produce a first separated trimmings (ST*). The first separated trimmings (ST*) is evacuated from the cyclone (TRX1) via a first dipleg (TRX1). A first trimmings depleted gas (FTDG) is evacuated from the cyclone (TRX1) and is introduced to a filter (TRX2*). In embodiments, insects are present within the *cannabis* introduced to the first and/or second trimmer (TR, TR*). In embodiments, insects are separated from the trimmings (TR2, TR2*) with the cyclone (TRX1*) and/or the filter (TRX2*).

The filter (TRX2*) has a filter element which is configured to remove additional trimmings from the first trimmings depleted gas (FTDG) to produce a second trimmings depleted gas (STDG) which has a reduced amount of trimmings relative to the first trimmings depleted gas (FTDG). In embodiments, the additional trimmings removed from the first trimmings depleted gas (FTDG) within the filter (TRX2) includes second separated trimmings (ST**). In embodiments, the first separated trimmings (ST*) and the second separated trimmings (ST**) are combined and send to the grinder (GR) as shown on FIG. 16, or to the cannabinoid tank for (6A3) as shown on FIG. 18, or to the volatiles extraction system (VES) on any one of FIGS. 17A, 17A', 17B, 17D, 17H, or to the mixing tank on FIG. 18E, combinations thereof.

In embodiments, the trimmed *cannabis* (TR1, TR1*) is sent to the grinder (GR) as shown on FIG. 16, the heater (on FIG. 17), or to the cannabinoid tank for (6A3) as shown on FIG. 18, or to the volatiles extraction system (VES) on any one of FIGS. 17A, 17A', 17B, 17D, 17H, or to the mixing tank on FIG. 18E, combinations thereof.

The second trimmings depleted gas (STDG) is evacuated from the filter (TRX2) and is introduced to fan (TRX3). The fan (TRX3) is configured to pull a vacuum on the filter (TRX3), the cyclone (TRX1), and the first and second trimmers (TR, TR). In embodiments, the vacuum pulled on the first and second trimmers (TR, TR*) pulls the trimmed *cannabis* (TR1, TR1*) up against the blades (CT2, CT2*) within each trimmer (TR, TR*). The fan (TRX3) is operated by a motor (TRX3). The fan (TRX2) is configured to configured to pull a vacuum on the filter (TRX3), the cyclone (TRX1), and the first and second trimmers (TR, TR) by applying a vacuum with a velocity pressure range from: between about 0.001 inches of water to about 0.005 inches of water; between about 0.005 inches of water to about 0.01 inches of water; between about 0.01 inches of water to about 0.02 inches of water; between about 0.02 inches of water to about 0.03 inches of water; between about 0.03 inches of water to about 0.04 inches of water; between about 0.04 inches of water to about 0.05 inches of water; between about 0.05 inches of water to about 0.06 inches of water; between about 0.06 inches of water to about 0.07 inches of water; between about 0.07 inches of water to about 0.08 inches of water; between about 0.08 inches of water to about 0.09 inches of water; between about 0.09 inches of water to about 0.1 inches of water; between about 0.1 inches of water to about 0.2 inches of water; between about 0.2 inches of water to about 0.3 inches of water; between about 0.3 inches of water to about 0.4 inches of water; between about 0.4 inches of water to about 0.5 inches of water; between about 0.5 inches of water to about 0.6 inches of water; between about 0.6 inches of water to about 0.7 inches of water; between about 0.7 inches of water to about 0.8 inches of water; between about 0.8 inches of water to about 0.9 inches of water; between about 0.9 inches of water to about 1 inch of water; between about 1 inch of water to about 1.25 inches of water; between about 1.25 inches of water to about 1.5 inches of water; between about 1.5 inches of water to about 2 inches of water; between about 2 inches of water to about 3 inches of water; between about 3 inches of water to about 4 inches of water; between about 4 inches of water to about 5 inches of water; between about 5 inches of water to about 6 inches of water; between about 6 inches of water to about 7 inches of water; between about 7 inches of water to about 8 inches of water; between about 8 inches of water to about 9 inches of water; between about 9 inches of water to about 10 inches of water; between about 10 inch of water to about 15 inches of water; between about 15 inches of water to about 25 inches of water; between about 25 inches of water to about 50 inches of water; between about 50 inches of water to about 75 inches of water; between about 75 inches of water to about 100 inches of water; between about 100 inches of water to about 150 inches of water; between about 150 inches of water to about 200 inches of water; between about 200 inches of water to about 250 inches of water; between about 250 inches of water to about 300 inches of water; between about 300 inches of water to about 350 inches of water; and, between about 350 inches of water to about 400 inches of water.

Gas is evacuated from the fan (TRX3) where it is then introduced to an adsorbent (TRX4). The adsorbent removes odor from the gas and produces a clean gas (TRX5). The clean gas (TRX5) has a reduced amount of volatile organic compounds within it relative to the gas that is evacuated from the fan (TRX3).

In embodiments, the harvested *cannabis* removed from the interior of the enclosure is immediately frozen within a freezer. In embodiments, the harvested *cannabis* removed from the interior of the enclosure is immediately frozen within a freezer to produce fresh frozen *cannabis*. In embodiments, the harvested *cannabis* removed from the interior of the enclosure is immediately frozen within a cryogenic liquid such as liquid nitrogen, liquid argon, liquid helium, liquid hydrogen, or liquid oxygen. In embodiments, the harvested *cannabis* removed from the interior of the enclosure is frozen at a temperature ranging from 32 degrees Fahrenheit to 0 degrees Fahrenheit, 0 degrees Fahrenheit to −10 degrees Fahrenheit, −10 degrees Fahrenheit to −20 degrees Fahrenheit, −20 degrees Fahrenheit to −30 degrees Fahrenheit, −30 degrees Fahrenheit to −40 degrees Fahrenheit, −40 degrees Fahrenheit to −50 degrees Fahrenheit, −50 degrees Fahrenheit to −75 degrees Fahrenheit, −75 degrees Fahrenheit to −100 degrees Fahrenheit, −100 degrees Fahrenheit to −125 degrees Fahrenheit, −135 degrees Fahrenheit to −150 degrees Fahrenheit, −150 degrees Fahrenheit to −250 degrees Fahrenheit, or −250 degrees Fahrenheit to −350 Fahrenheit.

In embodiments, the harvested *cannabis* removed from the interior of the enclosure is frozen immediately after it is harvested (to preserve terpenes) and then freeze dried (to remove water from the *cannabis*). In embodiments, the harvested *cannabis* removed from the interior of the enclosure is then freeze dried (to remove water from the *cannabis*).

In embodiments, the harvested *cannabis* removed from the interior of the enclosure is frozen immediately after it is harvested within a time duration after harvesting selected from the time durations inducing 0 minutes to 1 minute, 1 minutes to 3 minutes, 3 minutes to 5 minutes, 5 minutes to 7 minutes, 7 minutes to 9 minutes, 9 minutes to 11 minutes, 11 minutes to 13 minutes, 13 minutes to 15 minutes, 15 minutes to 20 minutes, 20 minutes to 25 minutes, 25 minutes to 30 minutes, 30 minutes to 35 minutes, 35 minutes to 40 minutes, 40 minutes to 45 minutes, 45 minutes to 50 minutes, 50 minutes to 55 minutes, 55 minutes to 60 minutes, 60 minutes to 75 minutes, 75 minutes to 90 minutes, 90 minutes to 105 minutes, or 105 minutes to 120 minutes.

FIG. 16

FIG. 16 shows a grinder (GR) that is configured to grind at least a portion of the cannabis (107, 207) that was growing in each growing assembly (100, 200). FIG. 16 also shows a grinder (GR) that is configured to grind at least a portion of the trimmed cannabis (TR1, TR1*, TR2, TR2*) that was trimmed by the trimmer (TR, TR*) as shown in FIG. 15.

A grinder (GR) generates a ground cannabis (GR1). The grinder may be used to grind (i) a portion of the cannabis (107, 207) harvested from each growing assembly (100, 200) or (ii) a portion of the trimmed cannabis (TR1) that is trimmed by the trimmer (TR) to produce ground cannabis (GR1). In embodiments, grinding of the cannabis is required for creating food products including a multifunctional composition, foodstuff, or animal food. In embodiments, the trimmings (TR2, TR2*) are provided to the grinder (GR) shown in FIG. 15.

In embodiments, the trimmings (TR2) from the first trimmer (TR) are provided to the grinder (GR) shown in FIG. 15. In embodiments, the trimmings (TR2*) from the second trimmer (TR*) are provided to the grinder (GR) shown in FIG. 15.

A grinder (GR) generates a ground cannabis (GR1) to a size ranging from 20 microns to 40 microns, 40 microns to 60 microns, 60 microns to 80 microns, 80 microns to 100 microns, 100 microns to 150 microns, 150 microns to 200 microns, 200 microns to 250 microns, 250 microns to 300 microns, 300 microns to 350 microns, 350 microns to 400 microns, 400 microns to 450 microns, 450 microns to 500 microns, 500 microns to 600 microns, 600 microns to 700 microns, 700 microns to 800 microns, 800 microns to 900 microns, 900 microns to 1000 microns, 1000 microns to 1250 microns, 1250 microns to 1500 microns, 1500 microns to 1750 microns, 1750 microns to 2000 microns, 2000 microns to 2250 microns, 2250 microns to 2500 microns, 2500 microns to 2750 microns, 2750 microns to 3000 microns, 3000 microns to 3500 microns, 3500 microns to 4000 microns, 4000 microns to 4500 microns, 4500 microns to 5000 microns, 5000 microns to 5500 microns, 5500 microns to 6000 microns, 6000 microns to 6500 microns, 6500 microns to 7000 microns, 7000 microns to 7500 microns, 7500 microns to 8000 microns, 8000 microns to 8500 microns, 8500 microns to 9000 microns, 9000 microns to 9500 microns, 9500 microns to 10000 microns, 10000 microns to 15000 microns, 15000 microns to 25000 microns, or 25000 microns to 35000 microns.

In embodiments, the ground cannabis (GR1) may be sent to the heater (on FIG. 17), or to the cannabinoid tank for (6A3) as shown on FIG. 18, or to the volatiles extraction system (VES) on any one of FIGS. 17A, 17A', 17B, 17D, 17H, or to the mixing tank on FIG. 18E, combinations thereof.

FIG. 17

FIG. 17 shows a heater (HTR1) that is configured to heat at least a portion of cannabis plants (107, 207) that was growing in each growing assembly (100, 200). FIG. 17 also shows a heater (HTR1) that is configured to heat at least a portion of the trimmed cannabis (TR1, TR1*, TR2, TR2*) that was trimmed by the trimmer (TR, TR*) as shown in FIG. 15. In embodiments, heating the cannabis is required for creating food products including a multifunctional composition, foodstuff, animal food.

FIG. 17 shows a heating unit (HTR1) that is configured to heat at least a portion of cannabis plants (107, 207) that was growing in each growing assembly (100, 200), and/or trimmed cannabis (TR1, TR1*), cannabis trimmings (TR2, TR2*), ground cannabis (GR1), or combinations thereof. FIG. 17 shows a heater (HTR1) that is configured to heat at least a portion of the cannabis (107, 207) that was growing in each growing assembly (100, 200). FIG. 17 also shows a heater (HTR1) that is configured to heat at least a portion of the trimmed cannabis (TR1, TR1*) that was trimmed by the trimmer (TR, TR*) as shown in FIG. 15. FIG. 17 also shows a heater (HTR1) that is configured to heat at least a portion of the ground cannabis (GR1) that was ground by the grinder (GR) as shown in FIG. 16. The heater (HTR1) may be used to heat (i) a portion of the cannabis (107, 207) harvested from each growing assembly (100, 200), (ii) a portion of the trimmed cannabis (TR1, TR1*, TR2, TR2*) that is trimmed by the trimmer (TR, TR*), (iii) a portion of the ground cannabis (GR1) that is ground by the cannabis (GR1), and/or (iv) frozen cannabis.

The heater (HTR1) generates a heated cannabis (HT1). The heater (HTR1) is configured to heat the cannabis (107, 207). In embodiments, the heater (HTR1) is configured to heat the cannabis (107, 207) as the cannabis (107, 207) passes through the heater (HTR1) via a conveyor (CVR1).

In embodiments, heating the cannabis (107, 207) removes carbon dioxide ($CO_2R$) from the cannabis (107, 207) to form a carbon dioxide depleted cannabis (CO2-1). In embodiments, the carbon dioxide depleted cannabis (CO2-1) is synonymous with the heated cannabis (HT1).

In embodiments, heating the cannabis (107, 207) decarboxylates the cannabis (107, 207) to produce a decarboxylated cannabis (DCX). In embodiments, heating the cannabis (107, 207) decarboxylates the tetrahydrocannabinolic acid (THCA) within the cannabis (107, 207) to form active tetrahydrocannabinol. In embodiments, decarboxylation is a chemical reaction that removes a carboxyl group and releases carbon dioxide ($CO_2R$). In embodiments, heating the cannabis (107, 207) removes carbon dioxide form the cannabis (107, 207) to form a carbon dioxide depleted cannabis (CO2-1).

The heater (HTR1) is equipped with a heater temperature sensor (HTR1T) that sends a signal (HTR1X) to the computer (COMP). In embodiments, the heater (HTR1) is operated within a temperature ranging from 185 degrees F. to 280 degrees F. In embodiments, the heater (HTR1) is operated within a temperature ranging from 205 degrees F. to 250 degrees F. In embodiments, the heater (HTR1) produces a heated cannabis (HT1) that has a temperature ranging from 185 degrees F. to 280 degrees F. In embodiments, the heater (HTR1) produces a heated cannabis (HT1) that has a temperature ranging from 205 degrees F. to 250 degrees F.

In embodiments, the heater (HTR1) is operated within a temperature ranging from 175 degrees Fahrenheit to 200 degrees Fahrenheit, 200 degrees Fahrenheit to 225 degrees Fahrenheit, 225 degrees Fahrenheit to 250 degrees Fahrenheit, 250 degrees Fahrenheit to 275 degrees Fahrenheit, 275 degrees Fahrenheit to 300 degrees Fahrenheit, 300 degrees Fahrenheit to 325 degrees Fahrenheit, 325 degrees Fahrenheit to 350 degrees Fahrenheit, 350 degrees Fahrenheit to 375 degrees Fahrenheit, 375 degrees Fahrenheit to 400 degrees Fahrenheit, or 400 degrees Fahrenheit to 425 degrees Fahrenheit.

In embodiments, the *cannabis* is dried at a temperature ranging from 50 to 60 degrees Fahrenheit, 60 to 65 degrees Fahrenheit, 65 to 70 degrees Fahrenheit, 70 to 75 degrees Fahrenheit, to 80 degrees Fahrenheit, 80 to 85 degrees Fahrenheit, 85 to 90 degrees Fahrenheit, 90 to 95 degrees Fahrenheit, 95 to 100 degrees Fahrenheit, 100 to 110 degrees Fahrenheit, 110 to 120 degrees Fahrenheit, 120 to 130 degrees Fahrenheit, 130 to 140 degrees Fahrenheit, 140 to 150 degrees Fahrenheit, 150 to 160 degrees Fahrenheit, or 160 to 175 degrees Fahrenheit.

In embodiments, the *cannabis* is heated to a temperature ranging from 50 to 60 degrees Fahrenheit, 60 to 65 degrees Fahrenheit, 65 to 70 degrees Fahrenheit, 70 to 75 degrees Fahrenheit, to 80 degrees Fahrenheit, 80 to 85 degrees Fahrenheit, 85 to 90 degrees Fahrenheit, 90 to 95 degrees Fahrenheit, 95 to 100 degrees Fahrenheit, 100 to 110 degrees Fahrenheit, 110 to 120 degrees Fahrenheit, 120 to 130 degrees Fahrenheit, 130 to 140 degrees Fahrenheit, 140 to 150 degrees Fahrenheit, 150 to 160 degrees Fahrenheit, or 160 to 175 degrees Fahrenheit.

In embodiments, a vacuum (VAC) is pulled on *cannabis* (107, 207) while the heater (HTR1) is heating the *cannabis* (107, 207) to aide in carbon dioxide removal. In embodiments, a vacuum (VAC) is pulled on the *cannabis* (107, 207) while the heater (HTR1) is heating the *cannabis* (107, 207) to a pressure that ranges from 0.5 inches of water to 30 inches of water. In embodiments, a vacuum (VAC) is pulled on the *cannabis* (107, 207) while the heater (HTR1) is heating the *cannabis* (107, 207) to a pressure that ranges from 5 inches of water to 90 inches of water. In embodiments, a vacuum (VAC) is pulled on the *cannabis* (107, 207) while the heater (HTR1) is heating the *cannabis* (107, 207) to a pressure that ranges from 2 pounds per square inch absolute to 14.69 pounds per square inch absolute. In embodiments, the *cannabis* (107, 207) is heated by the heater (HTR1) for a duration of 45 minutes to 2 hours. In embodiments, the *cannabis* (107, 207) is heated by the heater (HTR1) for a duration of 1 hour to 3 hours. In embodiments, the *cannabis* (107, 207) is heated by the heater (HTR1) for a duration of 2 hour to 24 hours.

In embodiments, the heated *cannabis* (HT1) may be sent to any number of locations of the FSS, such as, the cannabinoid tank for (6A3) as shown on FIG. 18, or to the volatiles extraction system (VES) on any one of FIGS. 17A, 17A', 17B, 17D, 17H, or to the mixing tank on FIG. 18E, combinations thereof.

FIG. 17A

FIG. 17A shows one non-limiting embodiment of a volatiles extraction system (VES) that is configured to extract volatiles (such as a cannabinoid) from *cannabis* (107, 207) with a first solvent (SOLV1). In embodiments, the volatiles extraction system (VES) is configured to extract volatiles (such as a cannabinoid) from the ground *cannabis* (GR1), trimmed *cannabis* (TR1, TR1*), *cannabis* trimmings (TR2, TR2*), heated *cannabis* (HT1) with a first solvent (SOLV1). In embodiments, the volatiles extraction system (VES) is configured to extract volatiles (such as a biosynthetic cannabinoid) from the genetically modified organisms as described in FIG. 18E. In embodiments, the volatiles extraction system (VES) is configured to extract an insect-derived cannabinoid glycoside from a source of insects containing the cannabinoid glycoside.

In embodiments, the biosynthetic cannabinoid comprises an insect produced cannabinoid compound. In embodiments, the biosynthetic cannabinoid comprises an insect produced cannabinoid compound comprising a cannabinoid glycoside. In embodiments, insects eat an enhanced feedstock including a first cannabinoid wherein the insects effectuate the glycosylation of the cannabinoid to produce second cannabinoid comprising a cannabinoid glycoside.

In embodiments, the cannabinoid glycoside includes glycosides of cannabinoid compounds, endocannabinoid compounds and/or vanilloid compounds. In embodiments, within the insects, a cannabinoid undergoes hydrolysis to produce the cannabinoid glycoside. In embodiments, an endocannabinoid refers to compounds including arachidonoyl ethanolamide (anandamide, AEA), 2-arachidonoyl ethanolamide (2-AG), 1-arachidonoyl ethanolamide (1-AG), and docosahexaenoyl ethanolamide (DHEA, synaptamide), oleoyl ethanolamide (OEA), eicsapentaenoyl ethanolamide, prostaglandin ethanolamide, docosahexaenoyl ethanolamide, linolenoyl ethanolamide, 5(Z),8(Z),11(Z)-eicosatrienoic acid ethanolamide (mead acid ethanolamide), heptadecanoul ethanolamide, stearoyl ethanolamide, docosaenoyl ethanolamide, nervonoyl ethanolamide, tricosanoyl ethanolamide, lignoceroyl ethanolamide, myristoyl ethanolamide, pentadecanoyl ethanolamide, palmitoleoyl ethanolamide, docosahexaenoic acid (DHA). Particularly preferred endocannabinoids are AEA, 2-AG, 1-AG, and DHEA. In embodiments, an vanilloid refers to compounds comprising a vanillyl group and which act on vanilloid receptors like TRPV1. "Vanilloid" compounds include, but are not limited to, vanillin, capsaicin and curcumin.

In embodiments, insects eat the cannabinoid in the feed and effectuate the glycosylation of a cannabinoid. In embodiments, an enzyme within the insects effectuate the glycosylation of a cannabinoid. In embodiments, insects eat an enhanced feedstock including tetrahydrocannabinolic acid (THCA), tetrahydrocannabinol (THC), Δ9-tetrahydrocannabinol (Δ9-THC), Δ8-tetrahydrocannabinol (Δ8-THC) wherein the insects effectuate the glycosylation of the cannabinoid to produce a cannabinoid glycoside. In embodiments, insects eat an enhanced feedstock including tetrahydrocannabinolic acid (THCA), tetrahydrocannabinol (THC), Δ9-tetrahydrocannabinol (Δ9-THC), Δ8-tetrahydrocannabinol (Δ8-THC) wherein the insects effectuate the glycosylation of the cannabinoid to produce a (THCV) Tetrahydrocannabivarin. The volatiles extraction system (VES) is configured to separate volatiles (VOLT) from *cannabis* (107, 207). The volatiles extraction system (VES) is configured to accept *cannabis* (107, 207), or heated *cannabis* (HT1), ground *cannabis* (GR1), trimmed *cannabis* (TR1), and/or combinations thereof. In embodiments, the *cannabis* (107, 207), heated *cannabis* (HT1), ground *cannabis* (GR1), and/or trimmed *cannabis* (TR1) may be weighed with a mass sensor (MS-VES) prior to being introduced to the volatiles extraction system (VES).

The volatiles (VOLT) include one or more from the group consisting of oil, wax, terpenes. The volatiles (VOLT) include at least one cannabinoid. In embodiments, the cannabinoid includes tetrahydrocannabinolic acid (THCA), active tetrahydrocannabinol, tetrahydrocannabinol (THC), Δ9-tetrahydrocannabinol (Δ9-THC), Δ8-tetrahydrocannabinol (Δ8-THC), tetrahydrocannabivarin (THCV), cannabidiolic acid (CBDA), cannabichromene (CBC), cannabidiol (CBD), cannabigerol (CBG), cannabinidiol (CBND), and/or cannabinol (CBN). In embodiments, the terpenes include one or more from the group consisting of limonene, humulene, pinene, linalool, caryophyllene, myrcene, eucalyptol, nerolidol, bisablol, and phytol.

In embodiments, the terpenes include one or more from the group consisting of alpha bisabolol, alpha pinene, beta caryophyllene, beta pinene, borneol, camphene, caryophyllene oxide, cineole, delta 3 carene, eucalyptol, fenchol, fenchone, geraniol, guaiol, humulene, isopulegol, limonene, linalool, myrcene, nerol, nerolidol, ocimene, phytol, pulegone, terpinene, terpineol, terpinolene, valencene, and combinations thereof.

In embodiments, the terpenes may be extracted from the volatiles. In embodiments, the terpenes may be extracted from the volatiles and then mixed with the concentrated volatiles. In embodiments, the terpenes may be extracted from the volatiles and then mixed with the concentrated volatiles after wax and solvent are removed from the volatiles. In embodiments, the terpenes mixed with the concentrated volatiles are not from a *cannabis* plant. In embodiments, the terpenes mixed with the concentrated volatiles are from a *cannabis* plant. In embodiments, the terpenes are produced by chemical synthesis from petrochemicals, hydrocarbons, plants, conifer trees, or insects. In embodiments, the terpenes include isoprenoids.

In embodiments, the terpenes include at least one organic carbon containing chemical compound. In embodiments, the terpenes include one or more from the group consisting of limonene, humulene, pinene, linalool, caryophyllene, myrcene, eucalyptol, nerolidol, bisablol, and phytol. In embodiments, limonene includes 1-Methyl-4-(1-methylethenyl)-cyclohexene. In embodiments, humulene includes 2,6,6,9-Tetramethyl-1,4-8-cycloundecatriene. In embodiments, pinene includes (1S,5S)-2,6,6-trimethylbicyclo [3.1.1]hept-2-ene. In embodiments, linalool includes 3,7-Dimethylocta-1,6-dien-3-ol. In embodiments, caryophyllene includes (1R,4E,9S)-4,11,11-Trimethyl-8-methylidenebicyclo[7.2.0]undec-4-ene. In embodiments, myrcene includes 7-Methyl-3-methylene-1,6-octadiene. In embodiments, eucalyptol includes 1,3,3-Trimethyl-2-oxabicyclo[2,2,2]octane. In embodiments, nerolidol includes 3,7,11-Trimethyl-1,6,10-dodecatrien-3-ol. In embodiments, bisablol includes 6-methyl-2-(4-methylcyclohex-3-en-1-yl) hept-5-en-2-ol. In embodiments, phytol includes (2E,7R, 11R)-3,7,11,15-tetramethyl-2-hexadecen-1-ol.

The volatiles extraction system (VES) extracts volatiles (VOLT) from *cannabis* with use of a first solvent (SOLV1). In embodiments, the first solvent (SOLV1) includes one or more from the group consisting of acetone, alcohol, oil, butane, butter, carbon dioxide, coconut oil, ethanol, gas, gaseous carbon dioxide, hexane, insect lipids, isobutane, isopropanol, liquid carbon dioxide, liquid, naphtha, olive oil, pentane, propane, R134 refrigerant gas, subcritical carbon dioxide, supercritical carbon dioxide, and vapor. In embodiments, the first solvent (SOLV1) includes one or more from the group consisting of petroleum ether, pentane, n-hexane, hexanes, diethyl ether, ethyl acetate, and ethanol.

In embodiments, the first solvent (SOLV1) includes an oil. In embodiments, the first solvent (SOLV1) includes one or more selected from the group consisting of acetone, alcohol, butane, butter, carbon dioxide, coconut oil, ethanol, an ethanol and water mixture, hexane, insect lipids, isobutane, isopropanol, liquid carbon dioxide, naphtha, olive oil, pentane, propane, R134 refrigerant gas, subcritical carbon dioxide, supercritical carbon dioxide, petroleum ether, pentane, n-hexane, hexanes, diethyl ether, ethyl acetate, and ethanol.

In embodiments, the first solvent (SOLV1) includes one or more selected from the group consisting of a medium-chain triglyceride, diglyceride, an ester, ethyl acetate, glycerin, glycerol, a hydrocarbon, isopropyl alcohol, methanol, a monoglyceride, a polyol, amylene hydrate, benzyl benzoate, butyl alcohol, carbon tetrachloride, chloroform, corn oil, cottonseed oil, ethyl acetate, glycerol, hexylene glycol, methylene chloride, methyl isobutyl ketone, mineral oil, peanut oil, propylene carbonate, and sesame oil.

The volatiles extraction system (VES) has an interior (VESI) that is configured to mix *cannabis*, frozen *cannabis*, heated *cannabis*, ground *cannabis*, trimmed *cannabis, cannabis* trimmings, insects, microorganisms, with a first solvent (SOLV1). The volatiles extraction system (VES) is configured to accept a first solvent (SOLV1). The first solvent (SOLV1) is configured to contact the *cannabis*, frozen *cannabis*, heated *cannabis*, ground *cannabis*, trimmed *cannabis, cannabis* trimmings, insects, microorganisms within the interior (VESI) of the volatiles extraction system (VES).

An output of the volatiles extraction system (VES) is a first solvent and volatiles mixture (FSVM). The first solvent and volatiles mixture (FSVM) is at least a mixture of volatiles (VOLT) and the first solvent (SOLV1). In embodiments, the first solvent and volatiles mixture (FSVM) is a mixture of oil, wax, terpenes and first solvent (SOLV1). In embodiments, the oil contains cannabinoids. In embodiments, the first solvent and volatiles mixture (FSVM) is a mixture of oil, wax, and first solvent (SOLV1). In embodiments, the first solvent and volatiles mixture (FSVM) is a mixture of a cannabinoid and the first solvent (SOLV1). In embodiments, the first solvent and volatiles mixture (FSVM) is a mixture of a biosynthetic cannabinoid and the first solvent (SOLV1). In embodiments, the first solvent and volatiles mixture (FSVM) is a mixture of a insect-derived cannabinoid glycoside and the first solvent (SOLV1).

In embodiments, the first solvent and volatiles mixture (FSVM) is a mixture of oil and first solvent (SOLV1). The first solvent and volatiles mixture (FSVM) is transferred from the volatiles extraction system (VES) to the first solvent separation system (SSS).

The first solvent separation system (SSS) is configured to separate the volatiles (VOLT) from the first solvent and volatiles mixture (FSVM). The first solvent separation system (SSS) has an interior (SSSI). The first solvent and volatiles mixture (FSVM) is transferred from the interior (VESI) of the volatiles extraction system (VES) to the interior (SSSI) of the first solvent separation system (SSS).

In embodiments, the interior (VEST) of the volatiles extraction system (VES) is in thermal contact with a first volatiles extraction heat exchanger (VS-HX1). The first volatiles extraction heat exchanger (VS-HX1) is configured to add and/or remove heat from the interior (VEST) of the volatiles extraction system (VES). The first volatiles extraction heat exchanger (VS-HX1) is configured to add and/or remove heat from the *cannabis* within the interior (VESI) of the volatiles extraction system (VES). the first volatiles extraction heat exchanger (VS-HX1) is configured to remove heat from the first solvent and volatiles mixture (FSVM) within the interior (VEST) of the volatiles extraction system (VES). In embodiments, the interior (SSSI) of the first solvent separation system (SSS) is in thermal contact with a second volatiles extraction heat exchanger (VS-HX2). The second volatiles extraction heat exchanger (VS-HX2) is configured to add and/or remove heat from the interior (SSSI) of the first solvent separation system (SSS).

The first volatiles extraction heat exchanger (VS-HX1) includes a first heat transfer medium (VF1C). The second volatiles extraction heat exchanger (VS-HX2) includes a second heat transfer medium (VF2C). In embodiments, the second coolant (VF2C) configured to add and/or remove heat from the interior (SSSI) of the first solvent separation system (SSS) is the first heat transfer medium (VF1C) that was used to add and/or remove heat from the interior (VESI) of the volatiles extraction system (VES). In embodiments, the first heat transfer medium (VF1C) configured to add and/or remove heat from the interior (VESI) of the volatiles extraction system (VES) is the second heat transfer medium (VF2C) used to add and/or remove heat from the interior (SSSI) of the first solvent separation system (SSS). In embodiments, the first heat transfer medium (VF1C) and/or the second heat transfer medium (VF2C) include a heated or cooled liquid. In embodiments, the first heat transfer medium (VF1C) and/or the second heat transfer medium (VF2C) include a refrigerated liquid, including water, an alcohol, ethylene glycol, ethylene alcohol, an oil, and an organic compound.

In embodiments, the first heat transfer medium (VF1C) maintains the interior (VESI) of the volatiles extraction system (VES) at a temperature range including one or more ranges selected from the group consisting of: between about 32 degrees Fahrenheit to about 40 degrees Fahrenheit; between about 40 degrees Fahrenheit to about 45 degrees Fahrenheit; between about 45 degrees Fahrenheit to about 50 degrees Fahrenheit; between about 50 degrees Fahrenheit to about 55 degrees Fahrenheit; between about 55 degrees Fahrenheit to about 60 degrees Fahrenheit; between about 60 degrees Fahrenheit to about 65 degrees Fahrenheit; between about 65 degrees Fahrenheit to about 70 degrees Fahrenheit; between about 70 degrees Fahrenheit to about 75 degrees Fahrenheit; between about 75 degrees Fahrenheit to about 80 degrees Fahrenheit; between about degrees Fahrenheit to about 85 degrees Fahrenheit; between about 85 degrees Fahrenheit to about 90 degrees Fahrenheit; between about 90 degrees Fahrenheit to about 95 degrees Fahrenheit; between about 95 degrees Fahrenheit to about 100 degrees Fahrenheit; between about 100 degrees Fahrenheit to about 105 degrees Fahrenheit; between about 105 degrees Fahrenheit to about 110 degrees Fahrenheit; between about 110 degrees Fahrenheit to about 115 degrees Fahrenheit; between about 115 degrees Fahrenheit to about 120 degrees Fahrenheit; between about 120 degrees Fahrenheit to about 130 degrees Fahrenheit; between about 130 degrees Fahrenheit to about 160 degrees Fahrenheit; between about 160 degrees Fahrenheit to about 190 degrees Fahrenheit; between about 190 degrees Fahrenheit to about 225 degrees Fahrenheit; between about 225 degrees Fahrenheit to about 250 degrees Fahrenheit; between about 250 degrees Fahrenheit to about 300 degrees Fahrenheit; between about 300 degrees Fahrenheit to about 400 degrees Fahrenheit; between about 400 degrees Fahrenheit to about 500 degrees Fahrenheit; between about 500 degrees Fahrenheit to about 600 degrees Fahrenheit; between about 600 degrees Fahrenheit to about 700 degrees Fahrenheit.

In embodiments, the second heat transfer medium (VF2C) maintains interior (SSSI) of the first solvent separation system (SSS) at a temperature range including one or more ranges selected from the group consisting of: between about 32 degrees Fahrenheit to about 40 degrees Fahrenheit; between about 40 degrees Fahrenheit to about 45 degrees Fahrenheit; between about 45 degrees Fahrenheit to about 50 degrees Fahrenheit; between about 50 degrees Fahrenheit to about 55 degrees Fahrenheit; between about 55 degrees Fahrenheit to about 60 degrees Fahrenheit; between about 60 degrees Fahrenheit to about 65 degrees Fahrenheit; between about 65 degrees Fahrenheit to about 70 degrees Fahrenheit; between about 70 degrees Fahrenheit to about 75 degrees Fahrenheit; between about 75 degrees Fahrenheit to about 80 degrees Fahrenheit; between about degrees Fahrenheit to about 85 degrees Fahrenheit; between about 85 degrees Fahrenheit to about 90 degrees Fahrenheit; between about 90 degrees Fahrenheit to about 95 degrees Fahrenheit; between about 95 degrees Fahrenheit to about 100 degrees Fahrenheit; between about 100 degrees Fahrenheit to about 105 degrees Fahrenheit; between about 105 degrees Fahrenheit to about 110 degrees Fahrenheit; between about 110 degrees Fahrenheit to about 115 degrees Fahrenheit; between about 115 degrees Fahrenheit to about 120 degrees Fahrenheit; between about 120 degrees Fahrenheit to about 130 degrees Fahrenheit; between about 130 degrees Fahrenheit to about 160 degrees Fahrenheit; between about 160 degrees Fahrenheit to about 190 degrees Fahrenheit; between about 190 degrees Fahrenheit to about 225 degrees Fahrenheit; between about 225 degrees Fahrenheit to about 250 degrees Fahrenheit; between about 250 degrees Fahrenheit to about 300 degrees Fahrenheit; between about 300 degrees Fahrenheit to about 400 degrees Fahrenheit; between about 400 degrees Fahrenheit to about 500 degrees Fahrenheit; between about 500 degrees Fahrenheit to about 600 degrees Fahrenheit; between about 600 degrees Fahrenheit to about 700 degrees Fahrenheit.

In embodiments, the pressure within the interior (VESI) of the volatiles extraction system (VES) is greater than the pressure within the interior (SSSI) of the first solvent separation system (SSS). In embodiments, the pressure within the interior (VESI) of the volatiles extraction system (VES) is less than the pressure within the interior (SSSI) of the first solvent separation system (SSS). In embodiments, the pressure within the interior (VESI) of the volatiles extraction system (VES) is equal to the pressure within the interior (SSSI) of the first solvent separation system (SSS).

The first solvent separation system (SSS) outputs a volatiles (VOLT) and a separated first solvent (SOLV1-S). The volatiles (VOLT) may be then mixed with a second solvent (SOLV2) as described in FIG. 17C. The volatiles (VOLT) may alternately by mixed with insects which include one or more from the group consisting of Orthoptera order of insects, grasshoppers, crickets, cave crickets, Jerusalem crickets, katydids, weta, lubber, acrida, locusts, cicadas, ants, mealworms, agave worms, worms, bees, centipedes, cockroaches, dragonflies, beetles, scorpions, tarantulas, termites, insect lipids, and insect oil.

The volatiles (VOLT) may alternately by mixed with insects which include one or more from the group consisting of Anthocoridae, minute pirate bugs, pirate bugs, flower bugs, the genus Orius, omnivorous bugs, carnivorous bugs, Orthoptera order of insects, grasshoppers, crickets, katydids, weta, lubber, acrida, locusts, mites, spider mites, predatory mites, *Neoseiulus fallacis*, genus of mites that are in the Phytoseiidae family, arthropods, hexapods, beetles, cicadas, beetles, nematodes, mealworms, bats, mammals of the order Chiroptera, yellow mealworm beetles, *Tenebrio Molitor, Tetranychus Urticae*, carnivorous arthropods, omnivorous arthropods, green lacewings, insects in the family Chrysopidae, insects in the order Neuroptera, mantidflies, black soldier flies, larvae, fly larvae, insect larvae, arthropod larvae, black soldier fly larvae, Hermetia illucens, antlions, mosquitos, Colorado potato beetle, *Leptinotarsa decemlineata*, Encarsia *Formosa*, whitefly parasites, ladybugs, spiders, dragonflies, orb-weaving spiders, arachnids, members of the spider family Araneidae, praying mantis, arachnids, eight-legged arthropods, six-legged arthropods, fall armyworm, *Spodoptera frugiperda*, species in the order Lepidoptera, diamondback moths, cabbage moths, moth species of the family Plutellidae and genus *Plutella*, moth species of the family Plutellidae, *drosophila* suzukii, spotted wing *drosophila*, *Ceratitis capitata*, Mediterranean fruit flies, and medfly.

The volatiles extraction system (VES) is configured to operate in a plurality of modes of operation. In a first mode of operation, the volatiles extraction system (VES) separates terpenes from the *cannabis*. The first mode of operation may take place at a first temperature and a first pressure. In a second mode of operation, the volatiles extraction system (VES) separates other volatiles (VOLT) from the *cannabis*, insects, and/or microorganisms. The second mode of operation may take place at a second temperature and a first pressure. In embodiments, the second temperature is greater than the first temperature. In embodiments, the second pressure is greater than the first pressure.

In embodiments, the interior (VEST) of the volatiles extraction system (VES) is configured to operate at a pressure range including one or more ranges selected from the group consisting of: 500 PSI to 1,000 PSI, 1,000 PSI to 1,500 PSI, 1,500 PSI to 2,000 PSI, 2,000 PSI to 2,500 PSI, 2,500 PSI to 3,000 PSI, 3,500 PSI to 4,000 PSI, 4,000 PSI to 4,500 PSI, 4,500 PSI to 5,000 PSI, and 5,000 PSI to 6,000 PSI.

In embodiments, the interior (SSSI) of the first solvent separation system (SSS) is configured to operate at a pressure range including one or more ranges selected from the group consisting of: 500 PSI to 1,000 PSI, 1,000 PSI to 1,500 PSI, 1,500 PSI to 2,000 PSI, 2,000 PSI to 2,500 PSI, 2,500 PSI to 3,000 PSI, 3,500 PSI to 4,000 PSI, 4,000 PSI to 4,500 PSI, 4,500 PSI to 5,000 PSI, and 5,000 PSI to 6,000 PSI.

In embodiments, the difference in pressure between the interior (VEST) of the volatiles extraction system (VES) and the interior (SSSI) of the first solvent separation system (SSS) including one or more ranges selected from the group consisting of: 100 PSI to 150 PSI, 150 PSI to 250 PSI, 250 PSI to 350 PSI, 350 PSI to 500 PSI, 500 PSI to 1,000 PSI, 1,000 PSI to 1,500 PSI, 1,500 PSI to 2,000 PSI, 2,000 PSI to 2,500 PSI, 2,500 PSI to 3,000 PSI, 3,500 PSI to 4,000 PSI, 4,000 PSI to 4,500 PSI, 4,500 PSI to 5,000 PSI, and 5,000 PSI to 6,000 PSI.

In embodiments, cannabinoids may extracted from the *cannabis* with ethanol for a time duration ranging from 1 minute to 2 minutes, 2 minutes to 4 minutes, 4 minutes to 6 minutes, 6 minutes to 8 minutes, 8 minutes to 10 minutes, 10 minutes to 12 minutes, 12 minutes to 14 minutes, 14 minutes to 16 minutes, 16 minutes to 18 minutes, 18 minutes to 20 minutes, 20 minutes to 25 minutes, 25 minutes to 30 minutes, 30 minutes to 35 minutes, 35 minutes to 40 minutes, 40 minutes to 45 minutes, 45 minutes to 50 minutes, 50 minutes to 55 minutes, 55 minutes to 1 hour, 1 hour to 1.5 hours, 1.5 hours to 2 hours, 2 hours to 2.5 hours, 2.5 hours to 3 hours, 3 hours to 3.5 hours, 3.5 hours to 4 hours, 4 hours to 4.5 hours, 4.5 hours to 5 hours, 5 hours to 5.5 hours, 5.5 hours to 6 hours, 6 hours to 18 hours, 18 hours to 24 hours, 24 hours to 36 hours, 36 hours to 48 hours, 48 hours to 60 hours, 60 hours to 72 hours, 72 hours to 84 hours, or 84 hours to 96 hours.

In embodiments, cannabinoids may extracted from the *cannabis* with the first solvent for a time duration ranging from 1 second to 15 seconds, 15 seconds to 30 seconds, 30 seconds to 1 minute, 1 minute to 2 minutes, 2 minutes to 4 minutes, 4 minutes to 6 minutes, 6 minutes to 8 minutes, 8 minutes to 10 minutes, 10 minutes to 12 minutes, 12 minutes to 14 minutes, 14 minutes to 16 minutes, 16 minutes to 18 minutes, 18 minutes to 20 minutes, 20 minutes to 25 minutes, 25 minutes to 30 minutes, 30 minutes to 35 minutes, 35 minutes to 40 minutes, 40 minutes to 45 minutes, 45 minutes to 50 minutes, 50 minutes to 55 minutes, 55 minutes to 1 hour, 1 hour to 1.5 hours, 1.5 hours to 2 hours, 2 hours to 2.5 hours, 2.5 hours to 3 hours, 3 hours to 3.5 hours, 3.5 hours to 4 hours, 4 hours to 4.5 hours, 4.5 hours to 5 hours, 5 hours to 5.5 hours, 5.5 hours to 6 hours, 6 hours to 18 hours, 18 hours to 24 hours, 24 hours to 36 hours, 36 hours to 48 hours, 48 hours to 60 hours, 60 hours to 72 hours, 72 hours to 84 hours, or 84 hours to 96 hours.

FIG. 17A'

FIG. 17A' shows one non-limiting embodiment of a volatiles extraction system (VES) that is configured to extract volatiles from *cannabis* (107, 207) with a chilled ethanol separation system (CESS).

In embodiments, the volatiles extraction system (VES) is configured to separate volatiles (VOLT) from *cannabis* (107, 207), insects, microorganisms. The volatiles extraction system (VES) is configured to accept *cannabis* (107, 207), or heated *cannabis* (HT1), ground *cannabis* (GR1), trimmed *cannabis* (TR1, TR1*), *cannabis* trimmings (TR2, TR2*), and optionally including a *cannabis* and insects mixture and/or microorganisms and/or combinations thereof. In embodiments, the *cannabis* (107, 207), or heated *cannabis* (HT1), ground *cannabis* (GR1), trimmed *cannabis* (TR1, TR1*), *cannabis* trimmings (TR2, TR2*), insects, microorganisms, and optionally including a *cannabis* and insects mixture may be weighed with a mass sensor (MS-VES) prior to being introduced to the volatiles extraction system (VES).

The volatiles (VOLT) include one or more from the group consisting of oil, wax, terpenes. The volatiles (VOLT) include cannabinoids. In embodiments, the terpenes may be extracted from the volatiles. In embodiments, the terpenes may be extracted from the volatiles and then mixed with the concentrated volatiles. In embodiments, the terpenes may be extracted from the volatiles and then mixed with the concentrated volatiles after wax and solvent are removed from the volatiles. In embodiments, the terpenes mixed with the concentrated volatiles are not from a *cannabis* plant. In embodiments, the terpenes mixed with the concentrated volatiles are from a *cannabis* plant.

The volatiles extraction system (VES) extracts volatiles (VOLT) from *cannabis* with use of a first solvent (SOLV1). In embodiments, the first solvent (SOLV1) includes chilled ethanol. In embodiments, the first solvent (SOLV1) includes a chilled ethanol and water mixture. In embodiments, the water within the chilled ethanol and water mixture includes treated water, the treated water may be distilled, membrane treated water, adsorbent treated water, cation and/or anion treated water, or any types of treated water mentioned in this specification.

The volatiles extraction system (VES) has an interior (VESI) that is configured to mix *cannabis* (107, 207), or heated *cannabis* (HT1), ground *cannabis* (GR1), trimmed *cannabis* (TR1, TR1*), *cannabis* trimmings (TR2, TR2*), etc. and optionally including a *cannabis* and insects mixture the first solvent (SOLV1). The volatiles extraction system (VES) is configured to accept a first solvent (SOLV1). The first solvent (SOLV1) is configured to contact the *cannabis* (107, 207), or heated *cannabis* (HT1), ground *cannabis* (GR1), trimmed *cannabis* (TR1), *cannabis* trimmings (TR2), and optionally including a *cannabis* and insects mixture within the interior (VESI) of the volatiles extraction system (VES).

In embodiments, the volatiles extraction system (VES) outputs a mixture of cannabinoids and ethanol as a first solvent and volatiles mixture (FSVM). The first solvent and volatiles mixture (FSVM) is at least a mixture of volatiles (VOLT) and the first solvent (SOLV1). In embodiments, the first solvent and volatiles mixture (FSVM) is a mixture of oil, wax, terpenes and first solvent (SOLV1). In embodiments, the oil contains cannabinoids. In embodiments, the first solvent and volatiles mixture (FSVM) is a mixture of oil, wax, and first solvent (SOLV1). In embodiments, the first solvent and volatiles mixture (FSVM) is a mixture of oil and first solvent (SOLV1). The first solvent and volatiles mixture (FSVM) is transferred from the volatiles extraction system (VES) to the first solids separation system (SSS). In embodiments, a first solids separation system (SSS) and a second solids separation system (SSS) may be used to remove the first solvent and volatiles mixture (FSVM) from the volatiles extraction system (VES).

The first solids separation system (SSS) is configured to separate the plant matter (leaves, stems, and/or buds), insect exoskeleton, microorganisms, from the first solvent and volatiles mixture (FSVM). The first solids separation system (SSS) has an interior (SSSI). The first solvent and volatiles mixture (FSVM) is transferred from the interior (VESI) of the volatiles extraction system (VES) to the interior (SSSI) of the first solids separation system (SSS).

In embodiments, the interior (VEST) of the volatiles extraction system (VES) is in thermal contact with a first volatiles extraction heat exchanger (VS-HX1). The first volatiles extraction heat exchanger (VS-HX1) is configured to add and/or remove heat from the interior (VEST) of the volatiles extraction system (VES). The first volatiles extraction heat exchanger (VS-HX1) is configured to add and/or remove heat from the *cannabis* within the interior (VESI) of the volatiles extraction system (VES). the first volatiles extraction heat exchanger (VS-HX1) is configured to remove heat from the first solvent and volatiles mixture (FSVM) within the interior (VEST) of the volatiles extraction system (VES). In embodiments, the interior (SSSI) of the first solids separation system (SSS) is in thermal contact with a second volatiles extraction heat exchanger (VS-HX2). The second volatiles extraction heat exchanger (VS-HX2) is configured to add and/or remove heat from the interior (SSSI) of the first solids separation system (SSS).

The first volatiles extraction heat exchanger (VS-HX1) includes a first heat transfer medium (VF1C). The second volatiles extraction heat exchanger (VS-HX2) includes a second heat transfer medium (VF2C). In embodiments, the second coolant (VF2C) configured to add and/or remove heat from the interior (SSSI) of the first solids separation system (SSS) is the first heat transfer medium (VF1C) that was used to add and/or remove heat from the interior (VESI) of the volatiles extraction system (VES). In embodiments, the first heat transfer medium (VF1C) configured to add and/or remove heat from the interior (VESI) of the volatiles extraction system (VES) is the second heat transfer medium (VF2C) used to add and/or remove heat from the interior (SSSI) of the first solids separation system (SSS). In embodiments, the first heat transfer medium (VF1C) and/or the second heat transfer medium (VF2C) include a heated or cooled liquid. In embodiments, the first heat transfer medium (VF1C) and/or the second heat transfer medium (VF2C) include a refrigerated liquid, including water, an alcohol, ethylene glycol, ethylene alcohol, an oil, liquid carbon dioxide, a refrigerant, and an organic compound.

In embodiments, the first heat transfer medium (VF1C) maintains the interior (VESI) of the volatiles extraction system (VES) at a temperature range including one or more ranges selected from the group consisting of: between about 32 degrees Fahrenheit to about 40 degrees Fahrenheit; between about 40 degrees Fahrenheit to about 45 degrees Fahrenheit; between about 45 degrees Fahrenheit to about 50 degrees Fahrenheit; between about 50 degrees Fahrenheit to about 55 degrees Fahrenheit; between about 55 degrees Fahrenheit to about 60 degrees Fahrenheit; between about 60 degrees Fahrenheit to about 65 degrees Fahrenheit; between about 65 degrees Fahrenheit to about 70 degrees Fahrenheit; between about 70 degrees Fahrenheit to about 75 degrees Fahrenheit; between about 75 degrees Fahrenheit to about 80 degrees Fahrenheit; between about 80 degrees Fahrenheit to about 85 degrees Fahrenheit; between about 85 degrees Fahrenheit to about 90 degrees Fahrenheit; between about 90 degrees Fahrenheit to about 95 degrees Fahrenheit; between about 95 degrees Fahrenheit to about 100 degrees Fahrenheit; between about 100 degrees Fahrenheit to about 105 degrees Fahrenheit; between about 105 degrees Fahrenheit to about 110 degrees Fahrenheit; between about 110 degrees Fahrenheit to about 115 degrees Fahrenheit; between about 115 degrees Fahrenheit to about 120 degrees Fahrenheit; between about 120 degrees Fahrenheit to about 130 degrees Fahrenheit; between about 130 degrees Fahrenheit to about 160 degrees Fahrenheit; between about 160 degrees Fahrenheit to about 190 degrees Fahrenheit; between about 190 degrees Fahrenheit to about 225 degrees Fahrenheit; between about 225 degrees Fahrenheit to about 250 degrees Fahrenheit; between about 250 degrees Fahrenheit to about 300 degrees Fahrenheit; between about 300 degrees Fahrenheit to about 400 degrees Fahrenheit; between about 400 degrees Fahrenheit to about 500 degrees Fahrenheit; between about 500 degrees Fahrenheit to about 600 degrees Fahrenheit; between about 600 degrees Fahrenheit to about 700 degrees Fahrenheit.

In embodiments, the first heat transfer medium (VF1C) maintains the interior (VESI) of the volatiles extraction system (VES) at a temperature range including one or more ranges selected from the group consisting of: 32 degrees Fahrenheit to 0 degrees Fahrenheit, 0 degrees Fahrenheit to −10 degrees Fahrenheit, −10 degrees Fahrenheit to −20 degrees Fahrenheit, −20 degrees Fahrenheit to −30 degrees Fahrenheit, −30 degrees Fahrenheit to −40 degrees Fahrenheit, −40 degrees Fahrenheit to −50 degrees Fahrenheit, −50 degrees Fahrenheit to −75 degrees Fahrenheit, −75 degrees Fahrenheit to −100 degrees Fahrenheit, −100 degrees Fahrenheit to −125 degrees Fahrenheit, or −135 degrees Fahrenheit to −150 degrees Fahrenheit.

In embodiments, the second heat transfer medium (VF2C) maintains interior (SSSI) of the first solids separation system (SSS) at a temperature range including one or more ranges selected from the group consisting of: between about 32 degrees Fahrenheit to about 40 degrees Fahrenheit; between about 40 degrees Fahrenheit to about 45 degrees Fahrenheit; between about 45 degrees Fahrenheit to about 50 degrees Fahrenheit; between about 50 degrees Fahrenheit to about 55 degrees Fahrenheit; between about 55 degrees Fahrenheit to about 60 degrees Fahrenheit; between about 60 degrees Fahrenheit to about 65 degrees Fahrenheit; between about 65 degrees Fahrenheit to about 70 degrees Fahrenheit; between about 70 degrees Fahrenheit to about 75 degrees Fahrenheit; between about 75 degrees Fahrenheit to about 80 degrees Fahrenheit; between about 80 degrees Fahrenheit to about 85 degrees Fahrenheit; between about 85 degrees Fahrenheit to about 90 degrees Fahrenheit; between about 90 degrees Fahrenheit to about 95 degrees Fahrenheit; between about 95 degrees Fahrenheit to about 100 degrees Fahrenheit; between about 100 degrees Fahrenheit to about 105 degrees Fahrenheit; between about 105 degrees Fahrenheit to about 110 degrees Fahrenheit; between about 110 degrees Fahrenheit to about 115 degrees Fahrenheit; between about 115 degrees Fahrenheit to about 120 degrees Fahrenheit; between about 120 degrees Fahrenheit to about 130 degrees Fahrenheit; between about 130 degrees Fahrenheit to about 160 degrees Fahrenheit; between about 160 degrees Fahrenheit to about 190 degrees Fahrenheit; between about 190 degrees Fahrenheit to about 225 degrees Fahrenheit; between about 225 degrees Fahrenheit to about 250 degrees Fahrenheit; between about 250 degrees Fahrenheit to about 300 degrees Fahrenheit; between about 300 degrees Fahrenheit to about 400 degrees Fahrenheit; between about 400 degrees Fahrenheit to about 500 degrees Fahrenheit; between about 500 degrees Fahrenheit to about 600 degrees Fahrenheit; between about 600 degrees Fahrenheit to about 700 degrees Fahrenheit.

In embodiments, the second heat transfer medium (VF2C) maintains interior (SSSI) of the first solids separation system (SSS) at a temperature range including one or more ranges selected from the group consisting of: 32 degrees Fahrenheit to 0 degrees Fahrenheit, 0 degrees Fahrenheit to −10 degrees Fahrenheit, −10 degrees Fahrenheit to −20 degrees Fahrenheit, −20 degrees Fahrenheit to −30 degrees Fahrenheit, −30 degrees Fahrenheit to −40 degrees Fahrenheit, −40 degrees Fahrenheit to −50 degrees Fahrenheit, −50 degrees Fahrenheit to −75 degrees Fahrenheit, −75 degrees Fahrenheit to −100 degrees Fahrenheit, −100 degrees Fahrenheit to −125 degrees Fahrenheit, or −135 degrees Fahrenheit to −150 degrees Fahrenheit.

In embodiments, the pressure within the interior (VESI) of the volatiles extraction system (VES) is greater than the pressure within the interior (SSSI) of the first solids separation system (SSS). In embodiments, the pressure within the interior (VESI) of the volatiles extraction system (VES) is less than the pressure within the interior (SSSI) of the first solids separation system (SSS). In embodiments, the pressure within the interior (VESI) of the volatiles extraction system (VES) is equal to the pressure within the interior (SSSI) of the first solids separation system (SSS).

The first solids separation system (SSS) outputs a volatiles and ethanol mixture (VOLT) and a separated solids (SOLIDSV), the solids (SOLIDSV) include plant matter, exoskeleton, and/or microorganisms. The volatiles and ethanol mixture (VOLT) includes volatiles (VOLT) and ethanol (SOLVETH). In embodiments, the ethanol (SOLVETH) includes a water and ethanol mixture. In embodiments, the water includes treated water. In embodiments, the water includes distilled water.

The volatiles (VOLT) may be then transferred to the solvent cooler (SOLV-C) as shown on FIG. 17C. The volatiles and ethanol mixture (VOLT) may be cooled together with carbon dioxide extracted *cannabis* oil and/or hydrocarbon extracted *cannabis* oil.

In embodiments, cannabinoids may extracted from the *cannabis* with the first solvent within the volatiles extraction system (VES) for a time duration ranging from 1 second to 15 seconds, 15 seconds to 30 seconds, 30 seconds to 1 minute, 1 minute to 2 minutes, 2 minutes to 4 minutes, 4 minutes to 6 minutes, 6 minutes to 8 minutes, 8 minutes to 10 minutes, 10 minutes to 12 minutes, 12 minutes to 14 minutes, 14 minutes to 16 minutes, 16 minutes to 18 minutes, 18 minutes to 20 minutes, 20 minutes to 25 minutes, 25 minutes to 30 minutes, 30 minutes to 35 minutes, 35 minutes to 40 minutes, 40 minutes to 45 minutes, 45 minutes to 50 minutes, 50 minutes to 55 minutes, 55 minutes to 1 hour, 1 hour to 1.5 hours, 1.5 hours to 2 hours, 2 hours to 2.5 hours, 2.5 hours to 3 hours, 3 hours to 3.5 hours, 3.5 hours to 4 hours, 4 hours to 4.5 hours, 4.5 hours to 5 hours, 5 hours to 5.5 hours, 5.5 hours to 6 hours. Preferably the shorter the duration of ethanol extraction is preferred so as to only separate volatiles from the *cannabis* and not other undesirable compounds such as chlorophyll and/or wax.

FIG. 17B

FIG. 17B shows a plurality of volatiles extraction systems (VES1, VES2) equipped with one first solvent separation system (SSS). The first volatiles extraction system (VES1) has an interior (VES1I) that is configured to mix *cannabis* (107, 207), heated *cannabis* (HT1), ground *cannabis* (GR1), trimmed *cannabis* (TR1, TR1*), *cannabis* trimmings (TR2, TR2*), insects, microorganisms, etc. with a first solvent (SOLV1). The second volatiles extraction system (VES2) has an interior (VES1I) that is configured to mix *cannabis* (107, 207), heated *cannabis* (HT1), ground *cannabis* (GR1), trimmed *cannabis* (TR1, TR1*), *cannabis* trimmings (TR2, TR2*), insects, and/or microorganisms with a first solvent (SOLV1).

FIG. 17B shows a first *cannabis* portion (FCS) introduced to the first volatiles extraction system (VES1) and a second *cannabis* portion (SCS) introduced to the second volatiles extraction system (VES2). The first *cannabis* portion (FCS) may be weighed prior to being introduced to the first volatiles extraction system (VES1). The second *cannabis* portion (SCS) may be weighed prior to being introduced to the second volatiles extraction system (VES2). The first *cannabis* portion (FCS) and/or the second *cannabis* portion (SCS) may be either *cannabis* (107, 207), heated *cannabis* (HT1), ground *cannabis* (GR1), trimmed *cannabis* (TR1, TR1*), *cannabis* trimmings (TR2, TR2*), insects, microorganisms, and/or combinations thereof.

A primary first solvent and volatiles mixture (FSVMA) is discharged from the first volatiles extraction system (VES1). A secondary first solvent and volatiles mixture (FSVMB) is discharged from the second volatiles extraction system (VES1). The primary first solvent and volatiles mixture (FSVMA) and secondary first solvent and volatiles mixture (FSVMB) are combined and introduced to the first solvent separation system (SSS).

FIG. 17C

FIG. 17C shows a volatiles and solvent mixing system (VSMS) that is configured to mix the volatiles (VOLT) with a second solvent (SOLV2). The volatiles (VOLT) that are introduced to the interior (VSMSI) of the volatiles and solvent mixing system (VSMS) are transferred from the volatiles extraction systems (VES, VES1, VES2) via the first solvent separation system (SSS) or extraction or purification systems as shown in FIGS. 17A, 17A', 17B, and/or 17H.

In embodiments, the second solvent (SOLV2) includes one or more from the group consisting of a liquid, acetone, alcohol, oil, ethanol. In embodiments, the second solvent (SOLV2) includes one or more selected from the group consisting of acetone, alcohol, butane, butter, carbon dioxide, coconut oil, ethanol, an ethanol and water mixture, hexane, insect lipids, isobutane, isopropanol, liquid carbon dioxide, naphtha, olive oil, pentane, propane, R134 refrigerant gas, subcritical carbon dioxide, supercritical carbon dioxide, petroleum ether, pentane, n-hexane, hexanes, diethyl ether, ethyl acetate, and ethanol. In embodiments, the second solvent (SOLV2) includes one or more selected from the group consisting of a medium-chain triglyceride, diglyceride, an ester, ethyl acetate, glycerin, glycerol, a hydrocarbon, isopropyl alcohol, methanol, a monoglyceride, a polyol, amylene hydrate, benzyl benzoate, butyl alcohol, carbon tetrachloride, chloroform, corn oil, cottonseed oil, ethyl acetate, glycerol, hexylene glycol, methylene chloride, methyl isobutyl ketone, mineral oil, peanut oil, propylene carbonate, and sesame oil.

In embodiments, the second solvent (SOLV2) includes one or more from the group consisting of petroleum ether, pentane, n-hexane, hexanes, diethyl ether, ethyl acetate, and ethanol. The second solvent (SOLV2) can be weighed with a mass sensor (MS-SOLV2) prior to being introduced to the interior (VSMSI) of the volatiles and solvent mixing system (VSMS). The volatiles (VOLT) may also be weighed with a mass sensor (MS-VOLT) prior to being introduced to the interior (VSMSI) of the volatiles and solvent mixing system (VSMS). The second solvent (SOLV2) and volatiles (VOLT) are mixed within the interior (VSMSI) of the volatiles and solvent mixing system (VSMS).

The volatiles (VOLT) and second solvent (SOLV2) may be mixed at varying mass ratios. The volatiles (VOLT) to second solvent (SOLV2) mixing mass ratio is the pounds of volatiles (VOLT) per pounds of second solvent (SOLV2). In embodiments, the mixing mass ratio of volatiles (VOLT) to the second solvent (SOLV2) ranges from 1 pound of volatiles (VOLT) per 1 pound of second solvent (SOLV2), so this would be a mixing mass ratio of 1/1 or 1; In embodiments, the mixing mass ratio of volatiles (VOLT) to the second solvent (SOLV2) ranges from 1 pound of volatiles (VOLT) per 2 pounds of second solvent (SOLV2), so this would be a mixing mass ratio of ½ or 0.5; In embodiments, the mixing mass ratio of volatiles (VOLT) to the second solvent (SOLV2) ranges from 1 pound of volatiles (VOLT) per 3 pounds of second solvent (SOLV2), so this would be a mixing mass ratio of 1/3 or 0.33; In embodiments, the mixing mass ratio of volatiles (VOLT) to the second solvent (SOLV2) ranges from 1 pound of volatiles (VOLT) per 4 pounds of second solvent (SOLV2), so this would be a mixing mass ratio of ¼ or 0.25; In embodiments, the mixing mass ratio of volatiles (VOLT) to the second solvent (SOLV2) ranges from 1 pound of volatiles (VOLT) per 5 pounds of second solvent (SOLV2), so this would be a mixing mass ratio of 1/5 or 0.2; In embodiments, the mixing mass ratio of volatiles (VOLT) to the second solvent (SOLV2) ranges from 1 pound of volatiles (VOLT) per 6 pounds of second solvent (SOLV2), so this would be a mixing mass ratio of 1/6 or 0.16; In embodiments, the mixing mass ratio of volatiles (VOLT) to the second solvent (SOLV2) ranges from 1 pound of volatiles (VOLT) per 7 pounds of second solvent (SOLV2), so this would be a mixing mass ratio of 1/7 or 0.14; In embodiments, the mixing mass ratio of volatiles (VOLT) to the second solvent (SOLV2) ranges from 1 pound of volatiles (VOLT) per 8 pounds of second solvent (SOLV2), so this would be a mixing mass ratio of 1/8 or 0.125; In embodiments, the mixing mass ratio of volatiles (VOLT) to the second solvent (SOLV2) ranges from 1 pound of volatiles (VOLT) per 9 pounds of second solvent (SOLV2), so this would be a mixing mass ratio of 1/9 or 0.11; In embodiments, the mixing mass ratio of volatiles (VOLT) to the second solvent (SOLV2) ranges from 1 pound of volatiles (VOLT) per 10 pounds of second solvent (SOLV2), so this would be a mixing mass ratio of 1/10 or 0.1; In embodiments, the mixing mass ratio of volatiles (VOLT) to the second solvent (SOLV2) ranges from 1 pound of volatiles (VOLT) per 12 pounds of second solvent (SOLV2), so this would be a mixing mass ratio of 1/12 or 0.08; In embodiments, the mixing mass ratio of volatiles (VOLT) to the second solvent (SOLV2) ranges from 1 pound of volatiles (VOLT) per 14 pounds of second solvent (SOLV2), so this would be a mixing mass ratio of 1/14 or 0.07; In embodiments, the mixing mass ratio of volatiles (VOLT) to the second solvent (SOLV2) ranges from 1 pound of volatiles (VOLT) per 16 pounds of second solvent (SOLV2), so this would be a mixing mass ratio of 1/16 or 0.06; In embodiments, the mixing mass ratio of volatiles (VOLT) to the second solvent (SOLV2) ranges from 1 pound of volatiles (VOLT) per 20 pounds of second solvent (SOLV2), so this would be a mixing mass ratio of 1/20 or 0.05; In embodiments, the mixing mass ratio of volatiles (VOLT) to the second solvent (SOLV2) ranges from 1 pound of volatiles (VOLT) per 60 pounds of second solvent (SOLV2), so this would be a mixing mass ratio of 1/60 or 0.016; In embodiments, the mixing mass ratio of volatiles (VOLT) to the second solvent (SOLV2) ranges from 1 pound of volatiles (VOLT) per 100 pounds of second solvent (SOLV2), so this would be a mixing mass ratio of 1/100 or 0.01. In embodiments, the mixing mass ratio of pounds of volatiles (VOLT) per pounds of second solvent (SOLV2) ranges from 0.01 to 1.

A volatiles and solvent mixture (SVSM) is discharged from the interior (VSMSI) of the volatiles and solvent mixing system (VSMS). FIG. 17D shows one non-limiting embodiment of the separation system (SEPSOL) wherein the separation system (SEPSOL) is configured to separate the second solvent (SOLV2) from the volatiles and solvent mixture (SVSM). In embodiments, the separation system (SEPSOL) is configured to evaporate at least a portion of the solvent (SOLV2) from the volatiles and solvent mixture (SVSM) to create concentrated volatiles (CVOLT). In embodiments, the separation system (SEPSOL) is configured to evaporate at least a portion of the cannabinoids from the solvent (SOLV2) to create concentrated volatiles (CVOLT) including the separated cannabinoid.

Concentrated volatiles (CVOLT) have a reduced amount of second solvent (SOLV2) relative to the volatiles and solvent mixture (SVSM). The separation system (SEPSOL) is configured to separate the second solvent (SOLV2) from the volatiles and solvent mixture (SVSM) to concentrate the volatiles (VOLT). In embodiments, concentrated volatiles (CVOLT) are mixed with terpenes that were separated out in the volatiles extraction system (VES). In embodiments, concentrated volatiles (CVOLT) are mixed with insects and/or insect lipids. In embodiments, concentrated volatiles (CVOLT) may be sent to the cannabinoid tank for (6A3) as shown on FIG. 18, returned or recycled to the volatiles extraction system (VES) on any one of FIGS. 17A, 17A', 17B, 17D, 17H, or sent to solvent separation of FIG. 17E, cannabinoid extraction/purification of FIG. 17H, emulsion mixing of FIG. 17J, encapsulation of FIG. 17K, shaping, cooking flavoring of FIG. 18A-18D, to the mixing tank on FIG. 18E, combinations thereof.

The separation system (SEPSOL) is configured to separate the second solvent (SOLV2) from the volatiles and solvent mixture (SVSM) by evaporation, rotary evaporation, distillation, crystallization, vacuum flashing, or wiped film evaporation, wherein the distillation includes a distillation column, with trays, packing, or a wiper, or a spinning-band. In embodiments, a vacuum may be pulled on the separation system (SEPSOL) to aide in evaporation of the second solvent (SOLV2) from the volatiles and solvent mixture (SVSM), as shown in FIG. 17D.

The separation system (SEPSOL) is configured to separate the second solvent (SOLV2) from the volatiles and solvent mixture (SVSM) with a rotary evaporator, falling film tubular evaporator, rising/falling film tubular evaporator, rising film tubular evaporator, forced circulation evaporator, internal pump forced circulation evaporator, plate evaporator, evaporative cooler, multiple-effect evaporator, thermal vapor recompression evaporator, mechanical vapor recompression evaporator, flash tank, a crystallizer, a draft tube crystallizer, a draft tube and baffle crystallizer, cooling crystallization, evaporative crystallization, fractional crystallization, and a distillation column, wherein the distillation includes a distillation column, with trays, packing, or a wiper, or a spinning-band. In embodiments, the separation system (SEPSOL) is a distillation system. In embodiments, the separation system (SEPSOL) is short-path molecular distillation system.

In embodiments, the second solvent (SOLV2) and volatiles (e.g., the cannabinoid) (VOLT) are miscible. In embodiments, the second solvent (SOLV2) and cannabinoid within the volatiles (VOLT) are miscible. In embodiments, the second solvent (SOLV2) and terpenes within the volatiles (VOLT) are miscible. In embodiments, the second solvent (SOLV2) and wax within the volatiles (VOLT) are miscible. In embodiments, the second solvent (SOLV2) and wax within the volatiles (VOLT) are immiscible.

In instances where the second solvent (SOLV2) and wax within the volatiles (VOLT) are immiscible, a solvent cooler (SOLV-C) is provided to cool the volatiles and solvent mixture (SVSM) that is evacuated from the interior (VSMSI) of the volatiles and solvent mixing system (VSMS). The solvent cooler (SOLV-C) lowers the temperature of the volatiles and solvent mixture (SVSM) to permit phase separation of the wax from the volatiles (VOLT). The volatiles and solvent mixture (SVSM) is a reduced temperature second volatiles and solvent mixture (RTSVSM) as it is leaves the solvent cooler (SOLV-C). In embodiments, the solvent cooler (SOLV-C) cools the filtered volatiles and ethanol mixture (VOLT) to produce a chilled volatiles and ethanol mixture (VOLT1).

In embodiments, the solvent cooler (SOLV-C) operates at a temperature range including one or more ranges selected from the group consisting of: 32 degrees Fahrenheit to 0 degrees Fahrenheit, 0 degrees Fahrenheit to −10 degrees Fahrenheit, −10 degrees Fahrenheit to −20 degrees Fahrenheit, −20 degrees Fahrenheit to −30 degrees Fahrenheit, −30 degrees Fahrenheit to −40 degrees Fahrenheit, −40 degrees Fahrenheit to −50 degrees Fahrenheit, −50 degrees Fahrenheit to −75 degrees Fahrenheit, −75 degrees Fahrenheit to −100 degrees Fahrenheit, −100 degrees Fahrenheit to −125 degrees Fahrenheit, or −135 degrees Fahrenheit to −150 degrees Fahrenheit. In embodiments, the solvent cooler (SOLV-C) operates at a temperature less than 50 degrees F. In embodiments, the solvent cooler (SOLV-C) operates at a temperature less than 40 degrees F. In embodiments, the solvent cooler (SOLV-C) operates at a temperature less than 30 degrees F. In embodiments, the solvent cooler (SOLV-C) operates at a temperature less than 20 degrees F. In embodiments, the solvent cooler (SOLV-C) operates at a temperature less than 10 degrees F. In embodiments, the solvent cooler (SOLV-C) operates at a temperature less than 00 degrees F. In embodiments, the reduced temperature second volatiles and solvent mixture (RTSVSM) leaves the solvent cooler (SOLV-C) at a temperature including one or more from the group consisting of: less than 50 degrees F., less than 40 degrees F., less than 30 degrees F., less than 20 degrees F., less than 10 degrees F., and less than 0 degrees F.

In embodiments, a solvent filter (SOLV-F) is configured to accept at least a portion of the volatiles and solvent mixture (SVSM) and/or the chilled volatiles and ethanol mixture (VOLT1). In embodiments, a solvent filter (SOLV-F) is configured to accept at least a portion of the reduced temperature second volatiles and solvent mixture (RTSVSM). In embodiments, the solvent filter (SOLV-F) is configured to separate wax (WAX) from the volatiles and solvent mixture (SVSM) and/or the chilled volatiles and ethanol mixture (VOLT1). In embodiments, the solvent filter (SOLV-F) is configured to separate wax (WAX) from the reduced temperature second volatiles and solvent mixture (RTSVSM). The solvent filter (SOLV-F) discharges a volatiles and solvent mixture (SVSM) volatiles and solvent mixture (SVSM) which may then be routed to the separation system (SEPSOL) of FIG. 17D. In embodiments, the wax (WAX) is used to produce cosmetics, drugs, lip balm, food ingredients, animal foods, and topicals which may or may not include insect lipids and/or a fatty acid, wherein the insect lipids and/or a fatty acid include fatty acids or lipids including lauric acid, palmitic acid, linoleic acid, alpha-linoleic acid, oleic acid, gamma-linoleic acid, or stearic acid.

In embodiments, the wax separated in the solvent filter (SOLV-F) is separated under vacuum conditions. In embodiments, the vacuum conditions are provided by a vacuum system, aspirator, eductor, or an ejector. In embodiments, the aspirator is a type of ejector-jet pump, which produces vacuum by means of the venturi effect. In embodiments, the wax separated in the solvent filter (SOLV-F) is filtered with filter paper. In embodiments, the filter paper includes filter paper, polyethersulfone (PES) membrane filter, glass filter, polytetrafluoroethylene (PTFE) filter, quartz filter, or cellulose filter paper. In embodiments, the wax separated in the solvent filter (SOLV-F) is filtered with a mixed cellulose ester membranes are comprised of cellulose acetate and cellulose nitrate. In embodiments, the wax separated in the solvent filter (SOLV-F) wherein the solvent filter (SOLV-F) includes pore sizes ranging from between: 0.01 microns to 0.02 microns, 0.02 microns to 0.03 microns, 0.03 microns to 0.04 microns, 0.04 microns to 0.05 microns, 0.05 microns to 0.06 microns, 0.06 microns to 0.07 microns, 0.07 microns to 0.08 microns, 0.08 microns to 0.09 microns, 0.09 microns to 0.10 microns, 0.10 microns to 0.11 microns, 0.11 microns to 0.12 microns, 0.12 microns to 0.13 microns, 0.13 microns to 0.14 microns, 0.14 microns to 0.15 microns, 0.15 microns to 0.16 microns, 0.16 microns to 0.17 microns, 0.17 microns to 0.18 microns, 0.18 microns to 0.19 microns, 0.19 microns to 0.20 microns, 0.20 microns to 0.25 microns, 0.25 microns to 0.30 microns, 0.30 microns to 0.35 microns, 0.35 microns to 0.40 microns, 0.40 microns to 0.45 microns, 0.45 microns to 0.50 microns, or 0.50 microns to 0.60 microns.

In embodiments, the wax separated in the solvent filter (SOLV-F) has a melting point ranging including one or more melting point ranges selected from the group consisting of 75.00 degrees Fahrenheit 77.50 Fahrenheit, 77.50 degrees Fahrenheit 80.00 Fahrenheit, 80.00 degrees Fahrenheit 82.50 Fahrenheit, 82.50 degrees Fahrenheit 85.00 Fahrenheit, 85.00 degrees Fahrenheit 87.50 Fahrenheit, 87.50 degrees Fahrenheit 90.00 Fahrenheit, 90.00 degrees Fahrenheit 92.50 Fahrenheit, 92.50 degrees Fahrenheit 95.00 Fahrenheit, 95.00 degrees Fahrenheit 97.50 Fahrenheit, 97.50 degrees Fahrenheit 100.00 Fahrenheit, 100.00 degrees Fahrenheit 102.50 Fahrenheit, 102.50 degrees Fahrenheit 105.00 Fahrenheit, 105.00 degrees Fahrenheit 107.50 Fahrenheit, 107.50 degrees Fahrenheit 110.00 Fahrenheit, 110.00 degrees Fahrenheit 112.50 Fahrenheit, 112.50 degrees Fahrenheit 115.00 Fahrenheit, 115.00 degrees Fahrenheit 117.50 Fahrenheit, 117.50 degrees Fahrenheit 120.00 Fahrenheit, 120.00 degrees Fahrenheit 122.50 Fahrenheit, 122.50 degrees Fahrenheit 125.00 Fahrenheit, 125.00 degrees Fahrenheit 127.50 Fahrenheit, 127.50 degrees Fahrenheit 130.00 Fahrenheit, 130.00 degrees Fahrenheit 132.50 Fahrenheit, 132.50 degrees Fahrenheit 135.00 Fahrenheit, 135.00 degrees Fahrenheit 137.50 Fahrenheit, 137.50 degrees Fahrenheit 140.00 Fahrenheit, 140.00 degrees Fahrenheit 142.50 Fahrenheit, 142.50 degrees Fahrenheit 145.00 Fahrenheit, 145.00 degrees Fahrenheit 147.50 Fahrenheit, 147.50 degrees Fahrenheit 150.00 Fahrenheit, 150.00 degrees Fahrenheit 152.50 Fahrenheit, 152.50 degrees Fahrenheit 155.00 Fahrenheit, 155.00 degrees Fahrenheit 157.50 Fahrenheit, 157.50 degrees Fahrenheit 160.00 Fahrenheit, 160.00 degrees Fahrenheit 162.50 Fahrenheit, 162.50 degrees Fahrenheit 165.00 Fahrenheit, 165.00 degrees Fahrenheit 167.50 Fahrenheit, 167.50 degrees Fahrenheit 170.00 Fahrenheit, 170.00 degrees Fahrenheit 172.50 Fahrenheit, 172.50 degrees Fahrenheit 175.00 Fahrenheit, 175.00 degrees Fahrenheit 177.50 Fahrenheit, or 177.50 degrees Fahrenheit 180.00 Fahrenheit.

In embodiments, the wax separated in the solvent filter (SOLV-F) is further mixed with one or more waxes selected from the group consisting of *acacia decurrens* flower cera (*mimosa* flower wax), almond wax, avocado wax, beery wax, bees wax, *cananga odorata* flower cera (ylang ylang flower wax), candelilla wax, *Cannabis sativa* oil, castor wax, cupuacu butter, floral wax, hemp wax, hydrogenated almond oil, hydrogenated animal-based oils, hydrogenated apricot kernel oil, hydrogenated avocado oil, hydrogenated brazil nut oil, hydrogenated canola oil, hydrogenated cashew oil, hydrogenated cocoa butter, hydrogenated coconut oil, hydrogenated coffee oil, hydrogenated corn oil, hydrogenated cottonseed oil, hydrogenated grapeseed oil, hydrogenated hazelnut oil, hydrogenated hemp oil, hydrogenated hop oil, hydrogenated insect oil, hydrogenated lard oil, hydrogenated lard, hydrogenated macadamia nut oil, hydrogenated mustard oil, hydrogenated olive oil, hydrogenated palm kernel oil, hydrogenated palm oil, hydrogenated peanut oil, hydrogenated peppermint oil, hydrogenated rapeseed oil, hydrogenated rice bran oil, hydrogenated rice oil, hydrogenated safflower oil, hydrogenated semi-refined sesame oil, hydrogenated semi-refined sunflower oil, hydrogenated sesame oil, hydrogenated soybean oil, hydrogenated walnut oil, *jasminum grandiflorum* flower cera (jasmine flower wax), *Lavandula angustifolia* flower cera (lavender flower wax), mmyrica fruit wax, olive wax, *prunus* amygdalus *dulcis* oil, rapeseed wax, rice bran wax, rosa damascene flower cera (rose flower wax), shea butter, soybean wax, sunflower wax, vegan wax, vegetable wax, wax from Mexican shrub *Euphorbia* anti syphilitica, and wax from the berries of *rhus* verniciflua.

In embodiments, the wax separated in the solvent filter (SOLV-F) is used to make a consumer product, the consumer product includes wax separated in the solvent filter (SOLV-F) mixed with one or more waxes selected from the group consisting of *acacia decurrens* flower cera (*mimosa* flower wax), almond wax, avocado wax, beery wax, bees wax, *cananga odorata* flower cera (ylang ylang flower wax), candelilla wax, *Cannabis sativa* oil, castor wax, cupuacu butter, floral wax, hemp wax, hydrogenated almond oil, hydrogenated animal-based oils, hydrogenated apricot kernel oil, hydrogenated avocado oil, hydrogenated brazil nut oil, hydrogenated canola oil, hydrogenated cashew oil, hydrogenated cocoa butter, hydrogenated coconut oil, hydrogenated coffee oil, hydrogenated corn oil, hydrogenated cottonseed oil, hydrogenated grapeseed oil, hydrogenated hazelnut oil, hydrogenated hemp oil, hydrogenated hop oil, hydrogenated insect oil, hydrogenated lard oil, hydrogenated lard, hydrogenated macadamia nut oil, hydrogenated mustard oil, hydrogenated olive oil, hydrogenated palm kernel oil, hydrogenated palm oil, hydrogenated peanut oil, hydrogenated peppermint oil, hydrogenated rapeseed oil, hydrogenated rice bran oil, hydrogenated rice oil, hydrogenated safflower oil, hydrogenated semi-refined sesame oil, hydrogenated semi-refined sunflower oil, hydrogenated sesame oil, hydrogenated soybean oil, hydrogenated walnut oil, *jasminum grandiflorum* flower cera (jasmine flower wax), *Lavandula angustifolia* flower cera (lavender flower wax), mmyrica fruit wax, olive wax, *prunus* amygdalus *dulcis* oil, rapeseed wax, rice bran wax, rosa damascene flower cera (rose flower wax), shea butter, soybean wax, sunflower wax, vegan wax, vegetable wax, wax from Mexican shrub *Euphorbia* anti syphilitica, and wax from the berries of *rhus* verniciflua.

In embodiments, the wax separated in the solvent filter (SOLV-F) includes a mixture of hydrocarbon molecules containing between twenty and fifty carbon atoms. In embodiments, the wax separated in the solvent filter (SOLV-F) includes a mixture of hydrocarbon molecules containing between twenty and forty carbon atoms. In embodiments, the wax separated in the solvent filter (SOLV-F) includes an aliphatic ester. In embodiments, the wax separated in the solvent filter (SOLV-F) includes diesters of 4-hydroxycinnamic acid. In embodiments, the wax separated in the solvent filter (SOLV-F) includes w-hydroxycarboxylic acids. In embodiments, the wax separated in the solvent filter (SOLV-F) includes fatty alcohols. In embodiments, the wax separated in the solvent filter (SOLV-F) can be further processed by bleaching. In embodiments, the wax separated in the solvent filter (SOLV-F) can be further processed with hydrogen peroxide. In embodiments, the wax separated in the solvent filter (SOLV-F) can be further processed with a mixture of water and hydrogen peroxide. In embodiments, the wax separated in the solvent filter (SOLV-F) can be further processed with a mixture of treated water and hydrogen peroxide.

FIG. 17D

FIG. 17D shows a separation system (SEPSOL) that is configured to separate at least a portion of the solvent (SOLV2) and/or volatiles and/or cannabinoids from the volatiles and solvent mixture (SVSM) to produce concentrated volatiles (CVOLT). FIG. 17D shows a separation system (SEPSOL) that is configured to separate at least a portion of the cannabinoid from the volatiles and solvent mixture (SVSM) to produce concentrated volatiles (CVOLT).

In embodiments, the separation system (SEPSOL) includes an evaporator (J11). FIG. 17D shows at least a portion of the volatiles and solvent mixture (SVSM) transferred to the separation system (SEPSOL) from the volatiles and solvent mixing system (VSMS) shown in FIG. 17C. The volatiles and solvent mixture (SVSM) is transferred from the solvent cooler (SOLV-C) or from the solvent filter (SOLV-F) of FIG. 17C to the separation system (SEPSOL) of FIG. 17D.

FIG. 17D displays the separation system (SEPSOL) as an evaporator (J11) which separates or evaporates the second solvent (SOLV2) from the volatiles and solvent mixture (SVSM) to produce concentrated volatiles (CVOLT). FIG. 17D displays the separation system (SEPSOL) as an evaporator (J11) which separates or evaporates the cannabinoid from the from the volatiles and solvent mixture (SVSM) to produce concentrated volatiles (CVOLT).

In embodiments, the evaporator (J11) is a wiped-film evaporator (J11A). In embodiments, the evaporator (J11) is comprised of one or more from the group consisting of a rotary evaporator, falling film tubular evaporator, rising/falling film tubular evaporator, rising film tubular evaporator, forced circulation evaporator, internal pump forced circulation evaporator, plate evaporator, evaporative cooler, multiple-effect evaporator, thermal vapor recompression evaporator, mechanical vapor recompression evaporator, flash tank, a crystallizer, a draft tube and baffle crystallizer, cooling crystallization, evaporative crystallization, fractional crystallization, and a distillation column, wherein the distillation includes a distillation column, with trays, packing, or a wiper, or a spinning-band. In embodiments, the separation system (SEPSOL) is a distillation system. In embodiments, the separation system (SEPSOL) is short-path molecular distillation system.

In embodiments, the evaporator (J11) includes a forced circulation evaporator including one or more from the group consisting of a falling film tubular evaporator, rising/falling film tubular evaporator, rising film tubular evaporator, falling film evaporator, rising/falling film evaporator, rising film evaporator, internal pump forced circulation evaporator, plate evaporator, evaporative cooler, multiple-effect evaporator, thermal vapor recompression evaporator, mechanical vapor recompression evaporator, a crystallizer, a draft tube and baffle crystallizer, cooling crystallization, evaporative crystallization, fractional crystallization, and a distillation column, wherein the distillation includes a distillation column, with trays, packing, or a wiper, or a spinning-band.

In embodiments, the evaporator (J11) includes a two or more of the following in series including a forced circulation evaporator, falling film tubular evaporator, rising/falling film tubular evaporator, rising film tubular evaporator, falling film evaporator, rising/falling film evaporator, rising film evaporator, internal pump forced circulation evaporator, plate evaporator, evaporative cooler, multiple-effect evaporator, thermal vapor recompression evaporator, mechanical vapor recompression evaporator, a crystallizer, a draft tube and baffle crystallizer, cooling crystallization, evaporative crystallization, fractional crystallization, and a distillation column, wherein the distillation includes a distillation column, with trays, packing, or a wiper, or a spinning-band.

In embodiments, the evaporator (J11) includes a falling film tubular evaporator, rising/falling film tubular evaporator, rising film tubular evaporator, having a tube velocity ranging from 5 to 10 feet per second (ft/s), 10 to 15 ft/s, 15 to 20 ft/s, or 20 to 25 ft/s.

In embodiments, the distillation system includes spinning band distillation system which uses a spinning helical band made of an inert material such as metal, Teflon, composites, or other materials to push the rising vapors and descending condensate to the sides of the column, coming into close contact with each other. In embodiments, the distillation system includes a spinning band distillation system which uses a rotating helical band to create a high number of theoretical plates.

In embodiments, the cannabinoid can be distilled with via spinning band distillation, which is known to a person of ordinary skill in the art and available from a variety of commercial vendors including from: EquiLab Canada Inc., see B/R 9400 and 9600 High Efficiency Distillation Systems, (http://www.equilabcanada.com); or from https://www.alibaba.com, Model Number: HSPD-2000, 2L Turnkey Spinning Band Distillation Short Path Unit; or from BR Instrument, 9119 Centreville Road Easton, MD 21601 USA (https://brinstrument.com). In embodiments, the spinning band distillation system is equipped to distill a variety of throughputs.

In embodiments, the spinning band distillation system is an automatic controlled distillation column having: a volume ranging from 1 to 2 liters, 2 to 5 liters, 5 to 10 liters, 10 liters to 100 liters, 100 liters to 1000 liters, 1000 liters to 1500 liters, 1500 liters to 5000 liters; a column diameter ranging from 0.5 to 1 inch, 1 inch to 1.5 inches, 1.5 inches to 2.5 inches, 2.5 inches to 3.5 inches, 3.5 inches to 5 inches, 5 inches to 10 inches; a column length ranging from 5 inches to inches, 10 inches to 20 inches, 20 inches to 30 inches, 30 inches to 40 inches, 40 inches to 50 inches, 50 inches to 60 inches, 60 inches to 80 inches, 80 inches to 100 inches; maximum theoretical plates, with a Teflon spinning band 10 to 15 maximum theoretical plates, 15 to 30 maximum theoretical plates, 30 to 45 maximum theoretical plates, 45 to 60 maximum theoretical plates; maximum theoretical plates, with a metal band 10 to 15 maximum theoretical plates, 15 to maximum theoretical plates, 30 to 45 maximum theoretical plates, 45 to 60 maximum theoretical plates. In embodiments, the spinning band distillation system operates in batch mode or continuously. In embodiments, the spinning band distillation system includes a plurality of is generated from a boiler and/or a steam drum (such as shown on FIG. 17F), wherein the boiler can be electrically heated of natural gas heated. In embodiments, the spinning band distillation system is electrically heated and operates at a voltage of 110 volts, 120 volts, 220 volts. In embodiments, the spinning band distillation system operates under vacuum conditions.

In embodiments, the distillation column includes a packed distillation column including packing. In embodiments, the packing within the packed distillation column includes structured packing or random packing. In embodiments, the distillation column includes a vertically oriented cylindrical, or rectangular, pressure vessel having a lower section, and an upper section, along with a central section that contains packing or trays. In embodiments, the packing within the packed distillation column includes raschig rings, pall rings, berl saddles, intalox packing, metal structured grid packing, hollow spherical packing, high performance thermoplastic packing, structured packing, synthetic woven fabric, or ceramic packing, or the like, wherein media is supported upon a suitable support grid system. In embodiments, the distillation column includes trays. In embodiments, the trays include valve trays, sieve trays, and bubble cap trays. In embodiments, the sieve trays have holes, wherein the holes have a diameter ranging in size from 0.0625 to 0.125 inches, 0.125 inches to 0.25 inches, 0.25 to 0.375 inches, or 0.375 inches to 0.5 inches.

In embodiments, each tray includes a weir, wherein the weir height ranges from 0.25 to 0.5 inches, 0.5 to 0.75 inches, 0.75 to 1 inches, 1 to 1.25 inches, 1.25 to 1.5 inches, 1.5 to 1.75 inches, 1.75 to 2 inches, 2 to 3, 3 to 3.5 inches, or 3.5 to 4 inches. In embodiments, the distillation column includes 2 to 3 trays, 3 to 4 trays, 4 to 5 trays, 5 to 6 trays, 6 to 7 trays, 7 to 8 trays, 8 to 9 trays, 9 to 10 trays, 10 to 15 trays, 15 to 20 trays, 20 to 30 trays, 30 to 40 trays, or 40 to 50 trays. In embodiments, the pressure drop across each tray ranges from 0.025 to 0.05 pounds per square inch (PSI), 0.05 to 0.075 PSI, 0.075 to 0.1 PSI, 0.1 to 0.125 PSI, 0.125 to 0.105 PSI, 0.105 to 0.175 PSI, 0.175 to 0.2 PSI, 0.2 to 0.3 PSI. In embodiments, the distillation column includes a tray spacing ranging from 2 to 4 inches, 4 to 6 inches, 6 to 8 inches, 8 to 10 inches, 10 to 12 inches, 12 to 14 inches, 14 to 16 inches, 16 to 18 inches, or 18 to 20 inches, wherein the tray spacing is the vertical height between trays within the distillation column.

In embodiments, the distillation column includes a liquid rate of 0.25 to 0.5 gpm/ft2 (gallons per minute per square foot), 0.5 to 1 gpm/ft2, 1 to 2 gpm/ft2, 2 to 3 gpm/ft2, 3 to 4 gpm/ft2, 4 to 5 gpm/ft2, 5 to 10 gpm/ft2, 10 to 15 gpm/ft2, 15 to 20 gpm/ft2, 20 to 25 gpm/ft2, or 25 to 30 gpm/ft2. In embodiments, the distillation column includes a reflux to feed ratio ranging from 0.1 to 0.2 mol/mol, 0.2 to 0.3 mol/mol, 0.3 to 0.4 mol/mol, 0.4 to 0.5 mol/mol, 0.5 to 0.6 mol/mol, 0.6 to 0.7 mol/mol, 0.7 to 0.8 mol/mol, or 0.8 to 0.9 mol/mol. In embodiments, the distillation column includes a reflux ratio ranging from 1 to 1.1, 1.2 to 1.2, 1.2 to 1.3, 1.3 to 1.4, 1.4 to 1.5, 1.5 to 1.6, 1.6 to 1.7, 1.7 to 1.8, 1.8 to 1.9, or 1.9 to 2.0. In embodiments, the velocity through the trays within the distillation column include 0.5 to 1 feet per second (ft/s), 1 to 1.5 ft/s, 1.5 to 2 ft/s, 2 to 2.5 ft/s, 2.5 to 3 ft/s, 3 to 3.5 ft/s, 3.5 to 4 ft/s, 4 to 4.5 ft/s, 4.5 to 5 ft/s, 5 to 5.5 ft/s, 5.5 to 6 ft/s, 6 to 7 ft/s, 7 to 8 ft/s, 8 to 9 ft/s, or 9 to 10 ft/s.

In embodiments, when referring to the evaporator and/or the rotary evaporator in this disclosure, the evaporator and/or rotary evaporator may include one or more selected from the group consisting of: an evaporator and/or rotary evaporator provided by: BUCHI Labortechnik AG; Eyela Tokyo Rikakikai Co. Ltd; Heidolph Instruments Gmbh & Co. KG.; IKA Works, Inc.; KNF Neuberger, Inc.; Labfirst Scientific Instruments (Shanghai) Co., Ltd.; Xian Yuanjian Instrument Equipment Co., Ltd.; Labtech S.R.L.; Hydrion Scientific Instruments Co., Ltd.; Shanghai HJ Lab Instruments Co., Ltd.; Stewart Equipment Co Inc.; Thermo Fisher Scientific, Fisher Clinical Services Inc; or Cole Parmer Instrument Co Ltd.

In embodiments, when referring to the rotary evaporator in this disclosure, the rotary evaporator may include one or more evaporation flask volumes selected from the group consisting of: 1 liter to 2 liters, 2 liters to 3 liters, 3 liters to 4 liters, 4 liters to 5 liters, 5 liter to 10 liters, 10 liters to 20 liters, 20 liters to 30 liters, 30 liters to 40 liters, or 40 liters to 50 liters.

In embodiments, the throughput of concentrated volatiles (CVOLT) includes one or more throughputs selected from the group consisting of: 0.1 pounds per day to 0.2 pounds per day, 0.2 pounds per day to 0.4 pounds per day, 0.4 pounds per day to 0.8 pounds per day, 0.8 pounds per day to 1.0 pounds per day, 1 pounds per day to 2 pounds per day, 2 pounds per day to 4 pounds per day, 4 pounds per day to 8 pounds per day, 8 pounds per day to 16 pounds per day, 16 pounds per day to 32 pounds per day, 32 pounds per day to 64 pounds per day, 64 pounds per day to 128 pounds per day, 128 pounds per day to 256 pounds per day, 256 pounds per day to 512 pounds per day, 512 pounds per day to 1024 pounds per day, 1024 pounds per day to 2048 pounds per day, 2048 pounds per day to 4096 pounds per day, 4096 pounds per day to 8192 pounds per day, 8192 pounds per day to 16384 pounds per day, 16384 pounds per day to 32768 pounds per day, 32768 pounds per day to 65536 pounds per day, 65536 pounds per day to 131072 pounds per day, 131072 pounds per day to 262144 pounds per day, 262144 pounds per day to 524288 pounds per day, 524288 pounds per day to 1048576 pounds per day, 1048576 pounds per day to 2097152 pounds per day, and 2097152 pounds per day to 4194304 pounds per day.

In embodiments, the FSS produces *cannabis* at a rate of: 0.5 tons per day to 1 tons per day, 1 tons per day to 2 tons per day, 2 tons per day to 4 tons per day, 4 tons per day to 8 tons per day, 8 tons per day to 16 tons per day, 16 tons per day to 25 tons per day, 25 tons per day to 50 tons per day, 50 tons per day to 75 tons per day, 75 tons per day to 100 tons per day, 100 tons per day to 150 tons per day, 150 tons per day to 200 tons per day, 200 tons per day to 250 tons per day, 250 tons per day to 300 tons per day, 300 tons per day to 350 tons per day, 350 tons per day to 400 tons per day, 400 tons per day to 450 tons per day, 450 tons per day to 500 tons per day, 500 tons per day to 600 tons per day, 600 tons per day to 700 tons per day, 700 tons per day to 800 tons per day, 800 tons per day to 900 tons per day, 900 tons per day to 1000 tons per day, 1000 tons per day to 1500 tons per day, 1500 tons per day to 2000 tons per day, 2000 tons per day to 2500 tons per day, 2500 tons per day to 3000 tons per day, 3000 tons per day to 3500 tons per day, 3500 tons per day to 4000 tons per day, 4000 tons per day to 4500 tons per day, 4500 tons per day to 5000 tons per day, 5000 tons per day to 6000 tons per day, 6000 tons per day to 7000 tons per day, 7000 tons per day to 8000 tons per day, 8000 tons per day to 9000 tons per day, or 9000 tons per day to 10000 tons per day.

The evaporator (J11) shown in FIG. 17D is that of a wiped-film evaporator (J11A). The evaporator (J11) has a vapor inlet (J12), an input (J16), a heating jacket (J17), a first output (J18), and a second output (J19). In embodiments, the evaporator (J11) is electrically heated. In embodiments, the vapor inlet (J12) is provided with a vapor (J12A) such as steam. The vapor inlet is connected to a vapor supply conduit (J13). A vapor supply valve (J14) is positioned on the vapor supply conduit (J13). The vapor supply valve (J14) is equipped with a controller (J15A) that is configured to input and output a signal (J15B) to the computer (COMP). In embodiments, the pressure drop across the vapor supply valve (J14) ranges from between 5 PSI to 10 PSI, 15 PSI to 25 PSI, 25 PSI to 35 PSI, 35 PSI to 45 PSI, 45 PSI to 55 PSI, 55 PSI to 65 PSI, 65 PSI to 75 PSI, 75 PSI to 85 PSI. In embodiments, the vapor supply valve (J14) percent open during normal operation ranges from 10% open to 25% open, 25% open to 35% open, 35% open to 45% open, 45% open to 55% open, 55% open to 65% open, 65% open to 75% open, 75% open to 80% open. In embodiment, the volatiles and solvent mixture (SVSM) transferred from the solvent filter (SOLV-F) is heated with a heat exchanger (JDHK) before being introduced to the separation system (SEPSOL). In embodiments, the heat exchanger (JDHK) heats tetrahydrocannabinolic acid within the solvent mixture to decarboxylate the tetrahydrocannabinolic acid to form active tetrahydrocannabinol. In embodiments, tetrahydrocannabinolic acid within the solvent mixture may be decarboxylated to form active tetrahydrocannabinol before the solvent is separated by vacuum evaporation and after filtration to remove the wax.

A separated vapor transfer conduit (J20) is connected to the first output (J18) and is configured to transfer vaporized solvent (J22) from the evaporator (J11) to a condenser (J26). In embodiments, the vaporized solvent (J22) is the second solvent (SOLV2) in vapor phase. When the second solvent (SOLV2) is evaporated or vaporized into a vaporized solvent (J22) the concentration of the volatiles (VOLT) within the volatiles and solvent mixture (SVSM) increases to form concentrated volatiles (CVOLT).

The condenser (J26) has a vaporized liquid input (J25) that is configured to transfer the vaporized solvent (J22) or vaporized second solvent (SOLV2), and/or the cannabinoid vaporized from the second solvent (SOLV2), from the separated vapor transfer conduit (J20) to the condenser (J26). The condenser (J26) is configured to accept vaporized solvent (J22) from the evaporator (J11) and condense the liquid into condensate (J27). In embodiments, the condensate (J27) is discharged from the condenser (J26) via a condenser condensate output (J30). In embodiments, the condensate (J27) includes the cannabinoid and is discharged from the condenser (J26) via a condenser condensate output (J30). In embodiments, the condensate (J27) is the second solvent (SOLV2) which can then be recovered and reused in the volatiles and solvent mixing system (VSMS). In embodiments, the condensate (J27) is are the concentrated volatiles (CVOLT) which may be sent to the cannabinoid tank for (6A3) as shown on FIG. 18, returned or recycled to the volatiles extraction system (VES) on any one of FIGS. 17A, 17A', 17B, 17D, 17H, or sent to solvent separation of FIG. 17E, cannabinoid extraction/purification of FIG. 17H, emulsion mixing of FIG. 17J, encapsulation of FIG. 17K, shaping, cooking flavoring of FIG. 18A-18D, to the mixing tank on FIG. 18E, combinations thereof.

The condenser is connected to a vacuum system (J32) via a gas/vapor transfer conduit (J33). Gas/vapor (J35) is evacuated from the condenser (J27) via a gas/vapor discharge (J37). The gas/vapor (J35) transferred from the condenser (J26) to the vacuum system (J32) may be comprised of one or more from the group consisting of second solvent, carbon dioxide, nitrogen, air, steam, water vapor, and non-condensables. The vacuum system (J32) may be any conceivable system configured to draw a vacuum on the condenser (J26). In embodiments, the vacuum system (J32) is that of a liquid-ring vacuum pump. A portion of the gas/vapor (J35) may be in turn condensed within the vacuum system (J26). A portion of the gas/vapor (J35) may be discharged from the vacuum system (J26) via a gas/vapor transfer line (J39).

In embodiments, the vacuum system (J32) pulls a vacuum on the evaporator (J11) at a pressure ranging from 0.25 pounds per square inch absolute (PSIA) to 0.0000005 PSIA to PSIA, 0.000005 PSIA to 0.00005 PSIA, 0.00005 PSIA to 0.0005 PSIA, 0.0005 PSIA to PSIA, 0.005 PSIA to 0.05 PSIA, 0.05 PSIA to 0.5 PSIA, 0.5 PSIA, 0.5 PSIA to 1 PSIA, 1 PSIA to 1.5 PSIA, 1.5 PSIA to 3 PSIA, 3 PSIA to 4.5 PSIA, 4.5 PSIA to 6 PSIA, 6 PSIA to 7.5 PSIA, 7.5 PSIA to 9 PSIA, 9 PSIA to 10.5 PSIA, 10.5 PSIA to 12 PSIA, 12 PSIA to 13.5 PSIA, 12 PSIA to 12.25 PSIA, 12.25 PSIA to 12.5 PSIA, 12.5 PSIA to 12.75 PSIA, 12.75 PSIA to 13 PSIA, 13 PSIA to 13.25 PSIA, 13.25 PSIA to 13.5 PSIA, 13.5 PSIA to 13.75 PSIA, 13.75 PSIA to 14 PSIA, 14 PSIA to 14.25 PSIA, 14.25 PSIA to 14.5 PSIA, or 14.5 PSIA to 14.75 PSIA.

The condenser (J26) is provided with a coolant input (J36) and a coolant output (J40). The coolant input (J36) is configured to accept a coolant supply (J38) and the coolant output (J40) is configured to discharge a coolant return (J42). The coolant supply (J38) is configured to reduce the temperature of the vaporized solvent (J22) within the condenser (J26) to convert the vaporized solvent (J22) into a liquid condensate (J27). In embodiments, the coolant includes treated water and a mixture of In embodiments, the coolant includes water. In embodiments, the coolant includes a mixture of treated water and glycerol, ethanol, methanol, glycerol, ethylene glycol, a glycol, propylene glycol, an alcohol, anti-freeze fluid, or a water-based synthetic liquid. In embodiments, the anti-freeze fluid includes mono ethylene glycol, or ono propylene glycol. In embodiments, the coolant includes a corrosion inhibitor.

In embodiments, a chiller (J26) recycles the coolant from the condenser to the chiller to maintain a constant temperature within the condenser (J26) to convert the vaporized solvent (J22) into a liquid condensate (J27), wherein the liquid condensate includes either the solvent and/or the cannabinoid, e.g., the concentrated volatiles. In embodiments, the liquid condensate (J27) condensed in the condenser is reused in the *cannabis* solvent extraction process.

In embodiments, the chiller (J26) provides a coolant to the condenser (J26), wherein the coolant has a temperature entering the coolant input (J36) of the condenser (J26) at a temperature ranging from 60 degrees Fahrenheit to 40 degrees Fahrenheit, 40 degrees Fahrenheit to 32 degrees Fahrenheit, 32 degrees Fahrenheit to 0 degrees Fahrenheit, 0 degrees Fahrenheit to −10 degrees Fahrenheit, −10 degrees Fahrenheit to −20 degrees Fahrenheit, −20 degrees Fahrenheit to −30 degrees Fahrenheit, −30 degrees Fahrenheit to −40 degrees Fahrenheit, −40 degrees Fahrenheit to −50 degrees Fahrenheit, −50 degrees Fahrenheit to −75 degrees Fahrenheit, −75 degrees Fahrenheit to −100 degrees Fahrenheit, −100 degrees Fahrenheit to −125 degrees Fahrenheit, or −135 degrees Fahrenheit to −150 degrees Fahrenheit.

In embodiments, a cold trap (J32) is installed in between the gas/vapor discharge (J37) of the condenser (J26) and the vacuum system (J32). The cold trap (J32) condenses any additional vapor within the gas/vapor (J35) so that no condensation occurs in the vacuum system (J26). In embodiments, a cold trap (J32) is installed in between the gas/vapor discharge (J37) of the condenser (J26) and the vacuum system (J32). The cold trap (J32) condenses any additional vapor within the gas/vapor (J35) so that no condensation occurs in the vacuum system (J26) to as to maximize the recovery of solvent within to reuse in the extraction of cannabinoids from the *cannabis*. In embodiments, a cold trap (J32) includes dry ice and a solvent, wherein the dry ice contacts the gas/vapor (J35) to condense solvent (and/or the cannabinoid). In embodiments, a cold trap (J32) includes dry ice and a solvent, wherein the solvent includes one or more selected from the group consisting of glycerol, ethanol, methanol, glycerol, ethylene glycol, a glycol, propylene glycol, an alcohol, anti-freeze fluid, or a water-based synthetic liquid.

The evaporator (J11) has an evaporator condensate output (J24) for evacuating condensate (J41) from the heating jacket (J17). The condensate (J41) discharged via the evaporator condensate output (J24) was provided to the evaporator heating jacket (J17) as the vapor (J12A) or steam. The heating jacket (J17) accepts a source of vapor (J12A), and evaporates second solvent (SOLV2) (or a cannabinoid) from the volatiles and solvent mixture (SVSM) to form vaporized solvent (J22) (or a vaporized cannabinoid) that is discharged from the evaporator (J11) and sent to the condenser (J26).

The heating jacket (J17) accepts a source of vapor (J12A), and evaporates second solvent (SOLV2) from the volatiles and solvent mixture (SVSM) to form concentrates volatiles (CVOLT) that has a reduced amount of second solvent (SOLV2) relative to the volatiles and solvent mixture (SVSM).

In embodiments, the evaporator (J11) takes the form of a wiped-film evaporator (J11A). In embodiments, the evaporator (J11) takes the form of a wiped-film distillation system (J11A). In embodiments, the wiped-film evaporator (J11A) has a motor (J42) and a wiper (J44). In embodiments, the motor (J42) and wiper (J44) act together to wipe at least one heat transfer surface within the evaporator (J11). In embodiments, the wiped-film evaporator includes a high vacuum (short path) distillation system. In embodiments, the wiped-film evaporator allows for short path evaporation (molecular distillation). In embodiments, the wiped-film evaporator includes a wper including a slotted wiper blade. In embodiments, the wiped-film evaporator is ideal for heat sensitive, high boiling, fouling, and viscous materials such as cannabinoids. In embodiments, the wiped-film evaporator includes: a size ranging, in square feet, ranging from 1 to 2, 2 to 5, 5 to 10, to 50, 50 to 100, 100 to 200, 200 o 300, 300 to 400, 400 to 500; and a jacket pressure, in pounds per square inch, ranging from 10 to 20, 20 to 40, 40 to 50, 50 to 100, 125 to 150, 150 to 100.

The input (J16) is configured to introduce the volatiles and solvent mixture (SVSM) to the evaporator (J11). In embodiments, the evaporator vaporizes the second solvent (SOLV2) from within the volatiles and solvent mixture (SVSM) to produce a vaporized solvent (J22) and concentrated volatiles (CVOLT).

In embodiments, the present disclosure describes a method to separate volatiles from *cannabis*, the method includes:
- (a) providing a source of *cannabis*;
- (b) after step (a), grinding the *cannabis* to form ground *cannabis*;
- (c) after step (b), extracting volatiles from the ground *cannabis* with a first solvent to form a first solvent and volatiles mixture; and
- (d) after step (c), separating at least a portion of the volatiles from the first solvent and volatiles mixture;

wherein:
  the volatiles include one or more from the group consisting of oil, wax, terpenes; the first solvent (SOLV1) includes one or more from the group consisting of acetone, alcohol, oil, butane, butter, carbon dioxide, coconut oil, ethanol, gas, gaseous carbon dioxide, hexane, insect lipids, isobutane, isopropanol, liquid carbon dioxide, liquid, naphtha, olive oil, pentane, propane, R134 refrigerant gas, subcritical carbon dioxide, supercritical carbon dioxide, vapor.

In embodiments, the present disclosure describes a method to separate volatiles from *cannabis*, the method includes:
- (a) providing INSECTERGY III or *cannabis*;
- (b) grinding INSECTERGY III or *cannabis* after step (a);
- (c) extracting volatiles (VOLT) from INSECTERGY III or *cannabis* after step (b) with a first solvent (SOLV1) to form a first solvent and volatiles mixture (FSVM);
- (d) separating at least a portion of the volatiles (VOLT) from the first solvent and volatiles mixture (FSVM);
- (e) mixing the volatiles with a second solvent (SOLV2) after step (d) to form a volatiles and solvent mixture (SVSM);
- (f) cooling the volatiles and solvent mixture (SVSM) after step (e);
- (g) filtering the volatiles and solvent mixture (SVSM); and
- (h) evaporating the second solvent (SOLV2) and/or the cannabinoid from the volatiles and solvent mixture (SVSM).

In embodiments, the present disclosure describes a method to separate volatiles from *cannabis*, the method includes:
- (a) providing INSECTERGY III or *cannabis*;
- (b) grinding INSECTERGY III or *cannabis* after step (a); and
- (c) extracting volatiles (VOLT) from INSECTERGY III or *cannabis* after step (b) with a first solvent (SOLV1) to form a first solvent and volatiles mixture (FSVM);
- (d) separating at least a portion of the volatiles (VOLT) from the first solvent and volatiles mixture (FSVM);
- (e) mixing the volatiles with a second solvent (SOLV2) after step (d) to form a volatiles and solvent mixture (SVSM);
- (f) separating at least a portion of the volatiles (VOLT) from the second solvent (SOLV2).

In embodiments, the present disclosure describes a method to separate volatiles from *cannabis*, the method includes:
- (a) providing INSECTERGY III or *cannabis*;
- (b) grinding INSECTERGY III or *cannabis* after step (a);
- (c) extracting volatiles (VOLT) from INSECTERGY III or *cannabis* after step (b) with a first solvent (SOLV1) to form a first solvent and volatiles mixture (FSVM);
- (d) separating at least a portion of the volatiles (VOLT) from the first solvent and volatiles mixture (FSVM);
- (e) producing a foodstuff from the volatiles (VOLT).

In embodiments, the present disclosure describes a method to separate volatiles from *cannabis*, the method includes:
- (a) providing INSECTERGY III or *cannabis*;
- (b) grinding INSECTERGY III or *cannabis* after step (a);
- (c) extracting volatiles (VOLT) from INSECTERGY III or *cannabis* after step (b) with a first solvent (SOLV1) to form a first solvent and volatiles mixture (FSVM);
- (d) separating at least a portion of the volatiles (VOLT) from the first solvent and volatiles mixture (FSVM);
- (e) mixing the volatiles (VOLT) with a second solvent (SOLV2) after step (d) to form a volatiles and solvent mixture (SVSM);
- (f) separating at least a portion of the volatiles (VOLT) from the volatiles and solvent mixture (SVSM).

In embodiments, the present disclosure describes a method to separate volatiles from *cannabis*, the method includes:
- (a) providing INSECTERGY III or *cannabis*;
- (b) grinding INSECTERGY III or *cannabis* after step (a); and (c) extracting volatiles (VOLT) from INSECTERGY III or *cannabis* after step (b) with a first solvent (SOLV1) to form a first solvent and volatiles mixture (FSVM);
- (d) separating at least a portion of the volatiles (VOLT) from the first solvent and volatiles mixture (FSVM);
- (e) mixing the volatiles (VOLT) with a second solvent (SOLV2) after step (d) to form a volatiles and solvent mixture (SVSM);
- (f) evaporating at least a portion of the second solvent (SOLV2) from the volatiles and solvent mixture (SVSM) to create concentrated volatiles (CVOLT) that have reduced amount of second solvent relative to the volatiles and solvent mixture (SVSM).

In embodiments, the present disclosure describes a method to separate volatiles from *cannabis*, the method includes:
- (a) providing a farming superstructure system (FSS), including:
  - (a1) a first water treatment unit (A1) including a cation configured to remove positively charged ions from water to form a positively charged ion depleted water (06A), the positively charged ions are comprised of one or more from the group consisting of calcium, magnesium, sodium, and iron;
  - (a2) a second water treatment unit (A2) including an anion configured to remove negatively charged ions from the positively charged ion depleted water (06A) to form a negatively charged ion depleted water (09A), the negatively charged ions are comprised of one or more from the group consisting of iodine, chloride, and sulfate;

(a3) an optional third water treatment unit (A3) including a membrane configured to remove undesirable compounds from the negatively charged ion depleted water (09A) to form an undesirable compounds depleted water (12A), the undesirable compounds are comprised of one or more from the group consisting of dissolved organic chemicals, viruses, bacteria, and particulates;

(a4) an enclosure (ENC) having an interior (ENC1);

(a5) a plurality of growing assemblies (100, 200) positioned within the interior (ENC1) of the enclosure (ENC), each growing assembly (100, 200) configured to grow INSECTERGY III (107, 207) or *cannabis* (107, 207);

(a6) a plurality of lights (L1, L2) configured to illuminate the interior (ENC1) of the enclosure (ENC);

(a7) a volatiles extraction system (VES) that is configured to separate volatiles (VOLT) from INSECTERGY III (107, 207) or *cannabis* (107, 207) with use of a first solvent (SOLV1), the volatiles extraction system (VES) has an interior (VESI) that is configured to contain INSECTERGY III (107, 207) or *cannabis* (107, 207), the volatiles extraction system (VES) is configured to accept a first solvent (SOLV1), the first solvent (SOLV1) is configured to contact the INSECTERGY III (107, 207) or *cannabis* (107, 207) within the interior (VEST) of the volatiles extraction system (VES), the volatiles extraction system (VES) outputs a first solvent and volatiles mixture (FSVM);

(a8) a first solvent separation system (SSS) that is configured to separate the volatiles (VOLT) from the first solvent and volatiles mixture (FSVM), the first solvent separation system (SSS) has an interior (SSSI), the first solvent and volatiles mixture (FSVM) is transferred from the interior (VEST) of the volatiles extraction system (VES) to the interior (SSSI) of the first solvent separation system (SSS), the first solvent separation system (SSS) outputs a volatiles (VOLT) and a separated first solvent (SOLV1-S);

(a9) a volatiles and solvent mixing system (VSMS) that is configured to mix the volatiles (VOLT) with a second solvent (SOLV2), the volatiles (VOLT) that are introduced to the interior (VSMSI) of the volatiles and solvent mixing system (VSMS) are transferred from the volatiles extraction systems (VES), a second volatiles and solvent mixture (SVSM) is discharged from the interior (VSMSI) of the volatiles and solvent mixing system (VSMS);

(a10) a second solvent separation system (SEPSOL) that is configured to separate at least a portion of the second solvent (SOLV2) from the second volatiles and solvent mixture (SVSM) to produce concentrated volatiles (CVOLT);

(b) providing a source of water;

(c) removing positively charged ions and negatively charged ions and optionally undesirable compounds from the water of step (b);

(d) mixing the water after step (c) with macro-nutrients, micro-nutrients, or a pH adjustment solution to form a liquid mixture;

(e) pressurizing the liquid mixture after step (d) to form a pressurized liquid mixture;

(f) transferring the pressurized liquid mixture of step (e) to the plurality of growing assemblies; and (g) illuminating the plurality of growing assemblies (100, 200) with the plurality of lights;

(h) growing INSECTERGY III or *cannabis* within the plurality of growing assemblies after step (g);

(i) harvesting INSECTERGY III or *cannabis* after growing INSECTERGY III or *cannabis* in step (h);

(j) grinding INSECTERGY III or *cannabis* after step (i); and (k) extracting volatiles (VOLT) from INSECTERGY III or *cannabis* after step (j) with a first solvent (SOLV1) to form a first solvent and volatiles mixture (FSVM);

(l) separating at least a portion of the volatiles (VOLT) from the first solvent and volatiles mixture (FSVM);

(m) mixing the volatiles (VOLT) with a second solvent (SOLV2) after step (l) to form a volatiles and solvent mixture (SVSM);

(n) cooling the volatiles and solvent mixture (SVSM) after step (m);

(o) filtering the volatiles and solvent mixture (SVSM) after step (n);

(p) evaporating the second solvent (SOLV2) from the second volatiles and solvent mixture (SVSM).

In embodiments, the present disclosure describes a method to separate volatiles from *cannabis*, the method includes:

(a) providing a farming superstructure system (FSS), including:

(a1) a cation configured to remove positively charged ions from water to form a positively charged ion depleted water (06A), the positively charged ions are comprised of one or more from the group consisting of calcium, magnesium, sodium, and iron;

(a2) an anion configured to remove negatively charged ions from the positively charged ion depleted water (06A) to form a negatively charged ion depleted water (09A), the negatively charged ions are comprised of one or more from the group consisting of iodine, chloride, and sulfate;

(a3) a membrane configured to remove undesirable compounds from the negatively charged ion depleted water (09A) to form an undesirable compounds depleted water (12A), the undesirable compounds are comprised of one or more from the group consisting of dissolved organic chemicals, viruses, bacteria, and particulates;

(a4) an enclosure (ENC) having an interior (ENC1);

(a5) a plurality of growing assemblies (100, 200) positioned within the interior (ENC1) of the enclosure (ENC), each growing assembly (100, 200) configured to grow INSECTERGY III (107, 207) or *cannabis* (107, 207);

(a6) a plurality of lights (L1, L2) configured to illuminate the interior (ENC1) of the enclosure (ENC);

(a7) a volatiles extraction system (VES) that is configured to separate volatiles (VOLT) from INSECTERGY III (107, 207) or *cannabis* (107, 207) with use of a first solvent (SOLV1), the volatiles extraction system (VES) has an interior (VEST) that is configured to contain INSECTERGY III (107, 207) or *cannabis* (107, 207), the volatiles extraction system (VES) is configured to accept a first solvent (SOLV1), the first solvent (SOLV1) is configured to contact the INSECTERGY III (107, 207) or *cannabis* (107, 207) within the interior (VEST) of the volatiles extraction system (VES), the volatiles extraction system (VES) outputs a first solvent and volatiles mixture (FSVM);

(a8) a first solvent separation system (SSS) that is configured to separate the volatiles (VOLT) from the first solvent and volatiles mixture (FSVM), the first solvent separation system (SSS) has an interior (SSSI), the first solvent and volatiles mixture (FSVM) is transferred from the interior (VEST) of the volatiles extraction system (VES) to the interior (SSSI) of the first solvent separation system (SSS), the first solvent separation system (SSS) outputs a volatiles (VOLT) and a separated first solvent (SOLV1-S);

(a9) a volatiles and solvent mixing system (VSMS) that is configured to mix the volatiles (VOLT) with a second solvent (SOLV2), the volatiles (VOLT) that are introduced to the interior (VSMSI) of the volatiles and solvent mixing system (VSMS) are transferred from the volatiles extraction systems (VES), a second volatiles and solvent mixture (SVSM) is discharged from the interior (VSMSI) of the volatiles and solvent mixing system (VSMS);

(a10) a second solvent separation system (SEPSOL) that is configured to separate at least a portion of the second solvent (SOLV2) from the second volatiles and solvent mixture (SVSM) to produce concentrated volatiles (CVOLT);

(b) providing a source of water;

(c) removing positively charged ions and negatively charged ions and optionally undesirable compounds from the water of step (b);

(d) mixing the water after step (c) with macro-nutrients, micro-nutrients, or a pH adjustment solution to form a liquid mixture;

(e) pressurizing the liquid mixture after step (d) to form a pressurized liquid mixture;

(f) transferring the pressurized liquid mixture of step (e) to the plurality of growing assemblies; and (g) illuminating the plurality of growing assemblies (100, 200) with the plurality of lights (L1, L2);

(h) growing INSECTERGY III or *cannabis* within the plurality of growing assemblies after step (g);

(i) harvesting INSECTERGY III or *cannabis* after growing INSECTERGY III or *cannabis* in step (h);

(j) grinding INSECTERGY III or *cannabis* after step (i); and (k) extracting volatiles (VOLT) from INSECTERGY III or *cannabis* after step (j) with a first solvent (SOLV1) to form a first solvent and volatiles mixture (FSVM);

(l) separating at least a portion of the volatiles (VOLT) from the first solvent and volatiles mixture (FSVM).

In embodiments, the present disclosure describes a method to separate volatiles from *cannabis*, the method includes:

(a) providing a farming superstructure system (FSS), including:

(a1) a first water treatment unit (A1) including a cation configured to remove positively charged ions from water to form a positively charged ion depleted water (06A), the positively charged ions are comprised of one or more from the group consisting of calcium, magnesium, sodium, and iron;

(a2) a second water treatment unit (A2) including an anion configured to remove negatively charged ions from the positively charged ion depleted water (06A) to form a negatively charged ion depleted water (09A), the negatively charged ions are comprised of one or more from the group consisting of iodine, chloride, and sulfate;

(a3) an optional third water treatment unit (A3) including a membrane configured to remove undesirable compounds from the negatively charged ion depleted water (09A) to form an undesirable compounds depleted water (12A), the undesirable compounds are comprised of one or more from the group consisting of dissolved organic chemicals, viruses, bacteria, and particulates;

(a4) an enclosure (ENC) having an interior (ENC1);

(a5) a plurality of growing assemblies (100, 200) positioned within the interior (ENC1) of the enclosure (ENC), each growing assembly (100, 200) configured to grow INSECTERGY III (107, 207) or *cannabis* (107, 207);

(a6) a plurality of lights (L1, L2) configured to illuminate the interior (ENC1) of the enclosure (ENC);

(a7) a volatiles extraction system (VES) that is configured to separate volatiles (VOLT) from INSECTERGY III (107, 207) or *cannabis* (107, 207) with use of a first solvent (SOLV1), the volatiles extraction system (VES) has an interior (VESI) that is configured to contain INSECTERGY III (107, 207) or *cannabis* (107, 207), the volatiles extraction system (VES) is configured to accept a first solvent (SOLV1), the first solvent (SOLV1) is configured to contact the INSECTERGY III (107, 207) or *cannabis* (107, 207) within the interior (VESI) of the volatiles extraction system (VES), the volatiles extraction system (VES) outputs a first solvent and volatiles mixture (FSVM);

(a8) a first solvent separation system (SSS) that is configured to separate the volatiles (VOLT) from the first solvent and volatiles mixture (FSVM), the first solvent separation system (SSS) has an interior (SSSI), the first solvent and volatiles mixture (FSVM) is transferred from the interior (VEST) of the volatiles extraction system (VES) to the interior (SSSI) of the first solvent separation system (SSS), the first solvent separation system (SSS) outputs a volatiles (VOLT) and a separated first solvent (SOLV1-S);

(a9) a volatiles and solvent mixing system (VSMS) that is configured to mix the volatiles (VOLT) with a second solvent (SOLV2), the volatiles (VOLT) that are introduced to the interior (VSMSI) of the volatiles and solvent mixing system (VSMS) are transferred from the volatiles extraction systems (VES), a second volatiles and solvent mixture (SVSM) is discharged from the interior (VSMSI) of the volatiles and solvent mixing system (VSMS);

(a10) a second solvent separation system (SEPSOL) that is configured to separate at least a portion of the second solvent (SOLV2) from the second volatiles and solvent mixture (SVSM) to produce concentrated volatiles (CVOLT);

(b) providing a source of water;

(c) removing positively charged ions and negatively charged ions and optionally undesirable compounds from the water of step (b);

(d) mixing the water after step (c) with macro-nutrients, micro-nutrients, or a pH adjustment solution to form a liquid mixture;

(e) pressurizing the liquid mixture after step (d) to form a pressurized liquid mixture;

(f) transferring the pressurized liquid mixture of step (e) to the plurality of growing assemblies; and (g) illuminating the plurality of growing assemblies (100, 200) with the plurality of lights (L1, L2);

(h) growing INSECTERGY III or *cannabis* within the plurality of growing assemblies after step (g);

(i) harvesting INSECTERGY III or *cannabis* after growing INSECTERGY III or *cannabis* in step (h);

(j) grinding INSECTERGY III or *cannabis* after step (i); and (k) extracting volatiles (VOLT) from INSECTERGY III or *cannabis* after step (j) with a first solvent (SOLV1) to form a first solvent and volatiles mixture (FSVM);

(l) separating at least a portion of the volatiles (VOLT) from the first solvent and volatiles mixture (FSVM);

(m) mixing the volatiles with a second solvent (SOLV2) after step (l) to form a second volatiles and solvent mixture (SVSM); and (n) separating at least a portion of the volatiles (VOLT) from the second volatiles and solvent mixture (SVSM).

In embodiments, the present disclosure describes a method to separate volatiles from *cannabis*, the method includes:

(a) providing a farming superstructure system (FSS), including:

(a1) a first water treatment unit (A1) including a cation configured to remove positively charged ions from water to form a positively charged ion depleted water (06A), the positively charged ions are comprised of one or more from the group consisting of calcium, magnesium, sodium, and iron;

(a2) a second water treatment unit (A2) including an anion configured to remove negatively charged ions from the positively charged ion depleted water (06A) to form a negatively charged ion depleted water (09A), the negatively charged ions are comprised of one or more from the group consisting of iodine, chloride, and sulfate;

(a3) an optional third water treatment unit (A3) including a membrane configured to remove undesirable compounds from the negatively charged ion depleted water (09A) to form an undesirable compounds depleted water (12A), the undesirable compounds are comprised of one or more from the group consisting of dissolved organic chemicals, viruses, bacteria, and particulates;

(a4) an enclosure (ENC) having an interior (ENC1);

(a5) a plurality of growing assemblies (100, 200) positioned within the interior (ENC1) of the enclosure (ENC), each growing assembly (100, 200) configured to grow INSECTERGY III (107, 207) or *cannabis* (107, 207);

(a6) a plurality of lights (L1, L2) configured to illuminate the interior (ENC1) of the enclosure (ENC);

(a7) a volatiles extraction system (VES) that is configured to separate volatiles (VOLT) from INSECTERGY III (107, 207) or *cannabis* (107, 207) with use of a first solvent (SOLV1), the volatiles extraction system (VES) has an interior (VESI) that is configured to contain INSECTERGY III (107, 207) or *cannabis* (107, 207), the volatiles extraction system (VES) is configured to accept a first solvent (SOLV1), the first solvent (SOLV1) is configured to contact the INSECTERGY III (107, 207) or *cannabis* (107, 207) within the interior (VEST) of the volatiles extraction system (VES), the volatiles extraction system (VES) outputs a first solvent and volatiles mixture (FSVM);

(a8) a first solvent separation system (SSS) that is configured to separate the volatiles (VOLT) from the first solvent and volatiles mixture (FSVM), the first solvent separation system (SSS) has an interior (SSSI), the first solvent and volatiles mixture (FSVM) is transferred from the interior (VESI) of the volatiles extraction system (VES) to the interior (SSSI) of the first solvent separation system (SSS), the first solvent separation system (SSS) outputs a volatiles (VOLT) and a separated first solvent (SOLV1-S);

(a9) a volatiles and solvent mixing system (VSMS) that is configured to mix the volatiles (VOLT) with a second solvent (SOLV2), the volatiles (VOLT) that are introduced to the interior (VSMSI) of the volatiles and solvent mixing system (VSMS) are transferred from the volatiles extraction systems (VES), a second volatiles and solvent mixture (SVSM) is discharged from the interior (VSMSI) of the volatiles and solvent mixing system (VSMS);

(a10) a second solvent separation system (SEPSOL) that is configured to separate at least a portion of the second solvent (SOLV2) from the second volatiles and solvent mixture (SVSM) to produce concentrated volatiles (CVOLT);

(b) providing a source of water;

(c) removing positively charged ions and negatively charged ions and optionally undesirable compounds from the water of step (b);

(d) mixing the water after step (c) with macro-nutrients, micro-nutrients, or a pH adjustment solution to form a liquid mixture;

(e) pressurizing the liquid mixture after step (d) to form a pressurized liquid mixture;

(f) transferring the pressurized liquid mixture of step (e) to the plurality of growing assemblies; and (g) illuminating the plurality of growing assemblies (100, 200) with the plurality of lights (L1, L2);

(h) growing INSECTERGY III or *cannabis* within the plurality of growing assemblies after step (g);

(i) harvesting INSECTERGY III or *cannabis* after growing INSECTERGY III or *cannabis* in step (h);

(j) grinding INSECTERGY III or *cannabis* after step (i); and (k) extracting volatiles (VOLT) from INSECTERGY III or *cannabis* after step (j) with a first solvent (SOLV1) to form a first solvent and volatiles mixture (FSVM);

(l) separating at least a portion of the volatiles (VOLT) from the first solvent and volatiles mixture (FSVM);

(m) mixing the volatiles with a second solvent (SOLV2) after step (l) to form a second volatiles and solvent mixture (SVSM); and (n) evaporating at least a portion of the second solvent (SOLV2) from the second volatiles and solvent mixture (SVSM).

In embodiments, the method to separate and concentrate volatiles from *cannabis*, also includes: (e) mixing a portion of the volatiles (VOLT) after step (d) with a fiber-starch material, a binding agent, a moisture improving textural supplement, a density improving textural supplement, and/or insects to produce a foodstuff comprising ada, bagels, baked goods, biscuits, bitterballen, bonda, breads, cakes, candies, cereals, chips, chocolate bars, chocolate, coffee, cokodok, confectionery, cookies, cooking batter, corn starch mixtures, crackers, crepes, croissants, croquettes, croutons, dolma, dough, doughnuts, energy bars, flapjacks, french fries, frozen custard, frozen desserts, frying cakes, fudge, gelatin mixes, granola bars, gulha, hardtack, ice cream, khandvi, khanom buang, krumpets, meze, mixed flours, muffins, multi-grain snacks, nachos, nian gao, noodles, nougat, onion rings, pakora, pancakes, panforte, pastas, pastries, pie crust, pita chips, pizza, poffertjes, pretzels, protein powders, pudding, rice krispie treats, sesame sticks, smoothies, snacks, specialty milk, tele-bhaja, tempura, toffee, tortillas, totopo, turkish delights, or waffles.

In embodiments, the method to separate and concentrate volatiles from *cannabis*, also includes: (f) cooling the volatiles and solvent mixture (SVSM) after step (e); and (g) filtering the volatiles and solvent mixture (SVSM).

In embodiments, the method to separate and concentrate volatiles from *cannabis*, also includes: in step (c), separating volatiles (VOLT) from *cannabis* using a method that includes: (1) separating terpenes from the *cannabis* at a first temperature and a first pressure; and (2) separating oil and wax from the *cannabis* at a second temperature and a second pressure; wherein: the second temperature is greater than the first temperature; the second pressure is greater than the first pressure; the terpenes include one or more from the group consisting of limonene, humulene, pinene, linalool, caryophyllene, myrcene, eucalyptol, nerolidol, bisablol, and phytol; the volatiles include one or more from the group consisting of oil, wax, terpenes, and tetrahydrocannabinol (THC). The volatiles includes a cannabinoid, such as tetrahydrocannabinolic acid (THCA), active tetrahydrocannabinol, tetrahydrocannabinol (THC), Δ9-tetrahydrocannabinol (Δ9-THC), Δ8-tetrahydrocannabinol (Δ8-THC), tetrahydrocannabivarin (THCV), cannabidiolic acid (CBDA), cannabichromene (CBC), cannabidiol (CBD), cannabigerol (CBG), cannabinidiol (CBND), and/or cannabinol (CBN).

In embodiments, an analyzer (J70) is used to analyze the concentrated volatiles (CVOLT), (e.g., the cannabinoid), the analyzer (J70) includes one or more analyzers selected from the group consisting of liquid chromatography-mass spectrometry, gas chromatography-mass spectrometry (GC-MS), and inductively coupled plasma mass spectrometry (ICP-MS). In embodiments, the analyzer (J70) is used to detect for the presence of solvents, mycotoxins, microbes, moisture content, metals, pesticides, terpenes, and potency.

In embodiments, the concentrated volatiles (CVOLT) includes: a nitrate (NO3) concentration having a maximum level of 1,000 mg NO3/kg of end-product; a mycotoxin analysis including: an ochratoxin A concentration having a maximum level of 10 µg/kg of end-product; a deoxynivalenol concentration having a maximum level of 2,000 µg/kg of end-product; a zearalenone concentration having a maximum level of 275 µg/kg of end-product; a fumonisins concentration having a maximum level of 2,500 µg/kg of end-product; a metals analysis including: a lead concentration having a maximum level of 0.5 mg/kg of end-product; a cadmium concentration having a maximum level of 0.5 mg/kg of end-product; a mercury concentration having a maximum level of 0.5 mg/kg of end-product; a 3-monochloropropane-1,2-diol (3-MCPD) concentration having a maximum level of 20 µg/kg of end-product; a dioxins and polychlorinated biphenyls (PCBs) concentration having a maximum level of 3 picogram/gram; a polycyclic aromatic hydrocarbon concentration having a maximum level of 5 µg/kg of end-product; a benzo(a)pyrene concentration having a maximum level of 2 or 5 µg/kg of end-product; a total concentration of benzo(a)pyrene, benz(a)anthracene, benzo (b)fluoranthene and chrysene having a maximum level of 15 or 30 µg/kg of end-product.

In embodiments, the present disclosure describes a *cannabis* traceability system includes a quality analysis of a *cannabis* plant, dried *cannabis*, ground *cannabis*, ground and dried *cannabis*, trimmed *cannabis, cannabis* trimmings, heated *cannabis*, a cannabinoid, a composition comprising the cannabinoid, and a foodstuff comprising the cannabinoid, including: a standard plate count (to test for total aerobic bacterial and total mold and yeasts) having less than: 500,000 colony forming unit per gram, 400,000 colony forming units per gram, 300,000 colony forming units per gram, 200,000 colony forming units per gram, 100,000 colony forming units per gram, 50,000 colony forming units per gram, 25,000 colony forming units per gram, or 5,000 colony forming units per gram; a coliform content less than 500 colony forming units per gram, 400 colony forming units per gram, 300 colony forming units per gram, 200 colony forming units per gram, 100 colony forming units per gram, 90 colony forming units per gram, 80 colony forming units per gram, 70 colony forming units per gram, 60 colony forming units per gram, 50 colony forming units per gram, 40 colony forming units per gram, 30 colony forming units per gram, 20 colony forming units per gram, or 10 colony forming units per gram; a coliform content less than 500,000 colony forming unit per gram, 400,000 colony forming units per gram, 300,000 colony forming units per gram, 200,000 colony forming units per gram, 100,000 colony forming units per gram, 50,000 colony forming units per gram, 25,000 colony forming units per gram, or 5,000 colony forming units per gram; a spore-forming sulphite reducing anaerobe content less than 500 colony forming units per gram, 400 colony forming units per gram, 300 colony forming units per gram, 200 colony forming units per gram, 100 colony forming units per gram, 90 colony forming units per gram, 80 colony forming units per gram, 70 colony forming units per gram, 60 colony forming units per gram, 50 colony forming units per gram, 40 colony forming units per gram, 30 colony forming units per gram, 20 colony forming units per gram, or 10 colony forming units per gram; a spore-forming sulphite reducing anaerobe content less than 500,000 colony forming unit per gram, 400,000 colony forming units per gram, 300,000 colony forming units per gram, 200,000 colony forming units per gram, 100,000 colony forming units per gram, 50,000 colony forming units per gram, 25,000 colony forming units per gram, or 5,000 colony forming units per gram; a *Pseudomonas aeruginosa* content less than 500 colony forming units per gram, 400 colony forming units per gram, 300 colony forming units per gram, 200 colony forming units per gram, 100 colony forming units per gram, 90 colony forming units per gram, 80 colony forming units per gram, 70 colony forming units per gram, 60 colony forming units per gram, 50 colony forming units per gram, 40 colony forming units per gram, 30 colony forming units per gram, 20 colony forming units per gram, or 10 colony forming units per gram; a *Pseudomonas aeruginosa* content less than 500,000 colony forming unit per gram, 400,000 colony forming units per gram, 300,000 colony forming units per gram, 200,000 colony forming units per gram, 100,000 colony forming units per gram, 50,000 colony forming units per gram, 25,000 colony forming units per gram, or 5,000 colony forming units per gram; a *E. coli* content less than 500 colony forming units per gram, 400 colony forming units per gram, 300 colony forming units per gram, 200 colony forming units per gram, 100 colony forming units per gram, 90 colony forming units per gram, 80 colony forming units per gram, 70 colony forming units per gram, 60 colony forming units per gram, 50 colony forming units per gram, 40 colony forming units per gram, 30 colony forming units per gram, 20 colony forming units per gram, or 10 colony forming units per gram; a *E. coli* content less than 500,000 colony forming unit per gram, 400,000 colony forming units per gram, 300,000 colony forming units per gram, 200,000 colony forming units per gram, 100,000 colony forming units per gram, 50,000 colony forming units per gram, 25,000 colony forming units per gram, or 5,000 colony forming units per gram.

In embodiments, the concentrated volatiles (*cannabis* plant derived cannabinoid, an insect-derived cannabinoid glycoside, a biosynthetically derived cannabinoid, a purified cannabinoid, distilled cannabinoid, a emulsion, a micro emulsion, a nano emulsion, a colloid suspension, etc.) may be mixed with one or more of a fiber-starch material, a binding agent, a moisture improving textural supplement, a density improving textural supplement, and/or insects to produce a foodstuff comprising ada, bagels, baked goods, biscuits, bitterballen, bonda, breads, cakes, candies, cereals, chips, chocolate bars, chocolate, coffee, cokodok, confectionery, cookies, cooking batter, corn starch mixtures, crackers, crepes, croissants, croquettes, croutons, dolma, dough, doughnuts, energy bars, flapjacks, french fries, frozen custard, frozen desserts, frying cakes, fudge, gelatin mixes, granola bars, gulha, hardtack, ice cream, khandvi, khanom buang, krumpets, meze, mixed flours, muffins, multi-grain snacks, nachos, nian gao, noodles, nougat, onion rings, pakora, pancakes, panforte, pastas, pastries, pie crust, pita chips, pizza, poffertj es, pretzels, protein powders, pudding, rice krispie treats, sesame sticks, smoothies, snacks, specialty milk, tele-bhaj a, tempura, toffee, tortillas, totopo, turkish delights, or waffles.

In embodiments, the concentrated volatiles (*cannabis* plant derived cannabinoid, an insect-derived cannabinoid glycoside, a biosynthetically derived cannabinoid, a purified cannabinoid, distilled cannabinoid, a emulsion, a micro emulsion, a nano emulsion, a colloid suspension, a cannabinoid powder, a water-soluble cannabinoid powder, a water soluble powder, etc.) may be used to produce a beverage, a topical, an animal food, a pet food, a human food, a shaped, cooked, and/or flavored composition.

In embodiments, the concentrated volatiles (*cannabis* plant derived cannabinoid, an insect-derived cannabinoid glycoside, a biosynthetically derived cannabinoid, a purified cannabinoid, distilled cannabinoid, a emulsion, a micro emulsion, a nano emulsion, a colloid suspension, a cannabinoid powder, a water-soluble cannabinoid powder, a water soluble powder, etc.)) may be mixed with one or more waxes selected from the group consisting of almond oil, an animal-based oil, apricot kernel oil, avocado oil, brazil nut oil, butter, canola oil, cashew oil, cocoa butter, coconut oil, cooking oil, corn oil, cottonseed oil, fish oil, grapeseed oil, hazelnut oil, hemp oil, insect oil, lard, lard oil, macadamia nut oil, mustard oil, olive oil, palm kernel oil, palm oil, peanut oil, rapeseed oil, rice oil, rice bran oil, safflower oil, semi-refined sesame oil, semi-refined sunflower oil, sesame oil, soybean oil, tallow of beef, tallow of mutton, vegetable oil, and walnut oil.

In embodiments, the concentrated volatiles (*cannabis* plant derived cannabinoid, an insect-derived cannabinoid glycoside, a biosynthetically derived cannabinoid, a purified cannabinoid, distilled cannabinoid, a emulsion, a micro emulsion, a nano emulsion, a colloid suspension, a cannabinoid powder, a water-soluble cannabinoid powder, a water soluble powder, etc.) may be mixed with one or more waxes selected from the group consisting of *acacia decurrens* flower cera (*mimosa* flower wax), almond wax, avocado wax, beery wax, bees wax, *cananga odorata* flower cera (ylang ylang flower wax), candelilla wax, *Cannabis sativa* oil, castor wax, cupuacu butter, floral wax, hemp wax, hydrogenated almond oil, hydrogenated animal-based oils, hydrogenated apricot kernel oil, hydrogenated avocado oil, hydrogenated brazil nut oil, hydrogenated canola oil, hydrogenated cashew oil, hydrogenated cocoa butter, hydrogenated coconut oil, hydrogenated coffee oil, hydrogenated corn oil, hydrogenated cottonseed oil, hydrogenated grapeseed oil, hydrogenated hazelnut oil, hydrogenated hemp oil, hydrogenated hop oil, hydrogenated insect oil, hydrogenated lard oil, hydrogenated lard, hydrogenated macadamia nut oil, hydrogenated mustard oil, hydrogenated olive oil, hydrogenated palm kernel oil, hydrogenated palm oil, hydrogenated peanut oil, hydrogenated peppermint oil, hydrogenated rapeseed oil, hydrogenated rice bran oil, hydrogenated rice oil, hydrogenated safflower oil, hydrogenated semi-refined sesame oil, hydrogenated semi-refined sunflower oil, hydrogenated sesame oil, hydrogenated soybean oil, hydrogenated walnut oil, *jasminum grandiflorum* flower cera (jasmine flower wax), *Lavandula angustifolia* flower cera (lavender flower wax), mmyrica fruit wax, olive wax, *prunus* amygdalus *dulcis* oil, rapeseed wax, rice bran wax, rosa damascene flower cera (rose flower wax), shea butter, soybean wax, sunflower wax, vegan wax, vegetable wax, wax from Mexican shrub *Euphorbia antisyphilitica*, and wax from the berries of *rhus* verniciflua.

In embodiments, the concentrated volatiles (*cannabis* plant derived cannabinoid, an insect-derived cannabinoid glycoside, a biosynthetically derived cannabinoid, a purified cannabinoid, distilled cannabinoid, a emulsion, a micro emulsion, a nano emulsion, a colloid suspension, a cannabinoid powder, a water-soluble cannabinoid powder, a water soluble powder, etc.) may be mixed with allspice berries, almond meal, anise seed, annato seed, arrowroot powder, basil, bay leaves, black pepper, buttermilk, capsaicin, caraway, cayenne, celery seed, cheese cultures, chervil, chile powder, chives, cilantro, cinnamon, citric acid, cloves, coconut shredded, coriander, corn oil, corn starch, cream of tartar, cubeb berries, cumin, curry, dextrose, dill, enzymes, fennel, fenugreek, file powder, garlic powder, ginger, grapefruit peel, green peppercorns, honey, horseradish powder, juniper berries, kaffir lime, lavender, lemon grass powder, lemon peel, lime peel, long pepper, marjoram, molasses, mustard, natural smoke flavor, nigella seeds, nutmeg, onion powder, orange peel, oregano, paprika, parsley, peppermint, poppy seed, powdered cheese, red pepper, rose petals, rosemary, saffron, sassafrass, sage, salt, savory, sesame seed, star anise, sugar, sugar maple, sumac, tamarind, tangerine peel, tarragon, thyme, tomatillo powder, tomato powder, turmeric, vanilla extract, wasabi powder, whey, or white peppercorns.

In embodiments, the concentrated volatiles (*cannabis* plant derived cannabinoid, an insect-derived cannabinoid glycoside, a biosynthetically derived cannabinoid, a purified cannabinoid, distilled cannabinoid, a emulsion, a micro emulsion, a nano emulsion, a colloid suspension, a cannabinoid powder, a water-soluble cannabinoid powder, a water soluble powder, etc.) may be mixed with serotonin, psilocybin, psilocin, baeocystin, lysergic acid diethylamide (LSD), ibogaine, and/or mescaline. In embodiments, the concentrated volatiles may be mixed with psilocybin mushrooms and/or the alimentary composition. In embodiments, the concentrated volatiles may be mixed with psilocybin extract, psilocin extract, baeocystin extract, and/or norbaeocystin extract. In embodiments, the concentrated volatiles may be mixed with milk, milk powder, whole milk powder, goat milk, soy milk, almond milk, coconut milk, oat milk, rice milk, cashew milk, macadamia milk, whole milk, 2% milk, 1% milk, organic milk, lactose-free milk, half and half, cream, buttermilk, or chocolate milk.

In embodiments, the concentrated volatiles (cannabis plant derived cannabinoid, an insect-derived cannabinoid glycoside, a biosynthetically derived cannabinoid, a purified cannabinoid, distilled cannabinoid, a emulsion, a micro emulsion, a nano emulsion, a colloid suspension, a cannabinoid powder, a water-soluble cannabinoid powder, a water soluble powder, etc.) may be further processed to create foodstuffs not only including ada, bagels, baked goods, biscuits, bitterballen, bonda, breads, cakes, candies, cereals, chips, chocolate bars, chocolate, coffee, cokodok, confectionery, cookies, cooking batter, corn starch mixtures, crackers, crepes, croissants, croquettes, croutons, dolma, dough, doughnuts, energy bars, flapjacks, french fries, frozen custard, frozen desserts, frying cakes, fudge, gelatin mixes, granola bars, gulha, hardtack, ice cream, khandvi, khanom buang, krumpets, meze, mixed flours, muffins, multi-grain snacks, nachos, nian gao, noodles, nougat, onion rings, pakora, pancakes, panforte, pastas, pastries, pie crust, pita chips, pizza, poffertjes, pretzels, protein powders, pudding, rice krispie treats, sesame sticks, smoothies, snacks, specialty milk, tele-bhaja, tempura, toffee, tortillas, totopo, turkish delights, or waffles.

In embodiments, the foodstuff includes a fiber-starch material, a binding agent, a moisture improving textural supplement, a density improving textural supplement, and/or insects. In embodiments, the fiber-starch materials may be comprised of singular or mixtures of cereal-grain-based materials, grass-based materials, nut-based materials, powdered fruit materials, root-based materials, tuber-based materials, or vegetable-based materials. In embodiments, the binding agents may be comprised of singular or mixtures of agar, agave, alginin, aspartame, arrowroot, carrageenan, collagen, cornstarch, egg whites, finely ground seeds, furcellaran, gelatin, guar gum, honey, katakuri starch, locust bean gum, pectin, potato starch, proteins, *psyllium* husks, sago, sugar, *stevia*, syrup, tapioca, vegetable gums, or xanthan gum. In embodiments, the moisture improving textural supplements may be comprised of singular or mixtures of almonds, brazil nuts, cacao, cashews, chestnuts, coconut, filberts, hazelnuts, Indian nuts, macadamia nuts, nut butters, nut oils, nut powders, peanuts, pecans, pili nuts, pine nuts, pinon nuts, pistachios, soy nuts, sunflower seeds, tiger nuts, walnuts, and oils extracted from any one of the aforesaid nuts and nuts listed herein and combinations thereof. In embodiments, the insects may be Orthoptera order of insects including grasshoppers, crickets, cave crickets, Jerusalem crickets, katydids, weta, lubber, acrida, and locusts. However, other orders of insects, such as cicadas, ants, mealworms, agave worms, worms, bees, centipedes, cockroaches, dragonflies, beetles, scorpions, tarantulas, termites, insect lipids, and insect oil, black soldier fly larvae, or any insects or insect products mentioned herein may be used as well. In embodiments, the density improving textural supplement may be comprised of singular or mixtures of extracted arrowroot starch, extracted corn starch, extracted lentil starch, extracted potato starch, or extracted tapioca starch.

In embodiments, the concentrated volatiles may be mixed with alpha-tocopherol, ascorbic acid, biotin, caffeine, calciferol, calcium, carotene, chloride, choline, chromium, citicoline, cobalamin, copper, fluoride, folacin, folate, folic acid, glucuronic acid, iodine, iron, L-phenylalanine, magnesium, malic acid, manganese, menadione, mineral, molybdenum, N-acetyl L tyrosine, niacin, pantothenic acid, phosphorus, phylloquinone, potassium, pyridoxine, retinal, retinoic acid, retinoids, retinol, retinyl esters, riboflavin, selenium, sodium, sulfur, taurine, thiamine, Vitamin A, Vitamin B1, vitamin B12, Vitamin B2, vitamin B3, vitamin B5, vitamin B6, vitamin B9, vitamin C, vitamin D, Vitamin E, vitamin H, vitamin K, or zinc. In embodiments, each serving size of the foodstuff includes a cannabidiol content in milligrams per serving ranging from 0 milligrams to 0.5 milligrams, 0.5 milligrams to 1 milligrams, 1 milligrams to 1.5 milligrams, 1.5 milligrams to 2 milligrams, 2 milligrams to 2.5 milligrams, 2.5 milligrams to 3 milligrams, 3 milligrams to 3.5 milligrams, 3.5 milligrams to 4 milligrams, 4 milligrams to 4.5 milligrams, 4.5 milligrams to 5 milligrams, 5 milligrams to 5.5 milligrams, 5.5 milligrams t 6 milligrams, 6 milligrams to 6.5 milligrams, 6.5 milligrams to 7 milligrams, 7 milligrams to 7.5 milligrams, 7.5 milligrams to 8 milligrams, 8 milligrams to 8.5 milligrams, 8.5 milligrams to 9 milligrams, 9 milligrams to 9.5 milligrams, 9.5 milligrams to 10 milligrams, 10 milligrams to 11 milligrams, 11 milligrams to 12 milligrams, 12 milligrams to 13 milligrams, 13 milligrams to 14 milligrams, 14 milligrams to 15 milligrams, 15 milligrams to 16 milligrams, 16 milligrams to 17 milligrams, 17 milligrams to 18 milligrams, 18 milligrams to 19 milligrams, 19 milligrams to 20 milligrams, 20 milligrams to 25 milligrams, 25 milligrams to 30 milligrams, 30 milligrams to 35 milligrams, 35 milligrams to 40 milligrams, 40 milligrams to 45 milligrams, 45 milligrams to 50 milligrams, 50 milligrams to 60 milligrams, 60 milligrams to 70 milligrams, 70 milligrams to 80 milligrams, 80 milligrams to 90 milligrams, 90 milligrams to 100 milligrams, 100 milligrams to 125 milligrams, 125 milligrams to 150 milligrams, 150 milligrams to 175 milligrams, 175 milligrams to 200 milligrams, 200 milligrams to 250 milligrams, 250 milligrams to 300 milligrams, 300 milligrams to 350 milligrams, 350 milligrams to 400 milligrams, 400 milligrams to 450 milligrams, or 450 milligrams to 500 milligrams.

In embodiments, each serving size of the foodstuff includes a tetrahydrocannabinol content in milligrams per serving ranging from 0 milligrams to 0.5 milligrams, 0.5 milligrams to 1 milligrams, 1 milligrams to 1.5 milligrams, 1.5 milligrams to 2 milligrams, 2 milligrams to 2.5 milligrams, 2.5 milligrams to 3 milligrams, 3 milligrams to 3.5 milligrams, 3.5 milligrams to 4 milligrams, 4 milligrams to 4.5 milligrams, 4.5 milligrams to 5 milligrams, 5 milligrams to 5.5 milligrams, 5.5 milligrams t 6 milligrams, 6 milligrams to 6.5 milligrams, 6.5 milligrams to 7 milligrams, 7 milligrams to 7.5 milligrams, 7.5 milligrams to 8 milligrams, 8 milligrams to 8.5 milligrams, 8.5 milligrams to 9 milligrams, 9 milligrams to 9.5 milligrams, 9.5 milligrams to 10 milligrams, 10 milligrams to 11 milligrams, 11 milligrams to 12 milligrams, 12 milligrams to 13 milligrams, 13 milligrams to 14 milligrams, 14 milligrams to 15 milligrams, 15 milligrams to 16 milligrams, 16 milligrams to 17 milligrams, 17 milligrams to 18 milligrams, 18 milligrams to 19 milligrams, 19 milligrams to 20 milligrams, 20 milligrams to 25 milligrams, 25 milligrams to 30 milligrams, 30 milligrams to 35 milligrams, 35 milligrams to 40 milligrams, 40 milligrams to 45 milligrams, 45 milligrams to 50 milligrams, 50 milligrams to 60 milligrams, 60 milligrams to 70 milligrams, 70 milligrams to 80 milligrams, 80 milligrams to 90 milligrams, 90 milligrams to 100 milligrams, 100 milligrams to 125 milligrams, 125 milligrams to 150 milligrams, 150 milligrams to 175 milligrams, 175 milligrams to 200 milligrams, 200 milligrams to 250 milligrams, 250 milligrams to 300 milligrams, 300 milligrams to 350 milligrams, 350 milligrams to 400 milligrams, 400 milligrams to 450 milligrams, or 450 milligrams to 500 milligrams.

In embodiments, each serving size of the foodstuff includes a psilocybin, psilocin, baeocystin, and/or norbaeocystin content in milligrams per serving ranging from 0 milligrams to milligrams, 0.5 milligrams to 1 milligrams, 1 milligrams to 1.5 milligrams, 1.5 milligrams to 2 milligrams, 2 milligrams to 2.5 milligrams, 2.5 milligrams to 3 milligrams, 3 milligrams to 3.5 milligrams, 3.5 milligrams to 4 milligrams, 4 milligrams to 4.5 milligrams, 4.5 milligrams to 5 milligrams, 5 milligrams to 5.5 milligrams, 5.5 milligrams t 6 milligrams, 6 milligrams to 6.5 milligrams, 6.5 milligrams to 7 milligrams, 7 milligrams to 7.5 milligrams, 7.5 milligrams to 8 milligrams, 8 milligrams to 8.5 milligrams, 8.5 milligrams to 9 milligrams, 9 milligrams to 9.5 milligrams, 9.5 milligrams to 10 milligrams, 10 milligrams to 11 milligrams, 11 milligrams to 12 milligrams, 12 milligrams to 13 milligrams, 13 milligrams to 14 milligrams, 14 milligrams to 15 milligrams, 15 milligrams to 16 milligrams, 16 milligrams to 17 milligrams, 17 milligrams to 18 milligrams, 18 milligrams to 19 milligrams, 19 milligrams to 20 milligrams, 20 milligrams to 25 milligrams, 25 milligrams to 30 milligrams, 30 milligrams to 35 milligrams, 35 milligrams to 40 milligrams, 40 milligrams to 45 milligrams, 45 milligrams to 50 milligrams, 50 milligrams to 60 milligrams, 60 milligrams to 70 milligrams, 70 milligrams to 80 milligrams, 80 milligrams to 90 milligrams, 90 milligrams to 100 milligrams, 100 milligrams to 125 milligrams, 125 milligrams to 150 milligrams, 150 milligrams to 175 milligrams, 175 milligrams to 200 milligrams, 200 milligrams to 250 milligrams, 250 milligrams to 300 milligrams, 300 milligrams to 350 milligrams, 350 milligrams to 400 milligrams, 400 milligrams to 450 milligrams, or 450 milligrams to 500 milligrams, 500 milligrams to 1 gram, 1 gram to 2 grams, 2 grams to 3 grams. In embodiments, each serving size of the foodstuff includes a serotonin, lysergic acid diethylamide (LSD), ibogaine, methylenedioxymethamphetamine, and/or mescaline content in milligrams per serving ranging from 0 milligrams to 0.5 milligrams, 0.5 milligrams to 1 milligrams, 1 milligrams to 1.5 milligrams, 1.5 milligrams to 2 milligrams, 2 milligrams to 2.5 milligrams, 2.5 milligrams to 3 milligrams, 3 milligrams to 3.5 milligrams, 3.5 milligrams to 4 milligrams, 4 milligrams to 4.5 milligrams, 4.5 milligrams to 5 milligrams, 5 milligrams to 5.5 milligrams, 5.5 milligrams t 6 milligrams, 6 milligrams to 6.5 milligrams, 6.5 milligrams to 7 milligrams, 7 milligrams to 7.5 milligrams, 7.5 milligrams to 8 milligrams, 8 milligrams to 8.5 milligrams, 8.5 milligrams to 9 milligrams, 9 milligrams to 9.5 milligrams, 9.5 milligrams to 10 milligrams, 10 milligrams to 11 milligrams, 11 milligrams to 12 milligrams, 12 milligrams to 13 milligrams, 13 milligrams to 14 milligrams, 14 milligrams to 15 milligrams, 15 milligrams to 16 milligrams, 16 milligrams to 17 milligrams, 17 milligrams to 18 milligrams, 18 milligrams to 19 milligrams, 19 milligrams to 20 milligrams, 20 milligrams to 25 milligrams, 25 milligrams to 30 milligrams, 30 milligrams to 35 milligrams, 35 milligrams to 40 milligrams, 40 milligrams to 45 milligrams, 45 milligrams to 50 milligrams, 50 milligrams to 60 milligrams, 60 milligrams to 70 milligrams, 70 milligrams to 80 milligrams, 80 milligrams to 90 milligrams, 90 milligrams to 100 milligrams, 100 milligrams to 125 milligrams, 125 milligrams to 150 milligrams.

In embodiments, the concentrated volatiles (CVOLT) include pharmaceutical grade purity tetrahydrocannabinol (THC). In embodiments, the concentrated volatiles (CVOLT) include pharmaceutical grade purity cannabidiol (CBD). In embodiments, the concentrated volatiles (CVOLT) include pharmaceutical grade purity Δ9-tetrahydrocannabinol Δ9-THC, Δ8-tetrahydrocannabinol Δ8-THC, cannabichromene CBC, cannabidiol CBD, cannabigerol CBG, cannabinidiol CBND, and/or cannabinol CBN. In embodiments, the concentrated volatiles (CVOLT) include distilled pharmaceutical grade purity tetrahydrocannabinol (THC). In embodiments, the concentrated volatiles (CVOLT) include distilled pharmaceutical grade purity cannabidiol (CBD). In embodiments, the concentrated volatiles (CVOLT) include distilled pharmaceutical grade purity Δ9-tetrahydrocannabinol Δ9-THC, Δ8-tetrahydrocannabinol Δ8-THC, cannabichromene CBC, cannabidiol CBD, cannabigerol CBG, cannabinidiol CBND, and/or cannabinol CBN.

In embodiments, the concentrated volatiles include concentrated volatiles (CVOLT). In embodiments, the concentrated volatiles (CVOLT) includes a cannabinoid. In embodiments, an analyzer (J50) is configured to analyze at least a portion of the concentrated volatiles (CVOLT). In embodiments, the analyzer (J50) is comprised of one or more analyzers selected from the group consisting of Fourier-transform infrared spectroscopy, gas chromatography, high-performance liquid chromatography, liquid chromatograph, liquid chromatography-mass spectrometry, mass spectrometry, and ultra-high performance liquid chromatography, and combinations thereof.

In embodiments, the concentrated volatiles may be sent to the cannabinoid tank (6A2) as shown on FIG. 18, returned to the volatiles extraction system (VES) on any one of FIGS. 17A, 17A', 17B, 17D, 17H, or sent to solvent separation of FIG. 17E, cannabinoid extraction/purification of FIG. 17H, emulsion mixing of FIG. 17J, encapsulation of FIG. 17K, shaping, cooking flavoring of FIG. 18A-18D, to the mixing tank on FIG. 18E, combinations thereof.

FIG. 17D'

FIG. 17D' shows a plurality of sequential separation systems (SEPSOL, SEPSOL, SEPSOL) that are configured to separate at least a portion of the solvent, volatiles, and/or cannabinoids from produce concentrated volatiles (CVOLT) and a plurality of different compounds (1SCM, 1SCM, 2SCM, 2SCM). Shown in FIG. 17D' is a first separation system (SEPSOL) as depicted in FIG. 17D'. The system shows three stages of separation, wherein at least one separator is used in each separation stage, the separators include: evaporation, rotary evaporation, vacuum evaporation, distillation, short path distillation, simulated moving bed purification, chromatography, filtration, adsorption, absorption, molecular distillation, crystallization, vacuum flashing, wiped-film evaporation, emulsification, filtration, spray drying, and/or chilled ethanol extraction:

(1) a first separation system (SEPSOL) is configured to separate at least a portion of the solvent (SOLV2) and/or volatiles and/or cannabinoids from the volatiles and solvent mixture (SVSM) to produce concentrated volatiles (CVOLT);

(2) a second separation system (SEPSOL) configured to separate volatiles and/or cannabinoids from the concentrated volatiles (CVOLT) to produce a first separated compound (1SCM) and a second separated compound (1SCM); and (3) a third separation system (SEPSOL) configured to separate volatiles and/or cannabinoids from the first separated compound (1SCM) and/or the second separated compound (1SCM) to produce a third separated compound (2SCM) and a fourth separated compound (2SCM).

The first separation system (SEPSOL) is configured to separate at least a portion of the solvent (SOLV2) and/or volatiles and/or cannabinoids from the volatiles and solvent mixture (SVSM) to produce concentrated volatiles (CVOLT). Shown in FIG. 17D' is a second separation system (SEPSOL) configured to separate volatiles and/or cannabinoids from the concentrated volatiles (CVOLT) to produce a first separated compound (1SCM) and a second separated compound (1SCM).

In embodiments, the first separated compound (1SCM) is a cannabinoid and a solvent. In embodiments, the second separated compound (1SCM) is THC and/or CBD and a solvent. In embodiments, the first separated compound (1SCM) is THC and terpenes and a solvent. In embodiments, the second separated compound (1SCM) is CBD and terpenes and a solvent. In embodiments, the first separated compound (1SCM) is THC oil. In embodiments, the second separated compound (1SCM) is CBD oil. In embodiments, the first separated compound (1SCM) is THC and/or CBD. In embodiments, the second separated compound (1SCM) is a solvent. In embodiments, the first separated compound (1SCM) is THC and CBD. In embodiments, the second separated compound (1SCM) is a solvent. In embodiments, the first separated compound (1SCM) is THC. In embodiments, the second separated compound (1SCM) is a CBD. In embodiments, the first separated compound (1SCM) is THC and/or CBD. In embodiments, the second separated compound (1SCM) is a solvent and terpenes. In embodiments, the first separated compound (1SCM) is THC and/or CBD. In embodiments, the second separated compound (1SCM) includes terpenes.

In embodiments, the first separated compound (1SCM) is a cannabinoid. In embodiments, the second separated compound (1SCM) includes terpenes. In embodiments, a second analyzer (J51) is configured to analyze at least a portion of the first separated compound (1SCM) and/or the second separated compound (1SCM). In embodiments, the analyzer (J50) is comprised of one or more analyzers selected from the group consisting of Fourier-transform infrared spectroscopy, gas chromatography, high-performance liquid chromatography, liquid chromatograph, liquid chromatography-mass spectrometry, mass spectrometry, and ultra-high performance liquid chromatography.

Shown in FIG. 17D' is a third separation system (SEPSOL) configured to separate volatiles and/or cannabinoids from the first separated compound (1SCM) and/or the second separated compound (1SCM) to produce a third separated compound (2SCM) and a fourth separated compound (2SCM). FIG. 17D' shows a third separation system (SEPSOL) configured to separate cannabinoids into separate isolated substantially pure and/or pure molecular compounds such as TCH and/or CBD. FIG. 17D' shows a third separation system (SEPSOL) configured to separate extracts into separate isolated molecular compounds such as a cannabinoid, a cannabinoid glycoside, and/or a biosynthetic cannabinoid.

In embodiments, the third separated compound (2SCM) is terpenes and a solvent. In embodiments, the fourth separated compound (2SCM) is a solvent. In embodiments, the third separated compound (2SCM) is terpenes. In embodiments, the fourth separated compound (2SCM) is a solvent. In embodiments, the third separated compound (2SCM) is THC and a solvent. In embodiments, the fourth separated compound (2SCM) is CBD and a solvent. In embodiments, the third separated compound (2SCM) is THC and terpenes and a solvent. In embodiments, the fourth separated compound (2SCM) is CBD and terpenes and a solvent. In embodiments, the third separated compound (2SCM) is THC. In embodiments, the fourth separated compound (2SCM) is CBD. In embodiments, the third separated compound (2SCM) is THC and/or CBD. In embodiments, the fourth separated compound (2SCM) is a solvent. In embodiments, the third separated compound (2SCM) is THC and/or CBD. In embodiments, the fourth separated compound (2SCM) is a solvent and terpenes. In embodiments, the third separated compound (2SCM) is THC and/or CBD. In embodiments, the fourth separated compound (2SCM) includes terpenes. In embodiments, the third separated compound (2SCM) is THC and/or CBD. In embodiments, the fourth separated compound (2SCM) includes terpenes.

In embodiments, a third analyzer (J52) is configured to analyze at least a portion of the third separated compound (2SCM) and/or fourth separated compound (2SCM). In embodiments, the analyzer (J50) is comprised of one or more analyzers selected from the group consisting of Fourier-transform infrared spectroscopy, gas chromatography, high-performance liquid chromatography, liquid chromatograph, liquid chromatography-mass spectrometry, mass spectrometry, and ultra-high performance liquid chromatography.

In embodiments, both of the first separated compound (1SCM) and second separated compound (1SCM) are introduced into the third separation system (SEPSOL). In embodiments, only one of the first separated compound (1SCM) or second separated compound (1SCM) are introduced into the third separation system (SEPSOL).

In embodiments, the cannabinoid can be separated from the *cannabis*, insect, and/or microorganism in the first or second stage separator if any one of the system of separation are used: evaporation, rotary evaporation, vacuum evaporation, distillation, short path distillation, simulated moving bed purification, chromatography, filtration, adsorption, absorption, molecular distillation, crystallization, vacuum flashing, wiped-film evaporation, emulsification, filtration, spray drying, or ethanol extraction In embodiments, the cannabinoid can be separated from the *cannabis*, insect, and/or microorganism in the second or third stage separator if any one of the system of separation are used: evaporation, rotary evaporation, vacuum evaporation, distillation, short path distillation, simulated moving bed purification, chromatography, filtration, adsorption, absorption, molecular distillation, crystallization, vacuum flashing, wiped-film evaporation, emulsification, filtration, spray drying, or ethanol extraction.

In embodiments, the crystallizer and/or spray drier may be configured to produce a crystalline cannabinoid. In embodiments, the crystallizer and/or spray drier produce a powder from the cannabinoid. In embodiments, *cannabis* is grown, grinded (to a reduced particle size), and mixed with ethanol for a duration of time selected from the group consisting of 1 second to 5 seconds, 5 seconds to 15 seconds, 15 seconds to 30 seconds, 30 seconds to 1 minute, 1 minute to 2 minutes, 2 minutes to 3 minutes, 3 minutes to 4 minutes, 4 minutes to 5 minutes, 5 minutes to 10 minutes, 10 minutes to 15 minutes, 15 minutes to 20 minutes, 20 minutes to 25 minutes, 25 minutes to 30 minutes, 30 minutes to 35 minutes, 35 minutes to 40 minutes, 40 minutes to 45 minutes, 45 minutes to 50 minutes, 50 minutes to 55 minutes, 55 minutes to 1 hours, 1 hours to 1.25 hours, 1.25 hours to 1.5 hours, 1.5 hours to 1.75 hours, 1.75 hours to 2 hours, 2 hours to 2.5 hours, 2.5 hours to 3 hours, 3 hours to 3.5 hours, 3.5 hours to 4 hours, 4 hours to 4.5 hours, 4.5 hours to 5 hours, 5 hours to 5.5 hours, 5.5 hours to 6 hours, 7 hours to 8 hours, 9 hours to 10 hours, 11 hours to 12 hours, 13 hours to 14 hours, 15 hours to 16 hours, 17 hours to 18 hours, 19 hours to 20 hours, 21 hours to 22 hours, 23 hours to 24 hours, 25 hours to 26 hours, 27 hours to 28 hours, 29 hours to 30 hours, 31 hours to 32 hours, 33 hours to 34 hours, 35 hours to 36 hours, 37 hours to 38 hours, 39 hours to 40 hours, 41 hours to 42 hours, 43 hours to 44 hours, 45 hours to 46 hours, 47 hours to 48 hours, 49 hours to 50 hours, 51 hours to 52 hours, 53 hours to 54 hours, 55 hours to 56 hours, 57 hours to 58 hours, 59 hours to 60 hours, 61 hours to 62 hours, 63 hours to 64 hours, 65 hours to 66 hours, 67 hours to 68 hours, 69 hours to 70 hours, or 71 hours to 72 hours.

In embodiments, the crystallizer has a crystal growth rate ranging from 0.05 to 0.1 millimeters per hour (mm/hr), 0.1 to 0.2 mm/hr, 0.2 to 0.3 mm/hr, 0.3 to 0.4 mm/hr, 0.4 to 0.5 mm/hr, 0.5 to 0.6 mm/hr, 0.6 to 0.7 mm/hr, 0.7 to 0.8 mm/hr, 0.8 to 0.9 mm/hr, 1 to 2 mm/hr, 2 to 3 mm/hr, 3 to 4 mm/hr, 4 to 5 mm/hr, 5 to 6 mm/hr, 6 to 7 mm/hr, 7 to 8 mm/hr, or 8 to 10 mm/hr. In embodiments, the crystallizer operates at a concentration to saturated concentration (C/Csat) ratio ranging from 1.01 to 1.02, 1.02 to 1.03, 1.03 to 1.04, 1.04 to 1.05, 1.05 to 1.1, 1.1 to 1.2, or 1.2 to 1.3.

The ethanol extracts any of the cannabinoid from the *cannabis*, insects, and/or microorganism to produce a liquid mixture. The liquid mixture than may be filtered to remove the solids to produce a solids depleted liquid mixture, the solids depleted liquid mixture has a reduced amount of solids relative to the liquid mixture. The liquid mixture can be used to make foodstuff or be mixed with any variety of insect and/or *cannabis* mixtures during any stage of processing disclosed in this patent specification (shaped compositions, cooked compositions, flavored compositions, cannabinoid beverages, cannabinoid emulsions, cannabinoid microemulsions, cannabinoid nanoemulsions, cannabinoid colloids, cannabinoid colloid suspensions, cannabinoid foodstuffs, cannabinoid alternative meat products, cannabinoid and insect foodstuffs and compositions, etc.).

In embodiments, the solids depleted liquid mixture is then introduced to an evaporation step to reduce the amount of ethanol in the solids depleted liquid mixture. The evaporator produces a concentrated volatiles mixture which has a reduced amount of solvent relative to the solids depleted liquid mixture. In embodiments the cannabinoids are referred to as a volatiles. The evaporator produces a concentrated volatiles mixture which has a reduced amount of solvent relative to the solids depleted liquid mixture and includes one or more selected from the group consisting of a cannabinoid.

FIG. 17D' shows a three-stage separation system for removing solvent from volatiles, then two stages of separating volatiles from one another including: the second stage separates one volatile from another (e.g. separating or purifying cannabinoids from one another), and the third stage for separating another (e.g. cannabinoid from one another). In embodiments, a second and third solvent and evaporation step are performed. In embodiments, at least one of the mixtures transferred from the second to the third stage is a liquid and is filtered. In embodiments, both of the mixtures transferred from the second to the third stage is a liquid and is filtered. In embodiments, none of the mixtures transferred from the second to the third stage is a liquid and is filtered. In embodiments, a second solvent is required to be added to the mixture of solvent and extract to be cooled and fileted as shown in FIG. 17C.

FIG. 17E

FIG. 17E shows one non-limiting embodiment of a solvent separation system that is configured to evaporate the second solvent from the second volatiles and solvent mixture (SVSM) by use of a spray dryer (KAP).

In embodiments, a plurality of separators are used to separate at least a small particulate portion (KCW) and a large particulate portion (KCY) from a volatiles and gas mixture (KBV) that is discharged in the drying chamber (KBG) of a spray dryer (KAP) evaporator (KAO). In embodiments, the spray dryer (KAP) spray dries a cannabinoid emulsion and/or a colloidal suspension of a cannabinoid and a solvent (for example, transferred from the emulsification system of FIG. 17J). In embodiments, the spray dryer accepts a cannabinoid, a cannabinoid and solvent mixture, a cannabinoid and liquid (or solvent) mixture from a variety of locations such as from 17A, 17A', 17B, 17C, 17D, 17D', 17E, 17H, 17J, 18A, 18E, and/or combinations thereof.

The spray dryer (KAP) is type of evaporator (KAO) that evaporates liquid from a cannabinoid and liquid mixture, such as the second volatiles and solvent mixture (SVSM), or any number of combinations and/or permutations of mixtures of a cannabinoid (extracted, distilled, purified, isolated, a slurry) and a liquid (such as an oil, a solvent, treated water, etc.), an emulsion, a nanoemulsion, a microemulsion, a colloid, a colloidal suspension, a mixture of a cannabinoid and a variety of other ingredients, such as a fiber-starch material, a binding agent, a moisture improving textural supplement, a density improving textural supplement, and/or insects.

A first separator (KCA), second separator (KCI), and a third separator (KCR) are configured to accept a cannabinoid mixture, such as a volatiles and gas mixture (KBV), from the drying chamber (KBG) of a spray dryer (KAP). In embodiments, the first separator (KCA) is a cyclone or a filter. In embodiments, the second separator (KCI) is a cyclone or a filter. In embodiments, the third separator (KCR) is a sifter or a filter. The third separator (KCR) accepts first separated volatiles (KCG) from the first separator (KCA) and second separated volatiles (KCP) from the second separator (KCI) and separates at least a small particulate portion (KCW) and a large particulate portion (KCY) therefrom. In embodiments, the small particulate portion (KCW) and a large particulate portion (KCY) are crystals, solids, and contain a cannabinoid.

The second volatiles and solvent mixture (SVSM) is introduced to a liquid input (KAR) of the spray dryer (KAP). The spray dryer (KAP) has a top (K-T) and a bottom (K-B). The spray dryer (KAP) has a vertical axis (KYY) and a horizontal axis (KXY). As shown in FIG. 17E, the liquid input (KAR) is located positioned towards the top (K-T) of the spray dryer (KAP). In embodiments, the liquid input (KAR) to the spray dryer (KAP) is positioned closer to the bottom (K-B) of the spray dryer (KAP).

In embodiments, the range of height of the drying chamber (KBG) is selected from one or more from the group 6 feet tall to 8 feet tall, 8 feet tall to 10 feet tall, 10 feet tall to 12 feet tall, 12 feet tall to 14 feet tall, 14 feet tall to 16 feet tall, 16 feet tall to 18 feet tall, 18 feet tall to 20 feet tall, 20 feet tall to 22 feet tall, 22 feet tall to 24 feet tall, 24 feet tall to 26 feet tall, 26 feet tall to 28 feet tall, 28 feet tall to 30 feet tall, 30 feet tall to 32 feet tall, 32 feet tall to 34 feet tall, 34 feet tall to 36 feet tall, 36 feet tall to 38 feet tall, 38 feet tall to 40 feet tall, and 40 feet tall to 50 feet tall.

In embodiments, the range of diameter of the drying chamber (KBG) is selected from one or more from the group 2 feet in diameter to 4 feet in diameter, 4 feet in diameter to 6 feet in diameter, 6 feet in diameter to 8 feet in diameter, 8 feet in diameter to 10 feet in diameter, 10 feet in diameter to 12 feet in diameter, 12 feet in diameter to 14 feet in diameter, 14 feet in diameter to 16 feet in diameter, 16 feet in diameter to 18 feet in diameter, 18 feet in diameter to 20 feet in diameter, 20 feet in diameter to 22 feet in diameter, 22 feet in diameter to 24 feet in diameter, 24 feet in diameter to 26 feet in diameter, 26 feet in diameter to 28 feet in diameter, 28 feet in diameter to 30 feet in diameter, 30 feet in diameter to 32 feet in diameter, 32 feet in diameter to 34 feet in diameter, 34 feet in diameter to 36 feet in diameter, 36 feet in diameter to 38 feet in diameter, and 38 feet in diameter to 40 feet in diameter. In embodiments, the drying chamber (KBG) is comprised of a material that is selected from one or more from the group consisting of carbon steel, graphite, Hastelloy alloy, nickel, stainless steel, tantalum, and titanium.

A flow sensor (KEQ) is made available to measure the flow to the second volatiles and solvent mixture (SVSM) prior to being introduced to the spray dryer (KAP). The flow sensor (KEQ) is configured to input or output a signal (KER) to the computer (COMP). The flow sensor (KEQ) measures the flow of the second volatiles and solvent mixture (SVSM) that is introduced to the liquid input (KAR) of the spray dryer (KAP). A valve (KEC) is positioned to regulate the flow of the second volatiles and solvent mixture (SVSM) prior to being introduced to the spray dryer (KAP). The valve (KEC) has a controller (KED) that is configured to input or output a signal (KEE) to the computer (COMP). The valve (KEC) and the flow sensor (KEQ) may be used together in a flow control loop to set the flowrate of spray dryer (KAP) to a flow rate that includes one or more from the group consisting of: 0.5 gallons per minute (GPM) to 1 GPM, 1 GPM to 1.5 GPM, 1.5 GPM to 2 GPM, 2 GPM to 2.5 GPM, 2.5 GPM to 3 GPM, 3 GPM to 3.5 GPM, 3.5 GPM to 4 GPM, 4 GPM to 4.5 GPM, 4.5 GPM to 5 GPM, 5 GPM to 5.5 GPM, 5.5 GPM to 6 GPM, 6 GPM to 6.5 GPM, 6.5 GPM to 7 GPM, 7 GPM to 7.5 GPM, 7.5 GPM to 8 GPM, 8 GPM to 8.5 GPM, 8.5 GPM to 9 GPM, 9 GPM to 9.5 GPM, 9.5 GPM to 10 GPM, and 10 GPM to 10.5 GPM.

In embodiments, the liquid and/or the second solvent content of the cannabinoid mixture that is transferred to the mixture input (KAR) of the spray dryer (KAP) ranges between 50 weight percent solvent and 95 weight percent liquid and/or the solvent. In embodiments, the liquid and/or the second solvent content of the cannabinoid mixture that is transferred to the mixture input (KAR) of the spray dryer (KAP) ranges between 60 weight percent solvent and 92 weight percent solvent.

In embodiments, the second volatiles and solvent mixture (SVSM) (e.g., a cannabinoid and liquid mixture) is pressurized. An inlet pressure sensor (KBE) is provided to measure the inlet pressure prior to the spray dryer (KAP). The inlet pressure sensor (KBE) measures the pressure of the second volatiles and solvent mixture (SVSM) that is introduced to the liquid input (KAR) of the spray dryer (KAP). The inlet pressure sensor (KBE) transmits a signal (KBF) to the computer (COMP).

In embodiments, the range of pressure that the inlet pressure sensor (KBE) transmits to the computer (COMP) ranges from one or more from the group consisting of: 5 pounds per square inch (PSI) to 10 PSI; 10 PSI to 15 PSI; 15 PSI to 20 PSI; 20 PSI to 25 PSI; 25 PSI to 30 PSI; 30 PSI to 35 PSI; 35 PSI to 40 PSI; 40 PSI to 45 PSI; 45 PSI to 50 PSI; 50 PSI to 55 PSI; 55 PSI to 60 PSI; 60 PSI to 65 PSI; 65 PSI to 70 PSI; 70 PSI to 75 PSI; 75 PSI to 80 PSI; 80 PSI to 85 PSI; PSI to 90 PSI; 90 PSI to 95 PSI; 95 PSI to 100 PSI; 100 PSI to 125 PSI; 125 PSI to 145 PSI; 145 PSI to 170 PSI; 170 PSI to 195 PSI; 195 PSI to 200 PSI; 200 PSI to 220 PSI; 220 PSI to 250 PSI; 250 PSI to 275 PSI; 275 PSI to 300 PSI; 300 PSI to 350 PSI; 350 PSI to 402 PSI; 402 PSI to 463 PSI; 463 PSI to 532 PSI; 532 PSI to 612 PSI; 612 PSI to 704 PSI; 704 PSI to 809 PSI; 809 PSI to 930 PSI; 930 PSI to 1070 PSI; 1,070 PSI to 1,231 PSI; 1,231 PSI to 1,415 PSI; 1,415 PSI to 1,627 PSI; 1,627 PSI to 1,872 PSI; 1,872 PSI to 2,152 PSI; 2,152 PSI to 2,475 PSI; 2,475 PSI to 2,846 PSI; 2,846 PSI to 3,273 PSI; 3,273 PSI to 3,764 PSI; 3,764 PSI to 4,329 PSI; 4,329 PSI to 4,978 PSI; 4,978 PSI to 5,725 PSI; 5,725 PSI to 6,584 PSI; 6,584 PSI to 7,571 PSI; 7,571 PSI to 8,707 PSI; 8,707 PSI to 10,013 PSI; 10,013 PSI to 11,515 PSI; and 11,515 PSI to 15,000 PSI.

In embodiments, the residence time of the second volatiles and solvent mixture (SVSM) and gas supply (KAG) within the spray dryer (KAP) or drying chamber (KBG) ranges from one or more from the group selected from: 0.1 seconds to 1 seconds, 1 seconds to 2 seconds, 2 seconds to 3 seconds, 3 seconds to 4 seconds, 4 seconds to 5 seconds, 5 seconds to 6 seconds, 6 seconds to 7 seconds, 7 seconds to 8 seconds, 8 seconds to 9 seconds, 9 seconds to 10 seconds, 10 seconds to 12 seconds, 12 seconds to 15 seconds, 15 seconds to 20 seconds, 20 seconds to 25 seconds, 25 seconds to 30 seconds, 30 seconds to 35 seconds, 35 seconds to 40 seconds, 40 seconds to 45 seconds, 45 seconds to 50 seconds, 50 seconds to 55 seconds, 55 seconds to 60 seconds, 60 seconds to 65 seconds, 65 seconds to 70 seconds, 70 seconds to 80 seconds, 80 seconds to 90 seconds, 90 seconds to 100 seconds, 100 seconds to 110 seconds, and 110 seconds to 120 seconds.

A gas supply (KAG) is made available to the spray dryer (KAP) via a gas input (KAQ). In embodiments, the gas supply (KAG) may include a gas. In embodiments, the gas supply (KAG) may include a carbon dioxide. In embodiments, the gas supply (KAG) may include air. In embodiments, the gas supply (KAG) may include an oxygen-containing gas which includes air, oxygen-enriched-air i.e. greater than 21 mole % 02, and substantially pure oxygen, i.e. greater than about 95 mole % oxygen (the remainder usually comprising N2 and rare gases). In embodiments, the gas supply (KAG) may include flue gas which includes a vapor or gaseous mixture containing varying amounts of nitrogen (N2), carbon dioxide (CO2), water (H2O), and oxygen (O2). Flue gas is generated from the thermochemical process of combustion. In embodiments, the gas supply (KAG) may include a combustion stream.

A filter (KAH) is made available to remove particulates from the gas supply (KAG) prior to being introduced to the gas input (KAQ) of the spray dryer (KAP). A filter (KAH) may include a sorbent (KAH) and be configured to adsorb and/or absorb at least one component that is contained within the gas supply (KAG) prior to being introduced to the gas input (KAQ) of the spray dryer (KAP). In embodiments, the filter (KAH) may be a dehumidifier. In embodiments, the filter (KAH) may remove water from the gas supply (KAG) using an adsorbent. In embodiments, the adsorbent used in the filter (KAH) be selected from one or more from the group consisting of 3 Angstrom molecular sieve, 3 Angstrom zeolite, 4 Angstrom molecular sieve, 4 Angstrom zeolite, activated alumina, activated carbon, adsorbent, alumina, carbon, catalyst, clay, desiccant, molecular sieve, polymer, resin, and silica gel. In embodiments, the filter (KAH) may include any conceivable means to remove moisture from the gas supply (KAG), such as an air conditioner, cooling tower, an adsorber, a plurality of adsorbers. In embodiments, the filter (KAH) may include a cooling tower followed by an adsorber. In embodiments, the filter (KAH) may include a cooling tower followed by a plurality of adsorbers. In embodiments, an adsorber is a packed bed of adsorbent. In embodiments, an adsorber is a moving bed of adsorbent. In embodiments, an adsorber contains an adsorbent.

A fan (KAI) is made available and is configured to introduce the gas supply (KAG) to the spray dryer (KAP). The fan (KAI) is equipped with a motor (KAJ) that has a controller (KAK) which is configured to input or output a signal (KAL) to the computer (COMP). In embodiments, the fan (KAI) operates within a range that is selected from one or more from the group consisting of: 350 standard cubic feet per minute (SCFM) to 3,500 SCFM; 700 SCFM to 7,000 SCFM; 1,050 SCFM to 10,500 SCFM; 1,400 SCFM to 14,000 SCFM; 1,750 SCFM to 17,500 SCFM; 2,100 SCFM to 21,000 SCFM; 2,450 SCFM to 24,500 SCFM; 2,800 SCFM to 28,000 SCFM; 3,150 SCFM to 31,500 SCFM; 3,500 SCFM to 35,000 SCFM; 3,850 SCFM to 38,500 SCFM; 4,200 SCFM to 42,000 SCFM; 4,550 SCFM to 45,500 SCFM; 4,900 SCFM to 49,000 SCFM; 5,250 SCFM to 52,500 SCFM; 5,600 SCFM to 56,000 SCFM; 5,950 SCFM to 59,500 SCFM; 6,300 SCFM to 63,000 SCFM; 6,650 SCFM to 66,500 SCFM; 7,000 SCFM to 70,000 SCFM; and 7,350 SCFM to 73,500 SCFM.

In embodiments, the spray dryer operates at a cannabinoid and liquid mixture (SVSM) flow rate of 0.5 to 1 GPM, the fan (KAI) operates in a range between 350 standard cubic feet per minute (SCFM) to 3,500 SCFM. In embodiments, the spray dryer operates at a cannabinoid and liquid mixture (SVSM) flow rate of 0.5 to 1 GPM, the fan (KAI) operates in a range between 700 SCFM to 7,000 SCFM. In embodiments, the spray dryer operates at a cannabinoid and liquid mixture (SVSM) flow rate of 1 to 1.5 GPM, the fan (KAI) operates in a range between 1,050 SCFM to SCFM. In embodiments, the spray dryer operates at a cannabinoid and liquid mixture (SVSM) flow rate of 1.5 to 5 GPM, the fan (KAI) operates in a range between 1,400 SCFM to 14,000 SCFM. In embodiments, the spray dryer operates at a cannabinoid and liquid mixture (SVSM) flow rate of 2 to 2.5 GPM, the fan (KAI) operates in a range between 1,750 SCFM to 17,500 SCFM. In embodiments, the spray dryer operates at a cannabinoid and liquid mixture (SVSM) flow rate of 2.5 to 3 GPM, the fan (KAI) operates in a range between 2,100 SCFM to 21,000 SCFM. In embodiments, the spray dryer operates at a cannabinoid and liquid mixture (SVSM) flow rate of 3 to 3.5 GPM, the fan (KAI) operates in a range between 2,450 SCFM to 24,500 SCFM. In embodiments, the spray dryer operates at a cannabinoid and liquid mixture (SVSM) flow rate of 3.5 to 4 GPM, the fan (KAI) operates in a range between 2,800 SCFM to 28,000 SCFM. In embodiments, the spray dryer operates at a cannabinoid and liquid mixture (SVSM) flow rate of 4 to 4.5 GPM, the fan (KAI) operates in a range between 3,150 SCFM to 31,500 SCFM. In embodiments, the spray dryer operates at a cannabinoid and liquid mixture (SVSM) flow rate of 4.5 to 5 GPM, the fan (KAI) operates in a range between 3,500 SCFM to SCFM. In embodiments, the spray dryer operates at a cannabinoid and liquid mixture (SVSM) flow rate of 5 to 5.5 GPM, the fan (KAI) operates in a range between 3,850 SCFM to 38,500 SCFM. In embodiments, the spray dryer operates at a cannabinoid and liquid mixture (SVSM) flow rate of 5.5 to 6 GPM, the fan (KAI) operates in a range between 4,200 SCFM to 42,000 SCFM. In embodiments, the spray dryer operates at a cannabinoid and liquid mixture (SVSM) flow rate of 6 to 6.5 GPM, the fan (KAI) operates in a range between 4,550 SCFM to SCFM. In embodiments, the spray dryer operates at a cannabinoid and liquid mixture (SVSM) flow rate of 6.5 to 7 GPM, the fan (KAI) operates in a range between 4,900 SCFM to 49,000 SCFM. In embodiments, the spray dryer operates at a cannabinoid and liquid mixture (SVSM) flow rate of 7 to 7.5 GPM, the fan (KAI) operates in a range between 5,250 SCFM to 52,500 SCFM. In embodiments, the spray dryer operates at a cannabinoid and liquid mixture (SVSM) flow rate of 7.5 to 8 GPM, the fan (KAI) operates in a range between 5,600 SCFM to 56,000 SCFM. In embodiments, the spray dryer operates at a cannabinoid and liquid mixture (SVSM) flow rate of 8 to 8.5 GPM, the fan (KAI) operates in a range between 5,950 SCFM to 59,500 SCFM. In embodiments, the spray dryer operates at a cannabinoid and liquid mixture (SVSM) flow rate of 8.5 to 9 GPM, the fan (KAI) operates in a range between 6,300 SCFM to 63,000 SCFM. In embodiments, the spray dryer operates at a cannabinoid and liquid mixture (SVSM) flow rate of 9 to 9.5 GPM, the fan (KAI) operates in a range between 6,650 SCFM to 66,500 SCFM. In embodiments, the spray dryer operates at a cannabinoid and liquid mixture (SVSM) flow rate of 9.5 to 10 GPM, the fan (KAI) operates in a range between 7,000 SCFM to SCFM. In embodiments, the spray dryer operates at a cannabinoid and liquid mixture (SVSM) flow rate of 10 to 10.5 GPM, the fan (KAI) operates in a range between 7,350 SCFM to 73,500 SCFM.

An air heater (KAF) is made available to heat the gas supply (KAG) prior to being introduced to the gas input (KAQ) of the spray dryer (KAP). FIG. 17E shows the gas supply (KAG) first entering the filter (KAH), then the fan (KAI), and then the air heater (KAF). It is to be noted that combinations of the filter (KAH), fan (KAI), and air heater (KAF) shown in FIG. 17E are non-limiting. For example, the fan (KAI) may be before the filter (KAH), the fan (KAI) may be after the air heater (KAF), the filter (KAH) may be after the fan (KAI), the filter (KAH) may be after the air heater (KAF), the air heater (KAF) may be before the fan (KAI). The air heater (KAF) provides a heated gas supply (KAG) to the spray dryer (KAP).

In embodiments, the ideal range that the temperature sensor (KAM) inputs into the computer (COMP) while measuring the heated gas supply (KAG) is preferably set to 250 degrees Fahrenheit to 600 degrees Fahrenheit, but more preferably to 300 degrees Fahrenheit to 5000 degrees Fahrenheit, but more preferably to 350 degrees Fahrenheit to 450 degrees Fahrenheit. In embodiments, the heated gas supply (KAG) has a temperature selected from the group consisting of: 250 degrees Fahrenheit to 275 degrees Fahrenheit; 275 degrees Fahrenheit to 300 degrees Fahrenheit; 300 degrees Fahrenheit to 325 degrees Fahrenheit; 325 degrees Fahrenheit to 350 degrees Fahrenheit; 350 degrees Fahrenheit to 375 degrees Fahrenheit; 375 degrees Fahrenheit to 400 degrees Fahrenheit; 400 degrees Fahrenheit to 425 degrees Fahrenheit; 425 degrees Fahrenheit to 450 degrees Fahrenheit; 450 degrees Fahrenheit to 475 degrees Fahrenheit; 475 degrees Fahrenheit to 500 degrees Fahrenheit; 500 degrees Fahrenheit to 525 degrees Fahrenheit; 525 degrees Fahrenheit to 550 degrees Fahrenheit; 550 degrees Fahrenheit to 575 degrees Fahrenheit; 575 degrees Fahrenheit to 600 degrees Fahrenheit; 600 degrees Fahrenheit to 625 degrees Fahrenheit; 625 degrees Fahrenheit to 650 degrees Fahrenheit; 650 degrees Fahrenheit to 675 degrees Fahrenheit; 675 degrees Fahrenheit to 700 degrees Fahrenheit; 700 degrees Fahrenheit to 725 degrees Fahrenheit; 725 degrees Fahrenheit to 750 degrees Fahrenheit; 750 degrees Fahrenheit to 775 degrees Fahrenheit; and 775 degrees Fahrenheit to 800 degrees Fahrenheit.

The temperature sensor (KAM) is configured to input a signal (KAN) to the computer (COMP). The computer (COMP), temperature sensor (KAM), and the motor (KAJ) of the fan (KAI) may be used together in a temperature control loop to maintain a constant pre-determined temperature of heated gas to the spray dryer (KAP).

In embodiments, the heated gas supply (KAG) is created by indirect contact with steam in the air heater (KAF). In embodiments, the air heater (KAF) may be electrically heated or heated by a combustion steam or flue gas. The heated gas supply (KAG) may also be a combustion stream. In embodiments, the air heater (KAF) accepts a source of steam from a steam drum (LBE) as shown on FIG. 17F. The steam drum (LBE) provides an eighth steam supply (LDM) to the air heater (KAF), as discussed below. The eighth steam supply (LDM) may be saturated or superheated steam. A steam flow control valve (KAA) is configured to regulate the flow of the steam that passes through the air heater (KAF). The steam flow control valve (KAA) is equipped with a controller (KAB) that sends a signal (KAC) to or from the computer (COMP).

A flow sensor (KAD) is configured to measure the flow of the steam that passes through the air heater (KAF). The flow sensor (KAD) sends a signal (KAE) to the computer (COMP). The computer (COMP), steam flow control valve (KAA), and the flow sensor (KAD) may be used in a control loop to control the flow of steam that is passed through the air heater (KAF). In embodiments, the computer (COMP), steam flow control valve (KAA), flow sensor (KAD), temperature sensor (KAM), and motor (KAJ) of the fan (KAI) may be used together in a temperature control loop to maintain a constant pre-determined temperature of heated gas to the spray dryer (KAP). The steam flow control valve (KAA) may be positioned before or after the air heater (KAF). The air heater (KAF) discharges an eighth condensate (LJA) to the condensate tank (LAP) that is shown on FIG. 17F. A condensate temperature sensor (KK1) is configured to measure the temperature of the eighth condensate (LJA) that leaves the air heater (KAF). The condensate temperature sensor (KK1) sends a signal (KK2) to the computer (COMP).

In embodiments, the solvent separation system separates liquid solvent from the second volatiles and solvent mixture (SVSM) by converting the liquid into a vapor. In embodiments, the solvent separation system evaporates liquid from within the second volatiles and solvent mixture (SVSM) by use of an evaporator (KAO). A spray dryer (KAP) is a type of evaporator (KAO). In embodiments, the spray dryer, and/or evaporator are operated under temperature-controlled conditions. In embodiments, the spray dryer, and/or evaporator are operated under pressure-controlled conditions.

In embodiments, the spray dryer (KAP) and/or evaporator (KAO) operate at a temperature greater than the boiling point of the liquid solvent within the second volatiles and solvent mixture (SVSM) to vaporize the liquid portion of the second volatiles and solvent mixture (SVSM) into a vapor. In embodiments, the spray dryer (KAP) is configured to mix a heated gas supply (KAG) with a second volatiles and solvent mixture (SVSM) under precise computer operated automated control to generate a volatiles and gas mixture (KBV).

In embodiments, the spray dryer (KAP) has an interior (KAP) which accepts both the heated gas supply (KAG) and the second volatiles and solvent mixture (SVSM). In embodiments, the spray dryer (KAP) has an interior (KAP) which accepts both the heated gas supply (KAG) via the gas input (KAQ) and the second volatiles and solvent mixture (SVSM) via the liquid input (KAR). In embodiments, the spray dryer (KAP) is equipped with a plurality of spray nozzles (KBC) that dispense the second volatiles and solvent mixture (SVSM) within the interior (KAP) of the spray dryer (KAP).

In embodiments the spray dryer (KAP) has a drying chamber (KBG) which evaporates liquid within the second volatiles and solvent mixture (SVSM). In embodiments, interior (KBG) of the drying chamber (KBG) is located within the interior (KAP) of the spray dryer (KAP). In embodiments the spray dryer (KAP) has an air distributor (KAT) that is configured to accept the heated gas supply (KAG) from the gas input (KAQ) and distribute it to the interior (KAP) of the drying chamber (KBG). In embodiments, the heated gas supply (KAG) is introduced to the interior (KAP) of the spray dryer (KAP) via the air distributor (KAT) using centrifugal momentum.

In embodiments, the second volatiles and solvent mixture (SVSM) is introduced to the interior (KAP) of the spray dryer (KAP) via a plurality of spray nozzles (KBC). In embodiments, the second volatiles and solvent mixture (SVSM) is introduced to the interior (KBG) of the drying chamber (KBG) via a plurality of spray nozzles (KBC). In embodiments, the second volatiles and solvent mixture (SVSM) is introduced to the interior (KAP) of the spray dryer (KAP) via a rotary atomizer (KAU) which may have a spray nozzle (KBC) or a plurality of spray nozzles (KBC). In embodiments, the second volatiles and solvent mixture (SVSM) is introduced to the interior (KBG) of the drying chamber (KBG) via a rotary atomizer (KAU). In embodiments, the rotary atomizer (KAU) dispenses second volatiles and solvent mixture (SVSM) or start-up liquid (KEO) into the interior (KBG) of the drying chamber (KBG) via an opening (KBD) or a plurality of openings (KBD) or a spray nozzle (KBC) or a plurality of spray nozzles (KBC).

In embodiments the pressure drop across the opening (KBD), plurality of openings (KBD), spray nozzle (KBC), or plurality of spray nozzles (KBC) includes one or more from the group consisting of: 5 pounds per square inch (PSI) to 10 PSI; 10 PSI to 15 PSI; 15 PSI to 20 PSI; 20 PSI to 25 PSI; 25 PSI to 30 PSI; 30 PSI to 35 PSI; 35 PSI to 40 PSI; 40 PSI to 45 PSI; 45 PSI to PSI; 50 PSI to 55 PSI; 55 PSI to 60 PSI; 60 PSI to 65 PSI; 65 PSI to 70 PSI; 70 PSI to 75 PSI; PSI to 80 PSI; 80 PSI to 85 PSI; 85 PSI to 90 PSI; 90 PSI to 95 PSI; 95 PSI to 100 PSI; 100 PSI to 125 PSI; 125 PSI to 145 PSI; 145 PSI to 170 PSI; 170 PSI to 195 PSI; 195 PSI to 200 PSI; 200 PSI to 220 PSI; 220 PSI to 250 PSI; 250 PSI to 275 PSI; 275 PSI to 300 PSI; 300 PSI to 350 PSI; 350 PSI to 402 PSI; 402 PSI to 463 PSI; 463 PSI to 532 PSI; 532 PSI to 612 PSI; 612 PSI to 704 PSI; 704 PSI to 809 PSI; 809 PSI to 930 PSI; 930 PSI to 1070 PSI; 1,070 PSI to 1,231 PSI; 1,231 PSI to 1,415 PSI; 1,415 PSI to 1,627 PSI; 1,627 PSI to 1,872 PSI; 1,872 PSI to 2,152 PSI; 2,152 PSI to 2,475 PSI; 2,475 PSI to 2,846 PSI; 2,846 PSI to 3,273 PSI; 3,273 PSI to 3,764 PSI; 3,764 PSI to 4,329 PSI; 4,329 PSI to 4,978 PSI; 4,978 PSI to 5,725 PSI; 5,725 PSI to 6,584 PSI; 6,584 PSI to 7,571 PSI; 7,571 PSI to 8,707 PSI; 8,707 PSI to 10,013 PSI; 10,013 PSI to 11,515 PSI; and 11,515 PSI to 15,000 PSI.

The rotary atomizer (KAU) has a motor (KAV) and a controller (KAW) that is configured to input or output a signal (KAX) to the computer (COMP). In embodiments, the motor (KAV) of the rotary atomizer (KAU) is connected to a shaft (KBA). In embodiments, the shaft (KBA) is connected to a disc (KBB). In embodiments, the disc (KBB) has an opening (KBD) or a plurality of openings (KBD) or spray nozzle (KBC) or a plurality of spray nozzles (KBC)

installed on it. In embodiments, the motor (KAV) rotates the shaft (KBA) which in turn rotates the disc (KBB) and then distributes the second volatiles and solvent mixture (SVSM) or start-up liquid (KEO) to the interior (KAP) of the spray dryer (KAP) or the interior (KBG) of the drying chamber (KBG).

In embodiments, the spray nozzle (KBC) or plurality of spray nozzles (KBC) each have an opening (KBD). In embodiments, the spray nozzle (KBC) or plurality of spray nozzles (KBC) each have a spray aperture (KK4). In embodiments, the spray nozzle (KBC) or plurality of spray nozzles (KBC) each have an orifice (KK5). In embodiments, the spray nozzle (KBC) or plurality of spray nozzles (KBC) each have an impingement surface (KK6).

In embodiments, at least a portion of the second volatiles and solvent mixture (SVSM) or start-up liquid (KEO) contact an impingement surface (KK6) prior to being dispensed to the interior (KAP) of the spray dryer (KAP) or the interior (KBG) of the drying chamber (KBG) via a spray aperture (KK4). In embodiments, at least a portion of the second volatiles and solvent mixture (SVSM) or start-up liquid (KEO) pass through an orifice (KK5) prior to being dispensed to the interior (KAP) of the spray dryer (KAP) or the interior (KBG) of the drying chamber (KBG) via a spray aperture (KK4). In embodiments, at least a portion of the second volatiles and solvent mixture (SVSM) or start-up liquid (KEO) pass through the spray nozzle (KBC) or plurality of spray nozzles (KBC) and contact an orifice (KK5) prior to being dispensed to the interior (KAP) of the spray dryer (KAP) or the interior (KBG) of the drying chamber (KBG).

In embodiments, the plurality of spray nozzles (KBC) have a spray pattern is a hollow cone, full cone, or a flat spray. In embodiments, the spray pattern includes is that of the whirling type. In embodiments, the whirling type spray nozzle sprays the second volatiles and solvent mixture (SVSM) or start-up liquid (KEO) while rotating the liquid (SVSM, KEO) across a portion of the spray nozzle (KBC). A whirling type spray nozzle (KBC) is one that sprays the second volatiles and solvent mixture (SVSM) or start-up liquid (KEO) while rotating the liquid (SVSM, KEO) across a portion of the spray nozzle (KBC) after a pressure drop has taken place. A whirling type spray nozzle (KBD) is one that sprays the second volatiles and solvent mixture (SVSM) or start-up liquid (KEO) while rotating the liquid (SVSM, KEO) across a portion of the spray nozzle after the liquid or slurry has passed through an orifice.

In embodiments, a whirling type spray nozzle (KBD) includes an orifice (KK5) and an impingement surface (KK6): the orifice (KK5) is configured to accept second volatiles and solvent mixture (SVSM) or start-up liquid (KEO) and drop the pressure from a first higher pressure to a second lower pressure, the first pressure being greater than the second pressure; an impingement surface (KK6) that is configured to accept the liquid (SVSM, KEO) at the second pressure at change its direction to impart rotational or centrifugal momentum.

A whirling type spray nozzle (KBD) is one that sprays a liquid (SVSM, KEO) under cyclone conditions. In embodiments, the spray nozzle (KBD) is comprised of ceramic, metal, brass, 316 stainless steel, 316L stainless steel, stainless steel, polytetrafluoroethylene (PTFE), or plastic, or a composite material. In embodiments, the spray nozzle (KBC) opening (KBD) ranges from 0.030 inches to 0.30 inches. In embodiments, the spray nozzle (KBC) opening (KBD) ranges from 0.03 inches to 0.16 inches. In embodiments, the spray nozzle (KBC) orifice (KK5) ranges from 0.030 inches to 0.30 inches. In embodiments, the spray nozzle (KBC) orifice (KK5) ranges from 0.03 inches to 0.16 inches.

In embodiments, the spray nozzle (KBC) has an orifice (KK5) and a spray aperture (KK4). In embodiments, the spray angle of the spray nozzle (KBC) ranges from 15° to 120°. In embodiments, the spray angle of the spray nozzle (KBC) ranges from 30° to 100°. In embodiments, the spray angle of the spray nozzle (KBC) ranges from 40° to 90°. In embodiments, the spray angle of the spray nozzle (KBC) ranges from 50° to 85°. In embodiments, the spray angle of the spray nozzle (KBC) ranges from 70° to 75°. In embodiments, the spray angle of the spray nozzle (KBC) ranges from 45° to 89°. In embodiments, the spray angle of the spray nozzle (KBC) ranges from 90° to 134°. In embodiments, the spray angle of the spray nozzle (KBC) ranges from 135° to 179°. In embodiments, the spray angle of the spray nozzle ranges (KBC) from 180° to 360°.

In embodiments, the spray nozzle (KBC) creates solid volatiles particulates that have a size selected from one or more from the group consisting of: 0.01 microns to 0.1 microns, 0.1 microns to 0.5 microns, 0.5 microns to 1 microns, 1 microns to 2 microns, 2 microns to 4 microns, 4 microns to 8 microns, 8 microns to 10 microns, 10 microns to 20 microns, 20 microns to 30 microns, 30 microns to 40 microns, 40 microns to 50 microns, 50 microns to 60 microns, 60 microns to 70 microns, 70 microns to 80 microns, 80 microns to 90 microns, 90 microns to 100 microns, and 100 microns to 200 microns.

In embodiments, the spray nozzle (KBC) creates solid volatiles particulates that have a size selected from one or more from the group consisting of: 0.001 microns to 0.002 microns; 0.002 microns to 0.004 microns; 0.004 microns to 0.008 microns; 0.008 microns to 0.016 microns; 0.016 microns to 0.032 microns; 0.032 microns to 0.064 microns; 0.064 microns to 0.122 microns; 0.128 microns to 0.251 microns; 0.256 microns to 0.512 microns; 0.512 microns to 1.0 microns; 1.0 microns to 1.5 microns; 1.5 microns to 2.3 microns; 2.3 microns to 3.5 microns; 3.5 microns to 5.2 microns; 5.2 microns to 7.8 microns; 7.8 microns to 12 microns; 12 microns to 17 microns; 17 microns to 26 microns; 26 microns to 39 microns; 39 microns to 59 microns; 59 microns to 89 microns; 89 microns to 133 microns; 133 microns to 199 microns; 199 microns to 299 microns; 299 microns to 448 microns; 448 microns to 673 microns; 673 microns to 1009 microns; 1009 microns to 1513 microns; 1513 microns to 2270 microns; 2270 microns to 3405 microns; 3405 microns to 5108 microns; and 5108 microns to 7661 microns.

In embodiments, each spray nozzle (KBC) is affixed to the disc (KAB) using one or more connectors selected from the group consisting of national pipe thread, British standard pipe thread, and welded. In embodiments, the spray nozzle (KBC) is connected to the disc (KAB) using 0.25 inch national pipe threads, 0.375 inch national pipe threads, 0.50 inch national pipe threads, 0.625 inch national pipe threads, 0.75 inch national pipe threads, 1 inch national pipe threads, 1.25 inch national pipe threads, 1.375 inch national pipe threads, 1.625 inch national pipe threads, 1.75 inch national pipe threads, 1.875 inch national pipe threads, or 2 inch national pipe threads. In embodiments, the spray nozzle (KBC) is connected to the disc (KAB) using a fitting that includes 0.25 inch pipe threads, 0.375 inch pipe threads, 0.50 inch pipe threads, 0.625 inch pipe threads, inch pipe threads, 1 inch pipe threads, 1.25 inch pipe threads, 1.375 inch pipe threads, 1.625 inch pipe threads, 1.75 inch pipe threads, 1.875 inch pipe threads, or 2 inch pipe threads.

In embodiments, the flow through the disc (KAB) is selected from one or more from the group consisting of 30 gallons per hour to 90 gallons per hour, 90 gallons per hour to 210 gallons per hour, 210 gallons per hour to 330 gallons per hour, 330 gallons per hour to 450 gallons per hour, and 450 gallons per hour to 630 gallons per hour.

In embodiments, the disc (KAB) is has a plurality of spray nozzles (KBC), the plurality of spray nozzles (KBC) is comprised of a quantity of spray nozzles that is selected from one or more from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, and 42 spray nozzles.

In embodiments, the disc (KAB) is has a plurality of spray nozzles (KBC), the quantity of spray nozzles (KBC) that are installed on the disc (KAB) is selected from one or more from the group consisting of: 1 spray nozzles to 3 spray nozzles, 3 spray nozzles to 6 spray nozzles, 6 spray nozzles to 9 spray nozzles, 9 spray nozzles to 12 spray nozzles, 12 spray nozzles to 15 spray nozzles, 15 spray nozzles to 18 spray nozzles, 18 spray nozzles to 21 spray nozzles, 21 spray nozzles to 24 spray nozzles, 24 spray nozzles to 27 spray nozzles, 27 spray nozzles to 30 spray nozzles, 30 spray nozzles to 33 spray nozzles, 33 spray nozzles to 36 spray nozzles, 36 spray nozzles to 39 spray nozzles, and 39 spray nozzles to 42 spray nozzles.

In embodiments, where 1 spray nozzles are used, the flow through each spray nozzle in gallons per hour (GPH) ranges from one of more from the group consisting of: 30 GPH to 90 GPH, GPH to 210 GPH, 210 GPH to 330 GPH, 330 GPH to 450 GPH, and 450 GPH to 630 GPH. In embodiments, where 2 spray nozzles are used, the flow through each spray nozzle ranges from one of more from the group consisting of: 15 GPH to 45 GPH, 45 GPH to 105 GPH, 105 GPH to 165 GPH, 165 GPH to 225 GPH, and 225 GPH to 315 GPH. In embodiments, where 3 spray nozzles are used, the flow through each spray nozzle ranges from one of more from the group consisting of: 10 GPH to 30 GPH 30 GPH to 70 GPH 70 GPH to 110 GPH 110 GPH to 150 GPH, and 150 GPH to 210 GPH.

In embodiments, where 4 spray nozzles are used, the flow through each spray nozzle ranges from one of more from the group consisting of: 8 GPH to 23 GPH, 23 GPH to 53 GPH, 53 GPH to 83 GPH, 83 GPH to 113 GPH, and 113 GPH to 158 GPH. In embodiments, where 5 spray nozzles are used, the flow through each spray nozzle ranges from one of more from the group consisting of: 6 GPH to 18 GPH, 18 GPH to 42 GPH, 42 GPH to 66 GPH, 66 GPH to 90 GPH, and 90 GPH to 126 GPH. In embodiments, where 6 spray nozzles are used, the flow through each spray nozzle ranges from one of more from the group consisting of: 15 GPH to 35 GPH, 35 GPH to 55 GPH, 55 GPH to 75 GPH, and 75 GPH to 105 GPH.

In embodiments, where 7 spray nozzles are used, the flow through each spray nozzle ranges from one of more from the group consisting of: 12.857 GPH and 30 GPH, 30 GPH and 47.143 GPH, 47.143 GPH and 64.286 GPH, and 64.286 GPH and 90 GPH. In embodiments, where 8 spray nozzles are used, the flow through each spray nozzle ranges from one of more from the group consisting of: 11.250 GPH to 26.250 GPH, 26.250 GPH to 41.250 GPH, 41.250 GPH to 56.250 GPH, and 56.250 GPH to 78.750 GPH. In embodiments, where 9 spray nozzles are used, the flow through each spray nozzle ranges from one of more from the group consisting of: 10.000 GPH to 23.333 GPH, 23.333 GPH to 36.667 GPH, 36.667 GPH to 50.000 GPH, and 50.000 GPH to 70.000 GPH.

In embodiments, where 10 spray nozzles are used, the flow through each spray nozzle ranges from one of more from the group consisting of: 9 GPH to 21 GPH, 21 GPH to 33 GPH, 33 GPH to 45 GPH, and 45 GPH to 63 GPH. In embodiments, where 11 spray nozzles are used, the flow through each spray nozzle ranges from one of more from the group consisting of: 8.182 GPH to 19.091 GPH, 19.091 GPH to 30.000 GPH, 30.000 GPH to 40.909 GPH, and 40.909 GPH to 57.273 GPH. In embodiments, where 12 spray nozzles are used, the flow through each spray nozzle ranges from one of more from the group consisting of: 7.5 GPH to 17.5 GPH, 17.5 GPH to 27.5 GPH, 27.5 GPH to 37.5 GPH, and 37.5 GPH to 52.5 GPH.

In embodiments, where 13 spray nozzles are used, the flow through each spray nozzle ranges from one of more from the group consisting of: 6.923 GPH to 16.154 GPH, 16.154 GPH to 25.385 GPH, 25.385 GPH to 34.615 GPH, and 34.615 GPH to 48.462 GPH. In embodiments, where 14 spray nozzles are used, the flow through each spray nozzle ranges from one of more from the group consisting of: 6.429 GPH to 15.000 GPH, 15.000 GPH to 23.571 GPH, 23.571 GPH to 32.143 GPH, and 32.143 GPH to 45.000 GPH. In embodiments, where 15 spray nozzles are used, the flow through each spray nozzle ranges from one of more from the group consisting of: 6 GPH to 14 GPH, 14 GPH to 22 GPH, 22 GPH to 30 GPH, and 30 GPH to 42 GPH.

In embodiments, where 16 spray nozzles are used, the flow through each spray nozzle ranges from one of more from the group consisting of: 13.125 GPH to 20.625 GPH, 20.625 GPH to 28.125 GPH, and 28.125 GPH to 39.375 GPH. In embodiments, where 17 spray nozzles are used, the flow through each spray nozzle ranges from one of more from the group consisting of: 12.353 GPH to 19.412 GPH, 19.412 GPH to 26.471 GPH, and 26.471 GPH to 37.059 GPH. In embodiments, where 18 spray nozzles are used, the flow through each spray nozzle ranges from one of more from the group consisting of: 11.667 GPH to 18.333 GPH, 18.333 GPH to 25.000 GPH, and 25.000 GPH to 35.000 GPH.

In embodiments, where 19 spray nozzles are used, the flow through each spray nozzle ranges from one of more from the group consisting of: 11.053 GPH to 17.368 GPH, 17.368 GPH to 23.684 GPH, and 23.684 GPH to 33.158 GPH. In embodiments, where 20 spray nozzles are used, the flow through each spray nozzle ranges from one of more from the group consisting of: 10.500 GPH to 16.500 GPH, 16.500 GPH to 22.500 GPH, and 22.500 GPH to 31.500 GPH. In embodiments, where 21 spray nozzles are used, the flow through each spray nozzle ranges from one of more from the group consisting of: 10.000 GPH to 15.714 GPH, 15.714 GPH to 21.429 GPH, and 21.429 GPH to 30.000 GPH.

In embodiments, where 22 spray nozzles are used, the flow through each spray nozzle ranges from one of more from the group consisting of: 9.545 GPH to 15.000 GPH, 15.000 GPH to 20.455 GPH, and 20.455 GPH to 28.636 GPH. In embodiments, where 23 spray nozzles are used, the flow through each spray nozzle ranges from one of more from the group consisting of: 9.130 GPH to 14.348 GPH, 14.348 GPH to 19.565 GPH, and 19.565 GPH to 27.391 GPH. In embodiments, where 24 spray nozzles are used, the flow through each spray nozzle ranges from one of more from the group consisting of: 8.75 GPH to 13.75 GPH, 13.75 GPH to 18.75 GPH, and 18.75 GPH to 26.25 GPH.

In embodiments, where 25 spray nozzles are used, the flow through each spray nozzle ranges from one of more from the group consisting of: 8.40 GPH to 13.20 GPH, 13.20

GPH to 18.00 GPH, and 18.00 GPH to 25.20 GPH. In embodiments, where 26 spray nozzles are used, the flow through each spray nozzle ranges from one of more from the group consisting of: 8.077 GPH to 12.692 GPH, 12.692 GPH to 17.308 GPH, and 17.308 GPH to 24.231 GPH. In embodiments, where 27 spray nozzles are used, the flow through each spray nozzle ranges from one of more from the group consisting of: 7.778 GPH to 12.222 GPH, 12.222 GPH to 16.667 GPH, and 16.667 GPH to 23.333 GPH.

In embodiments, where 28 spray nozzles are used, the flow through each spray nozzle ranges from one of more from the group consisting of: 7.500 GPH to 11.786 GPH, 11.786 GPH to 16.071 GPH, and 16.071 GPH to 22.500 GPH. In embodiments, where 29 spray nozzles are used, the flow through each spray nozzle ranges from one of more from the group consisting of: 7.241 GPH to 11.379 GPH, 11.379 GPH to 15.517 GPH, and 15.517 GPH to 21.724 GPH. In embodiments, where 30 spray nozzles are used, the flow through each spray nozzle ranges from one of more from the group consisting of: 7 GPH to 11 GPH, 11 GPH to 15 GPH, and 15 GPH to 21 GPH.

In embodiments, where 31 spray nozzles are used, the flow through each spray nozzle ranges from one of more from the group consisting of: 6.774 GPH to 10.645 GPH, 10.645 GPH to 14.516 GPH, and 14.516 GPH to 20.323 GPH. In embodiments, where 32 spray nozzles are used, the flow through each spray nozzle ranges from one of more from the group consisting of: 6.563 GPH to 10.313 GPH, 10.313 GPH to 14.063 GPH, and 14.063 GPH to 19.688 GPH. In embodiments, where 33 spray nozzles are used, the flow through each spray nozzle ranges from one of more from the group consisting of: 6.364 GPH to 10.000 GPH, 10.000 GPH to 13.636 GPH, and 13.636 GPH to 19.091 GPH.

In embodiments, where 34 spray nozzles are used, the flow through each spray nozzle ranges from one of more from the group consisting of: 6.176 GPH to 9.706 GPH, 9.706 GPH to 13.235 GPH, and 13.235 GPH to 18.529 GPH. In embodiments, where 35 spray nozzles are used, the flow through each spray nozzle ranges from one of more from the group consisting of: 6.000 GPH to 9.429 GPH, 9.429 GPH to 12.857 GPH, and 12.857 GPH to 18.000 GPH. In embodiments, where 36 spray nozzles are used, the flow through each spray nozzle ranges from 9.167 GPH to 12.500 GPH, or 12.500 GPH to 17.500 GPH. In embodiments, where 37 spray nozzles are used, the flow through each spray nozzle ranges from 8.919 GPH to 12.162 GPH, or 12.162 GPH to 17.027 GPH. In embodiments, where 38 spray nozzles are used, the flow through each spray nozzle ranges from 8.684 GPH to 11.842 GPH, or 11.842 GPH to 16.579 GPH. In embodiments, where 39 spray nozzles are used, the flow through each spray nozzle ranges from 8.462 GPH to 11.538 GPH, or 11.538 GPH to 16.154 GPH. In embodiments, where 40 spray nozzles are used, the flow through each spray nozzle ranges from 8.250 GPH to 11.250 GPH, or 11.250 GPH to GPH. In embodiments, where 41 spray nozzles are used, the flow through each spray nozzle ranges 8.049 GPH to 10.976 GPH, or 10.976 GPH to 15.366 GPH. In embodiments, where 42 spray nozzles are used, the flow through each spray nozzle ranges from 7.857 GPH to 10.714 GPH, or 10.714 GPH to 15.000 GPH.

In embodiments, the drying chamber (KBG) is equipped with a heating jacket (KBJ), the heating jacket (KBJ) has a heat transfer medium inlet (KBK) and a heat transfer medium outlet (KBL). FIG. 17E shows the heating jacket (KBJ) installed over a portion of the drying chamber (KBG) creating an interior (KBJ1) having an annular space within which a heat transfer medium flows. A source of steam is provided to the heat transfer medium inlet (KBK). This steam may be a steam supply (LDP) that is provided from a steam drum (LBE) as indicated on FIG. 17F.

In embodiments, a steam trap (KX6) is configured to accept steam, condensate, or non-condensable gases from the interior (KBJ1) of the heating jacket (KBJ) via a heat transfer medium outlet (KBL). Steam, condensate, or non-condensable gases are passed through the valve. During normal operation, only condensate flow through the steam trap (KX6). The condensate the flows through the steam trap (KX6) is the ninth condensate (LJB) that is passed to the condensate tank (LAP) as shown on FIG. 17F.

In embodiments, the steam trap (KX6) is a valve which automatically drains the condensate from the interior (KBJ1) of the heating jacket (KBJ) while remaining tight to live steam, or if necessary, allowing steam to flow at a controlled or adjusted rate. In embodiments, the steam trap (KX6) also allows non-condensable gases to pass through it while remaining tight to steam. In embodiments, the steam trap (KX6) is a mechanical trap such as a bucket trap or a floating ball trap. In embodiments, the steam trap (KX6) is a thermostatic trap such as a balanced pressure trap or a bimetallic trap. In embodiments, the steam trap (KX6) is a thermodynamic trap which work by using the difference in velocity between steam and condensate.

In embodiments, a steam flow control valve (KX1) is provided and is configured to regulate the flow of steam that is passes through the heating jacket (KBJ). The steam flow control valve (KX1) has a controller (KX2) which is configured to input or output a signal (KX3) to the computer (COMP). FIG. 17E shows the steam flow control valve (KX1) positioned to regulate steam that enters the heat transfer medium inlet (KBK) of the heating jacket (KBJ). It is to be noted that it is also contemplated that in certain instances, the steam flow control valve (KX1) may be positioned to regulate the heat transfer fluid that is discharged from the interior (KBJ1) of the heating jacket (KBJ) via the heat transfer medium outlet (KBL).

In embodiments, a flow sensor (KX4) is provided to measure the flow of heat transfer fluid that is passes through the heating jacket (KBJ). FIG. 17E shows the flow sensor (KX4) positioned to measure the flow of steam that enters the heat transfer medium inlet (KBK) of the heating jacket (KBJ). It is to be noted that it is also contemplated that in certain instances, the flow sensor (KX4) may be positioned to measure the heat transfer fluid (steam or steam condensate) that is discharged from the interior (KBJ1) of the heating jacket (KBJ) via the heat transfer medium outlet (KBL). The flow sensor (KX4) inputs a signal (KX5) to the computer (COMP).

In embodiment, the heating jacket (KBJ) is configured to maintain the wall (KWG) within the interior (KBG) drying chamber (KBG) at a constant temperature. In embodiments, the wall temperature ranges from one or more from the group consisting of between: 110 degrees Fahrenheit to 125 degrees Fahrenheit; 125 degrees Fahrenheit to 140 degrees Fahrenheit; 140 degrees Fahrenheit to 155 degrees Fahrenheit; 155 degrees Fahrenheit to 170 degrees Fahrenheit; 170 degrees Fahrenheit to 185 degrees Fahrenheit; 185 degrees Fahrenheit to 200 degrees Fahrenheit; 200 degrees Fahrenheit to 215 degrees Fahrenheit; 215 degrees Fahrenheit to 230 degrees Fahrenheit; 230 degrees Fahrenheit to 245 degrees Fahrenheit; 250 degrees Fahrenheit to 275 degrees Fahrenheit; 275 degrees Fahrenheit to 300 degrees Fahrenheit; 300 degrees Fahrenheit to 325 degrees Fahrenheit; 325 degrees Fahrenheit to 350 degrees Fahrenheit; 350 degrees Fahrenheit to 375 degrees Fahrenheit; 375 degrees Fahrenheit to 400 degrees Fahrenheit; 400 degrees Fahrenheit to 425 degrees Fahrenheit; 425 degrees Fahrenheit to 450 degrees Fahrenheit; 450 degrees Fahrenheit to 475 degrees Fahrenheit; 475 degrees Fahrenheit to 500 degrees Fahrenheit; 500 degrees Fahrenheit to 525 degrees Fahrenheit; 525 degrees Fahrenheit to 550 degrees Fahrenheit; 550 degrees Fahrenheit to 575 degrees Fahrenheit; 575 degrees Fahrenheit to 600 degrees Fahrenheit; 600 degrees Fahrenheit to 625 degrees Fahrenheit; 625 degrees Fahrenheit to 650 degrees Fahrenheit; 650 degrees Fahrenheit to 675 degrees Fahrenheit; 675 degrees Fahrenheit to 700 degrees Fahrenheit; 700 degrees Fahrenheit to 725 degrees Fahrenheit; 725 degrees Fahrenheit to 750 degrees Fahrenheit; 750 degrees Fahrenheit to 775 degrees Fahrenheit; and 775 degrees Fahrenheit to 800 degrees Fahrenheit.

In embodiments, it is desired to operate the heating jacket (KBJ) to maintain a wall (KWG) temperature sufficient to avoid sticking, deposition, burning of volatile particulates or liquid upon surface of the wall (KWG). In embodiments, the surface of the wall (KWG) transfers heat into the interior (KBG) of the drying chamber (KBG). In embodiments, it is desired to operate the heating jacket (KBJ) in a manner that is sufficient to maintain a wall (KWG) temperature that is known to now fouling of the heat surface by sticking, deposition, burning of volatile particulates or liquid upon surface of the wall (KWG). Powder build-up on the wall (KWG) within the interior (KBG) surface of the drying chamber (KBG) poses problems related to start-up and shutdown as discussed below.

In embodiments, the openings (KM4) of the screen (KM3) or mesh (KM3) are selected from one or more from the group consisting of 0.01 microns to 0.1 microns, 0.1 microns to 0.5 microns, 0.5 microns to 1 microns, 1 microns to 2 microns, 2 microns to 4 microns, 4 microns to 8 microns, 8 microns to 10 microns, 10 microns to 20 microns, 20 microns to 30 microns, 30 microns to 40 microns, 40 microns to 50 microns, 50 microns to 60 microns, 60 microns to 70 microns, 70 microns to 80 microns, 80 microns to 90 microns, 90 microns to 100 microns, and 100 microns to 200 microns.

In embodiments, the temperature sensor (KBY) positioned on the first transfer conduit (KBW) in between the second output (KBU) of the spray dryer (KAP) and the first input (KCB) of the first separator (KCA) that measures the temperature of the volatiles and gas mixture (KBV) is preferably optimized to be maintained at 120 degrees Fahrenheit to 400 degrees Fahrenheit, or between 135 degrees Fahrenheit to 300 degrees Fahrenheit, or between 140 degrees Fahrenheit to 160 degrees Fahrenheit, or between 146 degrees Fahrenheit to 154 degrees Fahrenheit. The temperature sensor (KBY) inputs a signal (KBX) to the computer (COMP).

In embodiments, the temperature sensor (KBY) positioned on the first transfer conduit (KBW) in between the second output (KBU) of the spray dryer (KAP) and the first input (KCB) of the first separator (KCA) that measures the temperature of the volatiles and gas mixture (KBV) is preferably optimized to be maintained at 150 degrees Fahrenheit to 250 degrees Fahrenheit, but more preferably to 135 degrees Fahrenheit to 180 degrees Fahrenheit, but more preferably to 145 degrees Fahrenheit to 155 degrees Fahrenheit.

In embodiments, the temperature of the volatiles and gas mixture (KBV) leaving the drying chamber (KBG) ranges from one or more from the group consisting of between: 110 degrees Fahrenheit to 125 degrees Fahrenheit; 125 degrees Fahrenheit to 140 degrees Fahrenheit; 140 degrees Fahrenheit to 155 degrees Fahrenheit; 155 degrees Fahrenheit to 170 degrees Fahrenheit; 170 degrees Fahrenheit to 185 degrees Fahrenheit; 185 degrees Fahrenheit to 200 degrees Fahrenheit; 200 degrees Fahrenheit to 215 degrees Fahrenheit; 215 degrees Fahrenheit to 230 degrees Fahrenheit; 230 degrees Fahrenheit to 245 degrees Fahrenheit; 250 degrees Fahrenheit to 275 degrees Fahrenheit; 275 degrees Fahrenheit to 300 degrees Fahrenheit; 300 degrees Fahrenheit to 325 degrees Fahrenheit; 325 degrees Fahrenheit to 350 degrees Fahrenheit; 350 degrees Fahrenheit to 375 degrees Fahrenheit; and 375 degrees Fahrenheit to 400 degrees Fahrenheit.

In embodiments, the difference in temperature between the heated gas supply (KAG) and the volatiles and gas mixture (KBV) ranges from between 110 degrees Fahrenheit to 125 degrees Fahrenheit; 125 degrees Fahrenheit to 140 degrees Fahrenheit; 140 degrees Fahrenheit to 155 degrees Fahrenheit; 155 degrees Fahrenheit to 170 degrees Fahrenheit; 170 degrees Fahrenheit to 185 degrees Fahrenheit; 185 degrees Fahrenheit to 200 degrees Fahrenheit; 200 degrees Fahrenheit to 215 degrees Fahrenheit; 215 degrees Fahrenheit to 230 degrees Fahrenheit; 230 degrees Fahrenheit to 245 degrees Fahrenheit; 250 degrees Fahrenheit to 275 degrees Fahrenheit; 275 degrees Fahrenheit to 300 degrees Fahrenheit; 300 degrees Fahrenheit to 325 degrees Fahrenheit; 325 degrees Fahrenheit to 350 degrees Fahrenheit; 350 degrees Fahrenheit to 375 degrees Fahrenheit; 375 degrees Fahrenheit to 400 degrees Fahrenheit; 400 degrees Fahrenheit to 425 degrees Fahrenheit; 425 degrees Fahrenheit to 450 degrees Fahrenheit; 450 degrees Fahrenheit to 475 degrees Fahrenheit; 475 degrees Fahrenheit to 500 degrees Fahrenheit.

In embodiments, a pressure sensor (KBH) is configured to measure the pressure within the interior (KBG) of the drying chamber (KBG) and output a signal (KBI) to the computer (COMP). In embodiments, the ranges of pressure within the interior (KBG) of the drying chamber (KBG) is selected from one of more from the group consisting of: 1.5 pounds per square inch absolute (PSIA) 3 PSIA, 3 PSIA to 4.5 PSIA, 4.5 PSIA to 6 PSIA, 6 PSIA to 7.5 PSIA, 7.5 PSIA to 9 PSIA, 9 PSIA to 10.5 PSIA, 10.5 PSIA to 12 PSIA, 12 PSIA to 13.5 PSIA, 12 PSIA to 12.25 PSIA, 12.25 PSIA to 12.5 PSIA, 12.5 PSIA to 12.75 PSIA, 12.75 PSIA to 13 PSIA, 13 PSIA to 13.25 PSIA, 13.25 PSIA to 13.5 PSIA, 13.5 PSIA to 13.75 PSIA, 13.75 PSIA to 14 PSIA, 14 PSIA to 14.25 PSIA, 14.25 PSIA to 14.5 PSIA, 14.5 PSIA to 14.75 PSIA, 14.75 PSIA to 15 PSIA, 15 PSIA to 16.5 PSIA, 16.5 PSIA to 18 PSIA, 18 PSIA to 19.5 PSIA, 19.5 PSIA to 21 PSIA, 21 PSIA to 22.5 PSIA, 22.5 PSIA to 24 PSIA, 24 PSIA to 25.5 PSIA, 25.5 PSIA to 27 PSIA, 27 PSIA to 28.5 PSIA, 28.5 PSIA to 30 PSIA, 30 PSIA to 31.5 PSIA, 31.5 PSIA to 33 PSIA, 33 PSIA to 34.5 PSIA, and 34.5 PSIA to 36 PSIA.

In embodiments, the ranges of pressure within the interior (KBG) of the drying chamber (KBG) is selected from one of more from the group consisting of: between about 0.001 inches of water to about 0.002 inches of water; between about 0.002 inches of water to about 0.003 inches of water; between about 0.003 inches of water to about 0.006 inches of water; between about 0.006 inches of water to about 0.012 inches of water; between about 0.012 inches of water to about 0.024 inches of water; between about 0.024 inches of water to about 0.050 inches of water; between about 0.050 inches of water to about 0.075 inches of water; between about 0.075 inches of water to about 0.150 inches of water; between about 0.150 inches of water to about 0.300 inches of water; between about 0.300 inches of water to about 0.450 inches of water; between about 0.450 inches of water to about 0.473 inches of water; between about 0.473 inches of water to about 0.496 inches of water; between about 0.496 inches of water to about 0.521 inches of water; between about 0.521 inches of water to about 0.547 inches of water; between about 0.547 inches of water to about 0.574 inches of water; between about 0.574 inches of water to about 0.603 inches of water; between about 0.603 inches of water to about 0.633 inches of water; between about 0.633 inches of water to about 0.665 inches of water; between about 0.665 inches of water to about 0.698 inches of water; between about 0.698 inches of water to about 0.733 inches of water; between about 0.733 inches of water to about 0.770 inches of water; between about 0.770 inches of water to about 0.808 inches of water; between about 0.808 inches of water to about 0.849 inches of water; between about 0.849 inches of water to about 0.891 inches of water; between about 0.891 inches of water to about 0.936 inches of water; between about 0.936 inches of water to about 0.982 inches of water; between about 0.982 inches of water to about 1.031 inches of water; between about 1.031 inches of water to about 1.083 inches of water; between about 1.083 inches of water to about 1.137 inches of water; between about 1.137 inches of water to about 1.194 inches of water; between about 1.194 inches of water to about 1.254 inches of water; between about 1.254 inches of water to about 1.316 inches of water; between about 1.316 inches of water to about 1.382 inches of water; between about 1.382 inches of water to about 1.451 inches of water; between about 1.451 inches of water to about 1.524 inches of water; between about 1.524 inches of water to about 2.286 inches of water; between about 2.286 inches of water to about 3.429 inches of water; between about 3.429 inches of water to about 5.143 inches of water; between about 5.143 inches of water to about 7.715 inches of water; between about 7.715 inches of water to about 11.572 inches of water; between about 11.572 inches of water to about 17.358 inches of water; between about 17.358 inches of water to about 26.037 inches of water; between about 26.037 inches of water to about 39.055 inches of water; between about 39.055 inches of water to about 58.582 inches of water; between about 58.582 inches of water to about 87.873 inches of water; between about 87.873 inches of water to about 131.810 inches of water; between about 131.810 inches of water to about 197.715 inches of water; between about 197.715 inches of water to about 296.573 inches of water; or, between about 296.573 inches of water to about 400 inches of water.

Spray dried volatiles (KBT) may be removed from the first output (KB S) of the drying chamber (KBG). In embodiments, the spray dried volatiles (KBT), removed from the first output (KB S) of the drying chamber (KBG), include a cannabinoid, and/or any additional ingredient, chemical, drug, additive, emulsifier, surfactant, etc., mentioned in this specification not only including such as a fiber-starch material, a binding agent, a moisture improving textural supplement, a density improving textural supplement, insects, psilocybin extract, psilocin extract, baeocystin extract, and/or norbaeocystin extract, a hallucinogen, serotonin, melatonin, psilocybin, psilocin, baeocystin, lysergic acid diethylamide (LSD), ibogaine, and/or mescaline, and combinations thereof.

In embodiments, the volatiles (KBT) removed from the first output (KB S) of the drying chamber (KBG) may be solid or may contain liquid. In embodiments, the volatiles (KBT) removed from the first output (KBS) of the drying chamber (KBG) are either too wet or too large, or both, to be evacuated from the second output (KBU) of the drying chamber (KBG). In embodiments, the volatiles (KBT) removed from the first output (KBS) may be mixed with one or more stream of separated volatiles, such first separated volatiles (KCG), second separated volatiles (KCP), third separated volatiles (KCV), a fourth separated volatiles (KCX), or a large particulate portion (KCY) to form combined volatiles (KM7) as shown in FIG. 17E.

In embodiments, a vibrator (KBN) is connected to the spray dryer (KAP) or drying chamber (KBG) via a connection (KBR). In embodiments, the spray dryer (KAP) or drying chamber (KBG) is equipped with a vibrator (KBN). In embodiments, a vibrator (KBN) vibrates at least a portion of the spray dryer (KAP) or drying chamber (KBG) to aide in removal of the spray dried volatiles (KBT) from the first output (KBS). In embodiments, the vibrator (KBN) is pneumatic. In embodiments, the vibrator (KBN) operates at a vibration range that is selected from one or more from the group consisting of 3,000 vibrations per minute (VPM) to 4000 VPM, 4,000 VPM to 5,000 VPM, 5,000 VPM to 5,500 VPM, 5,500 VPM to 6,000 VPM, 6,000 VPM to 6,500 VPM, 6,500 VPM to 7,000 VPM, 7,000 VPM to 7,500 VPM, 7,500 VPM to 8,000 VPM, 8,000 VPM to 8,500 VPM, 8,500 VPM to 9,000 VPM, 9,000 VPM to 9,500 VPM, 9,500 VPM to 10,000 VPM, 10,000 VPM to 15,000 VPM, 15,000 VPM to 20,000 VPM, 20,000 VPM to 25,000 VPM, 25,000 VPM to 30,000 VPM, 30,000 VPM to 35,000 VPM, 35,000 VPM to 40,000 VPM, 40,000 VPM to 45,000 VPM, and 45,000 VPM to 50,000 VPM. In embodiments, the vibrator (KBN) has a motor (KBO) with a controller (KBP) that is configured to input or output a signal (KBQ) to the computer (COMP).

In embodiments, the small particulate portion (KCW) has a liquid content that ranges from one or more from the group selected from 0.05 weight percent of liquid to 0.1 weight percent of liquid, 0.1 weight percent of liquid to 0.2 weight percent of liquid, 0.2 weight percent of liquid to weight percent of liquid, 0.4 weight percent of liquid to 0.8 weight percent of liquid, 0.8 weight percent of liquid to 1 weight percent of liquid, 1 weight percent of liquid to 2 weight percent of liquid, 2 weight percent of liquid to 3 weight percent of liquid, 3 weight percent of liquid to 4 weight percent of liquid, 4 weight percent of liquid to 5 weight percent of liquid, 5 weight percent of liquid to 6 weight percent of liquid, 6 weight percent of liquid to 7 weight percent of liquid, 7 weight percent of liquid to 8 weight percent of liquid, 8 weight percent of liquid to 9 weight percent of liquid, 9 weight percent of liquid to 10 weight percent of liquid, 10 weight percent of liquid to 11 weight percent of liquid, 11 weight percent of liquid to 12 weight percent of liquid, 12 weight percent of liquid to 13 weight percent of liquid, 13 weight percent of liquid to 14 weight percent of liquid, 14 weight percent of liquid to 15 weight percent of liquid, 15 weight percent of liquid to 16 weight percent of liquid, 16 weight percent of liquid to 17 weight percent of liquid, 17 weight percent of liquid to 18 weight percent of liquid, 18 weight percent of liquid to 19 weight percent of liquid, and 19 weight percent of liquid to 20 weight percent of liquid.

In embodiments, the small particulate portion (KCW) has a liquid content that ranges from one or more from the group selected from 0.05 weight percent of liquid to 0.1 weight percent of liquid, 0.1 weight percent of liquid to 0.2 weight percent of liquid, 0.2 weight percent of liquid to weight percent of liquid, 0.4 weight percent of liquid to 0.8 weight percent of liquid, 0.8 weight percent of liquid to 1 weight percent of liquid, 1 weight percent of liquid to 2 weight percent of liquid, 2 weight percent of liquid to 3 weight percent of liquid, 3 weight percent of liquid to 4 weight percent of liquid, 4 weight percent of liquid to 5 weight percent of liquid, 5 weight percent of liquid to 6 weight percent of liquid, 6 weight percent of liquid to 7 weight percent of liquid, 7 weight percent of liquid to 8 weight percent of liquid, 8 weight percent of liquid to 9 weight percent of liquid, 9 weight percent of liquid to 10 weight percent of liquid, 10 weight percent of liquid to 11 weight percent of liquid, 11 weight percent of liquid to 12 weight percent of liquid, 12 weight percent of liquid to 13 weight percent of liquid, 13 weight percent of liquid to 14 weight percent of liquid, 14 weight percent of liquid to 15 weight percent of liquid, 15 weight percent of liquid to 16 weight percent of liquid, 16 weight percent of liquid to 17 weight percent of liquid, 17 weight percent of liquid to 18 weight percent of liquid, 18 weight percent of liquid to 19 weight percent of liquid, and 19 weight percent of liquid to 20 weight percent of liquid.

In embodiments, the large particulate portion (KCY) has a liquid content that ranges from one or more from the group selected from 0.05 weight percent of liquid to 0.1 weight percent of liquid, 0.1 weight percent of liquid to 0.2 weight percent of liquid, 0.2 weight percent of liquid to weight percent of liquid, 0.4 weight percent of liquid to 0.8 weight percent of liquid, 0.8 weight percent of liquid to 1 weight percent of liquid, 1 weight percent of liquid to 2 weight percent of liquid, 2 weight percent of liquid to 3 weight percent of liquid, 3 weight percent of liquid to 4 weight percent of liquid, 4 weight percent of liquid to 5 weight percent of liquid, 5 weight percent of liquid to 6 weight percent of liquid, 6 weight percent of liquid to 7 weight percent of liquid, 7 weight percent of liquid to 8 weight percent of liquid, 8 weight percent of liquid to 9 weight percent of liquid, 9 weight percent of liquid to 10 weight percent of liquid, 10 weight percent of liquid to 11 weight percent of liquid, 11 weight percent of liquid to 12 weight percent of liquid, 12 weight percent of liquid to 13 weight percent of liquid, 13 weight percent of liquid to 14 weight percent of liquid, 14 weight percent of liquid to 15 weight percent of liquid, 15 weight percent of liquid to 16 weight percent of liquid, 16 weight percent of liquid to 17 weight percent of liquid, 17 weight percent of liquid to 18 weight percent of liquid, 18 weight percent of liquid to 19 weight percent of liquid, and 19 weight percent of liquid to 20 weight percent of liquid. In embodiments, the liquid may include a solvent, water, ethanol, an ethanol and water mixture, an oil, and/or combinations thereof.

In embodiments, the large particulate portion (KCY) has a liquid content that ranges from one or more from the group selected from 0.05 weight percent of liquid to 0.1 weight percent of liquid, 0.1 weight percent of liquid to 0.2 weight percent of liquid, 0.2 weight percent of liquid to 0.4 weight percent of liquid, 0.4 weight percent of liquid to 0.8 weight percent of liquid, 0.8 weight percent of liquid to 1 weight percent of liquid, 1 weight percent of liquid to 2 weight percent of liquid, 2 weight percent of liquid to 3 weight percent of liquid, 3 weight percent of liquid to 4 weight percent of liquid, 4 weight percent of liquid to 5 weight percent of liquid, 5 weight percent of liquid to 6 weight percent of liquid, 6 weight percent of liquid to 7 weight percent of liquid, 7 weight percent of liquid to 8 weight percent of liquid, 8 weight percent of liquid to 9 weight percent of liquid, 9 weight percent of liquid to 10 weight percent of liquid, 10 weight percent of liquid to 11 weight percent of liquid, 11 weight percent of liquid to 12 weight percent of liquid, 12 weight percent of liquid to 13 weight percent of liquid, 13 weight percent of liquid to 14 weight percent of liquid, 14 weight percent of liquid to 15 weight percent of liquid, 15 weight percent of liquid to 16 weight percent of liquid, 16 weight percent of liquid to 17 weight percent of liquid, 17 weight percent of liquid to 18 weight percent of liquid, 18 weight percent of liquid to 19 weight percent of liquid, and 19 weight percent of liquid to 20 weight percent of liquid.

In embodiments, the volatiles (KBT) removed the drying chamber (KBG) have a liquid content that ranges from one or more from the group selected from 0.05 weight percent of liquid to 0.1 weight percent of liquid, 0.1 weight percent of liquid to 0.2 weight percent of liquid, 0.2 weight percent of liquid to 0.4 weight percent of liquid, 0.4 weight percent of liquid to 0.8 weight percent of liquid, 0.8 weight percent of liquid to 1 weight percent of liquid, 1 weight percent of liquid to 2 weight percent of liquid, 2 weight percent of liquid to 3 weight percent of liquid, 3 weight percent of liquid to 4 weight percent of liquid, 4 weight percent of liquid to 5 weight percent of liquid, 5 weight percent of liquid to 6 weight percent of liquid, 6 weight percent of liquid to 7 weight percent of liquid, 7 weight percent of liquid to 8 weight percent of liquid, 8 weight percent of liquid to 9 weight percent of liquid, 9 weight percent of liquid to 10 weight percent of liquid, weight percent of liquid to 11 weight percent of liquid, 11 weight percent of liquid to 12 weight percent of liquid, 12 weight percent of liquid to 13 weight percent of liquid, 13 weight percent of liquid to 14 weight percent of liquid, 14 weight percent of liquid to 15 weight percent of liquid, 15 weight percent of liquid to 16 weight percent of liquid, 16 weight percent of liquid to 17 weight percent of liquid, 17 weight percent of liquid to 18 weight percent of liquid, 18 weight percent of liquid to 19 weight percent of liquid, and 19 weight percent of liquid to 20 weight percent of liquid.

In embodiments, the volatiles (KBT) removed the drying chamber (KBG) have a liquid content that ranges from one or more from the group selected from 0.05 weight percent of liquid to 0.1 weight percent of liquid, 0.1 weight percent of liquid to 0.2 weight percent of liquid, 0.2 weight percent of liquid to 0.4 weight percent of liquid, 0.4 weight percent of liquid to 0.8 weight percent of liquid, 0.8 weight percent of liquid to 1 weight percent of liquid, 1 weight percent of liquid to 2 weight percent of liquid, 2 weight percent of liquid to 3 weight percent of liquid, 3 weight percent of liquid to 4 weight percent of liquid, 4 weight percent of liquid to 5 weight percent of liquid, 5 weight percent of liquid to 6 weight percent of liquid, 6 weight percent of liquid to 7 weight percent of liquid, 7 weight percent of liquid to 8 weight percent of liquid, 8 weight percent of liquid to 9 weight percent of liquid, 9 weight percent of liquid to 10 weight percent of liquid, weight percent of liquid to 11 weight percent of liquid, 11 weight percent of liquid to 12 weight percent of liquid, 12 weight percent of liquid to 13 weight percent of liquid, 13 weight percent of liquid to 14 weight percent of liquid, 14 weight percent of liquid to 15 weight percent of liquid, 15 weight percent of liquid to 16 weight percent of liquid, 16 weight percent of liquid to 17 weight percent of liquid, 17 weight percent of liquid to 18 weight percent of liquid, 18 weight percent of liquid to 19 weight percent of liquid, and 19 weight percent of liquid to 20 weight percent of liquid.

In embodiments, the spray dryer (KAP) drying chamber (KBG) is configured to mix the heated gas supply (KAG) with the second volatiles and solvent mixture (SVSM) to form a volatiles and gas mixture (KBV). The volatiles and gas mixture (KBV) is discharged from the spray dryer (KAP) via a second output (KBU). The volatiles and gas mixture (KBV) include a spray dried volatiles portion (KBV), a vapor portion (KBV"), and a gas portion (KBV). In embodiments, the spray dried volatiles portion (KBV) may include solid particulates. In embodiments, the vapor portion (KBV") is the second solvent. In embodiments, the vapor portion (KBV") may include the vapor-phase of the liquid within the second volatiles and solvent mixture (SVSM) which may include the second solvent. In embodiments, the gas portion (KBV) includes whatever was within the gas supply (KAG).

The spray dryer (KAP) has a second output (KBU) that is configured to discharge a volatiles and gas mixture (KBV) from the interior (KBG) of the drying chamber (KBG). In embodiments, the volatiles and gas mixture (KBV) has a spray dried volatiles portion (KBV), vapor portion (KBV"), and a gas portion (KBV). The second output (KBU) of the spray dryer (KAP) is connected to the first-first input (KCB) of the first separator (KCA) via a first transfer conduit (KBW). In embodiments, the first separator (KCA) is a cyclone or a filter. FIG. 17E shows the first separator (KCA) as a cyclone.

The first transfer conduit (KBW) transfers the volatiles and gas mixture (KBV) from the interior (KBG) of the drying chamber (KBG) to the first separator (KCA). The first separator (KCA) separates first separated volatiles (KCG) from the volatiles and gas mixture (KBV) to create a first volatiles depleted gas stream (KCD). The first volatiles depleted gas stream (KCD) is discharged from the first separator (KCA) via a first-first output (KCC).

The first separator (KCA) has: a first-first input (KCB) for receiving the volatiles and gas mixture (KBV) from the spray dryer (KAP), a first-first output (KCC) for evacuating the first volatiles depleted gas stream (KCD) towards the second separator (KCI), and a first-second output (KCF) for transferring first separated volatiles (KCG) towards the third separator (KCR). The first volatiles depleted gas stream (KCD) is transferred from the first-first output (KCC) to the second-first input (KCK) of the second separator (KCI) via a second transfer conduit (KCE).

The first volatiles depleted gas stream (KCD) has a reduced amount of volatiles relative to the volatiles and gas mixture (KBV). The first volatiles depleted gas stream (KCD) has a reduced amount of spray dried volatiles portion (KBV) relative to the volatiles and gas mixture (KBV). The second transfer conduit (KCE) is connected at one end to the first-first output (KCC) of the first separator (KCA) and at another end to the second-first input (KCK) of the second separator (KCI).

The first separated volatiles (KCG) that are separated from the volatiles and gas mixture (KBV) are discharged from the first separator (KCA) via the first-second output (KCF). The third-first input (KCS) of the third separator (KCR) is configured to receive the first separated volatiles (KCG) via a first dipleg (KCH). The first dipleg (KCH) is connected at one end to the first-second output (KCF) of the first separator (KCA) and at a second end to the third-first input (KCS) of the third separator (KCR). The first separated volatiles (KCG) includes at least a portion of the spray dried volatiles portion (KBV) that were separated from the volatiles and gas mixture (KBV).

The second separator (KCI) separates second separated volatiles (KCP) from the first volatiles depleted gas stream (KCD) to create a second volatiles depleted gas stream (KCM). The second volatiles depleted gas stream (KCM) has a reduced amount of volatiles relative to the first volatiles depleted gas stream (KCD). The second volatiles depleted gas stream (KCM) has a reduced amount of spray dried volatiles portion (KBV) relative to the first volatiles depleted gas stream (KCD).

In embodiments, the second separator (KCI) is a cyclone or a filter. FIG. 17E shows the second separator (KCI) as a cyclone. The second volatiles depleted gas stream (KCM) is discharged from the second separator (KCI) via a second-first output (KCJ).

The second separator (KCI) has: a second-first input (KCK) for receiving the first volatiles depleted gas stream (KCD) from the first separator (KCA), a second-first output (KCJ) for evacuating the second volatiles depleted gas stream (KCM) towards the fourth separator (KCZ), and a second-second output (KCO) for transferring second separated volatiles (KCP) towards the third separator (KCR). The second volatiles depleted gas stream (KCM) is transferred from the second-first output (KCJ) to the fourth-first input (KDA) of the fourth separator (KCZ) via a third transfer conduit (KCN). The third transfer conduit (KCN) is connected at one end to the second-first output (KCJ) of the second separator (KCI) and at another end to the fourth-first input (KDA) of the fourth separator (KCZ).

The second separated volatiles (KCP) that are separated from the first volatiles depleted gas stream (KCD) are discharged from the second separator (KCI) via the second-second output (KCO). The third-first input (KCS) of the third separator (KCR) is configured to receive the second separated volatiles (KCP) via a second dipleg (KCQ). The second dipleg (KCQ) is connected at one end to the second-second output (KCO) of the second separator (KCI) and at a second end to the third-first input (KCS) of the third separator (KCR). The second separated volatiles (KCP) includes at least a portion of the volatiles that were separated from the first volatiles depleted gas stream (KCD). The second separated volatiles (KCP) includes at least a portion of the spray dried volatiles portion (KBV) that were separated from the first volatiles depleted gas stream (KCD).

The fourth separator (KCZ) separates an additional separated volatiles (KDF) from the second volatiles depleted gas stream (KCM) to create a third volatiles depleted gas stream (KDC). The third volatiles depleted gas stream (KDC) has a reduced amount of volatiles relative to the second volatiles depleted gas stream (KCM). The third volatiles depleted gas stream (KDC) has a reduced amount of spray dried volatiles portion (KBV) relative to the second volatiles depleted gas stream (KCM). In embodiments, the fourth separator (KCZ) is a cyclone, filter, scrubber, or electrostatic precipitator. In embodiments, the fourth separator (KCZ) is a scrubber that uses second solvent as the scrubbing liquid.

FIG. 17E shows the second separator (KCI) as an electrostatic precipitator. The electrostatic precipitator has an electrode (KM8) and a power supply (KM9) and is configured to separate volatiles from the second volatiles depleted gas stream (KCM). The electrode (KM8) and a power supply (KM9) apply an electrostatic charge to the second volatiles depleted gas stream (KCM) as it passes through the fourth separator (KCZ).

In other embodiments, the fourth separator (KCZ) is a scrubber. The scrubber, is preferably a vertically oriented cylindrical, or rectangular, pressure vessel having a lower section, and an upper section, along with a central section that contains a quantity of packed media either comprising raschig rings, pall rings, berl saddles, intalox packing, metal structured grid packing, hollow spherical packing, high performance thermoplastic packing, structured packing, synthetic woven fabric, or ceramic packing, or the like, wherein media is supported upon a suitable support grid system commonplace to industrial chemical equipment systems. The upper section of the scrubber preferably contains a demister to enhance the removal of liquid droplets entrained in a vapor stream and to minimize carry-over losses of the sorption liquid. In embodiments, the sorption liquid is second solvent. This demister is also positioned above the scrubber spray nozzle system, comprised of a plurality of spray nozzles, or spray balls, that introduce and substantially equally distribute the scrubbing absorption liquid to the scrubber onto the scrubbers central packing section, so it may gravity-flow down through the scrubber central section.

As the second volatiles depleted gas stream (KCM) passes up through the internal packing of the scrubber, excess vapor within the additional separated volatiles (KDF) comes into intimate contact with scrubbing liquid such as a portion of the second solvent, which are cooled prior to being introduced to the upper section of the scrubber through the scrubber spray nozzle system. Vapor from within the second volatiles depleted gas stream (KCM) is condensed into a liquid.

The third volatiles depleted gas stream (KDC) is discharged from the fourth separator (KCZ) via a fourth-first input (KDA). The fourth separator (KCZ) has: fourth-first input (KDA) for receiving the second volatiles depleted gas stream (KCM) from the second separator (KCI), a fourth-first output (KDB) for evacuating the third volatiles depleted gas stream (KDC) towards the condenser (KDH), and a fourth-second output (KDE) for transferring additional separated volatiles (KDF) towards the third separator (KCR).

The third volatiles depleted gas stream (KDC) is transferred from the fourth-first output (KDB) to the gas-vapor inlet (KDP) of the condenser (KDH) via a fourth transfer conduit (KDD). The fourth transfer conduit (KDD) is connected at one end to the fourth-second output (KDE) of the fourth separator (KCZ) and at another end to the gas-vapor inlet (KDP) of the condenser (KDH). The additional separated volatiles (KDF) that are separated from the second volatiles depleted gas stream (KCM) are discharged from the fourth separator (KCZ) via the fourth-second output (KDE). In embodiments, the third-first input (KCS) of the third separator (KCR) is configured to receive at least a portion of the additional separated volatiles (KDF) via a fifth transfer conduit (KDG). The fifth transfer conduit (KDG) is connected at one end to the fourth-second output (KDE) of the fourth separator (KCZ) and at a second end to the third-first input (KCS) of the third separator (KCR).

The third volatiles depleted gas stream (KDC) includes at least a portion of the vapor portion (KBV") or gas portion (KBV) of the volatiles and gas mixture (KBV) that was discharged from the drying chamber (KBG). The additional separated volatiles (KDF) includes at least a portion of the volatiles that were separated from the first volatiles depleted gas stream (KCD). The additional separated volatiles (KDF) include at least a portion of the volatiles that were separated from the second volatiles depleted gas stream (KCM). The additional separated volatiles (KDF) includes at least a portion of the spray dried volatiles portion (KBV) that were separated from the second volatiles depleted gas stream (KCM).

In embodiments, the additional separated volatiles (KDF) have a size range that is selected from one or more from the group consisting of 1 nanometer to 5 nanometers, 5 nanometers to 10 nanometers, 10 nanometers to 15 nanometers, 15 nanometers to 20 nanometers, 20 nanometers to nanometers, 25 nanometers to 30 nanometers, 30 nanometers to 35 nanometers, 35 nanometers to 40 nanometers, 40 nanometers to 45 nanometers, 45 nanometers to 50 nanometers, 50 nanometers to 55 nanometers, 55 nanometers to 60 nanometers, 60 nanometers to 65 nanometers, nanometers to 70 nanometers, 70 nanometers to 75 nanometers, 75 nanometers to 80 nanometers, 80 nanometers to 85 nanometers, 85 nanometers to 90 nanometers, 90 nanometers to nanometers, 95 nanometers to 100 nanometers, 100 nanometers to 200 nanometers, 200 nanometers to 300 nanometers, 300 nanometers to 400 nanometers, 400 nanometers to 500 nanometers, 500 nanometers to 600 nanometers, 600 nanometers to 700 nanometers, 700 nanometers to 800 nanometers, and 800 nanometers to 900 nanometers.

In embodiments, the additional separated volatiles (KDF) have a size range that is selected from one or more from the group consisting of 1 microns to 5 microns, 5 microns to 10 microns, microns to 30 microns, 30 microns to 50 microns, 50 microns to 70 microns, 70 microns to 90 microns, 90 microns to 110 microns, 110 microns to 130 microns, 130 microns to 150 microns, 150 microns to 170 microns, 170 microns to 190 microns, 190 microns to 210 microns, 210 microns to 230 microns, and 230 microns to 250 microns.

In embodiments, the additional separated volatiles (KDF) have a particle size distribution (PSD) that has a lesser or smaller PSD relative to the small particulate portion (KCW) separated in the solid-solid separator (SSS'). In embodiments, the additional separated volatiles (KDF) have a particle size distribution (PSD) that has a lesser or smaller PSD relative to the large particulate portion (KCY) separated in the solid-solid separator (SSS'). In embodiments, the particle size distribution of the small particulate portion (KCW) is lesser or smaller than the particle size distribution of the large particulate portion (KCY).

In embodiments, the small particulate portion (KCW) have a size range that is selected from one or more from the group consisting of 1 microns to 5 microns, 5 microns to 10 microns, microns to 30 microns, 30 microns to 50 microns, 50 microns to 70 microns, 70 microns to 90 microns, 90 microns to 110 microns, 110 microns to 130 microns, 130 microns to 150 microns, 150 microns to 170 microns, 170 microns to 190 microns, 190 microns to 210 microns, 210 microns to 230 microns, and 230 microns to 250 microns.

In embodiments, the large particulate portion (KCY) have a size range that is selected from one or more from the group consisting of 50 microns to 60 microns, 60 microns to 70 microns, 70 microns to 80 microns, 80 microns to 90 microns, 90 microns to 100 microns, 100 microns to 150 microns, 150 microns to 200 microns, 200 microns to 250 microns, 250 microns to 300 microns, 300 microns to 350 microns, 350 microns to 400 microns, 400 microns to 450 microns, 450 microns to 500 microns, 500 microns to 550 microns, 550 microns to 600 microns, 600 microns to 650 microns, 650 microns to 700 microns, 700 microns to 750 microns, 750 microns to 800 microns, 800 microns to 850 microns, 850 microns to 900 microns, 900 microns to 950 microns, and 950 microns to 1,000 microns.

As shown in FIG. 17E the third separator (KCR) accepts first separated volatiles (KCG) from the first separator (KCA), and second separated volatiles (KCP) from the second separator (KCI), and optionally a portion of the additional separated volatiles (KDF) from the fourth separator (KCZ), and separates at least a small particulate portion (KCW) and a large particulate portion (KCY) therefrom.

In embodiments, the third separator (KCR) includes solid-solid separator (SSS'). In embodiments, the third separator (KCR) includes a sifter as shown in FIG. 17E. In embodiments, the third separator (KCR) includes a filter. In embodiments, the third separator (KCR) has a third-first input (KCS) for receiving: first separated volatiles (KCG) via the first dipleg (KCH), second separated volatiles (KCP) via the second dipleg (KCQ), and additional separated volatiles (KDF) via the fifth transfer conduit (KDG). In embodiments, the third separator (KCR) has a third-first output (KCT) for discharging a third separated volatiles (KCV) which include a small particulate portion (KCW). In embodiments, the small particulate portion (KCW), large particulate portion (KCY), and/or the spray dried volatiles (KBT) may be transferred to the multifunctional composition tank (6F1) on FIG. 18, or to the cannabinoid tank (6A2) on FIG. 18 for foodstuff and/or beverage production on FIG. 18F in the mixing tank (G15).

In embodiments, the third separator (KCR) has a third-second output (KCU) for discharging a fourth separated volatiles (KCX) which include a large particulate portion (KCY). In embodiments, the large particulate portion (KCY) may be transferred to the cannabinoid tank (6A2) on FIG. 18. In embodiments, the third separator (KCR) separates a small particulate portion (KCW) from a large particulate portion (KCY) using a screen (KM3) or a mesh (KM3). The screen (KM3) or mesh (KM3) have openings (KM4) that permit the small particulate portion (KCW) to pass through the openings (KM4). The openings (KM4) in the screen (KM3) or mesh (KM3) are too small for the large particulate portion (KCY) to pass through.

In embodiments, the openings (KM4) in the screen (KM3) or mesh (KM3) include United States Sieve size number 18, 20, 25, 30, 35, 40, 45, 50, 60, 70, 80, 100, 120, 140, 170, 200, 230, 270, 325, or 400. In embodiments, the openings (KM4) in the screen (KM3) or mesh (KM3) have a size range that is selected from one or more from the group consisting of 37 microns to 44 microns, 44 microns to 53 microns, 53 microns to 63 microns, 63 microns to 74 microns, 74 microns to 88 microns, 88 microns to 105 microns, 105 microns to 125 microns, 125 microns to 149 microns, 149 microns to 177 microns, 177 microns to 210 microns, 210 microns to 250 microns, 250 microns to 297 microns, 297 microns to 354 microns, 354 microns to 420 microns, 420 microns to 500 microns, 500 microns to 595 microns, 595 microns to 707 microns, 707 microns to 841 microns, and 841 microns to 1,000 microns.

In embodiments, the screen (KM3) or mesh (KM3) may be cylindrical and located within a first chamber (KM5). In embodiments, the third separator (KCR) has a third-first input (KCS) that is configured to receive particulate volatiles that include first separated volatiles (KCG), second separated volatiles (KCP), and optionally additional separated volatiles (KDF). An auger (KM1) is configured to transfer the particulate volatiles from the third-first input (KCS) to a screen (KM3) or mesh (KM3) located within the first chamber (KM5) of the third separator (KCR). The auger (KM1) is equipped with a motor (KM2) that may be operated by the computer (COMP). The particulate volatiles transferred from the third-first input (KCS) are sifted using a cylindrical screen (KM3) or mesh (KM3) that is located within the first chamber (KM5).

The third-first output (KCT) is located at the bottom of the first chamber (KM5). The small particulate portion (KCW) may be removed from the third separator (KCR) via the third-first output (KCT) located in the first chamber (KM5). The large particulate portion (KCY) that are too large to pass through openings (KM4) of the screen (KM3) or a mesh (KM3) are transferred from the first chamber (KM5) to the second chamber (KM6) of the third separator (KCR). Since the openings (KM4) in the screen (KM3) or mesh (KM3) within the first chamber (KM5) are too small for the large particulate portion (KCY) to pass through, the large particulate portion (KCY) is transferred from the first chamber (KM5) to the second chamber (KM6) of the third separator (KCR). The large particulate portion (KCY) are removed from the second chamber (KM6) of the third separator (KCR) via the third-second output (KCU).

In embodiments, *cannabis* plants (107, 207) may be provided to the solid-solid separator (SSS') shown in FIG. 17E. In embodiments, the *cannabis* plants (107, 207) are transferred to the solid-solid separator (SSS') after harvesting and may be *cannabis* plants (107, 207), trimmed *cannabis* (TR1, TR1*), *cannabis* trimmings (TR2, TR2*), ground *cannabis* (GR1), heated *cannabis* (HT1), dried *cannabis*, freeze dried *cannabis*, and/or frozen *cannabis*. In embodiments, the solid-solid separator (SSS') includes a sifter configured to sift the *cannabis* to separate a cannabinoid from the *cannabis*. In embodiments, the solid-solid separator (SSS') sifts the *cannabis* to trichomes from the *cannabis* to produce crystals and/or a powder which includes the cannabinoid. In embodiments, the solid-solid separator (SSS') sifts the *cannabis* to produce hash. The *cannabis* may be added to the solid-solid separator (SSS') together with the spray-dried particulate, or separately to produce dry sifted hash separate from sifting the spray-dried particulate.

In embodiments, the sifter is provided by the Kason Corporation. In embodiments, sifter includes a vibratory screener or a centrifugal sifter. In embodiments, the sifter is provided by Kason Corporation and includes a VIBRO SCREEN® Circular Vibratory Screener and Separator, a CENTRI-SIFTER™ High Capacity Screener and Separator, a VIBRO-BED™ Circular Vibratory Fluid Bed Processor, or a CROSS-FLO High Capacity Static Sieve Screener and Separator.

In embodiments, the motor (KM2) of the third separator (KCR) is driven by a belt and ranges from 0.75 horsepower to 6 horsepower. In embodiments, the motor (KM2) of the third separator (KCR) is driven by a belt and ranges from 0.56 kilowatts to 4.48 kilowatts. In embodiments, the motor (KM2) of the third separator (KCR) is not driven by a belt and ranges from 0.5 horsepower to 4 horsepower. In embodiments, the motor (KM2) of the third separator (KCR) is driven by a belt and ranges from 0.37 kilowatts to 2.98 kilowatts.

The fourth separator (KCZ) is connected to the condenser (KDH) via a fourth transfer conduit (KDD). The third volatiles depleted gas stream (KDC) is transferred through the fourth transfer conduit (KDD) and enters the condenser (KDH). The third volatiles depleted gas stream (KDC) includes the vapor portion (KBV") and gas portion (KBV) that were transferred from the spray dryer (KAP).

The condenser (KDH) condenses the vapor portion (KBV") which may include the second solvent. Liquid is formed from condensing the vapor portion (KBV") of the third volatiles depleted gas stream (KDC) to form process condensate (KDO). Liquid is formed from condensing solvent contained within the third volatiles depleted gas stream (KDC) to form process condensate (KDO). The process condensate (KDO) is discharged from the condenser (KDH) via a liquid output (KDR).

The gas portion (KBV) of the third volatiles depleted gas stream (KDC) is not condensed within the condenser (KDH) and is instead released from the condenser (KDH) as a via the gas output (KDQ). The non-condensables (KDT) includes the gas portion (KBV) of the third volatiles depleted gas stream (KDC) and may include gas, air, nitrogen, carbon dioxide. The non-condensables (KDT) leave the gas output (KDQ) of the condenser (KDH) and are routed to a vacuum (KDM) via a gas transfer conduit (KDS).

In embodiments, the vacuum (KDM) is a vacuum pump, fan, or an eductor. A gas exhaust (KDN) is discharged from the vacuum (KDM). The gas exhaust (KDN) includes non-condensables (KDT) or the gas portion (KBV) of the third volatiles depleted gas stream (KDC) is not condensed within the condenser (KDH).

The condenser (KDH) is provided with a cooling water input (KDI) and a cooling water output (KDK). The cooling water input (KDI) is configured to accept a cooling water supply (KDJ) and the cooling water output (KDK) is configured to discharge a cooling water return (KDL). The cooling water supply (KDJ) is configured to condense a portion of the vapor that enters through the gas-vapor inlet (KDP).

Evaporator Operation: The system shown in FIG. 17E can operate in a plurality of modes of operation, including:
(1) preparation of the second volatiles and solvent mixture (SVSM);
(2) start-up;
(3) normal operation;
(4) emergency shut-down;
(5) resuming operations after the emergency shut-down.

As seen in FIG. 17E, the solvent separation system is equipped with a start-up/shut-down liquid system (KEZ). The purpose of the start-up/shut-down liquid system (KEZ) is to make a pressurized and optionally heated supply of liquid immediately available to the evaporator (KAO) whenever necessary. It is preferred that second solvent (SOLV2) is used within the start-up/shut-down liquid system (KEZ). Water, or an oil, a lipid, a fatty acid, and/or a first solvent (SOLV1), or a second solvent (SOLV2) may be used in the start-up/shut-down liquid system (KEZ).

In embodiments, the second solvent (SOLV2), as mentioned above, insome embodiments may include one or more from the group consisting of petroleum ether, pentane, n-hexane, hexanes, diethyl ether, ethyl acetate, and ethanol. In embodiments, the second solvent (SOLV2) includes one or more from the group consisting of liquid, acetone, alcohol, oil, ethanol. In embodiments, the second solvent (SOLV2) includes one or more from the group consisting of petroleum ether, a heptane, n-heptane, diethyl ether, and methyl tert butyl ether. In embodiments, the first solvent (SOLV1) includes one or more from the group consisting of petroleum ether, a heptane, n-heptane, diethyl ether, and methyl tert butyl ether. In embodiments, the second solvent (SOLV2) includes one or more selected from the group consisting of a medium-chain triglyceride, diglyceride, an ester, ethyl acetate, glycerin, glycerol, a hydrocarbon, isopropyl alcohol, methanol, a monoglyceride, a polyol, amylene hydrate, benzyl benzoate, butyl alcohol, carbon tetrachloride, chloroform, corn oil, cottonseed oil, ethyl acetate, glycerol, hexylene glycol, methylene chloride, methyl isobutyl ketone, mineral oil, peanut oil, propylene carbonate, and sesame oil.

In embodiments, the first solvent (SOLV1) includes a non-polar solvent selected from one or more of the group consisting of pentane, petroleum ether, hexanes, n-hexane, heptane, diisopropyl ether, toluene, chloroform, and methylene chloride; preferably petroleum ether, hexanes, n-hexane, heptane, and n-heptane.

In embodiments, the first solvent (SOLV1) includes a non-polar solvent selected from one or more of the group consisting of pentane, petroleum ether, hexanes, n-hexane, n-heptane, heptanes, diisopropyl ether, toluene, chloroform, and methylene chloride. In embodiments, the first solvent A in the binary solvent system is petroleum ether, a heptane, or n-heptane.

In embodiments, the second solvent (SOLV2) includes a non-polar solvent selected from one or more of the group consisting of pentane, petroleum ether, hexanes, n-hexane, heptane, diisopropyl ether, toluene, chloroform, and methylene chloride; preferably petroleum ether, hexanes, n-hexane, heptane, and n-heptane.

In embodiments, the second solvent (SOLV2) includes a non-polar solvent selected from one or more of the group consisting of pentane, petroleum ether, hexanes, n-hexane, n-heptane, heptanes, diisopropyl ether, toluene, chloroform, and methylene chloride. In embodiments, the first solvent in the binary solvent system is petroleum ether, a heptane, or n-heptane. It is also desired to be able to mix a known flow of treated, filtered, start-up/shut-down water (KEO) in with the second volatiles and solvent mixture (SVSM) to be used for start-up, shut-down or maintenance purposes such as cleaning.

A start-up/shut-down liquid tank (KEA) is provided and is configured to accept a stream of liquid (KEB), such as water, a first solvent, a second solvent, an emulsion, a nanoemulsion, a microemulsion, a colloid, a colloid suspension, which may or may not include a cannabinoid. In some embodiments, the liquid (KEB) transferred to the interior (KEA) of the start-up/shut-down liquid tank (KEA) can be passed through a filter (G23), activated carbon (G24), and/or an adsorbent (G25), and a polishing unit (G41). The polishing unit (G41) may be any type of conceivable device to improve the water quality such as an ultraviolet unit, ozone unit, microwave unit, filter, a distillation system or the like.

The start-up/shut-down liquid tank (KEA) may be equipped with a level sensor (KES) that sends a signal (KET) to the computer (COMP). A level control valve (KEU) may be used to control the amount of liquid (KEB) that is transferred to the interior (KEA) of the start-up/shut-down liquid tank (KEA). The level control valve (KEU) may be equipped with a controller (KEV) that is configured to input or output a signal (KEW) to the computer (COMP). The computer (COMP), level control valve (KEU), and level sensor (KES) may be used together in a level control loop to maintain a constant or batch supply of liquid to the interior (KEA) of the start-up/shut-down liquid tank (KEA).

In embodiments, a start-up heat exchanger (KEP) is configured to heat the liquid (KEB) that will be transferred to the evaporator (KAO). In embodiments, a start-up heat exchanger (KEP) is configured to heat the liquid (KEB) that will be transferred to the evaporator (KAO), spray dryer (KAP), rotary atomizer (KAU), spray nozzle (KBC) or plurality of spray nozzles (KBC), or openings (KBC) or plurality of openings (KBC) within the disc (KBB) of the rotary atomizer (KAU). The purpose of heating the liquid than will be transferred to the evaporator (KAO) is to not provide a thermal shock on the system while can result in fouled heat transfer surfaces of the outer wall (KWG) within the interior (KBG) of the drying chamber (KBG), and to prevent cloggage of either the disc (KBB), spray nozzle (KBC), plurality of spray nozzles (KBC), opening (KBD), plurality of openings (KBD), spray aperture (KK4), or orifice (KK5).

Is it desired to heat the liquid (KEO, KEB) that is transferred to the spray dryer (KAP) so that a seamless transition from liquid (KEO, KEB) to a cannabinoid and liquid mixture (SVSM) can be realized to attain steady-state conditions in the safest and most efficient manner as possible. In some embodiments, the a cannabinoid and liquid mixture is contained within the liquid tank (KEA), which may include recycled cannabinoids, off-spec liquid mixtures of cannabinoids and a liquid to minimize waste in the entire FSS processing system.

In embodiments, it is necessary to be able to heat the liquid (KEB) prior to adding to the evaporator (KAO) by itself, or add the liquid (KEB) to the evaporator (KAO) together while adding the second volatiles and solvent mixture (SVSM). Herein are disclosed methods to vary the flow of liquid (KEB) to an evaporator, such as a spray dryer, while varying either the flow of liquid (KEB) and/or the flow of second volatiles and solvent mixture (SVSM) to optimize operations and efficiency while reducing plant maintenance and cleaning.

FIG. 17E shows the start-up heat exchanger (KEP) positioned within the interior (KEA) start-up/shut-down liquid tank (KEA). In embodiments, the start-up heat exchanger (KEP) is located in between the start-up/shut-down liquid tank (KEA) and the evaporator (KAO).

In embodiments, a liquid pump (KEK) is provided and configured to transfer liquid from the start-up/shut-down liquid tank (KEA) and into the evaporator (KAO). The liquid pump (KEK) is equipped with a motor (KEL) and a controller (KEM) which is configured to input or output a signal (KEN) to the computer (COMP).

In embodiments, a liquid control valve (KEF) is provided to control the flow of start-up/shut-down liquid (KEB, KEO) transferred from the start-up/shut-down liquid tank (KEA) into the evaporator (KAO). The liquid control valve (KEF) is equipped with a controller (KEG) that is configured to input or output a signal (KEH) to the computer (COMP).

In embodiments, a liquid flow sensor (KEI) is provided to measure the flow of start-up/shut-down liquid (KEB, KEO) transferred from the start-up/shut-down liquid tank (KEA) into the evaporator (KAO). In embodiments, the computer (COMP), liquid control valve (KEF), liquid flow sensor (KEI), are used in a flow control loop to control the amount of liquid (KEB, KEO) that is provided into the evaporator (KAO).

FIG. 17E shows a co-current spray dryer (KAP) evaporator (KAO). In FIG. 17E the liquid input (KAR) is closer to the top (K-T) than the bottom (K-B). In FIG. 17E the gas input (KAQ) is closer to the top (K-T) than the bottom (K-B). In FIG. 17E the first output (KBS) is closer to the bottom (K-B) than the top (K-T). In FIG. 17E the second output (KBU) is closer to the bottom (K-B) than the top (K-T). Here, the heated gas supply (KAG) flows in the same direction of the second volatiles and solvent mixture (SVSM).

FIG. 17E-1

FIG. 17E-1 shows one non-limiting embodiment of a co-current type of spray dryer (KAP) that may be used with the solvent separation system described in FIG. 17E.

Shown in FIGS. 17E, 17E-1, 17E-2, 17E-3, and 17E-4, are different embodiments of a spray dryer (KAP) having a top (K-T) bottom (K-B) that are spaced apart along a vertical axis (KYY). The differences between the different types of spray dryers shown in FIGS. 17E-1, 17E-2, 17E-3, and 17E-4 are the differences in height of various inputs and outputs, specifically, the differences in relative heights of: (A) the liquid input (KAR) that introduces an second volatiles and solvent mixture (SVSM) to the interior (KAP) of the spray dryer (KAP); (B) the gas input (KAQ) that introduces a heated gas supply (KAG) to the interior (KAP) of the spray dryer (KAP); (C) first output (KBS) that discharges volatiles (KBT) from the from the interior (KAP) of the spray dryer (KAP); and (D) second output (KBU) that evacuates a volatiles and gas mixture (KBV) away from the interior (KAP) of the spray dryer (KAP).

In FIG. 17E-1 the liquid input (KAR) is closer to the top (K-T) than the bottom (K-B). In FIG. 17E-1 the gas input (KAQ) is closer to the top (K-T) than the bottom (K-B). In FIG. 17E-1 the first output (KBS) is closer to the bottom (K-B) than the top (K-T). In FIG. 17E-1 the second output (KBU) is closer to the bottom (K-B) than the top (K-T). FIG. 17E-1 shows a co-current spray dryer (KAP) evaporator (KAO) with the heated gas supply (KAG) flowing in the same direction of the second volatiles and solvent mixture (SVSM).

FIG. 17E-2

FIG. 17E-2 shows one non-limiting embodiment of a counter-current type of spray dryer (KAP) that may be used with the solvent separation system described in FIG. 17E.

In FIG. 17E-2 the liquid input (KAR) is closer to the top (K-T) than the bottom (K-B). In FIG. 17E-2 the gas input (KAQ) is closer to the bottom (K-B) than the top (K-T). In FIG. 17E-2 the first output (KBS) is closer to the bottom (K-B) than the top (K-T). In FIG. 17E-2 the second output (KBU) is closer to the top (K-T) than the bottom (K-B). FIG. 17E-2 shows a counter-current spray dryer (KAP) evaporator (KAO) with the heated gas supply (KAG) flowing in a direction that is opposite to the flow of the second volatiles and solvent mixture (SVSM). Here, the heated gas supply (KAG) flows upwards from the gas input (KAQ) to the second output (KBU), while the second volatiles and solvent mixture (SVSM) is sprayed in a downwards direction.

FIG. 17E-3

FIG. 17E-3 shows another non-limiting embodiment of a counter-current type of spray dryer (KAP) that may be used with the solvent separation system described in FIG. 17E.

In FIG. 17E-3 the liquid input (KAR) is closer to the bottom (K-B) than the top (K-T). In FIG. 17E-3 the gas input (KAQ) is closer to the top (K-T) than the bottom (K-B). In FIG. 17E-3 the first output (KBS) is closer to the bottom (K-B) than the top (K-T). In FIG. 17E-3 the second output (KBU) is closer to the bottom (K-B) than the top (K-T).

FIG. 17E-3 shows a counter-current spray dryer (KAP) evaporator (KAO) with the heated gas supply (KAG) flowing in a direction that is opposite to the flow of the second volatiles and solvent mixture (SVSM). Here, the heated gas supply (KAG) flows downwards from the gas input (KAQ) to the second output (KBU), while the second volatiles and solvent mixture (SVSM) is sprayed in an upwards direction.

FIG. 17E-4

FIG. 17E-4 shows one non-limiting embodiment of a mixed-flow type of spray dryer (KAP) that may be used with the solvent separation system described in FIG. 17E.

In FIG. 17E-4 the liquid input (KAR) is closer to the bottom (K-B) than the top (K-T). In FIG. 17E-4 the gas input (KAQ) is closer to the top (K-T) than the bottom (K-B). In FIG. 17E-4 the first output (KBS) is closer to the bottom (K-B) than the top (K-T). In FIG. 17E-4 the second output (KBU) is second output (KBU) is closer to the bottom (K-B) than the top (K-T), the other (KBU) is closer to the top (K-T) than the bottom (K-B).

FIG. 17E-4 shows a mixed-flow spray dryer (KAP) evaporator (KAO) with the heated gas supply (KAG) flowing in a direction that is opposite to the flow of the second volatiles and solvent mixture (SVSM). Here, the heated gas supply (KAG) flows both, in the same direction of the second volatiles and solvent mixture (SVSM), as well as opposite to the direction of the flow of the second volatiles and solvent mixture (SVSM). Here, the second volatiles and solvent mixture (SVSM) is sprayed in an upwards direction.

FIG. 17F

FIG. 17F shows a power production system (PPS) that is configured to generate electricity, heat, or steam for use in the farming superstructure system (FSS).

In embodiments, the power production system (PPS) shown in FIG. 17F can generate electricity for use in the farming superstructure system (FSS). In embodiments, the power production system (PPS) shown in FIG. 17F can generate steam and/or heat for use in the farming superstructure system (FSS). In embodiments, the power production system (PPS) shown in FIG. 17F can generate heat for use in the farming superstructure system (FSS). In embodiments, the power production system (PPS) includes a compressor (LEB), a combustor (LED), a turbine (LFE), a generator (LFH), a HRSG (heat recovery steam generator) (LFI), a steam drum (LBE), a steam distribution header (LCJ), and a condensate tank (LAP). In embodiments, the turbine (LFE) may be a wind turbine and turns the shaft with wind power.

An oxygen-containing gas (LEA) is made available to a compressor (LEB). In embodiments, the oxygen-containing gas may be air, oxygen-enriched-air i.e. greater than 21 mole % O2, and substantially pure oxygen, i.e. greater than about 95 mole % oxygen (the remainder usually comprising N2 and rare gases). In embodiments, the oxygen-containing gas may be flue gas or carbon dioxide. In embodiments, flue gas includes a vapor or gaseous mixture containing varying amounts of nitrogen (N2), carbon dioxide (CO2), water (H2O), and oxygen (O2). In embodiments, flue gas is generated from the thermochemical process of combustion. In embodiments, combustion is an exothermic (releases heat) thermochemical process wherein at least the stoichiometric oxidation of a carbonaceous material takes place to generate flue gas. In embodiments, the compressor (LEB) has a plurality of stages (LEC). In embodiments, the compressor (LEB) is an axial compressor. In embodiments, the compressor is configured to compress and pressurize the oxygen-containing gas (LEA) to form a compressed gas stream (LEK). In embodiments, the compressor is configured to compress and pressurize the oxygen-containing gas (LEA) to form a first compressed gas stream (LEK) and a second compressed gas stream (LEN). In embodiments, compressed gas stream (LEK) is provided to a combustor (LED). In embodiments, the first compressed gas stream (LEK) is provided to a first combustor (LED1). In embodiments, the second compressed gas stream (LEN) is provided to a second combustor (LED2).

In embodiments, the first combustor (LED1) has a first gas mixer (LEE). In embodiments, the second combustor (LED2) has a second gas mixer (LEH). In embodiments, the first gas mixer (LEE) or second gas mixer (LEH) is that of an annular type. In embodiments, the first combustor (LED1) or second combustor (LED2) is that of an annular type. In embodiments, the annular type gas mixer (LEE) mixes the fuel with the oxygen containing-gas within the combustor to form a fuel-and-oxygen-containing gas mixture, which is then combusted. In embodiments, the first combustor (LED1) has a first ignitor (LEF). In embodiments, the second combustor (LED2) has a second ignitor (LEI). In embodiments, the first ignitor (LEF) or second ignitor (LEI) include a torch ignitor. In embodiments, the first ignitor (LEF) or second ignitor (LEI) include a separate fuel supply to maintain a constantly burning torch. In embodiments, the first combustor (LED1) has a first flame detector (LEG). In embodiments, the second combustor (LED2) has a second flame detector (LEJ). In embodiments, the first flame detector (LEG) or second flame detector (LEJ) are selected from one or more from the group consisting of a UV flame detector, IR flame detector, UV/IR flame detector, multi-spectrum infrared flame detector, and a visual flame imaging flame detector.

In embodiments, the combustor (LED) mixes and combusts the compressed gas stream (LEK) with a first fuel (LEL) to produce a combustion stream (LEM). In embodiments, the first combustor (LED1) mixes and combusts the first compressed gas stream (LEK) with a first fuel (LEL) to produce a first combustion stream (LEM). In embodiments, the first combustion stream (LEM) is a first pressurized combustion stream (LEM). In embodiments, the second combustor (LED2) mixes and combusts the second compressed gas stream (LEN) with a second fuel (LEO) to produce a second combustion stream (LEP). In embodiments, the second combustion stream (LEP) is a second pressurized combustion stream (LEP).

A first fuel valve (LEW) is provided to regulate the flow of the compressor fuel source (LEU) to the first combustor (LED1) and the second combustor (LED2). The first fuel valve (LEW) is equipped with a controller (LEX) that is configured to input or output a signal (LEY) to the computer (COMP). FIG. 17F shows connector (K1) to show continuity between the second fuel (LEO) that is apportioned from the compressor fuel source (LEU) and transferred to the second combustor (LED2).

The combustion stream (LEM) is transferred to a turbine (LFE). In embodiments, the first combustion stream (LEM) is combined with the second combustion stream (LEP) before being transferred to the turbine (LFE). In embodiments, the turbine (LFE) has a plurality of stages (LFF). In embodiments, the first and second combustion streams (LEM, LEP) rotate a portion of the turbine (LFE), which in turn rotates a shaft (LFG), and a generator (LFH) to produce electricity (ELEC). In embodiments, the combustion stream (LEM) rotates the turbine (LFE), which in turn rotates a shaft (LFG), and a generator (LFH) to produce electricity (ELEC).

In embodiments, the compressor (LEB) is connected to the turbine (LFE) via a shaft (LFG). In embodiments, the turbine (LFE) is connected to the generator (LFH) via a shaft (LFG). In embodiments, the turbine (LFE) rotates the shaft (LFG) which in turn drives the compressor (LEB). In embodiments, the generator (LFH) is connected to the turbine (LFE) via a shaft (LFG). In embodiments, the turbine (LFE) rotates the shaft (LFG) which in turn drives the generator (LFH) to produce electricity for use in the farming superstructure system (FSS).

FIG. 17F shows the generator (LFH) producing electricity for use in the computer (COMP) within the farming superstructure system (FSS). In embodiments, the electricity (ELEC) may be used in the farming superstructure system (FSS) in any number of a plurality of: sensors, motors, pumps, heat exchangers, fans, actuators, controllers, compressors, analyzers, computers, lights, heaters, vacuum pumps, etc. Any asset, including sensors, motors, pumps, heat exchangers, fans, actuators, controllers, compressors, analyzers, computers, lights, heaters, vacuum pumps, disclosed in FIGS. 1A through 23 may be powered by the electricity (ELEC) generated by the generator (LFH) or generator (LCA).

A combustion stream (LFD) is discharged from the turbine (LFE) and is routed to a HRSG (LFI). In embodiments, the combustion stream (LFD) that is discharged from the turbine (LFE) is a depressurized combustion stream (LFD). In embodiments the depressurized combustion stream (LFD) has a pressure that is less than the pressure of the combustion stream (LEM, LEP) that is transferred to the turbine (LFE). The combustion stream (LFD) is transferred from the turbine (LFE) to the HRSG (LFI). The HRSG (LFI) is configured to remove heat from the combustion stream (LFD) by use of a heat transfer conduit (LBI) or a plurality of heat transfer conduits (LBI). At least one heat transfer conduit (LBI) generates steam through indirect heat transfer from the combustion stream (LFD).

In embodiments, the HRSG (LFI) is a fired-HRSG (LFJ). In embodiments, the fired-HRSG (LFJ) accepts a HRSG fuel source (LEV). In embodiments, the HRSG fuel source (LEV) is combusted with the combustion stream (LFD) that is transferred from the turbine (LFE) to form a combustion stream (LX0). In embodiments, the HRSG fuel source (LEV) is combusted with an oxygen-containing gas (LX0). In the instance where the HRSG fuel source (LEV) is combusted with an oxygen-containing gas (LX0), the compressor (LEB), a combustor (LED), a turbine (LFE), a generator (LFH) are optional. Thus, saturated steam (LBR) or superheated steam (LB S) may be generated within the steam drum (LBE) by combusting an oxygen-containing gas (LX0) with the compressor fuel source (LEU) to form a combustion stream (LX0).

In embodiments, a second fuel valve (LFA) is made available to regulate the amount of the HRSG fuel source (LEV) that is introduced to the fired-HRSG (LFJ). The second fuel valve (LFA) is equipped with a controller (LFB) that is configured to input or output a signal (LFC) to the computer (COMP). In embodiments, the compressor fuel source (LEU) and HRSG fuel source (LEV) come from a common fuel source (LEQ). A compressor fuel source (LEU) provides the fuel that is used as the first fuel (LEL) and second fuel (LEO). In embodiments, the fuel source (LEQ) that is made available as the compressor fuel source (LEU) or HRSG fuel source (LEV) may include a hydrocarbon. In embodiments, the fuel source (LEQ) that is made available as the compressor fuel source (LEU) or HRSG fuel source (LEV) may be a liquid, vapor, or a gas. In embodiments, the fuel source (LEQ) that is made available as the compressor fuel source (LEU) or HRSG fuel source (LEV) may be a methane containing gas such as natural gas. In embodiments, the fuel source (LEQ) that is made available as the compressor fuel source (LEU) or HRSG fuel source (LEV) may be naphtha, natural gas, gasoline, a hydrocarbon, diesel, or oil. In embodiments, the fuel source (LEQ, LET, LEU, LEV), may include a hydrocarbon, and may be a liquid, vapor, or a gas. In embodiments, the fuel source (LEQ, LET, LEU, LEV), may be a methane containing gas such as natural gas, or otherwise may be naphtha, natural gas, gasoline, a hydrocarbon, diesel, or oil.

In embodiments, a fuel source (LEQ) is made available to a fuel compressor (LER) to form a compressed fuel (LET). In embodiments, the fuel compressor (LER) has a plurality of stages (LES). A pressure sensor (LEQP) is provided to measure the pressure of the fuel source (LEQ) that is made available to the fuel compressor (LER). In embodiments, the compressor fuel source (LEU) and HRSG fuel source (LEV) are a compressed fuel (LET). In embodiments, the HRSG fuel source (LEV) is combusted within the fired-HRSG (LFJ) using a burner (LFK) such as a duct burner. In embodiments, the fired-HRSG (LFJ) or the burner (LFK) is lined with refractory material. In embodiments, the refractory material includes a ceramic, alumina, silica, magnesia, silicon carbide, or graphite.

In embodiments, heat is removed from the HRSG (LFI) and a flue gas (LFP) is evacuated from the HRSG (LFI). In embodiments, heat is removed from the fired-HRSG (LFJ) and a flue gas (LFP) is evacuated from the fired-HRSG (LFJ). A temperature sensor (LFM) is configured to measure the temperature within the HRSG (LFI, LFJ). A temperature sensor (LFM) is configured to measure the temperature of the flue gas (LFP) that is discharged from the HRSG (LFI, LFJ).

In embodiments, at least a portion of the flue gas (LFP) is made available as flue gas (FG1) that may be transferred to the thermal compressor (Q30) on FIG. 5C or 5E. In embodiments, at least a portion of the flue gas (LFP) is made available as flue gas (FG1) that may be transferred to the generator (Q50) within the thermal compressor (Q30) on FIG. 5C or 5E.

The steam generated in the plurality of heat transfer conduits (LBI) is routed to a steam drum (LBE). In embodiments, the steam drum (LBE) generates saturated steam (LBR) or superheated steam (LBS). In embodiments, saturated steam (LBR) is discharged from the steam drum (LBE) and is routed to a superheater (LX3) through a saturated steam transfer conduit (LX1). Heat is transferred from the combustion stream (LFD, LX0) to saturated steam (LBR) within the superheater (LX3) to produce superheated steam (LBS) which is routed to a superheated steam transfer conduit (LX2).

A steam distribution header (LCJ) is configured to accept at least a portion of the saturated steam (LBR) or superheated steam (LBS). In embodiments, a first portion (LBW) of either the saturated steam (LBR) or superheated steam (LBS) is transferred through a first steam transfer conduit (LBY) and into the steam distribution header (LCJ). In embodiments, a second portion (LBX) of either the saturated steam (LBR) or superheated steam (LBS) is transferred through a second steam transfer conduit (LSY) and into steam turbine (LBZ) to generate electricity via a generator (LCA). In embodiments, the steam turbine (LBZ) has a plurality of stages (LBZX). The steam turbine (LBZ) is connected to a generator (LCA) via a shaft (LCB). Depressurized steam (LCI) is evacuated from the steam turbine (LBZ) and is routed towards the steam distribution header (LCJ).

FIG. 17F shows a steam distribution header (LCJ) that is configured to accept at least a portion of the saturated steam (LBR) or superheated steam (LBS) that are routed through either the first steam transfer conduit (LBY) or second steam transfer conduit (LSY). A pressure sensor (LBO) is provided to measure the pressure within the interior of the steam drum (LBE). A temperature sensor (LBQ) is provided to measure the temperature of the saturated steam (LBR) or superheated steam (LBS) that are discharged from the steam drum (LBE). A pressure control valve (LBT) is positioned on the steam distribution header (LCJ). In embodiments, the pressure control valve (LBT) controls the pressure within the steam drum (LBE). In embodiments, the pressure control valve (LBT) controls the pressure within first steam transfer conduit (LBY) and second steam transfer conduit (LSY). The pressure control valve (LBT) is equipped with a controller (LBU) that sends a signal (LBV) to or from the computer (COMP). In embodiments, the computer (COMP), pressure control valve (LBT), and pressure sensor (LBO) are used in a control loop to regulate the pressure within the steam drum (LBE), first steam transfer conduit (LBY), or second steam transfer conduit (LSY).

In embodiments, the steam distribution header (LCJ) provides a source of steam to a variety of locations within the farming superstructure system (FSS). In embodiments, the velocity of steam within the steam distribution header (LCJ) ranges from one or more from the group selected from 50 feet per second (FPS) to 60 FPS, 60 FPS to 70 FPS, 70 FPS to 80 FPS, 80 FPS to 90 FPS, FPS to 100 FPS, 100 FPS to 110 FPS, 110 FPS to 120 FPS, 120 FPS to 130 FPS, 130 FPS to 140 FPS, 140 FPS to 150 FPS, 150 FPS to 160 FPS, 160 FPS to 180 FPS, 180 FPS to 200 FPS, 200 FPS to 225 FPS, and 225 FPS to 250 FPS.

In embodiments, the steam distribution header (LCJ) operates at a pressure range that is selected from one or more from the group consisting of 5 pounds per square inch (PSI) 10 PSI, 10 PSI 20 PSI, 20 PSI 30 PSI, 30 PSI 40 PSI, 40 PSI 50 PSI, 50 PSI 60 PSI, 60 PSI 70 PSI, 70 PSI 80 PSI, 80 PSI 90 PSI, 90 PSI 100 PSI, 100 PSI 125 PSI, 125 PSI 150 PSI, 150 PSI 175 PSI, 175 PSI 200 PSI, 200 PSI 225 PSI, 225 PSI 250 PSI, 250 PSI 275 PSI, 275 PSI 300 PSI, 300 PSI 325 PSI, 325 PSI 350 PSI, 350 PSI 375 PSI, 375 PSI 400 PSI, 400 PSI 425 PSI, 425 PSI 450 PSI, 450 PSI 475 PSI, 475 PSI 500 PSI, 500 PSI 525 PSI, 525 PSI 550 PSI, 550 PSI 575 PSI, 575 PSI 600 PSI, 600 PSI 700 PSI, 700 PSI 800 PSI, 800 PSI 900 PSI, and 900 PSI 1,000 PSI.

In embodiments, the steam distribution header (LCJ) is insulated with insulation (LCJ). In embodiments, the range of thickness of the insulation (LCJ) on the steam distribution header (LCJ) is selected from one or more from the group consisting of 1 inches to 1.5 inches, 1.5 inches to 2 inches, 2 inches to 2.5 inches, 2.5 inches to 3 inches, 3 inches to 3.5 inches, 3.5 inches to 4 inches, 4 inches to 4.5 inches, 4.5 inches to 5 inches, 5 inches to 5.5 inches, 5.5 inches to 6 inches, 6 inches to 6.5 inches, 6.5 inches to 7 inches, 7 inches to 7.5 inches, 7.5 inches to 8 inches, 8 inches to 8.5 inches, 8.5 inches to 9 inches, 9 inches to 9.5 inches, 9.5 inches to 10 inches, 10 inches to 11 inches, 11 inches to 12 inches, 12 inches to 13 inches, 13 inches to 14 inches, 14 inches to 15 inches, 15 inches to 16 inches, 16 inches to 17 inches, and 17 inches to 18 inches.

In embodiments, the steam distribution header (LCJ) provides a source of steam to a variety of locations including: a first steam supply (LCL) to FIG. 5C to the thermal compressor (Q30), a second steam supply (LCL) to FIG. 17D to the evaporator (J11), a third steam supply (LCL) to FIG. 17E to the spray dryer (KAP), a fourth steam supply (LCL) to FIG. 17E to the spray dryer (KAP) heating jacket (KBJ).

In embodiments, a first steam valve (LCM) is configured to regulate the amount of the first steam supply (LCL) to FIG. 5C to the thermal compressor (Q30). A first reducer (LCN) may be positioned upstream or downstream of the first steam valve (LCM) on the steam distribution header (LCJ).

In embodiments, a second steam valve (LDK) is configured to regulate the amount of the second steam supply (LDJ) to FIG. 17D to the evaporator (J11). A second reducer (LDL) may be positioned upstream or downstream of the second steam valve (LDK) on the steam distribution header (LCJ).

In embodiments, a third steam valve (LDN) is configured to regulate the amount of the third steam supply (LDM) to FIG. 17E to the spray dryer (KAP). A third reducer (LDO) may be positioned upstream or downstream of the third steam valve (LDN) on the steam distribution header (LCJ).

In embodiments, a fourth steam valve (LDQK) is configured to regulate the amount of the fourth steam supply (LDP) to FIG. 17E to the spray dryer (KAP) heating jacket (KBJ). A fourth reducer (LDR) may be positioned upstream or downstream of the fourth steam valve (LDQ) on the steam distribution header (LCJ).

In turn, a plurality of steam condensate streams are transferred from various locations within the FSS and are returned to a condensate tank (LAP) as indicated on FIG. 17F. In embodiments, the condensate tank (LAP) accepts steam condensate streams are transferred from various locations, including: a first condensate (LJC) from FIG. 5C from the thermal compressor (Q30), a second condensate (LAW) from FIG. 17D from the evaporator (J11), a third condensate (LJA) from FIG. 17E from the spray dryer (KAP), a fourth condensate (LJB) from FIG. 17E from the spray dryer (KAP) heating jacket (KBJ).

In embodiments, at least a portion are used again to remove heat within the HRSG (LFI, LFJ): first condensate (LJC), second condensate (LAW), third condensate (LJA), fourth condensate (LJB). In embodiments, feed water (LAX) (which may include condensate (LJC, LAW, LJA, LJB)) is pumped to the from the condensate tank (LAP) to the steam drum input (LBD) of the steam drum (LBE) via a pump (LAX).

A heat exchanger (LAZ) is provided to pre-heat the feed water (LAX) as it is transferred from the condensate tank (LAP) to the steam drum (LBE). A temperature sensor (LAY) is provided to measure the temperature of the feed water (LAX) before it enters the heat exchanger (LAZ). Another temperature sensor (LBC) is provided to measure the temperature of the feed water (LAX) after is exits the heat exchanger (LAZ).

In embodiments, the steam drum (LBE) is equipped with a level sensor (LBP) that is configured to regulate the amount of feed water (LAX) that is introduced to the steam drum (LBE). In embodiments, the steam drum (LBE) is equipped with a level control valve (LBP) that is configured to regulate the amount of feed water (LAX) that is introduced to the steam drum (LBE). In embodiments, the computer (COMP), level sensor (LBP), and level control valve (LBP) may be used in a control loop to regulate the amount of feed water (LAX) that is introduced to the steam drum (LBE).

In embodiments, the steam drum (LBE) is connected to a lower steam drum (LBF) via a plurality of heat transfer conduit (LBG, LBH, LBI). In embodiments, lower steam drum (LBF) is configured to discharge a blowdown (LBK) through a valve (LBN). In embodiments, the blowdown (LBK) includes suspended solids (LBL) and/or dissolved solids (LBM). In embodiments, the suspended solids (LBL) include solids such as bacteria, silt and mud. In embodiments, the dissolved solids (LBM) may include minerals, salts, metals, cations or anions dissolved in water. In embodiments, the dissolved solids (LBM) include inorganic salts including principally calcium, magnesium, potassium, sodium, bicarbonates, chlorides, and sulfates.

In embodiments, the condensate tank (LAP) also serves the purpose as a water tank (LAO) for accepting treated water (LAJ). Thus, treated water (LAJ) is added to the condensate tank (LAP) to make-up for water losses in the system. A source of water (LAA) is made available to a series of unit operations that are configured to improve the water. In embodiments, the source of water (LAA) is passed through a filter (LAC), a packed bed (LAD) of adsorbent (LAE), a cation (LAF), an anion (LAG), a membrane (LAH), followed by another cation/anion (LAI) to result in treated water (LAJ).

The treated water (LAJ) is then provided to the condensate tank (LAP)/water tank (LAO) via a pump (LAK). In embodiments, the treated water (LAJ) that is transferred to the condensate tank (LAP)/water tank (LAO) via a pump (LAK) is passed through a valve (LAL). The valve (LAL) is equipped with a controller (LAM) that is configured to input or output a signal (XAM) to the computer (COMP). A quality sensor (LAN) is provided as a quality control of the unit operations that are configured to improve the water. FIG. 17G FIG. 17G shows one non-limiting embodiment of a carbon dioxide removal system (GAE) that is configured to remove carbon dioxide from flue gas (LFP) for use as a source of carbon dioxide (CO2) in the farming superstructure system (FSS).

Flue gas (LFP) is provided from FIG. 17F to FIG. 17G. The flue gas (LFP) is routed to a first compressor (GAB), which may have a plurality of stages (GAC). A first pressure sensor (GAA) measures the inlet pressure to the first compressor (GAB). The first compressor (GAB) elevates the pressure of the flue gas to produce pressurized flue gas (GAD). A second pressure sensor (GAA) measures the outlet pressure to the first compressor (GAB). A carbon dioxide removal system (GAE) is provided to remove carbon dioxide (CO2) from flue gas (LFP) or from the pressurized flue gas (GAD). A carbon dioxide depleted flue gas is discharged from the carbon dioxide removal system (GAE). In embodiments, the carbon dioxide (CO2) that was removed from the flue gas (LFP, GAD) is provided to the carbon dioxide tank (CO2T), which is discussed in detail on FIGS. 1A and 1B. Alternately, the carbon dioxide (CO2) that was removed from the flue gas (LFP, GAD) may be directly made available to the first growing assembly (100) or second growing assembly (200).

In embodiments, carbon dioxide removal system (GAE) may include one or more from the group consisting of a membrane, an adsorber, a pressure swing adsorber, a temperature swing adsorber, a membrane, a solvent scrubber, a scrubber, an absorber, an amine scrubber, and an amine absorber.

In embodiments, the an adsorber, fixed bed adsorber, moving bed adsorber, a pressure swing adsorber, a temperature swing adsorber, may contain an adsorbent material. In embodiments, the adsorbent material may include regenerable and non-regenerable sorbents. In embodiments, the adsorbent material may be selected from one or more from the group consisting of 3 Angstrom molecular sieve, 3 Angstrom zeolite, 4 Angstrom molecular sieve, 4 Angstrom zeolite, activated alumina, activated carbon, adsorbent, alumina, carbon, catalyst, clay, desiccant, molecular sieve, zeolites, polymer, resin, and silica gel.

In embodiments, a second compressor (GAG) is provided to compress the carbon dioxide that is discharged from the carbon dioxide removal system (GAE). The second compressor (GAG) elevates the pressure of the carbon dioxide to produce carbon dioxide (GAI). In embodiments, the second compressor (GAG) has a plurality of stages (GAH).

As shown in FIG. 17G, the carbon dioxide tank (CO2T) is in fluid communication with the plurality of growing assemblies (100, 200) as shown on FIGS. 1A and 1B. The carbon dioxide tank (CO2T) contains pressurized carbon dioxide (CO2) and is equipped with a carbon dioxide pressure sensor (CO2P). A carbon dioxide supply header (CO2H) is connected to the carbon dioxide tank (CO2T). A first carbon dioxide supply valve (V10) is installed on the carbon dioxide supply header (CO2H) and is configured to take a pressure drop of greater than 50 pounds per square inch (PSI). In embodiments, range of the pressure drop across the first carbon dioxide supply valve (V10) is selected from one or more from the group consisting of 25 pounds per square inch (PSI) to 50 PSI, 50 PSI to 75 PSI, 75 PSI to 100 PSI, 100 PSI to 125 PSI, 125 PSI to 150 PSI, 150 PSI to 175 PSI, 175 PSI to 200 PSI, 200 PSI to 225 PSI, 225 PSI to 250 PSI, 250 PSI to 275 PSI, 275 PSI to 300 PSI, 300 PSI to 325 PSI, 325 PSI to 350 PSI, 350 PSI to 375 PSI, 375 PSI to 400 PSI, 400 PSI to 425 PSI, 425 PSI to 450 PSI, 450 PSI to 475 PSI, 475 PSI to 500 PSI, 500 PSI to 600 PSI, 600 PSI to 700 PSI, 700 PSI to 800 PSI, 800 PSI to 900 PSI, 900 PSI to 1000 PSI, 1,000 PSI to 1,250 PSI, 1,250 PSI to 1,500 PSI, 1,500 PSI to 1,750 PSI, 1,750 PSI to 2,000 PSI, 2,000 PSI to 2,250 PSI, 2,250 PSI to 2,500 PSI, 2,500 PSI to 2,750 PSI, 2,750 PSI to 3,000 PSI, 3,000 PSI to 3,250 PSI, 3,250 PSI to 3,500 PSI, 3,500 PSI to 3,750 PSI, 3,750 PSI to 4,000 PSI, 4,000 PSI to 4,500 PSI, and 4,500 PSI to 5,000 PSI.

As shown in FIGS. 1A and 1B, the carbon dioxide (CO2) transferred from the carbon dioxide tank (CO2T) the first growing assembly (100) is equipped with a CO2 input (115) that is connected to a CO2 supply conduit (116). The second growing assembly (200) is also equipped with a CO2 input (215) that is connected to a CO2 supply conduit (216). The CO2 supply conduit (116) of the first growing assembly (100) is connected to the carbon dioxide supply header (CO2H) via a CO2 header connection (115X). The CO2 supply conduit (116) of the first growing assembly (100) is configured to transfer carbon dioxide into the first interior (101) of the first growing assembly (100). In embodiments, a second carbon dioxide supply valve (V8) is installed on the CO2 supply conduit (116) of the first growing assembly (100). The second carbon dioxide supply valve (V8) is equipped with a controller (CV8) that sends a signal (XV8) to and from a computer (COMP). In embodiments, a CO2 flow sensor (FC1) is installed on the CO2 supply conduit (116) of the first growing assembly (100). The CO2 flow sensor (FC1) sends a signal (XFC1) to the computer (COMP). In embodiments, a gas quality sensor (GC1) is installed on the first growing assembly (100) to monitor the concentration of carbon dioxide within the first interior (101). The gas quality sensor (GC1) is equipped to send a signal (XGC1) to the computer (COMP).

The CO2 supply conduit (216) of the second growing assembly (200) is connected to the carbon dioxide supply header (CO2H) via a CO2 header connection (215X). The CO2 supply conduit (216) of the second growing assembly (200) is configured to transfer carbon dioxide into the second interior (201) of the second growing assembly (100). In embodiments, a third carbon dioxide supply valve (V9) is installed on the CO2 supply conduit (216) of the second growing assembly (200). The third carbon dioxide supply valve (V9) is equipped with a controller (CV9) that sends a signal (XV9) to and from a computer (COMP). In embodiments, a CO2 flow sensor (FC2) is installed on the CO2 supply conduit (216) of the second growing assembly (200). The CO2 flow sensor (FC2) sends a signal (XFC2) to the computer (COMP). In embodiments, a gas quality sensor (GC2) is installed on the second growing assembly (200) to monitor the concentration of carbon dioxide within the second interior (201). The gas quality sensor (GC2) is equipped to send a signal (XGC2) to the computer (COMP).

In embodiments, the range of the carbon dioxide concentration in the plurality of growing assemblies (100, 200) is selected from one or more from the group consisting of 390 part per million (PPM) to 400 PPM, 400 PPM to 410 PPM, 410 PPM to 420 PPM, 420 PPM to 430 PPM, 430 PPM to 440 PPM, 440 PPM to 450 PPM, 450 PPM to 460 PPM, 460 PPM to 470 PPM, 470 PPM to 480 PPM, 480 PPM to 490 PPM, 490 PPM to 500 PPM, 500 PPM to 510 PPM, 510 PPM to 520 PPM, 520 PPM to 530 PPM, 530 PPM to 540 PPM, 540 PPM to 550 PPM, 550 PPM to 560 PPM, 560 PPM to 570 PPM, 570 PPM to 580 PPM, 580 PPM to 590 PPM, 590 PPM to 600 PPM, 600 PPM to 620 PPM, 620 PPM to 640 PPM, 640 PPM to 660 PPM, 660 PPM to 680

PPM, 680 PPM to 700 PPM, 700 PPM to 720 PPM, 720 PPM to 740 PPM, 740 PPM to 760 PPM, 760 PPM to 780 PPM, 780 PPM to 800 PPM, 800 PPM to 820 PPM, 820 PPM to 840 PPM, 840 PPM to 860 PPM, 860 PPM to 880 PPM, 880 PPM to 900 PPM, 900 PPM to 920 PPM, 920 PPM to 940 PPM, 940 PPM to 960 PPM, 960 PPM to 980 PPM, 980 PPM to 1000 PPM, 1,000 PPM to 1,500 PPM, 1,500 PPM to 2,000 PPM, 2,000 PPM to 2,500 PPM, 2,500 PPM to 3,000 PPM, 3,000 PPM to 3,500 PPM, 3,500 PPM to 4,000 PPM, 4,000 PPM to 4,500 PPM, 4,500 PPM to 5,000 PPM, 5,000 PPM to 5,500 PPM, 5,500 PPM to 6,000 PPM, 6,000 PPM to 6,500 PPM, 6,500 PPM to 7,000 PPM, 7,000 PPM to 7,500 PPM, 7,500 PPM to 8,000 PPM, 8,000 PPM to 8,500 PPM, 8,500 PPM to 9,000 PPM, 9,000 PPM to 9,500 PPM, 9,500 PPM to 10,000 PPM, 10,000 PPM to 11,000 PPM, 11,000 PPM to 12,000 PPM, 12,000 PPM to 13,000 PPM, 13,000 PPM to 14,000 PPM, 14,000 PPM to 15,000 PPM, 15,000 PPM to 16,000 PPM, 16,000 PPM to 17,000 PPM, 17,000 PPM to 18,000 PPM, 18,000 PPM to 19,000 PPM, 19,000 PPM to 20,000 PPM, 20,000 PPM to 21,000 PPM, 21,000 PPM to 22,000 PPM, 22,000 PPM to 23,000 PPM, 23,000 PPM to 24,000 PPM, and 24,000 PPM to 25,000 PPM.

FIG. 17H

FIG. 17H shows a cannabinoid extraction and purification system including vessels, filters, pumps, and tubing/piping connecting flow between vessels and adsorbers, valving, controllers, pressure regulators, metering equipment, flow control, and microprocessor equipment, their construction, implementation, and functionality.

FIG. 17H shows one non-limiting embodiment of a cannabinoid extraction and purification system that is configured to adsorb and desorb at least a portion of cannabinoids (e.g., volatiles) from a cannabinoid and liquid mixture (SVSM) (e.g., volatiles and solvent mixture) by use of a plurality of adsorbers that contain an adsorbent. In embodiments, volatiles include cannabinoids. FIGS. 17H, 17J, and 17K show non-limiting schematics of process flow diagrams illustrating configurations of a continuous cannabinoid extraction, emulsification, colloidal suspension, and and softgel encapsulation system including:
  cannabis drying system;
  water treatment and pH adjustment system;
  cannabinoid extraction system;
  primary solvent filtration system;
  primary cannabinoid adsorption system;
  secondary solvent filtration system;
  secondary cannabinoid adsorption system;
  tertiary solvent filtration system;
  tertiary cannabinoid adsorption system;
  solvent recovery system;
  cannabinoid product processing (colloidal suspension preparation, emulsion mixing system, evaporation system, spray drying system, crystallization, beverage preparation, foodstuff preparation system, softgel encapsulation system, shaped/cooked/flavored composition preparation).

Disclosed is a continuous process for the purification of cannabinoids (e.g., cannabidiol and/or tetrahydrocannabinol, a cannabinoid glycoside) extracted from *cannabis*, insects, and/or genetically engineered microorganisms, and/or combinations thereof, using adsorption, chromatography, continuous simulated moving bed processes, and/or micro and nanofiltration to obtain a purified cannabinoid product. The purified cannabinoid can be used to create foodstuffs, shaped/cooked/flavored compositions, emulsions, colloids, drugs, topicals, pet food, animal food, meat substitutes, beverages, alcoholic beverages or for medicinal and/or recreational uses.

In embodiments, a method for purification and separation of cannabinoids from *cannabis*, insects, and/or genetically engineered microorganisms and continuous purification of cannabinoids and cannabinoid glycosides is disclosed. More particularly, the method relates to a process for the continuous purification of cannabinoids from *cannabis* using simulated moving bed chromatography. Most particularly, the method relates to a novel continuous process for the purification of cannabinoids using a continuous simulated moving bed process using a solvent (such as water, ethanol, an alcohol, an alcohol mixture, deionized water, treated water, membrane treated water) as the mobile phase desorbent without the addition of organic solvents to obtain a purified cannabinoid product comprising not only cannabidiol and/or tetrahydrocannabinol amongst other cannabinoids and/or insect-derived cannabinoid glycosides. The purified cannabinoid can be used to create foodstuffs, shaped/cooked/flavored compositions, emulsions, colloids, drugs, topicals, pet food, animal food, meat substitutes, beverages, alcoholic beverages or for medicinal and/or recreational uses.

In embodiments, *cannabis*, INSECTERGY III, insects, or genetically engineered microorganisms contain cannabinoids. In embodiments, cannabinoids are contained within volatiles. In embodiments, cannabinoids include cannabidiol and tetrahydrocannabinol. In embodiments, cannabinoids include Δ9-tetrahydrocannabinol Δ9-THC, Δ8-tetrahydrocannabinol Δ8-THC, cannabichromene CBC, cannabidiol CBD, cannabigerol CBG, cannabinidiol CBND, and/or cannabinol CBN. In embodiments, tetrahydrocannabinol has a molecular weight of 314.47 grams per mole. In embodiments, cannabidiol has a molecular weight of 314.47 grams per mole.

The cannabinoids within *cannabis* or INSECTERGY III are listed below and bear the IUPAC names (6aR-trans)-6a, 7,8,10a-tetrahydro-6,6,9-trim ethyl-3-pentyl-6H-dibenzo[b, d]pyran-1-ol or Δ9-THC, and (6aR-trans)-6a,7,10,10a-tetrahydro-6,6,9-trim ethyl-3-pentyl-6H-dibenzo[b,d]pyran-1-ol or Δ8-THC. Δ9-THC is also known under the designation of Dronabinol.

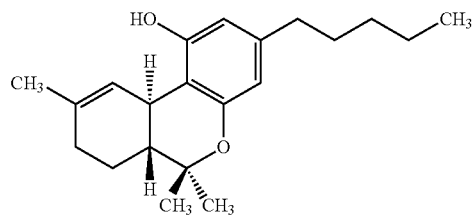

Tetrahydrocannabinol carboxylic acid

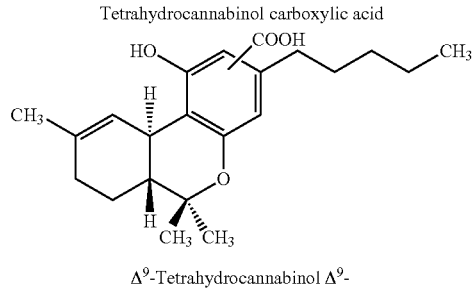

Δ9-Tetrahydrocannabinol Δ9-

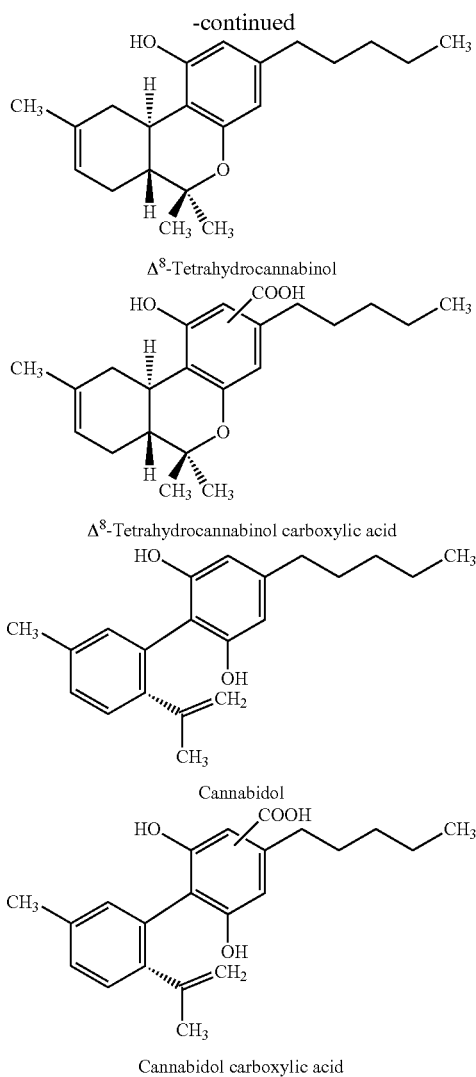

Δ8-Tetrahydrocannabinol

Δ8-Tetrahydrocannabinol carboxylic acid

Cannabidol

Cannabidol carboxylic acid

Table 17H illustrates various cannabinoids that are contained within *cannabis* or INSECTERGY III: Δ9-tetrahydrocannabinol Δ9-THC, Δ8-tetrahydrocannabinol Δ8-THC, cannabichromene CBC, cannabidiol CBD, cannabigerol CBG, cannabinidiol CBND, and/or cannabinol CBN.

Cannabinoids can be extracted from leaves, buds, stems, and/or volatiles, of *cannabis* or INSECTERGY III with use of a solvent, the solvent includes one or more from the group consisting of acetone, alcohol, ethanol, methanol, hexane, insect lipids, isobutane, isopropanol, liquid carbon dioxide, liquid, naphtha, and water, or any of the first or second solvents listed above. Cannabinoids can be extracted from volatiles that were separated from the *cannabis* or INSECTERGY III by use of carbon dioxide. In embodiments, carbon dioxide extracted volatiles contain cannabinoids. In embodiments, carbon dioxide extracted volatiles contain cannabinoids including cannabidiol and/or tetrahydrocannabinol, wherein the cannabidiol content ranges from 4 weight percent to 25 weight percent and the tetrahydrocannabinol content ranges from 4 weight percent to 66 weight percent.

In embodiments, cannabinoids are obtained from the leaves, buds, stems, and/or volatiles, of *cannabis* or INSECTERGY III. In embodiments, the cannabinoids are extracted with a heated solvent and the resulting aqueous extract is passed through an adsorption resin to trap and concentrate cannabinoids. Generally, the resin can be desorbed by washing the resin with organic solvents like methanol or ethanol to release the cannabinoids. Typically, the cannabinoid product is recrystallized with a solvent such as methanol or ethanol. Typically, the cannabinoid product is recrystallized with a solvent such as methanol. Ion-exchange resins have been used in the purification process. In embodiments, the final product is typically spray-dried as shown in FIG. 17E. In embodiments, the final product including a concentrated cannabinoid (CVOLT) is evaporated as shown in FIG. 17D.

As described herein, this disclosure provides for methods of supercritical fluid extraction and evaporator methods including evaporation, rotary evaporation, vacuum evaporation, distillation, crystallization, vacuum flashing, wiped film evaporation, emulsification, filtration, and spray drying. Methods for the recovery of terpenes and/or cannabidiol and/or tetrahydrocannabinol from *cannabis* using supercritical $CO_2$, filtration technology, and water or organic solvents, such as methanol and ethanol, may also be used.

FIG. 17H shows one non-limiting embodiment of a continuous cannabinoid extraction process. In embodiments, the *cannabis* (HAA) can be introduced to an extraction vessel (HAI). In embodiments, the *cannabis* (HAA) includes pieces or portions of harvested *cannabis*, trimmed *cannabis*, dried *cannabis*, wet *cannabis*, heated *cannabis*, or solvent extracted *cannabis*, insects, and/or genetically modified microorganisms comprising at least one cannabinoid. In embodiments, the *cannabis* (HAA) can first introduced to a water removal system (HZB) to reduce its moisture content. In embodiments, the water removal system (HZB) is a dryer (HZC). In embodiments, the dryer (HZC) includes a drum dryer, a vacuum dryer, rotary dryer, steam tube dryer, indirect dryer, direct dryer, indirectly-fired dryer, directly-fired dryer, tray dryer, tunnel dryer, roller dryers, pneumatic dryer, trough dryer, bin dryer, belt dryer, freeze dryer, or a microwave using microwave radiation and/or variable frequency microwave radiation. In embodiments, the dryer (HZC) includes an indirectly-fired dryer or a directly-fired dryer that is fired with a fuel, such as natural gas, propane, gasoline, fuel oil, oil, gaseous fuel, hydrocarbon, and liquid fuel.

In embodiments, water is removed from the *cannabis*, insects, and/or microorganism (HAA) with microwave radiation. In embodiments, the dryer (HZC) is a microwave. In embodiments, the dryer (HZC) is a variable frequency microwave. In embodiments, the microwave radiation is in the form of variable frequency microwave radiation. In embodiments, the variable frequency microwave radiation operates at a frequency between about 2 GHz to about 8 GHz. In embodiments, the variable frequency microwave radiation operates at a frequency of about 2.45 GHz. In embodiments, the variable frequency microwave radiation operates at a frequency selected from one or more from the group consisting of 2 GHz to 2.15 Ghz, 2.15 GHz to 2.25 Ghz, 2.25 GHz to 2.35 Ghz, 2.35 GHz to 2.45 Ghz, 2.45 GHz to 2.55 Ghz, 2.55 GHz to 2.65 Ghz, 2.65 GHz to 2.75 Ghz, 2.75 GHz to 2.85 Ghz, 2.85 GHz to 2.95 Ghz, 2.95 GHz to 3.05 Ghz, 3.05 GHz to 3.15 Ghz, 3.15 GHz to 3.25 Ghz, 3.25 GHz to 3.35 Ghz, 3.35 GHz to 3.45 Ghz, 3.45 GHz to 3.55 Ghz, 3.55 GHz to 3.65 Ghz, 3.65 GHz to 3.75 Ghz, 3.75 GHz to 3.85 Ghz, 3.85 GHz to 3.95 Ghz, 3.95 GHz to 4.05 Ghz, 4.05 GHz to 4.15 Ghz, 4.15 GHz to 4.25 Ghz, 4.25 GHz to 4.35 Ghz, 4.35 GHz to 4.45 Ghz, 4.45 GHz to 4.55 Ghz, 4.55 GHz to 4.65 Ghz, 4.65 GHz to 4.75 Ghz, 4.75 GHz to 4.85 Ghz, 4.85 GHz to 4.95 Ghz, 4.95

GHz to 5.05 Ghz, 5.05 GHz to 5.15 Ghz, 5.15 GHz to 5.25 Ghz, 5.25 GHz to 5.35 Ghz, 5.35 GHz to 5.45 Ghz, 5.45 GHz to 5.55 Ghz, GHz to 5.65 Ghz, 5.65 GHz to 5.75 Ghz, 5.75 GHz to 5.85 Ghz, 5.85 GHz to 5.95 Ghz, 5.95 GHz to 6.05 Ghz, 6.05 GHz to 6.15 Ghz, 6.15 GHz to 6.25 Ghz, 6.25 GHz to 6.35 Ghz, 6.35 GHz to 6.45 Ghz, 6.45 GHz to 6.55 Ghz, 6.55 GHz to 6.65 Ghz, 6.65 GHz to 6.75 Ghz, 6.75 GHz to 6.85 Ghz, 6.85 GHz to 6.95 Ghz, 6.95 GHz to 7.05 Ghz, 7.05 GHz to 7.15 Ghz, 7.15 GHz to 7.25 Ghz, 7.25 GHz to 7.35 Ghz, 7.35 GHz to 7.45 Ghz, 7.45 GHz to 7.55 Ghz, 7.55 GHz to 7.65 Ghz, 7.65 GHz to 7.75 Ghz, 7.75 GHz to 7.85 Ghz, 7.85 GHz to 7.95 Ghz, and 7.95 GHz to 8.00 Ghz.

In embodiments, the microwave has a power output that is measured in kilowatts (kW), the power output for the microwave operates at one or more selected from the group of power ranges consisting of 10 kw to 20 kw, 20 kw to 30 kw, 30 kw to 40 kw, 40 kw to 50 kw, 50 kw to 60 kw, kw to 70 kw, 70 kw to 80 kw, 80 kw to 90 kw, 90 kw to 100 kw, 100 kw to 110 kw, 110 kw to 120 kw, 120 kw to 130 kw, 130 kw to 140 kw, 140 kw to 150 kw, 150 kw to 160 kw, 160 kw to 170 kw, 170 kw to 180 kw, 180 kw to 190 kw, 190 kw to 200 kw, 200 kw to 210 kw, 210 kw to 220 kw, 220 kw to 230 kw, 230 kw to 240 kw, and 240 kw to 250 kw.

In embodiments, the microwave has a current that is measured in amps, the current for the microwave operates at one or more selected from the group of amp ranges consisting of 10 amps to 20 amps, 20 amps to 30 amps, 30 amps to 40 amps, 40 amps to 50 amps, 50 amps to 60 amps, amps to 70 amps, 70 amps to 80 amps, 80 amps to 90 amps, 90 amps to 100 amps, 100 amps to 110 amps, 110 amps to 120 amps, 120 amps to 130 amps, 130 amps to 140 amps, 140 amps to 150 amps, 150 amps to 160 amps, 160 amps to 170 amps, 170 amps to 180 amps, 180 amps to 190 amps, 190 amps to 200 amps, 200 amps to 210 amps, 210 amps to 220 amps, 220 amps to 230 amps, 230 amps to 240 amps, 240 amps to 250 amps, 250 amps to 260 amps, 260 amps to 270 amps, 270 amps to 280 amps, 280 amps to 290 amps, and 290 amps to 300 amps.

In embodiments, water is removed from the *cannabis*, insects, and/or microorganism (HAA) over a duration of time between about 0.1 seconds to about 500 seconds. In embodiments, water is removed from the *cannabis*, insects, and/or microorganism (HAA) over a duration of time between about 0.05 minutes to 0.1 minutes, 0.1 minutes to 0.5 minutes, 0.5 minutes to 1 minutes, 1 minute to 15 minutes, 15 minute to 30 minutes, 30 minute to 60 minutes, 60 minute to 2 hours, 2 hours to 3 hours, 3 hours to 4 hours, 4 hours to 5 hours, 5 hours to 6 hours, 6 hours to 7 hours, 7 hours to 8 hours, 8 hours to 9 hours, 9 hours to 10 hours, 10 hours to 11 hours, 11 hours to 12 hours, 12 hours to 13 hours, 13 hours to 14 hours, 14 hours to 15 hours, 15 hours to 16 hours, 16 hours to 17 hours, 17 hours to 18 hours, 18 hours to 19 hours, 19 hours to 20 hours, 20 hours to 24 hours, 24 hours to 1 day, 1 day to 2 days, 2 days to 3 days, 3 days to 4 days, 4 days to 5 days, 5 days to 6 days, 6 days to 7 days, 7 days to 8 days, 8 days to 9 days, 9 days to 10 days, or 10 days to 20 days.

In embodiments, the dryer (HZC) is a vacuum dryer that operates at a pressure that is selected from one of more from the group consisting of: between about 0.001 inches of water to about 0.002 inches of water; between about 0.002 inches of water to about 0.003 inches of water; between about 0.003 inches of water to about 0.006 inches of water; between about 0.006 inches of water to about 0.012 inches of water; between about 0.012 inches of water to about 0.024 inches of water; between about 0.024 inches of water to about 0.050 inches of water; between about 0.050 inches of water to about 0.075 inches of water; between about 0.075 inches of water to about 0.150 inches of water; between about 0.150 inches of water to about 0.300 inches of water; between about 0.300 inches of water to about 0.450 inches of water; between about 0.450 inches of water to about 0.473 inches of water; between about 0.473 inches of water to about 0.496 inches of water; between about 0.496 inches of water to about 0.521 inches of water; between about 0.521 inches of water to about 0.547 inches of water; between about 0.547 inches of water to about 0.574 inches of water; between about 0.574 inches of water to about 0.603 inches of water; between about 0.603 inches of water to about 0.633 inches of water; between about 0.633 inches of water to about 0.665 inches of water; between about 0.665 inches of water to about 0.698 inches of water; between about 0.698 inches of water to about 0.733 inches of water; between about 0.733 inches of water to about 0.770 inches of water; between about 0.770 inches of water to about 0.808 inches of water; between about 0.808 inches of water to about 0.849 inches of water; between about 0.849 inches of water to about 0.891 inches of water; between about 0.891 inches of water to about 0.936 inches of water; between about 0.936 inches of water to about 0.982 inches of water; between about 0.982 inches of water to about 1.031 inches of water; between about 1.031 inches of water to about 1.083 inches of water; between about 1.083 inches of water to about 1.137 inches of water; between about 1.137 inches of water to about 1.194 inches of water; between about 1.194 inches of water to about 1.254 inches of water; between about 1.254 inches of water to about 1.316 inches of water; between about 1.316 inches of water to about 1.382 inches of water; between about 1.382 inches of water to about 1.451 inches of water; between about 1.451 inches of water to about 1.524 inches of water; between about 1.524 inches of water to about 2.286 inches of water; between about 2.286 inches of water to about 3.429 inches of water; between about 3.429 inches of water to about 5.143 inches of water; between about 5.143 inches of water to about 7.715 inches of water; between about 7.715 inches of water to about 11.572 inches of water; between about 11.572 inches of water to about 17.358 inches of water; between about 17.358 inches of water to about 26.037 inches of water; between about 26.037 inches of water to about 39.055 inches of water; between about 39.055 inches of water to about 58.582 inches of water; between about 58.582 inches of water to about 87.873 inches of water; between about 87.873 inches of water to about 131.810 inches of water; between about 131.810 inches of water to about 197.715 inches of water; between about 197.715 inches of water to about 296.573 inches of water; or, between about 296.573 inches of water to about 400 inches of water.

In embodiments, the dryer (HZC) can be operated by electricity, flue gas, solar power from at least one solar panel (SOLAR), a fuel cell, or a combustion stream (LEM, LFD) as shown in FIG. 17F. The dryer (HZC) can reduce the moisture of the *cannabis*, insects, and/or microorganism (HAA) with a gas (HZA). In embodiments, the gas (HZA) includes an oxygen-containing gas which includes air, oxygen-enriched-air i.e. greater than 21 mole % 02, and substantially pure oxygen, i.e. greater than about 95 mole % oxygen (the remainder usually comprising N2 and rare gases). In embodiments, the gas (HZA) may include flue gas which includes a vapor or gaseous mixture containing varying amounts of nitrogen (N2), carbon dioxide (CO2), water ($H_2O$), and oxygen (O2). Flue gas is generated from the thermochemical process of combustion. In embodiments, the gas (HZA) may include a combustion stream.

In embodiments, a water-depleted *cannabis*, insects, and/or microorganism (HZE) or a dried *cannabis*, insects, and/or microorganism (HZE) is discharged from the water removal system (HZB) and has a moisture content (measured in weight percent of water) that is selected from one of more from the group consisting of: between about between 0.25 to 0.5, 0.5 to 1, 1 to 3, 3 to 5, to 7, 7 to 9, 9 to 11, 11 to 13, or 13 to 15.

A moisture content of the water-depleted *cannabis*, insects, and/or microorganism (HZE) or a dried *cannabis*, insects, and/or microorganism (HZE) may be measured with a moisture sensor (HZD). In embodiments, the moisture sensor (HZD) is selected from one or more from the group consisting of a halogen moisture sensor, mass spectrometer, Fourier transform infrared spectroscopy, infrared spectroscopy, radio frequency (RF), a DC resistance circuit, frequency domain reflectometry (FDR), time domain reflectometry (TDR), time domain transmissometry (TDT), oven drying, gravimetric testing, forced air oven, vacuum oven, microwave, variable frequency microwave radiation, IR drying, toluene distillation, Karl Fischer titration, or any conceivable instantaneous contact or non-contact moisture analyzer. In embodiments, time-domain reflectometry or TDR is a measurement technique used to determine the characteristics of *cannabis* (HAA) by observing reflected waveforms. In embodiments, time-domain transmissometry (TDT) is an analogous technique that measures the transmitted (rather than reflected) impulse of *cannabis* (HAA).

In embodiments, the moisture sensor (HZD) is configured to input a signal to the computer. In embodiments, the moisture content of the water-depleted *cannabis*, insects, and/or microorganism (HZE) may be obtained through thermo-gravimetry or the loss-on-drying principle. In embodiments, the moisture sensor (HZD) includes a mass sensor and a heat source. The starting weight is recorded by the mass sensor. The heat source applies heat to the *cannabis*, insects, and/or microorganism (HAA). The ending weight of the water-depleted *cannabis*, insects, and/or microorganism (HZE) or a dried *cannabis* (HZE) is then recorded via the mass sensor. The total loss in mass (the difference in mass of the water-depleted *cannabis* (HZE) and the *cannabis*, insects, and/or microorganism (HAA)) is used to obtain the moisture content.

In embodiments, the *cannabis*, insects, and/or microorganism (HAA) includes harvested *cannabis*, trimmed *cannabis*, dried *cannabis*, wet *cannabis*, heated *cannabis*, carbon dioxide extracted cannabidiol and/or tetrahydrocannabinol, extracted cannabidiol, cannabidiol, carbon dioxide extracted cannabidiol, terpenes, carbon dioxide extracted terpenes, and/or extracted terpenes, insects containing an insect-derived cannabinoid, and/or genetically engineered microorganism comprising a cannabinoid. The *cannabis*, insects, and/or microorganism (HAA, HAA) may come from any number of drawings disclosed within this specification and the *cannabis*, insects, and/or microorganism (HAA) can be grown in any number of ways.

A first sensor (HAC) is provided to measure the pressure, temperature, moisture, purity, pH, electrical conductivity, or elemental make-up of the *cannabis*, insects, and/or microorganism (HAA). A first flow valve (HAE) is provided to determine the content of *cannabis*, insects, and/or microorganism (HAA) that is introduced downstream to the extraction vessel (HAI). A second sensor (HAC) is provided to measure the pressure, temperature, moisture, purity, pH, electrical conductivity, or elemental make-up of the *cannabis*, insects, and/or microorganism (HAA) to the extraction vessel (HAI).

A solvent (HAB, HAB) is made available to the extraction vessel (HAI). The extraction vessel (HAI) is configured to accept a *cannabis*, insects, and/or microorganism (HAA, HAA) and a solvent (HAB, HAB). In embodiments, the solvent (HAB) includes water, ethanol, an alcohol, an alcohol mixture, deionized water, treated water, filtered water, and/or or any solvent mentioned above (e.g., a first solvent and/or a second solvent). In embodiments, the solvent (HAB) is pressurized and comes from a solvent treatment system (H-WTS) which may or may not treat solvent (such as water) that was passed on from a solvent recovery system. In embodiments, the solvent recovery system includes evaporation. In embodiments, the solvent recovery system includes distillation.

In embodiments, the solvent (HAB) includes a non-polar solvent selected from one or more of the group consisting of pentane, petroleum ether, hexanes, n-hexane, heptane, diisopropyl ether, toluene, chloroform, and methylene chloride; preferably petroleum ether, hexanes, n-hexane, heptane, and n-heptane.

In embodiments, the solvent (HAB) includes a non-polar solvent selected from one or more of the group consisting of pentane, petroleum ether, hexanes, n-hexane, n-heptane, heptanes, diisopropyl ether, toluene, chloroform, and methylene chloride. In embodiments, the first solvent in the binary solvent system is petroleum ether, a heptane, or n-heptane.

A first solvent sensor (HAD) is provided to measure the pressure, temperature, moisture, purity, pH, electrical conductivity, or elemental make-up of the solvent (HAB). A first solvent flow valve (HAF) is provided to determine the content of solvent (HAB) that is introduced downstream to the extraction vessel (HAI). A second solvent sensor (HAH) is provided to measure the pressure, temperature, moisture, purity, pH, electrical conductivity, or elemental make-up of the solvent (HAB) to the extraction vessel (HAI). In embodiments, insects and/or a microorganism are mixed with *cannabis* (HAA, HAA) prior to the extraction vessel (HAI).

In embodiments, the extraction vessel (HAI) is provided to accept at least a portion of the *cannabis*, insects, and/or microorganism (HAA, HAA). A solvent (HAB, HAB) is made available to the extraction vessel (HAI). The extraction vessel (HAI) is configured to accept the *cannabis*, insects, and/or microorganism (HAA, HAA) and a solvent (HAB, HAB). In embodiments, the extraction vessel (HAI) has an interior (HAJ). In embodiments, the interior (HAJ) of the extraction vessel (HAI) is the extraction zone (HAI) where cannabinoids and/or cannabinoid glycosides are extracted from the *cannabis*, insects, and/or microorganism (HAA, HAA) by use a solvent (HAB, HAB).

In embodiments, the extraction vessel (HAI) is a continuously stirred tank reactor having a jacketed reactor equipped with a steam supply system and at least one steam trap. In embodiments, the extraction vessel (HAI) is equipped with a level sensor (HAL) that is configured to input a signal (HAK) to the computer (COMP). In embodiments, the extraction vessel (HAI) is equipped with a pH sensor (HAL) that is configured to input a signal (HAK) to the computer (COMP). In embodiments, the extraction vessel (HAI) is equipped with an auger (HA1) that has a motor (HA2). The motor (HA2) of the auger (HAI) rotates the auger (HAI) to mix the contents within the interior (HAJ) of the extraction vessel (HAI). In embodiments, the extraction vessel (HAI) is equipped with a temperature sensor (HA3) that is configured to input a signal (HA4) to the computer (COMP). In embodiments, the extraction vessel (HAI) is equipped with a heat exchanger (HAM) to heat and/or cool the contents within the interior (HAJ) of the extraction vessel (HAI). In embodiments, the extraction vessel (HAI) outputs a crude cannabinoid extract (HAN).

In embodiments, the crude cannabinoids (including a cannabinoid, and/or a mixture of cannabinoids, a cannabinoid glycoside, and/or mixtures thereof) are admixed with water (membrane treated water, and/or ice produced from membrane treated water) or a solvent to provide a crude extract stream which comprises from one or more from the group consisting of 1 weight percent to 5 weight percent, 5 weight percent to 10 weight percent, 10 weight percent to 15 weight percent, 15 weight percent to 20 weight percent, 20 weight percent to 25 weight percent, weight percent to 30 weight percent, 30 weight percent to 35 weight percent, 35 weight percent to 40 weight percent, 40 weight percent to 45 weight percent, 45 weight percent to 50 weight percent, 50 weight percent to 55 weight percent, 55 weight percent to 60 weight percent, 60 weight percent to 65 weight percent, 65 weight percent to 70 weight percent, 70 weight percent to 75 weight percent, 75 weight percent to 80 weight percent, 80 weight percent to 85 weight percent, weight percent to 90 weight percent, and 90 to 100 weight percent.

Following the extraction of the cannabinoids and/or glycosides from leaves, buds, stems, and/or volatiles, of *cannabis* or INSECTERGY III, insects, and/or the microorganism, an extract stream comprising crude cannabinoids (and/or a cannabinoid glycoside) is withdrawn from the extraction zone (HAI). In embodiments, the crude cannabinoids are admixed with water or a solvent to provide a crude cannabinoid extract (HAN).

In embodiments, the crude cannabinoid extract (HAN) discharged from the extraction vessel (HAI) is made available to a crude cannabinoid extract pump (HAO). In embodiments, the crude cannabinoid extract pump (HAO) pressurizes and pumps the crude cannabinoid extract (HAN) to form a pressurized crude cannabinoid extract (HAX, HAX). In embodiments, the crude cannabinoid extract pump (HAO) is equipped with a motor (HAP) and a controller (HAQ) that is configured to input and/or output a signal (HAR) to the computer (COMP). A valve (HAU) may be provided to regulate the flow of the pressurized crude cannabinoid extract (HAX, HAX). In embodiments, the valve (HAU) is equipped with a controller (HAV) that is configured to input and/or output a signal (HAW) to the computer (COMP). In embodiments, a pressure sensor (HAS) is provided to measure the pressure of the pressurized crude cannabinoid extract (HAX, HAX) that is discharged from the crude cannabinoid extract pump (HAO). In embodiments, the pressure sensor (HAS) inputs a signal (HAT) to the computer (COMP).

In embodiments, the crude cannabinoid extract pump (HAO) pressurizes the crude cannabinoid extract (HAN) to form a pressurized crude cannabinoid extract (HAX, HAX) at a pressure that includes one or more pressure ranges selected from the group consisting of 10 pounds per square inch (PSI) to 20 PSI, 20 PSI to 40 PSI, 40 PSI to 60 PSI, 60 PSI to 80 PSI, 80 PSI to 100 PSI, 100 PSI to 125 PSI, 125 PSI to 150 PSI, 150 PSI to 175 PSI, 175 PSI to 200 PSI, 200 PSI to 225 PSI, 225 PSI to 250 PSI, 250 PSI to 275 PSI, 275 PSI to 300 PSI, 300 PSI to 325 PSI, 325 PSI to 350 PSI, 350 PSI to 375 PSI, 375 PSI to 400 PSI, 400 PSI to 425 PSI, 425 PSI to 450 PSI, 450 PSI to 475 PSI, and 475 PSI to 500 PSI. In embodiments, the crude cannabinoid extract pump (HAO) pressurizes the crude cannabinoid extract (HAN) to form a pressurized crude cannabinoid extract (HAX, HAX) which is then introduced to a heat exchanger (HAY). In embodiments, the heat exchanger (HAY) is provided with a heat transfer medium (HAZ) to heat or cool the pressurized crude cannabinoid extract (HAX, HAX).

In embodiments, at least a portion of the pressurized crude cannabinoid extract (HAX) is recycled back to the interior (HAJ) of the extraction vessel (HAI) via a bypass (HBB). A crude cannabinoid extract valve (HBA) is positioned on the bypass (HBB) to permit recycled pressurized crude cannabinoid extract (HAX) to flow back into the interior (HAJ) of the extraction vessel (HAI).

In embodiments, at least a portion of the pressurized crude cannabinoid extract (HAX) is introduced to a first filter (HBC) and a second filter (HBF). In embodiments, the first filter (HBC) has an interior (HBD) and at least one filter element (HBE). In embodiments, the second filter (HBF) has an interior (HBG) and at least one filter element (HBH). In embodiments, the first filtered crude cannabinoid extract (HBI) is discharged from the first filter (HBC) and a second filtered crude cannabinoid extract (HBI") is discharged from the second filter (HBF). In embodiments, the first filtered crude cannabinoid extract (HBI) and the second filtered crude cannabinoid extract (HBI") are combined to form a filtered crude cannabinoid extract (HBI) that has less solids in it relative to the pressurized crude cannabinoid extract (HAX). In embodiments, the first filter (HBC) and the second filter (HBF) also discharge solids (HBK) and solvent (HBJ). In embodiments, the solvent (HBJ) discharged from the first filter (HBC) and the second filter (HBF) is routed to the solvent treatment system (H-WTS) as discussed below.

In embodiments, the crude cannabinoid extract (HAN) is passed to the filter (HBC, HBF) to remove any solid particles to provide a filtered crude cannabinoid extract (HBI). In embodiments, the filtration is carried at a microfiltration temperature ranging from one or more from the group consisting of 30 degrees F. to 40 degrees F., 40 degrees F. to 50 degrees F., 50 degrees F. to 60 degrees F., 60 degrees F. to 70 degrees F., 70 degrees F. to 100 degrees F., 100 deg F to 110 deg F, 110 deg F to 120 deg F, 120 deg F to 130 deg F, 130 deg F to 140 deg F, 140 deg F to 150 deg F, 150 deg F to 160 deg F, 160 deg F to 170 deg F, 170 deg F to 180 deg F, 180 deg F to 190 deg F, 190 deg F to 200 deg F, 200 deg F to 210 deg F, 210 deg F to 212 deg F.

In embodiments, the filtration is carried out in a filter (HBC, HBF) has a pore size that ranges from rom one or more from the group consisting of 0.03 microns to 0.05 microns, 0.05 microns to 0.07 microns, 0.07 microns to 0.09 microns, 0.09 microns to 0.11 microns, 0.11 microns to 0.13 microns, 0.13 microns to 0.15 microns, 0.15 microns to 0.17 microns, 0.17 microns to 0.19 microns, 0.19 microns to 0.21 microns, 0.21 microns to 0.23 microns, 0.23 microns to 0.25 microns, 0.25 microns to 0.27 microns, 0.27 microns to 0.29 microns, 0.29 microns to 0.31 microns, 0.31 microns to 0.33 microns, 0.33 microns to 0.35 microns, 0.35 microns to 0.37 microns, 0.37 microns to 0.39 microns, 0.39 microns to 0.41 microns, 0.41 microns to 0.43 microns, 0.43 microns to 0.45 microns, 0.45 microns to 0.47 microns, 0.47 microns to 0.49 microns, 0.49 microns to 0.51 microns, 0.51 microns to 0.61 microns, 0.61 microns to 0.71 microns, 0.71 microns to 0.81 microns, 0.81 microns to 0.91 microns, 0.91 microns to 1.01 microns, 1.01 microns to 1.5 microns, 1.5 microns to 2 microns, 2 microns to 2.5 microns, 2.5 microns to 3 microns, 3 microns to 3.5 microns, 3.5 microns to 4 microns, 4 microns to 4.5 microns, 4.5 microns to 5 microns, 5 microns to 5.5 microns, 5.5 microns to 6 microns, 6 microns to 6.5 microns, 6.5 microns to 7 microns, 7 microns to 7.5 microns, 7.5 microns to 8 microns, 8 microns to 8.5 microns, 8.5 microns to 9 microns, 9 microns to 9.5 microns, and 9.5 microns to 10 microns, or at least 10 microns.

In embodiments, the filtration is carried out in a filter (HBC, HBF) that includes one or more filter types selected from the group consisting of a candle filter, a centrifuge cloth filter, filter press cloth filter, filter bag, vertical belt press cloth filter, basket filter, rotary vacuum filter, rotary filter, drum filter, leaf filter, plate filter, batch filter, and a continuous filter.

In embodiments, any of the pumps in this patent specification have a pump discharge velocity that is selected from one or more pump velocity ranges consisting of: 0.65 feet per second to 0.75 feet per second, 0.75 feet per second to 0.85 feet per second, 0.85 feet per second to 0.95 feet per second, 0.95 feet per second to 1.05 feet per second, 1.05 feet per second to 1.15 feet per second, 1.15 feet per second to 1.25 feet per second, 1.25 feet per second to 1.35 feet per second, 1.35 feet per second to 1.45 feet per second, 1.45 feet per second to 1.55 feet per second, 1.55 feet per second to 1.65 feet per second, 1.65 feet per second to 1.75 feet per second, 1.75 feet per second to 1.85 feet per second, 1.85 feet per second to 1.95 feet per second, 1.95 feet per second to 2.05 feet per second, 2.05 feet per second to 2.15 feet per second, 2.15 feet per second to 2.25 feet per second, 2.25 feet per second to 2.35 feet per second, 2.35 feet per second to 2.45 feet per second, 2.45 feet per second to 2.55 feet per second, 2.55 feet per second to 2.65 feet per second, 2.65 feet per second to 2.75 feet per second, 2.75 feet per second to 2.85 feet per second, 2.85 feet per second to 2.95 feet per second, 2.95 feet per second to 3.05 feet per second, 3.05 feet per second to 3.15 feet per second, 3.15 feet per second to 3.25 feet per second, 3.25 feet per second to 3.35 feet per second, 3.35 feet per second to 3.45 feet per second, 3.45 feet per second to 3.55 feet per second, 3.55 feet per second to 3.65 feet per second, 3.65 feet per second to 3.75 feet per second, 3.75 feet per second to 3.85 feet per second, 3.85 feet per second to 3.95 feet per second, 3.95 feet per second to 4.05 feet per second, 4.05 feet per second to 4.15 feet per second, 4.15 feet per second to 4.25 feet per second, 4.25 feet per second to 4.35 feet per second, 4.35 feet per second to 4.45 feet per second, 4.45 feet per second to 4.55 feet per second, 4.55 feet per second to 4.65 feet per second, 4.65 feet per second to 4.75 feet per second, 4.75 feet per second to 4.85 feet per second, 4.85 feet per second to 4.90 feet per second, and 4.90 feet per second to feet per second. This is true especially for all pumps on FIGS. 1-18F.

In embodiments, any of the pumps in this patent specification have a pump discharge velocity that is selected from one or more pump velocity ranges consisting of: 5.00 feet per second to 5.10 feet per second, 5.10 feet per second to 5.20 feet per second, 5.20 feet per second to 5.30 feet per second, 5.30 feet per second to 5.40 feet per second, 5.40 feet per second to 5.50 feet per second, 5.50 feet per second to 5.60 feet per second, 5.60 feet per second to 5.70 feet per second, feet per second to 5.80 feet per second, 5.80 feet per second to 5.90 feet per second, 5.90 feet per second to 6.00 feet per second, 6.00 feet per second to 6.10 feet per second, 6.10 feet per second to 6.20 feet per second, 6.20 feet per second to 6.30 feet per second, 6.30 feet per second to 6.40 feet per second, 6.40 feet per second to 6.50 feet per second, 6.50 feet per second to 6.60 feet per second, 6.60 feet per second to 6.70 feet per second, 6.70 feet per second to 6.80 feet per second, 6.80 feet per second to 6.90 feet per second, 6.90 feet per second to 7.00 feet per second, 7.00 feet per second to 7.10 feet per second, 7.10 feet per second to 7.20 feet per second, 7.20 feet per second to 7.30 feet per second, 7.30 feet per second to 7.40 feet per second, 7.40 feet per second to 7.50 feet per second, 7.50 feet per second to 7.60 feet per second, 7.60 feet per second to 7.70 feet per second, 7.70 feet per second to 7.80 feet per second, 7.80 feet per second to 7.90 feet per second, 7.90 feet per second to 8.00 feet per second, 8.00 feet per second to 8.10 feet per second, 8.10 feet per second to 8.20 feet per second, 8.20 feet per second to 8.30 feet per second, 8.30 feet per second to 8.40 feet per second, 8.40 feet per second to 8.50 feet per second, 8.50 feet per second to 8.60 feet per second, 8.60 feet per second to 8.70 feet per second, 8.70 feet per second to 8.80 feet per second, 8.80 feet per second to 8.90 feet per second, 8.90 feet per second to 9.00 feet per second, 9.00 feet per second to 9.10 feet per second, 9.10 feet per second to 9.20 feet per second, 9.20 feet per second to 9.30 feet per second, 9.30 feet per second to 9.40 feet per second, 9.40 feet per second to 9.50 feet per second, 9.50 feet per second to 9.60 feet per second, 9.60 feet per second to 9.70 feet per second, 9.70 feet per second to 9.80 feet per second, 9.80 feet per second to 9.90 feet per second, 9.90 feet per second to 10.00 feet per second, and 10.00 feet per second to 20.00 feet per second. This is true especially for all pumps on FIGS. 1-18F.

In embodiments, the filter (HBC, HBF) is comprised of one or more from the group consisting of membrane, hollow, nanofiltration, microfiltration, microfilter, nanofilter, metal, ceramic, cloth, particulate filter, candle filter, ceramic fiber, filter cartridge, fiber, and mesh. In embodiments, the filter is configured to have a face velocity during depressurization ranging from feet per minute to 50 feet per minute. In embodiments, the filter is configured to have a face velocity during filtration ranging from: 5 feet per minute to 10 feet per minute, 10 feet per minute to 15 feet per minute, 15 feet per minute to 20 feet per minute, 20 feet per minute to 25 feet per minute, 25 feet per minute to 30 feet per minute, 30 feet per minute to 35 feet per minute, 35 feet per minute to 40 feet per minute, 40 feet per minute to 45 feet per minute, 45 feet per minute to 50 feet per minute, 50 feet per minute to 55 feet per minute, 55 feet per minute to 60 feet per minute, feet per minute to 65 feet per minute, 65 feet per minute to 70 feet per minute, 70 feet per minute to 75 feet per minute, 75 feet per minute to 80 feet per minute, 80 feet per minute to 85 feet per minute, 85 feet per minute to 90 feet per minute, 90 feet per minute to 95 feet per minute, 95 feet per minute to 100 feet per minute, 100 feet per minute to 125 feet per minute, 125 feet per minute to 150 feet per minute, 150 feet per minute to 175 feet per minute, 175 feet per minute to 200 feet per minute, 200 feet per minute to 225 feet per minute, 225 feet per minute to 250 feet per minute, 250 feet per minute to 275 feet per minute, 275 feet per minute to 300 feet per minute, 300 feet per minute to 325 feet per minute, 325 feet per minute to 350 feet per minute, 350 feet per minute to 375 feet per minute, 375 feet per minute to 400 feet per minute, 400 feet per minute to 425 feet per minute, 425 feet per minute to 450 feet per minute, 450 feet per minute to 475 feet per minute, 475 feet per minute to 500 feet per minute, 500 feet per minute to 525 feet per minute, 525 feet per minute to 550 feet per minute, 550 feet per minute to 575 feet per minute, 575 feet per minute to 600 feet per minute, 600 feet per minute to 625 feet per minute, 625 feet per minute to 650 feet per minute, 650 feet per minute to 675 feet per minute, 675 feet per minute to 700 feet per minute, 700 feet per minute to 725 feet per minute, 725 feet per minute to 750 feet per minute, 750 feet per minute to 775 feet per minute, 775 feet per minute to 800 feet per minute, 800 feet per minute to 825 feet per minute, 825 feet per minute to 850 feet per minute, 850 feet per minute to 875 feet per minute, 875 feet per minute to 900 feet per minute, 900 feet per minute to 925 feet per minute, 925 feet per minute to 950 feet per minute, 950 feet per minute to 975 feet per minute, and 975 feet per minute to 1,000 feet per minute.

In embodiments, the crude cannabinoids are admixed with water or a solvent to provide a crude extract which comprises from one or more from the group consisting of 20.5 weight percent to 21 weight percent, 21 weight percent to 21.5 weight percent, 21.5 weight percent to 22 weight percent, 22 weight percent to 22.5 weight percent, 22.5 weight percent to 23 weight percent, 23 weight percent to 23.5 weight percent, 23.5 weight percent to 24 weight percent, 24 weight percent to 24.5 weight percent, 24.5 weight percent to 25 weight percent, 25 weight percent to 25.5 weight percent, 25.5 weight percent to 26 weight percent, 26 weight percent to 26.5 weight percent, 26.5 weight percent to 27 weight percent, 27 weight percent to 27.5 weight percent, 27.5 weight percent to 28 weight percent, 28 weight percent to 28.5 weight percent, 28.5 weight percent to 29 weight percent, 29 weight percent to 29.5 weight percent, 29.5 weight percent to 30 weight percent, 30 weight percent to 30.5 weight percent, 30.5 weight percent to 31 weight percent, 31 weight percent to 31.5 weight percent, 31.5 weight percent to 32 weight percent, 32 weight percent to 32.5 weight percent, 32.5 weight percent to 33 weight percent, 33 weight percent to 33.5 weight percent, 33.5 weight percent to 34 weight percent, 34 weight percent to 34.5 weight percent, 34.5 weight percent to 35 weight percent, 35 weight percent to 35.5 weight percent, 35.5 weight percent to 36 weight percent, 36 weight percent to 36.5 weight percent, 36.5 weight percent to 37 weight percent, 37 weight percent to 37.5 weight percent, 37.5 weight percent to 38 weight percent, 38 weight percent to 38.5 weight percent, 38.5 weight percent to 39 weight percent, 39 weight percent to 39.5 weight percent, and 39.5 weight percent to 40 weight percent.

In embodiments, the concentration of solids within the crude cannabinoid extract is selected from one or more from the group consisting of: 6.500 weight percent to 6.625 weight percent, 6.625 weight percent to 6.750 weight percent, 6.750 weight percent to 6.875 weight percent, 6.875 weight percent to 7.000 weight percent, 7.000 weight percent to 7.125 weight percent, 7.125 weight percent to 7.250 weight percent, 7.250 weight percent to 7.375 weight percent, 7.375 weight percent to 7.500 weight percent, 7.500 weight percent to 7.625 weight percent, 7.625 weight percent to 7.750 weight percent, 7.750 weight percent to 7.875 weight percent, 7.875 weight percent to 8.000 weight percent, 8.000 weight percent to 8.125 weight percent, 8.125 weight percent to 8.250 weight percent, 8.250 weight percent to 8.375 weight percent, 8.375 weight percent to 8.500 weight percent, 8.500 weight percent to 8.625 weight percent, 8.625 weight percent to 8.750 weight percent, 8.750 weight percent to 8.875 weight percent, 8.875 weight percent to 9.000 weight percent, 9.000 weight percent to 9.125 weight percent, 9.125 weight percent to 9.250 weight percent, 9.250 weight percent to 9.375 weight percent, 9.375 weight percent to 9.500 weight percent, 9.500 weight percent to 9.625 weight percent, 9.625 weight percent to 9.750 weight percent, 9.750 weight percent to 9.875 weight percent, 9.875 weight percent to 10.000 weight percent, 10.000 weight percent to 10.125 weight percent, 10.125 weight percent to 10.250 weight percent, 10.250 weight percent to 10.375 weight percent, 10.375 weight percent to 10.500 weight percent, 10.500 weight percent to 10.625 weight percent, 10.625 weight percent to 10.750 weight percent, 10.750 weight percent to 10.875 weight percent, 10.875 weight percent to 11.000 weight percent, 11.000 weight percent to 11.125 weight percent, 11.125 weight percent to 11.250 weight percent, 11.250 weight percent to 11.375 weight percent, 11.375 weight percent to 11.500 weight percent, 11.500 weight percent to 11.625 weight percent, 11.625 weight percent to 11.750 weight percent, 11.750 weight percent to 11.875 weight percent, 11.875 weight percent to 12.000 weight percent, 12.000 weight percent to 12.125 weight percent, 12.125 weight percent to 12.250 weight percent, 12.250 weight percent to 12.375 weight percent, 12.375 weight percent to 12.500 weight percent, 12.500 weight percent to 12.625 weight percent, 12.625 weight percent to 12.750 weight percent, 12.750 weight percent to 12.875 weight percent, 12.875 weight percent to 13.000 weight percent, 13.000 weight percent to 13.125 weight percent, 13.125 weight percent to 13.250 weight percent, 13.250 weight percent to 13.375 weight percent, 13.375 weight percent to 13.500 weight percent, 13.500 weight percent to 13.625 weight percent, 13.625 weight percent to 13.750 weight percent, 13.750 weight percent to 13.875 weight percent, 13.875 weight percent to 14.000 weight percent, 14.000 weight percent to 14.125 weight percent, 14.125 weight percent to 14.250 weight percent, 14.250 weight percent to 14.375 weight percent, 14.375 weight percent to 14.500 weight percent, 14.500 weight percent to 14.625 weight percent, 14.625 weight percent to 14.750 weight percent, 14.750 weight percent to 14.875 weight percent, 14.875 weight percent to 15.000 weight percent, 15.000 weight percent to 15.125 weight percent, 15.125 weight percent to 15.250 weight percent, 15.250 weight percent to 15.375 weight percent, 15.375 weight percent to 15.500 weight percent, 15.500 weight percent to 15.625 weight percent, 15.625 weight percent to 15.750 weight percent, 15.750 weight percent to 15.875 weight percent, 15.875 weight percent to 16.000 weight percent, 16.000 weight percent to 16.125 weight percent, 16.125 weight percent to 16.250 weight percent, 16.250 weight percent to 16.375 weight percent, 16.375 weight percent to 16.500 weight percent, 16.500 weight percent to 16.625 weight percent, 16.625 weight percent to 16.750 weight percent, 16.750 weight percent to 16.875 weight percent, 16.875 weight percent to 17.000 weight percent, 17.000 weight percent to 17.125 weight percent, 17.125 weight percent to 17.250 weight percent, 17.250 weight percent to 17.375 weight percent, 17.375 weight percent to 17.500 weight percent, 17.500 weight percent to 17.625 weight percent, 17.625 weight percent to 17.750 weight percent, 17.750 weight percent to 17.875 weight percent, 17.875 weight percent to 18.000 weight percent, 8.000 weight percent to 18.125 weight percent, 18.125 weight percent to 18.250 weight percent, 18.250 weight percent to 18.375 weight percent, 18.375 weight percent to 18.500 weight percent, 18.500 weight percent to 18.625 weight percent, 18.625 weight percent to 18.750 weight percent, 18.750 weight percent to 18.875 weight percent, 18.875 weight percent to 19.000 weight percent, 19.000 weight percent to 19.125 weight percent, 19.125 weight percent to 19.250 weight percent, 19.250 weight percent to 19.375 weight percent, 19.375 weight percent to 19.500 weight percent, 19.500 weight percent to 19.625 weight percent, 19.625 weight percent to 19.750 weight percent, 19.750 weight percent to 19.875 weight percent, and 19.875 weight percent to 20.000 weight percent.

In embodiments, the filtered crude cannabinoid extract (HBI, HBI, HBI") is passed from the first filter (HBC) and/or the second filter (HBF) and into a crude cannabinoid extract vessel (HCA). In embodiments, crude cannabinoid extract vessel (HCA) is configured to accept the filtered crude cannabinoid extract (HBI, HBI, HBI").

In embodiments, the crude cannabinoid extract vessel (HCA) is a continuously stirred tank reactor having a jacketed reactor equipped with a steam supply system and at least one steam trap. In embodiments, the crude cannabinoid extract vessel (HCA) is equipped with a level sensor (HCC) that is configured to input a signal (HCD) to the computer (COMP). In embodiments, the crude cannabinoid extract vessel (HCA) is equipped with a pH sensor (HCE) that is configured to input a signal (HCF) to the computer (COMP). In embodiments, the crude cannabinoid extract vessel (HCA) is equipped with an auger (HCG) that has a motor (HCH). The motor (HCH) of the auger (HCG) rotates the auger (HCG) to mix the contents within the interior (HCB) of the crude cannabinoid extract vessel (HCA). In embodiments, the crude cannabinoid extract vessel (HCA) is equipped with a temperature sensor that is configured to input a signal to the computer (COMP). In embodiments, the crude cannabinoid extract vessel (HCA) is equipped with a heat exchanger (HCI) to heat and/or cool the contents within the interior (HCB) of the crude cannabinoid extract vessel (HCA). In embodiments, the crude cannabinoid extract vessel (HCA) outputs a filtered crude cannabinoid extract (HCK).

A filtered crude cannabinoid extract (HCK) is discharged from the interior (HCB) of the crude cannabinoid extract vessel (HCA) and is transferred to a crude cannabinoid extract pump (HCO). The crude cannabinoid extract pump (HCO) is equipped with a motor (HCP) and a controller (HCQ) that is configured to input and/or output a signal (HCR) to the computer (COMP). The crude cannabinoid extract pump (HCO) pumps and pressurizes the filtered crude cannabinoid extract (HCK) to form a filtered and pressurized crude cannabinoid extract (HCM). In embodiments, the filtered and pressurized crude cannabinoid extract (HCM) is used as a backflush supply (HCN) to regenerate in-situ the first filter (HBC) and/or the second filter (HBF). In embodiments, a filter (HCJ) is provided to polish the filtered and pressurized crude cannabinoid extract (HCM) to remove any additional solids that are present. In embodiments, a pressure sensor (HCS) is provided to measure the pressure of the filtered and pressurized crude cannabinoid extract (HCM). In embodiments, the pressure sensor (HCS) is configured to input a signal (HCT) to the computer (COMP).

In embodiments, the crude cannabinoid extract pump (HCO) pressurizes the filtered crude cannabinoid extract (HCK) to form a filtered and pressurized crude cannabinoid extract (HCM) at a pressure that includes one or more pressure ranges selected from the group consisting of 10 pounds per square inch (PSI) to 20 PSI, 20 PSI to 40 PSI, 40 PSI to 60 PSI, 60 PSI to 80 PSI, 80 PSI to 100 PSI, 100 PSI to 125 PSI, 125 PSI to 150 PSI, 150 PSI to 175 PSI, 175 PSI to 200 PSI, 200 PSI to 225 PSI, 225 PSI to 250 PSI, 250 PSI to 275 PSI, 275 PSI to 300 PSI, 300 PSI to 325 PSI, 325 PSI to 350 PSI, 350 PSI to 375 PSI, 375 PSI to 400 PSI, 400 PSI to 425 PSI, 425 PSI to 450 PSI, 450 PSI to 475 PSI, and 475 PSI to 500 PSI.

In embodiments, the filtered and pressurized crude cannabinoid extract (HCM) is transferred from the crude cannabinoid extract pump (HCO) and into a first adsorber system (SMB1). In embodiments, the first adsorber system (SMB1) is configured to input a filtered and pressurized crude cannabinoid extract (HCM) and a first desorbent (HDC). In embodiments, the first adsorber system (SMB1) is configured to output a first extract (HDA) and a first raffinate (HDE). In embodiments, the first extract (HDA) can also be called a primary extract (HDB). In embodiments, the first adsorber system (SMB1) includes an adsorber or plurality of adsorbers containing an adsorbent.

In embodiments, the first adsorber system (SMB1) includes a plurality of adsorbers containing adsorbent is provided and may be called the stationary phase. In embodiments, the adsorbent positioned within the adsorber or plurality of adsorbers may be called the stationary phase. The bed of adsorbent that is contained within the adsorber does not move so therefore it is stationary. The plurality of beds of adsorbent that are contained within the plurality of adsorbers does not move so therefore it is stationary. In embodiments, at least a portion of *cannabis* is dissolved in a solvent (e.g.—the filtered and pressurized crude cannabinoid extract (HCM)) and may be called the mobile phase.

In embodiments, a first adsorber system (SMB1) operates as a simulated moving bed chromatography (SMB chromatography) which is a continuous process. This is implemented by arranging several preparative columns connected in series and periodically changing the valve setting so that a movement of the solid phase in the opposite direction of the flow of the liquid phase is simulated. In embodiments, the system is continuously fed with a feed mixture (e.g.—the filtered and pressurized crude cannabinoid extract (HCM)) comprising the compounds to be separated and an eluent (e.g.—the first desorbent (HDC) which is a liquid, water, treated water, or a solvent) while a raffinate and an extract are continuously withdrawn from the system.

In embodiments, the first adsorber system (SMB1) periodically switches the feed, eluent, extract and raffinate ports in the same direction. The basic premise of a simulated moving bed adsorber system is that the inlet and outlet ports are switched periodically in the direction of the fluid flow. This simulates the countercurrent movement of the phase in the process. Chromatography is a technique used to separate mixtures. In embodiments, the mixture may include cannabinoids and a solvent. In embodiments, the mixture may include a filtered and pressurized crude cannabinoid extract (HCM). In embodiments, the mixture may include cannabinoids from a first solvent and volatiles mixture (FSVM). In embodiments, the mixture may include cannabinoids from a second volatiles and solvent mixture (SVSM).

In embodiments, cannabinoids (e.g., a cannabinoid glycoside, tetrahydrocannabinolic acid (THCA), active tetrahydrocannabinol, tetrahydrocannabinol (THC), Δ9-tetrahydrocannabinol (Δ9-THC), Δ8-tetrahydrocannabinol (Δ8-THC), tetrahydrocannabivarin (THCV), cannabidiolic acid (CBDA), cannabichromene (CBC), cannabidiol (CBD), cannabigerol (CBG), cannabinidiol (CBND), and/or cannabinol (CBN)) are dissolved in a liquid solvent. The mixture of cannabinoids and the solvent may be called the mobile phase. The mobile phase is passed through an adsorber containing an adsorbent, the adsorbent within the adsorber may be called a stationary phase. In embodiments, a moving bed adsorber may be used in which the stationary phase would then move.

The mixture of cannabinoids and a liquid and/or a solvent are introduced into the adsorber and various constituents of the mixture travel at different speeds, causing them to separate. The separation is based on differential partitioning between the mobile and stationary phases. More than one adsorber may be used so there may be various stationary phases. Subtle differences in each of the cannabinoids partition coefficient result in differential retention on the stationary phase and thus affect the separation. For example, some cannabinoids are more hydrophilic than others and are mode readily soluble in a solvent such as lipids and alcohol. These compounds in turn have a relatively larger partition coefficient than the cannabinoids that are less hydrophilic.

In embodiments, a relatively less hydrophilic cannabinoid has a greater partition coefficient than a cannabinoid that is more hydrophilic. In embodiments, a relatively more hydrophobic cannabinoid has a greater partition coefficient than a cannabinoid that is less hydrophilic. In other embodiments, a relatively less hydrophilic cannabinoid has a greater partition coefficient than a cannabinoid that is more hydrophilic. In other embodiments, a relatively more hydrophilic cannabinoid has a lesser partition coefficient than a cannabinoid that is lesser hydrophilic.

In embodiments, tetrahydrocannabinol has a partition coefficient of 6.99. In embodiments, Δ9-tetrahydrocannabinol Δ9-THC has a partition coefficient of 6.99. In embodiments, cannabidiol has a partition coefficient of 5.79. In embodiments, tetrahydrocannabinol has a partition coefficient that is greater than cannabidiol. In embodiments, tetrahydrocannabinol is more hydrophobic than cannabidiol. In embodiments, cannabidiol is more hydrophilic than tetrahydrocannabinol.

Since tetrahydrocannabinol has a partition coefficient that is greater than cannabidiol, it will stay in the bed longer than the cannabidiol. In embodiments, the tetrahydrocannabinol will stay in the adsorber bed longer than the cannabidiol. In embodiments, the cannabidiol will stay in the adsorber bed longer than the tetrahydrocannabinol. In embodiments, the tetrahydrocannabinol will elute before the cannabidiol. In embodiments, the cannabidiol will elute before the tetrahydrocannabinol.

In embodiments, the first, second, and/or third adsorber systems (SMB1, SMB2, SMB3), are simulated moving bed processing systems and are cyclic steady state processes configured to obtain pure components (e.g.—concentrated volatiles, an emulsion, etc.) are production rates that include one or more selected from the group consisting of 0.0015 tons per day to 0.003 tons per day, 0.003 tons per day to 0.0045 tons per day, 0.0045 tons per day to 0.006 tons per day, 0.006 tons per day to 0.0075 tons per day, 0.0075 tons per day to 0.009 tons per day, 0.009 tons per day to 0.0105 tons per day, 0.0105 tons per day to 0.012 tons per day, 0.012 tons per day to 0.0135 tons per day, 0.0135 tons per day to 0.015 tons per day, 0.015 tons per day to 0.03 tons per day, 0.03 tons per day to 0.033 tons per day, 0.033 tons per day to 0.036 tons per day, 0.036 tons per day to 0.039 tons per day, 0.039 tons per day to 0.042 tons per day, 0.042 tons per day to 0.045 tons per day, 0.045 tons per day to 0.048 tons per day, 0.048 tons per day to 0.051 tons per day, 0.051 tons per day to 0.054 tons per day, 0.054 tons per day to 0.057 tons per day, 0.057 tons per day to 0.06 tons per day, 0.06 tons per day to 0.063 tons per day, 0.063 tons per day to 0.066 tons per day, 0.066 tons per day to 0.132 tons per day, 0.132 tons per day to 0.198 tons per day, 0.198 tons per day to 0.264 tons per day, 0.264 tons per day to 0.33 tons per day, 0.33 tons per day to 0.396 tons per day, 0.396 tons per day to 0.462 tons per day, 0.462 tons per day to 0.528 tons per day, 0.528 tons per day to 0.594 tons per day, 0.594 tons per day to 0.66 tons per day, 0.66 tons per day to 0.726 tons per day, 0.726 tons per day to 0.792 tons per day, 0.792 tons per day to 1.584 tons per day, 1.584 tons per day to 3.168 tons per day, 3.168 tons per day to 6.336 tons per day, 6.336 tons per day to 12.672 tons per day, 12.672 tons per day to 25.344 tons per day, 25.344 tons per day to 50.688 tons per day, 50.688 tons per day to 101.376 tons per day.

In embodiments, the extract is the more highly adsorbed component. In embodiments, the more highly adsorbed components are cannabinoids. In embodiments, the extract is desorbed with a desorbent to collect as the final product. Desorption may take place under pressure swing desorption, thermal swing desorption, or passing a heated and/or cooled desorbent liquid do desorb the extract from the adsorption sites within the adsorber. In embodiments, the desorption may take place under pressure swing desorption, thermal swing desorption, or passing a first heated desorbent liquid then a second cooled desorbent liquid do desorb the extract from the adsorption sites within the adsorber.

In embodiments, the raffinate includes poorly adsorbed components. The poorly adsorbed components adsorb less to the adsorption sites or the adsorbent within the adsorber or plurality of adsorbers in relation to the highly adsorbed components. In embodiments, the raffinate includes a liquid, first solvent, second solvent, water, alcohol, lipid. In embodiments, the raffinate includes a solvent, the solvent includes one or more from the group consisting of acetone, alcohol, ethanol, hexane, insect lipids, isobutane, isopropanol, liquid carbon dioxide, liquid, naphtha, and water. In embodiments, a mixture of cannabinoids and a solvent are provided to the simulated bed adsorber system. In embodiments, the cannabinoids are the extract and the solvent is the raffinate. In embodiments, the extract is more highly adsorbed components. In embodiments, the more highly adsorbed components are cannabinoids.

In embodiments, the raffinate includes cannabinoids. In embodiments, the raffinate includes cannabidiol. In embodiments, the raffinate includes THC. In embodiments, the raffinate includes a mixture of cannabinoids and water. In embodiments, the raffinate includes a mixture of cannabidiol and water. In embodiments, the raffinate includes a mixture of THC and water. In embodiments, the raffinate includes a mixture of cannabinoids and ethanol. In embodiments, the raffinate includes a mixture of cannabidiol and ethanol. In embodiments, the raffinate includes a mixture of THC and ethanol. In embodiments, the raffinate includes a mixture of cannabinoids and ethanol and water. In embodiments, the raffinate includes a mixture of cannabidiol and ethanol and water. In embodiments, the raffinate includes a mixture of THC and ethanol and water. In embodiments, the raffinate includes a mixture of cannabinoids and methanol. In embodiments, the raffinate includes a mixture of cannabidiol and methanol. In embodiments, the raffinate includes a mixture of THC and methanol.

In embodiments, the raffinate includes a mixture of cannabinoids and methanol and water. In embodiments, the raffinate includes a mixture of cannabidiol and methanol and water. In embodiments, the raffinate includes a mixture of THC and methanol and water.

In embodiments, the raffinate includes cannabinoids and ethanol at a cannabinoid-to-ethanol-raffinate-ratio selected from the group consisting of: 0.0001 pounds of cannabinoids to per pound of ethanol to 0.0002 pounds of cannabinoids to per pound of ethanol, 0.0002 pounds of cannabinoids to per pound of ethanol to 0.0004 pounds of cannabinoids to per pound of ethanol, pounds of cannabinoids to per pound of ethanol to 0.0008 pounds of cannabinoids to per pound of ethanol, 0.0008 pounds of cannabinoids to per pound of ethanol to 0.0016 pounds of cannabinoids to per pound of ethanol, 0.0016 pounds of cannabinoids to per pound of ethanol to pounds of cannabinoids to per pound of ethanol, 0.0032 pounds of cannabinoids to per pound of ethanol to 0.0064 pounds of cannabinoids to per pound of ethanol, 0.0064 pounds of cannabinoids to per pound of ethanol to 0.0128 pounds of cannabinoids to per pound of ethanol, 0.0128 pounds of cannabinoids to per pound of ethanol to 0.0256 pounds of cannabinoids to per pound of ethanol, 0.0256 pounds of cannabinoids to per pound of ethanol to 0.0512 pounds of cannabinoids to per pound of ethanol, 0.0512 pounds of cannabinoids to per pound of ethanol to pounds of cannabinoids to per pound of ethanol, 0.06 pounds of cannabinoids to per pound of ethanol to 0.07 pounds of cannabinoids to per pound of ethanol, 0.07 pounds of cannabinoids to per pound of ethanol to 0.08 pounds of cannabinoids to per pound of ethanol, 0.08 pounds of cannabinoids to per pound of ethanol to 0.09 pounds of cannabinoids to per pound of ethanol, 0.09 pounds of cannabinoids to per pound of ethanol to 0.1 pounds of cannabinoids to per pound of ethanol, 0.1 pounds of cannabinoids to per pound of ethanol to 0.233 pounds of cannabinoids to per pound of ethanol, 0.233 pounds of cannabinoids to per pound of ethanol to 0.366 pounds of cannabinoids to per pound of ethanol, 0.366 pounds of cannabinoids to per pound of ethanol to pounds of cannabinoids to per pound of ethanol, and 0.499 pounds of cannabinoids to per pound of ethanol to 0.632 pounds of cannabinoids to per pound of ethanol; wherein: the cannabinoid-to-ethanol-ratio is defined as the weight percent of the raffinate mixture including the pounds of cannabinoids divided by the pounds of ethanol.

In embodiments, the raffinate includes cannabinoids and methanol at a cannabinoid-to-methanol-raffinate-ratio selected from the group consisting of: 0.0001 pounds of cannabinoids to per pound of methanol to 0.0002 pounds of cannabinoids to per pound of methanol, 0.0002 pounds of cannabinoids to per pound of methanol to 0.0004 pounds of cannabinoids to per pound of methanol, 0.0004 pounds of cannabinoids to per pound of methanol to 0.0008 pounds of cannabinoids to per pound of methanol, 0.0008 pounds of cannabinoids to per pound of methanol to 0.0016 pounds of cannabinoids to per pound of methanol, 0.0016 pounds of cannabinoids to per pound of methanol to 0.0032 pounds of cannabinoids to per pound of methanol, 0.0032 pounds of cannabinoids to per pound of methanol to 0.0064 pounds of cannabinoids to per pound of methanol, 0.0064 pounds of cannabinoids to per pound of methanol to 0.0128 pounds of cannabinoids to per pound of methanol, 0.0128 pounds of cannabinoids to per pound of methanol to 0.0256 pounds of cannabinoids to per pound of methanol, 0.0256 pounds of cannabinoids to per pound of methanol to 0.0512 pounds of cannabinoids to per pound of methanol, 0.0512 pounds of cannabinoids to per pound of methanol to 0.06 pounds of cannabinoids to per pound of methanol, pounds of cannabinoids to per pound of methanol to 0.07 pounds of cannabinoids to per pound of methanol, 0.07 pounds of cannabinoids to per pound of methanol to 0.08 pounds of cannabinoids to per pound of methanol, 0.08 pounds of cannabinoids to per pound of methanol to pounds of cannabinoids to per pound of methanol, 0.09 pounds of cannabinoids to per pound of methanol to 0.1 pounds of cannabinoids to per pound of methanol, 0.1 pounds of cannabinoids to per pound of methanol to 0.233 pounds of cannabinoids to per pound of methanol, 0.233 pounds of cannabinoids to per pound of methanol to 0.366 pounds of cannabinoids to per pound of methanol, 0.366 pounds of cannabinoids to per pound of methanol to 0.499 pounds of cannabinoids to per pound of methanol, and 0.499 pounds of cannabinoids to per pound of methanol to 0.632 pounds of cannabinoids to per pound of methanol; wherein: the cannabinoid-to-methanol-ratio is defined as the weight percent of the raffinate mixture including the pounds of cannabinoids divided by the pounds of methanol.

In embodiments, the raffinate includes cannabinoids and water at a cannabinoid-to-water-raffinate-ratio selected from the group consisting of: 0.0001 pounds of cannabinoids to per pound of water to 0.0002 pounds of cannabinoids to per pound of water, 0.0002 pounds of cannabinoids to per pound of water to 0.0004 pounds of cannabinoids to per pound of water, 0.0004 pounds of cannabinoids to per pound of water to 0.0008 pounds of cannabinoids to per pound of water, pounds of cannabinoids to per pound of water to 0.0016 pounds of cannabinoids to per pound of water, 0.0016 pounds of cannabinoids to per pound of water to 0.0032 pounds of cannabinoids to per pound of water, 0.0032 pounds of cannabinoids to per pound of water to pounds of cannabinoids to per pound of water, 0.0064 pounds of cannabinoids to per pound of water to 0.0128 pounds of cannabinoids to per pound of water, 0.0128 pounds of cannabinoids to per pound of water to 0.0256 pounds of cannabinoids to per pound of water, 0.0256 pounds of cannabinoids to per pound of water to 0.0512 pounds of cannabinoids to per pound of water, pounds of cannabinoids to per pound of water to 0.06 pounds of cannabinoids to per pound of water, 0.06 pounds of cannabinoids to per pound of water to 0.07 pounds of cannabinoids to per pound of water, 0.07 pounds of cannabinoids to per pound of water to 0.08 pounds of cannabinoids to per pound of water, 0.08 pounds of cannabinoids to per pound of water to 0.09 pounds of cannabinoids to per pound of water, 0.09 pounds of cannabinoids to per pound of water to 0.1 pounds of cannabinoids to per pound of water, 0.1 pounds of cannabinoids to per pound of water to 0.233 pounds of cannabinoids to per pound of water, 0.233 pounds of cannabinoids to per pound of water to 0.366 pounds of cannabinoids to per pound of water, 0.366 pounds of cannabinoids to per pound of water to 0.499 pounds of cannabinoids to per pound of water, and 0.499 pounds of cannabinoids to per pound of water to 0.632 pounds of cannabinoids to per pound of water; wherein: the cannabinoid-to-water-ratio is defined as the weight percent of the raffinate mixture including the pounds of cannabinoids divided by the pounds of water.

In embodiments, the raffinate includes THC and ethanol at a THC-to-ethanol-raffinate-ratio selected from the group consisting of: 0.0001 pounds of THC to per pound of ethanol to 0.0002 pounds of THC to per pound of ethanol, 0.0002 pounds of THC to per pound of ethanol to pounds of THC to per pound of ethanol, 0.0004 pounds of THC to per pound of ethanol to pounds of THC to per pound of ethanol, 0.0008 pounds of THC to per pound of ethanol to pounds of THC to per pound of ethanol, 0.0016 pounds of THC to per pound of ethanol to pounds of THC to per pound of ethanol, 0.0032 pounds of THC to per pound of ethanol to 0.0064 pounds of THC to per pound of ethanol, 0.0064 pounds of THC to per pound of ethanol to pounds of THC to per pound of ethanol, 0.0128 pounds of THC to per pound of ethanol to pounds of THC to per pound of ethanol, 0.0256 pounds of THC to per pound of ethanol to pounds of THC to per pound of ethanol, 0.0512 pounds of THC to per pound of ethanol to pounds of THC to per pound of ethanol, 0.06 pounds of THC to per pound of ethanol to 0.07 pounds of THC to per pound of ethanol, 0.07 pounds of THC to per pound of ethanol to 0.08 pounds of THC to per pound of ethanol, 0.08 pounds of THC to per pound of ethanol to 0.09 pounds of THC to per pound of ethanol, 0.09 pounds of THC to per pound of ethanol to 0.1 pounds of THC to per pound of ethanol, 0.1 pounds of THC to per pound of ethanol to 0.233 pounds of THC to per pound of ethanol, 0.233 pounds of THC to per pound of ethanol to 0.366 pounds of THC to per pound of ethanol, 0.366 pounds of THC to per pound of ethanol to 0.499 pounds of THC to per pound of ethanol, and 0.499 pounds of THC to per pound of ethanol to 0.632 pounds of THC to per pound of ethanol; wherein: the THC-to-ethanol-ratio is defined as the weight percent of the raffinate mixture including the pounds of THC divided by the pounds of ethanol.

In embodiments, the raffinate includes THC and methanol at a THC-to-methanol-raffinate-ratio selected from the group consisting of: 0.0001 pounds of THC to per pound of methanol to 0.0002 pounds of THC to per pound of methanol, 0.0002 pounds of THC to per pound of methanol to 0.0004 pounds of THC to per pound of methanol, 0.0004 pounds of THC to per pound of methanol to 0.0008 pounds of THC to per pound of methanol, 0.0008 pounds of THC to per pound of methanol to 0.0016 pounds of THC to per pound of methanol, 0.0016 pounds of THC to per pound of methanol to 0.0032 pounds of THC to per pound of methanol, 0.0032 pounds of THC to per pound of methanol to 0.0064 pounds of THC to per pound of methanol, 0.0064 pounds of THC to per pound of methanol to 0.0128 pounds of THC to per pound of methanol, 0.0128 pounds of THC to per pound of methanol to 0.0256 pounds of THC to per pound of methanol, 0.0256 pounds of THC to per pound of methanol to 0.0512 pounds of THC to per pound of methanol, 0.0512 pounds of THC to per pound of methanol to 0.06 pounds of THC to per pound of methanol, 0.06 pounds of THC to per pound of methanol to 0.07 pounds of THC to per pound of methanol, 0.07 pounds of THC to per pound of methanol to 0.08 pounds of THC to per pound of methanol, 0.08 pounds of THC to per pound of methanol to 0.09 pounds of THC to per pound of methanol, 0.09 pounds of THC to per pound of methanol to 0.1 pounds of THC to per pound of methanol, 0.1 pounds of THC to per pound of methanol to 0.233 pounds of THC to per pound of methanol, 0.233 pounds of THC to per pound of methanol to 0.366 pounds of THC to per pound of methanol, 0.366 pounds of THC to per pound of methanol to 0.499 pounds of THC to per pound of methanol, and pounds of THC to per pound of methanol to 0.632 pounds of THC to per pound of methanol; wherein: the THC-to-methanol-ratio is defined as the weight percent of the raffinate mixture including the pounds of THC divided by the pounds of methanol.

In embodiments, the raffinate includes THC and water at a THC-to-water-raffinate-ratio selected from the group consisting of: 0.0001 pounds of THC to per pound of water to 0.0002 pounds of THC to per pound of water, 0.0002 pounds of THC to per pound of water to 0.0004 pounds of THC to per pound of water, 0.0004 pounds of THC to per pound of water to 0.0008 pounds of THC to per pound of water, 0.0008 pounds of THC to per pound of water to 0.0016 pounds of THC to per pound of water, 0.0016 pounds of THC to per pound of water to 0.0032 pounds of THC to per pound of water, 0.0032 pounds of THC to per pound of water to 0.0064 pounds of THC to per pound of water, 0.0064 pounds of THC to per pound of water to 0.0128 pounds of THC to per pound of water, 0.0128 pounds of THC to per pound of water to 0.0256 pounds of THC to per pound of water, 0.0256 pounds of THC to per pound of water to 0.0512 pounds of THC to per pound of water, 0.0512 pounds of THC to per pound of water to 0.06 pounds of THC to per pound of water, 0.06 pounds of THC to per pound of water to 0.07 pounds of THC to per pound of water, 0.07 pounds of THC to per pound of water to 0.08 pounds of THC to per pound of water, 0.08 pounds of THC to per pound of water to 0.09 pounds of THC to per pound of water, 0.09 pounds of THC to per pound of water to 0.1 pounds of THC to per pound of water, pounds of THC to per pound of water to 0.233 pounds of THC to per pound of water, 0.233 pounds of THC to per pound of water to 0.366 pounds of THC to per pound of water, 0.366 pounds of THC to per pound of water to 0.499 pounds of THC to per pound of water, and 0.499 pounds of THC to per pound of water to 0.632 pounds of THC to per pound of water; wherein: the THC-to-water-ratio is defined as the weight percent of the raffinate mixture including the pounds of THC divided by the pounds of water.

In embodiments, the raffinate includes CBD and ethanol at a CBD-to-ethanol-raffinate-ratio selected from the group consisting of: 0.0001 pounds of CBD to per pound of ethanol to pounds of CBD to per pound of ethanol, 0.0002 pounds of CBD to per pound of ethanol to pounds of CBD to per pound of ethanol, 0.0004 pounds of CBD to per pound of ethanol to pounds of CBD to per pound of ethanol, 0.0008 pounds of CBD to per pound of ethanol to 0.0016 pounds of CBD to per pound of ethanol, 0.0016 pounds of CBD to per pound of ethanol to pounds of CBD to per pound of ethanol, 0.0032 pounds of CBD to per pound of ethanol to pounds of CBD to per pound of ethanol, 0.0064 pounds of CBD to per pound of ethanol to pounds of CBD to per pound of ethanol, 0.0128 pounds of CBD to per pound of ethanol to pounds of CBD to per pound of ethanol, 0.0256 pounds of CBD to per pound of ethanol to pounds of CBD to per pound of ethanol, 0.0512 pounds of CBD to per pound of ethanol to 0.06 pounds of CBD to per pound of ethanol, 0.06 pounds of CBD to per pound of ethanol to 0.07 pounds of CBD to per pound of ethanol, 0.07 pounds of CBD to per pound of ethanol to 0.08 pounds of CBD to per pound of ethanol, 0.08 pounds of CBD to per pound of ethanol to 0.09 pounds of CBD to per pound of ethanol, 0.09 pounds of CBD to per pound of ethanol to 0.1 pounds of CBD to per pound of ethanol, 0.1 pounds of CBD to per pound of ethanol to 0.233 pounds of CBD to per pound of ethanol, 0.233 pounds of CBD to per pound of ethanol to 0.366 pounds of CBD to per pound of ethanol, 0.366 pounds of CBD to per pound of ethanol to 0.499 pounds of CBD to per pound of ethanol, and 0.499 pounds of CBD to per pound of ethanol to 0.632 pounds of CBD to per pound of ethanol; wherein: the CBD-to-ethanol-ratio is defined as the weight percent of the raffinate mixture including the pounds of CBD divided by the pounds of ethanol.

In embodiments, the raffinate includes CBD and methanol at a CBD-to-methanol-raffinate-ratio selected from the group consisting of: 0.0001 pounds of CBD to per pound of methanol to pounds of CBD to per pound of methanol, 0.0002 pounds of CBD to per pound of methanol to 0.0004 pounds of CBD to per pound of methanol, 0.0004 pounds of CBD to per pound of methanol to 0.0008 pounds of CBD to per pound of methanol, 0.0008 pounds of CBD to per pound of methanol to 0.0016 pounds of CBD to per pound of methanol, 0.0016 pounds of CBD to per pound of methanol to 0.0032 pounds of CBD to per pound of methanol, 0.0032 pounds of CBD to per pound of methanol to 0.0064 pounds of CBD to per pound of methanol, 0.0064 pounds of CBD to per pound of methanol to 0.0128 pounds of CBD to per pound of methanol, 0.0128 pounds of CBD to per pound of methanol to 0.0256 pounds of CBD to per pound of methanol, 0.0256 pounds of CBD to per pound of methanol to 0.0512 pounds of CBD to per pound of methanol, 0.0512 pounds of CBD to per pound of methanol to 0.06 pounds of CBD to per pound of methanol, 0.06 pounds of CBD to per pound of methanol to 0.07 pounds of CBD to per pound of methanol, 0.07 pounds of CBD to per pound of methanol to 0.08 pounds of CBD to per pound of methanol, 0.08 pounds of CBD to per pound of methanol to 0.09 pounds of CBD to per pound of methanol, 0.09 pounds of CBD to per pound of methanol to 0.1 pounds of CBD to per pound of methanol, 0.1 pounds of CBD to per pound of methanol to 0.233 pounds of CBD to per pound of methanol, 0.233 pounds of CBD to per pound of methanol to 0.366 pounds of CBD to per pound of methanol, 0.366 pounds of CBD to per pound of methanol to 0.499 pounds of CBD to per pound of methanol, and pounds of CBD to per pound of methanol to 0.632 pounds of CBD to per pound of methanol; wherein: the CBD-to-methanol-ratio is defined as the weight percent of the raffinate mixture including the pounds of CBD divided by the pounds of methanol.

In embodiments, the raffinate includes CBD and water at a CBD-to-water-raffinate-ratio selected from the group consisting of: 0.0001 pounds of CBD to per pound of water to 0.0002 pounds of CBD to per pound of water, 0.0002 pounds of CBD to per pound of water to 0.0004 pounds of CBD to per pound of water, 0.0004 pounds of CBD to per pound of water to 0.0008 pounds of CBD to per pound of water, 0.0008 pounds of CBD to per pound of water to 0.0016 pounds of CBD to per pound of water, 0.0016 pounds of CBD to per pound of water to 0.0032 pounds of CBD to per pound of water, 0.0032 pounds of CBD to per pound of water to 0.0064 pounds of CBD to per pound of water, 0.0064 pounds of CBD to per pound of water to 0.0128 pounds of CBD to per pound of water, 0.0128 pounds of CBD to per pound of water to 0.0256 pounds of CBD to per pound of water, 0.0256 pounds of CBD to per pound of water to 0.0512 pounds of CBD to per pound of water, 0.0512 pounds of CBD to per pound of water to 0.06 pounds of CBD to per pound of water, 0.06 pounds of CBD to per pound of water to 0.07 pounds of CBD to per pound of water, 0.07 pounds of CBD to per pound of water to 0.08 pounds of CBD to per pound of water, 0.08 pounds of CBD to per pound of water to 0.09 pounds of CBD to per pound of water, 0.09 pounds of CBD to per pound of water to 0.1 pounds of CBD to per pound of water, pounds of CBD to per pound of water to 0.233 pounds of CBD to per pound of water, 0.233 pounds of CBD to per pound of water to 0.366 pounds of CBD to per pound of water, 0.366 pounds of CBD to per pound of water to 0.499 pounds of CBD to per pound of water, and 0.499 pounds of CBD to per pound of water to 0.632 pounds of CBD to per pound of water; wherein: the CBD-to-water-ratio is defined as the weight percent of the raffinate mixture including the pounds of CBD divided by the pounds of water.

De Sorbent (Eluent)

In embodiments, the eluent is the first desorbent (HDC). In embodiments, the eluent is in a supercritical state. In embodiments, the eluent is not in a supercritical state. In embodiments, the eluent is a liquid. In embodiments, the eluent can be an aqueous alcohol. In embodiments, the aqueous alcohol can comprise water and one or more short chain alcohols. In embodiments, the short chain alcohol can have from 1 to 6 carbon atoms. In embodiments, the examples of suitable alcohols include methanol, ethanol, n-propanol, i-propanol, n-butanol, i-butanol, s-butanol and t-butanol. In some aspects of the present invention, methanol and ethanol can be used. In another aspect, methanol can be used. In embodiments, the eluent can be methyl tertiary butyl ether. In embodiments, the eluent is a mixture of methanol, tetrahydrofuran, and water. In embodiments, the eluent is treated water. In embodiments, the eluent ranges from between 30 degrees F. to 40 deg F, 40 deg F to 50 deg F, 50 deg F to 60 deg F, 60 deg F to deg F, 70 deg F to 80 deg F, 80 deg F to 90 deg F, 9 deg F to 100 deg F, 100 deg F to 110 deg F, 110 deg F to 120 deg F, 120 deg F to 130 deg F, 130 deg F to 140 deg F, 140 deg F to 150 deg F, 150 deg F to 160 deg F, 160 deg F to 170 deg F, 170 deg F to 180 deg F, 180 deg F to 190 deg F, 190 deg F to 200 deg F, 200 deg F to 210 deg F, 210 deg F to 212 deg F.

In embodiments, the weight percent of ethanol in the eluent includes one or more concentration ranges selected from the group consisting of: 15 weight percent to 20 weight percent, 20 weight percent to 25 weight percent, 25 weight percent to 30 weight percent, 30 weight percent to 35 weight percent, 35 weight percent to 40 weight percent, 40 weight percent to 45 weight percent, 45 weight percent to 50 weight percent, 50 weight percent to 55 weight percent, 55 weight percent to 60 weight percent, 60 weight percent to 65 weight percent, 65 weight percent to 70 weight percent, 70 weight percent to 75 weight percent, 75 weight percent to 80 weight percent, 80 weight percent to 85 weight percent, 85 weight percent to 90 weight percent, 90 to 95 weight percent, 95 weight percent to 99 weight percent, and 99 weight percent to 100 weight percent, and 100 weight percent.

In embodiments, the weight percent of methanol in the eluent includes one or more concentration ranges selected from the group consisting of: 15 weight percent to 20 weight percent, 20 weight percent to 25 weight percent, 25 weight percent to 30 weight percent, 30 weight percent to 35 weight percent, 35 weight percent to 40 weight percent, 40 weight percent to 45 weight percent, 45 weight percent to 50 weight percent, 50 weight percent to 55 weight percent, 55 weight percent to 60 weight percent, 60 weight percent to 65 weight percent, 65 weight percent to 70 weight percent, 70 weight percent to 75 weight percent, 75 weight percent to 80 weight percent, 80 weight percent to 85 weight percent, 85 weight percent to 90 weight percent, 90 to 95 weight percent, 95 weight percent to 99 weight percent, and 99 weight percent to 100 weight percent, and 100 weight percent.

In embodiments the weight percent of tetrahydrofuran in the eluent includes one or more concentration ranges selected from the group consisting of: 0 weight percent to 1 weight percent, 1 weight percent to 5 weight percent, 5 weight percent to 10 weight percent, 10 weight percent to 15 weight percent, 15 weight percent to 20 weight percent, 20 weight percent to 25 weight percent, weight percent to 30 weight percent, 30 weight percent to 35 weight percent, 35 weight percent to 40 weight percent, 40 weight percent to 45 weight percent, 45 weight percent to 50 weight percent, 50 weight percent to 55 weight percent, 55 weight percent to 60 weight percent, 60 weight percent to 65 weight percent, 65 weight percent to 70 weight percent, 70 weight percent to 75 weight percent, 75 weight percent to 80 weight percent, 80 weight percent to 85 weight percent, weight percent to 90 weight percent, 90 weight percent to 95 weight percent, 95 weight percent to 99 weight percent, and 99 to 100 weight percent to percent, and 100 weight percent.

In embodiments, the weight percent of water in the eluent includes one or more concentration ranges selected from the group consisting of: 0 weight percent to 1 weight percent, 1 weight percent to 5 weight percent, 5 weight percent to 10 weight percent, 10 weight percent to weight percent, 15 weight percent to 20 weight percent, 20 weight percent to 25 weight percent, weight percent to 30 weight percent, 30 weight percent to 35 weight percent, 35 weight percent to 40 weight percent, 40 weight percent to 45 weight percent, 45 weight percent to 50 weight percent, 50 weight percent to 55 weight percent, 55 weight percent to 60 weight percent, 60 weight percent to 65 weight percent, 65 weight percent to 70 weight percent, 70 weight percent to 75 weight percent, 75 weight percent to 80 weight percent, 80 weight percent to 85 weight percent, weight percent to 90 weight percent, 90 weight percent to 95 weight percent, 95 weight percent to 99 weight percent, and 99 weight percent to 100 weight percent, and 100 weight percent.

The process of the present invention relates to the purification of terpenes and/or cannabidiol and/or tetrahydrocannabinol directly from extracts of plant material in a process which uses novel chromatographic scheme. More specifically, Applicant has developed a sequence of purification steps and a novel simulated moving bed separation process (SMB) series of adsorbent/desorbent combinations and SMB configurations to bring about the enrichment and purification of terpenes and/or cannabidiol and/or tetrahydrocannabinol, to provide a purified terpenes and/or cannabinoid product and without using any potentially toxic organic solvent.

In embodiments, the adsorbent used in the simulated moving bed system employed is a combination of styrene-divinyl benzene copolymer, ion exchange and hydrophobic interaction based stationary phase adsorbents and a mobile phase comprising water in a combination of normal and reverse phase simulated moving bed separation zones to provide an enriched extract comprising major terpenes and/or a cannabinoid.

In embodiments, the terpenes that are extracted from the SMB process have a purity that includes one or more from the group consisting of 30 percent purity to 40 percent purity, 40 percent purity to 50 percent purity, 50 percent purity to 60 percent purity, 60 percent purity to 70 percent purity, 70 percent purity to 80 percent purity, 80 percent purity to 82 percent purity, 82 percent purity to 84 percent purity, 84 percent purity to 86 percent purity, 86 percent purity to 88 percent purity, 88 percent purity to 90 percent purity, 90 percent purity to 92 percent purity, 92 percent purity to 92.5 percent purity, 92.5 percent purity to 93 percent purity, 93 percent purity to 93.5 percent purity, 93.5 percent purity to 94 percent purity, 94 percent purity to 94.5 percent purity, 94.5 percent purity to 94.75 percent purity, 94.75 percent purity to 95 percent purity, 95 percent purity to 95.25 percent purity, 95.25 percent purity to 95.5 percent purity, 95.5 percent purity to 95.75 percent purity, 95.75 percent purity to 96 percent purity, 96 percent purity to 96.25 percent purity, 96.25 percent purity to 96.5 percent purity, 96.5 percent purity to 96.75 percent purity, 96.75 percent purity to 97 percent purity, 97 percent purity to 97.25 percent purity, 97.25 percent purity to 97.5 percent purity, 97.5 percent purity to 97.75 percent purity, 97.75 percent purity to 98 percent purity, 98 percent purity to 98.25 percent purity, 98.25 percent purity to 98.5 percent purity, 98.5 percent purity to 98.75 percent purity, 98.75 percent purity to 99 percent purity, 99 percent purity to 99.25 percent purity, 99.25 percent purity to 99.5 percent purity, 99.5 percent purity to 99.75 percent purity, and 99.75 percent purity to 100 percent purity.

In embodiments, the cannabidiol that are extracted from the SMB process have a purity that includes one or more from the group consisting of 30 percent purity to 40 percent purity, 40 percent purity to 50 percent purity, 50 percent purity to 60 percent purity, 60 percent purity to 70 percent purity, 70 percent purity to 80 percent purity, 80 percent purity to 82 percent purity, 82 percent purity to 84 percent purity, 84 percent purity to 86 percent purity, 86 percent purity to 88 percent purity, 88 percent purity to 90 percent purity, 90 percent purity to 92 percent purity, 92 percent purity to 92.5 percent purity, 92.5 percent purity to 93 percent purity, 93 percent purity to 93.5 percent purity, 93.5 percent purity to 94 percent purity, 94 percent purity to 94.5 percent purity, 94.5 percent purity to 94.75 percent purity, 94.75 percent purity to 95 percent purity, 95 percent purity to 95.25 percent purity, 95.25 percent purity to 95.5 percent purity, 95.5 percent purity to 95.75 percent purity, 95.75 percent purity to 96 percent purity, 96 percent purity to 96.25 percent purity, 96.25 percent purity to 96.5 percent purity, 96.5 percent purity to 96.75 percent purity, 96.75 percent purity to 97 percent purity, 97 percent purity to 97.25 percent purity, 97.25 percent purity to 97.5 percent purity, 97.5 percent purity to 97.75 percent purity, 97.75 percent purity to 98 percent purity, 98 percent purity to 98.25 percent purity, 98.25 percent purity to 98.5 percent purity, 98.5 percent purity to 98.75 percent purity, 98.75 percent purity to 99 percent purity, 99 percent purity to 99.25 percent purity, 99.25 percent purity to 99.5 percent purity, 99.5 percent purity to 99.75 percent purity, and 99.75 percent purity to 100 percent purity.

In embodiments, the tetrahydrocannabinol that are extracted from the SMB process have a purity that includes one or more from the group consisting of 30 percent purity to 40 percent purity, percent purity to 50 percent purity, 50 percent purity to 60 percent purity, 60 percent purity to 70 percent purity, 70 percent purity to 80 percent purity, 80 percent purity to 82 percent purity, 82 percent purity to 84 percent purity, 84 percent purity to 86 percent purity, 86 percent purity to 88 percent purity, 88 percent purity to 90 percent purity, 90 percent purity to 92 percent purity, 92 percent purity to 92.5 percent purity, 92.5 percent purity to 93 percent purity, 93 percent purity to 93.5 percent purity, 93.5 percent purity to 94 percent purity, 94 percent purity to 94.5 percent purity, 94.5 percent purity to 94.75 percent purity, 94.75 percent purity to 95 percent purity, 95 percent purity to 95.25 percent purity, 95.25 percent purity to 95.5 percent purity, 95.5 percent purity to 95.75 percent purity, 95.75 percent purity to 96 percent purity, 96 percent purity to 96.25 percent purity, 96.25 percent purity to 96.5 percent purity, 96.5 percent purity to 96.75 percent purity, 96.75 percent purity to 97 percent purity, 97 percent purity to 97.25 percent purity, 97.25 percent purity to 97.5 percent purity, 97.5 percent purity to 97.75 percent purity, 97.75 percent purity to 98 percent purity, 98 percent purity to 98.25 percent purity, 98.25 percent purity to 98.5 percent purity, 98.5 percent purity to 98.75 percent purity, 98.75 percent purity to 99 percent purity, 99 percent purity to 99.25 percent purity, 99.25 percent purity to 99.5 percent purity, 99.5 percent purity to 99.75 percent purity, and 99.75 percent purity to 100 percent purity.

In embodiments, the cannabinoids (e.g., cannabinoid glycoside, tetrahydrocannabinolic acid (THCA), active tetrahydrocannabinol, tetrahydrocannabinol (THC), Δ9-tetrahydrocannabinol (Δ9-THC), Δ8-tetrahydrocannabinol (Δ8-THC), tetrahydrocannabivarin (THCV), cannabidiolic acid (CBDA), cannabichromene (CBC), cannabidiol (CBD), cannabigerol (CBG), cannabinidiol (CBND), and/or cannabinol (CBN)) that are extracted from the SMB process have a purity that includes one or more from the group consisting of 30 percent purity to 40 percent purity, 40 percent purity to 50 percent purity, 50 percent purity to 60 percent purity, 60 percent purity to 70 percent purity, 70 percent purity to 80 percent purity, 80 percent purity to 82 percent purity, 82 percent purity to 84 percent purity, 84 percent purity to 86 percent purity, 86 percent purity to 88 percent purity, 88 percent purity to 90 percent purity, 90 percent purity to 92 percent purity, 92 percent purity to 92.5 percent purity, 92.5 percent purity to 93 percent purity, 93 percent purity to 93.5 percent purity, 93.5 percent purity to 94 percent purity, 94 percent purity to 94.5 percent purity, 94.5 percent purity to 94.75 percent purity, 94.75 percent purity to 95 percent purity, 95 percent purity to 95.25 percent purity, 95.25 percent purity to 95.5 percent purity, 95.5 percent purity to percent purity, 95.75 percent purity to 96 percent purity, 96 percent purity to 96.25 percent purity, 96.25 percent purity to 96.5 percent purity, 96.5 percent purity to 96.75 percent purity, 96.75 percent purity to 97 percent purity, 97 percent purity to 97.25 percent purity, 97.25 percent purity to 97.5 percent purity, 97.5 percent purity to 97.75 percent purity, 97.75 percent purity to 98 percent purity, 98 percent purity to 98.25 percent purity, 98.25 percent purity to 98.5 percent purity, 98.5 percent purity to 98.75 percent purity, 98.75 percent purity to 99 percent purity, 99 percent purity to 99.25 percent purity, 99.25 percent purity to 99.5 percent purity, 99.5 percent purity to 99.75 percent purity, and 99.75 percent purity to 100 percent purity.

In embodiments, a continuous process for the purification of cannabinoids from a crude cannabinoid extract to provide a purified cannabinoid product. The crude cannabinoid extract comprises cannabinoids which may include cannabidiol and/or tetrahydrocannabinol.

In embodiments, reversed-phase chromatography employs a polar (aqueous) mobile phase. As a result, hydrophobic molecules in the polar mobile phase tend to adsorb to the hydrophobic stationary phase, and hydrophilic molecules in the mobile phase will pass through an adsorber column and are eluted first.

The SMB system may be operated such that the adsorbent beds are operated individually or in parallel using a single rotary valve and associated control system. A column may comprise one or several beds containing chromatographic media. Feed tanks, filters, piping connecting flow between columns and/or beds where so connected, pumps, valving, pressure regulators, metering equipment, flow control and microprocessor equipment, their construction and function, and integration with the entire Farming Superstructure System (FSS) are all disclosed here.

Stationary Phase

In embodiments, the stationary phase adsorbent for use in the first swing bed simulated moving bed (SMB) chromatography zone is an aromatic non-polar copolymer of styrene-divinyl benzene adsorbent resin with an effective particle size of 0.25 mm and effective surface area of 590 square meters per gram (M2/g). Examples of suitable styrene-divinyl benzene adsorbent resins can be selected from the AMBERLITE XAD resin series (Available from Dow Chemical Company, Midland, Mich.), DIAION HP-20 (Available from Mitsubishi Chemical Company, Tokyo, Japan), or Stratosphere PL-PS/DVB (Available from Sigma-Aldrich, St. Louis, Mo.). In embodiments, the styrene-divinyl benzene adsorbent resin matrix provides an aromatic non-polar surface with selectivity for hydrophobic areas of molecules. In first swing bed simulated moving bed zone the cannabinoids are retained on the resin and are subsequently recovered in a first swing bed extract. Impurities such as wax, terpenes, and other undesirable cannabinoids are rejected into a first swing bed raffinate stream. In first swing bed simulated moving bed zone the cannabinoids are retained on the resin and are subsequently recovered in a first swing bed extract. In first swing bed simulated moving bed zone cannabidiol is retained on the resin and are subsequently recovered in a first swing bed extract. Impurities other cannabinoids are rejected into a first swing bed raffinate stream. In first swing bed simulated moving bed zone tetrahydrocannabinol is retained on the resin and are subsequently recovered in a first swing bed extract. Impurities other cannabinoids are rejected into a first swing bed raffinate stream. The stationary phase adsorbents may be disposed in a single adsorbent bed or may be disposed in within a single column or series of single columns containing multiple adsorbent bed zones.

In embodiments, the stationary phase adsorbent is comprised of one or more selected from the group consisting of silica gel, alumina, silica, cellulose powder, a polymer, polymeric beads, a macroporous adsorption resin, DOW XAD 418, molecular sieves, a polar macroporous adsorption resin, floridin, diatomite, zeolites, a catalyst, a resin, an ion-exchange resin, ion-exchange polymer, clay, ceramic material, activated carbon, a cation-exchange resin, an anion-exchange resin, bentonite, perlite, fly ash, chitin, charcoal, a solid substance, magnesia, titanium oxide, glass, fluorinated carbon, silicate, kaolin, a hollow substance, a porous substance.

In embodiments, the adsorbent includes Orpheus non-polar silica-based stationary phase adsorbent (available from Orochem Technologies Inc., Naperville, Ill., USA). In embodiments, the adsorbent includes C8, C18, or Polar C18 adsorbent (available from Orochem Technologies Inc., Naperville, Ill., USA).

In embodiments, the adsorber or the plurality of adsorbers are comprised of one or more corrosion resistant materials selected from the group consisting of stainless steel, corrosion resistant alloys, metals having a fluoropolymer coating, and mixtures thereof. In embodiments, the valve used to connect each of the adsorbers is a rotary valve. In embodiments, the adsorber or the plurality of adsorbers are non-rotating and are disposed in an asymmetrical manner about the axis of rotation of the rotary valve. In embodiments, the rotary valve is actuated by either hydraulics, electricity, or electromechanical actuation.

In embodiments, the adsorbent is comprised of one or more selected from the group consisting of a strongly acidic ion-exchange resin, a strongly basic ion-exchange resin, a weakly acidic ion-exchange resin and a weakly basic ion-exchange resin. In embodiments, the strongly acidic ion-exchange resin includes sulfonic acid groups, e.g. sodium polystyrene sulfonate or PolyAMPS, or poly(2-acrylamido-2-methyl-1-propanesulfonic acid)® (Trademark of The Lubrizol Corporation), is an organic polymer.

In embodiments, the strongly basic ion-exchange resin includes quaternary amino groups, for example, trimethylammonium groups, e.g. PolyAPTAC, or poly (acrylamido-N-propyltrimethylammonium chloride)® (Trademark of The Lubrizol Corporation), is an organic polymer. In embodiments, the weakly acidic ion-exchange resin includes carboxylic acid groups. In embodiments, the weakly basic ion-exchange resin includes primary, secondary, and/or tertiary amino groups, e.g. polyethylene amine.

In embodiments, the adsorbent is comprised of one or more selected from the group consisting of a powder, spheres, spherical pellets, rods, moldings, and monoliths. In embodiments, the adsorbent has pores. In embodiments, the range of size of the pores of the adsorbent are comprised of one or more selected from the group consisting of: 0.1 nanometers to 1 nanometer, 1 nanometer to 2 nanometers, 2 nanometers to 5 nanometers, 5 nanometers to 15 nanometers, 15 nanometers to 25 nanometers, 25 nanometers to 35 nanometers, 35 nanometers to 40 nanometers, nanometers to 50 nanometers, 50 nanometers to 100 nanometers, 100 nanometers to 150 nanometers, 150 nanometers to 200 nanometers, 200 nanometers to 1000 nanometers, and greater than 1000 nanometers.

In embodiments, the plurality of adsorbers are considered a simulated moving bed (SMB). In embodiments, the plurality of adsorbers are considered a simulated moving bed (SMB) and operate via chromatography. In embodiments, the SMB adsorption technique is a continuous. In embodiments, the plurality of adsorbers include more than one adsorber. In embodiments, the plurality of adsorbers include two adsorbers. In embodiments, the plurality of adsorbers include three adsorbers. In embodiments, the plurality of adsorbers include four adsorbers. In embodiments, the plurality of adsorbers include five adsorbers. In embodiments, the plurality of adsorbers include six adsorbers. In embodiments, the plurality of adsorbers include seven adsorbers. In embodiments, the plurality of adsorbers include eight adsorbers. In embodiments, the plurality of adsorbers include nine adsorbers. In embodiments, the plurality of adsorbers include ten adsorbers. In embodiments, the plurality of adsorbers include eleven adsorbers. In embodiments, the plurality of adsorbers include twelve adsorbers. In embodiments, the plurality of adsorbers include thirteen adsorbers. In embodiments, the plurality of adsorbers include fourteen adsorbers. In embodiments, the plurality of adsorbers include fifteen adsorbers. In embodiments, the plurality of adsorbers include sixteen adsorbers. In embodiments, the plurality of adsorbers include seventeen adsorbers. In embodiments, the plurality of adsorbers include eighteen adsorbers. In embodiments, the plurality of adsorbers include nineteen adsorbers. In embodiments, the plurality of adsorbers include twenty adsorbers. In embodiments, the plurality of adsorbers include twenty-one adsorbers. In embodiments, the plurality of adsorbers include twenty-two adsorbers. In embodiments, the plurality of adsorbers include twenty-three adsorbers. In embodiments, the plurality of adsorbers include twenty-four adsorbers. In embodiments, the plurality of adsorbers include twenty-five adsorbers. In embodiments, the plurality of adsorbers include twenty-six adsorbers. In embodiments, the plurality of adsorbers include twenty-seven adsorbers. In embodiments, the plurality of adsorbers include twenty-eight adsorbers. In embodiments, the plurality of adsorbers include twenty-nine adsorbers. In embodiments, the plurality of adsorbers include thirty adsorbers. In embodiments, the plurality of adsorbers include thirty-one adsorbers. In embodiments, the plurality of adsorbers include thirty-two adsorbers. In embodiments, the plurality of adsorbers include thirty-three adsorbers. In embodiments, the plurality of adsorbers include thirty-four adsorbers. In embodiments, the plurality of adsorbers include thirty-five adsorbers. In embodiments, the plurality of adsorbers include thirty-six adsorbers. In embodiments, the plurality of adsorbers include thirty-seven adsorbers. In embodiments, the plurality of adsorbers include thirty-eight adsorbers. In embodiments, the plurality of adsorbers include thirty-nine adsorbers. In embodiments, the plurality of adsorbers include forty adsorbers. In embodiments, the plurality of adsorbers include fifty adsorbers. In embodiments, the plurality of adsorbers include sixty adsorbers. In embodiments, the plurality of adsorbers include seventy adsorbers. In embodiments, the plurality of adsorbers include eighty adsorbers. In embodiments, the plurality of adsorbers include ninety adsorbers. In embodiments, the plurality of adsorbers include one hundred adsorbers.

In embodiments, the adsorbers operate at a pressure that is selected from one or more from the group consisting of between: 10 pounds per square inch (PSI) to 20 PSI, 20 PSI to 40 PSI, 40 PSI to 60 PSI, 60 PSI to 80 PSI, 80 PSI to 100 PSI, 100 PSI to 125 PSI, 125 PSI to 150 PSI, 150 PSI to 175 PSI, 175 PSI to 200 PSI, 200 PSI to 225 PSI, 225 PSI to 250 PSI, 250 PSI to 275 PSI, 275 PSI to 300 PSI, 300 PSI to 325 PSI, 325 PSI to 350 PSI, 350 PSI to 375 PSI, 375 PSI to 400 PSI, 400 PSI to 425 PSI, 425 PSI to 450 PSI, 450 PSI to 475 PSI, and 475 PSI to 500 PSI.

In embodiments, an analyzer is used to analyze the purified cannabidiol and/or tetrahydrocannabinol product. In embodiments, the analyzer is comprised of one or more analyzers selected from the group consisting of Fourier-transform infrared spectroscopy, gas chromatography, high-performance liquid chromatography, liquid chromatograph, liquid chromatography-mass spectrometry, mass spectrometry, and ultra-high performance liquid chromatography.

In embodiments, the adsorbent is comprised of one or more selected from the group consisting of a strongly acidic cation exchange resin include such as AMBERLITE IR-118 (Available from Dow Chemical Company, Midland, Mich.), or DIAION PK216LH (Available from Mitsubishi Chemical Company, Tokyo, Japan). Suitable examples of the weakly basic anion exchange resin include AMBERLITE IRA-70RF (Available from Dow Chemical Company, Midland, Mich.) or RELITE RAM2 (Available from Mitsubishi Chemical Company, Tokyo, Japan).

In embodiments, the first extract (HDA) or the primary extract (HDB) is transferred from the first adsorber system (SMB1) and into a primary extract vessel (HEE). In embodiments, the first raffinate (HDE) is transferred from the first adsorber system (SMB1) into the solvent treatment system (H-WTS) as discussed below.

In embodiments, the primary extract vessel (HEE) has an interior (HEF). In embodiments, the primary extract vessel (HEE) is a continuously stirred tank reactor having a jacketed reactor equipped with a steam supply system and at least one steam trap. In embodiments, the primary extract vessel (HEE) is equipped with a level sensor (HEG) that is configured to input a signal to the computer (COMP). In embodiments, the primary extract vessel (HEE) is equipped with a pH sensor (HEH) that is configured to input a signal to the computer (COMP). In embodiments, the primary extract vessel (HEE) is equipped with an auger (HEI) that has a motor. The motor of the auger (HEI) rotates the auger (HEI) to mix the contents within the interior (HEF) of the primary extract vessel (HEE). In embodiments, the primary extract vessel (HEE) is equipped with a temperature sensor that is configured to input a signal to the computer (COMP). In embodiments, the primary extract vessel (HEE) is equipped with a heat exchanger (HTA) to heat and/or cool the contents within the interior (HEF) of the primary extract vessel (HEE). In embodiments, the primary extract vessel (HEE) outputs a primary extract (HDB).

A primary extract pump (HTB) is configured to accept the primary extract (HDB) from the interior (HEF) of the primary extract vessel (HEE). The primary extract pump (HTB) pumps and pressurizes the primary extract (HDB) to produce a pressurized primary extract (HTC). A valve (HTD) and a pressure sensor (HTE) are installed on the discharged of the primary extract pump (HTB). In embodiments, the primary extract pump (HTB) pressurizes the primary extract (HDB) to form a pressurized primary extract (HTC) at a pressure that includes one or more pressure ranges selected from the group consisting of 10 pounds per square inch (PSI) to 20 PSI, 20 PSI to 40 PSI, 40 PSI to 60 PSI, 60 PSI to 80 PSI, 80 PSI to 100 PSI, 100 PSI to 125 PSI, 125 PSI to 150 PSI, 150 PSI to 175 PSI, 175 PSI to 200 PSI, 200 PSI to 225 PSI, 225 PSI to 250 PSI, 250 PSI to 275 PSI, 275 PSI to 300 PSI, 300 PSI to 325 PSI, 325 PSI to 350 PSI, 350 PSI to 375 PSI, 375 PSI to 400 PSI, 400 PSI to 425 PSI, 425 PSI to 450 PSI, 450 PSI to 475 PSI, and 475 PSI to 500 PSI.

In embodiments, the pressurized primary extract (HTC) is transferred from the primary extract pump (HTB) and into at least one filter (HEL, HEM, HEN). In embodiments, the pressurized primary extract (HTC) is transferred from the primary extract pump (HTB) and a primary extract filter system (HEK) that includes a first primary extract first filter (HEL), a first primary extract second filter (HEM), and a first primary extract third filter (HEN).

In embodiments, the first primary extract first filter (HEL) includes one or more selected from the group consisting of a cation, an anion, a membrane, a filter, activated carbon, an adsorbent, an absorbent, an ultraviolet unit, an ozone unit, a microwave unit, and/or a distillation system. In embodiments, the first primary extract second filter (HEM) includes one or more selected from the group consisting of a cation, an anion, a membrane, a filter, activated carbon, an adsorbent, an absorbent, an ultraviolet unit, an ozone unit, a microwave unit, and/or a distillation system. In embodiments, the first primary extract third filter (HEN) includes one or more selected from the group consisting of a cation, an anion, a membrane, a filter, activated carbon, an adsorbent, an absorbent, an ultraviolet unit, an ozone unit, a microwave unit, and/or a distillation system. In embodiments, the adsorbent includes one or more selected from the group consisting of 3 Angstrom molecular sieve, 3 Angstrom zeolite, 4 Angstrom molecular sieve, 4 Angstrom zeolite, activated alumina, activated carbon, adsorbent, alumina, carbon, catalyst, clay, desiccant, molecular sieve, polymer, resin, and silica gel.

In embodiments, the cation is configured to remove positively charged ions from the pressurized primary extract (HTC), the positively charged ions are comprised of one or more from the group consisting of calcium, magnesium, sodium, and iron. In embodiments, the anion is configured to remove negatively charged ions from the pressurized primary extract (HTC), the negatively charged ions are comprised of one or more from the group consisting of iodine, chloride, and sulfate. In embodiments, the membrane is configured to remove undesirable compounds from the pressurized primary extract (HTC), the undesirable compounds are comprised of one or more from the group consisting of dissolved organic chemicals, viruses, bacteria, and particulates. In embodiments, the membrane has a diameter that ranges from 1 inch to 6 inches and a pore size ranging from 0.0001 microns to 0.5 microns.

In embodiments, a filtered primary extract (HEO) is discharged from the primary extract filter system (HEK). In embodiments, the filtered primary extract (HEO) discharged from the primary extract filter system (HEK) is a pressurized filtered primary extract (HEP). In embodiments, a valve (HEQ) is configured to regulate the flow of the pressurized filtered primary extract (HEP) that leaves the primary extract filter system (HEK). In embodiments, a pressure sensor (HER) is configured to measure the pressure of the pressurized filtered primary extract (HEP).

In embodiments, the pressurized filtered primary extract (HEP) is passed from the primary extract filter system (HEK) and into a filtered primary extract vessel (HES). In embodiments, filtered primary extract vessel (HES) is configured to accept the filtered primary extract (HEO). In embodiments, the filtered primary extract vessel (HES) is a continuously stirred tank reactor having a jacketed reactor equipped with a steam supply system and at least one steam trap. In embodiments, the filtered primary extract vessel (HES) is equipped with a level sensor (HEU) that is configured to input a signal to the computer (COMP). In embodiments, the filtered primary extract vessel (HES) is equipped with a pH sensor (HEV) that is configured to input a signal to the computer (COMP). In embodiments, the filtered primary extract vessel (HES) is equipped with an auger (HEW) that has a motor. The motor of the auger (HEW) rotates the auger (HEW) to mix the contents within the interior (HET) of the filtered primary extract vessel (HES). In embodiments, the filtered primary extract vessel (HES) is equipped with a temperature sensor that is configured to input a signal to the computer (COMP). In embodiments, the filtered primary extract vessel (HES) is equipped with a heat exchanger (HEX) to heat and/or cool the contents within the interior (HET) of the filtered primary extract vessel (HES). In embodiments, the filtered primary extract vessel (HES) outputs a filtered primary extract.

In embodiments, a filtered primary extract is discharged from the interior (HET) of the filtered primary extract vessel (HES). In embodiments, a filtered primary extract is discharged from the interior (HET) of the filtered primary extract vessel (HES) and introduced to a filtered primary extract pump (HEY). The filtered primary extract pump (HEY) pumps and pressurizes the filtered primary extract to form a pressurized filtered primary extract (HEZ). In embodiments, a valve (HFA) is configured to regulate the flow of the pressurized filtered primary extract (HEZ) that leaves the filtered primary extract vessel (HES). In embodiments, a pressure sensor (HFB) is configured to measure the pressure of the pressurized filtered primary extract (HEZ) discharged from the filtered primary extract pump (HEY). In embodiments, a flow sensor (HFC) is configured to measure the flow of the pressurized filtered primary extract (HEZ) discharged from the filtered primary extract pump (HEY).

In embodiments, the pressurized filtered primary extract (HEZ) is transferred from the filtered primary extract pump (HEY) and into a second adsorber system (SMB2). In embodiments, the second adsorber system (SMB2) is configured to input a pressurized filtered primary extract (HEZ) and a second desorbent (HFG). In embodiments, the second adsorber system (SMB2) is configured to output a second extract (HFD) and a second raffinate (HFH). In embodiments, the second extract (HFD) can also be called a secondary extract (HFE). In embodiments, the second adsorber system (SMB2) includes an adsorber or a plurality of adsorbers each containing an adsorbent. In embodiments, the second desorbent (HFG) is pressurized and comes from a water treatment system (H-WTS) which may or may not treat solvent (such as water) that was passed on from a solvent recovery system. In embodiments, the second raffinate (HFH) is routed to the solvent treatment system (H-WTS) as discussed below.

In embodiments, the second adsorber system (SMB2) includes a plurality of adsorbers containing adsorbent is provided and may be called the stationary phase. In embodiments, the adsorbent positioned within the adsorber or plurality of adsorbers may be called the stationary phase. The bed of adsorbent that is contained within the adsorber does not move so therefore it is stationary. The plurality of beds of adsorbent that are contained within the plurality of adsorbers does not move so therefore it is stationary.

In embodiments, the second adsorber system (SMB2) periodically switches the feed, eluent, extract and raffinate ports in the same direction. The basic premise of a simulated moving bed adsorber system is that the inlet and outlet ports are switched periodically in the direction of the fluid flow. This simulates the countercurrent movement of the phase in the process. Chromatography is a technique used to separate mixtures. In embodiments, the mixture may include cannabinoids and a liquid and/or a solvent. In embodiments, chromatography may be used to separate mixtures of cannabinoids to produce a purified cannabinoid (e.g., separating CBD from THC, or separating TCH from CBD, or separating one cannabinoid from another cannabinoid).

In embodiments, the raffinate includes cannabinoids. In embodiments, the raffinate includes cannabidiol. In embodiments, the raffinate includes THC. In embodiments, the raffinate includes a mixture of cannabinoids and water. In embodiments, the raffinate includes a mixture of cannabidiol and water. In embodiments, the raffinate includes a mixture of THC and water. In embodiments, the raffinate includes a mixture of cannabinoids and ethanol. In embodiments, the raffinate includes a mixture of cannabidiol and ethanol. In embodiments, the raffinate includes a mixture of THC and ethanol. In embodiments, the raffinate includes a mixture of cannabinoids and ethanol and water. In embodiments, the raffinate includes a mixture of cannabidiol and ethanol and water. In embodiments, the raffinate includes a mixture of THC and ethanol and water. In embodiments, the raffinate includes a mixture of cannabinoids and methanol. In embodiments, the raffinate includes a mixture of cannabidiol and methanol. In embodiments, the raffinate includes a mixture of THC and methanol.

In embodiments, the raffinate includes a mixture of cannabinoids and methanol and water. In embodiments, the raffinate includes a mixture of cannabidiol and methanol and water. In embodiments, the raffinate includes a mixture of THC and methanol and water.

In embodiments, the second extract (HFD) or the secondary extract (HFE) is transferred from the second adsorber system (SMB2) and into a secondary extract vessel (HFI). In embodiments, the second raffinate (HFH) is transferred from the second adsorber system (SMB2) into the solvent treatment system (H-WTS) as discussed below.

In embodiments, the secondary extract vessel (HFI) has an interior (HFJ). In embodiments, the secondary extract vessel (HFI) is a continuously stirred tank reactor having a jacketed reactor equipped with a steam supply system and at least one steam trap. In embodiments, the secondary extract vessel (HFI) is equipped with a level sensor (HFK) that is configured to input a signal to the computer (COMP). In embodiments, the secondary extract vessel (HFI) is equipped with a pH sensor (HFL) that is configured to input a signal to the computer (COMP). In embodiments, the secondary extract vessel (HFI) is equipped with an auger that has a motor. The motor of the auger rotates the auger to mix the contents within the interior (HFJ) of the secondary extract vessel (HFI). In embodiments, the secondary extract vessel (HFI) is equipped with a temperature sensor that is configured to input a signal to the computer (COMP). In embodiments, the secondary extract vessel (HFI) is equipped with a heat exchanger (HFN) to heat and/or cool the contents within the interior (HFJ) of the secondary extract vessel (HFI). In embodiments, the secondary extract vessel (HFI) outputs a secondary extract.

A secondary extract pump (HFO) is configured to accept the second extract from the interior (HFJ) of the secondary extract vessel (HFI). The secondary extract pump (HFO) pumps and pressurizes the secondary extract to produce a pressurized secondary extract (HFP). A valve (HFQ) and a pressure sensor (HFR) are installed on the discharged of the secondary extract pump (HFO). In embodiments, the secondary extract pump (HFO) pressurizes the secondary extract to form a pressurized secondary extract (HFP) at a pressure that includes one or more pressure ranges selected from the group consisting of 10 pounds per square inch (PSI) to 20 PSI, 20 PSI to 40 PSI, PSI to 60 PSI, 60 PSI to 80 PSI, 80 PSI to 100 PSI, 100 PSI to 125 PSI, 125 PSI to 150 PSI, 150 PSI to 175 PSI, 175 PSI to 200 PSI, 200 PSI to 225 PSI, 225 PSI to 250 PSI, 250 PSI to 275 PSI, 275 PSI to 300 PSI, 300 PSI to 325 PSI, 325 PSI to 350 PSI, 350 PSI to 375 PSI, 375 PSI to 400 PSI, 400 PSI to 425 PSI, 425 PSI to 450 PSI, 450 PSI to 475 PSI, and 475 PSI to 500 PSI.

In embodiments, the pressurized secondary extract (HFP) is transferred from the secondary extract pump (HFO) and into a secondary extract filter system (HGA). In embodiments, the secondary extract filter system (HGA) includes one or more selected from the group consisting of a cation, an anion, a membrane, a filter, activated carbon, an adsorbent, an absorbent, an ultraviolet unit, an ozone unit, a microwave unit, and/or a distillation system. In embodiments, the adsorbent includes one or more selected from the group consisting of 3 Angstrom molecular sieve, 3 Angstrom zeolite, 4 Angstrom molecular sieve, 4 Angstrom zeolite, activated alumina, activated carbon, adsorbent, alumina, carbon, catalyst, clay, desiccant, molecular sieve, polymer, resin, and silica gel.

In embodiments, a filtered secondary extract (HGB) is discharged from the secondary extract filter system (HGA). In embodiments, the filtered secondary extract (HGB) is transferred to a filtered secondary extract vessel (HGD). In embodiments, the filtered secondary extract vessel (HGD) has an interior (HGE). In embodiments, the filtered secondary extract vessel (HGD) is a continuously stirred tank reactor having a jacketed reactor equipped with a steam supply system and at least one steam trap. In embodiments, the filtered secondary extract vessel (HGD) is equipped with a level sensor (HGF) that is configured to input a signal to the computer (COMP). In embodiments, the filtered secondary extract vessel (HGD) is equipped with a pH sensor that is configured to input a signal to the computer (COMP). In embodiments, the filtered secondary extract vessel (HGD) is equipped with an auger that has a motor. The motor of the auger rotates the auger to mix the contents within the interior (HGE) of the filtered secondary extract vessel (HGD). In embodiments, the filtered secondary extract vessel (HGD) is equipped with a temperature sensor that is configured to input a signal to the computer (COMP). In embodiments, the filtered secondary extract vessel (HGD) is equipped with a heat exchanger (HGG) to heat and/or cool the contents within the interior (HGE) of the filtered secondary extract vessel (HGD). In embodiments, the filtered secondary extract vessel (HGD) outputs a first pressurized filtered secondary extract (HGJ) and a second pressurized filtered secondary extract (HGK). In embodiments, the heat exchangers (HAM, HCL, HTA, HEX, HGA, HGG) shown in FIG. 17H may heat and/or cool the *cannabis*, cannabinoid, crude oil and solvent mixture.

In embodiments, the heat exchangers (HAM, HCL, HTA, HEX, HGA, HGG) may decarboxylate the cannabinoid to produce a decarboxylated cannabinoid (e.g., to produce active THC from THCA, and/or to produce active CBD from CBDA). In embodiments, heating the *cannabis*, cannabinoid, crude oil and solvent mixture decarboxylates the tetrahydrocannabinolic acid to form active tetrahydrocannabinol. In embodiments, heating the *cannabis*, cannabinoid, crude oil and solvent mixture decarboxylates the cannabidiolic acid to form active cannabidiol. In embodiments, decarboxylation is a chemical reaction that removes a carboxyl group and releases carbon dioxide from a cannabinoid. In embodiments, heating the *cannabis* removes carbon dioxide form the *cannabis* to form a carbon dioxide depleted *cannabis*.

In embodiments, the first pressurized filtered secondary extract (HGJ) is discharged from the interior (HGE) of the filtered secondary extract vessel (HGD) and transferred to a first filtered secondary extract pump (HGH). The first filtered secondary extract pump (HGH) pumps and pressurizes the filtered secondary extract to produce a first pressurized filtered secondary extract (HGJ).

In embodiments, the first pressurized filtered secondary extract (HGJ) may be transferred to FIGS. 17D, 17E, 17J, and/or FIG. 18A, 18B, 18C, 18D, 18E or any figure in this patent specification for evaporation, spray drying, colloid production, emulsion production, beverage production, encapsulation, foodstuff mixing, topical production, cosmetic production, manufacturing a shaped/cooked/flavored food and/or pet or animal food. In embodiments, the second pressurized filtered secondary extract (HGK) is discharged from the interior (HGE) of the filtered secondary extract vessel (HGD) and transferred to a second filtered secondary extract pump (HGI). The second filtered secondary extract pump (HGI) pumps and pressurizes the filtered secondary extract to produce a second pressurized filtered secondary extract (HGK). In embodiments, the second pressurized filtered secondary extract (HGK) may be transferred to a third adsorber system (SMB3).

In embodiments, the secondary extract (HGL) is transferred from the interior (HGE) of the filtered secondary extract vessel (HGD) and into a second filtered secondary extract pump (HGI). The second filtered secondary extract pump (HGI) pumps and pressurizes the filtered secondary extract to produce a second pressurized filtered secondary extract (HGK). In embodiments, a valve (HGM) is configured to regulate the flow of the second pressurized filtered secondary extract (HGK) that leaves the filtered secondary extract vessel (HGD). In embodiments, a pressure sensor (HFB) is configured to measure the pressure of the second pressurized filtered secondary extract (HGK) discharged from the second filtered secondary extract pump (HGI). In embodiments, a flow sensor (HFC) is configured to measure the flow of the second pressurized filtered secondary extract (HGK) discharged from the second filtered secondary extract pump (HGI).

In embodiments, the second pressurized filtered secondary extract (HGK) is transferred from the second filtered secondary extract pump (HGI) and into a third adsorber system (SMB3). In embodiments, the third adsorber system (SMB3) is configured to input a second pressurized filtered secondary extract (HGK) and a third desorbent (HHC). In embodiments, the third adsorber system (SMB3) is configured to output a third extract (HHA) and a third raffinate (HHD). In embodiments, the third extract (HHA) can also be called a tertiary extract (HHB). In embodiments, the third adsorber system (SMB3) includes an adsorber or a plurality of adsorbers each containing an adsorbent. In embodiments, the third desorbent (HHC) is pressurized and comes from a water treatment system (H-WTS) which may or may not treat solvent (such as water) that was passed on from a solvent recovery system. In embodiments, the third raffinate (HHD) is routed to the solvent treatment system (H-WTS) as discussed below.

In embodiments, the third adsorber system (SMB3) includes a plurality of adsorbers containing adsorbent is provided and may be called the stationary phase. In embodiments, the adsorbent positioned within the adsorber or plurality of adsorbers may be called the stationary phase. The bed of adsorbent that is contained within the adsorber does not move so therefore it is stationary. The plurality of beds of adsorbent that are contained within the plurality of adsorbers does not move so therefore it is stationary.

In embodiments, the third adsorber system (SMB3) periodically switches the feed, eluent, extract and raffinate ports in the same direction. The basic premise of a simulated moving bed adsorber system is that the inlet and outlet ports are switched periodically in the direction of the fluid flow. This simulates the countercurrent movement of the phase in the process. Chromatography is a technique used to separate mixtures. In embodiments, the mixture may include cannabinoids and a solvent. In embodiments, the third extract (HHA) may be transferred to FIGS. 17D, 17E, 17J, and/or FIG. 18A, 18B, 18C, 18D, 18E or any figure in this patent specification for evaporation, spray drying, colloid production, emulsion production, beverage production, encapsulation, foodstuff mixing, topical production, cosmetic production, manufacturing a shaped/cooked/flavored food and/or pet or animal food.

In embodiments, the first desorbent (HDC) for the first adsorber system (SMB1), second desorbent (HFG) for the second adsorber system (SMB2), third desorbent (HHC) for the third adsorber system (SMB3), are provided by a solvent treatment system (H-WTS).

In embodiments, the solvent (HBJ) from the first filter (HBC) and/or second filter (HBF), the first raffinate (HDE) from the first adsorber system (SMB1), the second raffinate (HFH) from the second adsorber system (SMB2), and the third raffinate (HHD) from the third adsorber system (SMB3), are provided by to a solvent treatment system (H-WTS). In embodiments, the solvent treatment system (H-WTS) includes a treatment unit (HIC). In embodiments, the treatment unit (HIC) includes one or more selected from the group consisting of a cation, an anion, a membrane, a filter, activated carbon, an adsorbent, an absorbent, an ultraviolet unit, an ozone unit, a microwave unit, and/or a distillation system. In embodiments, the adsorbent includes one or more selected from the group consisting of 3 Angstrom molecular sieve, 3 Angstrom zeolite, 4 Angstrom molecular sieve, 4 Angstrom zeolite, activated alumina, activated carbon, adsorbent, alumina, carbon, catalyst, clay, desiccant, molecular sieve, polymer, resin, and silica gel. In embodiments, the treatment unit (HIC) includes one or more selected from the group consisting of an evaporator, an anaerobic digestion system, a distillation column, a packed column, a reactor, liquid-liquid extraction, vacuum distillation, pressurized distillation, and reverse osmosis.

In embodiments, the first desorbent (HDC) for the first adsorber system (SMB1), second desorbent (HFG) for the second adsorber system (SMB2), third desorbent (HHC) for the third adsorber system (SMB3), are provided by a solvent treatment system (H-WTS). In embodiments, the solvent (HBJ) from the first filter (HBC) and/or second filter (HBF), the first raffinate (HDE) from the first adsorber system (SMB1), the second raffinate (HFH) from the second adsorber system (SMB2), and the third raffinate (HHD) from the third adsorber system (SMB3), are provided by to a solvent treatment system (H-WTS). In embodiments, a treated solvent (HIE) is discharged from the treatment unit (HIC) of the solvent treatment system (H-WTS). In embodiments, the treated solvent (HIE) has contaminants removed therefrom so that the solvent (water, ethanol, alcohol, oil, etc.) may be reused again in the solvent (HAB, HAB) or for the first desorbent (HDC) for the first adsorber system (SMB1), second desorbent (HFG) for the second adsorber system (SMB2), third desorbent (HHC) for the third adsorber system (SMB3).

In embodiments, the solvent (HAB) used within the extraction vessel (HAI) is water that comes from the solvent treatment system (H-WTS). In embodiments, a water supply (HJG) is made available to the solvent treatment system (H-WTS) for use as either a solvent (HABHAB) in the process or for use as the first desorbent (HDC) for the first adsorber system (SMB1), second desorbent (HFG) for the second adsorber system (SMB2), third desorbent (HHC) for the third adsorber system (SMB3). In embodiments, the water supply (HJG) is mixed with the treated solvent (HIE) (which may be water). In embodiments, a valve (HJI) is configured to regulate the flow of the water supply (HJG) that enters the first water treatment unit (HJK) of the solvent treatment system (H-WTS). In embodiments, a pressure sensor (HJH) is configured to measure the pressure of the water supply (HJG) that enters the first water treatment unit (HJK) of the solvent treatment system (H-WTS). In embodiments, the solvent treatment system (H-WTS) includes a first water treatment unit (HJK), second water treatment unit (HJL), and a third water treatment unit (HJM).

In embodiments, the first water treatment unit (HJK) includes one or more selected from the group consisting of a cation, an anion, a membrane, a filter, activated carbon, an adsorbent, an absorbent, an ultraviolet unit, an ozone unit, a microwave unit, and/or a distillation system. In embodiments, the second water treatment unit (HJL) includes one or more selected from the group consisting of a cation, an anion, a membrane, a filter, activated carbon, an adsorbent, an absorbent, an ultraviolet unit, an ozone unit, a microwave unit, and/or a distillation system. In embodiments, the third water treatment unit (HJM) includes one or more selected from the group consisting of a cation, an anion, a membrane, a filter, activated carbon, an adsorbent, an absorbent, an ultraviolet unit, an ozone unit, a microwave unit, and/or a distillation system. In embodiments, the adsorbent includes one or more selected from the group consisting of 3 Angstrom molecular sieve, 3 Angstrom zeolite, 4 Angstrom molecular sieve, 4 Angstrom zeolite, activated alumina, activated carbon, adsorbent, alumina, carbon, catalyst, clay, desiccant, molecular sieve, polymer, resin, and silica gel. In embodiments, the cation is configured to remove positively charged ions from the water supply (HJG), the positively charged ions are comprised of one or more from the group consisting of calcium, magnesium, sodium, and iron. In embodiments, the anion is configured to remove negatively charged ions from the water supply (HJG), the negatively charged ions are comprised of one or more from the group consisting of iodine, chloride, and sulfate. In embodiments, the membrane is configured to remove undesirable compounds from the water supply (HJG), the undesirable compounds are comprised of one or more from the group consisting of dissolved organic chemicals, viruses, bacteria, and particulates. In embodiments, the membrane has a diameter that ranges from 1 inch to 6 inches and a pore size ranging from 0.0001 microns to microns.

In embodiments, treated water (HJA) is discharged from the first water treatment unit (HJK), second water treatment unit (HJL), and/or the third water treatment unit (HJM). In embodiments, treated water (HJA) has less positively charged ions, negatively charged ions, and undesirable compounds relative to the supply (HJG) that enters the solvent treatment system (H-WTS). In embodiments, a valve (HJI) is configured to regulate the flow of the treated water (HJA) that leaves the first water treatment unit (HJK), second water treatment unit (HJL), and/or the third water treatment unit (HJM). In embodiments, a quality sensor (HJN) is configured to measure the quality of the treated water (HJA) that leaves the first water treatment unit (HJK), second water treatment unit (HJL), and/or the third water treatment unit (HJM). For example, the quality sensor (HJN) may measure the electrical conductivity of the treated water (HJA) to determine if either of the first water treatment unit (HJK), second water treatment unit (HJL), and/or the third water treatment unit (HJM) require maintenance and/or cleaning. In embodiments, the quality sensor (HJN) measures the electrical conductivity of the treatment unit (HJM) to ensure that the electrical conductivity ranges from 0.10 microsiemens per centimeter to 100 microsiemens per centimeter (or from 0.001 microsiemens per centimeter to 100 microsiemens per centimeter).

In embodiments, the quality sensor (HJN) measures the electrical conductivity of the treatment unit (HJM) to ensure that the electrical conductivity ranges from one or more selected from the group consisting of 0.1 µS to 0.5 µS, 0.5 µS to 1.00 µS, 1.00 µS to 1.25 µS, 1.25 µS to 1.50 µS, 1.500 to 1.75 µS, 1.75 µS to 2.00 µS, 2.000 to 2.25 µS, 2.250 to 2.50 µS, 2.50 µS to 2.75 µS, 2.75 µS to 3.00 µS, 3.00 µS to 3.25 µS, 3.25 µS to 3.50 µS, 3.50 µS to 3.75 µS, 3.75 µS to 4.00 µS, 4.00 µS to 4.25 µS, 4.25 µS to 4.50 µS, 4.50 µS to 4.75 µS, 4.75 µS to 5.00 µS to 5.25 µS, 5.25 µS to 5.50 µS, 5.50 µS to 5.75 µS, 5.75 µS to 6.00 µS, 6.00 µS to 6.25 µS, 6.25 µS to 6.50 µS, 6.50 µS to 6.75 µS, 6.75 µS to 7.00 µS, 7.00 µS to 7.25 µS, 7.25 µS to 7.50 µS, 7.500 to 7.75 µS, 7.75 µS to 8.00 µS, 8.00 µS to 8.25 µS, 8.250 to 8.50 µS, 8.50 µS to 8.75 µS, 8.75 µS to 9.00 µS, 9.00 µS to 9.25 µS, 9.25 µS to 9.50 µS, 9.50 µS to 9.75 µS, 9.75 µS to 10.00 µS, 10.00 µS to 12.50 µS, 12.50 µS to 15.00 µS, 15.00 µS to 17.50 µS, 17.50 µS to 20.00 µS to 22.50 µS, 22.50 µS to 25.00 µS, 25.00 µS to 27.50 µS, 27.50 µS to 30.00 µS, 30.00 µS to 32.50 µS, 32.50 µS to 35.00 µS, 35.00 µS to 37.50 µS, 37.50 µS to 40.00 µS to 42.50 µS, 42.50 µS to 45.00 µS, 45.00 µS to 47.50 µS, 47.50 µS to 50.00 µS, 50.00 µS to 52.50 µS, 52.50 µS to 55.00 µS, 55.00 µS to 57.50 µS, 57.50 µS to 60.00 µS, 60.00 µS to 62.50 µS, 62.50 µS to 65.00 µS, 65.00 µS to 67.50 µS, 67.50 µS to 70.00 µS, 70.00 µS to 72.50 µS, 72.50 µS to 75.00 µS, 75.00 µS to 77.50 µS, and 77.50 µS to 100.00 µS. In embodiments, µS means µS per centimeter.

In embodiments, the treated water used in the emulsion and/or colloidal suspension process, *cannabis* cloning/irrigation, etc. may in some instances conform to the following specifications: Bicarbonate (25 to 500 mg/L), Calcium (5 to 100 mg/L), Chloride (1 to 25 mg/L), Magnesium (1 to 25 mg/L), Sodium (1 to 25 mg/L), Sulfate (0.05 to 3 mg/L), Total Dissolved Solids (15 to 500 mg/L), Total Alkalinity (25 to 300 mg/L).

In embodiments, the treated solvent (HIE) is transferred from the first water treatment unit (HJK), second water treatment unit (HJL), or third water treatment unit (HJM) and into a treated water vessel (HJF). In embodiments, the treated water vessel (HJF) has an interior. In embodiments, the treated water vessel (HJF) is a continuously stirred tank reactor having a jacketed reactor equipped with a steam supply system and at least one steam trap. In embodiments, the treated water vessel (HJF) is equipped with a level sensor (HJPP) that is configured to input a signal to the computer (COMP). In embodiments, the treated water vessel (HJF) is equipped with a pH sensor (HJQ) that is configured to input a signal to the computer (COMP). In embodiments, the treated water vessel (HJF) is equipped with an auger that has a motor. The motor of the auger rotates the auger to mix the contents within the interior of the treated water vessel (HJF).

In embodiments, the treated water vessel (HJF) is equipped with a temperature sensor that is configured to input a signal to the computer (COMP). In embodiments, the treated water vessel (HJF) is equipped with a heat exchanger to heat the contents within the interior of the treated water vessel (HJF). In embodiments, the treated water vessel (HJF) outputs treated water (HJA).

In embodiments, the treated water (HJA) discharged from the treated water vessel (HJF) is provided to a treated water pump (HJD). In embodiments, the treated water pump (HJD) pumps and pressurizes the treated water (HJA) to form pressurized treated water (HJB). In embodiments, the pressurized treated water (HJB) provided by the treated water pump (HJD) is made available to the interior (HAJ) extraction zone (HAI) as a solvent (HAB). In embodiments, the pressurized treated water (HJB) provided by the treated water pump (HJD) is made available for use as the first desorbent (HDC) for the first adsorber system (SMB1), second desorbent (HFG) for the second adsorber system (SMB2), third desorbent (HHC) for the third adsorber system (SMB3). In embodiments, a treated water valve (HJE) is configured to regulate the flow of the pressurized treated water (HJB) that leaves the solvent treatment system (H-WTS). In embodiments, a pressure sensor (HJH) is configured to measure the pressure of the pressurized treated water (HJB) that is discharged from the treated water pump (HJD). In embodiments, a pH adjustment solution (HJR) is made available to the treated water vessel (HJF). In embodiments, the pH adjustment solution (HJR) passes through a valve (HJS) prior to being introduced to the interior of the treated water vessel (HJF).

In embodiments, the treated water (HJA) within the treated water vessel (HJF) is preferably maintained at a pH of 6.1 to 6.8. In embodiments, the treated water (HJA) within the treated water vessel (HJF) is preferably maintained at a pH including one or more selected from the group consisting of 5.00 to 5.05, 5.05 to 5.10, 5.10 to 5.15, 5.15 to 5.20, 5.20 to 5.25, 5.25 to 5.30, 5.30 to 5.35, 5.35 to 5.40, 5.40 to 5.45, 5.45 to 5.50, 5.50 to 5.55, 5.55 to 5.60, 5.60 to 5.65, 5.65 to 5.70, 5.70 to 5.75, 5.75 to 5.80, 5.80 to 5.85, 5.85 to 5.90, 5.90 to 5.95, 5.95 to 6.00, 6.00 to 6.05, 6.05 to 6.10, 6.10 to 6.15, 6.15 to 6.20, 6.20 to 6.25, 6.25 to 6.30, 6.30 to 6.35, 6.35 to 6.40, 6.40 to 6.45, 6.45 to 6.50, 6.50 to 6.55, 6.55 to 6.60, 6.60 to 6.65, 6.65 to 6.70, 6.70 to 6.75, 6.75 to 6.80, 6.80 to 6.85, 6.85 to 6.90, and 6.90 to 6.95.

In embodiments, the pH adjustment solution (HJR) is comprised of one or more from the group consisting of acid, nitric acid, phosphoric acid, potassium hydroxide, sulfuric acid, organic acids, citric acid, and acetic acid.

FIG. 17J

FIG. 17J shows one non-limiting embodiment of a cannabinoid emulsion and/or colloid production system.

Cannabinoids (THC, CBD, etc.) are lipophilic and hydrophobic. Cannabinoids (e.g., such as THC and CBD) are lipophilic and that they tend to combine with or dissolve in each other or in other compounds such as lipids or fats. Cannabinoids such as THC and CBD are hydrophobic and they tend to repel or fail to mix with water. An emulsion is a mixture of water and cannabinoids. An emulsion can be prepared from treated water having an electrical conductivity ranging from 0.10 microsiemens per centimeter to 100 microsiemens per centimeter.

An colloidal suspension, or a colloidal dispersion, includes is a mixture of a liquid and/or a solvent and a cannabinoid. In some embodiments, the solvent comprises an oil, a lipid, a medium chain triglyceride, and optionally a fatty acid, including lauric acid, palmitic acid, linoleic acid, alpha-linoleic acid, oleic acid, gamma-linoleic acid, or stearic acid, wherein the fatty acid may be derived from insects. In embodiments, the colloid, a colloidal suspension, and/or a colloidal dispersion, comprises a substance comprising a cannabinoid dispersed in a liquid and/or a solvent. In embodiments, the colloid may be added to water to provide a self-emulsifying means for cannabinoid delivery to a human and/or an animal.

In embodiments, the emulsion and/or colloid production system shown in FIG. 17J is specially equipped with a purge system to provide inert gases to the interior of the system to form a protective atmosphere (prevent oxidation and/or degradation of the emulsion and/or colloid or ingredients, improved product quality, clean good manufacturing practices as required by pharmaceutical industry, for cleaning in place, etc.) while creating the emulsion and/or the colloid dispersion.

In embodiments, the emulsion and/or colloid production system shown in FIG. 17J creates a microemulsion, a nanoemulsion, and/or a colloidal dispersion that is thermodynamically stable.

In embodiments, the emulsion and/or colloid produced has the following characteristics:

(i) a pH ranging from one or more selected from the group consisting of 6 to 6.25, 6.25 to 6.5, 6.5 to 6.75, 6.75 to 7, 7 to 7.05, 7.05 to 7.1, 7.1 to 7.15, 7.15 to 7.2, 7.2 to 7.25, 7.25 to 7.3, 7.3 to 7.35, 7.35 to 7.4, 7.4 to 7.45, 7.45 to 7.5, 7.5 to 7.55, 7.55 to 7.6, 7.6 to 7.65, 7.65 to 7.7, 7.7 to 7.75, 7.75 to 7.8, 7.8 to 7.85, 7.85 to 7.9, 7.9 to 7.95, 7.95 to 8, 8 to 8.05, 8.05 to 8.1, 8.1 to 8.15, 8.15 to 8.2, 8.2 to 8.25, 8.25 to 8.3, 8.3 to 8.35, 8.35 to 8.4, 8.4 to 8.45, 8.45 to 8.5, and 8.5 to 9.

(ii) a viscosity ranging from one or more selected from the group consisting of 0.9 centipoise (cps) to 1 cps, 1 cps to 1.1 cps, 1.1 cps to 1.2 cps, 1.2 cps to 1.3 cps, 1.3 cps to 1.4 cps, 1.4 cps to 1.5 cps, 1.5 cps to 1.6 cps, 1.6 cps to 1.7 cps, 1.7 cps to 1.8 cps, 1.8 cps to 1.9 cps, 1.9 cps to 2 cps, 2 cps to 2.1 cps, 2.1 cps to 2.2 cps, 2.2 cps to 2.3 cps, 2.3 cps to 2.4 cps, 2.4 cps to 2.5 cps, 2.5 cps to 2.6 cps, 2.6 cps to 2.7 cps, 2.7 cps to 2.8 cps, 2.8 cps to 2.9 cps, 2.9 cps to 3 cps, 3 cps to 5 cps, 5 cps to 10 cps, 10 cps to 20 cps, 20 cps to 30 cps, 30 cps to 40 cps, 40 cps to 50 cps, 50 cps to 60 cps, 60 cps to 70 cps, 70 cps to 80 cps, 80 cps to 90 cps, 90 cps to 100 cps, 100 cps to 125 cps, 125 cps to 150 cps, 150 cps to 175 cps, 175 cps to 200 cps, 200 cps to 225 cps, 225 cps to 250 cps, 250 cps to 275 cps, 275 cps to 300 cps, 300 cps to 325 cps, 325 cps to 350 cps, 350 cps to 375 cps, 375 cps to 400 cps, 400 cps to 425 cps, 425 cps to 450 cps, 450 cps to 475 cps, 475 cps to 500 cps, 500 cps to 550 cps, 550 cps to 600 cps, 600 cps to 650 cps, 650 cps to 700 cps, 700 cps to 750 cps, 750 cps to 800 cps, 800 cps to 850 cps, 850 cps to 900 cps, 900 cps to 950 cps, 950 cps to 1000 cps, 1,000 cps to 1,250 cps, 1,250 cps to 1,500 cps, 1,500 cps to 1,750 cps, 1,750 cps to 2,000 cps, 2,000 cps to 2,500 cps, 2,500 cps to 3,000 cps, 3,000 cps to 3,500 cps, 3,500 cps to 4,000 cps, 4,000 cps to 4,500 cps, 4,500 cps to 5,000 cps, 5,000 cps to 5,500 cps, 5,500 cps to 6,000 cps, 6,000 cps to 6,500 cps, 6,500 cps to 7,000 cps, 7,000 cps to 7,500 cps, 7,500 cps to 8,000 cps, 8,000 cps to 8,500 cps, 8,500 cps to 9,000 cps, 9,000 cps to 9,500 cps, 9,500 cps to cps, 10,000 cps to 11,000 cps, 11,000 cps to 12,000 cps, 12,000 cps to 13,000 cps, 13,000 cps to 14,000 cps, 14,000 cps to 15,000 cps, 15,000 cps to 16,000 cps, 16,000 cps to 17,000 cps, 17,000 cps to 18,000 cps, 18,000 cps to 19,000 cps, 19,000 cps to 20,000 cps, 20,000 cps to 21,000 cps, 21,000 cps to 22,000 cps, 22,000 cps to 23,000 cps, 23,000 cps to 24,000 cps, 24,000 cps to cps, and 25,000 cps to 26,000 cps.

(iii) a specific gravity ranging from one or more selected from the group consisting of 0.7 to 0.705, 0.705 to 0.71, 0.71 to 0.715, 0.715 to 0.72, 0.72 to 0.725, 0.725o 0.73, 0.73 to 0.735, 0.735 to 0.74, 0.74 to 0.745, 0.745 to 0.75, 0.75 to 0.755, 0.755 to 0.76, 0.76 to 0.765, 0.765 to 0.77 to 0.775, 0.775 to 0.78, 0.78 to 0.785, 0.785 to 0.79, 0.79 to 0.795, 0.795 to 0.8, 0.8 to 0.805 to 0.81, 0.81 to 0.815, 0.815 to 0.82, 0.82 to 0.825, 0.825 to 0.83, 0.83 to 0.835, 0.835 to 0.84, 0.84 to 0.845, 0.845 to 0.85, 0.85 to 0.855, 0.855 to 0.86, 0.86 to 0.865, 0.865 to 0.87, to 0.875, 0.875 to 0.88, 0.88 to 0.885, 0.885 to 0.89, 0.89 to 0.895, 0.895 to 0.9, 0.9 to 0.905, 0.905 to 0.91, 0.91 to 0.915, 0.915 to 0.92, 0.92 to 0.925, 0.925 to 0.93, 0.93 to 0.935, 0.935 to 0.94 to 0.945, 0.945 to 0.95, 0.95 to 0.955, 0.955 to 0.96, 0.96 to 0.965, 0.965 to 0.97, 0.97 to 0.975, 0.975 to 0.98, 0.98 to 0.985, 0.985 to 0.99, 0.99 to 0.995, 0.995 to 0.999, 0.999 to 1, 1 to 1.1, 1.1 to 1.2, and 1.2 to 1.3.

(iv) a conductivity ranging from one or more selected from the group consisting of 1.00 microsiemens ($\mu$S) to 1.25 $\mu$S, 1.25 $\mu$S to 1.50 $\mu$S, 1.50 $\mu$S to 1.75 $\mu$S, 1.75 $\mu$S to 2.00 $\mu$S, 2.00 $\mu$S to 2.25 $\mu$S, 2.25 $\mu$S to 2.50 $\mu$S, 2.50 $\mu$S to 2.75 $\mu$S, 2.75 $\mu$S to 3.00 $\mu$S, 3.00 $\mu$S to 3.25 $\mu$S, 3.25 $\mu$S to 3.50 $\mu$S, 3.50 $\mu$S to 3.75 $\mu$S, 3.75 $\mu$S to 4.00 $\mu$S, 4.00 $\mu$S to 4.25 $\mu$S, 4.25 $\mu$S to 4.50 $\mu$S, 4.50 $\mu$S to 4.75 $\mu$S, 4.75 $\mu$S to 5.00 $\mu$S, 5.00 $\mu$S to 5.25 $\mu$S, 5.25 $\mu$S to 5.50 $\mu$S, 5.50 $\mu$S to 5.75 $\mu$S, 5.75 $\mu$S to 6.00 $\mu$S, 6.00 $\mu$S to 6.25 $\mu$S, 6.25 $\mu$S to 6.50 $\mu$S, 6.50 $\mu$S to 6.75 $\mu$S, 6.75 $\mu$S to 7.00 $\mu$S, 7.00 $\mu$S to 7.25 $\mu$S, 7.25 $\mu$S to 7.50 $\mu$S, 7.50 $\mu$S to 7.75 $\mu$S, 7.75 $\mu$S to 8.00 $\mu$S, 8.00 $\mu$S to 8.25 $\mu$S, 8.25 $\mu$S to 8.50 $\mu$S, 8.50 $\mu$S to 8.75 $\mu$S, 8.75 $\mu$S to 9.00 $\mu$S, 9.00 $\mu$S to 9.25 $\mu$S, 9.25 $\mu$S to 9.50 $\mu$S, 9.50 $\mu$S to 9.75 $\mu$S, 9.75 $\mu$S to 10.00 $\mu$S, 10.00 $\mu$S to 12.50 $\mu$S, 12.50 $\mu$S to 15.00 $\mu$S, 15.00 $\mu$S to 17.50 $\mu$S, 17.50 $\mu$S to 20.00 $\mu$S, 20.00 $\mu$S to 22.50 $\mu$S, 22.50 $\mu$S to 25.00 $\mu$S, 25.00 $\mu$S to 27.50 $\mu$S, 27.50 $\mu$S to 30.00 $\mu$S, 30.00 $\mu$S to 32.50 $\mu$S, 32.50 $\mu$S to 35.00 $\mu$S, 35.00 $\mu$S to 37.50 $\mu$S, 37.50 $\mu$S to 40.00 $\mu$S, 40.00 $\mu$S to 42.50 $\mu$S, 42.50 $\mu$S to 45.00 $\mu$S, 45.00 $\mu$S to 47.50 $\mu$S, 47.50 $\mu$S to 50.00 $\mu$S, 50.00 $\mu$S to 52.50 $\mu$S, 52.50 $\mu$S to 55.00 $\mu$S, 55.00 $\mu$S to 57.50 $\mu$S, 57.50 $\mu$S to 60.00 $\mu$S, 60.00 $\mu$S to 62.50 $\mu$S, 62.50 $\mu$S to 65.00 $\mu$S, 65.00 $\mu$S to 67.50 $\mu$S, 67.50 $\mu$S to 70.00 $\mu$S, 70.00 $\mu$S to 72.50 $\mu$S, 72.50 $\mu$S to 75.00 $\mu$S, 75.00 $\mu$S to 77.50 $\mu$S, and 77.50 $\mu$S to 80.00 $\mu$S. In embodiments, $\mu$S means $\mu$S per centimeter.

(v) a conductivity ranging from one or more selected from the group consisting of 80 $\mu$S to 125 $\mu$S, 100 $\mu$S to 125 $\mu$S, 125 $\mu$S to 150 $\mu$S, 150 $\mu$S to 175 $\mu$S, 175 $\mu$S to 200 $\mu$S, 200 $\mu$S to 225 $\mu$S, 225 $\mu$S to 250 $\mu$S, 250 $\mu$S to 275 $\mu$S, 275 $\mu$S to 300 $\mu$S, 300 $\mu$S to 325 $\mu$S, 325 $\mu$S to 350 $\mu$S, 350 $\mu$S to 375 $\mu$S, 375 $\mu$S to 400 $\mu$S, 400 $\mu$S to 425 $\mu$S, 425 $\mu$S to 450 $\mu$S, 450 $\mu$S to 475 $\mu$S, 475 $\mu$S to 500 $\mu$S, 500 $\mu$S to 525 $\mu$S, 525 $\mu$S to 550 $\mu$S, 550 $\mu$S to 575 $\mu$S, 575 $\mu$S to 600 $\mu$S, 600 $\mu$S to 625 $\mu$S, 625 $\mu$S to 650 $\mu$S, 650 $\mu$S to 675 $\mu$S, 675 $\mu$S to 700 $\mu$S, 700 $\mu$S to 725 $\mu$S, 725 $\mu$S to 750 $\mu$S, 750 $\mu$S to 775 $\mu$S, 775 $\mu$S to 800 $\mu$S, 800 $\mu$S to 825 $\mu$S, 825 $\mu$S to 850 $\mu$S, 850 $\mu$S to 875 $\mu$S, 875 $\mu$S to 900 $\mu$S, 900 $\mu$S to 925 $\mu$S, 925 $\mu$S to 950 $\mu$S, 950 $\mu$S to 975 $\mu$S, 975 $\mu$S to 1,000 $\mu$S, 1,000 $\mu$S to 1,250 $\mu$S, 1,250 $\mu$S to 1,500 $\mu$S, 1,500 $\mu$S to 1,750 $\mu$S, 1,750 $\mu$S to 2,000 $\mu$S, 2,000 $\mu$S to 2,250 $\mu$S, 2,250 $\mu$S to 2,500 $\mu$S, 2,500 $\mu$S to 2,750 $\mu$S, 2,750 $\mu$S to 3,000 $\mu$S, 3,000 $\mu$S to 3,250 $\mu$S, 3,250 $\mu$S to 3,500 $\mu$S, 3,500 $\mu$S to 3,750 $\mu$S, 3,750 $\mu$S to 4,000 $\mu$S, 4,000 $\mu$S to 4,250 $\mu$S, 4,250 $\mu$S to 4,500 $\mu$S, 4,500 $\mu$S to 4,750 $\mu$S, 4,750 $\mu$S to 5,000 $\mu$S, 5,000 $\mu$S to $\mu$S, 5,250 $\mu$S to 5,500 $\mu$S, 5,500 $\mu$S to 5,750 $\mu$S, 5,750 $\mu$S to 6,000 $\mu$S, 6,000 $\mu$S to 6,250 $\mu$S, 6,250 $\mu$S to 6,500 $\mu$S, 6,500 $\mu$S to 6,750 $\mu$S, 6,750 $\mu$S to 7,000 $\mu$S, 7,000 $\mu$S to 7,250 $\mu$S, 7,250 $\mu$S to 7,500 $\mu$S, 7,500 $\mu$S to 7,750 $\mu$S, and 7,750 $\mu$S to 8,000 $\mu$S In embodiments, $\mu$S means $\mu$S per centimeter (vi) a preservation that includes: freezer, 0 degrees F. to 32 degrees F., 30 months to 40 months; refrigerator, 34 degrees F. to 45 degrees F., 30 months to 40 months; elevated temperature, 76 degrees F. to 98 degrees F., 4 months to 6 months; ambient temperature, 68 degrees F. to 76 degrees F., 30 months to 40 months.

Applicant has discovered an improved process to emulsify and or disperse a lipophilic and hydrophobic cannabinoid mixture for enhanced drug delivery. Applicant has discovered an improved process to emulsify and/or disperse a lipophilic and hydrophobic cannabinoid extract with water and/or a lipid. The simulated moving bed purification method utilized with an emulsification/colloid manufacturing procedure is a core concept of this disclosure shown in FIGS. 17G and 17H.

Lipophilic and hydrophobic cannabinoid mixtures do not easily disperse into water-based formulations. In embodiments, ultrasonic homogenizers can be used to produce stable nano-emulsions of cannabinoids in water or any aqueous phase. In embodiments, an emulsification system may be used for the production of *cannabis* oil-emulsions. In embodiments, the type of emulsification system varies. In embodiments, the type of emulsification system includes a homogenizer, agitator, sawtooth blade, closed rotor, rotor/stator, an ultrasonic homogenizer, rotor/stator generator, colloid mill, high pressure, piston pump, a microfluidizer, and a microfluidizer processor. In embodiments, the process described in FIG. 17J provides for a colloid and/or a colloidal suspension of a cannabinoid, a purified cannabinoid, a distilled cannabinoid with a liquid (such as a lipid, oil, a solvent, etc., as mentioned above).

Applicant has discovered a new microemulsion and nanoemulsion technology based water soluble platform to greatly enhance the bioavailability of water soluble cannabinoid (THC, CBD, etc.) powders, liquids, gels, and creams. In embodiments, the bioavailability of the cannabinoid emulsion is the proportion of the cannabinoid that enters the circulation of the human or animal when introduced into the body and so is able to have an active effect.

In embodiments, the bioavailability of the cannabinoid emulsion and/or colloid is the proportion of the cannabinoid that enters the circulation of the human or animal when introduced into the human or animal body and so is able to have an active effect. In embodiments, the bioavailability of the cannabinoid emulsion and/or colloid is selected from one or more bioavailability ranges selected from one or more from the group of bioavailability ranges consisting of: 30.00 percent to 40.00 percent, 40.00 percent to 50.00 percent, 50.00 percent to 60.00 percent, 60.00 percent to 70.00 percent, 70.00 percent to 72.50 percent, 72.50 percent to percent, 75.00 percent to 77.50 percent, 77.50 percent to 80.00 percent, 80.00 percent to 82.50 percent, 82.50 percent to 85.00 percent, 85.00 percent to 87.50 percent, 87.50 percent to percent, 90.00 percent to 90.50 percent, 90.50 percent to 91.00 percent, 91.00 percent to 91.50 percent, 91.50 percent to 92.00 percent, 92.00 percent to 92.50 percent, 92.50 percent to 93.00 percent, 93.00 percent to 93.50 percent, 93.50 percent to 94.00 percent, 94.00 percent to 94.50 percent, 94.50 percent to 95.00 percent, 95.00 percent to 95.50 percent, 95.50 percent to 96.00 percent, 96.00 percent to 96.50 percent, 96.50 percent to 97.00 percent, 97.00 percent to 97.50 percent, 97.50 percent to 98.00 percent, 98.00 percent to 98.50 percent, 98.50 percent to 99.00 percent, 99.00 percent to 99.50 percent, and 99.50 percent to 100.00 percent.

In embodiments, these new and advanced water-soluble technology formulations transforms cannabinoid oil (THC, CBD, etc.) into microemulsions and nanoemulsions and/or colloidal dispersions making them more absorbable when delivered orally, and much more permeable when administered topically. Applicant has discovered a method to make new water soluble powder and liquid cannabinoid drugs, foodstuffs, oils, crystals, and emulsions.

In embodiments, the emulsion is a nano-size emulsion or a nanoemulsion and has nano-size droplets. In embodiments, the emulsion is a micro-size emulsion or a microemulsion and has micro-sized droplets. In embodiments, emulsions, such as micro-sized or nano-sized emulsions, may be liquids, gels, of creams. In embodiments, emulsions, such as micro-sized or nano-sized emulsions, may be two immiscible fluids dispersed into one another. In embodiments, the emulsion contains cannabinoids and water. In embodiments, the emulsion contains cannabinoids and a solvent.

In embodiments, the colloid is a nano-size dispersion having nano-size droplets of cannabinoids in the lipid, oil, and/or solvent. In embodiments, the colloid is a micro-size dispersion having micro-size droplets of cannabinoids in the lipid, oil, and/or solvent.

In embodiments, the emulsion contains cannabinoids, a solvent, an emulsifier, a biocatalyst, and acid. In embodiments, the emulsion contains cannabinoids, a solvent, an emulsifier, a biocatalyst, an acid/caustic, and water. In embodiments, the emulsion contains cannabinoids, a water, an emulsifier, a biocatalyst, drugs, and an acid. In embodiments, the emulsion contains cannabinoids, a water, an emulsifier, a biocatalyst, drugs, an acid/caustic, and a pH adjustment solution. In embodiments, the emulsion contains cannabinoids and water. In embodiments, the emulsion contains cannabinoids and deionized water. In embodiments, the emulsion contains cannabinoids and deionized and membrane treated water. In embodiments, the emulsion contains cannabinoids and filtered and deionized water. In embodiments, the emulsion contains cannabinoids and distilled water. In embodiments, the emulsion contains cannabinoids and deionized, membrane treated, and distilled water. In embodiments, the emulsion contains cannabinoids and filtered, deionized, and distilled water. In embodiments, the emulsion has an average droplet size selected from one or more from the group consisting of between: 1 nanometers to 2 nanometers, 2 nanometers to 3 nanometers, 3 nanometers to 4 nanometers, 4 nanometers to 5 nanometers, 5 nanometers to 6 nanometers, 6 nanometers to 7 nanometers, 7 nanometers to 8 nanometers, 8 nanometers to 9 nanometers, 9 nanometers to 10 nanometers, 10 nanometers to 11 nanometers, 11 nanometers to 12 nanometers, 12 nanometers to 13 nanometers, 13 nanometers to 14 nanometers, 14 nanometers to 15 nanometers, 15 nanometers to 16 nanometers, 16 nanometers to 17 nanometers, 17 nanometers to 18 nanometers, 18 nanometers to 19 nanometers, 19 nanometers to 20 nanometers, 20 nanometers to 21 nanometers, 21 nanometers to 22 nanometers, 22 nanometers to 23 nanometers, 23 nanometers to 24 nanometers, 24 nanometers to 25 nanometers, 25 nanometers to 26 nanometers, 26 nanometers to 27 nanometers, 27 nanometers to 28 nanometers, 28 nanometers to 29 nanometers, 29 nanometers to 30 nanometers, 30 nanometers to 31 nanometers, 31 nanometers to 32 nanometers, 32 nanometers to 33 nanometers, 33 nanometers to 34 nanometers, 34 nanometers to 35 nanometers, 35 nanometers to 36 nanometers, 36 nanometers to 37 nanometers, 37 nanometers to 38 nanometers, 38 nanometers to 39 nanometers, 39 nanometers to 40 nanometers, 40 nanometers to 41 nanometers, 41 nanometers to 42 nanometers, 42 nanometers to 43 nanometers, 43 nanometers to 44 nanometers, 44 nanometers to 45 nanometers, 45 nanometers to 46 nanometers, 46 nanometers to 47 nanometers, 47 nanometers to 48 nanometers, 48 nanometers to 49 nanometers, 49 nanometers to 50 nanometers, nanometers to 75 nanometers, 75 nanometers to 100 nanometers, 100 nanometers to 150 nanometers, 150 nanometers to 250 nanometers, 250 nanometers to 500 nanometers, 500 nanometers to 750 nanometers, 750 nanometers to 1,000 nanometers, 1,000 nanometers to 1,500 nanometers, 1,500 nanometers to 2,000 nanometers, 2,000 nanometers to 3,000 nanometers, 3,000 nanometers to 4,000 nanometers, 4,000 nanometers to 5,000 nanometers, 5,000 nanometers to 6,000 nanometers, and 6,000 nanometers to 10,000 nanometers.

Applicant has discovered new and improved oil-in-water emulsions. Applicant has also discovered new and improved cannabinoid-in-oil colloidal dispersions. In embodiments, the emulsion is prepared by mixing the cannabinoid and solvent mixture with an emulsifier. In embodiments, the emulsifier used in Applicants cannabinoid emulsion process is selected from one or more emulsifiers selected from the group consisting of a surfactant, a nonionic surfactant, lecithin, polyethylene (40), stearate, polysorbate, Polyoxyethylene sorbitan monooleate, Polyoxyethylene (20) sorbitan monooleate, polysorbate 80, polysorbate 60, polysorbate 65, ammonium salts of phosphatidic acid, sucrose acetate isobutyrate, potassium pyrophosphate, sodium acid pyrophosphate, sodium pyrophosphate, potassium polymetaphosphate, sodium metaphosphate, insoluble or sodium polyphosphates, sodium polyphosphates, insoluble polyphosphates, glassy salts of fatty acids, mono- and di-glycerides of fatty acids, mono-glycerides of fatty acids, diglycerides of fatty acids, acetic and fatty acid esters of glycerol, lactic and fatty acid esters of glycerol, citric and fatty acid esters of glycerol, diacetyltartaric and fatty acid esters of glycerol, mixed fatty acid esters of glycerol, sucrose esters of fatty acids, polyglycerol esters of fatty acids, polyglycerol esters of interesterified ricinoleic acid, propylene glycol mono- and di-esters, propylene glycol di-esters, propylene glycol mono-esters, propylene glycol esters of fatty acids, propylene glycol esters, dioctyl sodium sulphosuccinate, sodium lactylate, sodium oleyl lactylate, sodium stearoyl lactylate, calcium lactylate, calcium oleyl lactylate, calcium stearoyl lactylate, sorbitan monostearate, maltodextrin, polyphosphates, formulated polyphosphates, and gum arabic.

In embodiments, the emulsion and/or colloid include a biocatalyst including one or more selected from the group consisting of a microorganism, bacteria, fungi, Lactobacilli, *Lactobacillus acidophilus, LactoBacillus bulgaricus, LactoBacillus plantarum, LactoBacillus rhamnosus, LactoBacillus fermentum, LactoBacillus caucasicus, LactoBacillus helveticus, LactoBacillus lactis, LactoBacillus reuteri, LactoBacillus casei, LactoBacillus brevis, LactoBacillus gasseri, LactoBacillus paracasei, LactoBacillus salivarius*, Bifidobacteria, *Bifidobacterium animalis, Bifidobacterium bifidum, Bifidobacterium breve, Bifidobacterium infantis, Bifidobacterium lactis, Bifidobacterium longum, Enterococcus faecium, Streptococcus thermophilus, Bacillus laterosporus,* and *Pediococcus acidilactici.*

In embodiments, the emulsion and/or colloid include a drug include one or more selected from the group consisting of a ayahuasca, biologically active organic compound with four rings, a nootropic drug, acetate, activated charcoal, an amphetamine, ascorbic acid, aspirin, butyrate, calcium, capsaicin, carnitine, carnosine, *cassia* cinnamon, chondroitin sulfate, chromium, coenzyme q-10, cannabinoids, cannabinoid drugs, water soluble powder cannabinoid drugs, liquid cannabinoid drugs, cranberry, creatine, curcumin, deprenyl, dimethyltryptamine, *echinacea*, fish oil, garlic, ginger, ginkgo, *ginseng*, gluconic acid, glucosamine, green tea, hoodia, human growth hormone, 7-hydroxymitragynine, inositol, iowaska, kratom, lactic acid, lithium, lions mane mushroom, lutein, magnesium, minerals, malate, melatonin, metformin, 3,4-methylenedioxy methamphetamine, milk thistle, n-acetylcysteine, niacin, niacinamide, nicotinamide riboside, omega-3 fatty acid, oxaloacetate, piracetam, psilocybin, pyruvate, resveratrol, *rhodiola*, saw palmetto, selenium, St. johns wort, steroid alternatives, steroids, testosterone, theaflavins, turmeric, valerian, vitamins, vitamin B3, vitamin C, and zinc.

In embodiments, the emulsion and/or colloid include a drug including one or more selected from the group consisting of basil, bergamot, black pepper, *cassia*, cedarwood, cinnamon, citronella, clary sage, clove, coffee, cypress, *eucalyptus*, evening primrose, fennel, fir needle, frankincense, *gardenia*, geranium, ginger, grapefruit, helichrysum, hop, hyssop, jasmine, juniper berry, lavender, lemon, lemongrass, mandarin, marjoram, *melaleuca*, melissa, myrrh, neroli, orange, oregano, palo santo, patchouli, peppermint, pine, chamomile, rose, rosemary, sandalwood, spikenard, tea tree, thyme, turmeric, vetiver, wintergreen, and ylang ylang.

In embodiments, the emulsion and/or colloid include a drug including one or more selected from the group consisting of barley, binding agents, brown rice, buckwheat flour, buckwheat, bulgur, carrageenan, corn meal, corn, cracked wheat, cricket flour, density improving textural supplements, farro, fiber-starch materials, insect flour, insects, mealworms, millet, moisture improving textural supplements, oatmeal, popcorn, *quinoa*, rice, rye, sorghum, triticale, wheat, whole farro, whole grain barley, whole grain corn, whole oats, whole rye, whole wheat flour, wild rice, fiber-starch materials, binding agents, density improving textural supplements, and moisture improving textural supplements.

In embodiments, the emulsion and/or colloid may be further processed to create foodstuffs not only including ada, bagels, baked goods, biscuits, bitterballen, bonda, breads, cakes, candies, cereals, chips, chocolate bars, chocolate, coffee, cokodok, confectionery, cookies, cooking batter, corn starch mixtures, crackers, crepes, croissants, croquettes, croutons, dolma, dough, doughnuts, energy bars, flapjacks, french fries, frozen custard, frozen desserts, frying cakes, fudge, gelatin mixes, granola bars, gulha, hardtack, ice cream, khandvi, khanom buang, krumpets, meze, mixed flours, muffins, multi-grain snacks, nachos, nian gao, noodles, nougat, onion rings, pakora, pancakes, panforte, pastas, pastries, pie crust, pita chips, pizza, poffertj es, pretzels, protein powders, pudding, rice krispie treats, sesame sticks, smoothies, snacks, specialty milk, tele-bhaja, tempura, toffee, tortillas, totopo, turkish delights, or waffles.

In embodiments, the fiber-starch materials may be comprised of singular or mixtures of cereal-grain-based materials, grass-based materials, nut-based materials, powdered fruit materials, root-based materials, tuber-based materials, or vegetable-based materials. In embodiments, the binding agents may be comprised of singular or mixtures of agar, agave, alginin, aspartame, arrowroot, carrageenan, collagen, cornstarch, egg whites, finely ground seeds, furcellaran, gelatin, guar gum, honey, katakuri starch, locust bean gum, pectin, potato starch, proteins, *psyllium* husks, sago, sugar, *stevia*, syrup, tapioca, vegetable gums, or xanthan gum. In embodiments, the moisture improving textural supplements may be comprised of singular or mixtures of almonds, brazil nuts, cacao, cashews, chestnuts, coconut, filberts, hazelnuts, Indian nuts, macadamia nuts, nut butters, nut oils, nut powders, peanuts, pecans, pili nuts, pine nuts, pinon nuts, pistachios, soy nuts, sunflower seeds, tiger nuts, walnuts, and oils extracted from any one of the aforesaid nuts and nuts listed herein and combinations thereof. In embodiments, the insects may be Orthoptera order of insects including grasshoppers, crickets, cave crickets, Jerusalem crickets, katydids, weta, lubber, acrida, and locusts. However, other orders of insects, such as cicadas, ants, mealworms, agave worms, worms, bees, centipedes, cockroaches, dragonflies, beetles, scorpions, tarantulas, termites, insect lipids, and insect oil, or any insects or insect products mentioned herein may be used as well.

In embodiments the emulsion and/or colloid is created in a continuously stirred tank reactor. In embodiments the emulsion is created in a homogenizer. In embodiments, the emulsion is created using ultrasound technology. In embodiments, the emulsion is created using ultrasonic homogenizer. In embodiments, the ultrasonic homogenizer includes an ultrasonic horn (also known as acoustic horn, sonotrode, acoustic waveguide, ultrasonic probe) is a tapering metal bar commonly used for augmenting the oscillation displacement amplitude provided by an ultrasonic transducer operating at the low end of the ultrasonic frequency spectrum. In embodiments, the ultrasonic homogenizer includes one or more ultrasonic homogenizers selected from the group consisting of an ultrasonic horn, a converging ultrasonic horn, and a barbell ultrasonic horn. In embodiments, a sonotrode is a tool that creates ultrasonic vibrations and applies this vibrational energy to a gas, liquid, solid or tissue. In embodiments, a sonotrode includes of a plurality of piezoelectric transducers attached to a tapering metal rod.

In embodiments, the ultrasonic homogenizer consumes power at a power consumption level ranging from one or more power consumption levels selected from the group consisting of kw to 0.25 kw, 0.25 kw to 0.5 kw, 0.5 kw to 1 kw, 1 kw to 2 kw, 2 kw to 3 kw, 3 kw to 4 kw, 4 kw to 5 kw, 5 kw to 6 kw, 6 kw to 7 kw, 7 kw to 8 kw, 8 kw to 9 kw, 9 kw to 10 kw, 10 kw to 11 kw, 11 kw to 12 kw, 12 kw to 13 kw, 13 kw to 14 kw, 14 kw to 15 kw, 15 kw to 16 kw, 16 kw to 17 kw, 17 kw to 18 kw, 18 kw to 19 kw, 19 kw to 20 kw, 20 kw to 25 kw, 25 kw to 30 kw, 30 kw to 35 kw, 35 kw to 40 kw, 40 kw to 45 kw, 45 kw to 50 kw, 50 kw to 55 kw, 55 kw to 60 kw, kw to 65 kw, 65 kw to 70 kw, 70 kw to 75 kw, 75 kw to 80 kw, 80 kw to 85 kw, 85 kw to 90 kw, 90 kw to 95 kw, 95 kw to 100 kw, 100 kw to 300 kw, 300 kw to 500 kw, and 500 kw to 1,000 kw.

In embodiments, the weight percent of emulsifier in the final emulsion product includes at least one emulsifier weight percent range that is selected from the emulsifier weight percent ranges selected from the group consisting of: 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, 14 weight percent to 15 weight percent, weight percent to 16 weight percent, 16 weight percent to 17 weight percent, 17 weight percent to 18 weight percent, 18 weight percent to 19 weight percent, 19 weight percent to 20 weight percent, 20 weight percent to 21 weight percent, 21 weight percent to 22 weight percent, 22 weight percent to 23 weight percent, 23 weight percent to 24 weight percent, 24 weight percent to 25 weight percent, 25 weight percent to 26 weight percent, 26 weight percent to 27 weight percent, 27 weight percent to 28 weight percent, 28 weight percent to 29 weight percent, 29 weight percent to 30 weight percent.

In embodiments, the weight percent of cannabinoids in the final emulsion product includes at least one cannabinoid weight percent range that is selected from the cannabinoid weight percent ranges selected from the group consisting of: 0.0001 weight percent to 0.001 weight percent, 0.001 weight percent to 0.05 weight percent, 0.05 weight percent to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight.

In embodiments, the weight percent of acid in the final emulsion product includes at least one acid weight percent range that is selected from the acid weight percent ranges selected from the group consisting of: 1 weight percent to 2 weight percent, 2 weight percent to 3 weight percent, 3 weight percent to 4 weight percent, 4 weight percent to 5 weight percent.

In embodiments, the weight percent of biocatalyst in the final emulsion product includes at least one biocatalyst weight percent range that is selected from the biocatalyst weight percent ranges selected from the group consisting of: 25 parts per million to 0.1 weight percent, 0.1 weight percent to 0.5 weight percent, 0.5 weight percent to 1 weight percent, 1 weight percent to 2 weight percent, 2 weight percent to 3 weight percent, 3 weight percent to 4 weight percent, 4 weight percent to 5 weight percent.

In embodiments, the weight percent of drugs (including a cannabinoid, and other drugs listed above) in the final emulsion product includes at least one drug weight percent range that is selected from the drug weight percent ranges selected from the group consisting of: 0.001 weight percent to 0.002 weight percent, 0.002 weight percent to 0.01 weight percent, 0.01 weight percent to 0.1 weight percent, 0.1 weight percent to 0.5 weight percent, 0.5 weight percent to 0.6 weight percent, 0.6 weight percent to 0.7 weight percent, 0.7 weight percent to 0.8 weight percent, 0.8 weight percent to 0.9 weight percent, 0.9 weight percent to 1.0 weight percent, 1.0 weight percent to 1.1 weight percent, 1.1 weight percent to 1.2 weight percent, 1.2 weight percent to 1.3 weight percent, 1.3 weight percent to 1.4 weight percent, 1.4 weight percent to 1.5 weight percent, 1.5 weight percent to 1.6 weight percent, 1.6 weight percent to 1.7 weight percent, 1.7 weight percent to 1.8 weight percent, 1.8 weight percent to 1.9 weight percent, 1.9 weight percent to 2.0 weight percent, 2.0 weight percent to 2.1 weight percent, 2.1 weight percent to 2.2 weight percent, 2.2 weight percent to 2.3 weight percent, 2.3 weight percent to 2.4 weight percent, 2.4 weight percent to 2.5 weight percent, 2.5 weight percent to 2.6 weight percent, 2.6 weight percent to 2.7 weight percent, 2.7 weight percent to 2.8 weight percent, 2.8 weight percent to 2.9 weight percent, 2.9 weight percent to 3.0 weight percent, 3.0 weight percent to 3.1 weight percent, 3.1 weight percent to 3.2 weight percent, 3.2 weight percent to 3.3 weight percent, 3.3 weight percent to 3.4 weight percent, 3.4 weight percent to 3.5 weight percent, 3.5 weight percent to 3.6 weight percent, 3.6 weight percent to 3.7 weight percent, 3.7 weight percent to 3.8 weight percent, 3.8 weight percent to 3.9 weight percent, 3.9 weight percent to 4.0 weight percent.

In embodiments, the weight percent of caustic in the final emulsion product includes at least one caustic weight percent range that is selected from the caustic weight percent ranges selected from the group consisting of: 1 weight percent to 2 weight percent, 2 weight percent to 3 weight percent, 3 weight percent to 4 weight percent, 4 weight percent to 5 weight percent.

In embodiments, the weight percent of water in the final emulsion product includes at least one caustic water percent range that is selected from the water weight percent ranges selected from the group consisting of: 80 to 85 weight percent, 85 to 90 weight percent, 90 to 95 weight percent, to 96 weight percent, 96 to 97 weight percent, 97 to 98 weight percent, 98 to 99 weight percent, 99 to 99.5 weight percent, 99.5 to 99.99 weight percent, and 99.99 to 99.999 weight percent.

In embodiments, the weight percent of treated water in the final emulsion product includes at least one treated water percent range that is selected from the treated water weight percent ranges selected from the group consisting of: 90 weight percent to 91 weight percent, 91 weight percent to 92 weight percent, 92 weight percent to 93 weight percent, 93 weight percent to 94 weight percent, 94 weight percent to 95 weight percent, 95 weight percent to 95.50 weight percent, 95.50 weight percent to 96.00 weight percent, 96.00 weight percent to 96.50 weight percent, 96.50 weight percent to 97.00 weight percent, 97.00 weight percent to 97.50 weight percent, 97.50 weight percent to 98.00 weight percent, 98.00 weight percent to 98.25 weight percent, 98.25 weight percent to 98.50 weight percent, 98.50 weight percent to 98.75 weight percent, 98.75 weight percent to 99.00 weight percent, 99.00 weight percent to 99.25 weight percent, 99.25 weight percent to 99.50 weight percent, 99.50 weight percent to 99.55 weight percent, 99.55 weight percent to 99.60 weight percent, 99.60 weight percent to 99.65 weight percent, 99.65 weight percent to 99.70 weight percent, 99.70 weight percent to 99.75 weight percent, 99.75 weight percent to 99.80 weight percent, 99.80 weight percent to 99.85 weight percent, 99.85 weight percent to 99.90 weight percent, 99.90 weight percent to 99.95 weight percent, 99.950 weight percent to 99.955 weight percent, 99.955 weight percent to 99.960 weight percent, 99.960 weight percent to 99.965 weight percent, 99.965 weight percent to 99.970 weight percent, 99.970 weight percent to 99.975 weight percent, 99.975 weight percent to 99.980 weight percent, 99.980 weight percent to 99.985 weight percent, 99.985 weight percent to 99.990 weight percent, 99.990 weight percent to 99.995 weight percent, 99.995 weight percent to 99.996 weight percent, 99.996 weight percent to 99.997 weight percent, 99.997 weight percent to 99.998 weight percent, 99.998 weight percent to 99.999 weight percent, and 99.999 weight percent to 99.9999 weight percent.

In embodiments, the weight percent of lipids and or an oil in the colloidal dispersion includes at least one caustic water percent range that is selected from the water weight percent ranges selected from the group consisting of: 80 to 85 weight percent, 85 to 90 weight percent, 90 to 95 weight percent, 95 to 96 weight percent, 96 to 97 weight percent, 97 to 98 weight percent, 98 to 99 weight percent, 99 to 99.5 weight percent, 99.5 to 99.99 weight percent, and 99.99 to 99.999 weight percent.

In embodiments, a homogenizer may be configured to homogenize a cannabinoid, a solvent, water, an emulsifier, the colloid, a lipid, a fatty acid, an oil, an acid/caustic, a biocatalyst, drugs, and a caustic material. In embodiments, homogenization may include any number of several processes used to make a mixture of two mutually non-soluble liquids the same throughout. In embodiments, homogenization is used to create an emulsion and/or the colloidal dispersion. In embodiments, an emulsification system may be configured to emulsify a cannabinoid, a cannabinoid glycoside, a solvent, water, an emulsifier, the colloid, a lipid, a fatty acid, an oil, an acid/caustic, a biocatalyst, drugs, and a caustic material, insects, and/or biomass. In embodiments, emulsification may include any number of several processes used to make a mixture of two mutually non-soluble liquids the same throughout. In embodiments, an emulsification system is used to create an emulsion.

In embodiments, a mixture of cannabinoids, solvents, an oil, lipids, water, an emulsifier, an acid/caustic, a biocatalyst, and drugs is introduced to an emulsification system at a pressure greater than the emulsion that is discharged from the emulsifier system. In embodiments, the pressure drop across the emulsification system is selected from one or more pressure drop ranges selected from the group consisting of 25 pounds per square inch (PSI) to 50 PSI, 50 PSI to 100 PSI, 100 PSI to 200 PSI, 200 PSI to 300 PSI, 300 PSI to 400 PSI, 400 PSI to 500 PSI, 500 PSI to 600 PSI, 600 PSI to 700 PSI, 700 PSI to 800 PSI, 800 PSI to 900 PSI, 900 PSI to 1,000 PSI, 1,000 PSI to 1,500 PSI, 1,500 PSI to 2,000 PSI, 2,000 PSI to 2,500 PSI, 2,500 PSI to 3,000 PSI, 3,000 PSI to 3,500 PSI, 3,500 PSI to 4,000 PSI, 4,000 PSI to 4,500 PSI, 4,500 PSI to 5,000 PSI, 5,000 PSI to 5,500 PSI, 5,500 PSI to 6,000 PSI, 6,000 PSI to 6,500 PSI, 6,500 PSI to 7,000 PSI, 7,000 PSI to 7,500 PSI, 7,500 PSI to 8,000 PSI, 8,000 PSI to 8,500 PSI, 8,500 PSI to 9,000 PSI, 9,000 PSI to 9,500 PSI, 9,500 PSI to 10,000 PSI, 10,000 PSI to 11,000 PSI, 11,000 PSI to 12,000 PSI, 12,000 PSI to 13,000 PSI, 13,000 PSI to 14,000 PSI, 14,000 PSI to 15,000 PSI, 15,000 PSI to 16,000 PSI, 16,000 PSI to 17,000 PSI, 17,000 PSI to 18,000 PSI, 18,000 PSI to 19,000 PSI, 19,000 PSI to 20,000 PSI, 20,000 PSI to 22,500 PSI, 22,500 PSI to 25,000 PSI, 25,000 PSI to 27,500 PSI, 27,500 PSI to 30,000 PSI, 30,000 PSI to 35,000 PSI. and 35,000 PSI to 40,000 PSI.

In embodiments the emulsion and/or the colloidal dispersion is produced under inert gas conditions in the presence of a gas such as and not only including carbon dioxide, nitrogen, or argon. In embodiments, an inert gas is introduced to the emulsion/colloid mixing tank to prolong the life of the emulsion and/or colloid product. The gas supply system is configured to continuously maintain a positive pressure in the vapor space within the emulsion/colloid mixing tank.

In embodiments, the beverage produced from the emulsion and/or the colloid includes carbon dioxide. In embodiments, the carbon dioxide is colorless, odorless, nonflammable, has a melting point or sublimination temperature ranging from −120 to −100 degrees Fahrenheit, a critical temperature ranging from 70 to 90 degrees Fahrenheit, a vapor pressure ranging from 800 to 875 PSIG, a vapor density ranging from 1.25 to 1.75, a specific volume ranging from 8 to 9 ft$^3$/lb, and a gas density ranging from 0.1 to 0.15 lb/ft$^3$.

In embodiments, the beverage includes carbon dioxide solubility coefficient. In embodiments, the solubility coefficient is the volume of carbon dioxide that can be dissolved by a unit volume of beverage (e.g. treated water) at a specified pressure and temperature. In embodiments, the solubility coefficient the solubility coefficient of carbon dioxide in the water-based beverage is the reciprocal of Henrys law coefficient H. In embodiments, Henrys law coefficient H applies to *cannabis*-derived beverages (or insect-derived beverages, psilocybin beverages, drug-infused beverages, etc.). and is a gas law that states that the amount of dissolved carbon dioxide in water within the beverage is proportional to its partial pressure above the beverage.

In embodiments, solubility of carbon dioxide in the beverage includes one or more solubility coefficient ranges selected from the group consisting of 0.50 to 1.00, 1.00 to 1.50, 1.50 to 2.00, 2.00 to 2.50, 2.50 to 3.00, 3.00 to 3.50, 3.50 to 4.00, 4.00 to 4.50, 4.50 to 5.00, 5.00 to 5.50 to 6.00, 6.00 to 6.50, 6.50 to 7.00, 7.00 to 7.50, 7.50 to 8.00, 8.00 to 8.50, 8.50 to 9.00, 9.00 to 9.50, 9.50 to 10.00, 10.00 to 10.50, 10.50 to 11.00, 11.00 to 11.50, 11.50 to 12.00, 12.00 to 12.50, 12.50 to 13.00, 13.00 to 13.50, 13.50 to 14.00, 14.00 to 14.50, and 14.50 to 15.00.

In embodiments, solubility of carbon dioxide in the beverage includes one or more Bunsen coefficient ranges selected from the group consisting of 0.50 to 1.00, 1.00 to 1.50, 1.50 to 2.00, 2.00 to 2.50, 2.50 to 3.00, 3.00 to 3.50, 3.50 to 4.00, 4.00 to 4.50, 4.50 to 5.00, 5.00 to 5.50, 5.50 to 6.00, 6.00 to 6.50, 6.50 to 7.00, 7.00 to 7.50, 7.50 to 8.00, 8.00 to 8.50, 8.50 to 9.00, 9.00 to 9.50, 9.50 to 10.00, 10.00 to 10.50, 10.50 to 11.00, 11.00 to 11.50, 11.50 to 12.00, 12.00 to 12.50, 12.50 to 13.00, 13.00 to 13.50, 13.50 to 14.00, 14.00 to 14.50, and 14.50 to 15.00, wherein: the Bunsen coefficient the number of milliliters of gas dissolved in a milliliter of liquid at atmospheric pressure (760 mm Hg) and a specified temperature.

In embodiments, solubility of carbon dioxide in the beverage is determined by the Zahm-Nagel technique which calculates carbon dioxide levels within the beverages using measurements of headspace of the tank or beverage, partial pressure, and beverage temperature.

In embodiments, solubility of carbon dioxide in the beverage is measured with a beverage carbonation tester. In embodiments, the beverages is bottled in a bottle, wherein the bottle is clear, brown, green, or amber colored. In embodiments, the beverages is bottled in a plastic bottle, wherein the plastic bottle is comprised of polyethylene terephthalate (PET or PETE or Polyester), high-density polyethylene (HDPE), polyvinyl chloride (PVC), low-density polyethylene (LDPE), polypropylene (PP), polystyrene (PS). In embodiments, the beverage is bottled in a metal can, wherein the metal can includes tin, aluminum, or copper, or mixtures of tin and aluminum.

In embodiments, solubility of carbon dioxide in the beverage is measured with a variety of instruments provided by Zahm & Nagel Co., Inc. of 210 Vermont Street, Holland, NY 14080 USA, which include: the Series 1000 carbon dioxide Volume Meter, the Series 6000 Zahm Model D.T. Piercing Device, the Series 7000 Zahm New Style Air Tester with Dial Thermometer, and the Series 11000 Zahm Modified Piercing Device.

The Series 1000 carbon dioxide Volume Meter (Part #1000D) is used to determine average carbon dioxide levels of gas in the beverage tank or bottle by using a piston release mechanism. In embodiments, the beverage is bottled in a glass bottle, wherein the glass bottle is clear, brown, green, or amber colored.

The Series 6000 Zahm Model D.T. Piercing Device (Part #6000) is used to test the carbonated beverage for volumes of carbon dioxide gas in glass/PET bottles and cans; this instrument uses a dual scale pressure gauge (0-60 psi &

0-4.2 kg/cm2) and an adjustable 2" dial thermometer (25/ 125° F. & −5/55° C.). It is available in one and three liter sizes. The Series 6000 Piercing Device will provide rapid and accurate determination of carbon dioxide gas volumes in beverages described herein.

The Series 7000 Zahm New Style Air Tester with Dial Thermometer (Part #7000) is used to test beverage or product for carbon dioxide gas and air content in either glass or PET containers and cans. It is automatically adjustable to various size bottles and cans and is available in either one or two liter sizes. This instrument can be used to determine the headspace "air" within the beverage bottle, wherein the headspace "air" is defined as atmospheric air picked up during the brewing or bottling process. In embodiments, the bottle's headspace is an inert gas, such as nitrogen and/or carbon dioxide.

The Series 11000 Zahm Modified Piercing Device (Part #11000) is used when a separately mounted burette is preferred for air testing or where a fast, simple closure piercing unit is required to measure pressure. Where samples are tested at room or known temperature, gas pressure can be quickly obtained to determine carbon dioxide gas volumes.

In embodiments, the solubility coefficient affects the type of beverage, stability, shelf-life, packing options, and sensory aspects of the beverage. In embodiments, the beverage has a shelf life ranging from 2 months to 4 months, 4 months to 6 months, 6 months to 8 months, 8 months to 10 months, 10 months to 12 months, 12 months to 14 months, 14 months to 16 months, 16 months to 18 months, 18 months to 20 months, 20 months to 22 months, 22 months to 24 months, 24 months to 26 months, 26 months to 28 months, 28 months to 30 months, 30 months to 32 months, 32 months to 34 months, 34 months to 36 months, 36 months to 38 months, 38 months to 40 months, 40 months to 42 months, 42 months to 44 months, 44 months to 46 months, 46 months to 48 months, 48 months to 50 months, 50 months to 52 months, 52 months to 54 months, 54 months to 56 months, 56 months to 58 months, and 58 months to 60 months. For example, in embodiments, the beverage has a shelf life ranging from 12 months to 24 months. For example, in embodiments, the beverage has a shelf life ranging from 18 months to 30 months. For example, in embodiments, the beverage has a shelf life ranging from 12 months to 48 months. For example, in embodiments, the beverage has a shelf life ranging from 14 months to 48 months.

FIG. 17J displays an acid-caustic distribution system (JAA) including an acid-caustic tank (JAB) that is configured to accept acid-caustic (JAD). The acid-caustic tank (JAB) has an interior (JAC), an acid-caustic input (JAF), an acid-caustic conveyor (JAG), and an acid-caustic conveyor output (JAH). The acid-caustic tank (JAB) accepts acid and/or caustic (JAD) to the interior (JAC) and regulates and controls an engineered amount of acid and/or caustic (JAD) downstream to be mixed to form an emulsion and/or a colloidal dispersion. The acid-caustic conveyor (6B5) has an integrated mass sensor (JAJ) that is configured to input and output a signal (JAK) to the computer (COMP). The acid-caustic conveyor motor (JAL) has a controller (JAM) that is configured to input and output a signal (JAN) to the computer (COMP). The mass sensor (JAJ), acid-caustic conveyor (JAG), and acid-caustic conveyor motor (JAL) are coupled so as to permit the conveyance, distribution, or output of a precise flow of acid and/or caustic (JAD) via an acid-caustic transfer line (JAI). It is to be noted that the acid-caustic may be in solid, powder, liquid, or slurry form. Transferring an engineered amount of acid and/or caustic (JAD) downstream to be mixed to form an emulsion and/or a colloidal dispersion is the premise of the disclosure and is not limited to regulating as a solid, powder, liquid, gel, slurry, or the equivalent.

FIG. 17J displays a biocatalyst distribution system (JBA) including a biocatalyst tank (JBB) that is configured to accept a biocatalyst (JBD). The biocatalyst tank (JBB) has an interior (JBC), a biocatalyst input (JBF), a biocatalyst conveyor (JBG), and a biocatalyst conveyor output (JBH). The biocatalyst tank (JBB) accepts a biocatalyst (JBD) to the interior (JBC) and regulates and controls an engineered amount of biocatalyst (JBD) downstream to be mixed to form an emulsion and/or a colloidal dispersion. The biocatalyst conveyor (6B5) has an integrated mass sensor (JBJ) that is configured to input and output a signal (JBK) to the computer (COMP). The biocatalyst conveyor motor (JBL) has a controller (JBM) that is configured to input and output a signal (JBN) to the computer (COMP). The mass sensor (JBJ), biocatalyst conveyor (JBG), and biocatalyst conveyor motor (JBL) are coupled so as to permit the conveyance, distribution, or output of a precise flow of biocatalyst (JBD) via a biocatalyst transfer line (JBI). It is to be noted that the biocatalyst may be in solid, powder, liquid, or slurry form. Transferring an engineered amount of biocatalyst (JBD) downstream to be mixed to form an emulsion and/or a colloidal dispersion is the premise of the disclosure and is not limited to regulating as a solid, powder, liquid, gel, slurry, or the equivalent.

FIG. 17J displays a drug distribution system (JCA) including a drug tank (JCB) that is configured to accept a drug (JCD). The drug tank (JCB) has an interior (JCC), a drug input (JCF), a drug conveyor (JCG), and a drug conveyor output (JCH). The drug tank (JCB) accepts drugs (JCD) to the interior (JCC) and regulates and controls an engineered amount of drugs (JCD) downstream to be mixed to form an emulsion and/or a colloidal dispersion. The drug conveyor (6B5) has an integrated mass sensor (JCJ) that is configured to input and output a signal (JCK) to the computer (COMP). The drug conveyor motor (JCL) has a controller (JCM) that is configured to input and output a signal (JCN) to the computer (COMP). The mass sensor (JCJ), drug conveyor (JCG), and drug conveyor motor (JCL) are coupled so as to permit the conveyance, distribution, or output of a precise flow of drugs (JCD) via a drug transfer line (JCI). It is to be noted that the drugs may be in solid, powder, liquid, or slurry form. Transferring an engineered amount of drugs (JCD) downstream to be mixed to form an emulsion and/or a colloidal dispersion is the premise of the disclosure and is not limited to regulating as a solid, powder, liquid, gel, slurry, or the equivalent.

FIG. 17J displays an emulsifier distribution system (JDA) including an emulsifier tank (JDB) that is configured to accept an emulsifier (JDD). The emulsifier tank (JDB) has an interior (JDC), an emulsifier input (JDF), an emulsifier conveyor (JDG), and an emulsifier conveyor output (JDH). The emulsifier tank (JDB) accepts an emulsifier (JDD) to the interior (JDC) and regulates and controls an engineered amount of emulsifier (JDD) downstream to be mixed to form an emulsion and/or a colloidal dispersion. The emulsifier conveyor (6B5) has an integrated mass sensor (JDJ) that is configured to input and output a signal (JDK) to the computer (COMP). The emulsifier conveyor motor (JDL) has a controller (JDM) that is configured to input and output a signal (JDN) to the computer (COMP). The mass sensor (JDJ), emulsifier conveyor (JDG), and emulsifier conveyor motor (JDL) are coupled so as to permit the conveyance, distribution, or output of a precise flow of emulsifier (JDD)

via an emulsifier transfer line (JDI). It is to be noted that the emulsifier may be in solid, powder, liquid, or slurry form. Transferring an engineered amount of emulsifier (JDD) downstream to be mixed to form an emulsion is the premise of the disclosure and is not limited to regulating as a solid, powder, liquid, gel, slurry, or the equivalent.

FIG. 17J displays an extract distribution system (JEA) including an extract tank (JEB) that is configured to accept an extract (JED). The extract tank (JEB) has an interior (JEC), an extract input (JEF), an extract conveyor (JEG), and an extract conveyor output (JEH). The extract tank (JEB) accepts an extract (JED) to the interior (JEC) and regulates and controls an engineered amount of extract (JED) downstream to be mixed to form an emulsion and/or a colloidal dispersion. The extract conveyor (6B5) has an integrated mass sensor (JEJ) that is configured to input and output a signal (JEK) to the computer (COMP). The extract conveyor motor (JEL) has a controller (JEM) that is configured to input and output a signal (JEN) to the computer (COMP). The mass sensor (JEJ), extract conveyor (JEG), and extract conveyor motor (JEL) are coupled so as to permit the conveyance, distribution, or output of a precise flow of extract (JED) via an extract transfer line (JEI). It is to be noted that the extract may be in solid, powder, liquid, or slurry form. Transferring an engineered amount of extract (JED) downstream to be mixed to form an emulsion and/or a colloidal dispersion is the premise of the disclosure and is not limited to regulating as a solid, powder, liquid, gel, slurry, or the equivalent.

In embodiments, the extract is not only including from: (VOLT) from FIG. 17A, 17A', 17B, a cannabinoid and liquid mixture (SVSM) from FIG. 17C, a concentrated cannabinoid (CVOLT) from FIG. 17D, 17D' (which may or may not include a solvent), cannabinoid powder/particulate from FIG. 17E, and/or extract from FIG. 17H. In embodiments, the extract comes from any disclosed Figure in this patent specification, such as from FIG. 18A, 18E, or 18F.

FIG. 17J displays a lipid distribution system (JFA) including a lipid tank (JFB) that is configured to accept a lipid (JFD). The lipid tank (JFB) has an interior (JFC), an lipid input (JFF), an insect conveyor (JFG) (or pump, the conveyors listed on FIG. 17J may be pumps to convey a liquid), and an lipid conveyor output (JFH). The lipid tank (JFB) accepts an lipid (JFD) to the interior (JFC) and regulates and controls an engineered amount of lipids (JFD) downstream to be mixed to form an emulsion. The lipid conveyor (6B5) has an integrated mass sensor (JFJ) that is configured to input and output a signal (JFK) to the computer (COMP). The lipid conveyor motor (JFL) has a controller (JFM) that is configured to input and output a signal (JFN) to the computer (COMP). The mass sensor (JFJ), lipid conveyor (JFG), and lipid conveyor motor (JFL) are coupled so as to permit the conveyance, distribution, or output of a precise flow of lipids (JFD) via an lipid transfer line (JFI). It is to be noted that the lipids may be in liquid, colloid, or slurry form. Transferring an engineered amount of lipids (JFD) downstream to be mixed to form an emulsion is the premise of the disclosure and is not limited to regulating as a solid, powder, liquid, gel, slurry, or the equivalent. In embodiments, the lipids (JFD) include one or more selected from the group consisting of neem oil, almond oil, animal-based oils, apricot kernel oil, avocado oil, brazil nut oil, butter, *cannabis* oil, canola oil, cashew oil, cocoa butter, coconut oil, cooking oil, corn oil, cottonseed oil, fish oil, grapeseed oil, hazelnut oil, hemp oil, insect oil, lard, lard oil, macadamia nut oil, mustard oil, olive oil, palm kernel oil, palm oil, peanut oil, rapeseed oil, rice oil, rice bran oil, safflower oil, semi-refined sesame oil, semi-refined sunflower oil, sesame oil, soybean oil, tallow of beef, tallow of mutton, vegetable oil, walnut oil, a medium chain triglyceride, insect lipids, a fatty acid, lauric acid, palmitic acid, linoleic acid, alpha-linoleic acid, oleic acid, gamma-linoleic acid, and/or stearic acid.

FIG. 17J displays a biomass distribution system (JGA) including a biomass tank (JGB) that is configured to accept biomass (JGD). The biomass tank (JGB) has an interior (JGC), a biomass input (JGF), a biomass conveyor (JGG), and a biomass conveyor output (JGH). The biomass tank (JGB) accepts biomass (JGD) to the interior (JGC) and regulates and controls an engineered amount of biomass (JGD) downstream to be mixed to form an emulsion. The biomass conveyor (6B5) has an integrated mass sensor (JGJ) that is configured to input and output a signal (JGK) to the computer (COMP). The biomass conveyor motor (JGL) has a controller (JGM) that is configured to input and output a signal (JGN) to the computer (COMP). The mass sensor (JGJ), biomass conveyor (JGG), and biomass conveyor motor (JGL) are coupled so as to permit the conveyance, distribution, or output of a precise flow of biomass (JGD) via a biomass transfer line (JGI). It is to be noted that the biomass may be in solid, powder, liquid, or slurry form. Transferring an engineered amount of biomass (JGD) downstream to be mixed to form an emulsion is the premise of the disclosure and is not limited to regulating as a solid, powder, liquid, gel, slurry, or the equivalent.

In embodiments, an emulsion/colloid mixing tank (JLE) is configured to accept acid and/or caustic (JAD) via an acid-caustic transfer line (JAI), biocatalyst (JBD) via a biocatalyst transfer line (JBI), drugs (JCD) via a drug transfer line (JCI), emulsifier (JDD) via an emulsifier transfer line (JDI), extract (JED) via an extract transfer line (JEI), as a first input (JLA) through a first input (JLA). In embodiments, an emulsion/colloid mixing tank (JLE) is configured to accept lipids (JFD) via an lipid transfer line (JFI), and biomass (JGD) via a biomass transfer line (JGI) as a second mixture (JLD) through a second input (JLC). It is to be noted that the first input (JLA) through a first input (JLA) and the second mixture (JLD) through a second input (JLC) are non-limiting and it is true that each of the acid and/or caustic (JAD), biocatalyst (JBD), drugs (JCD), emulsifier (JDD), extract (JED), lipids (JFD), and biomass (JGD) through one input or each having their own input to the emulsion/colloid mixing tank (JLE). In embodiments, the mixing tank (G15) as shown in FIG. 14G is the same vessel as the emulsion/colloid mixing tank (JLE) as shown in FIG. 17J.

In embodiments, a water supply (JKA) is made available to the emulsion/colloid mixing tank (JLE). In embodiments, a water supply (JKA) transferred to the emulsion/colloid mixing tank (JLE) is first treated in a first water treatment unit (JKB), second water treatment unit (JKC), and a third water treatment unit (JKD) to form treated water (JKE).

In embodiments, the first water treatment unit (JKB) includes one or more selected from the group consisting of a cation, an anion, a membrane, a filter, activated carbon, an adsorbent, an absorbent, an ultraviolet unit, an ozone unit, a microwave unit, and/or a distillation system. In embodiments, the second water treatment unit (JKC) includes one or more selected from the group consisting of a cation, an anion, a membrane, a filter, activated carbon, an adsorbent, an absorbent, an ultraviolet unit, an ozone unit, a microwave unit, and/or a distillation system. In embodiments, the third water treatment unit (JKD) includes one or more selected from the group consisting of a cation, an anion, a membrane, a filter, activated carbon, an adsorbent, an absorbent, an ultraviolet unit, an ozone unit, a microwave unit, and/or a distillation system. In embodiments, the adsorbent includes one or more selected from the group consisting of 3 Angstrom molecular sieve, 3 Angstrom zeolite, 4 Angstrom molecular sieve, 4 Angstrom zeolite, activated alumina, activated carbon, adsorbent, alumina, carbon, catalyst, clay, desiccant, molecular sieve, polymer, resin, and silica gel. In embodiments, the cation is configured to remove positively charged ions from the water supply (JKA), the positively charged ions are comprised of one or more from the group consisting of calcium, magnesium, sodium, and iron. In embodiments, the anion is configured to remove negatively charged ions from the water supply (JKA), the negatively charged ions are comprised of one or more from the group consisting of iodine, chloride, and sulfate. In embodiments, the membrane is configured to remove undesirable compounds from the water supply (JKA), the undesirable compounds are comprised of one or more from the group consisting of dissolved organic chemicals, viruses, bacteria, and particulates. In embodiments, the membrane has a diameter that ranges from 1 inch to 6 inches and a pore size ranging from 0.0001 microns to microns.

In embodiments, the water treatment unit in any embodiment described herein includes a distillation system. In embodiments, treated water is treated with a distillation system. In embodiments, the electrical conductivity of the treated water treated by the distillation system includes one or more selected from the group consisting of: 0.1 μS to 0.5 μS, 0.5 μS to 1.00 μS, 1.00 μS to 1.25 μS, 1.25 μS to 1.50 μS, 1.50 μS to 1.75 μS, 1.75 μS to 2.00 μS, 2.00 μS to 2.25 μS, 2.25 μS to 2.50 μS, 2.50 μS to 2.75 μS, 2.75 μS to 3.00 μS, 3.00 μS to 3.25 μS, 3.25 μS to 3.50 μS, 3.50 μS to 3.75 μS, 3.75 μS to 4.00 μS, 4.00 μS to 4.25 μS, 4.25 μS to 4.50 μS, 4.50 μS to 4.75 μS, 4.75 μS to 5.00 μS, 5.00 μS to 5.25 μS, 5.25 μS to 5.50 μS, 5.50 μS to 5.75 μS, 5.75 μS to 6.00 μS, 6.00 μS to 6.25 μS, 6.25 μS to 6.50 μS, 6.50 μS to 6.75 μS, 6.75 μS to 7.00 μS, 7.00 μS to 7.25 μS, 7.25 μS to 7.50 μS, 7.50 μS to 7.75 μS, 7.75 μS to 8.00 μS, 8.00 μS to 8.25 μS, 8.25 μS to 8.50 μS, 8.50 μS to 8.75 μS, 8.75 μS to 9.00 μS, 9.00 μS to 9.25 μS, 9.25 μS to 9.50 μS, 9.50 μS to 9.75 μS, 9.75 μS to 10.00 μS. In embodiments, μS means μS per centimeter.

In embodiments, treated water (JKE) is discharged from the first water treatment unit (JKB), second water treatment unit (JKC), and/or the third water treatment unit (JKD). In embodiments, treated water (JKE) has less positively charged ions, negatively charged ions, and undesirable compounds relative to the supply (JKA). In embodiments, a valve (HJI) is configured to regulate the flow of the treated water (HJA) that leaves the first water treatment unit (HJK), second water treatment unit (HJL), and/or the third water treatment unit (HJM). In embodiments, a quality sensor (JKG) is configured to measure the quality of the treated water (JKE) that leaves the first water treatment unit (HJK), second water treatment unit (HJL), and/or the third water treatment unit (HJM). For example, the quality sensor (JKG) may measure the electrical conductivity of the treated water (JKE) to determine if either of the first water treatment unit (HJK), second water treatment unit (HJL), and/or the third water treatment unit (HJM) require maintenance and/or cleaning. In embodiments, the quality sensor (HJN) measures the electrical conductivity of the treatment unit (HJM) to ensure that the electrical conductivity ranges from 0.10 microsiemens per centimeter to 100 microsiemens per centimeter.

In embodiments, a treated water pump (JKH) is provided and is configured to accept the treated water (JKE) from either one of the first water treatment unit (HJK), second water treatment unit (HJL), and/or the third water treatment unit (HJM). In embodiments, a valve (JKK) is configured to regulate the flow of the treated water (JKE) that leaves the treated water pump (JKH). In embodiments, a pressure sensor (HFB) is configured to measure the pressure of the treated water (JKE) that leaves the treated water pump (JKH). In embodiments, a flow sensor (HFC) is configured to measure the flow of the treated water (JKE) that leaves the treated water pump (JKH). In embodiments, the treated water (JKE) that leaves the treated water pump (JKH) has a pressure that includes one or more pressure ranges selected from the group consisting of 10 pounds per square inch (PSI) to 20 PSI, 20 PSI to 40 PSI, 40 PSI to 60 PSI, 60 PSI to 80 PSI, 80 PSI to 100 PSI, 100 PSI to 125 PSI, 125 PSI to 150 PSI, 150 PSI to 175 PSI, 175 PSI to 200 PSI, 200 PSI to 225 PSI, 225 PSI to 250 PSI, 250 PSI to 275 PSI, 275 PSI to 300 PSI, 300 PSI to 325 PSI, 325 PSI to 350 PSI, 350 PSI to 375 PSI, 375 PSI to 400 PSI, 400 PSI to 425 PSI, 425 PSI to 450 PSI, 450 PSI to 475 PSI, and 475 PSI to 500 PSI.

In embodiments, an emulsion/colloid mixing tank (JLE) is provided to mix the acid and/or caustic (JAD), biocatalyst (JBD), drugs (JCD), emulsifier (JDD), extract (JED), lipids (JFD), and biomass (JGD) through one input or each having their own input to the emulsion/colloid mixing tank (JLE).

In embodiments, an emulsion/colloid mixing tank (JLE) has an interior (JLF). In embodiments, the emulsion/colloid mixing tank (JLE) has have a heating jacket (JLN) to serve the purpose of the heat exchanger (JLM). The emulsion/colloid mixing tank (JLE) with a heating jacket (JLN) is a vessel that is designed for controlling the temperature of its contents, by using a heating jacket around the vessel through which a heat transfer medium (e.g.—steam) is circulated. The heating jacket (JLN) is a cavity external to the interior (JLF) of the emulsion/colloid mixing tank (JLE) that permits the uniform exchange of heat between the heat transfer medium circulating in it and the walls of the emulsion/colloid mixing tank (JLE). FIG. 17J shows the heating jacket (JLN) installed over a portion of the emulsion/colloid mixing tank (JLE) creating an interior (JLO) having an annular space within which a heat transfer medium flows.

The heating jacket (JLN) has a heat transfer medium inlet (JLP) and a heat transfer medium outlet (JLQ). Steam (JLR) is introduced to the heat transfer medium inlet (JLP). Steam condensate (JLT) is discharged from the heat transfer medium outlet (JLQ). Steam (JLR) is introduced to the heat transfer medium inlet (JLP) of the heating jacket (JLN) of the emulsion/colloid mixing tank (JLE) via a steam inlet conduit (JLS). The steam inlet conduit (JLS) is connected to the heat transfer medium inlet (JLP) and is configured to transfer steam (JLR) to the interior (JLO) of the heating jacket (JLN).

In embodiments, a steam supply (LDM) is provided to the heating jacket (JLN) and/or to the heat exchanger (JLM) and is provided from FIG. 17F. In embodiments, the steam condensate (JLT) that is discharged from the heat transfer medium outlet (JLQ) is transferred to the condensate tank (LAP) shown in FIG. 17F.

A steam supply valve (JLU) is interposed on the steam inlet conduit (JLS). The steam supply valve (JLU) is equipped with a controller (JLV) that inputs and outputs a signal (JLW) to the computer (COMP). In embodiments, the steam supply valve (JLU) is positioned to regulate the mass of heat transfer medium that leaves the heating jacket (JLN) via the discharged from the heat transfer medium outlet (JLQ).

In embodiments, a temperature sensor (JMA) measures the temperature of the contents within the interior (JLF) of the emulsion/colloid mixing tank (JLE). The temperature sensor (JMA) is configured to output a signal (JMB) to the computer (COMP). A pre-determined setpoint for the emulsion/colloid mixing tank (JLE) temperature sensor (JMA) may be inputted to the computer (COMP). In response to the pre-determined setpoint, the computer (COMP) regulates the modulation of the steam supply valve (JLU). The preferred modulation range of the steam supply valve (JLU) ranges from 33% open to 66% open. In embodiments, the preferred modulation range of the steam supply valve (JLU) ranges from: 5% open to 10% open; 10% open to 15% open; 15% open to 20% open; 20% open to 30% open; 30% open to 40% open; 40% open to 50% open; 50% open to 60% open; 60% open to 70% open.

In embodiments, the emulsion/colloid mixing tank (JLE) has a plurality of baffles (ThI, JLJ) that are positioned within the interior (JLF). Each baffle (JLI, JLJ) is configured to promote mixing and increase heat transfer and to create an emulsion.

The pressure drop across the steam supply valve (JLU) ranges from between: 1 pound per square inch (PSI) to 2 PSI; 2 pounds per square inch (PSI) to 5 PSI; 5 pounds per square inch (PSI) to 10 PSI; 10 pounds per square inch (PSI) to 20 PSI; 20 pounds per square inch (PSI) to 40 PSI; pounds per square inch (PSI) to 60 PSI; 60 pounds per square inch (PSI) to 80 PSI; 80 pounds per square inch (PSI) to 100 PSI; 100 pounds per square inch (PSI) to 125 PSI; 125 pounds per square inch (PSI) to 150 PSI; 150 pounds per square inch (PSI) to 200 PSI.

The velocity of steam in the steam inlet conduit (JLR) ranges from: 35 feet per second to 45 feet per second; 45 feet per second to 55 feet per second; 55 feet per second to 65 feet per second; 65 feet per second to 75 feet per second; 75 feet per second to 85 feet per second; 85 feet per second to 95 feet per second; 95 feet per second to 105 feet per second; 105 feet per second to 115 feet per second; 115 feet per second to 125 feet per second; 125 feet per second to 135 feet per second; 135 feet per second to 145 feet per second; 145 feet per second to 155 feet per second; 155 feet per second to 175 feet per second. The velocity of steam condensate discharged from the heat transfer medium outlet (G91) is less than 3 feet per second.

In embodiments, the heat transfer medium inlet (JLP) is comprised of one or more from the group consisting of: a Class 150 flange, a Class 300 flange, sanitary clamp fitting, national pipe thread, or compression fitting. In embodiments, the heat transfer medium outlet (JLQ) is comprised of one or more from the group consisting of: a Class 150 flange, a Class 300 flange, sanitary clamp fitting, national pipe thread, or compression fitting. In embodiments, the emulsion/colloid mixing tank (JLE) is comprised of stainless steel or carbon steel and may be ceramic or glass-lined. In embodiments, the heating jacket (JLN) is comprised of stainless steel or carbon steel and may be ceramic or glass-lined.

In embodiments, the temperature of the mixture within the interior (JLF) of the emulsion/colloid mixing tank (JLE) ranges from between: 50 degrees F. to 60 degrees F.; 60 degrees F. to 70 degrees F.; 70 degrees F. to 80 degrees F.; 80 degrees F. to 90 degrees F.; 90 degrees F. to 100 degrees F.; 100 degrees F. to 110 degrees F.; 110 degrees F. to 120 degrees F.; 120 degrees F. to 130 degrees F.; 130 degrees F. to 140 degrees F.; 140 degrees F. to 150 degrees F.; 150 degrees F. to 160 degrees F.; 160 degrees F. to 170 degrees F.; 170 degrees F. to 180 degrees F.; 180 degrees F. to 190 degrees F.; 190 degrees F. to 200 degrees F.; 200 degrees F. to 212 degrees F.

In embodiments, the mixture may mixed within the interior (JLF) of the emulsion/colloid mixing tank (JLE) ranges from between: 1 minute to 5 minutes, 5 minutes to 10 minutes; 10 minutes to 20 minutes; 20 minutes to 30 minutes; 30 minutes to 40 minutes; 40 minutes to 50 minutes; 50 minutes to 1 hour; 1 hour to 1.5 hours; 1.5 hour to 2 hours; 2 hour to 3 hours; 3 hour to 4 hours; 4 hour to 5 hours; 5 hour to 6 hours; 6 hour to 12 hours; 12 hour to 18 hours; 18 hour to 24 hours; 1 day to 2 days; 2 days to 3 days; 3 days to 4 days; 4 days to 5 days; 5 days to 1 week.

In embodiments, the emulsion/colloid mixing tank (JLE) is equipped with a pH sensor (JMC) that is configured to input a signal (JMD) to the computer (COMP). In embodiments, the emulsion/colloid mixing tank (JLE) is equipped with a first emulsifier system (JME). In embodiments, the first emulsifier system (JME) is an ultrasonic homogenizer (JME). In embodiments, the ultrasonic homogenizer (JME) is equipped with a controller (JMF) that is equipped to send a signal (JMG) to and from the computer (COMP).

In embodiments, the emulsion/colloid mixing tank (JLE) has a mixture output (JMH) that discharges a mixture (JMI) from within the interior (JLF) of the emulsion/colloid mixing tank (JLE). In embodiments, the mixture (JMI) that is discharged from the interior (JLF) of the emulsion/colloid mixing tank (JLE) is an emulsion (JMX). In embodiments, the mixture (JMI) that is discharged from the interior (JLF) of the emulsion/colloid mixing tank (JLE) is transferred to a mixture pump (JMJ). In embodiments, the mixture pump (JMJ) pumps and pressurizes the mixture (JMI) that is discharged from the interior (JLF) of the emulsion/colloid mixing tank (JLE) to form a pressurized mixture (JMK). A pressure sensor (JML) is installed to measure the pressure of the pressurized mixture (JMK) and transmit a signal (JMM) to the computer (COMP). In embodiments, the pressurized mixture (JMK) is transferred to a second emulsifier system (JMN).

In embodiments, the second emulsifier system (JMN) accepts the pressurized mixture (JMK) via a mixture input (JMV). In embodiments, the second emulsifier system (JMN) has an emulsion output (JMW) for discharging an emulsion (JMX). In embodiments, the pressurized mixture (JMK) is a first emulsion (JMY) and the emulsion (JMX) discharged from the second emulsifier system (JMN) is the second emulsion (JMZ). In embodiments, at least a portion of the emulsion (JMX) discharged from the second emulsifier system (JMN) is returned to the interior (JLF) of the emulsion/colloid mixing tank (JLE) via a recycle conduit (JNA) and a recycle input (JNB). In embodiments, at least a portion of the emulsion (JMX) discharged from the second emulsifier system (JMN) is an emulsion and/or colloid product (JNC) or a pressurized emulsion product (JND).

A flow sensor (JNE) is configured to measure the flow rate of the emulsion product (JNC) and input a signal (JNF) to the computer (COMP). An emulsion product valve (JNG) is configured to regulate the flow of the emulsion product (JNC) and the emulsion product valve (JNG) is equipped with a controller (JNH) that inputs or outputs a signal (JNI) to the computer (COMP). In embodiments, the second emulsifier system (JMN) has an interior (JMO) and is equipped with a motor (JMP) that has a controller (JMQ) and is configured to input or output a signal (JMR) to the computer (COMP). In embodiments, the second emulsifier system (JMN) is equipped with a piston (JMS), a rotor-stator (JMT), or a valve and seat (JMU).

The emulsion/colloid mixing tank (JLE) may be equipped with a mixer (JLK) for mixing the contents of the interior (JLF) of the emulsion/colloid mixing tank (JLE). The mixer (JLK) may be of an auger or blade type that is equipped with a motor (JLL).

In embodiments, when the low-level sensor (JLH) sends a signal to the computer (COMP), the valve (JKK) on the discharge of the water pump (JKH) may be opened to introduce water into the interior (JLF) of the emulsion/colloid mixing tank (JLE) until the high-level sensor (JLG) is triggered thus sending a signal to the computer (COMP) to close the valve (JKK). This level control loop including the high-level sensor (JLG) for detecting a high level and a low-level sensor (JLH) for detecting a lower level may be coupled to the operation of the water supply valve (JKK) for introducing a treated water (JKE) through a first water treatment unit (JKB), a second water treatment unit (JKC), and a third water treatment unit (JKD) and into the interior (JLF) of the emulsion/colloid mixing tank (JLE).

In embodiments, the treated water (JKL) is transferred from the water pump (JKH) to form pressurized treated water (JKL). In embodiments, the pressurized treated water (JKL) is transferred through a water transfer conduit (JKM) and through a valve (JKK). In embodiments, as the pressurized treated water (JKL) passes through the valve (JKK) on the water transfer conduit (JKM), the pressurized treated water (JKL) is reduced in pressure to form a depressurized treated water (JKN) which is then introduced to the interior (JLF) of the emulsion/colloid mixing tank (JLE) via a water input (JKO).

In embodiments, a gas tank (JJA) is provided. In embodiments, the gas tank (JJA) contains a gas (JJB). In embodiments, the gas (JJB) is transferred from the gas tank (JJA) and is made available to the interior (JLF) of the emulsion/colloid mixing tank (JLE) as a gas supply (JJC). A pressure sensor (JJD) is installed to measure the pressure of the gas (JJB) within the gas tank (JJA). A pressure regulating valve (JJE) is provided to set a pressure of the gas supply conduit (JJP) to transfer gas (JJB) from the gas tank (JJA) into the interior (JLF) of the emulsion/colloid mixing tank (JLE).

A pressure sensor (JJI) is provided to measure the pressure within the gas supply conduit (JJP) and input a signal (JJH) to the computer (COMP). In embodiments, a first gas valve (JJJ) is provided to regulate the flow of gas (JJB) from the gas supply conduit (JJP) and into the interior (JLF) of the emulsion/colloid mixing tank (JLE). The first gas valve (JJJ) has a controller (JJF) that is equipped to input or output a signal (JJG) to the computer (COMP). In embodiments, a second gas valve (JJK) is provided to regulate the flow of gas (JJB) from the gas supply conduit (JJP) and into the interior (JLF) of the emulsion/colloid mixing tank (JLE). The second gas valve (JJK) has a controller (JJL) that is equipped to input or output a signal (JJM) to the computer (COMP). A pressure sensor (110) is provided to measure the pressure within the gas supply conduit (JJP) downstream of both the first gas valve (JJJ) and second gas valve (JJK) and input a signal (JJN) to the computer (COMP). A first one-way valve (JJT) is installed on the gas supply conduit (JJP) downstream of both of the first gas valve (JJJ) and second gas valve (JJK) and before the gas input (JJY) of the emulsion/colloid mixing tank (JLE). In embodiments, a second one-way valve (JJU) is provided to prevent backflow of recycled carbon dioxide (JJX) from the gas input (JJY) of the emulsion/colloid mixing tank (JLE) backwards to the CO2 recovery system on FIG. 17G.

In embodiments, the cannabinoid, cannabinoid emulsion, and/or the colloidal dispersion may be mixed with: an acidifying agent (acetic acid, glacial acetic acid, citric acid, fumaric acid, hydrochloric acid, diluted hydrochloric acid, malic acid, nitric acid, phosphoric acid, diluted phosphoric acid, sulfuric acid, and/or tartaric acid).

In embodiments, the cannabinoid, cannabinoid emulsion, and/or the colloidal dispersion may be mixed with: an alkalizing agent (ammonia solution, ammonium carbonate, diethanolamine, diisopropanolamine, potassium hydroxide, sodium bicarbonate, sodium borate, sodium carbonate, sodium hydroxide, and/or trolamine).

In embodiments, the cannabinoid, cannabinoid emulsion, and/or the colloidal dispersion may be mixed with: an antifoaming agent (dimethicone and/or simethicone).

In embodiments, the cannabinoid, cannabinoid emulsion, and/or the colloidal dispersion may be mixed with: an antimicrobial preservative (benzalkonium chloride, benzalkonium chloride solution, benzethonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, and/or thymol).

In embodiments, the cannabinoid, cannabinoid emulsion, and/or the colloidal dispersion may be mixed with: an antioxidant (ascorbic acid, ascorbyl palmitate, butylated hydroxyanisole, butylated hydroxytoluene, hypophosphorous acid, monothioglycerol, propyl gallate, sodium formaldehyde sulfoxylate, sodium metabisulfite, sodium thiosulfate, sulfur dioxide, tocopherol, and/or tocopherols excipient).

In embodiments, the cannabinoid, cannabinoid emulsion, and/or the colloidal dispersion may be mixed with: a buffering agent (acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, and/or monobasic sodium phosphate).

In embodiments, the cannabinoid, cannabinoid emulsion, and/or the colloidal dispersion may be mixed with: a chelating agent (edetate disodium, ethylenediaminetetraacetic acid and salts, and/or edetic acid).

In embodiments, the cannabinoid, cannabinoid emulsion, and/or the colloidal dispersion may be mixed with: a coating agent (sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyvinyl acetate phthalate, shellac, sucrose, titanium dioxide, carnauba wax, microcrystalline wax, and/or zein);

In embodiments, the cannabinoid, cannabinoid emulsion, and/or the colloidal dispersion may be mixed with: a colorants (caramel, red, yellow, black or blends, ferric oxide).

In embodiments, the cannabinoid, cannabinoid emulsion, and/or the colloidal dispersion may be mixed with: a complexing agent (ethylenediaminetetraacetic acid and salts (EDTA), edetic acid, gentisic acid ethanolamide, oxyquinoline sulfate).

In embodiments, the cannabinoid, cannabinoid emulsion, and/or the colloidal dispersion may be mixed with: a desiccant (calcium chloride, calcium sulfate, and/or silicon dioxide).

In embodiments, the cannabinoid, cannabinoid emulsion, and/or the colloidal dispersion may be mixed with: an emulsifying and/or a solubilizing agent (*acacia*, cholesterol, diethanolamine (adjunct), glyceryl monostearate, lanolin alcohols, mono- and di-glycerides, monoethanolamine (adjunct), lecithin, oleic acid (adjunct), oleyl alcohol (stabilizer), poloxamer, polyoxyethylene 50 stearate, polyoxyl 35 castor oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate polysorbate 80, diacetate, monostearate, sodium lauryl sulfate, sodium stearate, sorbitan monolaurate, sorbitan monooleate, sorbitan monopalmitate, sorbitan monostearate, stearic acid, trolamine, and/or emulsifying wax).

In embodiments, the cannabinoid, cannabinoid emulsion, and/or the colloidal dispersion may be mixed with: a filtering aid (powdered cellulose, and/or purified siliceous earth);

In embodiments, the cannabinoid, cannabinoid emulsion, and/or the colloidal dispersion may be mixed with: a flavor and/or a perfume (anethole, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, and/or vanillin).

In embodiments, the cannabinoid, cannabinoid emulsion, and/or the colloidal dispersion may be mixed with: a humectant (glycerol, hexylene glycol, and/or sorbitol).

In embodiments, the cannabinoid, cannabinoid emulsion, and/or the colloidal dispersion may be mixed with: a plasticizer (castor oil, diacetylated monoglycerides, diethyl phthalate, glycerol, mono- and di-acetylated monoglycerides, propylene glycol, triacetin, and/or triethyl citrate).

In embodiments, the cannabinoid, cannabinoid emulsion, and/or the colloidal dispersion may be mixed with: polymers (cellulose acetate, alkyl celluloses, hydroxyalkyl, acrylic polymer, and/or an acrylic copolymers).

In embodiments, the cannabinoid, cannabinoid emulsion, and/or the colloidal dispersion may be mixed with: a solvent (listed above and/or acetone, alcohol, diluted alcohol, amylene hydrate, benzyl benzoate, butyl alcohol, carbon tetrachloride, chloroform, corn oil, cottonseed oil, ethyl acetate, glycerol, hexylene glycol, isopropyl alcohol, methyl alcohol, methylene chloride, methyl isobutyl ketone, mineral oil, peanut oil, propylene carbonate, sesame oil, and/or treated water).

In embodiments, the cannabinoid, cannabinoid emulsion, and/or the colloidal dispersion may be mixed with: a sorbent (powdered cellulose, charcoal, and/or purified siliceous earth).

In embodiments, the cannabinoid, cannabinoid emulsion, and/or the colloidal dispersion may be mixed with: a carbon dioxide sorbents (barium hydroxide, lime, and/or soda lime).

In embodiments, the cannabinoid, cannabinoid emulsion, and/or the colloidal dispersion may be mixed with: a stiffening agent (hydrogenated castor oil, cetostearyl alcohol, cetyl alcohol, cetyl esters wax, hard fat, paraffin, polyethylene excipient, stearyl alcohol, emulsifying wax, white wax, and/or yellow wax).

In embodiments, the cannabinoid, cannabinoid emulsion, and/or the colloidal dispersion may be mixed with: a suspending and/or a viscosity-increasing agent (*acacia*, agar, alginic acid, aluminum monostearate, bentonite, purified bentonite, magma bentonite, carbomer, carboxymethylcellulose calcium, carboxymethylcellulose sodium, carboxymethylcellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, alginate, silicon dioxide, colloidal silicon dioxide, sodium alginate, tragacanth, and/or xanthan gum).

In embodiments, the cannabinoid, cannabinoid emulsion, and/or the colloidal dispersion may be mixed with: a sweetening agent (aspartame, a dextrate, dextrose, excipient dextrose, fructose, mannitol, saccharin, calcium saccharin, sodium saccharin, sorbitol, solution sorbitol, sucrose, compressible sugar, confectioners sugar, and/or a syrup).

In embodiments, the cannabinoid, cannabinoid emulsion, and/or the colloidal dispersion may be mixed with: a surfactant (simethicone).

In embodiments, the cannabinoid, cannabinoid emulsion, and/or the colloidal dispersion may be mixed with: a tablet binder (*acacia*, alginic acid, sodium carboxymethylcellulose, microcrystalline cellulose, dextrin, ethylcellulose, gelatin, liquid glucose, guar gum, hydroxypropyl methylcellulose, methylcellulose, polyethylene oxide, povidone, and/or pregelatinized starch).

In embodiments, the cannabinoid, cannabinoid emulsion, and/or the colloidal dispersion may be mixed with: a tablet and/or a capsule diluent (calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, and/or compressible sugar).

In embodiments, the cannabinoid, cannabinoid emulsion, and/or the colloidal dispersion may be mixed with: a tablet disintegrant (alginic acid, microcrystalline cellulose, croscarmellose sodium, crospovidone, polacrilin potassium, sodium starch glycolate, starch, and/or pregelatinized starch).

In embodiments, the cannabinoid, cannabinoid emulsion, and/or the colloidal dispersion may be mixed with: a tablet and/or a capsule lubricant (calcium stearate, glyceryl behenate, magnesium stearate, light mineral oil, sodium stearyl fumarate, stearic acid, purified stearic acid, talc, hydrogenated vegetable oil, and/or zinc stearate).

In embodiments, the cannabinoid, cannabinoid emulsion, and/or the colloidal dispersion may be mixed with: a thickening agent (gelatin having a Bloom strength of 50-100, an animal-free gelatin, a vegan gelatin, agar, agar-agar, kanten, carrageenan, carragean, or Irish moss vegan jel (vegetable gum adipic acid, tapioca dextrin, calcium phosphate, and/or potassium citrate)).

In embodiments, the cannabinoid, cannabinoid emulsion, and/or the colloidal dispersion may be mixed with: a tonicity agent (dextrose, glycerol, mannitol, potassium chloride, and/or sodium chloride).

In embodiments, the cannabinoid, cannabinoid emulsion, and/or the colloidal dispersion may be mixed with: a flavoring and/or a sweetener (aromatic elixir, compound benzaldehyde elixir, iso-alcoholic elixir, peppermint water, sorbitol solution, syrup, and/or tolu balsam syrup).

In embodiments, the cannabinoid, cannabinoid emulsion, and/or the colloidal dispersion may be mixed with: an oleaginous compound (MCT oil, a medium chain tryglyceride, fatty acids, almond oil, corn oil, cottonseed oil, ethyl oleate, isopropyl myristate, isopropyl palmitate, mineral oil, light mineral oil, myristyl alcohol, octyl dodecanol, olive oil, peanut oil, persic oil, sesame oil, soybean oil, and/or squalane).

In embodiments, the cannabinoid, cannabinoid emulsion, and/or the colloidal dispersion may be mixed with: a sterile compound (Bacteriostatic water for injection, and/or bacteriostatic sodium chloride injection)

In embodiments, the cannabinoid, cannabinoid emulsion, and/or the colloidal dispersion may be mixed with: a viscosity-increasing agent (suspending agents, agar agar, calcium alginate, curdlan, gelatin, gellan gum, glycerol esters of wood rosin, hydroxypropyl methyl cellulose, jelly powder, konjac gum, microcrystalline cellulose (MCC), pectin, propylene glycol alginate (PGA) semi-refined carrageenan, sodium alginate, sodium carboxymethyl cellulose, tamarind gum polysaccharide, tara gum, and/or xanthan gum).

In embodiments, the cannabinoid, cannabinoid emulsion, and/or the colloidal dispersion may be mixed with: a water repelling agent (cyclomethicone, dimethicone, and/or simethicone).

In embodiments, the cannabinoid, cannabinoid emulsion, and/or the colloidal dispersion may be mixed with: a solubilizing agent (benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaurate, sorbitan monooleate, sorbitan monopalmitate, sorbitan monostearate, and/or tyloxapol).

In embodiments, the cannabinoid, cannabinoid emulsion, and/or the colloidal dispersion may be mixed with: one or more waxes selected from the group consisting of *acacia decurrens* flower cera (*mimosa* flower wax), almond wax, avocado wax, beery wax, bees wax, *cananga odorata* flower cera (ylang ylang flower wax), candelilla wax, *Cannabis sativa* oil, castor wax, cupuacu butter, floral wax, hemp wax, hydrogenated almond oil, hydrogenated animal-based oils, hydrogenated apricot kernel oil, hydrogenated avocado oil, hydrogenated brazil nut oil, hydrogenated canola oil, hydrogenated cashew oil, hydrogenated cocoa butter, hydrogenated coconut oil, hydrogenated coffee oil, hydrogenated corn oil, hydrogenated cottonseed oil, hydrogenated grapeseed oil, hydrogenated hazelnut oil, hydrogenated hemp oil, hydrogenated hop oil, hydrogenated insect oil, hydrogenated lard oil, hydrogenated lard, hydrogenated macadamia nut oil, hydrogenated mustard oil, hydrogenated olive oil, hydrogenated palm kernel oil, hydrogenated palm oil, hydrogenated peanut oil, hydrogenated peppermint oil, hydrogenated rapeseed oil, hydrogenated rice bran oil, hydrogenated rice oil, hydrogenated safflower oil, hydrogenated semi-refined sesame oil, hydrogenated semi-refined sunflower oil, hydrogenated sesame oil, hydrogenated soybean oil, hydrogenated walnut oil, *jasminum grandiflorum* flower cera (jasmine flower wax), *Lavandula angustifolia* flower cera (lavender flower wax), mmyrica fruit wax, olive wax, *prunus* amygdalus *dulcis* oil, rapeseed wax, rice bran wax, rosa damascene flower cera (rose flower wax), shea butter, soybean wax, sunflower wax, vegan wax, vegetable wax, wax from Mexican shrub *Euphorbia antisyphilitica*, and/or wax from the berries of *rhus* verniciflua.

In embodiments, the cannabinoid, cannabinoid emulsion, and/or the colloidal dispersion may be mixed with: esterified insect lipids.

In embodiments, the cannabinoid, cannabinoid emulsion, and/or the colloidal dispersion may be mixed with: psilocybin mushrooms, psilocybin extract, psilocin extract, baeocystin extract, and/or norbaeocystin extract.

In embodiments, the cannabinoid, cannabinoid emulsion, and/or the colloidal dispersion may be mixed with: psilocybin mushrooms and/or the alimentary composition to produce the psilocybin extract, psilocin extract, baeocystin extract, and/or norbaeocystin extract, drugs, a hallucinogen, serotonin, psilocybin, psilocin, baeocystin, lysergic acid diethylamide (LSD), ibogaine, and/or mescaline.

In embodiments, the cannabinoid, cannabinoid emulsion, and/or the colloidal dispersion may be mixed with: psilocybin mushrooms to produce the cannabinoid extract (such as THC extract and/or CBD extract) along with a psilocybin extract, a psilocin extract, a baeocystin extract, and/or a norbaeocystin extract. In embodiments, the *cannabis* described in any of FIGS. can be mixed with the psilocybin mushrooms and/or the alimentary composition to produce the cannabinoid extract (such as THC oil and/or CBD oil) along with a psilocybin extract, a psilocin extract, a baeocystin extract, and/or a norbaeocystin extract. In embodiments, the *cannabis* described in any of FIGS. includes a fungus to produce an isolated or purified cannabinoid.

In embodiments, the cannabinoid, cannabinoid emulsion, and/or the colloidal dispersion may be mixed with: vitamin E (tocophersolan), a monoglyceride, a diglyceride, and/or a flavoring; wherein the flavoring includes the flavoring includes one or more flavorings selected from the group consisting of allspice berries, almond meal, anise seed, annato seed, arrowroot powder, basil, bay leaves, black pepper, buttermilk, *cannabis*, capsaicin, caraway, cayenne, celery seed, cheese cultures, chervil, Chile powder, chives, cilantro, cinnamon, citric acid, cloves, coconut shredded, coriander, corn oil, corn starch, cream of tartar, cubeb berries, cumin, curry, dextrose, dill, enzymes, fennel, fenugreek, file powder, garlic powder, ginger, grapefruit peel, green peppercorns, honey, horseradish powder, juniper berries, kaffir lime, lavender, lemon grass powder, lemon peel, lime peel, long pepper, marjoram, molasses, mustard, natural smoke flavor, nigella seeds, nutmeg, onion powder, orange peel, oregano, paprika, parsley, peppermint, poppy seed, powdered cheese, red pepper, rose petals, rosemary, saffron, *sassafras*, sage, salt, savory, sesame seed, star anise, sugar, sugar maple, sumac, tamarind, tangerine peel, tarragon, thyme, tomatillo powder, tomato powder, torula yeast, turmeric, vanilla extract, wasabi powder, whey, white peppercorns, yeast extract, and yeast.

FIG. 17K

FIG. 17K shows one non-limiting embodiment of a cannabinoid softgel encapsulation system (17K).

FIG. 17K displays an extract distribution system (KEA) including an extract tank (KEB) that is configured to accept an extract (KED). In embodiments, the extract tank (KEB) accept the extract (KED) including a cannabinoid from either of FIGS. 17A, 17B, 17C, 17D, 17E, 17H, 17J, 18, 18A, and/or 18E including *cannabis* volatiles, a cannabinoid extracted from *cannabis* plants, a cannabinoid extracted from insects containing an insect-derived cannabinoid glycoside, and/or a cannabinoid derived from genetically engineered microorganisms, whether the extract is raw in form and not purified, a purified extract, an isolated cannabinoid subject to a purification process, a distilled cannabinoid, adsorption and/or chromatography purified cannabinoid, or any liquid and cannabinoid mixture (such as with a solvent, a lipid, water, etc.), or any liquid cannabinoid.

The extract tank (KEB) has an interior (KEC), an extract input (KEF), an extract conveyor (KEG) (such as a conveyor, a pump, or any means to convey the extract from one location to another), and an extract conveyor output (KEH). The extract tank (KEB) accepts an extract (KED) to the interior (KEC) and regulates and controls an engineered amount of extract (KED) downstream to be mixed to form the softgel (KCC). The extract conveyor (KB5) has an integrated mass sensor (KEJ) that is configured to input and output a signal (KEK) to the computer (COMP). The extract conveyor motor (KEL) has a controller (KEM) that is configured to input and output a signal (KEN) to the computer (COMP). The mass sensor (KEJ), extract conveyor (KEG), and extract conveyor motor (KEL) are coupled so as to permit the conveyance, distribution, or output of a precise flow of extract (KED) via an extract transfer line (KEI) into the input (KDF) of the cannabinoid softgel encapsulation system (17K). It is to be noted that the extract may be in solid, powder, crystal, liquid, slurry, emulsion, microemulsion, nanoemulsion, colloidal dispersion form. Transferring an engineered amount of extract (KED) downstream to be mixed to form a softgel (KCC) is the premise of the disclosure and is not limited at all whatsoever.

The cannabinoid softgel encapsulation system (JKB) shown in FIG. 17K is configured to produce cannabinoid softgels (KCC). In embodiments, a softgel (KCC) is an oral dosage form for medicine similar to capsules. In embodiments, softgels (KCC) are comprised of a gelatin based shell surrounding a liquid fill. In embodiments, the liquid fill is either an emulsion, volatiles from *cannabis* or INSECTERGY III, or any number of combinations and permutations of cannabinoids, distilled cannabinoid, a purified cannabinoid, a cannabinoid glycoside, cannabinoid emulsion, cannabinoid microemulsion, cannabinoid nanoemulsion, and/or the colloidal dispersion and/or any additional ingredient, chemical, drug, additive, emulsifier, surfactant, etc., mentioned in this specification not only including such as a fiber-starch material, a binding agent, a moisture improving textural supplement, a density improving textural supplement, insects, psilocybin extract, psilocin extract, baeocystin extract, and/or norbaeocystin extract, a hallucinogen, serotonin, melatonin, psilocybin, psilocin, baeocystin, lysergic acid diethylamide (LSD), ibogaine, and/or mescaline, and combinations thereof. In embodiments, the softgel includes a cannabinoid including THC and/or CBD as disclosed in this patent specification.

In embodiments, softgel shells are a combination of cannabinoids, gelatin, water, and a plasticiser such as glycerin or sorbitol. In embodiments, the plasticiser is used to increase the plasticity or decrease the viscosity of a material for the encapsulation of cannabinoids. In embodiments, the plasticiser is an emulsifier. In embodiments, softgel shells are a combination of cannabinoids, an emulsifier, medium chain triglycerides, beta caryophyllene, and a gelatin shell that includes bovine-derived gelatin, a vegan gelatin, glycerin, sorbitol, and deionized water, adsorbent treated water, membrane treated water, ion exchange resin treated water, catalyst treated water. In embodiments, medium chain triglycerides are triglycerides whose fatty acids have an aliphatic tail of 6-12 carbon atoms. In embodiments, triglycerides include esters derived from glycerol and three fatty acids (from tri- and glyceride). In embodiments, the gelatin shell that includes gelatin having a Bloom strength of 50-100, an animal-free gelatin, a vegan gelatin, agar, agar-agar, kanten, carrageenan, carrageen, or irish moss vegan j el (vegetable gum adipic acid, tapioca dextrin, calcium phosphate, and potassium citrate). In embodiments, each softgel contains cannabinoids at a cannabinoid concentration ranging from one or more cannabinoid concentrations selected from the group consisting of 5 mg to 10 mg, 10 mg to 15 mg, 15 mg to 20 mg, 20 mg to 25 mg, 25 mg to 30 mg, 30 mg to 35 mg, 35 mg to 40 mg, 40 mg to 45 mg, 45 mg to 50 mg, 50 mg to 55 mg, 55 mg to 60 mg, 60 mg to 65 mg, 65 mg to 70 mg, 70 mg to 75 mg, 75 mg to 80 mg, mg to 85 mg, 85 mg to 90 mg, 90 mg to 95 mg, 95 mg to 100 mg, 100 mg to 125 mg, 125 mg to 150 mg, 150 mg to 175 mg, 175 mg to 200 mg, 200 mg to 225 mg, 225 mg to 250 mg, 250 mg to 275 mg, 275 mg to 300 mg, 300 mg to 325 mg, 325 mg to 350 mg, 350 mg to 375 mg, 375 mg to 400 mg, 400 mg to 425 mg, 425 mg to 450 mg, 450 mg to 475 mg, 475 mg to 500 mg, 500 mg to 550 mg, 550 mg to 600 mg, 600 mg to 650 mg, 650 mg to 700 mg, 700 mg to 750 mg, 750 mg to 800 mg, 800 mg to 850 mg, 850 mg to 900 mg, 900 mg to 950 mg, 950 mg to 1,000 mg, 1,000 mg to 2,000 mg, 2,000 mg to 3,000 mg, 3,000 mg to 4,000 mg, 4,000 mg to 5,000 mg, 5,000 mg to 6,000 mg, 6,000 mg to 7,000 mg, 7,000 mg to 8,000 mg, 8,000 mg to 9,000 mg, and 9,000 mg to 10,000 mg.

In embodiments, the cannabinoid softgel encapsulation system (JKB) includes a rotary die encapsulation system (KAA). In embodiments, rotary die encapsulation system (KAA) includes a gelatin tank (KBA) having an interior (KBB). In embodiments, gelatin (KBC) is contained within the interior (KBB) of the gelatin tank (KBA). In embodiments, gelatin (KBC) is discharged from the gelatin tank (KBA) and is passed through a valve (KBD). A gas supply may pressurize the gelatin tank (KBA), the gas supply system of FIG. 17J can be used as similar to the way that the gas supply is provided to the emulsion process. The valve (KBD) has a controller (KBE) and is configured to input and output a signal (KBF) to the computer (COMP). A flow sensor (KBG) is provided to measure the amount of gelatin (KBC) transferred from the gelatin tank (KBA) and into the rotary die encapsulation system (KAA).

In embodiments, the rotary die encapsulation system (KAA) includes a roller (KBH), conveyor (KBI), and a ribbon (KBJ) of gelatin (KBC) (provided from the gelatin tank (KBA)), and a first roller (KCA) and a second roller (KCB). A softgel (KCC) is created by passing the liquid mixture from within the mixture tank (KDD) through the first roller (KCA) and a second roller (KCB) where the liquid mixture is encapsulated by the ribbon (KBJ) of gelatin (KBC).

In embodiments, each softgel has a length and a width. In embodiments, the length of each softgel falls within a range of length that is selected from one or more length ranges consisting from the group including 0.125 inches to 0.250 inches, 0.250 inches to 0.375 inches, 0.375 inches to 0.500 inches, 0.500 inches to 0.625 inches, 0.625 inches to 0.750 inches, 0.750 inches to 0.875 inches, and 0.875 inches to 1.000 inch. In embodiments, the width of each softgel falls within a range of length that is selected from one or more width ranges consisting from the group including inches to 0.250 inches, 0.250 inches to 0.375 inches, 0.375 inches to 0.500 inches, 0.500 inches to 0.625 inches, 0.625 inches to 0.750 inches, 0.750 inches to 0.875 inches, and 0.875 inches to 1.000 inch. In embodiments, the length is about 0.5 inches and the width is about 0.313 inches.

In embodiments, each softgel has a mass. In embodiments, the mass of each softgel falls within a range of mass that is selected from one or more mass ranges consisting from the group including 0.500 grams to 0.550 grams, 0.550 grams to 0.600 grams, 0.600 grams to 0.650 grams, grams to 0.700 grams, 0.700 grams to 0.750 grams, 0.750 grams to 0.800 grams, 0.800 grams to 0.850 grams, 0.850 grams to 0.900 grams, 0.900 grams to 0.950 grams, and 0.950 grams to 1.000 grams.

In embodiments, the thickness of the ribbon (KBJ) of gelatin (KBC) in the rotary die encapsulation system (KAA) includes one or more selected from the group of ribbon thickness ranges consisting of 0.0050 inches to 0.0053 inches, 0.0053 inches to 0.0055 inches, 0.0055 inches to 0.0058 inches, 0.0058 inches to 0.0061 inches, 0.0061 inches to 0.0064 inches, 0.0064 inches to 0.0067 inches, 0.0067 inches to 0.0070 inches, 0.0070 inches to 0.0074 inches, 0.0074 inches to 0.0078 inches, 0.0078 inches to 0.0081 inches, 0.0081 inches to 0.0086 inches, 0.0086 inches to 0.0090 inches, 0.0090 inches to 0.0094 inches, 0.0094 inches to 0.0099 inches, 0.0099 inches to 0.0104 inches, 0.0104 inches to 0.0109 inches, 0.0109 inches to 0.0115 inches, 0.0115 inches to 0.0120 inches, 0.0120 inches to 0.0126 inches, 0.0126 inches to 0.0133 inches, 0.0133 inches to 0.0139 inches, 0.0139 inches to 0.0146 inches, 0.0146 inches to 0.0154 inches, 0.0154 inches to 0.0161 inches, 0.0161 inches to 0.0169 inches, 0.0169 inches to 0.0178 inches, 0.0178 inches to 0.0187 inches, 0.0187 inches to 0.0196 inches, 0.0196 inches to 0.0206 inches, 0.0206 inches to 0.0216 inches, 0.0216 inches to 0.0227 inches, 0.0227 inches to 0.0238 inches, 0.0238 inches to 0.0250 inches, 0.0250 inches to 0.0263 inches, 0.0263 inches to 0.0276 inches, 0.0276 inches to 0.0290 inches, 0.0290 inches to 0.0304 inches, 0.0304 inches to 0.0319 inches, 0.0319 inches to 0.0335 inches, 0.0335 inches to 0.0352 inches, 0.0352 inches to 0.0370 inches, 0.0370 inches to 0.0388 inches, 0.0388 inches to 0.0407 inches, 0.0407 inches to 0.0428 inches, 0.0428 inches to 0.0449 inches, 0.0449 inches to 0.0472 inches, 0.0472 inches to 0.0495 inches, 0.0495 inches to 0.0520 inches, 0.0520 inches to 0.0546 inches, 0.0546 inches to 0.0573 inches, 0.0573 inches to 0.0602 inches, 0.0602 inches to 0.0632 inches, and 0.0632 inches to 0.0664 inches.

In embodiments, the cannabinoid softgel encapsulation system (JKB) includes a washing system (KFA) and a drying system (FGA) that are configured to first wash the softgels (KCC) with a wash liquid (KEF) and then dry the washed softgels (KEJ) in a dryer (KEH) to produce washed and dried softgels (KEK). In embodiments, the wash liquid (KEF) includes treated water (see water treatment system on FIG. 17H). In embodiments, the wash liquid (KEF) includes an alcohol or a liquid. In embodiments, the wash liquid (KEF) includes ethanol. In embodiments, the washing system (KFA) includes a conveyor (KEA) that is configured to accept the softgels (KCC) from the first roller (KCA) and a second roller (KCB).

In embodiments, the first roller (KCA) and a second roller (KCB) rotate to form the softgels (KEJ) at a revolutions per minute (RPM) that is selected from one or more from RPMs from the group consisting of 2 rpm to 4 rpm, 4 rpm to 6 rpm, 6 rpm to 8 rpm, 8 rpm to 10 rpm, 10 rpm to 12 rpm, 12 rpm to 14 rpm, 14 rpm to 16 rpm, 16 rpm to 18 rpm, 18 rpm to 20 rpm, 20 rpm to 22 rpm, 22 rpm to 24 rpm, 24 rpm to 26 rpm, 26 rpm to 28 rpm, 28 rpm to 30 rpm, 30 rpm to 32 rpm, 32 rpm to 34 rpm, 34 rpm to 36 rpm, 36 rpm to 38 rpm, 38 rpm to 40 rpm, 40 rpm to 42 rpm, 42 rpm to 44 rpm, 44 rpm to 46 rpm, 46 rpm to 48 rpm, 48 rpm to 50 rpm, 50 rpm to 52 rpm, 52 rpm to 54 rpm, 54 rpm to 56 rpm, 56 rpm to 58 rpm, 58 rpm to 60 rpm, 60 rpm to 62 rpm, 62 rpm to 64 rpm, 64 rpm to 66 rpm, 66 rpm to 68 rpm, 68 rpm to 70 rpm, and 70 rpm to 85 rpm.

The conveyor (KEA) is equipped with a motor (KEB) and a controller (KEC). The controller (KEC) sends a signal (KED) to and/or from the computer (COMP). In embodiments, the conveyor (KEA) is configured to convey the softgels (KCC) past a washing system (KFA). In embodiments, the washing system (KFA) is configured to wash the softgels (KCC) with a wash liquid (KEF) that is dispensed onto the softgels (KCC) through a spray nozzle (KEE) or a plurality of spray nozzles (KEE) to produce washed softgels (KEJ). In embodiments, the pressure drop across the spray nozzle (KEE) or a plurality of spray nozzles (KEE) includes one or more pressure drop ranges selected from the group consisting of 5 pounds per square inch (PSI) to 10 PSI, 10 PSI to 20 PSI, 20 PSI to 30 PSI, 30 PSI to 40 PSI, 40 PSI to 50 PSI, 50 PSI to 60 PSI, 60 PSI to 70 PSI, 70 PSI to 80 PSI, 80 PSI to 90 PSI, 90 PSI to 100 PSI, 100 PSI to 125 PSI, 125 PSI to 150 PSI, 150 PSI to 175 PSI, 175 PSI to 200 PSI, 200 PSI to 225 PSI, 225 PSI to 250 PSI, 250 PSI to 275 PSI, 275 PSI to 300 PSI, 300 PSI to 400 PSI, 400 PSI to 500 PSI, 500 PSI to 600 PSI, 600 PSI to 700 PSI, 700 PSI to 800 PSI, 800 PSI to 900 PSI, and 900 PSI to 1,000 PSI.

In embodiments, the washed softgels (KEJ) are conveyed away from the washing system (KFA) and are introduced to the input (KEG) of a drying system (FGA). In embodiments, the drying system (FGA) includes a dryer (KEH) that is configured to dry the washed softgels (KEJ) to produce washed and dried softgels (KEK). In embodiments, the dryer (KEH) is a rotary dryer (KEI) that rotates to dry the washed softgels (KEJ) and produce washed and dried softgels (KEK). In embodiments, the rotary dryer (KEI) rotates to dry the washed softgels (KEJ) and produce washed and dried softgels (KEK) at a revolutions per minute (RPM) that is selected from one or more from RPMs from the group consisting of 2 rpm to 4 rpm, 4 rpm to 6 rpm, 6 rpm to 8 rpm, 8 rpm to 10 rpm, 10 rpm to 12 rpm, 12 rpm to 14 rpm, 14 rpm to 16 rpm, 16 rpm to 18 rpm, 18 rpm to 20 rpm, 20 rpm to 22 rpm, 22 rpm to 24 rpm, 24 rpm to 26 rpm, 26 rpm to 28 rpm, 28 rpm to rpm, 30 rpm to 32 rpm, 32 rpm to 34 rpm, 34 rpm to 36 rpm, 36 rpm to 38 rpm, 38 rpm to 40 rpm, 40 rpm to 42 rpm, 42 rpm to 44 rpm, 44 rpm to 46 rpm, 46 rpm to 48 rpm, 48 rpm to 50 rpm, rpm to 52 rpm, 52 rpm to 54 rpm, 54 rpm to 56 rpm, 56 rpm to 58 rpm, 58 rpm to 60 rpm, 60 rpm to 62 rpm, 62 rpm to 64 rpm, 64 rpm to 66 rpm, 66 rpm to 68 rpm, 68 rpm to 70 rpm, and 70 rpm to 85 rpm.

In embodiments, the cannabinoid softgel encapsulation system (17K) produces softgels (KCC) that may be in bulk or bottled form. In embodiments, the cannabinoid softgel encapsulation system (17K) produces washed and dried softgels (KEK) that may be in bulk or bottled form. In embodiments, the softgels (KCC, KEK) have a bulk density that includes one or more bulk density ranges selected from the group consisting of 8 pounds per cubic foot to 10 pounds per cubic foot, pounds per cubic foot to 12 pounds per cubic foot, 12 pounds per cubic foot to 14 pounds per cubic foot, 14 pounds per cubic foot to 16 pounds per cubic foot, 16 pounds per cubic foot to 18 pounds per cubic foot, 18 pounds per cubic foot to 20 pounds per cubic foot, 20 pounds per cubic foot to 22 pounds per cubic foot, 22 pounds per cubic foot to 24 pounds per cubic foot, 24 pounds per cubic foot to 26 pounds per cubic foot, 26 pounds per cubic foot to 28 pounds per cubic foot, 28 pounds per cubic foot to 30 pounds per cubic foot, 30 pounds per cubic foot to 32 pounds per cubic foot, 32 pounds per cubic foot to 34 pounds per cubic foot, 34 pounds per cubic foot to 36 pounds per cubic foot, 36 pounds per cubic foot to 38 pounds per cubic foot, 38 pounds per cubic foot to 40 pounds per cubic foot, 40 pounds per cubic foot to 42 pounds per cubic foot, 42 pounds per cubic foot to 44 pounds per cubic foot, 44 pounds per cubic foot to 46 pounds per cubic foot, 46 pounds per cubic foot to 48 pounds per cubic foot, 48 pounds per cubic foot to 50 pounds per cubic foot, 50 pounds per cubic foot to 52 pounds per cubic foot, 52 pounds per cubic foot to 54 pounds per cubic foot, 54 pounds per cubic foot to 56 pounds per cubic foot, 56 pounds per cubic foot to 58 pounds per cubic foot, 58 pounds per cubic foot to 60 pounds per cubic foot, 60 pounds per cubic foot to 62 pounds per cubic foot, 62 pounds per cubic foot to 64 pounds per cubic foot, 64 pounds per cubic foot to 66 pounds per cubic foot, 66 pounds per cubic foot to 68 pounds per cubic foot, 68 pounds per cubic foot to 70 pounds per cubic foot, 70 pounds per cubic foot to 72 pounds per cubic foot, 72 pounds per cubic foot to 74 pounds per cubic foot, 74 pounds per cubic foot to 76 pounds per cubic foot, 76 pounds per cubic foot to 78 pounds per cubic foot, and 78 pounds per cubic foot to 80 pounds per cubic foot.

Example

A softgel including a mixture encapsulated within a shell, the mixture comprises a cannabinoid colloidal dispersion, a vitamin, and a medium chain triglyceride; the shell comprises bovine-derived gelatin and glycerin; and the softgel comprises a cannabinoid concentration ranging from 15 to 40 milligrams, the cannabinoid is derived from carbon dioxide *cannabis* oil; and the softgel comprises: a mass ranging from between 0.55 to 0.75 grams; and a length and a width; the length ranges from between 0.125 to 1.000 inch; and the width ranges from between to 0.313 inches. In embodiments, the softgel includes the shell comprises a wall thickness ranging from 0.0050 to 0.0664 inches. In embodiments, the softgel includes the medium chain triglycerides comprise triglycerides including fatty acids comprising an aliphatic tail of 6 to 12 carbon atoms. In embodiments, the softgel includes the triglycerides include esters derived from glycerol and fatty acids. In embodiments, the softgel includes psilocybin. In embodiments, the softgel includes a terpene. In embodiments, the softgel includes mono- and di-glycerides of fatty acids. In embodiments, the softgel includes one of more fatty acids selected from the group consisting of palmitic acid, linoleic acid, alpha-linoleic acid, oleic acid, gamma-linoleic acid, and stearic acid. In embodiments, the softgel includes the fatty acids are derived from insects. In embodiments, the softgel includes an acid, the acid includes acetic acid, ascorbic acid, citric acid, formic acid, fumaric acid, lactic acid, malic acid, nitric acid, organic acids, phosphoric acid, propionic acid, salicylic acid, and/or tartaric acid. In embodiments, the softgel includes lysergic acid diethylamide. In embodiments, the softgel includes mescaline, dimethyltryptamine, ibogaine, and/or iowaska. In embodiments, the softgel includes the cannabinoid includes cannabidiol and/or tetrahydrocannabinol. In embodiments, the softgel includes the cannabinoid includes a distilled cannabinoid, a simulated moving bed purified cannabinoid, an adsorption purified cannabinoid, an ion exchange resin purified cannabinoid, and/or a chromatography purified cannabinoid. In embodiments, the softgel includes the shell comprises deionized water, adsorbent treated water, membrane treated water, ion exchange resin treated water, catalyst treated water. In embodiments, the softgel includes 3,4-methylenedioxymethamphetamine. In embodiments, the softgel includes black pepper and curcumin. In embodiments, the softgel includes a microemulsion and/or a nanoemulsion. In embodiments, the softgel includes tea, rosemary, lavender, and/or coffee. In embodiments, the vitamin includes vitamin E (tocophersolan).

FIG. 18

FIG. 18 shows a simplistic diagram illustrating a multifunctional composition mixing module that is configured to generate a multifunctional composition from at least a portion of *cannabis* plants (107, 207) that was harvested from each growing assembly (100, 200), and/or any extracted and/or purified cannabinoid described in this entire specification including but not limited to *cannabis* plants (107, 207), trimmed *cannabis* (TR1, TR1*), *cannabis* trimmings (TR2, TR2*), ground *cannabis* (GR1), heated *cannabis* (HT1), a cannabinoid emulsion and/or colloidal dispersion (JNC), powdered cannabinoid, cannabinoid crystals, spray-dried cannabinoids, cannabinoids, *cannabis* volatiles, a cannabinoid and liquid mixture, a cannabinoid and a solvent mixture, trimmed *cannabis* buds, *cannabis* seeds, *cannabis* stems, *cannabis* roots, a mixture of *cannabis* with insects and/or arachnids, concentrated volatiles, a concentrated cannabinoid, a *cannabis* plant derived cannabinoid, an insect-derived cannabinoid glycoside, a biosynthetically derived cannabinoid, a secondary extract, a purified cannabinoid, a distilled cannabinoid, a cannabinoid emulsion, a micro emulsion, a nano emulsion, a cannabinoid colloid suspension, a cannabinoid colloid dispersion, a mixture of a biosynthetic cannabinoid and a genetically engineered microorganism, and combinations thereof.

In embodiments, the *cannabis* and/or the cannabinoid (or a biosynthetically derived from an insect and/or microorganism) is first trimmed, ground, heated, decarboxylated, extracted, purified, mixed with a solvent, evaporated, distilled, spray-dried, isolated, emulsified, or put into a colloidal dispersion, before being mixed with one or more from the group consisting of fiber-starch, binding agent, density improving textural supplement, moisture improving textural supplement, and insects.

FIG. 18 displays a cannabinoid distribution module (6A) including a cannabinoid tank (6A2) that is configured to accept the cannabinoid, which is preferably provided from at least a portion of the *cannabis* (107, 207), insects, and/or genetically engineered microorganisms that were harvested from each growing assembly (100, 200), or insects that were fed a cannabinoid (to produce the insect-derived cannabinoid glycoside), and/or biosynthetically produced within the a bioreactor of the FSS.

The cannabinoid tank (6A2) has an interior (6A3), a cannabinoid input (6A4), a cannabinoid conveyor (6A5), and a cannabinoid conveyor output (6A6). The cannabinoid tank (6A2) accepts *cannabis* to the interior (6A3) and regulates and controls an engineered amount of the cannabinoid (6A1) downstream to be mixed to form a multifunctional composition. In embodiments, the cannabinoid tank (6A2) accepts the cannabinoid to the interior (6A3) of the tank.

The cannabinoid conveyor (6A5) has an integrated cannabinoid mass sensor (6A7) that is configured to input and output a signal (6A8) to the computer (COMP). The cannabinoid conveyor motor (6A9) has a controller (6A10) that is configured to input and output a signal (6A11) to the computer (COMP). The cannabinoid mass sensor (6A7), cannabinoid conveyor (6A5), and cannabinoid conveyor motor (6A9) are coupled so as to permit the conveyance, distribution, or output of a precise flow of the cannabinoid via a cannabinoid transfer line (6A12).

FIG. 18 displays a fiber-starch distribution module (6B) including a fiber-starch tank (6B2) that is configured to accept fiber-starch (6B1). The fiber-starch tank (6B2) has an interior (6B3), a fiber-starch input (6B4), a fiber-starch conveyor (6B5), and a fiber-starch conveyor output (6B6). The fiber-starch tank (6B2) accepts fiber-starch (6B1) to the interior (6B3) and regulates and controls an engineered amount of fiber-starch (6B1) downstream to be mixed to form a multifunctional composition. The fiber-starch conveyor (6B5) has an integrated fiber-starch mass sensor (6B7) that is configured to input and output a signal (6B8) to the computer (COMP). The fiber-starch conveyor motor (6B9) has a controller (6B10) that is configured to input and output a signal (6B11) to the computer (COMP). The fiber-starch mass sensor (6B7), fiber-starch conveyor (6B5), and fiber-starch conveyor motor (6B9) are coupled so as to permit the conveyance, distribution, or output of a precise flow of fiber-starch (6B1) via a fiber-starch transfer line (6B12).

FIG. 18 displays a binding agent distribution module (6C) including a binding agent tank (6C2) that is configured to accept a binding agent (6C1). The binding agent tank (6C2) has an interior (6C3), a binding agent input (6C4), a binding agent conveyor (6C5), and a binding agent conveyor output (6C6). The binding agent tank (6C2) accepts binding agent (6C1) to the interior (6C3) and regulates and controls an engineered amount of a binding agent (6C1) downstream to be mixed to form a multifunctional composition. The binding agent conveyor (6C5) has an integrated binding agent mass sensor (6C7) that is configured to input and output a signal (6C8) to the computer (COMP). The binding agent conveyor motor (6C9) has a controller (6C10) that is configured to input and output a signal (6C11) to the computer (COMP). The binding agent mass sensor (6C7), binding agent conveyor (6C5), and binding agent conveyor motor (6C9) are coupled so as to permit the conveyance, distribution, or output of a precise flow of binding agent (6C1) via a binding agent transfer line (6C12).

FIG. 18 displays a density improving textural supplement distribution module (6D) including a density improving textural supplement tank (6D2) that is configured to accept a density improving textural supplement (6D1). The density improving textural supplement tank (6D2) has an interior (6D3), a density improving textural supplement input (6D4), a density improving textural supplement conveyor (6D5), and a density improving textural supplement conveyor output (6D6). The density improving textural supplement tank (6D2) accepts density improving textural supplement (6D1) to the interior (6D3) and regulates and controls an engineered amount of a density improving textural supplement (6D1) downstream to be mixed to form a multifunctional composition. The density improving textural supplement conveyor (6D5) has an integrated density improving textural supplement mass sensor (6D7) that is configured to input and output a signal (6D8) to the computer (COMP). The density improving textural supplement conveyor motor (6D9) has a controller (6D10) that is configured to input and output a signal (6D11) to the computer (COMP). The density improving textural supplement mass sensor (6D7), density improving textural supplement conveyor (6D5), and density improving textural supplement conveyor motor (6D9) are coupled so as to permit the conveyance, distribution, or output of a precise flow of density improving textural supplement (6D1) via a density improving textural supplement transfer line (6D12).

FIG. 18 displays a moisture improving textural supplement distribution module (6E) including a moisture improving textural supplement tank (6E2) that is configured to accept a moisture improving textural supplement (6E1). The moisture improving textural supplement tank (6E2) has an interior (6E3), a moisture improving textural supplement input (6E4), a moisture improving textural supplement conveyor (6E5), and a moisture improving textural supplement conveyor output (6E6). The moisture improving textural supplement tank (6E2) accepts a moisture improving textural supplement (6E1) to the interior (6E3) and regulates and controls an engineered amount of a moisture improving textural supplement (6E1) downstream to be mixed to form a multifunctional composition. The moisture improving textural supplement conveyor (6E5) has an integrated moisture improving textural supplement mass sensor (6E7) that is configured to input and output a signal (6E8) to the computer (COMP). The moisture improving textural supplement conveyor motor (6E9) has a controller (6E10) that is configured to input and output a signal (6E11) to the computer (COMP). The moisture improving textural supplement mass sensor (6E7), moisture improving textural supplement conveyor (6E5), and moisture improving textural supplement conveyor motor (6E9) are coupled so as to permit the conveyance, distribution, or output of a precise flow of moisture improving textural supplement (6E1) via a moisture improving textural supplement transfer line (6E12).

FIG. 18 displays an insect distribution module (6G) including an insect tank (6G2) that is configured to accept insects (6G1). The insect tank (6G2) has an interior (6G3), an insect input (6G4), an insect conveyor (6G5), and an insect conveyor output (6G6). The insect tank (6G2) accepts insects (6G1) to the interior (6G3) and regulates and controls an engineered amount of insects (6G1) downstream to be mixed to form a multifunctional composition. The insect conveyor (6G5) has an integrated insect mass sensor (6G7) that is configured to input and output a signal (6G8) to the computer (COMP). The insect conveyor motor (6G9) has a controller (6G10) that is configured to input and output a signal (6G11) to the computer (COMP). The insect mass sensor (6G7), insect conveyor (6G5), and insect conveyor motor (6G9) are coupled so as to permit the conveyance, distribution, or output of a precise flow of insects (6G1) via an insect transfer line (6G12). In embodiments, the insects may be Orthoptera order of insects including grasshoppers, crickets, cave crickets, Jerusalem crickets, katydids, weta, lubber, acrida, and locusts in a solid, frozen, ground, spray-dried, lipid extracted, freeze dried, or slurry form. However, other orders of insects, such as cicadas, ants, mealworms, agave worms, worms, bees, centipedes, cockroaches, dragonflies, beetles, scorpions, tarantulas, termites, insect lipids, and insect oil, or any insects mentioned herein may be used as well, such as one or more selected from the group consisting of Hermetia illucens, Orthoptera order of insects, cockroaches, crickets, locusts, cicadas, black soldier fly larvae, black soldier fly prepupae, black soldier fly pupae, beetles, mealworms, yellow mealworm beetles, *Tenebrio molitor*, eight-legged arthropods, and six-legged arthropods. In embodiments, the insects also include Anthocoridae, minute pirate bugs, pirate bugs, flower bugs, the genus Orius, omnivorous bugs, carnivorous bugs, Orthoptera order of insects, grasshoppers, crickets, katydids, weta, lubber, acrida, locusts, mites, spider mites, predatory mites, *Neoseiulus fallacis*, genus of mites that are in the Phytoseiidae family, arthropods, hexapods, beetles, cicadas, beetles, nematodes, mealworms, bats, mammals of the order Chiroptera, yellow mealworm beetles, *Tenebrio Molitor, Tetranychus Urticae*, carnivorous arthropods, omnivorous arthropods, green lacewings, insects in the family Chrysopidae, insects in the order Neuroptera, mantidflies, black soldier flies, black soldier fly larvae, butterflies, larvae, fly larvae, insect larvae, arthropod larvae, black soldier fly larvae, Hermetia illucens, antlions, mosquitos, Colorado potato beetle, *Leptinotarsa decemlineata*, moths, diamondback moth, *Plutella xylostella*, moth species of the family Plutellidae and genus *Plutella. Encarsia Formosa*, insects in the macrolepidopteran Glade Rhopalocera from the order Lepidoptera, whitefly parasites, ladybugs, spiders, dragonflies, orb-weaving spiders, arachnids, *Spodoptera frugiperda*, members of the spider family Araneidae, praying mantis, and/or arachnids.

FIG. 18 displays a multifunctional composition mixing module (6F) including a multifunctional composition tank (6F1) that is configured to accept a mixture including the cannabinoid (6A1), fiber-starch (6B1), binding agent (6C1), density improving textural supplement (6D1), moisture improving textural supplement (6E1), and insects (6G1) via a multifunctional composition transfer line (6F0).

The multifunctional composition tank (6F1) has an interior (6F2), a multifunctional composition tank input (6F3), screw conveyor (6F9), multifunctional composition output (6F10). The multifunctional composition tank (6F1) accepts the cannabinoid (6A1), fiber-starch (6B1), binding agent (6C1), density improving textural supplement (6D1), moisture improving textural supplement (6E1), and insects (6G1) to the interior (6F2) and mixes, regulates, and outputs a weighed multifunctional composition stream (6F22).

The multifunctional composition tank (6F1) has a top section (6F4), bottom section (6F5), at least one side wall (6F6), with a level sensor (6F7) positioned thereon that is configured to input and output a signal (6F8) to the computer (COMP). The screw conveyor (6F9) has a multifunctional composition conveyor motor (6F11) with a controller (6F12) that is configured to input and output a signal (6F13) to the computer (COMP). From the multifunctional composition output (6F10) of the multifunctional composition tank (6F1) is positioned a multifunctional composition weigh screw (6F14) that is equipped with a multifunctional composition weigh screw input (6F15), a multifunctional composition weigh screw output (6F16), and a mass sensor (6F17) that is configured to input and output a signal (6F18) to the computer (COMP). The multifunctional composition weigh screw (6F14) also has a weigh screw motor (6F19) with a controller (6F20) that is configured to input and output a signal (6F21) to the computer (COMP).

The multifunctional composition mixing module (6000) involves mixing the cannabinoid with one or more of the fiber-starch material, binding agent, density improving textural supplement, moisture improving textural supplement, and insect, to form a multifunctional composition.

The multifunctional composition may be further processed to create a shaped, cooked, and flavored multifunctional composition which may be used in foodstuffs, pet foods, animal foods, etc. The multifunctional composition may be further processed to create foodstuffs not only including ada, bagels, baked goods, biscuits, bitterballen, bonda, breads, cakes, candies, cereals, chips, chocolate bars, chocolate, coffee, cokodok, confectionery, cookies, cooking batter, corn starch mixtures, crackers, crepes, croissants, croquettes, croutons, dolma, dough, doughnuts, energy bars, flapjacks, french fries, frozen custard, frozen desserts, frying cakes, fudge, gelatin mixes, granola bars, gulha, hardtack, ice cream, khandvi, khanom buang, krumpets, meze, mixed flours, muffins, multi-grain snacks, nachos, nian gao, noodles, nougat, onion rings, pakora, pancakes, panforte, pastas, pastries, pie crust, pita chips, pizza, poffertj es, pretzels, protein powders, pudding, rice krispie treats, sesame sticks, smoothies, snacks, specialty milk, tele-bhaja, tempura, toffee, tortillas, totopo, turkish delights, or waffles.

In embodiments, the fiber-starch materials may be comprised of singular or mixtures of cereal-grain-based materials, grass-based materials, nut-based materials, powdered fruit materials, root-based materials, tuber-based materials, or vegetable-based materials. In embodiments, the fiber-starch mass ratio ranges from between about 33 pounds of fiber-starch per ton of multifunctional composition to about 600 pounds of fiber-starch per ton of multifunctional composition.

In embodiments, the binding agents may be comprised of singular or mixtures of agar, agave, alginin, arrowroot, carrageenan, collagen, cornstarch, egg whites, finely ground seeds, furcellaran, gelatin, guar gum, honey, katakuri starch, locust bean gum, pectin, potato starch, proteins, *psyllium* husks, sago, sugar, syrup, tapioca, vegetable gums, or xanthan gum. In embodiments, the binding agent mass ratio ranges from between about 5 pounds of binding agent per ton of multifunctional composition to about 300 pounds of binding agent per ton of multifunctional composition.

In embodiments, the density improving textural supplements may be comprised of singular or mixtures of extracted arrowroot starch, extracted corn starch, extracted lentil starch, extracted potato starch, or extracted tapioca starch. In embodiments, the density improving textural supplement mass ratio ranges from between about 5 pounds of density improving textural supplement per ton of multifunctional composition to about 300 pounds of density improving textural supplement per ton of multifunctional composition.

In embodiments, the moisture improving textural supplements may be comprised of singular or mixtures of almonds, brazil nuts, cacao, cashews, chestnuts, coconut, filberts, hazelnuts, Indian nuts, macadamia nuts, nut butters, nut oils, nut powders, peanuts, pecans, pili nuts, pine nuts, pinon nuts, pistachios, soy nuts, sunflower seeds, tiger nuts, and walnuts. In embodiments, the moisture improving textural supplement mass ratio ranges from between about pounds of moisture improving textural supplement per ton of multifunctional composition to about 1000 pounds of moisture improving textural supplement per ton of multifunctional composition.

In embodiments, insects may be added to the multifunctional composition. In embodiments, the insect mass ratio ranges from between about 250 pounds of insects per ton of multifunctional composition to about 1500 pounds of insects per ton of multifunctional composition.

In embodiments, the cannabinoid ratio ranges from between about 25 pounds of cannabinoid per ton of multifunctional composition to about 1800 pounds of cannabinoid per ton of multifunctional composition.

In embodiments, the cannabinoid ratio ranges from between about 1 pounds of cannabinoid per ton of multifunctional composition to about 10 pounds of cannabinoid per ton of multifunctional composition. In embodiments, the cannabinoid ratio ranges from between about pounds of cannabinoid per ton of multifunctional composition to about 100 pounds of cannabinoid per ton of multifunctional composition. In embodiments, the cannabinoid ratio ranges from between about 100 pounds of cannabinoid per ton of multifunctional composition to about 300 pounds of cannabinoid per ton of multifunctional composition. In embodiments, the multifunctional composition includes N-acetylglucosamine, bacteria, and/or a fungus.

The multifunctional composition may solid or liquid and may be include pet foods by further mixing with animal fat, animal protein, animal skin, antibiotics, beef by-product meal, beef meal, beef, carcasses of beef, carcasses of chicken, carcasses of fish, carcasses of lamb, carcasses of pigs, chicken by-product meal, chicken meal, chicken, chicken eggs, eggs, fish meal, fish oil, fish scales, flaxseed, lamb by-product meal, lamb meal, lamb, mammal by-product meal, mammal meal, pork by-product meal, pork meal, pork, shrimp, soybean oil, or sugar. The compositions disclosed herein may include foods including cannabinoids including CBD or THC to alleviate arthritis and anxiety in animals or humans. Compositions disclosed herein may include pet and animal foods including cannabinoids including CBD or THC to alleviate arthritis and anxiety. Compositions disclosed herein may include pet and animal foods derived from psilocybin mushrooms or drugs or additives.

In embodiments, the pet food or animal food is fed to pets or animals, the pets or animals include dogs and cats. In embodiments, the pet food or animal food is shaped, cooked, and flavored. In embodiments, the pet food of animal food is fed to pets or animals, the pets or animals include amphibians, arachnids, arthropods, hexapods, aviary birds, bats, burros, canaries, cats, centipedes, chickens, chinchillas, cockatiels, crabs, crickets, dogs, doves, ducks, falcons, ferrets, finches, freshwater fish, geese, gerbils, goats, guinea pigs, hamsters, hawks, hedgehogs, horses, invertebrates, insects, land invertebrates, lizards, llamas, lorikeets, lovebirds, mice, miniature horses, mites, worms, mynah birds, octopus, parakeets, parrots, pheasants, pigeons, pond fish, ponies, pot-bellied pigs, quail, rabbits, raccoons, rats, ringtail possum, saltwater fish, scorpions, short-tailed possum, shrimp, snails, squirrels, sugar gliders, tarantulas, tortoises, toucans, turkeys, or turtles.

In embodiments, the pet food or animal food is fed to pets or animals, the pets or animals include Anthocoridae, minute pirate bugs, pirate bugs, flower bugs, the genus Orius, omnivorous bugs, carnivorous bugs, Orthoptera order of insects, grasshoppers, crickets, katydids, weta, lubber, acrida, locusts, mites, spider mites, predatory mites, Neoseiulus fallacis, genus of mites that are in the Phytoseiidae family, arthropods, hexapods, beetles, cicadas, beetles, nematodes, mealworms, bats, mammals of the order Chiroptera, yellow mealworm beetles, Tenebrio Molitor, Tetranychus Urticae, carnivorous arthropods, omnivorous arthropods, green lacewings, insects in the family Chrysopidae, insects in the order Neuroptera, mantidflies, black soldier flies, black soldier fly larvae, butterflies, larvae, fly larvae, insect larvae, arthropod larvae, black soldier fly larvae, Hermetia illucens, antlions, mosquitos, Colorado potato beetle, Leptinotarsa decemlineata, moths, diamondback moth, Plutella xylostella, moth species of the family Plutellidae and genus Plutella. Encarsia Formosa, insects in the macrolepidopteran Glade Rhopalocera from the order Lepidoptera, whitefly parasites, ladybugs, spiders, dragonflies, orb-weaving spiders, arachnids, Spodoptera frugiperda, members of the spider family Araneidae, praying mantis, arachnids, eight-legged arthropods, and six-legged arthropods.

In embodiments, the pet food is shaped, cooked, flavored as disclosed herein. In embodiments, the pet food is kibble, wet, or canned. In embodiments, the pet food includes a water content ranging from between 1 weight percent of water to 2 weight percent of water, 2 weight percent of water to 3 weight percent of water, 3 weight percent of water to 4 weight percent of water, 4 weight percent of water to 5 weight percent of water, 5 weight percent of water to 6 weight percent of water, 6 weight percent of water to 7 weight percent of water, 7 weight percent of water to 8 weight percent of water, 8 weight percent of water to 9 weight percent of water, 9 weight percent of water to 10 weight percent of water, 10 weight percent of water to 11 weight percent of water, 11 weight percent of water to 12 weight percent of water, 12 weight percent of water to 13 weight percent of water, 13 weight percent of water to 14 weight percent of water, 14 weight percent of water to 15 weight percent of water, 15 weight percent of water to 16 weight percent of water, 16 weight percent of water to 17 weight percent of water, 17 weight percent of water to 18 weight percent of water, 18 weight percent of water to 19 weight percent of water, and 19 weight percent of water to 20 weight percent of water, 20 weight percent of water to 25 weight percent of water, 25 weight percent of water to 30 weight percent of water, 30 weight percent of water to 35 weight percent of water, 35 weight percent of water to 40 weight percent of water, 40 weight percent of water to 50 weight percent of water, 50 weight percent of water to 60 weight percent of water, 60 weight percent of water to 65 weight percent of water, 65 weight percent of water to 70 weight percent of water.

FIG. 18A:

FIG. 18A shows one non-limiting embodiment of a liquid mixing module (LMM) that is configured to mix water with multifunctional composition (6F23) provided from the multifunctional composition mixing module as shown in FIG. 18.

FIG. 18A shows one non-limiting embodiment of a liquid mixing module (LMM) that includes a first water treatment unit (C10), a second water treatment unit (C11), and a third water treatment unit (C12), that provide a third contaminant depleted water (C13) to the interior (C14) of a mixing tank (C15). The mixing tank (C15) mixes a water supply (C16) with multifunctional composition (6F23) provided from the multifunctional composition mixing module as shown in FIG. 18 to form a multifunctional composition and water mixture (C17). The multifunctional composition (6F23) introduced to the mixing tank (C15) may be a multifunctional composition (6F23) and/or a weighed multifunctional composition stream (6F22) provided from FIG. 18.

The multifunctional composition and water mixture (C17) is transferred from the mixing tank (C15) to the shaping module (14D) of FIG. 18B. In embodiments, the multifunctional composition and water mixture (C17) is transferred and pressurized using a pump (C18) from the mixing tank (C15) to the shaping module (14D) of FIG. 18A. In embodiments, the multifunctional composition and water mixture (C17) is transferred and pressurized using a screw auger, a pump, or a conveyor (C19) from the mixing tank (C15) to the shaping module (14D) of FIG. 18B.

FIG. 18A depicts the first water treatment unit (C10) to include a cation, a second water treatment unit (C11) to include an anion, and a third water treatment unit (C13) to include a membrane. A first water pressure sensor (C20) is positioned on the water input conduit (C21) that is introduced to the first input (C22) to the first water treatment unit (C10). In embodiments, a filter (C23), activated carbon (C24), and/or an adsorbent (C25), are positioned on the water input conduit (C21) prior to introducing the water supply (C16) to the first water treatment unit (C10). The water supply (C16) may be considered a contaminant-laden water (C26) that includes positively charged ions, negatively charged ions, and undesirable compounds. In embodiments, any type of treated water may be provided to the mixing tank (C15), such as distilled water, membrane treated water, adsorbent treated water, ion exchange treated water, catalyst treated water, ultraviolent treated water, and/or combinations thereof.

In embodiments, the positively charged ions are comprised of one or more from the group consisting of calcium, magnesium, sodium, and iron. In embodiments, the positively charged ions are comprised of one or more from the group consisting of aluminum, barium, beryllium, calcium, chromium(III), copper(I), copper(II), hydrogen, iron(II), iron(III), lead(II), lead(IV), lithium, magnesium, manganese (II), mercury(II), potassium, silver, sodium, strontium, tin (II), tin(IV), and zinc. In embodiments, the negatively charged ions are comprised of one or more from the group consisting of iodine, chloride, and sulfate. In embodiments, the negatively charged ions are comprised of one or more from the group consisting of acetate, aluminum silicate, anions from organic acids, azide, bromide, carbonate, chlorate, chloride, chromate, cyanide, dichromate, dihydrogen phosphate, fluoride, formate, hydride, hydrogen carbonate, hydrogen sulfate, hydrogen sulfite, hydroxide, hypochlorite, iodide, metasilicate, monohydrogen phosphate, nitrate, nitride, nitrite, oxalate, oxide, perchlorate, permanganate, peroxide, phosphate, silicate, sulfate, sulfide, sulfite, superoxide, and thiosulfate. In embodiments, the undesirable compounds are comprised of one or more from the group consisting of dissolved organic chemicals, viruses, bacteria, and particulates.

A first contaminant depleted water (C27) is discharged by the first water treatment unit (C10) by a first output (C28). The first contaminant depleted water (C27) may be a positively charged ion depleted water (C29). The first contaminant depleted water (C27) is then transferred to the second water treatment unit (C11) via a second input (C30). A second contaminant depleted water (C31) is discharged by the second water treatment unit (C11) by a second output (C32). The second contaminant depleted water (C31) may be a negatively charged ion depleted water (C33). The second contaminant depleted water (C31) is then transferred to the third water treatment unit (C12) via a third input (C34). A third contaminant depleted water (C13) is discharged by the third water treatment unit (C12) by a third output (C35). The third contaminant depleted water (C13) may be an undesirable compounds depleted water (C36). The third contaminant depleted water (C13) is then transferred to the interior (C14) of a mixing tank (C15) via a water supply conduit (C37) and water input (C38).

Within the interior (C14) of a mixing tank (C15), the water is mixed with multifunctional composition (6F23) provided from the multifunctional composition mixing module as shown in FIG. 18. In embodiments, a cation (C39), an anion (C40), and a polishing unit (C41), are positioned on the water supply conduit (C37) in between the third water treatment unit (C12) and the water input (C38) of the mixing tank (C15). The polishing unit (C41) may be any type of conceivable device to improve the water quality such as an membrane, a catalyst, ultraviolet unit, ozone unit, microwave unit, filter, a distillation system or the like.

In embodiments, the mixing tank (C15) is equipped with a sensor (C44). In embodiments, the mixing tank (C15) is equipped with a first sensor (C44) and a second sensor (C45). The first sensor (C44) is used for detecting a high level and the second sensor (C45) is used for detecting a low level. The first sensor (C44) is configured to output a signal to the computer (COMP) when the first sensor (C44) is triggered by a high level of liquid within the mixing tank (C15). The second sensor (C45) is configured to output a signal to the computer (COMP) when the second sensor (C45) is triggered by a low level of liquid within the mixing tank (C15). In embodiments, the mixing tank (C15) is equipped with a sensor (C44) wherein the sensor includes a dialysis unit. In embodiments, the dialysis unit is configured to remove toxins and/or waste from the mixing tank (C15). In embodiments, the dialysis unit includes at least one semipermeable membrane.

In embodiments, the insects (6G1) introduced to the mixing tank (C15) may include insect cells. In embodiments, the insects (6G1) may include oligoclonal recombinant baculovirus; oligoclonal insect cells infected with a monoclonal recombinant baculovirus; monoclonal insect cells; monoclonal insect cells infected with a baculovirus; monoclonal insect cells infected with a recombinant baculovirus; monoclonal insect cells infected with a polyclonal recombinant baculovirus; monoclonal insect cells infected with an oligoclonal recombinant baculovirus; and/or monoclonal insect cells infected with a monoclonal recombinant baculovirus.

In embodiments, the insects, and/or insect cells, (6G1) within the bioreactor (C15) of FIG. 18A include: cloned insects; transgenic insects; genetically engineered insects; insects that are infected with a recombinant baculovirus; insects that are infected with a cloned recombinant baculovirus; insects that are infected with a polyclonal recombinant baculovirus; insects that are infected with an oligoclonal recombinant baculovirus; and/or insects that are infected with a monoclonal recombinant baculovirus.

In embodiments, the insects, and/or insect cells, (6G1) within the bioreactor (C15) of FIG. 18A include: cloned insects; transgenic insects; genetically engineered insects; insects that are infected with a recombinant baculovirus; insects that are infected with a cloned recombinant baculovirus; insects that are infected with a polyclonal recombinant baculovirus; insects that are infected with an oligoclonal recombinant baculovirus; and/or insects that are infected with a monoclonal recombinant baculovirus.

In embodiments, the insects and/or insect cells then produce a variety of pharmaceutical compositions, including a cannabinoid, a cannabinoid glycoside, a recombinant protein, vaccine, antibody, peptide, or chemical and various other therapeutics and cosmetic personal products from insects using high-tech advancements in bioprocessing, chemical, and controls, and automation engineering technologies. In embodiments, the chemical includes one or more selected from the group consisting of cellular ribonucleic acid (RNA), ribosomal ribonucleic acid (RNA), messenger ribonucleic acid (RNA), transfer ribonucleic acid (RNA), competing endogenous RNA, microRNAs (miRNAs), messenger ribonucleic acid (mRNA), double-strand ribonucleic acid (dsRNA), plasmid deoxyribonucleic acid, and combinations thereof. In embodiments, the chemical includes a bioinsecticide. In embodiments, the chemical includes an insecticide. In embodiments, the chemical includes a fungicide. In embodiments, the chemical includes an insecticide. In embodiments, the chemical includes a steroid.

FIG. 18A shows a mixing tank discloses bioreactor (C15) configured to produce an insect-derived pharmaceutical composition from a source a mixture of water and genetically engineered insects to realize a biopharmaceutical manufacturing system with increased productivity, selectivity, flexibility, and reduction of cost and simplicity using a single use processing architecture.

In embodiments, the insect cell life support system includes a dialysis unit configured to remove contaminants away from the mixture of insect cells and treated water. In embodiments, a mixture of insect cells and treated water are purified to extract the antibodies and/or lectins and or a insect-derived cannabinoid from the bioreactor (C15). In embodiments, the pharmaceutical compositions, including the recombinant proteins, antibodies, and/or lectins are purified via chromatography purification, distillation, evaporation, adsorption, or crystallization. In embodiments, the insect-derived cannabinoid, recombinant protein, vaccine, antibody, peptide, or chemical is purified via chromatography purification, distillation, evaporation, adsorption, or crystallization. In embodiments, the bioreactor (C15) includes one or more ingredients selected from the group consisting of methylenedioxymethamphetamine, psilocybin, psilocin, baeocystin, norbaeocystin, cannabidiol, tetrahydrocannabinol, distilled cannabidiol, distilled tetrahydrocannabinol, serotonin, melatonin, lysergic acid diethylamide (LSD), ibogaine, and/or mescaline and combinations thereof. In embodiments, the pharmaceutical compositions produced in the bioreactor (C15) may be mixed with one or more ingredients selected from the group consisting of methylenedioxymethamphetamine, psilocybin, psilocin, baeocystin, norbaeocystin, cannabidiol, tetrahydrocannabinol, purified cannabinoid, a distilled cannabinoid, amongst other types listed above, and/or combinations thereof.

In embodiments, water supply valve (C42) is positioned on the water supply conduit (C37) in between the third water treatment unit (C12) and the water input (C38) of the mixing tank (C15). The water supply valve (C42) is equipped with a controller (C43) that inputs or outputs a signal from a computer (COMP). In embodiments, the mixing tank (C15) is equipped with a high-level sensor (C44) and a second sensor (C45). The first sensor (C44) is used for detecting a high level and the second sensor (C45) is used for detecting a low level. The first sensor (C44) is configured to output a signal to the computer (COMP) when the first sensor (C44) is triggered by a high level of liquid within the mixing tank (C15). The second sensor (C45) is configured to output a signal to the computer (COMP) when the second sensor (C45) is triggered by a low level of liquid within the mixing tank (C15).

In embodiments, when the second sensor (C45) sends a signal to the computer (COMP), the water supply valve (C42) on the water supply conduit (C37) is opened and introduces water into the mixing tank (C15) until the first sensor (C44) is triggered thus sending a signal to the computer (COMP) to close the water supply valve (C42). This level control loop including the first sensor (C44) for detecting a high level and a second sensor (C45) for detecting a lower level may be coupled to the operation of the water supply valve (C42) for introducing a water supply (C16) through a first water treatment unit (C10), a second water treatment unit (C11), and a third water treatment unit (C12), to provide a third contaminant depleted water (C13) to the interior (C14) of a mixing tank (C15).

The mixing tank (C15) may be placed on a load cell (C46) for measuring the mass of the tank. The mixing tank (C15) may be equipped with a mixer (C47) for mixing water with multifunctional composition (6F23). The multifunctional composition (6F23) is introduced to the interior (C14) of the mixing tank (C15) via an input (C51). In embodiments, the mixer (C47) may be of an auger or blade type that is equipped with a motor (C48).

The mixing tank (C15) has a multifunctional composition and water mixture output (C49) that is connected to a discharge conduit (C50). In embodiments, the mixer (C47) may be a wet grinder, a rotor/stator, or a high shear device. In embodiments, the wet grinder includes a rotor/stator with a single stage rotor that turns at high speed within a stationary stator. In embodiments, the mixer includes the rotor/stator and is positioned nearby the bottom of the mixing tank, and slightly off center. In embodiments, the mixer (C47) includes the rotor/stator and is positioned in the center of the mixing tank. In embodiments, the mixer (C47) includes a wet grinder. In embodiments, the wet grinder includes a rotor/stator. In embodiments, the wet grinder includes a high shear device.

In embodiments, the mixer (C47) includes a homogenizer, agitator, sawtooth blade, closed rotor, rotor/stator, an ultrasonic homogenizer, rotor/stator generator, colloid mill, high pressure, piston pump, a microfluidizer, and a microfluidizer processor. In embodiments, the ultrasonic homogenizer includes an ultrasonic horn (also known as acoustic horn, sonotrode, acoustic waveguide, ultrasonic probe) is a tapering metal bar commonly used for augmenting the oscillation displacement amplitude provided by an ultrasonic transducer operating at the low end of the ultrasonic frequency spectrum. In embodiments, the ultrasonic homogenizer includes one or more ultrasonic homogenizers selected from the group consisting of an ultrasonic horn, a converging ultrasonic horn, and a barbell ultrasonic horn. In embodiments, a sonotrode is a tool that creates ultrasonic vibrations and applies this vibrational energy to a gas, liquid, solid or tissue. In embodiments, a sonotrode includes of a plurality of piezoelectric transducers attached to a tapering metal rod.

In embodiments, the mixer includes two mixers, first, a rotor/stator, and second an ultrasonic homogenizer, wherein the ultrasonic homogenizer consumes power at a power consumption level ranging from one or more power consumption levels selected from the group consisting of 0.1 kw to 0.25 kw, 0.25 kw to 0.5 kw, 0.5 kw to 1 kw, 1 kw to 2 kw, 2 kw to 3 kw, 3 kw to 4 kw, 4 kw to 5 kw, 5 kw to 6 kw, 6 kw to 7 kw, 7 kw to 8 kw, 8 kw to 9 kw, 9 kw to 10 kw, kw to 11 kw, 11 kw to 12 kw, 12 kw to 13 kw, 13 kw to 14 kw, 14 kw to 15 kw, 15 kw to 16 kw, 16 kw to 17 kw, 17 kw to 18 kw, 18 kw to 19 kw, 19 kw to 20 kw, 20 kw to 25 kw, 25 kw to kw, 30 kw to 35 kw, 35 kw to 40 kw, 40 kw to 45 kw, 45 kw to 50 kw, 50 kw to 55 kw, 55 kw to 60 kw, 60 kw to 65 kw, 65 kw to 70 kw, 70 kw to 75 kw, 75 kw to 80 kw, 80 kw to 85 kw, 85 kw to 90 kw, 90 kw to 95 kw, 95 kw to 100 kw, 100 kw to 300 kw, 300 kw to 500 kw, and 500 kw to 1,000 kw.

The discharge conduit (C50) is connected at one end to the multifunctional composition and water mixture output (C49) of the mixing tank (C15) and at another end to a supply pump (C18) or a screw auger (C19). The supply pump (C18) or a screw auger (C19) provides a pressurized source of multifunctional composition and water mixture (C17) to the downstream shaping module (14D) as shown in FIG. 18A. The multifunctional composition and water mixture (C17) may be a pressurized multifunctional composition and water mixture (C17A).

In embodiments, a flow sensor (C51) and/or a flow totalizer (C52) may be installed on the water supply conduit (C37) to determine the mass or volume of water that is sent to the interior (C14) of the mixing tank (C15). In embodiments, the mixing tank (C15) is equipped with a heat exchanger (C53) to heat the mixture of water and multifunctional composition. The heat exchanger (C53) may be electrically heated or provided with a source of steam or hot oil. In embodiments, the heat exchanger (C53) accepts a third steam supply (LCT) that is provided by FIG. 17F. In embodiments, a third condensate (LAS) is discharged from the heat exchanger (C53) and is provided to the condensate tank (LAP) on FIG. 17F.

In embodiments, the mass of water or multifunctional composition within the mixing tank (C15) can be measured via the load cell (C46). In embodiments, water can be added to the mixing tank (C15) and the mass of water is measured, following by adding the multifunctional composition to the interior (C14) of the mixing tank (C15) to know the mass of the total mixture. The contents within the mixing tank (C15) can be mixed with the mixer and/or heated.

FIG. 18B:

FIG. 18B shows one non-limiting embodiment of a shaping module (14D) configured to shape the multifunctional composition and water mixture (C17) to produce a shaped multifunctional composition (D10).

Many shaping technologies are available to shape the multifunctional composition and water mixture (C17) including one or more from the group consisting of extrusion, sheet rolling, cutting rolls, a 3D printer, a hydraulic press, a mechanical press, a pneumatic press, a gummy candy making machine, a capsule filler machine, a candy making machine, and a pill making machine.

For example, extrusion is a process used to create a shaped multifunctional composition (D10) having a fixed cross-sectional profile. The shaped multifunctional composition may also be shaped in a variety of shapes, including the shape of an insect (if insects are added to the multifunctional composition mixing), for example, shaped into: a cow (if beef is added to the multifunctional composition mixing), a lamb (if lamb is added to the multifunctional composition mixing), a fish (if fish is added to the multifunctional composition mixing), a pig (if pork is added to the multifunctional composition mixing), a chicken (if chicken is added to the multifunctional composition mixing), a mushroom (if mushrooms are added to the multifunctional composition mixing), a dog (if the product will be a dog food), a dog (if the product will be a cat food), or into the shape of a *cannabis* leaf, or an insect (with a body and head) with a *cannabis* leaf surrounding the head.

In embodiments, a die (D15) has a fixed cross-sectional profile and is configured to accept the multifunctional composition and water mixture (C17) and press it into an extrudate (D11). The multifunctional composition and water mixture (C17) is pushed through a die of the desired cross-section to create an extrudate (D11) or a shaped multifunctional composition (D10) which may then be cooked in a cooking module (14E) as shown in FIG. 14E.

In embodiments, the shaping module (14D) includes an extrusion system (D12). In embodiments, the extrusion system (D12) includes an input hopper (D13), an auger (D14), and a die (D15). The auger (D14) is driven by a motor (D16). The multifunctional composition and water mixture (C17) is transferred from the liquid mixing module (LMM) as shown in FIG. 18A and provided to the input hopper (D13) of the extrusion system (D12).

The multifunctional composition and water mixture (C17) is transferred through the die (D15) by the rotating motion of an auger (D14). As the multifunctional composition and water mixture (C17) is pressed through the die (D15) by the auger (D14), friction causes at least a portion of the extrusion system (D12) to generate heat. In embodiments, the temperature within the extrusion system (D12) can increase due to the friction caused by formation of the extrudate (D11). This requires the extrusion system (D12) to require a source of coolant, such as cooling water, to cool regulate temperature and prevent overheating. In embodiments, the auger (D14) is cooled with a coolant.

The auger (D14) is equipped with a shaft (D17) and flights (D18) and is configured to applying pressure on the multifunctional composition and water mixture (C17) sufficient to squeeze through the die (D15). The shaped multifunctional composition (D10) or an extrudate (D11) is discharged from the extrusion system (D12) via an extrudate output (D19). The extrusion system (D12) is equipped with a stand (D20) to elevate it off the ground.

The shaped multifunctional composition (D10) or an extrudate (D11) is discharged from the extrusion system (D12) via an extrudate output (D19) and is transferred to a conveyor (D21). The conveyor (D21) transfers the extrudate (D11) to the cooking module (14E) as shown in FIG. 14E. The conveyor (D21) may be mechanical, pneumatic, air conveyor, elevating conveyor, conveyor belt, a drag-chain conveyor, bucket elevator, or any conceivable means to transfer extrudate (D11) from the extrusion system (D12) to the cooking module (14E).

In embodiments, the extrusion system (D12) is equipped with an extrusion pressure sensor (D21) configured to input or output a signal (D22) to the computer (COMP). In embodiments, the extrusion pressure sensor (D21) reads a pressure within the extrusion system (D12) ranging from: between 0.25 PSI to 49.99 PSI; between 50 PSI to 99.99 PSI; between 100 PSI to 149.99 PSI; between 150 PSI to 199.99 PSI; between 200 PSI to 249.99 PSI; between 250 PSI to 299.99 PSI; between 300 PSI to 349.99 PSI; between 350 PSI to 399.99 PSI; between 400 PSI to 449.99 PSI; between 450 PSI to 499.99 PSI; between 500 PSI to 549.99 PSI; between 550 PSI to 599.99 PSI; between 600 PSI to 649.99 PSI; between 650 PSI to 699.99 PSI; between 700 PSI to 749.99 PSI; between 750 PSI to 799.99 PSI; between 800 PSI to 8549.99 PSI; between 850 PSI to 899.99 PSI; between 900 PSI to 949.99 PSI; between 950 PSI to 999.99 PSI; between 1,000 PSI to 1,499.99 PSI; between 1,500 PSI to 1,999.99 PSI; between 2,000 PSI to 2,499.99 PSI; between 2,500 PSI to 2,999.99 PSI; between 3,000 PSI to 3,499.99 PSI; between 3,500 PSI to 3,999.99 PSI; between 4,000 PSI to 4,499.99 PSI; between 4,500 PSI to 4,999.99 PSI; between 5,000 PSI to 5,499.99 PSI; between 5,500 PSI to 5,999.99 PSI; between 6,000 PSI to 6,499.99 PSI; between 6,500 PSI to 6,999.99 PSI; between 7,000 PSI to 7,499.99 PSI; between 7,500 PSI to 7,999.99 PSI; between 8,000 PSI to 8,499.99 PSI; between 8,500 PSI to 8,999.99 PSI; between 9,000 PSI to 9,499.99 PSI; between 9,500 PSI to 9,999.99 PSI; between 10,000 PSI to 15,499.99 PSI; between 15,500 PSI to 19,999.99 PSI; between 20,000 PSI to 25,499.99 PSI; between 25,500 PSI to 29,999.99 PSI; between 30,000 PSI to 35,499.99 PSI; and, between 35,500 PSI to 40,000 PSI.

In embodiments, operation of the extrusion system (D12) includes maintaining the extrusion pressure sensor (D21) at a pressure less than 250 PSI. Nonetheless, all the above pressures may work as intended to realize a shaped multifunctional composition (D10).

The extrusion system (D12) may be equipped with a coolant input (D23) and a coolant output (D24). A coolant input temperature sensor (D25) is configured to input and output a signal (D26) to the computer (COMP) and measures the temperature of coolant that passes into the coolant input (D23). A coolant output temperature sensor (D27) is configured to input and output a signal (D28) to the computer (COMP) and measures the temperature of coolant that leaves the coolant output (D24). A coolant (D29) passes from the coolant input (D23) to the coolant output (D24) and accepts heat from at least a portion of the extrusion system (D12). The temperature of the coolant (D29) measured at the coolant output temperature sensor (D27) is greater than the temperature measured by the coolant input temperature sensor (D25).

In embodiments, the coolant input temperature sensor (D25) reads a temperature ranging from between 60 degrees Fahrenheit to 150 degrees Fahrenheit. In embodiments, the coolant output temperature sensor (D27) reads a temperature ranging from between 150.999 degrees Fahrenheit to 210 degrees Fahrenheit.

In embodiments, a cutting roll may be used to shape the multifunctional composition and water mixture (C17). In embodiments, the cutting roll includes cutting a continuous ribbon of shaped dough (e.g., the multifunctional composition, and/or the multifunctional composition and water mixture) suitable for cooking in the cooking module. In embodiments, the shaping module (14D) produces a burger patty that does not contain meat and contains a cannabinoid. In embodiments, the shaping module (14D) produces a burger patty that does not contain meat and contains a insects and/or or any number of combinations and permutations of cannabinoids, distilled cannabinoid, a purified cannabinoid, a cannabinoid glycoside, cannabinoid emulsion, cannabinoid microemulsion, cannabinoid nanoemulsion, and/or the colloidal dispersion and/or any additional ingredient, chemical, drug, additive, emulsifier, surfactant, etc., mentioned in this specification not only including such as a fiber-starch material, a binding agent, a moisture improving textural supplement, a density improving textural supplement, insects, psilocybin extract, psilocin extract, baeocystin extract, and/or norbaeocystin extract, a hallucinogen, serotonin, melatonin, psilocybin, psilocin, baeocystin, lysergic acid diethylamide (LSD), ibogaine, and/or mescaline, and combinations thereof.

In embodiments, the shaping module (14D) produces a burger patty that includes beans, especially soybeans and tofu, nuts, grains, seeds or fungi such as mushrooms or mycoprotein. In embodiments, the shaping module (14D) produces a burger patty that includes a cannabinoid and/or insects. In embodiments, the shaping module (14D) produces a burger patty that includes beans, especially soybeans and tofu, nuts, grains, seeds or fungi such as mushrooms or mycoprotein.

In embodiments, the shaping module (14D) produces a burger patty including an oil, the oil includes one or more oils selected from the group consisting of neem oil, almond oil, animal-based oils, apricot kernel oil, avocado oil, brazil nut oil, butter, *cannabis* oil, canola oil, cashew oil, cocoa butter, coconut oil, cooking oil, corn oil, cottonseed oil, fish oil, grapeseed oil, hazelnut oil, hemp oil, insect oil, lard, lard oil, macadamia nut oil, mustard oil, olive oil, palm kernel oil, palm oil, peanut oil, rapeseed oil, rice oil, rice bran oil, safflower oil, semi-refined sesame oil, semi-refined sunflower oil, sesame oil, soybean oil, tallow of beef, tallow of mutton, vegetable oil, and walnut oil.

In embodiments, the shaping module (14D) produces an insect-burger patty including a cannabinoid. In embodiments, the shaping module (14D) produces a burger patty including a cannabinoid. In embodiments, the shaping module (14D) includes a hydraulic press to produce a-burger patty. In embodiments, the shaping module (14D) produces a burger patty to emulate beef burgers. In embodiments, the insect-burger patty is a meat substitute or a meat analogue. In embodiments, the cannabinoid and/or the cannabinoid glycoside-infused burger patty is a meat substitute or a meat analogue. In embodiments, the burger patty is a meat substitute or a meat analogue. In embodiments, the burger patty is includes animal fat, animal protein, animal skin, an antibiotic, beef by-product meal, beef meal, beef, carcasses of beef, carcasses of chicken, carcasses of fish, carcasses of lamb, carcasses of pigs, chicken by-product meal, chicken meal, chicken, chicken eggs, eggs, fish meal, fish oil, fish scales, flaxseed, lamb by-product meal, lamb meal, lamb, pork by-product meal, pork meal, pork, and/or shrimp.

In embodiments, the shaped composition includes a pet food or animal food that is fed to pets or animals, the pets or animals include dogs and cats. In embodiments, the pet food of animal food is fed to pets or animals, the pets or animals include amphibians, arachnids, arthropods, hexapods, aviary birds, bats, burros, *canaries*, cats, centipedes, chickens, chinchillas, cockatiels, crabs, crickets, dogs, doves, ducks, falcons, ferrets, finches, freshwater fish, geese, gerbils, goats, guinea pigs, hamsters, hawks, hedgehogs, horses, invertebrates, insects, land invertebrates, lizards, llamas, lorikeets, lovebirds, mice, miniature horses, mites, worms, mynah birds, octopus, parakeets, parrots, pheasants, pigeons, pond fish, ponies, pot-bellied pigs, quail, rabbits, raccoons, rats, ring-tail possum, saltwater fish, scorpions, short-tailed possum, shrimp, snails, squirrels, sugar gliders, tarantulas, tortoises, toucans, turkeys, or turtles.

In embodiments, the burger patty includes insects, fungi, fruit, and/or a legume. In embodiments, the burger patty includes a fungi, wherein the fungi includes one or more selected from the group consisting of an edible mushroom, a mycoprotein, fistulina *hepatica*, laetiporus, and lyophyllum decastes. In embodiments, the edible mushroom includes one or more selected from the group consisting of *Agaricus bisporus, Pleurotus species, Lentinula edodes, Auricularia* auricula-judae, *Volvariella volvacea*, Flammulina velutipes, Tremella fuciformis, *Hypsizygus* tessellatus, *Stropharia* rugosoannulata, Cyclocybe aegerita, and Hericium *erinaceus*.

In embodiments, the edible mushroom includes psilocybin mushroom or Copelandia, Gymnopilus, *Inocybe*, Panaeolus, Pholiotina, Pluteus, and Psilocybe. In embodiments, the mycoprotein includes a form of a single-cell protein, also known as fungal protein, it is able to provide greater satiety than traditional protein sources such as chicken, while also being rich in protein and low in caloric content. In embodiments, the fistulina *hepatica* is a common mushroom known as beefsteak fungus. In embodiments, the laetiporus is a mushroom which is also named chicken of the woods. In embodiments, the lyophyllum decastes is a mushroom known as fried chicken mushroom. In embodiments, the fruit includes one or more selected from the group consisting of jackfruit, breadfruit, coconut, sapal, coconut pulp, young green jackfruit pulp, and eggplant. In embodiments, the fruit includes one or more selected from the group consisting of acerola, pomme, apple, apricot, avocado, banana, blackberries, blackcurrant, blueberries, breadfruit, cantaloupe, carambola, cherimoya, cherries, clementine, coconut meat, cranberries, custard-apple, date fruit, durian, elderberries, feijoa, figs, fruit extract, gooseberries, grapefruit, grapes, guava, honeydew melon, jackfruit, java-plum, jujube fruit, kiwifruit, kumquat, lemon, lime, lime, longan, loquat, lychee, mandarin, mango, mangosteen, mulberries, nectarine, olives, orange, *papaya*, passion fruit, peaches, pear, persimmon, pitaya, pineapple, pitanga, plantain, plums, pomegranate, prickly pear, prunes, pummelo, quince, raspberries, rhubarb, rose-apple, sapodilla, sapote, soursop, strawberries, sugar-apple, tamarind, tangerine, and watermelon.

In embodiments, the burger patty includes insects and a vegetable, wherein the vegetable includes one or more vegetables selected from the group consisting of artichoke, aubergine, eggplant, asparagus, legumes, alfalfa sprouts, azuki beans, adzuki, bean sprouts, black beans, black-eyed peas, borlotti bean, broad beans, chickpeas, garbanzos, ceci beans, green beans, kidney beans, lentils, lima beans, butter bean, mung beans, navy beans, peanuts, pinto beans, runner beans, split peas, soy beans, peas, mangetout, snap peas, broccoflower, broccoli, calabrese, brussels sprouts, cabbage, kohlrabi, Savoy cabbage, red cabbage, cauliflower, celery, endive, fiddleheads, frisee, fennel, greens, bok choy, chard, beet greens, collard greens, kale, mustard greens, spinach, herbs, anise, basil, caraway, coriander, chamomile, daikon, fennel, lavender, cymbopogon, lemongrass, marjoram, oregano, parsley, rosemary, thyme, lettuce, arugula, mushrooms, a fungus, nettles, New Zealand spinach, okra, onions, chives, garlic, peppers, bell pepper, chili pepper, jalapeno, habanero, paprika, tabasco pepper, cayenne pepper, ghost pepper, carolina reaper pepper, leek, onion, shallot, scallion, radicchio, rhubarb, root vegetables, beetroot, beet, mangelwurzel, carrot, celeriac, corms, eddoe, konjac, taro, water chestnut, ginger, parsnip, rutabaga, radish, wasabi, horseradish, Diakon radish, white radish, tubers, jicama, j erusalem artichoke, potato, sweet potato, yam, turnip, spinach, salsif, skirret, sweetcorn, topinambur, squash, acorn squash, bitter melon, butternut squash, banana squash, courgette, Zucchini, cucumber, delicata, gem squash, hubbard squash, spaghetti squash, tat soi, tomato, and watercress.

In embodiments, the burger patty includes a cannabinoid and/or a cannabinoid glycoside and an emulsifier, the emulsifier includes one or more selected from the group consisting of a surfactant, a nonionic surfactant, lecithin, polyethylene (40), stearate, polysorbate, Polyoxyethylene sorbitan monooleate, Polyoxyethylene (20) sorbitan monooleate, polysorbate 80, polysorbate 60, polysorbate 65, ammonium salts of phosphatidic acid, sucrose acetate isobutyrate, potassium pyrophosphate, sodium acid pyrophosphate, sodium pyrophosphate, potassium polymetaphosphate, sodium metaphosphate, insoluble or sodium polyphosphates, sodium polyphosphates, insoluble polyphosphates, glassy salts of fatty acids, mono- and di-glycerides of fatty acids, mono-glycerides of fatty acids, di-glycerides of fatty acids, acetic and fatty acid esters of glycerol, lactic and fatty acid esters of glycerol, citric and fatty acid esters of glycerol, diacetyltartaric and fatty acid esters of glycerol, mixed fatty acid esters of glycerol, sucrose esters of fatty acids, polyglycerol esters of fatty acids, polyglycerol esters of interesterified ricinoleic acid, propylene glycol mono- and di-esters, propylene glycol di-esters, propylene glycol mono-esters, propylene glycol esters of fatty acids, propylene glycol esters, dioctyl sodium sulphosuccinate, sodium lactylate, sodium oleyl lactylate, sodium stearoyl lactylate, calcium lactylate, calcium oleyl lactylate, calcium stearoyl lactylate, sorbitan monostearate, maltodextrin, polyphosphates, formulated polyphosphates, and gum arabic.

In embodiments, the burger patty includes a cannabinoid and/or a cannabinoid glycoside and a biocatalyst, the biocatalyst includes one or more selected from the group consisting of an *acetobacter*, actoBacillus *acidophilus, LactoBacillus acidophilus, ananas* comorus, *Ananas comosus, Aspergillus* melleus, *Aspergillus niger, Aspergillus oryzae*, bacilliales, *Bacillus licheniformis, Bacillus subtilis* var. natto, *Bacillus subtilis*, bifidobacteriales, *Bifidobacterium bifidum*, bromelain, *Candida utilis, Carica papaya*, casein, an enzyme, eurotiales, a fungus, lactobacilliales, *lactobacillus LactoBacillus casei, LactoBacillus helveticus, LactoBacillus plantarum*, a microorganism, papain, peptidase, phaffia rhodozyma, protease A, protease, rhodospirillales, *Saccharomyces cerevisiae*, saccharomycetales, *streptococcus* thermopilus, *Yarrowia lipolytica*, and yeast.

In embodiments, the burger patty includes a cannabinoid and/or a cannabinoid glycoside and an acid, acetic acid, ascorbic acid, citric acid, formic acid, fumaric acid, lactic acid, malic acid, nitric acid, organic acids, phosphoric acid, propionic acid, salicylic acid, and tartaric acid. In embodiments, the burger patty includes a cannabinoid and/or a cannabinoid glycoside and a preservative, the preservative includes one or more selected from the group consisting of antioxidant, benzoate, butylated hydroxyanisole (BHA), butylated hydroxytoluene (BHT), calcium silicate, calcium sorbate, carrageenan, chelating agent, corn syrup, dextrin, dextrose, disodium ethylenediaminetetraacetic acid (EDTA), disodium guanylate, disodium inosinate, maltodextrain, modified food starch, nitrite, polyphosphate, potassium bisulfite, potassium chloride, potassium metabisulfite, potassium sorbate, propionate, sodium bisulfite, sodium metabisulfite, sodium phosphate, sodium sorbate, sodium sulfite, sorbate, and sulfite.

In embodiments, the legume includes one or more selected from the group consisting of burmese tofu (water, chickpea flour, and turmeric), falafel, ganmodoki, thawed and sliced frozen tofu, koya-dofu, oncom, soy protein, soybean meal, soy pulp, tempeh, textured vegetable protein, tofu, tofurkey, vegetarian bacon, vegan hot dog, vegan sausage, vegan burger, vegetarian hot dog, vegetarian sausage, veggie burger, and meat substitute.

Example 1: A burger patty including a cannabinoid and two or more ingredients selected from the group consisting of insects, a fungi, a fruit, and a legume; wherein: the fungi includes one or more selected from the group consisting of an edible mushroom, a mycoprotein, fistulina *hepatica*, laetiporus, and lyophyllum decastes; the fruit includes one or more selected from the group consisting of j ackfruit, breadfruit, coconut, sapal, coconut pulp, young green jackfruit pulp, and eggplant; the legume includes one or more selected from the group consisting of burmese tofu, falafel, ganmodoki, thawed and sliced frozen tofu, koya-dofu, oncom, soy protein, soybean meal, soy pulp, tempeh, textured vegetable protein, tofu, tofurkey, vegetarian bacon, vegan hot dog, vegan sausage, vegan burger, vegetarian hot dog, vegetarian sausage, veggie burger, and a meat substitute.

In embodiments, the edible mushroom includes one or more selected from the group consisting of *Agaricus bisporus, Pleurotus species, Lentinula edodes, Auricularia* auricula-judae, *Volvariella volvacea*, Flammulina velutipes, Tremella fuciformis, *Hypsizygus* tessellatus, *Stropharia* rugosoannulata, Cyclocybe aegerita, and Hericium *erinaceus*. In embodiments, the edible mushroom includes one or more selected from the group consisting of Copelandia, Gymnopilus, *Inocybe*, Panaeolus, Pholiotina, Pluteus, and Psilocybe.

In embodiments, the burger patty includes a cannabinoid and/or a cannabinoid glycoside and an oil, the oil includes one or more oils selected from the group consisting of neem oil, almond oil, animal-based oils, apricot kernel oil, avocado oil, brazil nut oil, butter, *cannabis* oil, canola oil, cashew oil, cocoa butter, coconut oil, cooking oil, corn oil, cottonseed oil, fish oil, grapeseed oil, hazelnut oil, hemp oil, insect oil, lard, lard oil, macadamia nut oil, mustard oil, olive oil, palm kernel oil, palm oil, peanut oil, rapeseed oil, rice oil, rice bran oil, safflower oil, semi-refined sesame oil, semi-refined sunflower oil, sesame oil, soybean oil, tallow of beef, tallow of mutton, vegetable oil, and walnut oil.

In embodiments, the burger patty includes a cannabinoid and/or a cannabinoid glycoside and a flavoring, the flavoring includes one or more flavorings selected from the group consisting of allspice berries, almond meal, anise seed, annato seed, arrowroot powder, basil, bay leaves, black pepper, buttermilk, *cannabis*, capsaicin, caraway, cayenne, celery seed, cheese cultures, chervil, Chile powder, chives, cilantro, cinnamon, citric acid, cloves, coconut shredded, coriander, corn oil, corn starch, cream of tartar, cubeb berries, cumin, curry, dextrose, dill, enzymes, fennel, fenugreek, file powder, garlic powder, ginger, grapefruit peel, green peppercorns, honey, horseradish powder, juniper berries, kaffir lime, lavender, lemon grass powder, lemon peel, lime peel, long pepper, marjoram, molasses, mustard, natural smoke flavor, nigella seeds, nutmeg, onion powder, orange peel, oregano, paprika, parsley, peppermint, poppy seed, powdered cheese, red pepper, rose petals, rosemary, saffron, *sassafras*, sage, salt, savory, sesame seed, star anise, sugar, sugar maple, sumac, tamarind, tangerine peel, tarragon, tetrahydrocannabinol, thyme, tomatillo powder, tomato powder, torula yeast, turmeric, vanilla extract, wasabi powder, whey, white peppercorns, yeast extract, and yeast.

In embodiments, the burger patty includes a cannabinoid and/or a cannabinoid glycoside and a preservative, the preservative includes one or more selected from the group consisting of antioxidant, benzoate, butylated hydroxyanisole (BHA), butylated hydroxytoluene (BHT), calcium silicate, calcium sorbate, carrageenan, chelating agent, corn syrup, dextrin, dextrose, disodium ethylenediaminetetraacetic acid (EDTA), disodium guanylate, disodium inosinate, maltodextrain, modified food starch, nitrite, polyphosphate, potassium bisulfite, potassium chloride, potassium metabisulfite, potassium sorbate, propionate, sodium bisulfite, sodium metabisulfite, sodium phosphate, sodium sorbate, sodium sulfite, sorbate, and sulfite.

In embodiments, the burger patty includes a cannabinoid and/or a cannabinoid glycoside and an acid, acetic acid, ascorbic acid, citric acid, formic acid, fumaric acid, lactic acid, malic acid, nitric acid, organic acids, phosphoric acid, propionic acid, salicylic acid, and tartaric acid.

In embodiments, the burger patty includes a cannabinoid and/or a cannabinoid glycoside and a biocatalyst, the biocatalyst includes one or more selected from the group consisting of an *acetobacter*, actoBacillus *acidophilus, LactoBacillus acidophilus, ananas* comorus, *Ananas comosus, Aspergillus* melleus, *Aspergillus niger, Aspergillus oryzae*, bacilliales, *Bacillus licheniformis, Bacillus subtilis* var. natto, *Bacillus subtilis*, bifidobacteriales, *Bifidobacterium bifidum*, bromelain, *Candida utilis, Carica papaya*, casein, an enzyme, eurotiales, a fungus, lactobacilliales, *lactobacillus LactoBacillus casei, LactoBacillus helveticus, LactoBacillus plantarum*, a microorganism, papain, peptidase, phaffia rhodozyma, protease A, protease, rhodospirillales, *Saccharomyces cerevisiae*, saccharomycetales, *streptococcus* thermopilus, *Yarrowia lipolytica*, and yeast.

In embodiments, the burger patty includes a cannabinoid and/or a cannabinoid glycoside and an emulsifier, the emulsifier includes one or more selected from the group consisting of a surfactant, a nonionic surfactant, lecithin, polyethylene (40), stearate, polysorbate, Polyoxyethylene sorbitan monooleate, Polyoxyethylene (20) sorbitan monooleate, polysorbate 80, polysorbate 60, polysorbate 65, ammonium salts of phosphatidic acid, sucrose acetate isobutyrate, potassium pyrophosphate, sodium acid pyrophosphate, sodium pyrophosphate, potassium polymetaphosphate, sodium metaphosphate, insoluble or sodium polyphosphates, sodium polyphosphates, insoluble polyphosphates, glassy salts of fatty acids, mono- and di-glycerides of fatty acids, mono-glycerides of fatty acids, di-glycerides of fatty acids, acetic and fatty acid esters of glycerol, lactic and fatty acid esters of glycerol, citric and fatty acid esters of glycerol, diacetyltartaric and fatty acid esters of glycerol, mixed fatty acid esters of glycerol, sucrose esters of fatty acids, polyglycerol esters of fatty acids, polyglycerol esters of interesterified ricinoleic acid, propylene glycol mono- and di-esters, propylene glycol di-esters, propylene glycol mono-esters, propylene glycol esters of fatty acids, propylene glycol esters, dioctyl sodium sulphosuccinate, sodium lactylate, sodium oleyl lactylate, sodium stearoyl lactylate, calcium lactylate, calcium oleyl lactylate, calcium stearoyl lactylate, sorbitan monostearate, maltodextrin, polyphosphates, formulated polyphosphates, and gum arabic.

In embodiments, the burger patty includes a cannabinoid and/or a cannabinoid glycoside and a vegetable, wherein the vegetable includes one or more vegetables selected from the group consisting of artichoke, aubergine, eggplant, asparagus, legumes, alfalfa sprouts, azuki beans, adzuki, bean sprouts, black beans, black-eyed peas, borlotti bean, broad beans, chickpeas, garbanzos, ceci beans, green beans, kidney beans, lentils, lima beans, butter bean, mung beans, navy beans, peanuts, pinto beans, runner beans, split peas, soy beans, peas, mangetout, snap peas, broccoflower, broccoli, calabrese, brussels sprouts, cabbage, kohlrabi, Savoy cabbage, red cabbage, cauliflower, celery, endive, fiddleheads, frisee, fennel, greens, bok choy, chard, beet greens, collard greens, kale, mustard greens, spinach, herbs, anise, basil, caraway, coriander, chamomile, daikon, fennel, lavender, cymbopogon, lemongrass, marjoram, oregano, parsley, rosemary, thyme, lettuce, arugula, mushrooms, a fungus, nettles, New Zealand spinach, okra, onions, chives, garlic, peppers, bell pepper, chili pepper, jalapeno, habanero, paprika, tabasco pepper, cayenne pepper, ghost pepper, carolina reaper pepper, leek, onion, shallot, scallion, radicchio, rhubarb, root vegetables, beetroot, beet, mangel-wurzel, carrot, celeriac, corms, eddoe, konjac, taro, water chestnut, ginger, parsnip, rutabaga, radish, wasabi, horseradish, Diakon radish, white radish, tubers, jicama, jerusalem artichoke, potato, sweet potato, yam, turnip, spinach, salsif, skirret, sweetcorn, topinambur, squash, acorn squash, bitter melon, butternut squash, banana squash, courgette, Zucchini, cucumber, delicata, gem squash, hubbard squash, spaghetti squash, tat soi, tomato, and watercress.

In embodiments, the burger patty includes a cannabinoid and/or a cannabinoid glycoside and the fruit further includes one or more selected from the group consisting of acerola, pomme, apple, apricot, avocado, banana, blackberries, blackcurrant, blueberries, breadfruit, cantaloupe, carambola, cherimoya, cherries, clementine, coconut meat, cranberries, custard-apple, date fruit, durian, elderberries, feijoa, figs, fruit extract, gooseberries, grapefruit, grapes, guava, honeydew melon, jackfruit, java-plum, jujube fruit, kiwifruit, kumquat, lemon, lime, lime, longan, loquat, lychee, mandarin, mango, mangosteen, mulberries, nectarine, olives, orange, *papaya*, passion fruit, peaches, pear, persimmon, pitaya, pineapple, pitanga, plantain, plums, pomegranate, prickly pear, prunes, pummelo, quince, raspberries, rhubarb, rose-apple, sapodilla, sapote, soursop, strawberries, sugar-apple, tamarind, tangerine, and watermelon.

In embodiments, the burger patty is fried in an oil, wherein the oil includes one or more oils selected from the group consisting of neem oil, almond oil, animal-based oils, apricot kernel oil, avocado oil, brazil nut oil, butter, *cannabis* oil, canola oil, cashew oil, cocoa butter, coconut oil, cooking oil, corn oil, cottonseed oil, fish oil, grapeseed oil, hazelnut oil, hemp oil, insect oil, lard, lard oil, macadamia nut oil, mustard oil, olive oil, palm kernel oil, palm oil, peanut oil, rapeseed oil, rice oil, rice bran oil, safflower oil, semi-refined sesame oil, semi-refined sunflower oil, sesame oil, soybean oil, tallow of beef, tallow of mutton, vegetable oil, and walnut oil. In embodiments, the burger patty is cooked, baked, freeze dried, frozen, and/or dehydrated.

In embodiments, the burger patty includes a diameter ranging from 2.5 to 4 inches. In embodiments, the burger patty includes: a serving size ranging from 37 to 170 grams. In embodiments, the burger patty includes: one, two, or three or more selected from the group consisting of: a fat content ranging from 1 to 27 grams per serving; a sodium content ranging from 0.1 to 0.6 grams per serving; a carbohydrate content ranging from 2 to 15 grams per serving; a fiber content ranging from 0.5 to 5 grams per serving; and a protein content ranging from 5 to 30 grams per serving.

In embodiments, the burger patty includes: one, two, or three or more selected from the group consisting of: a calcium content ranging from 0.05 to 3 grams per serving; an iron content ranging from 0.001 to 0.15 grams per serving; an potassium content ranging from 0.1 to 1.5 grams per serving; a zinc content ranging from 0.0001 to 0.005 grams per serving; a copper content ranging from 0.0001 to 0.005 grams per serving; and a manganese content ranging from 0.0001 to grams per serving.

In embodiments, the burger patty includes: one or more selected from the group consisting of crickets, black soldier fly larvae, black soldier fly prepupa, black soldier fly pupae, beetles, and beetle larvae. In embodiments, the burger patty includes: frozen insects, whole insects, insect powder, ground insects, spray-dried insects, fermented insects, lipid depleted insects, cooked whole insects, roasted whole crickets, dehydrated whole insects, and free-dried whole insects, and combinations thereof. In embodiments, the burger patty is produced according to a method, comprising: providing a source of insects; mixing the insects with water and the two or more ingredients selected from the group consisting of a fungi, a fruit, and a legume, to produce a mixture; shaping the mixture to produce the burger patty.

In embodiments, the burger patty is frozen and packaged. In embodiments, the burger patty is packaged in plastic. In embodiments, the burger patty is packaged in plastic and carboard. In embodiments, the burger patty is packaged in biodegradable plastic and recycled carboard. In embodiments, the burger patty is packaged in biodegradable plastic. In embodiments, the burger patty is packaged in biodegradable plastic, wherein: the biodegradable plastic is derived from a renewable raw material, a microorganism, a petrochemicals, or combinations thereof. In embodiments, the burger patty is packaged in a bio-based plastic. In embodiments, the burger patty is packaged in a bio-based plastic, wherein the bio-based plastic includes one or more selected from the group consisting of plants, animals, and microorganisms. In embodiments, the burger patty is packaged in a bio-based plastic derived from insects.

In embodiments, the burger patty is packaged in a bio-based plastic, wherein the bio-based plastic includes polyhydroxyalkanoates. In embodiments, the burger patty is packaged in a bio-based plastic, wherein the bio-based plastic is derived from bacteria including *cupriavidus* necator, *Alcaligenes latus*, and/or *Pseudomonas putida*. In embodiments, the burger patty is packaged in a bio-based plastic, wherein the bio-based plastic includes a thermoplastic aliphatic polyester. In embodiments, the burger patty is packaged in a bio-based plastic, wherein the bio-based plastic includes polylactic acid. In embodiments, the burger patty is packaged in a bio-based plastic, wherein the bio-based plastic includes a thermoplastic polymer comprising starch and a plasticizer. In embodiments, the burger patty is packaged in a bio-based plastic, wherein the bio-based plastic includes a thermoplastic polymer comprising starch/polylactic acid, starch/polycaprolactone, and/or starch/polybutylene-adipate-co-terephthalate. In embodiments, the burger patty is packaged in a bio-based plastic, wherein the bio-based plastic includes a cellulose ester, cellulose acetate and nitrocellulose, and/or a lignin-based polymer composite.

In embodiments, the shaped multifunctional composition is frozen and packaged. In embodiments, the shaped multifunctional composition is packaged in plastic. In embodiments, the shaped multifunctional composition is packaged in plastic and carboard. In embodiments, the shaped multifunctional composition is packaged in biodegradable plastic and recycled carboard. In embodiments, the shaped multifunctional composition is packaged in biodegradable plastic. In embodiments, the shaped multifunctional composition is packaged in biodegradable plastic, wherein: the biodegradable plastic is derived from a renewable raw material, a microorganism, a petrochemicals, or combinations thereof. In embodiments, the shaped multifunctional composition is packaged in a bio-based plastic. In embodiments, the shaped multifunctional composition is packaged in a bio-based plastic, wherein the bio-based plastic includes one or more selected from the group consisting of plants, animals, and microorganisms. In embodiments, the shaped multifunctional composition is packaged in a bio-based plastic derived from insects. In embodiments, the shaped multifunctional composition is packaged in a bio-based plastic, wherein the bio-based plastic includes polyhydroxyalkanoates. In embodiments, the shaped multifunctional composition is packaged in a bio-based plastic, wherein the bio-based plastic is derived from bacteria including *cupriavidus* necator, *Alcaligenes latus*, and/or *Pseudomonas putida*. In embodiments, the shaped multifunctional composition is packaged in a bio-based plastic, wherein the bio-based plastic includes a thermoplastic aliphatic polyester. In embodiments, the shaped multifunctional composition is packaged in a bio-based plastic, wherein the bio-based plastic includes polylactic acid. In embodiments, the shaped multifunctional composition is packaged in a bio-based plastic, wherein the bio-based plastic includes a thermoplastic polymer comprising starch and a plasticizer. In embodiments, the shaped multifunctional composition is packaged in a bio-based plastic, wherein the bio-based plastic includes a thermoplastic polymer comprising starch/polylactic acid, starch/polycaprolactone, and/or starch/polybutylene-adipate-co-terephthalate. In embodiments, the shaped multifunctional composition is packaged in a bio-based plastic, wherein the bio-based plastic includes a cellulose ester, cellulose acetate and nitrocellulose, and/or a lignin-based polymer composite.

In embodiments, the cooked and cooked and shaped multifunctional composition is frozen and packaged. In embodiments, the cooked and shaped multifunctional composition is packaged in plastic. In embodiments, the cooked and shaped multifunctional composition is packaged in plastic and carboard. In embodiments, the cooked and shaped multifunctional composition is packaged in biodegradable plastic and recycled carboard. In embodiments, the cooked and shaped multifunctional composition is packaged in biodegradable plastic. In embodiments, the cooked and shaped multifunctional composition is packaged in biodegradable plastic, wherein: the biodegradable plastic is derived from a renewable raw material, a microorganism, a petrochemicals, or combinations thereof. In embodiments, the cooked and shaped multifunctional composition is packaged in a bio-based plastic. In embodiments, the cooked and shaped multifunctional composition is packaged in a bio-based plastic, wherein the bio-based plastic includes one or more selected from the group consisting of plants, animals, and microorganisms. In embodiments, the cooked and shaped multifunctional composition is packaged in a bio-based plastic derived from insects. In embodiments, the cooked and shaped multifunctional composition is packaged in a bio-based plastic, wherein the bio-based plastic includes polyhydroxyalkanoates. In embodiments, the cooked and shaped multifunctional composition is packaged in a bio-based plastic, wherein the bio-based plastic is derived from bacteria including *cupriavidus* necator, *Alcaligenes latus*, and/or *Pseudomonas putida*. In embodiments, the cooked and shaped multifunctional composition is packaged in a bio-based plastic, wherein the bio-based plastic includes a thermoplastic aliphatic polyester. In embodiments, the cooked and shaped multifunctional composition is packaged in a bio-based plastic, wherein the bio-based plastic includes polylactic acid. In embodiments, the cooked and shaped multifunctional composition is packaged in a bio-based plastic, wherein the bio-based plastic includes a thermoplastic polymer comprising starch and a plasticizer. In embodiments, the cooked and shaped multifunctional composition is packaged in a bio-based plastic, wherein the bio-based plastic includes a thermoplastic polymer comprising starch/polylactic acid, starch/polycaprolactone, and/or starch/polybutylene-adipate-co-terephthalate. In embodiments, the cooked and shaped multifunctional composition is packaged in a bio-based plastic, wherein the bio-based plastic includes a cellulose ester, cellulose acetate and nitrocellulose, and/or a lignin-based polymer composite.

FIG. 18C:

FIG. 18C shows one non-limiting embodiment of a cooking module (14E) configured to cook the shaped multifunctional composition (D10) provided from the shaping module (14D) to form a cooked multifunctional composition (E18A).

FIG. 18C shows one non-limiting embodiment of a cooking module (14E) configured to cook the shaped multifunctional composition (D10) (e.g., wherein the shaped multifunctional composition has been subjected to extrusion, sheet rolling, cutting rolls, 3D printing, hydraulic press, mechanical press, a pneumatic press, a gummy candy making machine, a capsule filler machine, a candy making machine, a pill making machine) provided from the shaping module (14D) to form a cooked multifunctional composition (E18A).

The cooking module (14E) as shown in FIG. 18C includes a cooking system (E10). The cooking system (E10) shown in FIG. 18C includes an oven (E11) or a fryer (E12). In embodiments, the fryer (E12) cooks the extrudate (D11), and/or the shaped multifunctional composition (D10), in an oil (E19). In embodiments, the oil (E19) are lipids extracted from insects. In embodiments, the oil (E19) may be comprised of one or more from the group consisting of almond oil, animal-based oils, apricot kernel oil, avocado oil, brazil nut oil, butter, *cannabis* oil, canola oil, cashew oil, cocoa butter, coconut oil, cooking oil, corn oil, cottonseed oil, fish oil, grapeseed oil, hazelnut oil, hemp oil, insect oil, lard, lard oil, macadamia nut oil, mustard oil, olive oil, palm kernel oil, palm oil, peanut oil, rapeseed oil, rice oil, rice bran oil, safflower oil, semi-refined sesame oil, semi-refined sunflower oil, sesame oil, soybean oil, tallow of beef, tallow of mutton, vegetable oil, and walnut oil.

In embodiments, the cooking system (E10) includes a heat exchanger (E20) that cooks the shaped multifunctional composition (D10). In embodiments, the heat exchanger (E20) accepts a fourth steam supply (LCX) that is provided from FIG. 17F. In embodiments, the heat exchanger (E20) outputs a fourth condensate (LAT) and is provided to the condensate tank (LAP) on FIG. 17F. In embodiments, the fryer (E12) has a heat exchanger (E20) that heats an oil (E19) which in turn cooks the shaped multifunctional composition (D10). In embodiments, the heat exchanger (E20)

accepts a fourth steam supply (LCX) that is provided from FIG. 17F. In embodiments, the heat exchanger (E20) outputs a fourth condensate (LAT) and is provided to the condensate tank (LAP) on FIG. 17F. The cooking system (E10) may also include a dryer (E13), pressure cooker (E14), dehydrator (E15), freeze dryer (E16), and may operate in a batch or continuous mode.

In embodiments, the cooking system (E10) employs electricity to cook the shaped multifunctional composition (D10), wherein the electricity is provided by either the power production system of FIG. 17F and/or the solar panels (SOLAR) that provide electricity for the farming superstructure system (FSS) as shown on FIG. 3.

In embodiments, the shaping system (D11) employs electricity to shape the multifunctional composition, wherein the electricity is provided by either the power production system of FIG. 17F and/or the solar panels (SOLAR) that provide electricity for the farming superstructure system (FSS) as shown on FIG. 3.

A conveyor (E17) may be integrated with the cooking system (E10). The conveyor (E17) may be mechanical, pneumatic, air operated, electricity operated, an elevating conveyor, conveyor belt, drag-chain conveyor, or the like.

The cooking system (E10) cooks the extrudate (D11) and/or the shaped multifunctional composition (D10) provided from the shaping module (14D) to form a cooked extrudate (E18) and/or a cooked multifunctional composition (E18A). The cooked extrudate (E18) or cooked multifunctional composition (E18A) is transferred to the flavoring module (14F) as shown in FIG. 18C. In embodiments, the cooked multifunctional composition (E18A) is a cooked extrudate (E18). In embodiments, the cooked multifunctional composition (E18A) is a cooked extrudate, a cooked portion of a rolled sheet of dough, cooked dough cut by rolls, a cooked multifunctional composition shaped by a cutting rolls, a cooked multifunctional composition shaped by sheet rolling, a 3D printed cooked multifunctional composition, a cooked multifunctional composition shaped by a hydraulic press, a cooked multifunctional composition shaped by a mechanical press, a cooked multifunctional composition shaped by a pneumatic press, a cooked multifunctional composition shaped by a gummy candy making machine, a cooked multifunctional composition shaped by a capsule filler machine, a cooked multifunctional composition shaped by a candy making machine, and/or a cooked multifunctional composition shaped by a pill making machine.

In embodiments, the cooked multifunctional composition (E18A) is cooked under vacuum conditions. In embodiments, the cooked multifunctional composition (E18A) is cooked under vacuum conditions at a pressure below atmospheric pressure ranging from one of more pressures selected from the group consisting of 0.25 pounds per square inch absolute (PSIA) to 0.5 PSIA, 0.5 PSIA to 1 PSIA, 1 PSIA to 1.5 PSIA, 1.5 PSIA to 3 PSIA, 3 PSIA to 4.5 PSIA, 4.5 PSIA to 6 PSIA, 6 PSIA to 7.5 PSIA, 7.5 PSIA to 9 PSIA, 9 PSIA to 10.5 PSIA, 10.5 PSIA to 12 PSIA, 12 PSIA to 13.5 PSIA, 12 PSIA to 12.25 PSIA, 12.25 PSIA to 12.5 PSIA, 12.5 PSIA to 12.75 PSIA, 12.75 PSIA to 13 PSIA, 13 PSIA to 13.25 PSIA, 13.25 PSIA to 13.5 PSIA, 13.5 PSIA to 13.75 PSIA, 13.75 PSIA to 14 PSIA, and 14 PSIA to 14.25 PSIA.

In embodiments, the cooking system (E10) cooks the extrudate (D11) at a temperature ranging from between: 60 degrees F. to 70 degrees F., 70 degrees F. to 80 degrees F., 80 degrees F. to 90 degrees F., 90 degrees F. to 100 degrees F., 100 degrees F. to 124.99 degrees F.; 125 degrees F. to 149.99 degrees F.; 150 degrees F. to 174.99 degrees F.; 175 degrees F. to 199.99 degrees F.; 200 degrees F. to 224.99 degrees F.; 225 degrees F. to 249.99 degrees F.; 250 degrees F. to 274.99 degrees F.; 275 degrees F. to 299.99 degrees F.; 300 degrees F. to 324.99 degrees F.; 325 degrees F. to 349.99 degrees F.; 350 degrees F. to 374.99 degrees F.; 375 degrees F. to 399.99 degrees F.; 400 degrees F. to 550 degrees F.

In embodiments, the cooking system (E10) cooks the shaped multifunctional composition over a time duration ranging from between: 1 second to 5 seconds, 5 seconds to 15 seconds; 15 seconds to 30 seconds; 30 seconds to 1 minute; 1 minute to 2 minutes; 2 minutes to 3 minutes; 3 minutes to 4 minutes; 4 minutes to 5 minutes; 5 minutes to 6 minutes; 6 minutes to 7 minutes; 7 minutes to 8 minutes; 8 minutes to 9 minutes; 9 minutes to 10 minutes; 11 minutes to 12 minutes; 12 minutes to 13 minutes; 13 minutes to 14 minutes; 14 minutes to 15 minutes; 15 minutes to 16 minutes; 16 minutes to 17 minutes; 17 minutes to 18 minutes; 18 minutes to 19 minutes; 19 minutes to 60 minutes.

In embodiments, an air-oil heat exchanger (E21), an oil pump (E24), temperature sensor (E25), and a computer (E26) are integrated with the cooking system (E10). Hot oil (E19) is pumped from the fryer (E12) via an oil pump (E24) to the air-oil heat exchanger (E21) where heat is removed from the oil (E19) and transferred to the air (E23) by use of a fan (E22) to heat the air (E23) that is located above the cooking system (E10).

In embodiments, the temperature sensor (E26) measures the temperature of the air (E23) above the cooking system (E10) and sends a signal (E27) to the computer (COMP). A pre-determined air temperature is entered into the computer (COMP) which may include one or more from the group consisting of 60 degrees F. to 70 degrees F., 70 degrees F. to 80 degrees F., 80 degrees F. to 90 degrees F., and 90 degrees F. to 100 degrees F.

When the temperature of the air (E23) located above the cooking system (E10) falls below the pre-determined air temperature, the computer (COMP) sends a signal (E28) to the motor (E29) of the oil pump (E24) to pump oil (E19) to the air/oil heat exchanger (E21). Also, when the temperature of the air (E23) located above the cooking system (E10) falls below the pre-determined air temperature, the computer (COMP) sends a signal (E30) to the motor (E31) of the fan (E22) to blow air (E23) across the surface of the air/oil heat exchanger (E21). This in turn transfer heat from the hot oil (E19) to the air (E23) that is located above the cooking system (E10). The air/oil heat exchanger (E21) discharged cooled oil (E33) back to the fryer (E12) where to be mixed with oil (E19) and heated using the fourth steam supply (LCX) that is provided from FIG. 17F.

In embodiments, the cooking system (E10) shown in FIG. 18C can be used to produce cooked-*cannabis*. In embodiments, *cannabis* may be introduced to the cooking system (E10) shown in FIG. 18C to produce cooked *cannabis*. In embodiments, the cooking system (E10) shown in FIG. 18C can be used to produce cooked *cannabis* from a variety of sources of *cannabis* from the FSS, including heated *cannabis*, ground *cannabis, cannabis* trimmings, *cannabis* buds, *cannabis* seeds, *cannabis* stems, *cannabis* roots, a *cannabis* enhancer, and mixtures of *cannabis* with insects which then may or may not include a cannabinoid, and/or any additional ingredient, chemical, drug, additive, emulsifier, surfactant, etc., mentioned in this specification not only including such as a fiber-starch material, a binding agent, a moisture improving textural supplement, a density improving textural supplement, insects, psilocybin extract, psilocin extract, baeocystin extract, and/or norbaeocystin extract, a hallucinogen, serotonin, melatonin, psilocybin, psilocin, baeocystin, lysergic acid diethylamide (LSD), ibogaine, and/or mescaline, and combinations thereof.

FIG. 18D:

FIG. 18D shows one non-limiting embodiment of a flavoring module (14F) configured to flavor the cooked multifunctional composition (E18A) provided from the cooking module (14E) to form a flavored multifunctional composition (F10).

FIG. 18D shows one non-limiting embodiment of a flavoring module (14F) configured to flavor the cooked extrudate (E18) provided from the cooking module (14E) to form a flavored cooked extrudate (F10).

The flavoring module (14F) as shown in FIG. 18D includes a flavoring system (F11). The flavoring system (F11) shown in FIG. 18D includes a flavoring machine (F12) shown in the form of a tumbler (F13). The tumbler (F13) has a motor (F14) and a controller (F15) and is configured to be operated by a computer (COMP). The flavoring machine (F12) has a cooked extrudate input (F16) for receiving the cooked extrudate (E18) from the cooking module (14E).

The flavoring machine (F12) has a flavoring input (F17) for receiving flavoring (F18). The flavoring (F18) are comprised of one or more from the group consisting of allspice berries, almond meal, anise seed, annato seed, arrowroot powder, basil, bay leaves, black pepper, buttermilk, *cannabis*, capsaicin, caraway, cayenne, celery seed, cheese cultures, chervil, Chile powder, chives, cilantro, cinnamon, citric acid, cloves, coconut shredded, coriander, corn oil, corn starch, cream of tartar, cubeb berries, cumin, curry, dextrose, dill, enzymes, fennel, fenugreek, file powder, garlic powder, ginger, grapefruit peel, green peppercorns, honey, horseradish powder, juniper berries, kaffir lime, lavender, lemon grass powder, lemon peel, lime peel, long pepper, marjoram, molasses, mustard, natural smoke flavor, nigella seeds, nutmeg, onion powder, orange peel, oregano, paprika, parsley, peppermint, poppy seed, powdered cheese, red pepper, rose petals, rosemary, saffron, *sassafras*, sage, salt, savory, sesame seed, star anise, sugar, sugar maple, sumac, tamarind, tangerine peel, tarragon, tetrahydrocannabinol, thyme, tomatillo powder, tomato powder, torula yeast, turmeric, vanilla extract, wasabi powder, whey, white peppercorns, yeast extract, and yeast.

In embodiments, the flavoring (F18) includes one or more from the group consisting of heated *cannabis*, ground *cannabis, cannabis* trimmings, *cannabis* buds, *cannabis* seeds, *cannabis* stems, *cannabis* roots, a *cannabis* enhancer, and mixtures of *cannabis* with insects which then may or may not include a cannabinoid, and/or any additional ingredient, chemical, drug, additive, emulsifier, surfactant, etc., mentioned in this specification not only including such as a fiber-starch material, a binding agent, a moisture improving textural supplement, a density improving textural supplement, insects, psilocybin extract, psilocin extract, baeocystin extract, and/or norbaeocystin extract, a hallucinogen, serotonin, melatonin, psilocybin, psilocin, baeocystin, lysergic acid diethylamide (LSD), ibogaine, and/or mescaline, and combinations thereof.

In embodiments, flavoring (F18) includes: an acidifying agent (acetic acid, glacial acetic acid, citric acid, fumaric acid, hydrochloric acid, diluted hydrochloric acid, malic acid, nitric acid, phosphoric acid, diluted phosphoric acid, sulfuric acid, and/or tartaric acid).

In embodiments, flavoring (F18) includes: an alkalizing agent (ammonia solution, ammonium carbonate, diethanolamine, diisopropanolamine, potassium hydroxide, sodium bicarbonate, sodium borate, sodium carbonate, sodium hydroxide, and/or trolamine).

In embodiments, flavoring (F18) includes: an antifoaming agent (dimethicone and/or simethicone).

In embodiments, flavoring (F18) includes: an antimicrobial preservative (benzalkonium chloride, benzalkonium chloride solution, benzethonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, and/or thymol).

In embodiments, flavoring (F18) includes: an antioxidant (ascorbic acid, ascorbyl palmitate, butylated hydroxyanisole, butylated hydroxytoluene, hypophosphorous acid, monothioglycerol, propyl gallate, sodium formaldehyde sulfoxylate, sodium metabisulfite, sodium thiosulfate, sulfur dioxide, tocopherol, and/or tocopherols excipient).

In embodiments, flavoring (F18) includes: a buffering agent (acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, and/or monobasic sodium phosphate).

In embodiments, flavoring (F18) includes: a chelating agent (edetate disodium, ethylenediaminetetraacetic acid and salts, and/or edetic acid).

In embodiments, flavoring (F18) includes: a coating agent (sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyvinyl acetate phthalate, shellac, sucrose, titanium dioxide, carnauba wax, microcrystalline wax, zein);

In embodiments, flavoring (F18) includes: a colorant (caramel, red, yellow, black or blends, and/or ferric oxide).

In embodiments, flavoring (F18) includes: a complexing agent (ethylenediaminetetraacetic acid and salts (EDTA), edetic acid, gentisic acid ethanolamide, and/or oxyquinoline sulfate).

In embodiments, flavoring (F18) includes: a desiccant (calcium chloride, calcium sulfate, and/or silicon dioxide).

In embodiments, flavoring (F18) includes: an emulsifying and/or a solubilizing agent (*acacia*, cholesterol, diethanolamine (adjunct), glyceryl monostearate, lanolin alcohols, mono- and di-glycerides, monoethanolamine (adjunct), lecithin, oleic acid (adjunct), oleyl alcohol (stabilizer), poloxamer, polyoxyethylene 50 stearate, polyoxyl 35 castor oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, diacetate, monostearate, sodium lauryl sulfate, sodium stearate, sorbitan monolaurate, sorbitan monooleate, sorbitan monopalmitate, sorbitan monostearate, stearic acid, trolamine, and/or emulsifying wax).

In embodiments, flavoring (F18) includes: a filtering aid (powdered cellulose, purified siliceous earth).

In embodiments, flavoring (F18) includes: a flavor and/or a perfume (anethole, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, and/or vanillin).

In embodiments, flavoring (F18) includes: a humectant (glycerol, hexylene glycol, and/or sorbitol).

In embodiments, flavoring (F18) includes: a plasticizer (e.g., castor oil, diacetylated monoglycerides, diethyl phthalate, glycerol, mono- and di-acetylated monoglycerides, propylene glycol, triacetin, and/or triethyl citrate).

In embodiments, flavoring (F18) includes: a polymer (e.g., cellulose acetate, alkyl celluloses, hydroxyalkyl, an acrylic polymers, and/or an acrylic copolymer).

In embodiments, flavoring (F18) includes: a solvent (listed above and/or acetone, alcohol, diluted alcohol, amylene hydrate, benzyl benzoate, butyl alcohol, carbon tetrachloride, chloroform, corn oil, cottonseed oil, ethyl acetate, glycerol, hexylene glycol, isopropyl alcohol, methyl alcohol, methylene chloride, methyl isobutyl ketone, mineral oil, peanut oil, propylene carbonate, sesame oil, and/or treated water).

In embodiments, flavoring (F18) includes: a sorbent (powdered cellulose, charcoal, and/or purified siliceous earth).

In embodiments, flavoring (F18) includes: a carbon dioxide sorbent (barium hydroxide, lime, and/or soda lime).

In embodiments, flavoring (F18) includes: a stiffening agent (hydrogenated castor oil, cetostearyl alcohol, cetyl alcohol, cetyl esters wax, hard fat, paraffin, polyethylene excipient, stearyl alcohol, emulsifying wax, white wax, and/or yellow wax).

In embodiments, flavoring (F18) includes: a suspending and/or a viscosity-increasing agent (*acacia*, agar, alginic acid, aluminum monostearate, bentonite, purified bentonite, magma bentonite, carbomer, carboxymethylcellulose calcium, carboxymethylcellulose sodium, carboxymethylcellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, alginate, silicon dioxide, colloidal silicon dioxide, sodium alginate, tragacanth, and/or xanthan gum).

In embodiments, flavoring (F18) includes: a sweetening agent (aspartame, a dextrate, dextrose, excipient dextrose, fructose, mannitol, saccharin, calcium saccharin, sodium saccharin, sorbitol, solution sorbitol, sucrose, compressible sugar, confectioners sugar, and/or a syrup).

In embodiments, flavoring (F18) includes: a surfactant (simethicone).

In embodiments, flavoring (F18) includes: a tablet binder (*acacia*, alginic acid, sodium carboxymethylcellulose, microcrystalline cellulose, dextrin, ethylcellulose, gelatin, liquid glucose, guar gum, hydroxypropyl methylcellulose, methylcellulose, polyethylene oxide, povidone, pregelatinized starch, and/or a syrup).

In embodiments, flavoring (F18) includes: a tablet and/or capsule diluent (calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, and/or confectioners sugar).

In embodiments, flavoring (F18) includes: a tablet disintegrant (alginic acid, microcrystalline cellulose, croscarmellose sodium, crospovidone, polacrilin potassium, sodium starch glycolate, starch, and/or pregelatinized starch).

In embodiments, flavoring (F18) includes: a tablet and/or a capsule lubricant (calcium stearate, glyceryl behenate, magnesium stearate, light mineral oil, sodium stearyl fumarate, stearic acid, purified stearic acid, talc, hydrogenated vegetable oil, and/or zinc stearate).

In embodiments, flavoring (F18) includes: a thickening agent (gelatin having a Bloom strength of 50-100, an animal-free gelatin, a vegan gelatin, agar, agar-agar, kanten, carrageenan, carrageen, and/or Irish moss vegan jel (vegetable gum adipic acid, tapioca dextrin, calcium phosphate, and/or potassium citrate)).

In embodiments, flavoring (F18) includes: a tonicity agent (dextrose, glycerol, mannitol, potassium chloride, and/or sodium chloride).

In embodiments, flavoring (F18) includes: a flavoring and/or a sweetener (aromatic elixir, compound benzaldehyde elixir, iso-alcoholic elixir, peppermint water, sorbitol solution, and/or tolu balsam syrup).

In embodiments, flavoring (F18) includes: an oleaginous compound (MCT oil, a medium chain tryglyceride, fatty acids, almond oil, corn oil, cottonseed oil, ethyl oleate, isopropyl myristate, isopropyl palmitate, mineral oil, light mineral oil, myristyl alcohol, octyl dodecanol, olive oil, peanut oil, persic oil, sesame oil, soybean oil, and/or squalane).

In embodiments, flavoring (F18) includes: a sterile compound (Bacteriostatic water for injection, and/or bacteriostatic sodium chloride injection)

In embodiments, flavoring (F18) includes: a viscosity-increasing agent (suspending agents, agar agar, calcium alginate, curdlan, gelatin, gellan gum, glycerol esters of wood rosin, hydroxypropyl methyl cellulose, jelly powder, konjac gum, microcrystalline cellulose (MCC), pectin, propylene glycol alginate (PGA) semi-refined carrageenan, sodium alginate, sodium carboxymethyl cellulose, tamarind gum polysaccharide, tara gum, and/or xanthan gum).

In embodiments, flavoring (F18) includes: a water repelling agent (cyclomethicone, dimethicone and/or simethicone).

In embodiments, flavoring (F18) includes: a solubilizing agent (benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaurate, sorbitan monooleate, sorbitan monopalmitate, sorbitan monostearate, and/or tyloxapol).

In embodiments, flavoring (F18) includes: one or more waxes selected from the group consisting of *acacia decurrens* flower cera (*mimosa* flower wax), almond wax, avocado wax, beery wax, bees wax, *cananga odorata* flower cera (ylang ylang flower wax), candelilla wax, *Cannabis sativa* oil, castor wax, cupuacu butter, floral wax, hemp wax, hydrogenated almond oil, hydrogenated animal-based oils, hydrogenated apricot kernel oil, hydrogenated avocado oil, hydrogenated brazil nut oil, hydrogenated canola oil, hydrogenated cashew oil, hydrogenated cocoa butter, hydrogenated coconut oil, hydrogenated coffee oil, hydrogenated corn oil, hydrogenated cottonseed oil, hydrogenated grapeseed oil, hydrogenated hazelnut oil, hydrogenated hemp oil, hydrogenated hop oil, hydrogenated insect oil, hydrogenated lard oil, hydrogenated lard, hydrogenated macadamia nut oil, hydrogenated mustard oil, hydrogenated olive oil, hydrogenated palm kernel oil, hydrogenated palm oil, hydrogenated peanut oil, hydrogenated peppermint oil, hydrogenated rapeseed oil, hydrogenated rice bran oil, hydrogenated rice oil, hydrogenated safflower oil, hydrogenated semi-refined sesame oil, hydrogenated semi-refined sunflower oil, hydrogenated sesame oil, hydrogenated soybean oil, hydrogenated walnut oil, *jasminum grandiflorum* flower cera (jasmine flower wax), *Lavandula angustifolia* flower cera (lavender flower wax), mmyrica fruit wax, olive wax, *prunus* amygdalus *dulcis* oil, rapeseed wax, rice bran wax, rosa damascene flower cera (rose flower wax), shea butter, soybean wax, sunflower wax, vegan wax, vegetable wax, wax from Mexican shrub *Euphorbia antisyphilitica*, and/or wax from the berries of *rhus* verniciflua.

In embodiments, flavoring (F18) includes: esterified insect lipids.

In embodiments, flavoring (F18) includes: psilocybin mushrooms, psilocybin extract, psilocin extract, baeocystin extract, and/or norbaeocystin extract.

In embodiments, flavoring (F18) includes: psilocybin mushrooms and/or the alimentary composition to produce the psilocybin extract, psilocin extract, baeocystin extract, and/or norbaeocystin extract, drugs, a hallucinogen, serotonin, psilocybin, psilocin, baeocystin, lysergic acid diethylamide (LSD), ibogaine, and/or mescaline.

In embodiments, the flavoring machine (F12) provides intimate contact between the flavoring (F18) and the cooked extrudate (E18) to form a flavored cooked extrudate (F10).

In embodiments, the flavoring machine (F12) provides intimate contact between the flavoring (F18) and the cooked multifunctional composition (E18A) to form a flavored multifunctional composition (F10A). In embodiments, the tumbler (F13) rotates and provides intimate contact between the flavoring (F18) and the cooked extrudate (E18) to form a flavored cooked extrudate (F10) or a flavored multifunctional composition (F10A). The flavoring machine (F12) has a flavored cooked extrudate output (F19) for discharging the flavored cooked extrudate (F10) or flavored multifunctional composition (F10A). In embodiments, the tumbler (F13) rotates at a revolution per minute (RPM) ranging from between: 3 RPM to 4 RPM; 4 RPM to 5 RPM; 6 RPM to 7 RPM; 7 RPM to 8 RPM; 8 RPM to 9 RPM; 9 RPM to 10 RPM; 10 RPM to 11 RPM; 11 RPM to 12 RPM; 13 RPM to 14 RPM; 14 RPM to 15 RPM; 15 RPM to 16 RPM; 16 RPM to 17 RPM; 17 RPM to 18 RPM; 18 RPM to 19 RPM; 19 RPM to 20 RPM.

In embodiments, the flavored multifunctional composition (F10A) is a flavored cooked extrudate (F10). A conveyor (F20) is equipped to accept the flavored cooked extrudate (F10) from the flavored cooked extrudate output (F19). The conveyor (F20) may be mechanical, pneumatic, air operated, an elevating conveyor, conveyor belt, drag-chain conveyor, or any conceivable device to transport flavored multifunctional composition (F10) away from the flavoring machine (F12). The conveyor (F20) may be equipped with a metal detector (F21). The metal detector (F21) may be an electronic instrument which detects the presence of metal within the flavored multifunctional composition (F10A).

In embodiments, the flavoring system (F11) employs electricity to flavor the cooked multifunctional composition (E18A), wherein the electricity is provided by either the power production system of FIG. 17F and/or the solar panels (SOLAR) that provide electricity for the farming superstructure system (FSS) as shown on FIG. 3.

FIG. 18E:

FIG. 18E shows one non-limiting embodiment of a biocatalyst mixing module (14G) that is configured to mix a cannabinoid, with insects, water, biocatalyst, and/or an acid to create an cannabinoid and biocatalyst mixture (G09).

FIG. 18E shows one non-limiting embodiment of a biocatalyst mixing module (14G) that includes a first water treatment unit (G10), a second water treatment unit (G11), and a third water treatment unit (G12), that provide a third contaminant depleted water (G13) to the interior (G14) of a mixing tank (G15). The mixing tank (G15) mixes a water supply (C16) with insects and biocatalyst. In embodiments, the insects introduced to the mixing tank (G15) may be ground insects or whole insects (which may be dead or alive and include live insect cells). In embodiments, the first water treatment unit (G10), a second water treatment unit (G11), and a third water treatment unit (G12) are optional. In embodiments, only one of the first water treatment unit (G10), second water treatment unit (G11), or third water treatment unit (G12) may be used. In embodiments, two of the first water treatment unit (G10), second water treatment unit (G11), or third water treatment unit (G12) may be used. In embodiments, a water supply (C16) is provided to the interior (G14) of the mixing tank (G15).

In embodiments, the insects introduced to the mixing tank (G15) may have an insect bulk density ranging from between 3.5 pounds per cubic foot to 14.999 pounds per cubic foot or a ground insect bulk density ranging from between 15 pounds per cubic foot to 50 pounds per cubic foot.

The whole insects (G07) or ground insects (G08) introduced to the mixing tank (G15) may be a weighed. In embodiments, the whole insects (G07) introduced to the mixing tank (G15) may be have an insect bulk density ranging from between 3.5 pounds per cubic foot to 14.999 pounds per cubic foot. In embodiments, the ground insects (G08) have a ground insect bulk density ranging from between 15 pounds per cubic foot to 50 pounds per cubic foot.

The insect liquid biocatalyst mixture (G09) is transferred from the mixing tank (G15) to the solid separation module (14H) of FIG. 18E. In embodiments, the insect liquid biocatalyst mixture (G09) is transferred and pressurized using a pump (G18) from the mixing tank (G15) to the solid separation module (14H) of FIG. 18F. In embodiments, the insect liquid biocatalyst mixture (G09) is transferred and pressurized using a screw auger (G19) from the mixing tank (G15) to the solid separation module (14H) of FIG. 18F.

FIG. 14G depicts the first water treatment unit (G10) to include a cation, a second water treatment unit (G11) to include an anion, and a third water treatment unit (G13) to include a membrane. A first water pressure sensor (G20) is positioned on the water input conduit (G21) that is introduced to the first input (G22) to the first water treatment unit (G10). In embodiments, a filter (G23), activated carbon (G24), and/or an adsorbent (G25), are positioned on the water input conduit (G21) prior to introducing the water supply (G16) to the first water treatment unit (G10). The water supply (G16) may be considered a contaminant-laden water (G26) that includes positively charged ions, negatively charged ions, and undesirable compounds. In embodiments, the positively charged ions are comprised of one or more from the group consisting of calcium, magnesium, sodium, and iron. In embodiments, the positively charged ions are comprised of one or more from the group consisting of aluminum, barium, beryllium, calcium, chromium(III), copper(I), copper(II), hydrogen, iron(II), iron(III), lead(II), lead(IV), lithium, magnesium, manganese(II), mercury(II), potassium, silver, sodium, strontium, tin(II), tin(IV), and zinc. In embodiments, the negatively charged ions are comprised of one or more from the group consisting of iodine, chloride, and sulfate. In embodiments, the negatively charged ions are comprised of one or more from the group consisting of acetate, aluminum silicate, anions from organic acids, azide, bromide, carbonate, chlorate, chloride, chromate, cyanide, dichromate, dihydrogen phosphate, fluoride, formate, hydride, hydrogen carbonate, hydrogen sulfate, hydrogen sulfite, hydroxide, hypochlorite, iodide, metasilicate, monohydrogen phosphate, nitrate, nitride, nitrite, oxalate, oxide, perchlorate, permanganate, peroxide, phosphate, silicate, sulfate, sulfide, sulfite, superoxide, and thiosulfate. The undesirable compounds are comprised of one or more from the group consisting of dissolved organic chemicals, viruses, bacteria, and particulates.

A first contaminant depleted water (G27) is discharged by the first water treatment unit (G10) by a first output (G28). The first contaminant depleted water (G27) may be a positively charged ion depleted water (G29). The first contaminant depleted water (G27) is then transferred to the second water treatment unit (G11) via a second input (G30). A second contaminant depleted water (G31) is discharged by the second water treatment unit (G11) by a second output (G32). The second contaminant depleted water (G31) may be a negatively charged ion depleted water (G33). The second contaminant depleted water (G31) is then transferred to the third water treatment unit (G12) via a third input (G34). A third contaminant depleted water (G13) is discharged by the third water treatment unit (G12) by a third output (G35). The third contaminant depleted water (G13) may be an undesirable compounds depleted water (G36). The third contaminant depleted water (G13) is then transferred to the interior (G14) of a mixing tank (G15) via a water supply conduit (G37) and water input (G38). In embodiments, a diptube (G38A) is provided to introduce water to beneath the liquid level of the contents within the interior (G14) of the mixing tank (G15).

Within the interior (G14) of a mixing tank (G15), the water is mixed with insects, a genetically modified microorganism, and/or biocatalyst. In embodiments, a cation (G39), an anion (G40), and a polishing unit (G41), are positioned on the water supply conduit (G37) in between the third water treatment unit (G12) and the water input (G38) of the mixing tank (G15). The polishing unit (G41) may be any type of conceivable device to improve the water quality such as an ultraviolet unit, ozone unit, microwave unit, filter, a distillation system, or the like. In embodiments, the polishing unit (G41) may be a distillation system. In embodiments, the electrical conductivity of the treated water treated by the distillation system includes one or more selected from the group consisting of: 0.1 μS to 0.5 μS, 0.5 μS to 1.00 μS, 1.00 μS to 1.25 μS, 1.25 μS to 1.50 μS, 1.50 μS to 1.75 μS, 1.75 μS to 2.00 μS, 2.00 μS to 2.25 μS, 2.25 μS to 2.50 μS, 2.50 μS to 2.75 μS, 2.75 μS to 3.00 μS, 3.00 μS to 3.25 μS, 3.25 μS to 3.50 μS, 3.50 μS to 3.75 μS, 3.75 μS to 4.00 μS, 4.00 μS to 4.25 μS, 4.25 μS to 4.50 μS, 4.50 μS to 4.75 μS, 4.75 μS to 5.00 μS, μS to 5.25 μS, 5.25 μS to 5.50 μS, 5.50 μS to 5.75 μS, 5.75 μS to 6.00 μS, 6.00 μS to 6.25 μS, 6.25 μS to 6.50 μS, 6.50 μS to 6.75 μS, 6.75 μS to 7.00 μS, 7.00 μS to 7.25 μS, 7.25 μS to 7.50 μS, 7.50 μS to 7.75 μS, 7.75 μS to 8.00 μS, 8.00 μS to 8.25 μS, 8.25 μS to 8.50 μS, 8.50 μS to 8.75 μS, 8.75 μS to 9.00 μS, 9.00 μS to 9.25 μS, 9.25 μS to 9.50 μS, 9.50 μS to 9.75 μS, 9.75 μS to 10.00 μS. In embodiments, μS means μS per centimeter.

In embodiments, water supply valve (G42) is positioned on the water supply conduit (G37) in between the third water treatment unit (G12) and the water input (G38) of the mixing tank (G15). The water supply valve (G42) is equipped with a controller (G43) that inputs or outputs a signal from a computer (COMP). In embodiments, the mixing tank (G15) is equipped with a high-level sensor (G44) and a low-level sensor (G45). The high-level sensor (G44) is used for detecting a high level and the low-level sensor (G45) is used for detecting a low level. The high-level sensor (G44) is configured to output a signal to the computer (COMP) when the high-level sensor (G44) is triggered by a high level of liquid within the mixing tank (G15). The low-level sensor (G45) is configured to output a signal to the computer (COMP) when the low-level sensor (G45) is triggered by a low level of liquid within the mixing tank (G15).

In embodiments, when the low-level sensor (G45) sends a signal to the computer (COMP), the water supply valve (G42) on the water supply conduit (G37) is opened and introduces water into the mixing tank (G15) until the high-level sensor (G44) is triggered thus sending a signal to the computer (COMP) to close the water supply valve (G42). This level control loop including the high-level sensor (G44) for detecting a high level and a low-level sensor (G45) for detecting a lower level may be coupled to the operation of the water supply valve (G42) for introducing a water supply (G16) through a first water treatment unit (G10), a second water treatment unit (G11), and a third water treatment unit (G12), to provide a third contaminant depleted water (G13) to the interior (G14) of a mixing tank (G15).

The mixing tank (GC15) may be placed on a load cell (G46) for measuring the mass of the tank. The mixing tank (G15) may be equipped with a mixer (G47) for mixing water with insects, the genetically engineered microorganism, and/or the biocatalyst. The insects, the genetically engineered microorganism, and/or the biocatalyst may be introduced to the interior (G14) of the mixing tank (G15) via an input (G51). The mixer (G47) may be of an auger or blade type that is equipped with a motor (G48). The mixing tank (G15) has an insect liquid biocatalyst mixture output (G49) that is connected to a transfer conduit (G50).

The transfer conduit (G50) is connected at one end to the insect liquid biocatalyst mixture output (G49) of the mixing tank (G15) and at another end to a supply pump (G18) or a screw auger (G19). The supply pump (G18) or a screw auger (G19) provides a pressurized insect liquid biocatalyst mixture (GO9B) to the solid separation module (14H) of FIG. 18F.

In embodiments, a flow sensor (G51) and/or a flow totalizer (G52) may be installed on the water supply conduit (G37) to determine the mass or volume of water that is sent to the interior (G14) of the mixing tank (G15). In embodiments, the mixing tank (G15) is equipped with a heat exchanger (G53) to heat the mixture of water, biocatalyst, and insects. The heat exchanger (G53) may be electrically heated or provided with a heat transfer medium such as a source of steam or hot oil.

The mixing tank (G15) may have a heating jacket (G53J) to serve the purpose of the heat exchanger (G53). The mixing tank (G15) or bioreactor may have a heating jacket (G53J) and includes a cylindrical tank. In embodiments, the cylindrical tank (G15) includes a length to diameter ratio ranging from 2 to 5. The cylindrical tank (G15) includes a length to diameter ratio ranging from 1 to 2, 2 to 3, 3 to 4, 4 to 5, 5 to 6. In embodiments, the cylindrical tank (G15) is vertically oriented and is mounted on legs or brackets. In embodiments, the cylindrical tank (G15) is horizontally oriented and is mounted on legs or brackets. In embodiments, the cylindrical tank (G15) is horizontally oriented and is mounted on a saddle support. In embodiments, the cylindrical tank (G15) is vertically oriented and has a flat bottom and/or a concrete foundation with a length to diameter ratio ranging from 0.5 to 1, 1 to 1.5, 1.5 to 2, 2 to 2.5.

The mixing tank (G15) with a heating jacket (G53J) is a vessel that is designed for controlling the temperature of its contents, by using a heating jacket around the vessel through which a heat transfer medium (e.g.—steam) is circulated.

The heating jacket (G53J) is a cavity external to the interior (G14) of the mixing tank (G15) that permits the uniform exchange of heat between the heat transfer medium circulating in it and the walls of the mixing tank (G15). FIG. 18E shows the heating jacket (G53J) installed over a portion of the mixing tank (G15) creating an interior (G53J-1) having an annular space within which a heat transfer medium flows.

The heating jacket (G53J) has a heat transfer medium inlet (G90) and a heat transfer medium outlet (G91). Steam (G92) is introduced to the heat transfer medium inlet (G90). Steam condensate (G93) is discharged from the heat transfer medium outlet (G91). Steam (G92) is introduced to the heat transfer medium inlet (G90) of the heating jacket (G53J) of the mixing tank (G15) via a steam inlet conduit (G94). The steam inlet conduit (G94) is connected to the heat transfer medium inlet (G90) and is configured to transfer steam to the interior (G53J-1) of the heating jacket (G53J).

In embodiments, a fifth steam supply (LDB) is provided to the heating jacket (G53J) and/or to the heat exchanger (G53) and is provided from FIG. 17F. In embodiments, the steam condensate (G93) that is discharged from the heat transfer medium outlet (G91) is transferred to the condensate tank (LAP) shown in FIG. 17F as a fifth condensate (LAU).

A steam supply valve (G95) is interposed on the steam inlet conduit (G94). The steam supply valve (G95) is equipped with a controller (G96) that inputs and outputs a signal (G97) to the computer (COMP). In embodiments, the steam supply valve (G95) is positioned to regulate the mass of heat transfer medium that leaves the heating jacket (G53J) via the discharged from the heat transfer medium outlet (G91).

In embodiments, a temperature sensor (G54) measures the temperature of the contents within the interior (G14) of the mixing tank (G15). The temperature sensor (G54) is configured to output a signal (G55) to the computer (COMP). A pre-determined setpoint for the mixing tank (G15) temperature sensor (G54) may be inputted to the computer (COMP). In response to the pre-determined setpoint, the computer (COMP) regulates the modulation of the steam supply valve (G95). The preferred modulation range of the steam supply valve (G95) ranges from 33% open to 66% open. In embodiments, the preferred modulation range of the steam supply valve (G95) ranges from: 5% open to 10% open; 10% open to 15% open; 15% open to 20% open; 20% open to 30% open; 30% open to 40% open; 40% open to 50% open; 50% open to 60% open; 60% open to 70% open.

In embodiments, the mixing tank (G15) has a plurality of baffles (G55A, G55B) that are positioned within the interior (G14). Each baffle (G55A, G55B) is configured to promote mixing and increase heat transfer and chemical reaction rate of the biocatalyst with the insects.

The pressure drop across the steam supply valve (G95) ranges from between: 1 pound per square inch (PSI) to 2 PSI; 2 pounds per square inch (PSI) to 5 PSI; 5 pounds per square inch (PSI) to 10 PSI; 10 pounds per square inch (PSI) to 20 PSI; 20 pounds per square inch (PSI) to 40 PSI; pounds per square inch (PSI) to 60 PSI; 60 pounds per square inch (PSI) to 80 PSI; 80 pounds per square inch (PSI) to 100 PSI; 100 pounds per square inch (PSI) to 125 PSI; 125 pounds per square inch (PSI) to 150 PSI; 150 pounds per square inch (PSI) to 200 PSI.

The velocity of steam in the steam inlet conduit (G94) ranges from: 35 feet per second to 45 feet per second; 45 feet per second to 55 feet per second; 55 feet per second to 65 feet per second; 65 feet per second to 75 feet per second; 75 feet per second to 85 feet per second; 85 feet per second to 95 feet per second; 95 feet per second to 105 feet per second; 105 feet per second to 115 feet per second; 115 feet per second to 125 feet per second; 125 feet per second to 135 feet per second; 135 feet per second to 145 feet per second; 145 feet per second to 155 feet per second; 155 feet per second to 175 feet per second. The velocity of steam condensate discharged from the heat transfer medium outlet (G91) is less than 3 feet per second.

In embodiments, the heat transfer medium inlet (G90) is comprised of one or more from the group consisting of: a Class 150 flange, a Class 300 flange, sanitary clamp fitting, national pipe thread, or compression fitting. In embodiments, the heat transfer medium outlet (G91) is comprised of one or more from the group consisting of: a Class 150 flange, a Class 300 flange, sanitary clamp fitting, national pipe thread, or compression fitting. In embodiments, the mixing tank (G15) is comprised of stainless steel or carbon steel and may be ceramic or glass-lined. In embodiments, the heating jacket (G53J) is comprised of stainless steel or carbon steel and may be ceramic or glass-lined or fluoropolymer-lined. In embodiments, the mixing tank (G15) is comprised of stainless steel or carbon steel and may be ceramic or glass-lined or fluoropolymer-lined.

In embodiments, the temperature of the water, insect, and biocatalyst mixture within the interior (G14) of the mixing tank (G15) ranges from between: 50 degrees F. to 60 degrees F.; 60 degrees F. to 70 degrees F.; 70 degrees F. to 80 degrees F.; 80 degrees F. to 90 degrees F.; 90 degrees F. to 100 degrees F.; 100 degrees F. to 110 degrees F.; 110 degrees F. to 120 degrees F.; 120 degrees F. to 130 degrees F.; 130 degrees F. to 140 degrees F.; 140 degrees F. to 150 degrees F.; 150 degrees F. to 160 degrees F.; 160 degrees F. to 170 degrees F.; 170 degrees F. to 180 degrees F.; 180 degrees F. to 190 degrees F.; 190 degrees F. to 200 degrees F.; 200 degrees F. to 212 degrees F.

In embodiments, the water, insect, and biocatalyst mixture may mixed within the interior (G14) of the mixing tank (G15) ranges from between: 5 minutes to 10 minutes; 10 minutes to 20 minutes; 20 minutes to 30 minutes; 30 minutes to 40 minutes; 40 minutes to 50 minutes; 50 minutes to 1 hour; 1 hour to 1.5 hours; 1.5 hour to 2 hours; 2 hour to 3 hours; 3 hour to 4 hours; 4 hour to hours; 5 hour to 6 hours; 6 hour to 12 hours; 12 hour to 18 hours; 18 hour to 24 hours; 1 day to 2 days; 2 days to 3 days; 3 days to 4 days; 4 days to 5 days; 5 days to 1 week.

In embodiments, the mass of water, biocatalyst, or insects within the mixing tank (G15) can be measured via the load cell (G46). In embodiments, water can be added to the mixing tank (G15) and the mass of water is measured, following by adding the insects and/or biocatalyst to the interior (G14) of the mixing tank (G15) to know the mass of the total mixture. The contents within the mixing tank (G15) can be mixed with the mixer and heated.

Insect Distribution Module (14G1)

FIG. 14G displays an insect distribution module (14G1) including an insect tank (G55) that is configured to accept insects (G56). The insects (G56) may be whole insects which may be alive or dead. The insects (G56) may be pieces and portions of insects, including insect wings, insect legs, insect chitin, insect protein, live insect cells, and/or insect lipids. The insects (G56) may be a mixture of insects and *cannabis* plants. The insects (G56) may be a mixture of insects and *cannabis* plants that have undergone a processing step, such as grinding and/or trimming (provided from the *cannabis* trimmer as trimmed *cannabis* (TR1*, TR1**) and/or from the *cannabis* grinder as ground *cannabis* (GR1*) on FIGS. 15' and/or 16', respectively.

*Cannabis* may be used in place of the insects (G56), or the mixture may be a mixture of insects and *cannabis* plants (107, 207), trimmed *cannabis* (TR1, TR1*), *cannabis* trimmings (TR2, TR2*), ground *cannabis* (GR1), heated *cannabis* (HT1), or alternatively a cannabinoid emulsion and/or colloidal dispersion (JNC), powdered cannabinoid, cannabinoid crystals, spray-dried cannabinoids, cannabinoids, *cannabis* volatiles, a cannabinoid and liquid mixture, a cannabinoid and a solvent mixture, trimmed *cannabis* buds, *cannabis* seeds, *cannabis* stems, *cannabis* roots, a mixture of *cannabis* with insects and/or arachnids, concentrated volatiles, a concentrated cannabinoid, a *cannabis* plant derived cannabinoid, an insect-derived cannabinoid glycoside, a biosynthetically derived cannabinoid, a secondary extract, a purified cannabinoid, a distilled cannabinoid, a cannabinoid emulsion, a micro emulsion, a nano emulsion, a cannabinoid colloid suspension, a cannabinoid colloid dispersion, a mixture of a biosynthetic cannabinoid and a genetically engineered microorganism, and combinations thereof.

The insects (G56) may be a mixture of insects and *cannabis* plants that have undergone heat treatment step and may be heated *cannabis* (HT1*) including *cannabis* and insects as provided from the *cannabis* heater (HTR1*) on FIG. 17.

The insects (G56) may be first transported though interstate commerce via at least one vehicle having three or more axles and having an engine and/or a fuel cell, transported though interstate commerce via at least one vehicle having two axles and having an internal combustion engine, electric battery, of fuel cell powered.

The insect tank (G55) has an interior (G57), an insect input (G58), an insect conveyor (G59), and an insect conveyor output (G60). The insect tank (G55) accepts insects (G56) to the interior (G57) and regulates and controls an engineered amount of insects (G56) downstream to be mixed in the mixing tank (G15). The insect conveyor (G59) has an integrated insect mass sensor (G61) that is configured to input and output a signal (G61A) to the computer (COMP). The insect conveyor motor (G62) has a controller (G63) that is configured to input and output a signal (G64) to the computer (COMP). The insect mass sensor (G61), insect conveyor (G59), and insect conveyor motor (G62) are coupled so as to permit the conveyance, distribution, or output of a precise flow of insects (G56) via an insect transfer line (G65).

Ground Insect Distribution Module (14G2)

FIG. 14G displays a ground insect distribution module (14G2) including an insect tank (G66) that is configured to accept ground insects (G67).

In embodiments, the ground insects (G67) may be ground but contain live insect cells. In embodiments, the ground insects (G67) may include ovary cells from an insect. In embodiments, the ground insects (G67) may include cells from an insect reproductive system. In embodiments, the insect cells are infected with a baculovirus. In embodiments, the insect cells are infected with a recombinant baculovirus. In embodiments, the insect cells are infected with a genetically engineered baculovirus. In embodiments, the insect cells, or the insects, are genetically engineered. In embodiments, the insect cells, or the insects, contain an insect derived cannabinoid glycoside.

In embodiments, the ground insects (G67) may include liquid-depleted insects subject to a lipid extraction process. In embodiments, the ground insects (G67) have had undergone spray drying.

The ground insects (G67) may be first transported though interstate commerce via at least one vehicle having three or more axles and having an engine and/or a fuel cell, transported though interstate commerce via at least one vehicle having two axles and having an internal combustion engine, electric battery, of fuel cell powered.

The insect tank (G66) has an interior (G68), an insect input (G69), an insect conveyor (G70), and an insect conveyor output (G71). The insect tank (G66) accepts ground insects (G67) to the interior (G68) and regulates and controls an engineered amount of ground insects (G67) downstream to be mixed in the mixing tank (G15). The insect conveyor (G70) has an integrated insect mass sensor (G72) that is configured to input and output a signal (G73) to the computer (COMP). The insect conveyor motor (G74) has a controller (G75) that is configured to input and output a signal (G76) to the computer (COMP). The insect mass sensor (G72), insect conveyor (G70), and insect conveyor motor (G74) are coupled so as to permit the conveyance, distribution, or output of a precise flow of ground insects (G67) via a ground insect transfer line (G77).

Biocatalyst Distribution Module (14G3)

FIG. 14G displays a biocatalyst mixing module (14G3) including a biocatalyst tank (G78) that is configured to accept at least one biocatalyst (G79). The biocatalyst (G79) may be comprised of one or more from the group consisting of *acetobacter*, actoBacillus *acidophilus, Lactobacillus acidophilus, ananas* comorus, *Ananas comosus, Aspergillus melleus, Aspergillus niger, Aspergillus oryzae*, bacilliales, *Bacillus licheniformis, Bacillus subtilis* var. natto, *Bacillus subtilis*, bifidobacteriales, *Bifidobacterium bifidum*, bromelain, *Candida utilis, Carica papaya*, casein, an enzyme, eurotiales, a fungus, lactobacilliales, *LactoBacillus LactoBacillus casei, lactobacillus helveticus, LactoBacillus plantarum*, a microorganism, papain, peptidase, phaffia rhodozyma, protease A, protease, rhodospirillales, *Saccharomyces cerevisiae*, saccharomycetales, *streptococcus* thermopilus, *Yarrowia lipolytica*, and yeast. In embodiments, mixing of the biocatalyst (G79) is optional.

In embodiments, the biocatalyst includes yeast. In embodiments, the yeast may be ale yeast, the "top-fermenting" type, *Saccharomyces cerevisiae*. In embodiments, the yeast may be lager yeast, the "bottom-fermenting" type, *Saccharomyces uvarum*, or *Saccharomyces carlsbergensis*. In embodiments, the yeast is liquid or powder. Yeasts are eukaryotic, single-celled microorganisms classified as members of the fungus kingdom.

In embodiments, the insects may be mixed with water, a biocatalyst, *cannabis*, and grain, barley, honey, and/or hops. In embodiments, the water, a biocatalyst, optionally *cannabis*, and at least one from the group consisting of grain, barley, honey, and hops may be fermented to produce ethyl alcohol. In embodiments, the water, a biocatalyst, optionally *cannabis*, and at least one from the group consisting of grain, barley, honey, and hops may be fermented to produce ethanol.

In embodiments, the water, a biocatalyst, optionally *cannabis*, and at least one from the group consisting of malt, grain, barley, honey, and hops may be fermented to produce a mixture of water and ethanol. Alcohol by volume (abbreviated as ABV, abv, or alc/vol) is a standard measure of how much ethanol is contained in a given volume of an alcoholic beverage (expressed as a volume percent). In embodiments, the mixture of water and ethanol has a range of alcohol by volume that is selected from one or more from the group consisting of 2.5 ABV to 3 ABV, 3 ABV to 3.5 ABV, 3.5 ABV to 4 ABV, 4 ABV to 4.5 ABV, 4.5 ABV to 5 ABV, 5

ABV to 5.5 ABV, 5.5 ABV to 6 ABV, 6 ABV to 6.5 ABV, 6.5 ABV to 7 ABV, 7 ABV to 7.5 ABV, 7.5 ABV to 8 ABV, 8 ABV to 8.5 ABV, 8.5 ABV to 9 ABV, 9 ABV to 9.5 ABV, 9.5 ABV to 10 ABV, 10 ABV to 10.5 ABV, 10.5 ABV to 11 ABV, 11 ABV to 11.5 ABV, 11.5 ABV to 12 ABV, and 12 ABV to 12.5 ABV.

In embodiments, the beverage has a serving size of 0.10 fluid ounce to 0.5 fluid ounces, fluid ounce to 1 fluid ounce, 1.0 fluid ounce to 1.5 fluid ounces, 1.5 fluid ounce to 2.0 fluid ounces, 2.0 fluid ounce to 2.5 fluid ounces, 2.5 fluid ounce to 3.0 fluid ounces, 3.0 fluid ounce to 3.5 fluid ounces, 3.5 fluid ounce to 4.0 fluid ounces, 4.0 fluid ounce to 4.5 fluid ounces, 4.5 fluid ounce to 5.0 fluid ounces, 5.0 fluid ounce to 5.5 fluid ounces, 5.5 fluid ounce to 6 fluid ounces, 6 fluid ounces, 8 fluid ounces or 12 fluid ounces. In embodiments, the beverage has a serving size of 1 fluid ounce to 2 fluid ounces, 2 fluid ounces to 3 fluid ounces, 3 fluid ounces to 4 fluid ounces, 4 fluid ounces to 5 fluid ounces, 5 fluid ounces to 6 fluid ounces, 6 fluid ounces to 7 fluid ounces, 7 fluid ounces to 8 fluid ounces, 8 fluid ounces to 9 fluid ounces, 9 fluid ounces to 10 fluid ounces, fluid ounces to 11 fluid ounces, 11 fluid ounces to 12 fluid ounces, 12 fluid ounces to 13 fluid ounces, 13 fluid ounces to 14 fluid ounces, 14 fluid ounces to 15 fluid ounces, 15 fluid ounces to 16 fluid ounces, 16 fluid ounces to 17 fluid ounces, 17 fluid ounces to 18 fluid ounces, 18 fluid ounces to 19 fluid ounces, 19 fluid ounces to 20 fluid ounces, 20 fluid ounces to 21 fluid ounces, 21 fluid ounces to 22 fluid ounces, 22 fluid ounces to 24 fluid ounces, 24 fluid ounces to 26 fluid ounces, 26 fluid ounces to 28 fluid ounces, 28 fluid ounces to 30 fluid ounces, 30 fluid ounces to 32 fluid ounces, 32 fluid ounces to 34 fluid ounces, 34 fluid ounces to 36 fluid ounces, 36 fluid ounces to 38 fluid ounces, or 38 fluid ounces to 40 fluid ounces.

In embodiments, each serving size of the beverage includes a cannabidiol content in milligrams per serving ranging from 0 milligrams to 0.5 milligrams, 0.5 milligrams to 1 milligrams, 1 milligrams to 1.5 milligrams, 1.5 milligrams to 2 milligrams, 2 milligrams to 2.5 milligrams, 2.5 milligrams to 3 milligrams, 3 milligrams to 3.5 milligrams, 3.5 milligrams to 4 milligrams, 4 milligrams to 4.5 milligrams, 4.5 milligrams to 5 milligrams, 5 milligrams to 5.5 milligrams, 5.5 milligrams t 6 milligrams, 6 milligrams to 6.5 milligrams, 6.5 milligrams to 7 milligrams, 7 milligrams to 7.5 milligrams, 7.5 milligrams to 8 milligrams, 8 milligrams to 8.5 milligrams, 8.5 milligrams to 9 milligrams, 9 milligrams to 9.5 milligrams, 9.5 milligrams to 10 milligrams, 10 milligrams to 11 milligrams, 11 milligrams to 12 milligrams, 12 milligrams to 13 milligrams, 13 milligrams to 14 milligrams, 14 milligrams to 15 milligrams, 15 milligrams to 16 milligrams, 16 milligrams to 17 milligrams, 17 milligrams to 18 milligrams, 18 milligrams to 19 milligrams, 19 milligrams to 20 milligrams, 20 milligrams to 25 milligrams, 25 milligrams to 30 milligrams, 30 milligrams to 35 milligrams, 35 milligrams to 40 milligrams, 40 milligrams to 45 milligrams, 45 milligrams to 50 milligrams, 50 milligrams to 60 milligrams, 60 milligrams to 70 milligrams, 70 milligrams to 80 milligrams, 80 milligrams to 90 milligrams, 90 milligrams to 100 milligrams, 100 milligrams to 125 milligrams, 125 milligrams to 150 milligrams, 150 milligrams to 175 milligrams, 175 milligrams to 200 milligrams, 200 milligrams to 250 milligrams, 250 milligrams to 300 milligrams, 300 milligrams to 350 milligrams, 350 milligrams to 400 milligrams, 400 milligrams to 450 milligrams, or 450 milligrams to 500 milligrams.

In embodiments, each serving size of the beverage includes a tetrahydrocannabinol content in milligrams per serving ranging from 0 milligrams to 0.5 milligrams, 0.5 milligrams to 1 milligrams, 1 milligrams to 1.5 milligrams, 1.5 milligrams to 2 milligrams, 2 milligrams to 2.5 milligrams, 2.5 milligrams to 3 milligrams, 3 milligrams to 3.5 milligrams, 3.5 milligrams to 4 milligrams, 4 milligrams to 4.5 milligrams, 4.5 milligrams to 5 milligrams, 5 milligrams to 5.5 milligrams, 5.5 milligrams t 6 milligrams, 6 milligrams to 6.5 milligrams, 6.5 milligrams to 7 milligrams, 7 milligrams to 7.5 milligrams, 7.5 milligrams to 8 milligrams, 8 milligrams to 8.5 milligrams, 8.5 milligrams to 9 milligrams, 9 milligrams to 9.5 milligrams, 9.5 milligrams to 10 milligrams, 10 milligrams to 11 milligrams, 11 milligrams to 12 milligrams, 12 milligrams to 13 milligrams, 13 milligrams to 14 milligrams, 14 milligrams to 15 milligrams, 15 milligrams to 16 milligrams, 16 milligrams to 17 milligrams, 17 milligrams to 18 milligrams, 18 milligrams to 19 milligrams, 19 milligrams to 20 milligrams, 20 milligrams to 25 milligrams, 25 milligrams to 30 milligrams, 30 milligrams to 35 milligrams, 35 milligrams to 40 milligrams, 40 milligrams to 45 milligrams, 45 milligrams to 50 milligrams, 50 milligrams to 60 milligrams, 60 milligrams to 70 milligrams, 70 milligrams to 80 milligrams, 80 milligrams to 90 milligrams, 90 milligrams to 100 milligrams, 100 milligrams to 125 milligrams, 125 milligrams to 150 milligrams, 150 milligrams to 175 milligrams, 175 milligrams to 200 milligrams, 200 milligrams to 250 milligrams, 250 milligrams to 300 milligrams, 300 milligrams to 350 milligrams, 350 milligrams to 400 milligrams, 400 milligrams to 450 milligrams, or 450 milligrams to 500 milligrams. In embodiments, the beverage has zero calories per serving size. In embodiments, the beverage has a calories per serving ranging from 0 to 1, 1 to 2, 2 to 3, 3 to 4, 4 to 5, 5 to 6, 6 to 7, 7 to 8, 8 to 9, 9 to 10 to 15, 15 to 20, 20 to 25, 25 to 30, 30 to 35, 35 to 40, 40 to 45, 45 to 50, 50 to 55, 55 to 60, 60 to 65, 65 to 70, 70 to 75, 75 to 80, 80 to 85, 85 to 90, 90 to 95, 95 to 100, 100 to 110, 110 to 120, 120 to 130, 130 to 140, 140 to 150, 150 to 160, 160 to 170, 170 to 180, 180 to 190, 190 to 200, 200 to 210, 210 to 220, 220 to 230, 230 to 240, 240 to 250, 250 to 260, 260 to 270, 270 to 280, 280 to 290, 290 to 300, or 300 to 310.

In embodiments, the beverage has a sodium content (in milligrams per serving) ranging from 0 to 1, 1 to 2, 2 to 3, 3 to 4, 4 to 5, 5 to 6, 6 to 7, 7 to 8, 8 to 9, 9 to 10, 10 to 11, 11 to 12, 12 to 13, 13 to 14, 14 to 15, 15 to 16, 16 to 17, 17 to 18, 18 to 19, 19 to 20, 20 to 25, 25 to 30, 30 to 35, 35 to 40, 40 to 45, 45 to 50, 50 to 55, 55 to 60, 60 to 65, 65 to 70, 70 to 75, 75 to 80, 80 to 85, to 90, 90 to 95, 95 to 100.

In embodiments, the beverage has a carbohydrate content (in grams per serving) ranging from 0 to 1, 1 to 2, 2 to 3, 3 to 4, 4 to 5, 5 to 6, 6 to 7, 7 to 8, 8 to 9, 9 to 10, 10 to 11, 11 to 12, 12 to 13, 13 to 14, 14 to 15, 15 to 16, 16 to 17, 17 to 18, 18 to 19, 19 to 20, 20 to 25, 25 to 30, 30 to 35, 35 to 40, 40 to 45, 45 to 50, 50 to 55, 55 to 60, 60 to 65, 65 to 70, 70 to 75, 75 to 80, 80 to 85, to 90, 90 to 95, 95 to 100.

In embodiments, the beverage includes aspartame, sodium, sodium chloride, sucrose, sugar, dextrose, citric acid, monopotassium phosphate, and brominated vegetable oil (as a stabilizer), magnesium chloride, calcium chloride, niacinamide (vitamin B3), vitamin pyridoxine hydrochloride (B6), cyanocobalamin (vitamin B12).

In embodiments, the beverage includes a zero-calorie sweetener. In embodiments, the beverage includes low-calorie sweetener. In embodiments, the beverage includes an artificial sweetener. In embodiments, the beverage includes honey, sugar, aspartame, acesulfame potassium, saccharin, sucralose, neotame, erythritol, *stevia, stevia* leaf extract. In embodiments, the beverage includes a sugar alcohol and/or a polyol. In embodiments, the beverage includes electrolytes including sodium, potassium, magnesium, calcium. In embodiments, the beverage includes fruit juice concentrate, citric acid, white tea extract, malic acid, beta carotene, ascorbic acid (vitamin C), sodium citrate.

In embodiments, the beverage includes a coloring agent that is configured to color the beverage a color that includes one or more colors selected from the group consisting of: light green (144C), yellow (001A) or yellow green (001A), dark green (144A) with shades of yellow (001A), yellow orange (011A), orange (024A), orange red (033B), orange pink (027A), red (033A), dark purple red (046A), light red pink (039C), red pink (043C), dark pink red (045D), purple red (054A), light blue pink (055C), purple (058A), purple red (059D), blue pink (062A), light blue violet (069C), violet blue (089A), violet (075A), dark violet (079A), blue violet (083D), blue (100A), dark blue (103A), light blue (104D), light green blue (110C), green blue (111A), grey blue (115C), green blue (125C), white (155A), orange brown (169A), brown (172A), brown purple (178A), orange pink (179D) (The Royal Horticultural Society Colour Chart, 1995 Ed.).

In embodiments, the water, a biocatalyst, optionally *cannabis*, and at least one from the group consisting of malt, grain, barley, honey, and hops may be fermented at a temperature that ranges from one or more from the group consisting of 50 degrees Fahrenheit to 52 degrees Fahrenheit, 52 degrees Fahrenheit to 54 degrees Fahrenheit, 54 degrees Fahrenheit to 56 degrees Fahrenheit, 56 degrees Fahrenheit to 58 degrees Fahrenheit, 58 degrees Fahrenheit to 60 degrees Fahrenheit, 60 degrees Fahrenheit to 62 degrees Fahrenheit, 62 degrees Fahrenheit to 64 degrees Fahrenheit, 64 degrees Fahrenheit to 66 degrees Fahrenheit, 66 degrees Fahrenheit to 68 degrees Fahrenheit, 68 degrees Fahrenheit to 70 degrees Fahrenheit, 70 degrees Fahrenheit to 72 degrees Fahrenheit, 72 degrees Fahrenheit to 74 degrees Fahrenheit, 74 degrees Fahrenheit to 76 degrees Fahrenheit, 76 degrees Fahrenheit to 78 degrees Fahrenheit, 78 degrees Fahrenheit to 80 degrees Fahrenheit, 80 degrees Fahrenheit to 82 degrees Fahrenheit, 82 degrees Fahrenheit to 84 degrees Fahrenheit, 84 degrees Fahrenheit to 86 degrees Fahrenheit, 86 degrees Fahrenheit to 88 degrees Fahrenheit, 88 degrees Fahrenheit to 90 degrees Fahrenheit, 90 degrees Fahrenheit to 92 degrees Fahrenheit, and 92 degrees Fahrenheit to 94 degrees Fahrenheit.

In embodiments, the yeast within the mixture of water, yeast, optionally *cannabis*, and at least one or more from the group consisting of malt, grain, barley, honey, and hops has a range of attenuation that is selected from one or more from the group consisting of 50 percent to 52 percent, 52 percent to 54 percent, 54 percent to 56 percent, 56 percent to 58 percent, 58 percent to 60 percent, 60 percent to 62 percent, 62 percent to 64 percent, 64 percent to 66 percent, 66 percent to 68 percent, 68 percent to 70 percent, 70 percent to 72 percent, 72 percent to 74 percent, 74 percent to 76 percent, 76 percent to 78 percent, 78 percent to 80 percent, 80 percent to 82 percent, 82 percent to 84 percent, 84 percent to 86 percent, 86 percent to 88 percent, 88 percent to 90 percent, percent to 92 percent, and 92 percent to 94 percent. The term attenuation is a percentage that is used to describe the percent of sugar within the malt, grain, barley, honey, or hops that is converted by the yeast into ethanol and carbon dioxide.

The biocatalyst tank (G78) has an interior (G80), a biocatalyst input (G81), a biocatalyst conveyor (G82), and a biocatalyst conveyor output (G83). The biocatalyst tank (G78) accepts biocatalyst (G79) to the interior (G80) and regulates and controls an engineered amount of biocatalyst (G79) downstream to be mixed in the mixing tank (G15). The biocatalyst conveyor (G82) has an integrated biocatalyst mass sensor (G84) that is configured to input and output a signal (G85) to the computer (COMP). The biocatalyst conveyor motor (G86) has a controller (G87) that is configured to input and output a signal (G88) to the computer (COMP). The biocatalyst mass sensor (G84), biocatalyst conveyor (G82), and biocatalyst conveyor motor (G86) are coupled so as to permit the conveyance, distribution, or output of a precise flow of biocatalyst (G79) via a biocatalyst transfer line (G89). In embodiments, the biocatalyst transfer line (G89) has a diameter that ranges from: 0.5 inches to 0.75 inches, 0.75 inches to 1 inch, 1 inch to 1.5 inches, 2 inches to 3 inches, 3 inches to 4 inches.

In embodiments, the biocatalyst includes a SCOBY which is an acronym for a "Symbiotic Culture Of Bacteria and Yeast" which is a syntrophic mixed culture of bacteria and yeast used in production of several traditional foods and beverages, such as Kombucha. In embodiments, the beverage includes Kombucha.

In embodiments, the beverage includes Kombucha which can be stored at room temperature or without the need for refrigeration. This type of Kombucha has been fermented with a SCOBY and is then filtered to remove bacteria and yeast from the beverage, either by pasteurization or filtration. Kombucha, if it is raw and unpasteurized, includes live, beneficial bacteria and yeast colonies, wherein to increase the shelf-life is it cooked, heated, or pasteurized or filtered to remove the live, beneficial bacteria and yeast colonies to prevent the beverage from going bad and spoiling. In embodiments, the beverage is refrigerated before sale to prevent further fermentation from occurring. In embodiments, the beverage is not refrigerated before sale since cooking, heating, or pasteurization or filtration takes place.

Acid Distribution Module (14G3')

FIG. 14G displays an acid mixing module (14G3') including an acid tank (G78') that is configured to accept at least one acid (G79'). The acid (G79') may be comprised of one or more from the group consisting of an acid, abscic acid, acetic acid, ascorbic acid, benzoic acid, citric acid, formic acid, fumaric acid, hydrochloric acid, lactic acid, malic acid, nitric acid, organic acids, phosphoric acid, potassium hydroxide, propionic acid, salicylic acid, sulfamic acid, sulfuric acid, and tartaric acid.

In embodiments, insects (G56) and/or ground insects (G67) have a pH that is greater than 7. In embodiments, insects (G56) and/or ground insects (G67) have a pH that is basic and ranges from greater than 7 to less than 8.75. In embodiments, insects (G56) and/or ground insects (G67) added to the interior (G14) of the mixing tank (G15) is required to lower the pH of the water, insect, biocatalyst mixture to a pH that is sufficient for the biocatalyst to digest or hydrolyze the insects. In embodiments, addition of an acid (G79') to the interior (G14) of the mixing tank (G15) is required to maintain the liquid mixture of biocatalyst, insects, and water within the mixing tank (G15) to be at a desired range from within 6.25 to 7.5.

The acid tank (G78') has an interior (G80'), an acid input (G81'), an acid conveyor (G82'), and an acid conveyor output (G83'). The acid tank (G78') accepts acid (G79') to the interior (G80') and regulates and controls an engineered amount of acid (G79') downstream to be mixed in the mixing tank (G15).

The acid conveyor (G82') has an integrated acid mass sensor (G84') that is configured to input and output a signal (G85') to the computer (COMP). The acid conveyor motor (G86') has a controller (G87') that is configured to input and output a signal (G88') to the computer (COMP). The acid mass sensor (G84'), acid conveyor (G82'), and acid conveyor motor (G86') are coupled so as to permit the conveyance, distribution, or output of a precise flow of acid (G79') via an acid transfer line (G89'). In embodiments, the acid transfer line (G89') has a diameter that ranges from: inches to 0.75 inches, 0.75 inches to 1 inch, 1 inch to 1.5 inches, 2 inches to 3 inches, 3 inches to 4 inches.

In embodiments, the mixing tank (G15) is equipped with a pH sensor (PHG) that is configured to output a signal (PHG') to the computer (COMP). In embodiments, the pH sensor (PHG) is used in a control loop with the acid mass sensor (G84'), acid conveyor (G82'), and acid conveyor motor (G86') to permit output of a precise flow of acid (G79') to the interior (G14) of the mixing tank (G15) to maintain a predetermined pH within the mixing tank (G15).

FIG. 14G shows the insects (G56), ground insects (G67), biocatalyst (G79), and acid (G79') introduced to the interior (G14) of the mixing tank (G15) via an input (G100). It is not required that the insects (G56), ground insects (G67), biocatalyst (G79), and acid (G79') are combined into a combined stream (G101) for input (G100) to the interior (G14) of the mixing tank (G15). It is apparent to those skilled in the art to which it pertains that each insects (G56), ground insects (G67), biocatalyst (G79), and acid (G79') can have their own input to the interior (G14) of the mixing tank (G15) as well.

In embodiments, another alternate liquid (G102) may be added to the interior (G14) of the mixing tank (G15) to replace or be mixed with the source of water (01). In embodiments, the alternate liquid (G102) are comprised of one or more from the group consisting of alcohol, diglycerides, esters, ethanol, butanol, n-butanol, sec-butanol, isobutanol, tert-butanol, ethyl acetate, glycerin, glycerol, hexane, hydrocarbon, insect lipids, isopropyl alcohol, methanol, Monoglycerides, oil, and solvent.

In embodiments, at least a portion of the first contaminant depleted water (G27), second contaminant depleted water (G31), or third contaminant depleted water (G13) may be introduced to the start-up/shut-down liquid tank (KEA) for use as a source of start-up/shut-down water (KEB) as indicated on FIG. 18E. In embodiments, at least a portion of the first contaminant depleted water (G27), second contaminant depleted water (G31), or third contaminant depleted water (G13) may be introduced to start-up and/or shut-down the rotary atomizer (KAU) of FIG. 14K and used as start-up/shut-down water (KEB).

Methods for producing a partially biosynthetic cannabinoid distillate is described. The method includes mixing partially biosynthetic cannabinoids with plant derived cannabinoids to produce a cannabinoid distillate that includes both plant-derived cannabinoids together with partially biosynthetic cannabinoids. Methods to produce the biosynthetic cannabinoid are described and include use of a bioreactor including a liquid nutrient medium, or culture medium, used for culturing genetically modified microorganisms and a cannabinoid is produced within the bioreactor by the genetically modified microorganisms which either contain the cannabinoid within the cells of the microorganisms (and later extracted from the microorganisms) or secrete the cannabinoid which accumulates within the liquid nutrient medium. Purification and extraction of the cannabinoids from the genetically modified microorganisms then takes place to produce a source of biosynthetic cannabinoid distillate which is then mixed with plant-derived cannabinoids to produce a cannabinoid distillate that includes both plant-derived cannabinoids together with partially biosynthetic cannabinoids.

In embodiments, the bioreactor includes a liquid nutrient medium, or culture medium, used for culturing genetically modified microorganisms and a cannabinoid is produced within the bioreactor by the genetically modified microorganisms which either contain the cannabinoid within the cells of the microorganisms (and later extracted from the microorganisms) or secrete the cannabinoid which accumulates within the liquid nutrient medium. In embodiments, the cannabinoid includes tetrahydrocannabinolic acid (THCA), active tetrahydrocannabinol, tetrahydrocannabinol (THC), Δ9-tetrahydrocannabinol Δ9-THC, Δ8-tetrahydrocannabinol Δ8-THC, cannabichromene CBC, cannabidiol CBD, cannabigerol CBG, cannabinidiol CBND, and/or cannabinol CBN. In embodiments, the bioreactor includes a liquid nutrient medium, or culture medium, used for culturing the microorganisms and terpenes is produced within the bioreactor by the microorganisms which either contain the terpenes within the cells of the microorganisms (and later extracted from the microorganisms) secrete the terpenes which accumulate within the liquid nutrient medium, wherein the terpenes include one or more from the group consisting of limonene, humulene, pinene, linalool, caryophyllene, myrcene, eucalyptol, nerolidol, bisablol, and phytol.

In embodiments, the bioreactor (G15) includes a liquid nutrient medium, or culture medium, used for culturing microorganisms including genetically modified algae and a cannabinoid is produced within the bioreactor by the genetically modified algae which either contain the cannabinoid within the cells of the microorganisms (and later extracted from the microorganisms) or secrete the cannabinoid which accumulates within the liquid nutrient medium. In embodiments, the cannabinoid includes tetrahydrocannabinolic acid (THCA), active tetrahydrocannabinol, tetrahydrocannabinol (THC), Δ9-tetrahydrocannabinol Δ9-THC, Δ8-tetrahydrocannabinol Δ8-THC, cannabichromene CBC, cannabidiol CBD, cannabigerol CBG, cannabinidiol CBND, and/or cannabinol CBN. In embodiments, the bioreactor includes a liquid nutrient medium, or culture medium, used for culturing the genetically modified algae and terpenes is produced within the bioreactor by the genetically modified algae which either contain the terpenes within the cells of the genetically modified algae (and later extracted from the microorganisms) or secrete the terpenes which accumulate within the liquid nutrient medium, wherein the terpenes include one or more from the group consisting of limonene, humulene, pinene, linalool, caryophyllene, myrcene, eucalyptol, nerolidol, bisablol, and phytol.

In embodiments, the microorganisms used within the bioreactor (G15) include bacteria, archaea, fungi, protozoa, algae, and viruses. In embodiments, the microorganisms used within the bioreactor include genetically modified photosynthetic microalgae or a cyanobacterium. In embodiments, the microorganisms used within the bioreactor include genetically modified organisms. In embodiments, the microorganisms used within the bioreactor include genetically modified algae. In embodiments, the microorganisms used within the bioreactor do not include genetically modified organisms. In embodiments, the microorganisms used within the bioreactor include gas fermenting organisms. In embodiments, the microorganisms used within the bioreactor undergo anaerobic respiration. In embodiments, the microorganisms used within the bioreactor undergo fermentation. In embodiments, the microorganisms used within the bioreactor include anaerobic bacteria.

In embodiments, the microorganisms used within the bioreactor (G15) include genetically modified algae. In embodiments, the genetically modified algae include cloned algae cells. In embodiments, the genetically modified algae includes one or more selected from the group consisting of: polyclonal genetically modified algae cells, polyclonal genetically modified algae cells infected with a virus, polyclonal genetically modified algae cells infected with a recombinant virus, polyclonal genetically modified algae cells infected with a polyclonal recombinant virus, polyclonal genetically modified algae cells infected with an oligoclonal recombinant virus, polyclonal genetically modified algae cells infected with a monoclonal recombinant virus, and combinations thereof.

In embodiments, the genetically modified algae includes one or more selected from the group consisting of: oligoclonal genetically modified algae cells, oligoclonal genetically modified algae cells infected with a virus, oligoclonal genetically modified algae cells infected with a recombinant virus, oligoclonal genetically modified algae cells infected with a polyclonal recombinant virus, oligoclonal genetically modified algae cells infected with an oligoclonal recombinant virus, oligoclonal genetically modified algae cells infected with a monoclonal recombinant virus, and combinations thereof.

In embodiments, the genetically modified algae includes one or more selected from the group consisting of: monoclonal genetically modified algae cells, monoclonal genetically modified algae cells infected with a virus, monoclonal genetically modified algae cells infected with a recombinant virus, monoclonal genetically modified algae cells infected with a polyclonal recombinant virus, monoclonal genetically modified algae cells infected with an oligoclonal recombinant virus, monoclonal genetically modified algae cells infected with a monoclonal recombinant virus, and combinations thereof.

In embodiments, the microorganisms used within the bioreactor include genetically modified cyanobacterium. In embodiments, the genetically modified cyanobacterium include cloned cyanobacterium cells. In embodiments, the genetically modified cyanobacterium includes one or more selected from the group consisting of: polyclonal genetically modified cyanobacterium cells, polyclonal genetically modified cyanobacterium cells infected with a virus, polyclonal genetically modified cyanobacterium cells infected with a recombinant virus, polyclonal genetically modified cyanobacterium cells infected with a polyclonal recombinant virus, polyclonal genetically modified cyanobacterium cells infected with an oligoclonal recombinant virus, polyclonal genetically modified cyanobacterium cells infected with a monoclonal recombinant virus, and combinations thereof.

In embodiments, the genetically modified cyanobacterium includes one or more selected from the group consisting of: oligoclonal genetically modified cyanobacterium cells, oligoclonal genetically modified cyanobacterium cells infected with a virus, oligoclonal genetically modified cyanobacterium cells infected with a recombinant virus, oligoclonal genetically modified cyanobacterium cells infected with a polyclonal recombinant virus, oligoclonal genetically modified cyanobacterium cells infected with an oligoclonal recombinant virus, oligoclonal genetically modified cyanobacterium cells infected with a monoclonal recombinant virus, and combinations thereof.

In embodiments, the genetically modified cyanobacterium includes one or more selected from the group consisting of: monoclonal genetically modified cyanobacterium cells, monoclonal genetically modified cyanobacterium cells infected with a virus, monoclonal genetically modified cyanobacterium cells infected with a recombinant virus, monoclonal genetically modified cyanobacterium cells infected with a polyclonal recombinant virus, monoclonal genetically modified cyanobacterium cells infected with an oligoclonal recombinant virus, monoclonal genetically modified cyanobacterium cells infected with a monoclonal recombinant virus, and combinations thereof.

In embodiments, the bioreactor (G15) includes a single-use bioreactor. In embodiments, the single-use bioreactor includes a disposable bioreactor. In embodiments, the disposable bioreactor is a disposable bag instead of a culture vessel. In embodiments, the disposable bioreactor is a disposable bag. In embodiments, the bioreactor (G15) is transparent or translucent.

In embodiments, the disposable bag includes a three-layer plastic foil, comprising: a first layer including a first polymer configured to provide mechanical stability, wherein the first polymer includes polyethylene terephthalate or low-density polyethylene (LDPE); a second layer including a second polymer configured to act as a gas barrier, wherein the second polymer includes a first thermoplastic polymer, wherein the first thermoplastic polymer includes an aliphatic rubbery synthetic polymer, a material of the polyvinyl ester family, polyvinyl chloride, polyvinyl, or vinyl; and a third layer including a third polymer configured to contact the liquid within the bioreactor, wherein the liquid includes a culture medium including at least treated water, wherein the third polymer includes a second thermoplastic polymer, wherein the second thermoplastic polymer includes an aliphatic rubbery synthetic polymer, a material of the polyvinyl ester family, polyvinyl acetate (PVA, PVAc, poly(ethenyl ethanoate), polypropylene, or polypropene.

In embodiments, the liquid or culture medium within the disposable bioreactor is agitated. In embodiments, the disposable bioreactor includes a stirrer within bag to agitate the culture medium or liquid within the bioreactor. In embodiments, the stirrer is integrated into the disposable bag. In embodiments, the disposable bioreactor is pre-sterilized. In embodiments, the liquid or culture medium within the disposable bioreactor is agitated by a rocking motion. In embodiments, the liquid or culture medium within the disposable bioreactor is not agitated. In embodiments, the disposable bioreactor includes a stirrer within bag to agitate the culture medium. In embodiments, the disposable bioreactor reduces risk of cross-contamination between batches while providing flexibility, minimizing turnaround time, reducing cleaning costs, and easing validation restrictions.

In embodiments, the bioreactor (G15) provides scalable and robust stirred-tank or disposable performance in both cGMP and non-cGMP environments. In embodiments, the bioreactor (G15) includes a volume, in liters, ranging from 1, 5, 10, 50, 200, 500, 1000, or 2000. In embodiments, the bioreactor (G15) includes a perfusion bioreactor. In embodiments, the bioreactor (G15) is configured to operate in a plurality of modes, including: batch, fed-batch and perfusion bioreactor modes.

In embodiments, the filter (H11) includes one or more filter types selected from the group consisting of: a batch filter, a continuous filter, a continuous-batch filter, a leaf filter, a filter press, a centrifuge, a plate and frame filter, a recessed filter plate, a membrane filter press, a disc filter, a centrifugal filter, a hydroclone, an s-type filter belt press, a klampress belt press, a belt press, a basket filter, a chromatography column, a packed column, a packed bed, a chromatography filtration, adsorber, absorber, a membrane, ion exchange resin. In embodiments, the filter (H11) includes one or more filter types selected from the group consisting of microfiltration, depth filtration, ultrafiltration, diafiltration, tangential flow filtration (TFF) system, sterile filtration, and rotary vacuum drum filtration. In embodiments, the filter (H44) includes a General Electric AKTA liquid chromatography system.

In embodiments, the filter (H11) includes an adsorbent comprising one or more selected from the group consisting of a strongly acidic cation exchange resin include such as AMBERLITE IR-118 (Available from Dow Chemical Company, Midland, Mich.), or DIAION PK216LH (Available from Mitsubishi Chemical Company, Tokyo, Japan). Suitable examples of the weakly basic anion exchange resin include AMBERLITE IRA-70RF (Available from Dow Chemical Company, Midland, Mich.) or RELITE RAM2 (Available from Mitsubishi Chemical Company, Tokyo, Japan).

In embodiments, the adsorbent used in the filter (H11) employed is a combination of styrene-divinyl benzene copolymer, ion exchange and hydrophobic interaction based stationary phase adsorbents and a mobile phase comprising water in a combination of normal and reverse phase simulated moving bed separation zones to provide a first purified recombinant protein.

In embodiments, the filter (H11) includes one or more filters or purification systems selected from the group consisting of affinity chromatography (AC), ion exchange chromatography (IEX), hydrophobic interaction chromatography (HIC), gel filtration (GF) chromatography, reversed phase chromatography (RPC), and combinations thereof.

In embodiments, the filter (H11) includes a detergent purification system, wherein the detergent includes a surfactant, ionic detergent, non-ionic detergent, and/or a zwitterionic detergent. In embodiments, the filter (H11) includes a detergent purification system, wherein the detergent includes one or more detergents selected from the group consisting of a surfactant, a nonionic surfactant, lecithin, polyethylene (40), stearate, polysorbate, Polyoxyethylene sorbitan monooleate, Polyoxyethylene (20) sorbitan monooleate, polysorbate 80, polysorbate 60, polysorbate 65, ammonium salts of phosphatidic acid, sucrose acetate isobutyrate, potassium pyrophosphate, sodium acid pyrophosphate, sodium pyrophosphate, potassium polymetaphosphate, sodium metaphosphate, insoluble or sodium polyphosphates, sodium polyphosphates, insoluble polyphosphates, glassy salts of fatty acids, mono- and di-glycerides of fatty acids, mono-glycerides of fatty acids, di-glycerides of fatty acids, acetic and fatty acid esters of glycerol, lactic and fatty acid esters of glycerol, citric and fatty acid esters of glycerol, diacetyltartaric and fatty acid esters of glycerol, mixed fatty acid esters of glycerol, sucrose esters of fatty acids, polyglycerol esters of fatty acids, polyglycerol esters of interesterified ricinoleic acid, propylene glycol mono- and di-esters, propylene glycol di-esters, propylene glycol mono-esters, propylene glycol esters of fatty acids, propylene glycol esters, dioctyl sodium sulphosuccinate, sodium lactylate, sodium oleyl lactylate, sodium stearoyl lactylate, calcium lactylate, calcium oleyl lactylate, calcium stearoyl lactylate, sorbitan monostearate, maltodextrin, polyphosphates, formulated polyphosphates, and gum arabic.

In embodiments, the present discloses relates to a method to produce a biosynthetic cannabinoid distillate, the method includes:
 (a) in a photo-bioreactor, growing microalgae which have been genetically modified to produce a biosynthetic cannabinoid, in a liquid nutrient medium;
 (b) separating the grown, genetically modified microalgae from the liquid nutrient medium;
 (c) extracting the biosynthetic cannabinoid from the grown, genetically modified microalgae to produce an extracted biosynthetic cannabinoid; and
 (d) distilling the extracted biosynthetic cannabinoid to produce the biosynthetic cannabinoid distillate.

In embodiments, the biosynthetic cannabinoid distillate can be used to produce a beverage, a nanoemulsion, a spray-dried water-soluble powder by spray drying the nanoemulsion. In embodiments, the biosynthetic cannabinoid and/or the biosynthetic cannabinoid distillate can mixed with *cannabis* plant derived terpenes and/or non-biosynthetic plant derived cannabinoids. In embodiments, the biosynthetic cannabinoid and/or the biosynthetic cannabinoid distillate can mixed with non-biosynthetic plant derived cannabinoids to produce new products having high quality and repeatability and uniformity.

In embodiments, the biosynthetic cannabinoid and/or the biosynthetic cannabinoid distillate can be used to produce a foodstuff from the biosynthetic cannabinoid distillate, the foodstuff includes one or more selected from the group consisting of ada, bagels, baked goods, beverages, biscuits, bitterballen, bonda, breads, cakes, candies, cereals, chips, chocolate bars, carbonated soft drinks, carbonated drinks, chocolate, coffee, cokodok, confectionery, cookies, cooking batter, corn starch mixtures, crackers, crepes, croissants, croquettes, croutons, dolma, dough, doughnuts, energy bars, flapjacks, french fries, frozen custard, frozen desserts, frying cakes, fudge, gelatin mixes, granola bars, gulha, hardtack, ice cream, khandvi, khanom buang, krumpets, meze, mixed flours, muffins, multi-grain snacks, nachos, nian gao, noodles, nougat, onion rings, pakora, pancakes, panforte, pastas, pastries, pie crust, pita chips, pizza, poffertjes, pretzels, protein powders, pudding, rice krispie treats, sesame sticks, smoothies, snacks, soft drinks, sport drinks, sparkling drinks, specialty milk, tele-bhaja, tempura, toffee, tortillas, totopo, turkish delights, or waffles. In embodiments, the biosynthetic cannabinoid and/or the biosynthetic cannabinoid distillate can be used to produce a cosmetic product or a topical from the biosynthetic cannabinoid distillate.

In embodiments, the liquid nutrient medium includes treated water, the treated water is treated with an adsorbent, ion exchange resin, and/or a membrane. In embodiments, the gas may be introduced to the liquid nutrient medium, the gas includes carbon dioxide. In embodiments, the photo-bioreactor includes a superficial gas velocity ranging from between 0.1 to 15 inches per second, or 1 to 15, or 5 to 15, or 1 to 5 inches per second. In embodiments, the liquid nutrient medium includes one or more selected from the group consisting of a carbohydrate, a micronutrient, a macronutrient, an acid, and combinations thereof.

In embodiments, the genetically modified microalgae are grown within a photo-bioreactor at a residence time ranging from 1 to 5 days or 2 to 4 days. In embodiments, the photo-bioreactor operates at a photosynthetic photon flux density ranging from ranging from 50 to 1,000 micromole per second and square meter. In embodiments, the photo-bioreactor is provided with a photon flux density source including one or more selected from the group consisting of compact fluorescent lights, incandescent lights, fluorescent lights, halogen lights, metal halide lamps, high-intensity discharge gas discharge lamps, low pressure sodium lamps, sodium lamps, quartz halogen lamps, and combinations thereof. In embodiments, the photo-bioreactor is provided with a photon flux density source light emitting diodes, wherein the light emitting diodes operate at a wave length ranging from 390 to 700 nanometers. In embodiments, the photo-bioreactor is transparent and/or translucent. In embodiments, the photo-bioreactor has a volume ranging from 50 to 2000 liters. In embodiments, the extracted biosynthetic cannabinoid can be distilled with via spinning band distillation, which is known to a person of ordinary skill in the art and available from a variety of commercial vendors including from: EquiLab Canada Inc., see B/R 9400 and 9600 High Efficiency Distillation Systems, (http://www.equilabcanada.com); or from https://www.alibaba.com, Model Number: HSPD-2000, 2L Turnkey Spinning Band Distillation Short Path Unit; or from BR Instrument, 9119 Centreville Road Easton, MD 21601 USA (https://brinstrument.com). In embodiments, the spinning band distillation system is equipped to distill a variety of throughputs.

In embodiments, the spinning band distillation system is an automatic controlled distillation column having: a volume ranging from 1 to 2 liters, 2 to 5 liters, 5 to 10 liters, 10 liters to 100 liters, 100 liters to 1000 liters, 1000 liters to 1500 liters, 1500 liters to 5000 liters; a column diameter ranging from 0.5 to 1 inch, 1 inch to 1.5 inches, 1.5 inches to 2.5 inches, 2.5 inches to 3.5 inches, 3.5 inches to 5 inches, 5 inches to 10 inches; a column length ranging from 5 inches to inches, 10 inches to 20 inches, 20 inches to 30 inches, 30 inches to 40 inches, 40 inches to 50 inches, 50 inches to 60 inches, 60 inches to 80 inches, 80 inches to 100 inches; maximum theoretical plates, with a Teflon spinning band 10 to 15 maximum theoretical plates, 15 to 30 maximum theoretical plates, 30 to 45 maximum theoretical plates, 45 to 60 maximum theoretical plates; maximum theoretical plates, with a metal band 10 to 15 maximum theoretical plates, 15 to maximum theoretical plates, 30 to 45 maximum theoretical plates, 45 to 60 maximum theoretical plates. In embodiments, the spinning band distillation system operates in batch mode or continuously. In embodiments, the spinning band distillation system includes a plurality of is generated from a boiler, wherein the boiler can be electrically heated of natural gas heated. In embodiments, the spinning band distillation system is electrically heated and operates at a voltage of 110 volts, 120 volts, 220 volts. In embodiments, the spinning band distillation system operates under vacuum conditions.

In embodiments, the present discloses relates to a method to produce biosynthetic cannabinoid, the method includes:
(a) in a photo-bioreactor, growing microalgae and/or cyanobacterium which have been genetically modified to produce a biosynthetic cannabinoid, in a liquid nutrient medium and in the presence of carbon dioxide, the liquid nutrient medium including water treated with an adsorbent, ion exchange resin, and/or a membrane;
(b) separating the grown, genetically modified microalgae and/or the genetically modified cyanobacterium from the liquid nutrient medium; and
(c) extracting the biosynthetic cannabinoid from the grown, genetically modified microalgae and/or the genetically modified cyanobacterium to produce an extracted biosynthetic cannabinoid.

The present disclosure relates to methods to produce synthetic extracted and distilled cannabinoids and methods to prepare foods, drugs, chemicals, pharmaceuticals. One of ordinary skill in the art would know how to produce genetically modified microorganisms, as in genetically modified microalgae by viewing existing patents related to production of genetically modified microalgae as viewed in: WO2019210404 assigned to Algae-C Inc. and titled Engineered Microorganism For The Production Of Cannabinoid Biosynthetic Pathway Products.

FIG. 18F:

FIG. 18F shows one non-limiting embodiment of a solids separation module (14H) that is configured to remove the solids contained within the cannabinoid and biocatalyst mixture (G09).

FIG. 18f shows the solid separation module (14H) (e.g., a separation system) configured to remove solids (exoskeleton and/or microorganism cell walls, and/or solid portion of the microorganism) from insects that are contained within the insect liquid biocatalyst mixture (G09). In embodiments, where the biocatalyst (G79) within the biocatalyst mixing module (14G) is optional, the solid separation module (14H) is configured to remove solids contained within a liquid mixture (G09A) as depicted in FIG. 18F.

In embodiments, exoskeleton is chitin. In embodiments, exoskeleton is a long-chain polymer of an N-acetylglucosamine, a derivative of glucose. In embodiments, the exoskeleton is provided to insects within the FSS to eat.

The insect liquid biocatalyst mixture (G09) or an insect and liquid mixture (G09A) is transferred from the mixing tank (G15) to the solid separation module (14H) of FIG. 18F via a transfer conduit (G50). FIG. 18F displays the solid separation module (14H) including an solids separator (H10). In embodiments, the solids separator (H10) is a filter (H11) having at least one side wall (H65). In embodiments, the filter (H11) is cylindrical. In embodiments, the filter (H11) is a candle filter (H12) that has at least one filter element (H13) contained within its interior (H64). In embodiments, the filter (H11) has a top (H14) and a bottom (H15).

FIG. 18F shows a separator input (H16) positioned on the side wall (H65) of the solids separator (H10). The separator input (H16) is configured to introduce an exoskeleton-laden insect mixture (H17) to the interior (H64) of the filter (H11). In embodiments, the insect liquid biocatalyst mixture (G09) or an insect and liquid mixture (G09A) may be considered an exoskeleton-laden insect mixture (H17).

In embodiments, the insects and/or the genetically engineered microorganisms within the mixing tank/bioreactor (G15) of FIG. 18E are transferred to the filter (H11) on FIG. 18F. The solid portions may be separated and sent to any one of FIGS. 17A, 17A', 17B, 17D', 17H for extraction of the biosynthetically-derived cannabinoid (from the genetically modified microorganisms) and/or the insect-derived cannabinoid glycoside (from the insects).

In embodiments, the filter (H11) is configured to remove solids from the liquid mixture (G09A). In embodiments, the filter (H11) is configured to remove a recombinant protein from the insect and liquid mixture (G09A). In embodiments, the filter (H11) is configured to remove a cannabinoid, the biomass (cell walls, microorganisms) including the cannabinoid (for use in extraction of the cannabinoid from the biomass), a recombinant protein, vaccine, antibody, peptide, or chemical from the insect and liquid mixture (G09A).

In embodiments, the bioreactor includes one or more type of bioreactors selected from the group consisting of a continuous stirred tank bioreactor, a bubble column bioreactor, a microbubble reactor, an airlift bioreactor, a fluidized bed bioreactor, a packed bed bioreactor, a photo-bioreactor, a WAVE Bioreactor™ system from GE Healthcare, and combinations thereof. Further, photo-bioreactors are well known in the art and are available from a variety of commercial vendors, such as from: https://www.alibaba.com, Model Number: HXDYKZ-12, which is a photo-bioreactor comprising translucent plastic tubes provides a suitable environment for sunlight supply, algae growth and culture density; and also, from https://www.alibaba.com, Model Number: SF-100L, which is a photo-bioreactor comprising a jacketed glass reactor; and also, https://www.ika.com, Algaemaster 10 Control Bioreactor.

In embodiments, the a photo-bioreactor is used is provided with the source of light, and microorganisms are grown at a photosynthetic photon flux density within the photo-bioreactor (in micromole per second and square meter (µmol/m2/s)) ranging from 20 to 40, 40 to 50, 50 to 60, to 70, 70 to 80, 80 to 90, 90 to 100, 100 to 110, 110 to 120, 120 to 130, 130 to 140, 140 to 150, 150 to 160, 160 to 170, 170 to 180, 180 to 190, 190 to 200, 200 to 210, 210 to 220, 220 to 230, 230 to 240, 240 to 250, 250 to 260, 260 to 270, 270 to 280, 280 to 290, 290 to 300, 300 to 400, 400 to 500, 500 to 1,000, 1,000 to 2,000, 2,000 to 5,000. In embodiments, the microorganisms within the photo-bioreactor are provided with the source of light, and are grown at a photosynthetic photon flux density (in micromole per second and square meter (µmol/m2/s)) ranging from 100 to 110 to 130.

In embodiments, the photosynthetic photon flux density is based on the number of photons in a certain waveband incident per unit time (s) on a unit area (m2) divided by the Avogadro constant ($6.022 \times 10^{23}$ mol-1). In embodiments, the photo-bioreactor utilizes a light source to cultivate the microorganisms wherein the microorganisms may be phototrophic or photosynthetic which use photosynthesis. In embodiments, phototrophic or photosynthetic genetically modified microorganisms produce cannabinoids from light within the interior of the bioreactor.

In embodiments, the bioreactor grows the cultivating genetically modified microorganisms to fix carbon dioxide and produce target products, such as not only including biosynthetic cannabinoids for to produce pharmaceuticals and food. This disclosure is aimed at energy-efficient, low cost, bioreactors with carefully designed control systems to monitor the performance of the microorganisms for large-scale or industrial-scale pharmaceutical and food production.

In embodiments, the insect cells used within the bioreactor include genetically modified insect cells. In embodiments, the insect cells used within the bioreactor do not include genetically modified insect cells. In embodiments, the insect cells used within the bioreactor include gas fermenting insect cells. In embodiments, the insect cells used within the bioreactor undergo anaerobic respiration. In embodiments, the insect cells used within the bioreactor undergo fermentation. In embodiments, the insect cells used within the bioreactor include anaerobic insect cells. In embodiments, the bioreactor includes a liquid nutrient medium, or culture medium, used for culturing the insect cells and the a cannabinoid, a *cannabis* glycoside, a recombinant protein, vaccine, antibody, peptide, or chemical is produced within the bioreactor by the insect cells which either contain the cannabinoid within the insects and/or insect cells (and later optionally extracted from the insects and/or insect cells) or secrete the cannabinoid, recombinant protein, vaccine, antibody, peptide, or chemical which accumulates within the liquid nutrient medium. In embodiments, the chemical includes ethanol. In embodiments, the chemical includes a cannabinoid.

In embodiments, the bioreactor includes a liquid nutrient medium, or culture medium, used for culturing the insect cells is produced within the bioreactor by the insect cells which either contain a chemical within the insects and/or insect cells (and later optionally extracted from the insects and/or insect cells) or secrete the chemical which accumulates within the liquid nutrient medium. In embodiments, the chemical includes a cannabinoid.

In embodiments, the cannabinoid includes tetrahydrocannabinolic acid (THCA), active tetrahydrocannabinol, tetrahydrocannabinol (THC), Δ9-tetrahydrocannabinol (Δ9-THC), Δ8-tetrahydrocannabinol (Δ8-THC), tetrahydrocannabivarin (THCV), cannabidiolic acid (CBDA), cannabichromene (CBC), cannabidiol (CBD), cannabigerol (CBG), cannabinidiol (CBND), and/or cannabinol (CBN).

In embodiments, the cannabinoid glycoside includes glycosides of cannabinoid compounds, endocannabinoid compounds and/or vanilloid compounds. In embodiments, within the insects, a cannabinoid undergoes hydrolysis to produce the cannabinoid glycoside. In embodiments, an endocannabinoid refers to compounds including arachidonoyl ethanolamide (anandamide, AEA), 2-arachidonoyl ethanolamide (2-AG), 1-arachidonoyl ethanolamide (1-AG), and docosahexaenoyl ethanolamide (DHEA, synaptamide), oleoyl ethanolamide (OEA), eicsapentaenoyl ethanolamide, prostaglandin ethanolamide, docosahexaenoyl ethanolamide, linolenoyl ethanolamide, 5(Z),8(Z),11(Z)-eicosatrienoic acid ethanolamide (mead acid ethanolamide), heptadecanoul ethanolamide, stearoyl ethanolamide, docosaenoyl ethanolamide, nervonoyl ethanolamide, tricosanoyl ethanolamide, lignoceroyl ethanolamide, myristoyl ethanolamide, pentadecanoyl ethanolamide, palmitoleoyl ethanolamide, docosahexaenoic acid (DHA). Particularly preferred endocannabinoids are AEA, 2-AG, 1-AG, and DHEA. In embodiments, an vanilloid refers to compounds comprising a vanillyl group and which act on vanilloid receptors like TRPV1. "Vanilloid" compounds include, but are not limited to, vanillin, capsaicin and curcumin.

In embodiments, insects eat the cannabinoid in the feed and effectuate the glycosylation of a cannabinoid. In embodiments, an enzyme within the insects effectuate the glycosylation of a cannabinoid. In embodiments, insects eat an enhanced feedstock including tetrahydrocannabinolic acid (THCA), tetrahydrocannabinol (THC), Δ9-tetrahydrocannabinol (Δ9-THC), Δ8-tetrahydrocannabinol (Δ8-THC) wherein the insects effectuate the glycosylation of the cannabinoid to produce a cannabinoid glycoside. In embodiments, insects eat an enhanced feedstock including tetrahydrocannabinolic acid (THCA), tetrahydrocannabinol (THC), Δ9-tetrahydrocannabinol (Δ9-THC), Δ8-tetrahydrocannabinol (Δ8-THC) wherein the insects effectuate the glycosylation of the cannabinoid to produce a (THCV) Tetrahydrocannabivarin.

In embodiments, insects eat the cannabinoid emulsion and/or colloidal dispersion (JNC), powdered cannabinoid, cannabinoid crystals, spray-dried cannabinoids, cannabinoids, *cannabis* volatiles, a cannabinoid and liquid mixture, a cannabinoid and a solvent mixture, trimmed *cannabis* buds, *cannabis* seeds, *cannabis* stems, *cannabis* roots, a mixture of *cannabis* with insects and/or arachnids, concentrated volatiles, a concentrated cannabinoid, a *cannabis* plant derived cannabinoid, an insect-derived cannabinoid glycoside, a biosynthetically derived cannabinoid, a secondary extract, a purified cannabinoid, a distilled cannabinoid, a cannabinoid emulsion, a micro emulsion, a nano emulsion, a cannabinoid colloid suspension, a cannabinoid colloid dispersion, a mixture of a biosynthetic cannabinoid and a genetically engineered microorganism, and combinations thereof.

In embodiments, insects eat the biosynthetic cannabinoid and a genetically engineered microorganisms to produce the cannabinoid glycoside including glycosides of cannabinoid compounds, endocannabinoid compounds and/or vanilloid compounds. The bioreactor is a "psu-pull" bioreactor in the sense that the insects inject a first cannabinoid to produce the second cannabinoid, wherein the second cannabinoid includes the insect-derived cannabinoid glycoside. In embodiments, within the insects, a cannabinoid undergoes hydrolysis to produce the cannabinoid glycoside. In embodiments, an endocannabinoid refers to compounds including arachidonoyl ethanolamide (anandamide, AEA), 2-arachidonoyl ethanolamide (2-AG), 1-arachidonoyl ethanolamide (1-AG), and docosahexaenoyl ethanolamide (DHEA, synaptamide), oleoyl ethanolamide (OEA), eicsapentaenoyl ethanolamide, prostaglandin ethanolamide, docosahexaenoyl ethanolamide, linolenoyl ethanolamide, 5(Z),8(Z),11(Z)-eicosatrienoic acid ethanolamide (mead acid ethanolamide), heptadecanoul ethanolamide, stearoyl ethanolamide, docosaenoyl ethanolamide, nervonoyl ethanolamide, tricosanoyl ethanolamide, lignoceroyl ethanolamide, myristoyl ethanolamide, pentadecanoyl ethanolamide, palmitoleoyl ethanolamide, docosahexaenoic acid (DHA). Particularly preferred endocannabinoids are AEA, 2-AG, 1-AG, and DHEA. In embodiments, an vanilloid refers to compounds comprising a vanillyl group and which act on vanilloid receptors like TRPV1. "Vanilloid" compounds include, but are not limited to, vanillin, capsaicin and curcumin.

In embodiments, the bioreactor includes a liquid nutrient medium, or culture medium, used for culturing the insect cells and terpenes is produced within the bioreactor by the insect cells which either contain the cannabinoid within the insects and/or insect cells (and later optionally extracted from the insects and/or insect cells) or secrete the terpenes which accumulate within the liquid nutrient medium, wherein the terpenes include one or more from the group consisting of limonene, humulene, pinene, linalool, caryophyllene, myrcene, eucalyptol, nerolidol, bisabolol, and phytol. In embodiments, the *cannabis* enhancer includes an emulsion of a cannabinoid and water. In embodiments, the *cannabis* enhancer includes an microemulsion of a cannabinoid and water. In embodiments, the *cannabis* enhancer includes an nanoemulsion of a cannabinoid and water. In embodiments, the *cannabis* enhancer includes an emulsion of a cannabinoid and treated water, wherein the treated water is treated with one or more water treatment units selected from the group consisting of an ultraviolet unit, ozone unit, microwave unit, a distillation system filter, an ion exchange resin, a cation, an anion, a membrane, an adsorbent, and activated carbon.

Methods to produce the biosynthetic chemicals are described and include use of a bioreactor including a liquid nutrient medium, or culture medium, used for culturing genetically modified microorganisms and a chemical is produced within the bioreactor by the genetically modified microorganisms which either contain the chemical within the cells of the microorganisms (and later extracted from the microorganisms) or secrete the chemical which accumulates within the liquid nutrient medium. Purification and extraction of the chemicals from the genetically modified microorganisms then takes place to produce a source of biosynthetic chemical distillate which is then mixed with plant-derived chemicals to produce a chemical distillate that includes both plant-derived chemicals together with partially biosynthetic chemicals.

In embodiments, the bioreactor includes a liquid nutrient medium, or culture medium, used for culturing genetically modified microorganisms and a chemical is produced within the bioreactor by the genetically modified microorganisms which either contain the chemical within the cells of the microorganisms (and later extracted from the microorganisms) or secrete the chemical which accumulates within the liquid nutrient medium. In embodiments, the chemical includes a cannabinoid including one or more selected from the group consisting of tetrahydrocannabinolic acid (THCA), active tetrahydrocannabinol, tetrahydrocannabinol (THC), Δ9-tetrahydrocannabinol (Δ9-THC), Δ8-tetrahydrocannabinol (Δ8-THC), tetrahydrocannabivarin (THCV), cannabidiolic acid (CBDA), cannabichromene (CBC), cannabidiol (CBD), cannabigerol (CBG), cannabinidiol (CBND), and/or cannabinol (CBN). In embodiments, the bioreactor includes a liquid nutrient medium, or culture medium, used for culturing the microorganisms and terpenes is produced within the bioreactor by the microorganisms which either contain the terpenes within the cells of the microorganisms (and later extracted from the microorganisms) secrete the terpenes which accumulate within the liquid nutrient medium, wherein the terpenes include one or more from the group consisting of limonene, humulene, pinene, linalool, caryophyllene, myrcene, eucalyptol, nerolidol, bisabolol, and phytol.

In embodiments, the bioreactor (G15) includes a liquid nutrient medium, or culture medium, used for culturing microorganisms including genetically modified algae and a chemical is produced within the bioreactor by the genetically modified algae which either contain the chemical within the cells of the microorganisms (and later extracted from the microorganisms) or secrete the chemical which accumulates within the liquid nutrient medium. In embodiments, the chemical includes a cannabinoid including one or more selected from the group consisting of tetrahydrocannabinolic acid (THCA), active tetrahydrocannabinol, tetrahydrocannabinol (THC), Δ9-tetrahydrocannabinol Δ9-THC, Δ8-tetrahydrocannabinol Δ8-THC, tetrahydrocannabivarin (THCV), cannabidiolic acid (CBDA), cannabichromene (CBC), cannabidiol (CBD), cannabigerol (CBG), cannabinidiol (CBND), and/or cannabinol (CBN). In embodiments, the bioreactor includes a liquid nutrient medium, or culture medium, used for culturing the genetically modified algae and terpenes is produced within the bioreactor by the genetically modified algae which either contain the terpenes within the cells of the genetically modified algae (and later extracted from the microorganisms) or secrete the terpenes which accumulate within the liquid nutrient medium, wherein the terpenes include one or more from the group consisting of limonene, humulene, pinene, linalool, caryophyllene, myrcene, eucalyptol, nerolidol, bisabolol, and phytol.

In embodiments, the microorganisms used within the bioreactor (G15) include bacteria, archaea, fungi, protozoa, algae, and viruses. In embodiments, the microorganisms used within the bioreactor include genetically modified photosynthetic microalgae or a cyanobacterium. In embodiments, the microorganisms used within the bioreactor include genetically modified organisms. In embodiments, the microorganisms used within the bioreactor include genetically modified algae. In embodiments, the microorganisms used within the bioreactor do not include genetically modified organisms. In embodiments, the microorganisms used within the bioreactor include gas fermenting organisms. In embodiments, the microorganisms used within the bioreactor undergo anaerobic respiration. In embodiments, the microorganisms used within the bioreactor undergo fermentation. In embodiments, the microorganisms used within the bioreactor include anaerobic bacteria.

In embodiments, the microorganisms used within the bioreactor (G15) include genetically modified algae. In embodiments, the genetically modified algae include cloned algae cells. In embodiments, the genetically modified algae includes one or more selected from the group consisting of: polyclonal genetically modified algae cells, polyclonal genetically modified algae cells infected with a virus, polyclonal genetically modified algae cells infected with a recombinant virus, polyclonal genetically modified algae cells infected with a polyclonal recombinant virus, polyclonal genetically modified algae cells infected with an oligoclonal recombinant virus, polyclonal genetically modified algae cells infected with a monoclonal recombinant virus, and combinations thereof.

In embodiments, the genetically modified algae includes one or more selected from the group consisting of: oligoclonal genetically modified algae cells, oligoclonal genetically modified algae cells infected with a virus, oligoclonal genetically modified algae cells infected with a recombinant virus, oligoclonal genetically modified algae cells infected with a polyclonal recombinant virus, oligoclonal genetically modified algae cells infected with an oligoclonal recombinant virus, oligoclonal genetically modified algae cells infected with a monoclonal recombinant virus, and combinations thereof.

In embodiments, the genetically modified algae includes one or more selected from the group consisting of: monoclonal genetically modified algae cells, monoclonal genetically modified algae cells infected with a virus, monoclonal genetically modified algae cells infected with a recombinant virus, monoclonal genetically modified algae cells infected with a polyclonal recombinant virus, monoclonal genetically modified algae cells infected with an oligoclonal recombinant virus, monoclonal genetically modified algae cells infected with a monoclonal recombinant virus, and combinations thereof.

In embodiments, the microorganisms used within the bioreactor include genetically modified cyanobacterium. In embodiments, the genetically modified cyanobacterium includes cloned cyanobacterium cells. In embodiments, the genetically modified cyanobacterium includes one or more selected from the group consisting of: polyclonal genetically modified cyanobacterium cells, polyclonal genetically modified cyanobacterium cells infected with a virus, polyclonal genetically modified cyanobacterium cells infected with a recombinant virus, polyclonal genetically modified cyanobacterium cells infected with a polyclonal recombinant virus, polyclonal genetically modified cyanobacterium cells infected with an oligoclonal recombinant virus, polyclonal genetically modified cyanobacterium cells infected with a monoclonal recombinant virus, and combinations thereof.

In embodiments, the genetically modified cyanobacterium includes one or more selected from the group consisting of: oligoclonal genetically modified cyanobacterium cells, oligoclonal genetically modified cyanobacterium cells infected with a virus, oligoclonal genetically modified cyanobacterium cells infected with a recombinant virus, oligoclonal genetically modified cyanobacterium cells infected with a polyclonal recombinant virus, oligoclonal genetically modified cyanobacterium cells infected with an oligoclonal recombinant virus, oligoclonal genetically modified cyanobacterium cells infected with a monoclonal recombinant virus, and combinations thereof.

In embodiments, the genetically modified cyanobacterium includes one or more selected from the group consisting of: monoclonal genetically modified cyanobacterium cells, monoclonal genetically modified cyanobacterium cells infected with a virus, monoclonal genetically modified cyanobacterium cells infected with a recombinant virus, monoclonal genetically modified cyanobacterium cells infected with a polyclonal recombinant virus, monoclonal genetically modified cyanobacterium cells infected with an oligoclonal recombinant virus, monoclonal genetically modified cyanobacterium cells infected with a monoclonal recombinant virus, and combinations thereof.

In embodiments, the bioreactor (G15) includes a single-use bioreactor. In embodiments, the single-use bioreactor includes a disposable bioreactor. In embodiments, the disposable bioreactor is a disposable bag instead of a culture vessel. In embodiments, the disposable bioreactor is a disposable bag. In embodiments, the bioreactor (G15) is transparent or translucent.

In embodiments, the disposable bag includes a three-layer plastic foil, comprising: a first layer including a first polymer configured to provide mechanical stability, wherein the first polymer includes polyethylene terephthalate or low-density polyethylene (LDPE); a second layer including a second polymer configured to act as a gas barrier, wherein the second polymer includes a first thermoplastic polymer, wherein the first thermoplastic polymer includes an aliphatic rubbery synthetic polymer, a material of the polyvinyl ester family, polyvinyl chloride, polyvinyl, or vinyl; and a third layer including a third polymer configured to contact the liquid within the bioreactor, wherein the liquid includes a culture medium including at least treated water, wherein the third polymer includes a second thermoplastic polymer, wherein the second thermoplastic polymer includes an aliphatic rubbery synthetic polymer, a material of the polyvinyl ester family, polyvinyl acetate (PVA), PVAc, poly(ethenyl ethanoate), polypropylene, or polypropene.

In embodiments, the liquid or culture medium within the disposable bioreactor is agitated. In embodiments, the disposable bioreactor includes a stirrer within bag to agitate the culture medium or liquid within the bioreactor. In embodiments, the stirrer is integrated into the disposable bag. In embodiments, the disposable bioreactor is pre-sterilized. In embodiments, the liquid or culture medium within the disposable bioreactor is agitated by a rocking motion. In embodiments, the liquid or culture medium within the disposable bioreactor is not agitated. In embodiments, the disposable bioreactor includes a stirrer within bag to agitate the culture medium. In embodiments, the disposable bioreactor reduces risk of cross-contamination between batches while providing flexibility, minimizing turnaround time, reducing cleaning costs, and easing validation restrictions.

In embodiments, the bioreactor (G15) provides scalable and robust stirred-tank or disposable performance in both cGiVIP and non-cGMP environments. In embodiments, the bioreactor (G15) includes a volume, in liters, ranging from 1, 5, 10, 50, 200, 500, 1000, or 2000. In embodiments, the bioreactor (G15) includes a perfusion bioreactor. In embodiments, the bioreactor (G15) is configured to operate in a plurality of modes, including: batch, fed-batch and perfusion bioreactor modes.

In embodiments, the bioreactor (G15) equipped with an insect cell life support system which includes at least one sensor (G44). In embodiments, the insect cell life support system is configured to maintain the insect cells and/or microorganisms and keep them alive to allow the to produce the cannabinoid compositions. In embodiments, the insect cell life support system is configured to maintain the insect cells to produce the cannabinoid glycoside and keep them alive to allow the cells to produce the insect-derived cannabinoid and to allove the genetically engineered microorgamisms to produce the biosynthetic cannabinoid within the bioreactor.

In embodiments, the filter (H11) includes one or more filter types selected from the group consisting of: a batch filter, a continuous filter, a continuous-batch filter, a leaf filter, a filter press, a centrifuge, a plate and frame filter, a recessed filter plate, a membrane filter press, a disc filter, a centrifugal filter, a hydroclone, an s-type filter belt press, a klampress belt press, a belt press, a basket filter, a chromatography column, a packed column, a packed bed, a chromatography filtration, adsorber, absorber, a membrane, ion exchange resin. In embodiments, the filter (H11) includes one or more filter types selected from the group consisting of microfiltration, depth filtration, ultrafiltration, diafiltration, tangential flow filtration (TFF) system, sterile filtration, and rotary vacuum drum filtration. In embodiments, the filter (H44) includes a General Electric AKTA liquid chromatography system.

In embodiments, the filter (H11) includes an adsorbent comprising one or more selected from the group consisting of a strongly acidic cation exchange resin include such as AMBERLITE IR-118 (Available from Dow Chemical Company, Midland, Mich.), or DIAION PK216LH (Available from Mitsubishi Chemical Company, Tokyo, Japan). Suitable examples of the weakly basic anion exchange resin include AMBERLITE IRA-70RF (Available from Dow Chemical Company, Midland, Mich.) or RELITE RAM2 (Available from Mitsubishi Chemical Company, Tokyo, Japan).

In embodiments, the adsorbent used in the filter (H11) employed is a combination of styrene-divinyl benzene copolymer, ion exchange and hydrophobic interaction based stationary phase adsorbents and a mobile phase comprising water in a combination of normal and reverse phase simulated moving bed separation zones to provide a first purified recombinant protein.

In embodiments, the filter (H11) includes one or more filters or purification systems selected from the group consisting of affinity chromatography (AC), ion exchange chromatography (IEX), hydrophobic interaction chromatography (HIC), gel filtration (GF) chromatography, reversed phase chromatography (RPC), and combinations thereof.

In embodiments, the filter (H11) includes a detergent purification system, wherein the detergent includes a surfactant, ionic detergent, non-ionic detergent, and/or a zwitterionic detergent. In embodiments, the filter (H11) includes a detergent purification system, wherein the detergent includes one or more detergents selected from the group consisting of a surfactant, a nonionic surfactant, lecithin, polyethylene (40), stearate, polysorbate, Polyoxyethylene sorbitan monooleate, Polyoxyethylene (20) sorbitan monooleate, polysorbate 80, polysorbate 60, polysorbate 65, ammonium salts of phosphatidic acid, sucrose acetate isobutyrate, potassium pyrophosphate, sodium acid pyrophosphate, sodium pyrophosphate, potassium polymetaphosphate, sodium metaphosphate, insoluble or sodium polyphosphates, sodium polyphosphates, insoluble polyphosphates, glassy salts of fatty acids, mono- and di-glycerides of fatty acids, mono-glycerides of fatty acids, di-glycerides of fatty acids, acetic and fatty acid esters of glycerol, lactic and fatty acid esters of glycerol, citric and fatty acid esters of glycerol, diacetyltartaric and fatty acid esters of glycerol, mixed fatty acid esters of glycerol, sucrose esters of fatty acids, polyglycerol esters of fatty acids, polyglycerol esters of interesterified ricinoleic acid, propylene glycol mono- and di-esters, propylene glycol di-esters, propylene glycol mono-esters, propylene glycol esters of fatty acids, propylene glycol esters, dioctyl sodium sulphosuccinate, sodium lactylate, sodium oleyl lactylate, sodium stearoyl lactylate, calcium lactylate, calcium oleyl lactylate, calcium stearoyl lactylate, sorbitan monostearate, maltodextrin, polyphosphates, formulated polyphosphates, and gum arabic.

In embodiments, the biocatalyst (G79) and acid (G79') within the mixing tank (G15) hydrolyzes chitosan. In embodiments, the biocatalyst (G79) and acid (G79') hydrolyze the chitosan within the mixing tank (G15). In embodiments, the biocatalyst (G79) and acid (G79') hydrolyze deacetylated insects (1570") within the mixing tank (G15). In embodiments, the biocatalyst (G79) and acid (G79') hydrolyze the biopolymer (1570') within the mixing tank (G15).

In embodiments, introducing biocatalyst (G79), acid (G79'), and deacetylated insects (1570") to the mixing tank (G15) hydrolyzes the deacetylated insects (1570") to produce an oligosaccharide (G09'). In embodiments, introducing biocatalyst (G79), acid (G79'), and biopolymer (1570') to the mixing tank (G15) hydrolyzes the biopolymer (1570') to produce a hydrolyzed-biopolymer (G09") containing at least an oligosaccharide (G09'). In embodiments, introducing the biocatalyst (G79), acid (G79'), and insects (G07), that include deacetylated insects (1570"), to the mixing tank (G15) hydrolyzes the deacetylated insects (1570") to produce an oligosaccharide (G09'). In embodiments, introducing the biocatalyst (G79), acid (G79'), and insects (G07) that include deacetylated insects (1570") to the mixing tank (G15) hydrolyzes the deacetylated insects (1570") to produce a hydrolyzed-biopolymer (G09"). In embodiments, the insect liquid biocatalyst mixture (G09) includes an oligosaccharide (G09'). In embodiments, the insect liquid biocatalyst mixture (G09) includes a hydrolyzed-biopolymer (G09").

A supply valve (H61) equipped with a controller (H62) and configured to input and output a signal (H63) to the computer (COMP) is positioned on the transfer conduit (G50) in between the mixing tank (G15) of FIG. 14G and the separator input (H16) positioned on the side wall (H65) of the solids separator (H10).

The filter (H11) has a first output (H18) positioned on the top (H14). The first output (H18) is configured to discharge an exoskeleton-depleted insect liquid mixture (H19) via an exoskeleton-depleted mixture conduit (H20). A discharge valve (H21) equipped with a controller (H22) and configured to input and output a signal (H23) to the computer (COMP) is positioned on the exoskeleton-depleted mixture conduit (H20). The filter (H11) is configured to remove exoskeleton (H46) from either the insect liquid biocatalyst mixture (G09) or the insect and liquid mixture (G09A) to form an exoskeleton-depleted insect liquid mixture (H19). The exoskeleton-depleted insect liquid mixture (H19) has a reduced amount of exoskeleton (H46) relative to the insect liquid biocatalyst mixture (G09) or an insect and liquid mixture (G09A).

In embodiments, a flow sensor (H24) and a secondary filter (H25) are both installed on the exoskeleton-depleted mixture conduit (H20). The flow sensor (H24) can be an electronic instrument, but a manual paddle-wheel type flow sensor or a totalizer are preferred. Alternately, the flow sensor (H24) may be of a rotameter, variable-area flow meter, a bullseye type flow sensor, or a sight-glass type sensor and configured to allow one to visually observe the clarity, and lack of exoskeleton solids within the exoskeleton-depleted insect liquid mixture (H19). The secondary filter (H25) is used as an emergency filter to prevent contamination of the downstream exoskeleton-depleted insect liquid mixture tank (H26). In embodiments, the exoskeleton-depleted insect liquid mixture tank (H26) is synonymous with an insect liquid mixture tank (H26).

In embodiments, a centrifuge (H11) is configured to remove a recombinant protein from the insect and liquid mixture (G09A). In embodiments, a centrifugal filter (H11) is configured to remove a recombinant protein from the insect and liquid mixture (G09A). In embodiments, the recombinant protein separated from the insect and liquid mixture (G09A) is then purified. In embodiments, the recombinant protein separated from the insect and liquid mixture (G09A) is transferred to the insect liquid mixture tank (H26).

The secondary filter (H25) is preferably installed to mitigate any risk of contamination downstream in the event that the filter element (H13) becomes ruptured and solid exoskeleton particles are transferred via the exoskeleton-depleted mixture conduit (H20) and into the interior (H27) of the exoskeleton-depleted insect liquid mixture tank (H26).

An exoskeleton-depleted insect liquid mixture tank (H26) is connected to the exoskeleton-depleted mixture conduit (H20) and configured to receive the exoskeleton-depleted insect liquid mixture (H19) from the solids separator (H10). The exoskeleton-depleted mixture conduit (H20) is connected at one end to the first output (H18) of the solids separator (H10) and at another end to the input (H28) of the exoskeleton-depleted insect liquid mixture tank (H26).

The exoskeleton-depleted insect liquid mixture tank (H26) has an input (H28) through which an exoskeleton-depleted insect liquid mixture (H19) is received to the interior (H27). A diptube (H29) may be installed on the input (H28) of the exoskeleton-depleted insect liquid mixture tank (H26) to introduce the exoskeleton-depleted insect liquid mixture (H19) to the interior (H27) beneath the liquid level. An upper level sensor (H30) and lower level sensor (H31) are installed on the exoskeleton-depleted insect liquid mixture tank (H26). A mixer (H32) with a motor (H33) may also be installed on the exoskeleton-depleted insect liquid mixture tank (H26) to provide agitation of the liquid contents within the interior (H27). A heat exchanger (H34) may be installed to heat a portion of the exoskeleton-depleted insect liquid mixture (H19) within the exoskeleton-depleted insect liquid mixture tank (H26). A temperature sensor (H35) may be installed on the exoskeleton-depleted insect liquid mixture tank (H26). A mass sensor (H36) may be installed on the exoskeleton-depleted insect liquid mixture tank (H26). In embodiments, a sixth steam supply (LDF) is made available to the heat exchanger (H34) to heat the liquid slurry within the interior (H27) of the exoskeleton-depleted insect liquid mixture tank (H26). In embodiments, the heat exchanger (H34) discharges a sixth condensate (LAV) to the condensate tank (LAP) that is shown on FIG. 17F.

The exoskeleton-depleted insect liquid mixture tank (H26) has an output (H37) that is configured to discharge an exoskeleton-depleted insect liquid mixture (H39) from the interior (H27). An exoskeleton-depleted insect liquid mixture conduit (H38) is connected to the output (H37) and configured to transfer exoskeleton-depleted insect liquid mixture (H39) away from the interior (H27) and towards the liquid separation module (LSM) shown in FIGS. 14i and 14J.

A pump (H40) is interposed on the exoskeleton-depleted insect liquid mixture conduit (H38) and configured to pressurize the exoskeleton-depleted insect liquid mixture (H39) to form a pressurized exoskeleton-depleted insect liquid mixture (H41). A pressure sensor (H42) is installed on the exoskeleton-depleted insect liquid mixture conduit (H38). In embodiments, the pump (H40) is configured to pressurize the exoskeleton-depleted insect liquid mixture (H39) to a pressure that ranges from between 10 pounds per square inch (PSI) to 20 PSI; 20 PSI to 30 PSI; 30 PSI to 40 PSI; 40 PSI to 50 PSI; 50 PSI to 60 PSI; 60 PSI to 70 PSI; 70 PSI to 80 PSI; 80 PSI to 90 PSI; 90 PSI to 100 PSI; 100 PSI to 125 PSI; 125 PSI to 150 PSI; 150 PSI to 200 PSI; 200 PSI to 300 PSI; 300 PSI to 500 PSI.

A recirculation conduit (H43) may be positioned on the exoskeleton-depleted insect liquid mixture conduit (H38) and configured to transport a portion of the pressurized exoskeleton-depleted insect liquid mixture (H41) back to the interior (H27) of the exoskeleton-depleted insect liquid mixture tank (H26). A filter (H44) may be positioned on the recirculation conduit (H43) to remove any particulates from the pressurized exoskeleton-depleted insect liquid mixture (H41) before being sent back to the interior (H27) of the exoskeleton-depleted insect liquid mixture tank (H26). A filter (H44) may be positioned on the recirculation conduit (H43) to purify the recombinant protein from the pressurized exoskeleton-depleted insect liquid mixture (H41) before being sent back to the interior (H27) of the exoskeleton-depleted insect liquid mixture tank (H26). In embodiments, the filter (H44) includes a protein purification system.

In embodiments, the recombinant protein separated from the insect and liquid mixture (G09A) is transferred from the insect liquid mixture tank (H26) to the filter (H44). In embodiments, the filter (H44) includes one or more filter types selected from the group consisting of: a batch filter, a continuous filter, a continuous-batch filter, a leaf filter, a filter press, a centrifuge, a plate and frame filter, a recessed filter plate, a membrane filter press, a disc filter, a centrifugal filter, a hydroclone, an s-type filter belt press, a klampress belt press, a belt press, a basket filter, a chromatography column, a packed column, a packed bed, a chromatography filtration, adsorber, a membrane, absorber, ion exchange resin. In embodiments, the filter (H44) includes one or more filter types selected from the group consisting of microfiltration, depth filtration, ultrafiltration, diafiltration, tangential flow filtration (TFF) system, sterile filtration, and rotary vacuum drum filtration. In embodiments, the filter (H44) includes a General Electric AKTA liquid chromatography system.

In embodiments, the filter (H44) includes an adsorbent comprising one or more selected from the group consisting of a strongly acidic cation exchange resin include such as AMBERLITE IR-118 (Available from Dow Chemical Company, Midland, Mich.), or DIAION PK216LH (Available from Mitsubishi Chemical Company, Tokyo, Japan). Suitable examples of the weakly basic anion exchange resin include AMBERLITE IRA-70RF (Available from Dow Chemical Company, Midland, Mich.) or RELITE RAM2 (Available from Mitsubishi Chemical Company, Tokyo, Japan).

In embodiments, the adsorbent used in the filter (H44) employed is a combination of styrene-divinyl benzene copolymer, ion exchange and hydrophobic interaction based stationary phase adsorbents and a mobile phase comprising water in a combination of normal and reverse phase simulated moving bed separation zones to provide a second purified recombinant protein.

In embodiments, the filter (H44) includes one or more purification systems selected from the group consisting of affinity chromatography (AC), ion exchange chromatography (IEX), hydrophobic interaction chromatography (HIC), gel filtration (GF) chromatography, reversed phase chromatography (RPC), and combinations thereof.

In embodiments, the filter (H44) includes a detergent purification system, wherein the detergent includes a surfactant, ionic detergent, non-ionic detergent, and/or a zwitterionic detergent. In embodiments, the filter (H44) includes a detergent purification system, wherein the detergent includes one or more detergents selected from the group consisting of a surfactant, a nonionic surfactant, lecithin, polyethylene (40), stearate, polysorbate, Polyoxyethylene sorbitan monooleate, Polyoxyethylene (20) sorbitan monooleate, polysorbate 80, polysorbate 60, polysorbate 65, ammonium salts of phosphatidic acid, sucrose acetate isobutyrate, potassium pyrophosphate, sodium acid pyrophosphate, sodium pyrophosphate, potassium polymetaphosphate, sodium metaphosphate, insoluble or sodium polyphosphates, sodium polyphosphates, insoluble polyphosphates, glassy salts of fatty acids, mono- and di-glycerides of fatty acids, mono-glycerides of fatty acids, di-glycerides of fatty acids, acetic and fatty acid esters of glycerol, lactic and fatty acid esters of glycerol, citric and fatty acid esters of glycerol, diacetyltartaric and fatty acid esters of glycerol, mixed fatty acid esters of glycerol, sucrose esters of fatty acids, polyglycerol esters of fatty acids, polyglycerol esters of interesterified ricinoleic acid, propylene glycol mono- and di-esters, propylene glycol di-esters, propylene glycol mono-esters, propylene glycol esters of fatty acids, propylene glycol esters, dioctyl sodium sulphosuccinate, sodium lactylate, sodium oleyl lactylate, sodium stearoyl lactylate, calcium lactylate, calcium oleyl lactylate, calcium stearoyl lactylate, sorbitan monostearate, maltodextrin, polyphosphates, formulated polyphosphates, and gum arabic.

The filter (H11) has a second output (H45) positioned on the bottom (H15). Exoskeleton (H46) may be separated from the insect liquid biocatalyst mixture (G09) or an insect and liquid mixture (G09A). A separated exoskeleton transfer conduit (H47) is connected to the second output (H45) positioned on the bottom (H15) of the filter (H11). An exoskeleton conveyor (H48) is equipped to receive exoskeleton (H46) from the separated exoskeleton transfer conduit (H47).

An exoskeleton drying gas (H49) may be applied to a portion of the exoskeleton (H46) to remove liquid therefrom and form dehydrated exoskeleton (H50). In embodiments, the exoskeleton drying gas (H49) is heated to a temperature ranging from between 80 degrees F. to 90 degrees F.; 90 degrees F. to 100 degrees F.; 100 degrees F. to 110 degrees F.; 110 degrees F. to 120 degrees F.; 120 degrees F. to 140 degrees F.; 140 degrees F. to 160 degrees F.; 160 degrees F. to 180 degrees F.; 180 degrees F. to 200 degrees F.; 200 degrees F. to 250 degrees F.; 250 degrees F. to 300 degrees F.; 300 degrees F. to 400 degrees F.

An exoskeleton discharge valve (H51) equipped with a controller (H52) and configured to input and output a signal (H53) to the computer (COMP) is installed on the separated exoskeleton transfer conduit (H47).

A backflush fluid (H54) may be provided to the filter (H11) to regenerate the filter element (H13). FIG. 14H shows the backflush fluid (H54) entering the exoskeleton-depleted mixture conduit (H20) and then entering the interior (H64) of the filter (H11) via the first output (H18). In embodiments, the backflush fluid (H54) is a liquid. In embodiments, the backflush fluid (H54) is a gas.

A backflush fluid transfer conduit (H55) is connected to the exoskeleton-depleted mixture conduit (H20) via a connection (H70) in between the discharge valve (H21) and the first output (H18). A backflush fluid supply valve (H56) equipped with a controller (H57) and configured to input and output a signal (H58) to the computer (COMP) is positioned on the backflush fluid transfer conduit (H55). In embodiments, a backflush fluid pressure regulating valve (H59) with a backflush pressure sensor (H60) is positioned upstream of the backflush fluid supply valve (H56). In embodiments, the backflush fluid pressure regulating valve (H59) may be adjusted to a pressure that is less than the rupture pressure of that of the filter element (H13). It is preferred to counter currently backflush the filter element (H13) by setting the pressure of the backflush fluid pressure regulating valve (H59) to a pressure of 0.25 PSI to 0.5 PSI; 0.5 PSI to 1.5 PSI; 1.5 PSI to 3 PSI; 3 PSI to 6 PSI; 6 PSI to 9 PSI; 9 PSI to 15 PSI.

The best mode of operation for realizing a continuous filtrate stream depleted of exoskeleton and encompasses operating the filtration system in a manner which allows for periodic back flushing of the filter element cloth surface in-situ by providing a counter-current flow of backflush fluid to the filter element. The backwashing dislodges any accumulated exoskeleton, in the form of a filter cake, allowing it to sink to the bottom of the filter for removal of the system as a thick, paste-like, filter cake substance.

It is preferred to utilize differential pressure across a filter bundle as the main variable to determine when to undergo a back-flushing cycle, as opposed to using manual predetermined periodic time duration intervals, or using the reduction in flow through the filter bundles as the variable dictating when to commence filter back flushing, (synonymously termed 'filter cleaning', or 'filter backwashing', 'in-situ filter cleaning', or 'filter surface in-situ regeneration'). Filter element differential pressure between 0.25 and 15 PSI is commensurate with preferable cake thickness of 20 to 35 millimeters. In contrast, using manual predetermined periodic time duration intervals as the sole mechanism to determine when to commence filter cleaning, often results in operational impairment, in that 'cake bridging' more readily occurs. 'Cake bridging' may be described as a large mass of agglomerated exoskeleton suspended solids filling the spaces between the filter elements and thus posing a challenge to regenerate in-situ, frequently requiring process interruption for physical cleaning and removal of the heavy, gelatinous exoskeleton filter cake.

In-situ filter cleaning may be accomplished by reversing the flow of liquid or gas through the filter element thereby dislodging exoskeleton filter cake from the cloth surface thus allowing it to sink to the bottom of the interior of the filter. This affords operations the luxury of minimizing losses of valuable solvent while draining the filter cake from the system.

Filter Operating Procedure

Herein is described the preferred operating procedure for continuous filtration of exoskeleton. Filtration [step 950] cooperates with the cyclic-batch filter in-situ cleaning steps of: filter element [step 952]; filter backflush [step 954]; filter cake sedimentation [step 956]; filter cake discharge start [step 958]; filter cake discharge end [step 960]; and filtration restart preparation [step 962].

In step 950, (filtration), filtration proceeds and the filter pressure drop is monitored. As a filtration cycle progresses, solid exoskeleton particles are deposited onto the surface of the filter element and adhere to its surface until a nominal target differential pressure drop between around to 15 PSI is attained, which is proportionate to a predetermined thickness of 20 to 35 millimeters. If the filter pressure drop is lower than the nominal target differential pressure drop, the filtering cycle continues until the nominal target differential pressure drop is reached. When a filter has reached its nominal target differential pressure drop, a filter cleaning cycle will commence, which begins with step 952 (filter bundle isolation). The sequential steps encompassing filtration and filter cleaning can be further illuminated by using FIG. 14H, which visually indicate some of the valve sequencing involved, as indicated by open and closed valve positions, illustrated by 'non-darkened-in valves' and 'darkened-in valves', respectively, wherein: supply valve (H61) is open; discharge valve (H21) is open; backflush fluid supply valve (H56) is closed; exoskeleton discharge valve (H51) is closed.

When a nominal target pressure drop across a filter is attained, the exoskeleton filter cake material must be dislodged from the filter element, and thus step 952 (filter isolation) proceeds, which involves isolating the filter by closing the supply valve (H61) and discharge valve.

Once both the supply valve (H61) and discharge valve are closed, to isolate the filter, step 954 may proceed. Step 954, (filtrate backflush), involves transferring a backflush fluid (liquid or gas) to backflush the filter. In embodiments, a typical backflush, in step 954, requires that the backflush fluid supply valve (H56) need be left open for a duration between: 5 seconds to 10 seconds; 10 seconds to 30 seconds; 30 seconds to 1 minute; 1 minute to 5 minutes; 5 minutes to minutes; 15 minutes to 30 minutes; 30 minutes to 60 minutes; 60 minutes to 90 minutes.

After the backflush fluid (H54) has been introduced to the filter, and once the backflush fluid supply valve (H56) has been returned to a closed position, step 956 may commence. Step 956 (exoskeleton filter cake sedimentation) entails allowing the dislodged exoskeleton filter cake solids to sink to the bottom of the filter.

Step 958 (exoskeleton filter cake discharge start) involves opening the exoskeleton discharge valve (H51) to allow transference of an agglomerated exoskeleton particulate filter cake material from the system. The backflush fluid (H54) may be liquid or gas or a combination of both during Step 958. In embodiments, a gas may be used to dry the exoskeleton and then dislodge the dried exoskeleton from the surface of the filter element (H13).

Step 960 (filter cake discharge end) entails closing the exoskeleton discharge valve (H51) since exoskeleton have been discharged from the system. After step 960 has transpired, step 962 (filtration restart preparation) may commence which entails opening the supply valve (H61) and discharge valve (H21) to again commence filtration on the regenerated filter bundle, thus allowing step 950 to commence again, then allowing the filtration and regeneration cycle to repeat itself.

In embodiments, the pharmaceutical composition includes a chemical, a cannabinoid, recombinant protein, vaccine, antibody, peptide, or chemical, or lectin. In embodiments, the pharmaceutical composition is derived from: a recombinant baculovirus. In embodiments, the virus includes a polyclonal recombinant baculovirus; and the recombinant baculovirus includes a genetically modified baculovirus where a foreign gene is inserted into to produce a protein. In embodiments, the pharmaceutical composition includes a protein produced from the recombinant baculovirus includes a chemical, a cannabinoid, recombinant protein, vaccine, antibody, peptide, or chemical.

In embodiments, the pharmaceutical composition is derived from: cloned insect cells; polyclonal insect cells; polyclonal insect cells infected with a baculovirus; polyclonal insect cells infected with a recombinant baculovirus; polyclonal insect cells infected with a polyclonal recombinant baculovirus; polyclonal insect cells infected with an oligoclonal recombinant baculovirus; polyclonal insect cells infected with a monoclonal recombinant baculovirus; oligoclonal insect cells; oligoclonal insect cells infected with a baculovirus; oligoclonal insect cells infected with a recombinant baculovirus; oligoclonal insect cells infected with a polyclonal recombinant baculovirus; oligoclonal insect cells infected with an oligoclonal recombinant baculovirus; oligoclonal insect cells infected with a monoclonal recombinant baculovirus; monoclonal insect cells; monoclonal insect cells infected with a baculovirus; monoclonal insect cells infected with a recombinant baculovirus; monoclonal insect cells infected with a polyclonal recombinant baculovirus; monoclonal insect cells infected with an oligoclonal recombinant baculovirus; and/or monoclonal insect cells infected with a monoclonal recombinant baculovirus.

In embodiments, the pharmaceutical composition is derived from: genetically modified microorganisms, algae, cloned insects; transgenic insects; genetically engineered insects; insects that are infected with a recombinant baculovirus; insects that are infected with a cloned recombinant baculovirus; insects that are infected with a polyclonal recombinant baculovirus; insects that are infected with an oligoclonal recombinant baculovirus; and/or insects that are infected with a monoclonal recombinant baculovirus.

In embodiments, the present disclosure describes:

Paragraph A. A method to produce a biosynthetic cannabinoid distillate, the method includes: (a) in a photobioreactor, growing microalgae which have been genetically modified to produce a biosynthetic cannabinoid, in a liquid nutrient medium;

(b) separating the grown, genetically modified microalgae from the liquid nutrient medium;

(c) extracting the biosynthetic cannabinoid from the grown, genetically modified microalgae to produce an extracted biosynthetic cannabinoid; and (d) distilling the extracted biosynthetic cannabinoid to produce the biosynthetic cannabinoid distillate.

Paragraph B. The method according to Paragraph A, comprising:

(e) producing a beverage from the biosynthetic cannabinoid distillate.

Paragraph C. The method according to Paragraph A, wherein:

(e) producing a nanoemulsion from the biosynthetic cannabinoid distillate.

Paragraph D. The method according to Paragraph C, wherein:

(f) spray drying the nanoemulsion to produce a spray-dried water-soluble powder.

Paragraph E. The method according to Paragraph A, comprising:

(e) mixing the biosynthetic cannabinoid distillate with *cannabis* plant derived terpenes.

Paragraph F. The method according to Paragraph A, comprising:

(e) mixing the biosynthetic cannabinoid distillate with non-biosynthetic plant derived cannabinoids.

Paragraph G. The method according to Paragraph A, comprising:
(e) producing a foodstuff from the biosynthetic cannabinoid distillate, the foodstuff includes one or more selected from the group consisting of ada, bagels, baked goods, beverages, biscuits, bitterballen, bonda, breads, cakes, candies, cereals, chips, chocolate bars, carbonated soft drinks, carbonated drinks, chocolate, coffee, cokodok, confectionery, cookies, cooking batter, corn starch mixtures, crackers, crepes, croissants, croquettes, croutons, dolma, dough, doughnuts, energy bars, flapjacks, french fries, frozen custard, frozen desserts, frying cakes, fudge, gelatin mixes, granola bars, gulha, hardtack, ice cream, khandvi, khanom buang, krumpets, meze, mixed flours, muffins, multi-grain snacks, nachos, nian gao, noodles, nougat, onion rings, pakora, pancakes, panforte, pastas, pastries, pie crust, pita chips, pizza, poffertjes, pretzels, protein powders, pudding, rice krispie treats, sesame sticks, smoothies, snacks, soft drinks, sport drinks, sparkling drinks, specialty milk, tele-bhaj a, tempura, toffee, tortillas, totopo, turkish delights, or waffles.

Paragraph H. The method according to Paragraph A, comprising:
(f) producing a cosmetic product or a topical from the biosynthetic cannabinoid distillate.

Paragraph I. The method according to Paragraph A, wherein:
the liquid nutrient medium includes treated water, the treated water is treated with an adsorbent, ion exchange resin, a membrane, and/or an ultraviolet unit.

Paragraph J. The method according to Paragraph A, wherein:
in step (a), introducing a gas to the liquid nutrient medium, the gas includes carbon dioxide.

Paragraph K. The method according to Paragraph J, wherein:
the photo-bioreactor includes a superficial gas velocity ranging from between 0.1 to 15 inches per second.

Paragraph L. T The method according to Paragraph A, wherein:
in step (a), the liquid nutrient medium includes one or more selected from the group consisting of a carbohydrate, a micronutrient, a macronutrient, an acid, and combinations thereof.

Paragraph M. The method according to Paragraph A, wherein:
The method according to claim 1, wherein:
in step (a), growing the genetically modified microalgae within a photo-bioreactor at a residence time ranging from 1 to 5 days.

Paragraph NM. The method according to Paragraph A, wherein:
in step (a), the photo-bioreactor operates at a photosynthetic photon flux density ranging from ranging from 50 to 1,000 micromole per second and square meter.

Paragraph O. The method according to Paragraph A, wherein:
in step (a), the photo-bioreactor is provided with a photon flux density source including one or more selected from the group consisting of compact fluorescent lights, incandescent lights, fluorescent lights, halogen lights, metal halide lamps, high-intensity discharge gas discharge lamps, low pressure sodium lamps, sodium lamps, quartz halogen lamps, and combinations thereof.

Paragraph P. The method according to Paragraph A wherein:
in step (a), the photo-bioreactor is provided with a photon flux density source light emitting diodes, wherein the light emitting diodes operate at a wave length ranging from 390 to 700 nanometers.

Paragraph Q. T The method according to Paragraph A, wherein:
in step (a), the photo-bioreactor is transparent and/or translucent.

Paragraph R. The method according to Paragraph A, wherein:
in step (a), the photo-bioreactor has a volume ranging from 50 to 2000 liters.

Paragraph S. The method according to Paragraph A, wherein:
in step (d), distilling the extracted biosynthetic cannabinoid via spinning band distillation.

Paragraph T. A method to produce an extracted biosynthetic cannabinoid, the method includes:
(a) in a photo-bioreactor, growing microalgae and/or cyanobacterium which have been genetically modified to produce a biosynthetic cannabinoid, in a liquid nutrient medium and in the presence of carbon dioxide, the liquid nutrient medium including water treated with an adsorbent, ion exchange resin, and/or a membrane;
(b) separating the grown, genetically modified microalgae and/or the genetically modified cyanobacterium from the liquid nutrient medium; and
(c) extracting the biosynthetic cannabinoid from the grown, genetically modified microalgae and/or the genetically modified cyanobacterium to produce an extracted biosynthetic cannabinoid.

FIG. 19
FIG. 19 illustrates a single fully-grown INSECTERGY III plant.

FIG. 20
FIG. 20 illustrates zoomed-in view of a budding or flowering plant.

FIG. 21
FIG. 21 illustrates a single leaf of INSECTERGY III.

FIG. 22
FIG. 22 illustrates a trimmed and dried bud (reproductive structure) of INSECTERGY III.

FIGS. 19-22 illustrate the overall appearance of the INSECTERGY III. These photographs show the colors as true as it is reasonably possible to obtain in reproductions of this type. Colors in the photographs may differ slightly from the color values cited in the detailed botanical description which accurately describe the colors of INSECTERGY III.

This disclosure relates to a new and distinct hybrid plant named INSECTERGY III characterized by a mixture of *Cannabis sativa* L. ssp. *Sativa*×*Cannabis sativa* L. ssp. Indica (Lam.);

Within the leaves, seeds, stems, roots, or any reproductive structures, INSECTERGY III has a:
(a) a cannabidiol content ranging from 0.125 weight percent to less than 5 weight percent;
(b) a tetrahydrocannabinol ranging from 5 weight percent to 63 weight percent;
(c) an energy content ranging from between 2,500 British Thermal Units per pound to 15,000 British Thermal Units per pound;
(d) a carbon content ranging from between 20 weight percent to 65 weight percent;
(e) an oxygen content ranging from between 12 weight percent to 55 weight percent;

(f) a hydrogen content ranging from between 2 weight percent to 20 weight percent;
(g) an ash content ranging from between 2.5 weight percent to 30 weight percent;
(h) volatiles content ranging from between 30 weight percent to 90 weight percent;
(i) a nitrogen content ranging from between 1 weight percent to 10 weight percent;
(j) a sulfur content ranging from between 0.01 weight percent to 8 weight percent;
(k) a chlorine content ranging from 0.05 weight percent to 5 weight percent;
(l) a sodium content ranging from 0.02 weight percent to 15 weight percent;
(m) a potassium content ranging from 0.05 weight percent to 15 weight percent;
(n) an iron content ranging from 0.01 weight percent to 13 weight percent;
(o) a magnesium content ranging from 0.02 weight percent to 10 weight percent;
(p) a phosphorous content ranging from 0.05 weight percent to 12 weight percent;
(q) a calcium content ranging from 0.03 weight percent to 10 weight percent;
(r) a zinc content ranging from 0.01 weight percent to 5 weight percent;
(s) a cellulose content ranging from 25 weight percent to 75 weight percent;
(t) a lignin content ranging from 3 weight percent to 35 weight percent;
(u) a hemicellulose content ranging from 3 weight percent to 30 weight percent;
(v) a fat content ranging from 5 weight percent to 35 weight percent;
(w) a fiber content ranging from 5 weight percent to 75 weight percent; and
(x) a protein content ranging from 5 weight percent to 35 weight percent;
wherein:
the *Cannabis Sativa* L. ssp *indica* content ranges from 15% to 65%;
the *Cannabis Sativa* L. ssp *sativa* content ranges from 20% to 70%.

In embodiments, INSECTERGY III also includes: a N-acetylglucosamine content ranging from between: 0.050 parts per million to 0.100 parts per million, 0.100 parts per million to 0.200 parts per million, 0.200 parts per million to 0.400 parts per million, 0.400 parts per million to 0.800 parts per million, 0.800 parts per million to 1.600 parts per million, 1.600 parts per million to 3.200 parts per million, 3.200 parts per million to 6.400 parts per million, 6.4 parts per million to 12.8 parts per million, 12.8 parts per million to 25.6 parts per million, 25 parts per million to 50 parts per million, 50 parts per million to 100 parts per million, 100 parts per million to 200 parts per million, 200 parts per million to 400 parts per million, 400 parts per million to 800 parts per million, 800 parts per million to 1600 parts per million, 1600 parts per million to 3200 parts per million, 3200 parts per million to 6400 parts per million, 6400 parts per million to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, 14 weight percent to 15 weight percent, 15 weight percent to 16 weight percent, 16 weight percent to 17 weight percent, 17 weight percent to 18 weight percent, 18 weight percent to 19 weight percent, 19 weight percent to 20 weight percent, 20 weight percent to 21 weight percent, 21 weight percent to 22 weight percent, 22 weight percent to 23 weight percent, 23 weight percent to 24 weight percent, 24 weight percent to 25 weight percent, 25 weight percent to 30 weight percent, 30 weight percent to 35 weight percent, 35 weight percent to 40 weight percent, weight percent to 45 weight percent, 45 weight percent to 50 weight percent, 50 weight percent to 55 weight percent, 55 weight percent to 60 weight percent, 60 weight percent to 65 weight percent, 65 weight percent to 70 weight percent, 70 weight percent to 75 weight percent, 75 weight percent to 80 weight percent, 80 weight percent to 85 weight percent, 85 weight percent to 90 weight percent, 90 weight percent to 95 weight percent, 95 weight percent to 95.25 weight percent, weight percent to 95.50 weight percent, 95.50 weight percent to 95.75 weight percent, 95.75 weight percent to 96.00 weight percent, 96.00 weight percent to 96.25 weight percent, 96.25 weight percent to 96.50 weight percent, 96.50 weight percent to 96.75 weight percent, 96.75 weight percent to 97.00 weight percent, 97.00 weight percent to 97.25 weight percent, 97.25 weight percent to 97.50 weight percent, 97.50 weight percent to 97.75 weight percent, 97.75 weight percent to 98.00 weight percent, 98.00 weight percent to 98.25 weight percent, 98.25 weight percent to 98.50 weight percent, 98.50 weight percent to 98.75 weight percent, 98.75 weight percent to 99.00 weight percent, 99.00 weight percent to 99.25 weight percent, 99.25 weight percent to 99.50 weight percent, 99.50 weight percent to 99.75 weight percent, and 99.75 weight percent to 99.99 weight percent.

In embodiments, INSECTERGY III also includes: a fungus content ranging from between: 0.050 parts per million to 0.100 parts per million, 0.100 parts per million to 0.200 parts per million, 0.200 parts per million to 0.400 parts per million, 0.400 parts per million to 0.800 parts per million, 0.800 parts per million to 1.600 parts per million, 1.600 parts per million to 3.200 parts per million, 3.200 parts per million to 6.400 parts per million, 6.4 parts per million to 12.8 parts per million, 12.8 parts per million to 25.6 parts per million, 25 parts per million to 50 parts per million, 50 parts per million to 100 parts per million, 100 parts per million to 200 parts per million, 200 parts per million to 400 parts per million, 400 parts per million to 800 parts per million, 800 parts per million to 1600 parts per million, 1600 parts per million to 3200 parts per million, 3200 parts per million to 6400 parts per million, 6400 parts per million to 1 weight percent.

In embodiments, INSECTERGY III also includes: a bacteria content ranging from between: 0.05 colony-forming units per gram (CFU/g) to 0.100 CFU/g, 0.1 CFU/g to 0.2 CFU/g, 0.2 CFU/g to 0.4 CFU/g, 0.4 CFU/g to 0.8 CFU/g, 0.8 CFU/g to 1.6 CFU/g, 1.6 CFU/g to 3.2 CFU/g, 3.2 CFU/g to 6.4 CFU/g, 6.4 CFU/g to 12.8 CFU/g, 12.8 CFU/g to 25 CFU/g, 25 CFU/g to 50 CFU/g, 50 CFU/g to 100 CFU/g, 100 CFU/g to 200 CFU/g, 200 CFU/g to 400 CFU/g, 400 CFU/g to 800 CFU/g, 800 CFU/g to 1,600 CFU/g, 1,600 CFU/g to 3,200 CFU/g, 3,200 CFU/g to 6,400 CFU/g, 32,000 CFU/g to 320,000 CFU/g, 320,000 CFU/g to 3,200,000 CFU/g, 3,200,000 CFU/g to 32,000,000 CFU/g.

In embodiments, INSECTERGY III also includes: a fungus content ranging from between: colony-forming units per gram (CFU/g) to 0.100 CFU/g, 0.1 CFU/g to 0.2 CFU/g, 0.2 CFU/g to 0.4 CFU/g, 0.4 CFU/g to 0.8 CFU/g, 0.8 CFU/g to 1.6 CFU/g, 1.6 CFU/g to 3.2 CFU/g, 3.2 CFU/g to 6.4 CFU/g, 6.4 CFU/g to 12.8 CFU/g, 12.8 CFU/g to 25 CFU/g, 25 CFU/g to 50 CFU/g, 50 CFU/g to 100 CFU/g, 100 CFU/g to 200 CFU/g, 200 CFU/g to 400 CFU/g, 400 CFU/g to 800 CFU/g, 800 CFU/g to 1,600 CFU/g, 1,600 CFU/g to 3,200 CFU/g, 3,200 CFU/g to 6,400 CFU/g, 32,000 CFU/g to 320,000 CFU/g, 320,000 CFU/g to 3,200,000 CFU/g, 3,200,000 CFU/g to 32,000,000 CFU/g.

In embodiments, INSECTERGY III also includes: an alanine content ranging from between: 500 parts per million to 1000 parts per million, 1000 parts per million to 5000 parts per million, 5000 parts per million to 7500 parts per million, 7500 parts per million to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, or 14 weight percent to 15 weight percent.

In embodiments, INSECTERGY III also includes: an arginine content ranging from between: 500 parts per million to 1000 parts per million, 1000 parts per million to 5000 parts per million, 5000 parts per million to 7500 parts per million, 7500 parts per million to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, or 14 weight percent to 15 weight percent.

In embodiments, INSECTERGY III also includes: an aspartic acid content ranging from between: 500 parts per million to 1000 parts per million, 1000 parts per million to 5000 parts per million, 5000 parts per million to 7500 parts per million, 7500 parts per million to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, or 14 weight percent to 15 weight percent.

In embodiments, INSECTERGY III also includes: a glutamic acid content ranging from between: 500 parts per million to 1000 parts per million, 1000 parts per million to 5000 parts per million, 5000 parts per million to 7500 parts per million, 7500 parts per million to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, or 14 weight percent to 15 weight percent.

In embodiments, INSECTERGY III also includes: a glycine content ranging from between: 500 parts per million to 1000 parts per million, 1000 parts per million to 5000 parts per million, 5000 parts per million to 7500 parts per million, 7500 parts per million to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, or 14 weight percent to 15 weight percent.

In embodiments, INSECTERGY III also includes: a histidine content ranging from between: 500 parts per million to 1000 parts per million, 1000 parts per million to 5000 parts per million, 5000 parts per million to 7500 parts per million, 7500 parts per million to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, or 14 weight percent to 15 weight percent.

In embodiments, INSECTERGY III also includes: an isoleucine content ranging from between: 500 parts per million to 1000 parts per million, 1000 parts per million to 5000 parts per million, 5000 parts per million to 7500 parts per million, 7500 parts per million to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, or 14 weight percent to 15 weight percent.

In embodiments, INSECTERGY III also includes: a Leucine content ranging from between: 500 parts per million to 1000 parts per million, 1000 parts per million to 5000 parts per million, 5000 parts per million to 7500 parts per million, 7500 parts per million to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, or 14 weight percent to 15 weight percent.

In embodiments, INSECTERGY III also includes: a lysine content ranging from between: 500 parts per million to 1000 parts per million, 1000 parts per million to 5000 parts per million, 5000 parts per million to 7500 parts per million, 7500 parts per million to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, or 14 weight percent to 15 weight percent.

In embodiments, INSECTERGY III also includes: a proline content ranging from between: 500 parts per million to 1000 parts per million, 1000 parts per million to 5000 parts per million, 5000 parts per million to 7500 parts per million, 7500 parts per million to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, or 14 weight percent to 15 weight percent.

In embodiments, INSECTERGY III also includes: a serine content ranging from between: 500 parts per million to 1000 parts per million, 1000 parts per million to 5000 parts per million, 5000 parts per million to 7500 parts per million, 7500 parts per million to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, or 14 weight percent to 15 weight percent.

In embodiments, INSECTERGY III also includes: a threonine content ranging from between: 500 parts per million to 1000 parts per million, 1000 parts per million to 5000 parts per million, 5000 parts per million to 7500 parts per million, 7500 parts per million to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, or 14 weight percent to 15 weight percent.

In embodiments, INSECTERGY III also includes: a tyrosine content ranging from between: 500 parts per million to 1000 parts per million, 1000 parts per million to 5000 parts per million, 5000 parts per million to 7500 parts per million, 7500 parts per million to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, or 14 weight percent to 15 weight percent.

In embodiments, INSECTERGY III also includes: a valine content ranging from between: 500 parts per million to 1000 parts per million, 1000 parts per million to 5000 parts per million, 5000 parts per million to 7500 parts per million, 7500 parts per million to 1 weight percent, 1 weight percent to 2 weight percent, 2 weight percent to 3 weight percent, 3 weight percent to 4 weight percent, 4 weight percent to 5 weight percent, 5 weight percent to 6 weight percent, 6 weight percent to 7 weight percent, 7 weight percent to 8 weight percent, 8 weight percent to 9 weight percent, 9 weight percent to 10 weight percent, 10 weight percent to 11 weight percent, 11 weight percent to 12 weight percent, 12 weight percent to 13 weight percent, 13 weight percent to 14 weight percent, or 14 weight percent to 15 weight percent.

In embodiments, INSECTERGY III also includes: a pH ranging from between: 6.00 to 6.05, 6.05 to 6.10, 6.10 to 6.15, 6.15 to 6.20, 6.20 to 6.25, 6.25 to 6.30, 6.30 to 6.35, 6.35 to 6.40, 6.40 to 6.45, 6.45 to 6.50, 6.50 to 6.55, 6.55 to 6.60, 6.60 to 6.65, 6.65 to 6.70, 6.70 to 6.75, 6.75 to 6.80, 6.80 to 6.85, 6.85 to 6.90, 6.90 to 6.95, 6.95 to 7.00, 7.00 to 7.05, 7.05 to 7.10, 7.10 to 7.15, 7.15 to 7.20, 7.20 to 7.25, 7.25 to 7.30, 7.30 to 7.35, 7.35 to 7.40, 7.40 to 7.45, 7.45 to 7.50, 7.50 to 7.55, 7.55 to 7.60, 7.60 to 7.65, 7.65 to 7.70, 7.70 to 7.75, 7.75 to 7.80, 7.80 to 7.85, 7.85 to 7.90, 7.90 to 7.95, 7.95 to 8.00, 8.00 to 8.05, 8.05 to 8.10, 8.10 to 8.15, 8.15 to 8.20, 8.20 to 8.25, 8.25 to 8.30, 8.30 to 8.35, 8.35 to 8.40, 8.40 to 8.45, or 8.45 to 8.50.

In embodiments, INSECTERGY III also includes: a water activity (Aw) ranging from between: 0.05 to 0.1, 0.1 to 0.15, 0.15 to 0.2, 0.2 to 0.25, 0.25 to 0.3, 0.3 to 0.35, 0.35 to 0.4, 0.4 to 0.45, 0.45 to 0.5, 0.5 to 0.6, or 0.6 to 0.7, 0.7 to 0.8, or 0.8 to 0.9.

The present plant was developed in the United States. In embodiments, the plant may be propagated from seed. In embodiments, the plant is asexually propagated using stem cuttings especially for large-scale production. In embodiments, the stem cutting may be ground, shredded, smashed, milled, crushed, and blended into a slurry or a liquid or gel with treated water and/or a hormone and then incubated in a first growing medium in a cloning enclosure to develop roots. It is preferred that the first growing medium includes a hormone and a gel and the gel includes one or more selected from the group consisting of *acacia*, agar, agave, alginate, alginic acid, alginin, aluminum monostearate, arrowroot, bentonite, bovine-derived gelatin, carbomer, carboxymethylcellulose calcium, carboxymethylcellulose sodium, carboxymethylcellulose sodium 12, carboxymethylcellulose sodium cellulose, carrageenan, collagen, colloidal silicon dioxide, cornstarch, dextrin, furcellaran, gelatin, glycerin, guar gum, honey, hydroxyethyl cellulose, hydroxypropyl cellulose, hydroxypropyl methylcellulose, katakuri starch, locust bean gum, magma bentonite, magnesium aluminum silicate, methylcellulose, microcrystalline cellulose, pectin, polyethylene oxide, polyvinyl alcohol, potato starch, povidone, *psyllium* husks, purified bentonite, sago, silicon dioxide, sodium alginate, sorbitol, sugar, syrup, tapioca, tragacanth, vegan gelatin, vegetable gum, xanthan gum, and combinations thereof; and, wherein, the hormone is comprised of one or more from the group consisting of auxins, cytokinins gibberellins, abscic acid, brassinosteroids, salicylic acid, jasmonates, plant peptide hormones, polyamines, nitric oxide, strigolactones, and triacontanol.

The plant may be grown indoors, such as for example in a greenhouse, building, or other suitable indoor growing environment under controlled conditions. In embodiments, the plant is grown outdoors. The density of the plant ranges from 3.5 pounds per cubic foot to about 14.999 pounds per cubic foot or a ground bulk density ranging from between 15 pounds per cubic foot to pounds per cubic foot.

In embodiments, the plants undergoes a deliberately stressed training method, including: (a) providing a branch of a *cannabis* plant; (b) after step (a), squeezing and/or bending the branch; (c) after step (b), allowing the plant to heal. In embodiments, after step (b) and before step (c), inspecting the plant for tears in the outside plant tissue and optionally taping the branch that was squeezed and/or bended.

Plant

Exposed Plant Structure: This is an aggressive annual, dioecious plant. The natural height at 6 months old for indoor growth is 40 inches to 120 inches, and, and for outdoor growth is 50 inches to 160 inches. A detailed list of characteristics follows:

Botanical Classification:

Mixture of *Cannabis sativa* L. ssp. Sativa×*Cannabis sativa* L. ssp. Indica (Lam.).

Percentages:

A new and distinct hybrid plant named INSECTERGY III, as illustrated and described herein characterized by a mixture of:
(i) *Cannabis Sativa* L. ssp indica, and
(ii) *Cannabis Sativa* L. ssp *sativa*;
within the leaves, seeds, stems, roots, or any reproductive structures, INSECTERGY III has a:
(a) a cannabidiol content ranging from 0.125 weight percent to less than 5 weight percent;
(b) a tetrahydrocannabinol ranging from 5 weight percent to 63 weight percent;
(c) an energy content ranging from between 2,500 British Thermal Units per pound to 15,000 British Thermal Units per pound;
(d) a carbon content ranging from between 20 weight percent to 65 weight percent;
(e) an oxygen content ranging from between 12 weight percent to 55 weight percent;
(f) a hydrogen content ranging from between 2 weight percent to 20 weight percent;
(g) an ash content ranging from between 2.5 weight percent to 30 weight percent;
(h) volatiles content ranging from between 30 weight percent to 90 weight percent;
(i) a nitrogen content ranging from between 1 weight percent to 10 weight percent;
(j) a sulfur content ranging from between 0.01 weight percent to 8 weight percent;
(k) a chlorine content ranging from 0.05 weight percent to 5 weight percent;
(l) a sodium content ranging from 0.02 weight percent to 15 weight percent;
(m) a potassium content ranging from 0.05 weight percent to 15 weight percent;
(n) an iron content ranging from 0.01 weight percent to 13 weight percent;
(o) a magnesium content ranging from 0.02 weight percent to 10 weight percent;
(p) a phosphorous content ranging from 0.05 weight percent to 12 weight percent;
(q) a calcium content ranging from 0.03 weight percent to 10 weight percent;
(r) a zinc content ranging from 0.01 weight percent to 5 weight percent;
(s) a cellulose content ranging from 25 weight percent to 75 weight percent;
(t) a lignin content ranging from 3 weight percent to 35 weight percent;
(u) a hemicellulose content ranging from 3 weight percent to 30 weight percent;
(v) a fat content ranging from 5 weight percent to 35 weight percent;
(w) a fiber content ranging from 5 weight percent to 75 weight percent; and
(x) a protein content ranging from 5 weight percent to 35 weight percent;
wherein:
the *Cannabis Sativa* L. ssp indica content ranges from 15% to 65%;
the *Cannabis Sativa* L. ssp *sativa* content ranges from 20% to 70%.

PROPAGATION: This Plant May be Perpetuated by Stem Cuttings. Seed Propagation is Possible but not preferred due to lack of efficiency when compared to asexual reproduction.

TIME TO INITIATE ROOTS IN SUMMER: about 4 to 20 days.

PLANT DESCRIPTION: Annual, dioecious flowering shrub; multi-stemmed; vigorous; freely branching; removal of the terminal bud enhances lateral branch development.

In embodiments, the turgor pressure within the plants includes the force within the cell that pushes the plasma membrane against the cell wall. In embodiments, the turgor pressure within the plants includes one or more pressure ranges selected from the group consisting of: 0.5 bars to 0.6 bars, 0.6 bars to 0.7 bars, 0.7 bars to 0.8 bars, 0.8 bars to 0.9 bars, 0.9 bars to 1 bars, 1 bars to 1.1 bars, 1.1 bars to 1.2 bars, 1.2 bars to 1.3 bars, 1.3 bars to 1.4 bars, 1.4 bars to 1.5 bars, 1.5 bars to 1.6 bars, 1.6 bars to 1.7 bars, 1.7 bars to 1.8 bars, 1.8 bars to 1.9 bars, 1.9 bars to 2 bars, 2 bars to 2.1 bars, 2.1 bars to 2.2 bars, 2.2 bars to 2.3 bars, 2.3 bars to 2.4 bars, 2.4 bars to 2.5 bars, 2.5 bars to 2.6 bars, 2.6 bars to 2.7 bars, 2.7 bars to 2.8 bars, 2.8 bars to 2.9 bars, and 2.9 bars to 3 bars.

MATURE HABIT: Tap-rooted annual, with extensive fibrous root system, upright and much branched aerial portion of plant. The growth form of all cloned plants was highly manipulated by systematic removal of terminal buds, inducing a greater branching habit. Many petiole scars on stems from systematic removal of large shade leaves. In this habit, these are obviously very vigorous annual herbs.

First Year Stems:
Shape: Round. Moderate to fine pubescence.
First year stem strength: Medium to Strong.
First year stem color:

In embodiments, the young stem has a color that is comprised of one or more from the group consisting of: light green (144C), yellow (001A) or yellow green (001A), dark green (144A) with shades of yellow (001A), yellow orange (011A), orange (024A), orange red (033B), orange pink (027A), red (033A), dark purple red (046A), light red pink (039C), red pink (043C), dark pink red (045D), purple red (054A), light blue pink (055C), purple (058A), purple red (059D), blue pink (062A), light blue violet (069C), violet blue (089A), violet (075A), dark violet (079A), blue violet (083D), blue (100A), dark blue (103A), light blue (104D), light green blue (110C), green blue (111A), grey blue (115C), green blue (125C), white (155A), orange brown (169A), brown (172A), brown purple (178A), orange pink (179D) (The Royal Horticultural Society Colour Chart, 1995 Ed.).

In embodiments, the older stem has a color that is comprised of one or more from the group consisting of: light green (144C), yellow (001A) or yellow green (001A), dark green (144A) with shades of yellow (001A), yellow orange (011A), orange (024A), orange red (033B), orange pink (027A), red (033A), dark purple red (046A), light red pink (039C), red pink (043C), dark pink red (045D), purple red (054A), light blue pink (055C), purple (058A), purple red (059D), blue pink (062A), light blue violet (069C), violet blue (089A), violet (075A), dark violet (079A), blue violet (083D), blue (100A), dark blue (103A), light blue (104D), light green blue (110C), green blue (111A), grey blue (115C), green blue (125C), white (155A), orange brown (169A), brown (172A), brown purple (178A), orange pink (179D) (The Royal Horticultural Society Colour Chart, 1995 Ed.).

Stem Diameter:

In embodiments, the stem diameter at the soil line is 1.05 inches to 7.15 inches. In embodiments, the middle of plant average stem diameter is 0.2 inches to 1.5 inches.

In embodiments, the stem diameter at the soil line is 0.75 inches to 4 inches. In embodiments, the middle of plant average stem diameter is 0.2 inches to 1.5 inches.

In embodiments, the stem diameter at the soil line is 0.25 inches to 2 inches. In embodiments, the middle of plant average stem diameter is 0.1 inches to 0.75 inches.

Stem Height:

In embodiments, the stem height is 3 feet to 9 feet. In embodiments, the stem height is 3 feet to 9 feet. In embodiments, the stem height is 1.5 feet to 4.5 feet. In embodiments, the stem height is 5.5 feet to 11.25 feet. In embodiments, the stem height is 10 feet to 20 feet. In embodiments, the stem height is 11 feet to 24.5 feet. In embodiments, the stem height is 18 feet to 32 feet.

Stem Strength:

In embodiments, lateral stems are strong but benefit from being staked during flowering. In embodiments, the stem has a hollow cross-section. In embodiments, the stem is ribbed having ribs that run parallel to the stem. In embodiments, the stem is hollow.

Internode Spacing:

In embodiments, from between 1.15 inches to 2 inches at the top half of the plant. In embodiments, from between 1.15 inches to 3.15 inches at the bottom half of the plant. In embodiments, from between 0.75 inches to 5 inches at the bottom half of the plant. In embodiments, from between 0.35 inches to 3.15 inches at the bottom half of the plant. In embodiments, from between 0.35 inches to 4.15 inches at the bottom half of the plant. In embodiments, from between 1.15 inches to 7.15 inches at the bottom half of the plant. In embodiments, from between 2 inches to 9 inches at the bottom half of the plant. In embodiments, from between 2 inches to 9 inches at the bottom half of the plant.

Foliage Description:

Texture (upper and lower surfaces): Upper surface scabrid with non-visible stiff hairs; lower surface more or less densely pubescent, covered with sessile glands.

Branch strength: Strong to medium to weak.

Branch description: In embodiments, branches may be short, dense with short, broad leaflets. In embodiments, branches may be medium length, dense with long, broad or compact leaflets. In embodiments, lateral branches off the main stem may be fine and of medium strength, they contain few leaves with many bud sites extending up the branch. In embodiments, branches may be long and sparse.

Leaf Arrangement: In embodiments, palmately compound (digitate) leaves with 5 to 9 serrates leaflets per leaf. In embodiments, palmately compound (digitate) leaves with 3 to 7 serrates leaflets per leaf. In embodiments, palmately compound (digitate) leaves with 7 to 11 serrates leaflets per leaf. In embodiments, palmately compound (digitate) leaves with 3 to 11 serrates leaflets per leaf. In embodiments, palmately compound (digitate) leaves with 5 to 11 serrates leaflets per leaf. In embodiments, the bottom two leaflets may be angled upwards at about a 45-degree angle towards the middle leaflet. In embodiments, the bottom two leaflets extend out from the petiole at approximately 180 degrees.

Leaf width: In embodiments, the average leaf width ranges from between 1.5 inches to 12 inches. In embodiments, the average leaf width ranges from between 1.5 inches to 3 inches. In embodiments, the average leaf width ranges from between 1.5 inches to 4 inches. In embodiments, the average leaf width ranges from between 1.5 inches to 5 inches. In embodiments, the average leaf width ranges from between 1.5 inches to 6 inches. In embodiments, the average leaf width ranges from between 1.5 inches to 7 inches. In embodiments, the average leaf width ranges from between 1.5 inches to 8 inches. In embodiments, the average leaf width ranges from between 1.5 inches to 10 inches.

Leaf length: In embodiments, the average leaf length ranges from between 1.5 inches to 12 inches. In embodiments, the average leaf length ranges from between 1.5 inches to 3 inches. In embodiments, the average leaf length ranges from between 1.5 inches to 4 inches. In embodiments, the average leaf length ranges from between 1.5 inches to 5 inches. In embodiments, the average leaf length ranges from between 1.5 inches to 6 inches. In embodiments, the average leaf length ranges from between 1.5 inches to 7 inches. In embodiments, the average leaf length ranges from between 1.5 inches to 8 inches. In embodiments, the average leaf length ranges from between 1.5 inches to 10 inches.

Leaf venation pattern: Venation of each leaf is palmately compound (digitate), with serrated leaflets. In embodiments, the lateral venation extends off the main vein to each serrated tip. In embodiments, the sublateral veins extend to the notch of each serration rather than the tip. In embodiments, each serration has a lateral vein extending to its tip from the central (primary) vein of the leaflet. In embodiments, the from each lateral vein there is usually a single spur vein (sublateral vein) extending to the notch of each serration.

Leaf venation Color: Leaf venation is very colorful with one or more from the group consisting of: light green (144C), dark green (144A), yellow (001A), yellow orange (011A), orange (024A), orange red (033B), orange pink (027A), red (033A), dark purple red (046A), light red pink (039C), red pink (043C), dark pink red (045D), purple red (054A), light blue pink (055C), purple (058A), purple red (059D), blue pink (062A), light blue violet (069C), violet blue (089A), violet (075A), dark violet (079A), blue violet (083D), blue (100A), dark blue (103A), light blue (104D), light green blue (110C), green blue (111A), grey blue (115C), green blue (125C), green (130A), dark green (132A), light green (149B), white (155A), orange brown (169A), brown (172A), brown purple (178A), orange pink (179D) (The Royal Horticultural Society Colour Chart, 1995 Ed.).

Petiole length: Average length of petiole of fan leaves 1.5 inches to 8 inches. In embodiments, Petioles are very study and appear a light brown (166C) or light green (144C) (The Royal Horticultural Society Colour Chart, 1995 Ed.). Petioles are very study.

Petiole Color: Petioles are very colorful with one or more from the group consisting of: light green (144C), dark green (144A), yellow (001A), yellow orange (011A), orange (024A), orange red (033B), orange pink (027A), red (033A), dark purple red (046A), light red pink (039C), red pink (043C), dark pink red (045D), purple red (054A), light blue pink (055C), purple (058A), purple red (059D), blue pink (062A), light blue violet (069C), violet blue (089A), violet (075A), dark violet (079A), blue violet (083D), blue (100A), dark blue (103A), light blue (104D), light green blue (110C), green blue (111A), grey blue (115C), green blue (125C), green (130A), dark green (132A), light green (149B), white (155A), orange brown (169A), brown (172A), brown purple (178A), orange pink (179D) (The Royal Horticultural Society Colour Chart, 1995 Ed.).

Color of emerging foliage (upper surface): In embodiments, the color of emerging foliage is have a color comprised of one or more from the group consisting of: light green (144C), dark green (144A), yellow (001A), yellow orange (011A), orange (024A), orange red (033B), orange pink (027A), red (033A), dark purple red (046A), light red pink (039C), red pink (043C), dark pink red (045D), purple red (054A), light blue pink (055C), purple (058A), purple red (059D), blue pink (062A), light blue violet (069C), violet blue (089A), violet (075A), dark violet (079A), blue violet (083D), blue (100A), dark blue (103A), light blue (104D), light green blue (110C), green blue (111A), grey blue (115C), green blue (125C), green (130A), dark green (132A), light green (149B), white (155A), orange brown (169A), brown (172A), brown purple (178A), orange pink (179D) (The Royal Horticultural Society Colour Chart, 1995 Ed.).

Vegetative bud (reproductive structure) description: In embodiments, the dried flower buds (reproductive structures) are a light green (144C), green (124A), or dark green (144A), small to large in nature, diffuse and airy, and coated with glandular trichomes. In embodiments, the fragrance may be quite spicy with an earthy aroma with noticeable hints of pine, clove, citrus, pepper, candy, and tropical fruit. In embodiments, the fragrance is slightly sweet, having a fruity, fresh, musky, cotton-candy, or grape-soda type smell.

Flower description: In embodiments, inflorescence (buds, or reproductive structures) may be conical, spherical, cylindrical, tubular, oblong, or rectangular. In embodiments, the flower, bud, or reproductive structures may be devoid of any petals. In embodiments, the flower, bud, or reproductive structures are comprised of a cluster of false spikes with single flowers. These flowers are often paired and enclosed by a bracteole. In embodiments, the wet flower buds have a color comprised of one or more from the group consisting of: light green (144C), dark green (144A), yellow (001A), yellow orange (011A), orange (024A), orange red (033B), orange pink (027A), red (033A), dark purple red (046A), light red pink (039C), red pink (043C), dark pink red (045D), purple red (054A), light blue pink (055C), purple (058A), purple red (059D), blue pink (062A), light blue violet (069C), violet blue (089A), violet (075A), dark violet (079A), blue violet (083D), blue (100A), dark blue (103A), light blue (104D), light green blue (110C), green blue (111A), grey blue (115C), green blue (125C), green (130A), dark green (132A), light green (149B), white (155A), orange brown (169A), brown (172A), brown purple (178A), orange pink (179D) (The Royal Horticultural Society Colour Chart, 1995 Ed.). In embodiments, the wet flower buds have many long white (155A) pistils (hairs), which may become brown (172A) a week before harvest (The Royal Horticultural Society Colour Chart, 1995 Ed.).

Seed description: In embodiments, the seeds typically brown (172A). In embodiments, the seeds are brown (172A) and have stripes that include one or more colors from the group consisting of light green (144C), dark green (144A), yellow (001A), yellow orange (011A), orange (024A), orange red (033B), orange pink (027A), red (033A), dark purple red (046A), light red pink (039C), red pink (043C), dark pink red (045D), purple red (054A), light blue pink (055C), purple (058A), purple red (059D), blue pink (062A), light blue violet (069C), violet blue (089A), violet (075A), dark violet (079A), blue violet (083D), blue (100A), dark blue (103A), light blue (104D), light green blue (110C), green blue (111A), grey blue (115C), green blue (125C), green (130A), dark green (132A), light green (149B), white (155A), orange brown (169A), brown (172A), brown purple (178A), orange pink (179D) (The Royal Horticultural Society Colour Chart, 1995 Ed.). In embodiments, the wet flower buds have many long white (155A) pistils (hairs), which may become brown (172A) a week before harvest (The Royal Horticultural Society Colour Chart, 1995 Ed.). In embodiments, the seeds are on average about 0.1 inches to 0.2 inches in diameter. In embodiments, the seeds are on average about 0.075 inches to 0.4 inches in diameter. The seeds have a high fat content ranging from 4 weight percent to 45 weight percent, with an energy content ranging up to or less than 65,000 British Thermal Units per pound.

Vegetative bud (reproductive structure) color: In embodiments, the dried flower buds are very colorful and are comprised of a vast array of different colors including one or more from the group consisting of light green (144C), green (124A), dark green (144A), yellow (001A), yellow orange (011A), orange (024A), orange red (033B), orange pink (027A), red (033A), dark purple red (046A), light red pink (039C), red pink (043C), dark pink red (045D), purple red (054A), light blue pink (055C), purple (058A), purple red (059D), blue pink (062A), light blue violet (069C), violet blue (089A), violet (075A), dark violet (079A), blue violet (083D), blue (100A), dark blue (103A), light blue (104D), light green blue (110C), green blue (111A), grey blue (115C), green blue (125C), white (155A), orange brown (169A), brown (172A), brown purple (178A), orange pink (179D), (The Royal Horticultural Society Colour Chart, 1995 Ed.).

Vegetative bud (reproductive structure) & pistils color: In embodiments, the dried flower buds (including reproductive structures) are comprised of one or more from the group consisting of: green (144C or 144A) with yellow (001A) pistils, green (144C or 144A) with yellow orange (011A) pistils, green (144C or 144A) with orange (024A) pistils, green (144C or 144A) with orange red (033B) pistils, green (144C or 144A) with orange pink (027A) pistils, green (144C or 144A) with red (033A) pistils, green (144C or 144A) with dark purple red (046A) pistils, green (144C or 144A) with light red pink (039C) pistils, green (144C or 144A) with red pink (043C) pistils, green (144C or 144A) with dark pink red (045D) pistils, green (144C or 144A) with purple red (054A) pistils, green (144C or 144A) with light blue pink (055C) pistils, green (144C or 144A) with purple (058A) pistils, green (144C or 144A) with purple red (059D) pistils, green (144C or 144A) with blue pink (062A) pistils, green (144C or 144A) with light blue violet (069C) pistils, green (144C or 144A) with violet blue (089A) pistils, green (144C or 144A) with violet (075A) pistils, green (144C or 144A) with dark violet (079A) pistils, green (144C or 144A) with blue violet (083D) pistils, green (144C or 144A) with blue (100A) pistils, green (144C or 144A) with dark blue (103A) pistils, green (144C or 144A) with light blue (104D) pistils, green (144C or 144A) with light green blue (110C) pistils, green (144C or 144A) with green blue (111A) pistils, green (144C or 144A) with grey blue (115C) pistils, green (144C or 144A) with green (124A) pistils, green (144C or 144A) with green blue (125C) pistils, green (144C or 144A) with green (130A) pistils, green (144C or 144A) with dark green (132A) pistils, green (144C or 144A) with light green (149B) pistils, green (144C or 144A) with white (155A) pistils, green (144C or 144A) with orange brown (169A) pistils, green (144C or 144A) with brown (172A) pistils, green (144C or 144A) with brown purple (178A) pistils, green (144C or 144A) with orange pink (179D) (The Royal Horticultural Society Colour Chart, 1995 Ed.).

Bud (reproductive structures) length: In embodiments, the bud spike length ranges from inches to 10 inches. In embodiments, the bud spike length ranges from 0.75 inches to 20 inches. In embodiments, the bud spike length ranges from 0.75 inches to 30 inches. In embodiments, the bud spike length ranges from 0.75 inches to 40 inches.

Bud (reproductive structures) diameter: Flower size is approximately: 0.25 inches to 3 inches in diameter; and approximately 0.35 to 10 inches in height.

Flowering time: In embodiments, flowering time ranges from 5 weeks to 18 weeks. In embodiments, flowering time ranges from 5 weeks to 28 weeks. In embodiments, flowering time ranges from 25 weeks to 37 weeks. In embodiments, flowering time ranges from 35 weeks to 60 weeks. In embodiments, flowering time ranges from 45 weeks to 101 weeks.

Peduncles: Peduncle strength is weak to medium to strong. In embodiments, they can bend horizontally from weight of flower buds. In embodiments, the average diameter of the peduncles ranges from between 0.2 to 0.5 inches in diameter. In embodiments, the average diameter of the peduncles ranges from between 0.1 to 0.3 inches in diameter. In embodiments, the average diameter of the peduncles ranges from between 0.3 to 1 inches in diameter. In embodiments, the average diameter of the peduncles ranges from between 1 to 2 inches in diameter. In embodiments, texture is smooth with few hairs. In embodiments, texture is moderately smooth, glabrous. In embodiments, texture is coarse with many hairs. In embodiments, pedicels are short to medium length, with visible hairs. They may be scabrid with sessile glands. In embodiments, pedicels are short to medium length, scabrid with sessile glands and visible hairs.

Peduncles color: In embodiments, peduncles are very colorful with many varied colors including having one or more from the group selected from: light green (144C), dark green (144A), yellow (001A), yellow orange (011A), orange (024A), orange red (033B), orange pink (027A), red (033A), dark purple red (046A), light red pink (039C), red pink (043C), dark pink red (045D), purple red (054A), light blue pink (055C), purple (058A), purple red (059D), blue pink (062A), light blue violet (069C), violet blue (089A), violet (075A), dark violet (079A), blue violet (083D), blue (100A), dark blue (103A), light blue (104D), light green blue (110C), green blue (111A), grey blue (115C), green blue (125C), green (130A), dark green (132A), light green (149B), white (155A), orange brown (169A), brown (172A), brown purple (178A), orange pink (179D) (The Royal Horticultural Society Colour Chart, 1995 Ed.).

Pedicel color: Pedicels are very colorful with many varied colors including having one or more from the group selected from: light green (144C), dark green (144A), yellow (001A), yellow orange (011A), orange (024A), orange red (033B), orange pink (027A), red (033A), dark purple red (046A), light red pink (039C), red pink (043C), dark pink red (045D), purple red (054A), light blue pink (055C), purple (058A), purple red (059D), blue pink (062A), light blue violet (069C), violet blue (089A), violet (075A), dark violet (079A), blue violet (083D), blue (100A), dark blue (103A), light blue (104D), light green blue (110C), green blue (111A), grey blue (115C), green blue (125C), green (130A), dark green (132A), light green (149B), white (155A), orange brown (169A), brown (172A), brown purple (178A), orange pink (179D) (The Royal Horticultural Society Colour Chart, 1995 Ed.).

Seed production on this plant is difficult. Seed production can be induced using colloidal silver solution but even with this step male inflorescence production is marginal. Pollen generated from this procedure may then be collected and used to self-cross with a non-treated female. The relative proportion of male plants is medium/high.

The inflorescences (e.g.—flowers, buds, reproductive structures) of the female plant are used for medical purposes. This plant is very versatile. It can be used to treat a wide range of health disorders. It has many beneficial medicinal qualities. Some uses include: stimulant, anti-inflammatory, pain management, sleep disorders, Tourette syndrome, Parkinsons disease, spasms, post-traumatic stress disorder (PTSD), epilepsy, multiple sclerosis, digestive disorders, INSECTERGY III prefers water having an electrical conductivity ranging from 0.10 microsiemens per centimeter to 100 microsiemens per centimeter. Other water sources with other electrical conductivity may be suitable but just not as efficient. INSECTERGY III prefers water having an electrical conductivity ranging from 0.10 microsiemens per centimeter to 100 microsiemens per centimeter is provided by:
  (a1) a first water treatment unit (A1) including a cation,
  (a2) a second water treatment unit (A2) including an anion, and
  (a3) a third water treatment unit (A3) including a membrane.

In embodiments, INSECTERGY III is grown using a method by providing water having an electrical conductivity ranging from 0.10 microsiemens per centimeter to 100 microsiemens per centimeter, the method includes:
  (a) providing:
    (a1) a first water treatment unit (A1) including a cation configured to remove positively charged ions from water to form a positively charged ion depleted water (06A), the positively charged ions are comprised of one or more from the group consisting of calcium, magnesium, sodium, and iron;
    (a2) a second water treatment unit (A2) including an anion configured to remove negatively charged ions from the positively charged ion depleted water (06A) to form a negatively charged ion depleted water (09A), the negatively charged ions are comprised of one or more from the group consisting of iodine, chloride, and sulfate;
    (a3) a third water treatment unit (A3) including a membrane configured to remove undesirable compounds from the negatively charged ion depleted water (09A) to form an undesirable compounds depleted water (12A), the undesirable compounds are comprised of one or more from the group consisting of dissolved organic chemicals, viruses, bacteria, and particulates;
  (b) providing a source of water;
  (c) removing positively charged ions from the water of step (b) to form a positively charged ion depleted water;
  (d) removing negatively charged ions from the water after step (c) to form a negatively charged ion depleted water;

(e) removing undesirable compounds from the water after step (d) to form an undesirable compound depleted water;
(f) mixing the undesirable compounds depleted water after step (e) with one or more from the group consisting of macro-nutrients, micro-nutrients, and a pH adjustment to form a liquid mixture;
(g) pressurizing the liquid mixture of step (f) to form a pressurized liquid mixture;
(h) splitting the pressurized liquid mixture into a plurality of pressurized liquid mixtures;
(i) transferring the plurality of pressurized liquid mixtures to each growing assembly;
wherein:
the macro-nutrients are comprised of one or more from the group consisting of nitrogen, phosphorus, potassium, calcium, magnesium, and sulfur;
the micro-nutrients are comprised of one or more from the group consisting of iron, manganese, boron, molybdenum, copper, zinc, sodium, chlorine, and silicon;
the pH adjustment solution is comprised of one or more from the group consisting acid, nitric acid, phosphoric acid, potassium hydroxide, sulfuric acid, organic acids, citric acid, and acetic acid.

This new and remarkable variety of plant prefers that lights illuminate the plant at an illumination on-off ratio ranging from between 0.5 and 5, the illumination on-off ratio is defined as the duration of time when the lights are on and illuminate the plant in hours divided by the subsequent duration of time when the lights are off and are not illuminating the plant in hours before the lights are turned on again. In embodiments, this variety of plant thrives at a carbon dioxide concentration that between 400 parts per million (ppm) to 500 ppm, 500 ppm to 600 ppm, 600 ppm to 700 ppm, 700 ppm to 800 ppm, 800 ppm to 900 ppm, 900 ppm to 1000 ppm, 1000 ppm to 1500 ppm, 1500 ppm to 2000 ppm, 2000 ppm to 2500 ppm, 2500 ppm to 3000 ppm, 3000 ppm to 3500 ppm, 3500 ppm to 4000 ppm, 4000 ppm to 4500 ppm, 4500 ppm to 5000 ppm, 5000 ppm to 5500 ppm, 5500 ppm to 6000 ppm, 6000 ppm to 6500 ppm, 6500 ppm to 7000 ppm, 7000 ppm to 7500 ppm, 7500 ppm to 8000 ppm, 8000 ppm to 8500 ppm, 8500 ppm to 9000 ppm, 9000 ppm to 9500 ppm, or 9500 ppm to 10000 ppm.

In embodiments, the INSECTERGY III is grown in a farming superstructure system (FSS) as described here and is grown while the FSS system is operated in a manner that switches from one mode of operation to another mode of operation.

In embodiments, the farming superstructure system (FSS) is operated in a manner that switches on a cyclical basis from: a first mode of operation to the second mode of operation; a second mode of operation to the first mode of operation. In embodiments, the farming superstructure system (FSS) is operated in a manner that switches on a cyclical basis from: a third mode of operation to the fourth mode of operation; a fourth mode of operation to the third mode of operation. It is preferred to turn on and off at least one valves (V1, V3, V4) in a cyclical manner to prevent the roots of the *cannabis* from receiving too much mist or spray or liquid water or water or nutrients.

In embodiments, the first mode of operation lasts for 5 seconds open followed by the second mode of operation lasting for 600 seconds closed. In embodiments, the third mode of operation lasts for 5 seconds open followed by the fourth mode of operation lasting for 600 seconds closed. In embodiments, water is transferred to the first growing assembly (100) for 5 seconds followed by not transferring water to the first growing assembly (100) for 600 seconds. In embodiments, water is transferred to the second growing assembly (200) for 5 seconds followed by not transferring water to the second growing assembly (200) for 600 seconds. In embodiments, water is transferred to both the first and second growing assemblies (100, 200) for 5 seconds followed by not transferring water to both the first and second growing assemblies (100, 200) for 600 seconds. 5 divided by 600 is 0.008.

In embodiments, the first mode of operation lasts for 60 seconds open followed by the second mode of operation lasting for 180 seconds closed. In embodiments, the third mode of operation lasts for 60 seconds open followed by the fourth mode of operation lasting for 180 seconds closed. In embodiments, water is transferred to the first growing assembly (100) for 60 seconds followed by not transferring water to the first growing assembly (100) for 180 seconds. In embodiments, water is transferred to the second growing assembly (200) for 60 seconds followed by not transferring water to the second growing assembly (200) for 180 seconds. 60 divided by 180 is 0.333.

The duration of time when liquid is transferred to at least one growing assembly (100, 200) divided by the duration of time when liquid is not transferred to at least one growing assembly (100, 200) may be considered an open-close ratio. The open-close ratio may be the duration of time when at least one valve (V1, V3, V4) is open in seconds divided by the subsequent duration of time when the same valve is closed in seconds before the same valve opens again. In embodiments, the open-close ratio ranges from between 0.008 to 0.33. In embodiments, the computer (COMP) opens and closes the valve (V1, V3, V4) to periodically introduce the pressurized liquid mixture into to each growing assembly with an open-close ratio ranging from between 0.008 to 0.33, the open-close ratio is defined as the duration of time when the valve (V1, V3, V4) is open in seconds divided by the subsequent duration of time when the same valve is closed in seconds before the same valve opens again. The computer (COMP) opens and closes the valves (V1, V3, V4) to periodically introduce the pressurized liquid mixture into to each growing assembly with an open-close ratio ranging from between 0.008 to 0.33.

In embodiments, the open-close ratio varies. The open-close ratio may vary throughout the life of the *cannabis* contained within the growing assemblies (100, 200). The open-close ratio may vary throughout the stage of development of the *cannabis* contained within the growing assemblies (100, 200). Stages of development of the *cannabis* include flowering, pollination, fertilization. In embodiments, the open-close ratio is greater during flowering and less during pollination. In embodiments, the open-close ratio is greater during pollination and less during fertilization. In embodiments, the open-close ratio is greater during flowering and less during fertilization. In embodiments, the open-close ratio is less during flowering and greater during pollination. In embodiments, the open-close ratio is less during pollination and greater during fertilization. In embodiments, the open-close ratio is less during flowering and greater during fertilization.

The open-close ratio may vary throughout a 24-hour duration of time. In embodiments, the open-close ratio is increased during the day-time and decreased during the night-time relative to one another. In embodiments, the open-close ratio varies increased during the night-time and decreased during the day-time relative to one another. Night-time is defined as the time between evening and morning. Day-time is defined as the time between morning and evening.

In embodiments, carbohydrates may be made available to INSECTERGY III. The carbohydrates are comprised of one or more from the group consisting of sugar, sucrose, molasses, and plant syrup.

In embodiments, enzymes may be made available to INSECTERGY III. The enzymes are comprised of one or more from the group consisting of amino acids, orotidine 5-phosphate decarboxylase, OMP decarboxylase, glucanase, beta-glucanase, cellulase, xylanase, HYGROZYME®, CANNAZYME®, MICROZYME®, and SENSIZYME®.

In embodiments, vitamins may be made available to INSECTERGY III. The vitamins are comprised of one or more from the group consisting of vitamin B, vitamin C, vitamin D, and vitamin E.

In embodiments, hormones may be made available to INSECTERGY III. The hormones are comprised of one or more from the group consisting of auxins, cytokinins gibberellins, abscic acid, brassinosteroids, salicylic acid, jasmonates, plant peptide hormones, polyamines, nitric oxide, strigolactones, and triacontanol.

In embodiments, microorganisms may be made available to INSECTERGY III. The microorganisms are comprised of one or more from the group consisting of bacteria, diazotroph bacteria, diazotroph archaea, *azotobacter vinelandii, Clostridium pasteurianum*, fungi, arbuscular mycorrhizal fungi, *glomus aggregatum, glomus etunicatum, glomus intraradices, Rhizophagus irregularis*, and *glomus mosseae*. Permits and Patent Licenses are Required for Growth of Insectergy III in the United States of America and Internationally.

The claims and specification are in conformity with 37 CFR 1.163, this specification and especially claimed ranges of elements (a) through (x) and other elements of the claims contain as full and complete a disclosure as possible of the plant and the characteristics thereof that distinguish the same over related known varieties, and its antecedents, and particularly point out where and in what manner the variety of plant has been asexually reproduced. Further, in the case of this newly found plant, this specification particularly points out the location and character of the area where the plant was discovered. Applicant is based out of Baltimore, Maryland, 21202.

The claims and specification are in conformity with 35 U.S.C. 112(a), since this specification and especially claimed ranges of elements (a) through (x) and other elements of the claims contain a written description of the invention, and of the manner and process of making and using it, in such full, clear, concise, and exact terms as to enable any person skilled in the art to which it pertains, or with which it is most nearly connected, to make and use the same, and shall set forth the best mode contemplated by the inventor or joint inventor of carrying out the invention.

Complete botanical description and the characteristics which distinguish over related known varieties are herein provided. The new variety differs from parents and related (similar) cultivars of *Cannabis sativa* L. ssp. *Sativa* and *Cannabis sativa* L. ssp. Indica (Lam.). The new variety differs from parents and related (similar) cultivars because INSECTERGY III has a precise and unique engineered concentrations of: cannabidiol, tetrahydrocannabinol, energy, carbon, oxygen, hydrogen, ash, volatiles, nitrogen, sulfur, chlorine, sodium, potassium, iron, magnesium, phosphorous, calcium, zinc, cellulose, lignin, hemicellulose, fat, fiber, protein, as well as specific *Cannabis sativa* L. ssp. *Sativa* and *Cannabis sativa* L. ssp. Indica (Lam.) contents and ratios. The new plant differs from its parents and related cultivars because it is engineered to more effectively alleviate inflammation, manage pain, treat post-traumatic stress disorder (PTSD), and digestive disorders, while also helping to prevent sleep disorders. It provides adequate stimulant to cure attention deficit disorder but does not so act as such a stimulating drug to prevent normal sleep, dietary, and exercise patterns. Because of this remarkable new plant, and combination of ingredients, individuals seeking to medicate with tetrahydrocannabinol can now use this plant as medicine while having little-to-no side effects at all whatsoever and at a very low dosage compared to its parents and related cultivars.

Applicant has specifically identified the characteristic of improved medicinal benefits through extensive trial and error and has a claim which is the result of quantifiable, experimental, and empirical data characterizing the difference between INSECTERGY III and *Cannabis sativa* L. ssp. *Sativa* or *Cannabis sativa* L. ssp. Indica (Lam.) alone. Most importantly, INSECTERGY III possesses a volatiles content ranging from between 30 weight percent to 90 weight percent, and a *Cannabis sativa* L. ssp. *Sativa* content ranges from 20 weight percent to 70 weight percent, and a *Cannabis sativa* L. ssp. Indica (Lam.) content ranges from 15 weight percent to 65 weight percent. Whereas the patents and cultivars possess 100 weight percent of each of *Cannabis sativa* L. ssp. *Sativa* content and a *Cannabis sativa* L. ssp. Indica (Lam.), applicants research and development has resulted in a new and distinct plant that has an engineered amount of volatiles while mixing *Cannabis sativa* L. ssp. *Sativa* content and a *Cannabis sativa* L. ssp. Indica (Lam.) at varying ratios to achieve a preferred cannabidiol content ranging from 0.125 weight percent to weight percent. Applicant has realized that the tetrahydrocannabinol content ranging from 5 weight percent to 63 weight percent is specifically tailored to maximize dosage while having a volatiles content ranging from between 30 weight percent to 90 weight percent. The combination of INSECTERGY III having a volatiles content ranging from between 30 weight percent to 90 weight percent together with the tetrahydrocannabinol content ranging from 5 weight percent to 63 weight percent provides a remarkable new plant. Because of this, a user can use less of the plant to achieve the required dosage.

The application conforms to 37 CFR 1.163(a) since the specification particularly points out that Applicant is based out of Baltimore, Maryland, USA in zip code 21202 which was the location that Applicant realized that he can take stem cuttings and asexually reproduce plants in a manner disclosed in this specification. This disclosure conforms to 37 CFR 1.163(a) since the specification particularly points out that Baltimore, Maryland, USA in zip code 21202, indoor propagation, growing, and cultivation were the location and character of the area where the plant was discovered.

Applicant has generated the ranges of claimed ranges of elements (a) through (x) were discovered through comprehensive compositional analysis, particle-induced X-ray emission analysis, elemental analysis, proximate analysis, and ultimate analysis immediately available from a variety of different laboratories in the USA. Obtaining the appropriate ranges of varying concentrations of *Cannabis sativa* L. ssp. *Sativa* and *Cannabis sativa* L. ssp. Indica (Lam.) were performed on a trial and error basis. The tetrahydrocannabinol concentration is provided as a measurement of INSECTERGY IIIs leaves, seeds, stems, roots, or any reproductive structures on a dry basis.

The age and growing conditions of this plant shown in FIGS. 1-4 may be: adult plant of 14 weeks, average temperature 70 degrees F. to 80 degrees F., humidity 45 to 55 percent humidity, water pH from 5.15 to 6.8, water having an electrical conductivity ranging from 0.10 microsiemens per centimeter to 100 microsiemens per centimeter, an illumination on-off ratio ranging from between 0.5 and 5 (the illumination on-off ratio is defined as the duration of time when the lights are on and illuminate the *cannabis* in hours divided by the subsequent duration of time when the lights are off and are not illuminating the *cannabis* in hours before the lights are turned on again), a carbon dioxide concentration that is greater than 400 parts per million and less than 3,000 parts per million, a LED lighting wavelength ranging from 400 nm to 700 nm, air velocity ranging from feet per second to 50 feet per second.

The parents of the instant plant are known and are comprised of *Cannabis sativa* L. ssp. *Sativa*×*Cannabis sativa* L. ssp. Indica (Lam.). Seeds from either are commercially available from many vendors throughout the USA. Applicant devised various plant hybrids of *Cannabis sativa* L. ssp. *Sativa*×*Cannabis sativa* L. ssp. Indica (Lam.) to create a plant best suited to accommodate industrial, commercial, recreation and medicinal popular demand.

The idea of a superior and precisely engineered composition that embodies INSECTERGY III as described and disclosed herein was discovered by the applicants in his garden where the inventor was asexually reproducing and cultivating many plants, in many different containers, of many different species. Applicants work with plants has resulted in the discovery of a cross between *Cannabis sativa* L. ssp. *Sativa*×*Cannabis sativa* L. ssp. Indica (Lam.) described herein. Applicant has discovered that INSECTERGY III can be reproduced asexually, by taking cuttings of the plants of origin resulting in a remarkable new plant. The discovered female plant can be asexually reproduced by cuttings.

The invention employs a novel plant variety. Since the plant is essential to the claimed invention it must be obtainable by the following method. A method to asexually clone a plurality of INSECTERGY III plants, the method includes:

(a) providing:
   (a0) a plurality of INSECTERGY III (107, 207) plants;
   (a1) a cutting tool (CT1);
   (a2) a liquid, powder, or gel rooting solution (RS), the rooting solution includes one or more from the group consisting of water, carbohydrates, enzymes, vitamins, hormones, and microorganisms;
   (a3) a growing medium (GM), the growing medium includes one or more from the group consisting of rockwool, perlite, amorphous volcanic glass, vermiculite, clay, clay pellets, LECA (lightweight expanded clay aggregate), coco-coir, fibrous coconut husks, soil, dirt, peat, peat moss, sand, soil, compost, manure, fir bark, foam, gel, oasis cubes, lime, gypsum, quartz, plastic, polyethylene, high-density polyethylene (HDPE), low-density polyethylene (LDPE), polyethylene terephthalate (PET), polyacrylonitrile, and polypropylene; and
   (a4) a plurality of containers (TY1, TY2, TY3, $TY^N$, $TY^{N+1}$) configured to accept the rooting solution (RS) and the growing medium (GM), the plurality of containers are configured to be positioned within a cloning enclosure (CHD);
   (a5) the cloning enclosure (CHD) has an interior (CHD-1), the cloning enclosure (CHD) is configured to contain water vapor within the interior (CHD-1) to provide a humid environment for plants within the interior (CHD-1);

(b) introducing the rooting solution and the growing medium to the plurality of containers;

(c) using the cutting tool to sever the tips from a plurality of INSECTERGY III plants to form a plurality of severed plants (107X, 207X);

(d) inserting the plurality of severed plants (107X, 207X) of step (c) into the plurality of containers;

(e) placing the plurality of containers within the interior of the cloning enclosure;

(f) illuminating the plants after step (e);

(g) growing the plants for 4 to 20 days or until roots are formed; and (h) optionally venting the interior of the cloning enclosure;

wherein:

the carbohydrates are comprised of one or more from the group consisting of sugar, sucrose, molasses, and plant syrup;

the enzymes are comprised of one or more from the group consisting of amino acids, orotidine 5-phosphate decarboxylase, OMP decarboxylase, glucanase, beta-glucanase, cellulase, xylanase, HYGROZYME®, CANNAZYME®, MICROZYME®, and SENSIZYME®, the vitamins are comprised of one or more from the group consisting of vitamin B, vitamin C, vitamin D, and vitamin E;

the hormones are comprised of one or more from the group consisting of auxins, cytokinins gibberellins, abscic acid, brassinosteroids, salicylic acid, jasmonates, plant peptide hormones, polyamines, nitric oxide, strigolactones, and triacontanol;

the microorganisms are comprised of one or more from the group consisting of bacteria, diazotroph bacteria, diazotroph archaea, *Azotobacter vinelandii*, *Clostridium pasteurianum*, fungi, arbuscular mycorrhizal fungi, mycorrhiza, *Glomus aggregatum*, *Glomus etunicatum*, *Glomus intraradices*, *Rhizophagus irregularis*, and *Glomus mosseae*.

TABLE 1

USDA Plants Growth Habit Code: FB;
Vigor: 5;
Productivity: Good;
Flowering timing: 5 weeks to 18 weeks;
Flowering score: 7.5;
Branches: strong to medium to weak;
(a) a cannabidiol content ranging from 0.125 weight percent to less than 25 weight percent;
(b) a tetrahydrocannabinol ranging from 5 weight percent to 63 weight percent;
(c) an energy content ranging from between 2,500 British Thermal Units per pound to 15,000 British Thermal Units per pound;
(d) a carbon content ranging from between 20 weight percent to 65 weight percent;
(e) an oxygen content ranging from between 12 weight percent to 55 weight percent;
(f) a hydrogen content ranging from between 2 weight percent to 20 weight percent;
(g) an ash content ranging from between 2.5 weight percent to 30 weight percent;
(h) volatiles content ranging from between 30 weight percent to 90 weight percent;
(i) a nitrogen content ranging from between 1 weight percent to 10 weight percent;
(j) a sulfur content ranging from between 0.01 weight percent to 8 weight percent;

TABLE 1-continued (k) a chlorine content ranging from 0.05 weight percent to 5 weight percent;
(l) a sodium content ranging from 0.02 weight percent to 15 weight percent;
(m) a potassium content ranging from 0.05 weight percent to 15 weight percent;
(n) an iron content ranging from 0.01 weight percent to 13 weight percent;
(o) a magnesium content ranging from 0.02 weight percent to 10 weight percent;
(p) a phosphorous content ranging from 0.05 weight percent to 12 weight percent;
(q) a calcium content ranging from 0.03 weight percent to 10 weight percent;
(r) a zinc content ranging from 0.01 weight percent to 5 weight percent;
(s) a cellulose content ranging from 25 weight percent to 75 weight percent;
(t) a lignin content ranging from 3 weight percent to 35 weight percent;
(u) a hemicellulose content ranging from 3 weight percent to 30 weight percent;
(v) a fat content ranging from 5 weight percent to 35 weight percent;
(w) a fiber content ranging from 5 weight percent to 75 weight percent; and
(x) a protein content ranging from 5 weight percent to 35 weight percent;
wherein:
the *Cannabis Sativa* L. ssp *indica* content ranges from 15% to 65%;
the *Cannabis Sativa* L. ssp *sativa* content ranges from 20% to 70%;

In embodiments, INSECTERGY III has a cannabidiol content including a weight percent on a dry basis comprising one or more weight percents selected from the group consisting of: 0.125 to 0.156, 0.156 to 0.195, 0.195 to 0.244, 0.244 to 0.305, 0.305 to 0.381, 0.381 to 0.477, 0.477 to 0.596, 0.596 to 0.745, 0.745 to 0.931, 0.931 to 1.164, 1.164 to 1.455, 1.455 to 1.819, 1.819 to 2.274, 2.274 to 2.842, 2.842 to 3.553, 3.553 to 4.441, 4.441 to 5.551, 5.551 to 6.939, 6.939 to 8.674, 8.674 to 10.842, 10.842 to 13.553, 13.553 to 16.941, 16.941 to 21.176, and 21.176 to 25.000.

In embodiments, INSECTERGY III has a tetrahydrocannabinol content including a weight percent on a dry basis comprising one or more weight percents selected from the group consisting of: 5 to 10, 10 to 15, 15 to 20, 20 to 25, 25 to 30, 30 to 35, 35 to 40, 40 to 45, 45 to 50, 50 to 55, to 60, and 60 to 63.

In embodiments, INSECTERGY III has an energy content including British Thermal Units per pound on a dry basis comprising one or more selected from the group consisting of: 2500 to 3000, 3000 to 3500, 3500 to 4000, 4000 to 4500, 4500 to 5000, 5000 to 5500, 5500 to 6000, 6000 to 6500, 6500 to 7000, 7000 to 7500, 7500 to 8000, 8000 to 8500, 8500 to 9000, 9000 to 9500, 9500 to 10000, 10000 to 10500, 10500 to 11000, 11000 to 11500, 11500 to 12000, 12000 to 12500, 12500 to 13000, 13000 to 13500, 13500 to 14000, 14000 to 14500, and 14500 to 15000.

In embodiments, INSECTERGY III has a carbon content including a weight percent on a dry basis comprising one or more weight percents selected from the group consisting of: 20 to 25, 25 to 30, 30 to 35, 35 to 40, 40 to 45, 45 to 50, 50 to 55, 55 to 60, and 60 to 65.

In embodiments, INSECTERGY III has an oxygen content including a weight percent on a dry basis comprising one or more weight percents selected from the group consisting of: 12 to 17, 17 to 22, 22 to 27, 27 to 32, 32 to 37, 37 to 42, 42 to 47, 47 to 52, and 52 to 55.

In embodiments, INSECTERGY III has a hydrogen content including a weight percent on a dry basis comprising one or more weight percents selected from the group consisting of: 2 to 4, 4 to 6, 6 to 8, 8 to 10, 10 to 12, 12 to 14, 14 to 16, 16 to 18, and 18 to 20.

In embodiments, INSECTERGY III has an ash content including a weight percent on a dry basis comprising one or more weight percents selected from the group consisting of: 2.5 to 5.0, to 7.5, 7.5 to 10.0, 10.0 to 12.5, 12.5 to 15.0, 15.0 to 17.5, 17.5 to 20.0, 20.0 to 22.5, 22.5 to 25.0, 25.0 to 27.5, and 27.5 to 30.0.

In embodiments, INSECTERGY III has a volatiles content including a weight percent on a dry basis comprising one or more weight percents selected from the group consisting of: 30 to 35 to 40, 40 to 45, 45 to 50, 50 to 55, 55 to 60, 60 to 65, 65 to 70, 70 to 75, 75 to 80, 80 to 85, and 85 to 90.

In embodiments, INSECTERGY III has a nitrogen content including a weight percent on a dry basis comprising one or more weight percents selected from the group consisting of: 1.0 to 1.5, 1.5 to 2.0, 2.0 to 2.5, 2.5 to 3.0, 3.0 to 3.5, 3.5 to 4.0, 4.0 to 4.5, 4.5 to 5.0, 5.0 to 5.5, 5.5 to 6.0, 6.0 to 6.5, 6.5 to 7.0, 7.0 to 7.5, 7.5 to 8.0, 8.0 to 8.5, 8.5 to 9.0, 9.0 to 9.5, and 9.5 to 10.0.

In embodiments, INSECTERGY III has a sulfur content including a weight percent on a dry basis comprising one or more weight percents selected from the group consisting of: 0.01 to 0.02 to 0.04, 0.04 to 0.08, 0.08 to 0.16, 0.16 to 0.32, 0.32 to 0.64, 0.64 to 1.28, 1.28 to 1.92, 1.92 to 2.88, 2.88 to 4.32, 4.32 to 6.48, and 6.48 to 8.00.

In embodiments, INSECTERGY III has a chlorine content including a weight percent on a dry basis comprising one or more weight percents selected from the group consisting of: 0.05 to 0.10 to 0.20, 0.20 to 0.40, 0.40 to 0.80, 0.80 to 1.60, 1.60 to 3.20, 3.20 to 4.80, and 4.80 to 5.00.

In embodiments, INSECTERGY III has a sodium content including a weight percent on a dry basis comprising one or more weight percents selected from the group consisting of: 0.02 to 0.04 to 0.08, 0.08 to 0.16, 0.16 to 0.32, 0.32 to 0.64, 0.64 to 1.28, 1.28 to 1.92, 1.92 to 2.88, 2.88 to 4.32, 4.32 to 6.48, 6.48 to 9.72, 9.72 to 12.15, and 12.15 to 15.00.

In embodiments, INSECTERGY III has a potassium content including a weight percent on a dry basis comprising one or more weight percents selected from the group consisting of: 0.05 to 0.10 to 0.20, 0.20 to 0.40, 0.40 to 0.80, 0.80 to 1.60, 1.60 to 3.20, 3.20 to 4.80, 4.80 to 6.00, 6.00 to 7.50, 7.50 to 9.38, 9.38 to 11.72, 11.72 to 14.65, and 14.65 to 15.00.

In embodiments, INSECTERGY III has an iron content including a weight percent on a dry basis comprising one or more weight percents selected from the group consisting of: 0.01 to 0.02 to 0.04, 0.04 to 0.08, 0.08 to 0.16, 0.16 to 0.32, 0.32 to 0.64, 0.64 to 0.96, 0.96 to 1.20, 1.20 to 1.50, 1.50 to 1.88, 1.88 to 2.34, 2.34 to 2.93, 2.93 to 3.66, 3.66 to 4.58, 4.58 to 5.72, 5.72 to 7.15, 7.15 to 8.94, 8.94 to 11.18, and 11.18 to 13.00.

In embodiments, INSECTERGY III has a magnesium content including a weight percent on a dry basis comprising one or more weight percents selected from the group consisting of: 0.02 to 0.04, 0.04 to 0.08, 0.08 to 0.16, 0.16 to 0.32, 0.32 to 0.64, 0.64 to 1.28, 1.28 to 1.92, 1.92 to 2.40, 2.40 to 3.00, 3.00 to 3.75, 3.75 to 4.69, 4.69 to 5.86, 5.86 to 7.32, 7.32 to 9.16, and 9.16 to 10.00.

In embodiments, INSECTERGY III has a phosphorous content including a weight percent on a dry basis comprising one or more weight percents selected from the group consisting of: 0.05 to 0.10, 0.10 to 0.20, 0.20 to 0.40, 0.40 to 0.80, 0.80 to 1.60, 1.60 to 3.20, 3.20 to 4.80, 4.80 to 6.00, 6.00 to 7.50, 7.50 to 9.38, 9.38 to 11.72, and 11.72 to 12.00.

In embodiments, INSECTERGY III has a calcium content including a weight percent on a dry basis comprising one or more weight percents selected from the group consisting of: 0.03 to 0.06, 0.06 to 0.12, 0.12 to 0.24, 0.24 to 0.48, 0.48 to 0.96, 0.96 to 1.92, 1.92 to 3.84, 3.84 to 7.68, and 7.68 to 10.00.

In embodiments, INSECTERGY III has a zinc content including a weight percent on a dry basis comprising one or more weight percents selected from the group consisting of: 0.01 to 0.02, to 0.04, 0.04 to 0.08, 0.08 to 0.16, 0.16 to 0.32, 0.32 to 0.64, 0.64 to 0.80, 0.80 to 1.00, 1.00 to 1.25, 1.25 to 1.56, 1.56 to 1.95, 1.95 to 2.44, 2.44 to 3.05, 3.05 to 3.81, 3.81 to 4.77, and 4.77 to 5.00.

In embodiments, INSECTERGY III has a cellulose content including a weight percent on a dry basis comprising one or more weight percents selected from the group consisting of: 25 to 30 to 35, 35 to 40, 40 to 45, 45 to 50, 50 to 55, 55 to 60, 60 to 65, 65 to 70, and 70 to 75.

In embodiments, INSECTERGY III has a lignin content including a weight percent on a dry basis comprising one or more weight percents selected from the group consisting of: 3 to 6, 6 to 9, 9 to 12, 12 to 15, 15 to 18, 18 to 21, 21 to 24, 24 to 27, 27 to 30, 30 to 33, and 33 to 35.

In embodiments, INSECTERGY III has a hemicellulose content including a weight percent on a dry basis comprising one or more weight percents selected from the group consisting of: 3 to 6, 6 to 9, 9 to 12, 12 to 15, 15 to 18, 18 to 21, 21 to 24, 24 to 27, and 27 to 30. In embodiments, INSECTERGY III has a fat content including a weight percent on a dry basis comprising one or more weight percents selected from the group consisting of: 5 to 10, 10 to 15 to 20, 20 to 25, 25 to 30, and 30 to 35.

In embodiments, INSECTERGY III has a fiber content including a weight percent on a dry basis comprising one or more weight percents selected from the group consisting of: 5 to 10, 10 to 15, 15 to 20, 20 to 25, 25 to 30, 30 to 35, 35 to 40, 40 to 45, 45 to 50, 50 to 55, 55 to 60, 60 to 65, to 70, and 70 to 75.

In embodiments, INSECTERGY III has a protein content including a weight percent on a dry basis comprising one or more weight percents selected from the group consisting of: 5 to 10, to 15, 15 to 20, 20 to 25, 25 to 30, and 30 to 35.

In embodiments, INSECTERGY III has a *Cannabis Sativa* L. ssp indica content ranges from: 15 to 20, 20 to 25, 25 to 30, 30 to 35, 35 to 40, 40 to 45, 45 to 50, 50 to 55, 55 to 60, or 60 to 65.

In embodiments, INSECTERGY III has a *Cannabis Sativa* L. ssp *sativa* content ranges from: 20 to 25, 25 to 30, 30 to 35, 35 to 40, 40 to 45, 45 to 50, 50 to 55, 55 to 60, 60 to 65, or 65 to 70.

In embodiments, the terpenes concentration of INSECTERGY III *cannabis* plant includes on a dry basis: 25 parts per million (ppm) to 50 ppm, 50 ppm to 100 ppm, 100 ppm to 200 ppm, 200 ppm to 400 ppm, 400 ppm to 800 ppm, 800 ppm to 1600 ppm, 1600 ppm to 3200 ppm, 3200 ppm to 6400 ppm, 6400 ppm to 9600 ppm, 9600 ppm to 14400 ppm, 14400 ppm to 21600 ppm, 21600 ppm to 32400 ppm, 32400 ppm to 48600 ppm, 48600 ppm to 72900 ppm, 72900 ppm to 109350 ppm, 109350 ppm to 164025 ppm, 164025 ppm to 246038 ppm, 246038 ppm to 369056 ppm, 369056 ppm to 553584 ppm, and combinations thereof of various different terpenes and terpene concentrations.

In embodiments, the INSECTERGY III *cannabis* plant includes a natural mutation. In embodiments, the INSECTERGY III *cannabis* plant includes an induced mutation. In embodiments, the INSECTERGY III *cannabis* plant is distinguished over the parent plants or related varieties in that is possesses unique characteristics, including specific ranges of various characteristics and components which make up the plant. In embodiments, the INSECTERGY III *cannabis* plant has different levels of chemical constituents as compared with the parents as described in the Comparison To Parents section of this patent specification. In embodiments, the main differences between the INSECTERGY III *cannabis* plant and its parents are described in the Comparison To Parents section of this patent specification.

Applicant believes that the description presents a full, clear and complete botanical description of the *cannabis* plant named INSECTERGY III and the characteristics which define the plant and which distinguish the plant from related known cultivars and antecedents. Applicant has carefully compared the *cannabis* plant named INSECTERGY III with the botanical descriptions set forth in the specification and has ensured completeness and accuracy and to distinguish the plant.

Comparison to Parents:

The parents of INSECTERGY III were INSECTERGY I and INSECTERGY II.

| INSECTERGY I |
| --- |
| USDA Plants Growth Habit Code: FB; |
| Vigor: 5; |
| Productivity: Good; |
| Flowering timing: 5 weeks to 18 weeks; |
| Flowering score: 7.5; |
| Branches: strong to medium to weak; |
| (a) a cannabidiol content ranging from 0.1 weight percent to less than 28 weight percent; |
| (b) a tetrahydrocannabinol ranging from 3 weight percent to 65 weight percent; |
| (c) an energy content ranging from between 2,400 British Thermal Units per pound to 15,500 British Thermal Units per pound; |
| (d) a carbon content ranging from between 18 weight percent to 66 weight percent; |
| (e) an oxygen content ranging from between 10 weight percent to 60 weight percent; |
| (f) a hydrogen content ranging from between 1 weight percent to 25 weight percent; |
| (g) an ash content ranging from between 2 weight percent to 35 weight percent; |
| (h) volatiles content ranging from between 25 weight percent to 95 weight percent; |
| (i) a nitrogen content ranging from between 0.5 weight percent to 12 weight percent; |
| (j) a sulfur content ranging from between 0.005 weight percent to 10 weight percent; |
| (k) a chlorine content ranging from 0.01 weight percent to 7 weight percent; |
| (l) a sodium content ranging from 0.01 weight percent to 16 weight percent; |
| (m) a potassium content ranging from 0.04 weight percent to 16 weight percent; |
| (n) an iron content ranging from 0.008 weight percent to 15 weight percent; |
| (o) a magnesium content ranging from 0.01 weight percent to 12 weight percent; |
| (p) a phosphorous content ranging from 0.01 weight percent to 14 weight percent; |
| (q) a calcium content ranging from 0.02 weight percent to 12 weight percent; |
| (r) a zinc content ranging from 0.005 weight percent to 6 weight percent; |
| (s) a cellulose content ranging from 20 weight percent to 78 weight percent; |
| (t) a lignin content ranging from 2 weight percent to 38 weight percent; |
| (u) a hemicellulose content ranging from 2 weight percent to 32 weight percent; |
| (v) a fat content ranging from 4 weight percent to 38 weight percent; |

-continued (w) a fiber content ranging from 4 weight percent to 77 weight percent; and
(x) a protein content ranging from 4 weight percent to 38 weight percent;
wherein:
the Cannabis Sativa L. ssp *indica* content ranges from 10% to 70%;
the Cannabis Sativa L. ssp *sativa* content ranges from 15% to 75%;

INSECTERGY II

USDA Plants Growth Habit Code: FB;
Vigor: 5;
Productivity: Good;
Flowering timing: 5 weeks to 18 weeks;
Flowering score: 7.5;
Branches: strong to medium to weak;
(a) a cannabidiol content ranging from 0.15 weight percent to less than 24 weight percent;
(b) a tetrahydrocannabinol ranging from 8 weight percent to 60 weight percent;
(c) an energy content ranging from between 3,000 British Thermal Units per pound to 14,500 British Thermal Units per pound;
(d) a carbon content ranging from between 22 weight percent to 60 weight percent;
(e) an oxygen content ranging from between 15 weight percent to 50 weight percent;
(f) a hydrogen content ranging from between 3 weight percent to 18 weight percent;
(g) an ash content ranging from between 3 weight percent to 28 weight percent;
(h) volatiles content ranging from between 35 weight percent to 85 weight percent;
(i) a nitrogen content ranging from between 1.5 weight percent to 9.5 weight percent;
(j) a sulfur content ranging from between 0.015 weight percent to 7.5 weight percent;
(k) a chlorine content ranging from 0.08 weight percent to 4.5 weight percent;
(l) a sodium content ranging from 0.03 weight percent to 14 weight percent;
(m) a potassium content ranging from 0.06 weight percent to 14 weight percent;
(n) an iron content ranging from 0.02 weight percent to 12 weight percent;
(o) a magnesium content ranging from 0.03 weight percent to 9 weight percent;
(p) a phosphorous content ranging from 0.06 weight percent to 11 weight percent;
(q) a calcium content ranging from 0.04 weight percent to 9 weight percent;
(r) a zinc content ranging from 0.02 weight percent to 4.5 weight percent;
(s) a cellulose content ranging from 26 weight percent to 70 weight percent;
(t) a lignin content ranging from 4 weight percent to 33 weight percent;
(u) a hemicellulose content ranging from 4 weight percent to 28 weight percent;
(v) a fat content ranging from 6 weight percent to 33 weight percent;
(w) a fiber content ranging from 6 weight percent to 70 weight percent; and
(x) a protein content ranging from 6 weight percent to 33 weight percent;
wherein:
the Cannabis Sativa L. ssp *indica* content ranges from 20% to 60%;
the Cannabis Sativa L. ssp *sativa* content ranges from 25% to 65%;

FIG. 23

FIG. 23 shows one non-limiting embodiment of a *cannabis* cloning assembly (CA). In embodiments, the *cannabis* cloning assembly (CA) includes a plurality of containers (TY1, TY2, TY3, $TY^N$, $TY^{N+1}$) connected to at least one cloning enclosure (CHD). The cloning enclosure (CHD) when placed upon the plurality of containers (TY1, TY2, TY3, $TY^N$, $TY^{N+1}$) forms an interior (CHD-1). In embodiments, the cloning enclosure (CHD) does not let humidity, water vapor, carbon dioxide, or air to escape from within the interior (CHD-1). The cloning enclosure (CHD) is configured to contain humidity in the interior (CHD-1) above the plurality of containers (TY1, TY2, TY3, $TY^N$, $TY^{N+1}$). In embodiments, insects are grown within the *cannabis* cloning assembly (CA). In embodiments, the *cannabis* plants are cloned using aeroponic methodologies as described in detail above.

The *cannabis* cloning assembly (CA) is configured to asexually reproduce INSECTERGY III (107, 207) that grow within in each growing assembly (100, 200). The present disclosure provides for a method to asexually clone a plurality of INSECTERGY III (107, 207) plants, the method includes:
(a) providing:
(a0) a plurality of INSECTERGY III (107, 207) plants;
(a1) a cutting tool (CT1);
(a2) a liquid, powder, or gel rooting solution (RS), the rooting solution includes one or more from the group consisting of water, carbohydrates, enzymes, vitamins, hormones, and microorganisms;
(a3) a growing medium (GM), the growing medium includes one or more from the group consisting of rockwool, perlite, amorphous volcanic glass, vermiculite, clay, clay pellets, LECA (lightweight expanded clay aggregate), coco-coir, fibrous coconut husks, soil, dirt, peat, peat moss, sand, soil, compost, manure, fir bark, foam, gel, oasis cubes, lime, gypsum, quartz, plastic, polyethylene, high-density polyethylene (HDPE), low-density polyethylene (LDPE), polyethylene terephthalate (PET), polyacrylonitrile, and polypropylene;
(a4) a plurality of containers (TY1, TY2, TY3, $TY^N$, $TY^{N+1}$) configured to accept the rooting solution (RS) and the growing medium (GM), the plurality of containers are configured to be positioned within a cloning enclosure (CHD);
(a5) the cloning enclosure (CHD) has an interior (CHD-1), the cloning enclosure (CHD) is configured to contain water vapor within the interior (CHD-1) to provide a humid environment for plants within the interior (CHD-1);
(b) introducing the rooting solution and the growing medium to the plurality of containers;
(c) using the cutting tool to sever the tips from a plurality of *Cannabis* plants to form a plurality of severed plants (107X, 207X);
(d) inserting the plurality of severed plants (107X, 207X) of step (c) into the plurality of containers;
(e) placing the plurality of containers within the interior of the cloning enclosure;
(f) illuminating the plants after step (e);
(g) growing the plants until roots are formed; and
(h) optionally venting the interior of the cloning enclosure;
wherein:
the carbohydrates are comprised of one or more from the group consisting of sugar, sucrose, molasses, and plant syrup;
the enzymes are comprised of one or more from the group consisting of amino acids, orotidine 5-phosphate decarboxylase, OMP decarboxylase, glucanase, beta-glucanase, cellulase, xylanase, HYGROZYME®, CANNAZYME®, MICROZYME®, and SENSIZYMEg;
the vitamins are comprised of one or more from the group consisting of vitamin B, vitamin C, vitamin D, and vitamin E;
the hormones are comprised of one or more from the group consisting of auxins, cytokinins gibberellins, abscic acid, brassinosteroids, salicylic acid, jasmonates, plant peptide hormones, polyamines, nitric oxide, strigolactones, and triacontanol;

the microorganisms are comprised of one or more from the group consisting of bacteria, diazotroph bacteria, diazotroph archaea, azotobacter vinelandii, Clostridium pasteurianum, fungi, arbuscular mycorrhizal fungi, mycorrhiza, *Glomus aggregatum, Glomus etunicatum, Glomus intraradices, Rhizophagus irregularis,* and *Glomus mosseae.*

The *cannabis* cloning assembly (CA) is configured to asexually reproduce INSECTERGY III (107, 207) that grow within in each growing assembly (100, 200). The present disclosure provides for a method to asexually clone a plurality of INSECTERGY III (107, 207) plants, the method includes:

(a) providing:
  (a0) a plurality of INSECTERGY III (107, 207) plants;
  (a1) a cutting tool (CT1);
  (a2) a liquid, powder, or gel rooting solution (RS), the rooting solution includes one or more from the group consisting of water, carbohydrates, enzymes, vitamins, hormones, and microorganisms;
  (a3) a growing medium (GM), the growing medium includes a gel;
  (a4) a plurality of containers (TY1, TY2, TY3, TY$^N$, TY$^{N+1}$) configured to accept the rooting solution (RS) and the growing medium (GM), the plurality of containers are configured to be positioned within a cloning enclosure (CHD);
  (a5) the cloning enclosure (CHD) has an interior (CHD-1), the cloning enclosure (CHD) is configured to contain water vapor within the interior (CHD-1) to provide a humid environment for plants within the interior (CHD-1);
(b) introducing the rooting solution and the growing medium to the plurality of containers;
(c) using the cutting tool to sever the tips from a plurality of *Cannabis* plants to form a plurality of severed plants (107X, 207X), and blending the tips into a slurry comprising water, and mixing the slurry with the rooting solution (RS) and the growing medium (GM);
(d) introducing the slurry of step (c) into the plurality of containers;
(e) placing the plurality of containers within the interior of the cloning enclosure;
(f) illuminating the slurry after step (e);
(g) growing the slurry until roots are formed; and
(h) optionally venting the interior of the cloning enclosure;
wherein:
the carbohydrates are comprised of one or more from the group consisting of sugar, sucrose, molasses, and plant syrup;
the enzymes are comprised of one or more from the group consisting of amino acids, orotidine 5-phosphate decarboxylase, OMP decarboxylase, glucanase, beta-glucanase, cellulase, xylanase, HYGROZYME®, CANNAZYME®, MICROZYME®, and SENSIZYMEg;
the vitamins are comprised of one or more from the group consisting of vitamin B, vitamin C, vitamin D, and vitamin E;
the hormones are comprised of one or more from the group consisting of auxins, cytokinins gibberellins, abscic acid, brassinosteroids, salicylic acid, jasmonates, plant peptide hormones, polyamines, nitric oxide, strigolactones, and triacontanol;

the microorganisms are comprised of one or more from the group consisting of bacteria, diazotroph bacteria, diazotroph archaea, azotobacter vinelandii, Clostridium pasteurianum, fungi, arbuscular mycorrhizal fungi, mycorrhiza, *Glomus aggregatum, Glomus etunicatum, Glomus intraradices, Rhizophagus irregularis,* and *Glomus mosseae.*

FIG. 24:

FIG. 24 includes one non-limiting embodiment of a *cannabis*-related product traceability system flow chart. In embodiments, the present disclosure provides for a *cannabis*-related product traceability system. In embodiments, the *cannabis*-related product traceability system is specifically tailored towards the unique challenges related to tracking, accountability, food safety, and state and federal government compliance of the *cannabis*-related product industry, either for food (for humans or animals), drugs, chemicals, and medicine. In embodiments, the present disclosure provides for an *cannabis*-related product traceability system that is used to verify the history, location, or application of an item by means of documented recorded identification. In embodiments, the *cannabis*-related product traceability system flow chart may also be a traceability system to trace the cloning, growing, processing of *cannabis* plants.

In embodiments, the *cannabis*-related product traceability system has been developed to track inventory to end-product (distilled cannabinoids, cannabinoid isolates, purified cannabinoids, cannabinoid crystals, cannabinoid powders, cannabinoid water-soluble particulates, cannabinoid emulsions, cannabinoid microemulsions, cannabinoid nanoemulsions, cannabinoid colloidal dispersions, cannabinoid liquid mixtures, distilled biosynthetic cannabinoids, biosynthetic cannabinoids, insect-derived cannabinoid glycosides, insects, beverages, softgels, topicals, cosmetics, foodstuffs, shaped foodstuffs, candies, gummies, chocolates, cannabinoid burger patties, cannabinoid insect meat replacements, cannabinoid foodstuffs, pet foods, animal foods, trimmed *cannabis* buds, *cannabis* trimmings, *cannabis* plants, *cannabis* seeds, *cannabis* clones, *cannabis* stems, *cannabis*-derived fibers and/or textiles, etc.). In embodiments, the *cannabis*-related product traceability system includes a *cannabis*-related product end-product laboratory analytical testing component.

In embodiments, the *cannabis*-related product traceability system and method includes production of a first product and an analytical or laboratory testing component of that first product. Determination of a measure of quality of the first product is determined in the analytical or laboratory testing component of that first product. In embodiments, the *cannabis*-related product traceability system includes production of a second product from the first product and an analytical or laboratory testing component of that second product.

In embodiments, the traceability system and method incorporate a server having tables comprising a database for receiving, processing and storing data. In embodiments, the traceability system includes a computer network providing electronic communication between the server and other computers and/or mobile devices. In embodiments, blockchain technology can be implemented with the traceability system.

In embodiments, the traceability system tracks data including:

(A) times and dates *cannabis* plants were germinated, cloned, fed, watered, fertilized, frozen, trimmed, grinded, heated, decarboxylated, cannabinoid extraction, purification, provided with an insecticide, provided with a fungicide, provided with a miticide, subjected to extraction, purification, formulation and processing including evaporation, distillation, crystallization, spray-dried, emulsifier, preparade into an emulsion, prepared into a microemulsion, prepared into a nanoemulsion, processed to produce a colloidal dispersion, a softgel, a foodstuff, a beverage, a mixed with other ingredients, mixed with drugs, mixed with additives, mixed to produce a multifunctional composition, cooked, flavored, manufactured into a food stuff and/or a beverage, biosynthesis of biosynthetic cannabinoids derived from genetically modified microorganisms, production of an insect-derived *cannabis* glycoside, preparation of a pet food, preparation of an animal food, and processed to be heated, ground, spray-dried, filtered, evaporated, pressurized, fermented, reacted, analyzed, mixed with water, liquid, gas, solvent (and type of solvent), acid, enzyme, fungus, or mixed with a fiber-starch material, a binding agent, a density improving textural supplement, a moisture improving textural supplement, and other insects (either whole, ground, powder, slurry, particulate, frozen, heated, dehydrated, cooked, raw, ground, whole insects, whole insect cells, cloned insect cells, cloned insects, or wherein the *cannabis* plants are exposed to arachnids and/or insects) and whether any of the aforementioned products and/or any supplies needed are sold, leased, borrowed, processed, traded, and/or bartered;

(B) *cannabis* plant growing material composition, growing chamber temperature, humidity, mass/length/width of each *cannabis* plant, mass/length/width of each insect purposefully introduced to a *cannabis* plant, average insect mass/length/width, genus, species, *cannabis* composition including bacteria, fungi, ecoli, water activity, moisture content, and contents of the *cannabis* plant including cannabidiol, tetrahydrocannabinol, energy, carbon, oxygen, hydrogen, ash, volatiles, nitrogen, sulfur, chlorine, sodium, potassium, iron, magnesium, phosphorous, calcium, zinc, cellulose, lignin, hemicellulose, fat, fiber, protein, *Cannabis sativa* L. ssp. *Sativa* content, and *Cannabis sativa* L. ssp. Indica (Lam.) content in weight percentages;

(C) entity purchased (first product, second product, insects, arachnids, *cannabis* plants, *cannabis* seeds, insect eggs, arachnid eggs, *cannabis* clone, cannabinoid containing foodstuffs, beverages, compositions, extracts, pet food), end customer; growing chamber plant cycle time, temp, humidity, growing medium moisture and temperature and watering cycle, lighting cycle and/or wavelength, bacteria content of growing medium, pH, type of fish used in water used to feed *cannabis* plants; *cannabis* plant information (analytical results, composition, vendor information, MSDS, bacteria content, fungus content, water content, method of preparation of the enhanced *cannabis*, feed rate, production capacity and/or rate, revenue, debts, liens, mortgages, leases, utility bills, and/or licenses).

FIG. 24 includes one non-limiting embodiment of a *cannabis*-related product traceability system or method flow chart. First, the initial inventory is tracked, not only including: *cannabis* seeds, *cannabis* clones, growing mediums, insects, arachnids, bats, insect eggs, arachnid eggs, insects at various stages of development, arachnids at various stages of development, *cannabis* pants at various stages of development, carbohydrates, micronutrients, macronutrients, acid, biocatalysts, fungicides, miticides, insecticides, surfactants, heat transfer equipment, lighting, carbon dioxide, water treatment units, adsorbents, absorbents, catalysts, ion exchange resins, water, water quality, water contaminants, contaminants removed in from the water, type of water treatment unit (adsorbent, catalyst, ion-exchange resin, polymer, alumina, etc.), water quality in and out of the water treatment unit, odor control system (adsorbent, sorbent, filter element), enzymes, solvents, chemicals, acid, drugs, hallucinogens, additives, and/or ingredients.

Second, the *cannabis* plants are grown, and the cannabinoids within the *cannabis* plants (or insects and/or genetically modified microorganisms) are extracted, purified, and formulated within the farming superstructure system (FSS). The *cannabis* may be trimmed, ground, heated, decarboxylated to form a first product which includes trimmed *cannabis* buds, *cannabis* trimmings, *cannabis* plants, *cannabis* seeds, *cannabis* clones, *cannabis* stems, and/or *cannabis*-derived fibers and/or textiles. Various wastes are generated while making the first product. In embodiments, the wastes include growing mediums, fish, insects, water treatment supplies, pots, pans, trays, spent growing medium (that can no longer be re-used), regenerable adsorbent, non-regenerable adsorbent, catalysts, ion-exchange resins, polymers, alumina, filters, lights, mirrors, solar panels, fuel cells, humidity and/or temperature control equipment, computers, servers, hard drives, office supplies, and/or refrigerants. In embodiments, some of the waste is discarded. In embodiments, some of the waste is sold or recycled or used on site to grow insects and/or *cannabis* plants in.

In embodiments, the waste includes insect frass comprising solid excreta of insects from the insects growing together with the *cannabis* plants. In embodiments, the waste includes guano comprising solid excreta of bats growing together with the insects, arachnids, and *cannabis* plants. In embodiments, the insect frass includes water. In embodiments, the insect frass may be used as a fertilizer. In embodiments, the insect frass may be used as a fertilizer for plants. In embodiments, the waste includes insects which is then fed to bats to eat to maintain a healthy population of insects and/or arachnids on the *cannabis* plants in the FSS. In embodiments, the insect frass may be used as a fertilizer for *cannabis* plants. In embodiments, the insect frass includes chitin. In embodiments, the waste includes bats. In embodiments, the waste includes worms and/or nematodes. In embodiments, the waste includes insects. In embodiments, the waste includes arachnids.

In embodiments, the waste includes *cannabis* stems which are upcycled to fibers and/or textiles. In embodiments, the waste includes solid waste. In embodiments, the waste includes rockwool. In embodiments, the waste includes rockwool. In embodiments, the waste includes fertilizer. In embodiments, the waste includes liquid waste.

Quality testing takes place of the first product to ensure that recalls may be instituted if necessary. In embodiments, the quality testing includes testing the first product prior to entering the stream of interstate commerce (or prior to making the second product) for: pH, chemicals, contaminants, bacteria, pathogens, yeast, mold, allergens, pesticides, metals, mycotoxins, toxins, quality, taste, appearance, texture, water content, and/or water activity.

In embodiments, the *cannabis*-related traceability system includes a quality analysis of a the first product that includes: a nitrate (NO3) concentration having a maximum level of 1,000 mg NO3/kg of end-product; a mycotoxin analysis including: an ochratoxin A concentration having a maximum level of 10 µg/kg of end-product; a deoxynivalenol concentration having a maximum level of 2,000 µg/kg of end-product; a zearalenone concentration having a maximum level of 275 µg/kg of end-product; a fumonisins concentration having a maximum level of 2,500 µg/kg of end-product; a metals analysis including: a lead concentration having a maximum level of 0.5 mg/kg of end-product; a cadmium concentration having a maximum level of 0.5 mg/kg of end-product; a mercury concentration having a maximum level of 0.5 mg/kg of end-product; a 3-monochloropropane-1,2-diol (3-MCPD) concentration having a maximum level of 20 µg/kg of end-product; a dioxins and polychlorinated biphenyls (PCBs) concentration having a maximum level of 3 picogram/gram; a polycyclic aromatic hydrocarbon concentration having a maximum level of 5 µg/kg of end-product; a benzo(a)pyrene concentration having a maximum level of 2 or µg/kg of end-product; a total concentration of benzo(a)pyrene, benz(a)anthracene, benzo(b)fluoranthene and chrysene having a maximum level of 15 or 30 µg/kg of end-product.

In embodiments, the *cannabis*-related traceability system includes a quality analysis of a the first product that includes: a standard plate count (to test for total aerobic bacterial and total mold and yeasts) having less than: 500,000 colony forming unit per gram, 400,000 colony forming units per gram, 300,000 colony forming units per gram, 200,000 colony forming units per gram, 100,000 colony forming units per gram, 50,000 colony forming units per gram, 25,000 colony forming units per gram, or 5,000 colony forming units per gram; a coliform content less than 500 colony forming units per gram, 400 colony forming units per gram, 300 colony forming units per gram, 200 colony forming units per gram, 100 colony forming units per gram, 90 colony forming units per gram, 80 colony forming units per gram, 70 colony forming units per gram, 60 colony forming units per gram, 50 colony forming units per gram, 40 colony forming units per gram, 30 colony forming units per gram, 20 colony forming units per gram, or 10 colony forming units per gram; a coliform content less than 500,000 colony forming unit per gram, 400,000 colony forming units per gram, 300,000 colony forming units per gram, 200,000 colony forming units per gram, 100,000 colony forming units per gram, 50,000 colony forming units per gram, 25,000 colony forming units per gram, or 5,000 colony forming units per gram; a spore-forming sulphite reducing anaerobe content less than 500 colony forming units per gram, 400 colony forming units per gram, 300 colony forming units per gram, 200 colony forming units per gram, 100 colony forming units per gram, 90 colony forming units per gram, 80 colony forming units per gram, 70 colony forming units per gram, 60 colony forming units per gram, 50 colony forming units per gram, 40 colony forming units per gram, 30 colony forming units per gram, 20 colony forming units per gram, or colony forming units per gram; a spore-forming sulphite reducing anaerobe content less than 500,000 colony forming unit per gram, 400,000 colony forming units per gram, 300,000 colony forming units per gram, 200,000 colony forming units per gram, 100,000 colony forming units per gram, 50,000 colony forming units per gram, 25,000 colony forming units per gram, or 5,000 colony forming units per gram; a *Pseudomonas aeruginosa* content less than 500 colony forming units per gram, 400 colony forming units per gram, 300 colony forming units per gram, 200 colony forming units per gram, 100 colony forming units per gram, 90 colony forming units per gram, 80 colony forming units per gram, 70 colony forming units per gram, 60 colony forming units per gram, 50 colony forming units per gram, 40 colony forming units per gram, 30 colony forming units per gram, 20 colony forming units per gram, or 10 colony forming units per gram; a *Pseudomonas aeruginosa* content less than 500,000 colony forming unit per gram, 400,000 colony forming units per gram, 300,000 colony forming units per gram, 200,000 colony forming units per gram, 100,000 colony forming units per gram, 50,000 colony forming units per gram, 25,000 colony forming units per gram, or 5,000 colony forming units per gram; a *E. coli* content less than 500 colony forming units per gram, 400 colony forming units per gram, 300 colony forming units per gram, 200 colony forming units per gram, 100 colony forming units per gram, 90 colony forming units per gram, 80 colony forming units per gram, 70 colony forming units per gram, 60 colony forming units per gram, 50 colony forming units per gram, 40 colony forming units per gram, 30 colony forming units per gram, 20 colony forming units per gram, or 10 colony forming units per gram; a *E. coli* content less than 500,000 colony forming unit per gram, 400,000 colony forming units per gram, 300,000 colony forming units per gram, 200,000 colony forming units per gram, 100,000 colony forming units per gram, 50,000 colony forming units per gram, 25,000 colony forming units per gram, or 5,000 colony forming units per gram.

Fourth, after (and/or if) the first product has passed product testing they may be further processed to make a second product. In embodiments, the second product includes distilled cannabinoids, cannabinoid isolates, purified cannabinoids, cannabinoid crystals, cannabinoid powders, cannabinoid water-soluble particulates, hash, a sifted cannabinoid, cannabinoid emulsions, cannabinoid microemulsions, cannabinoid nanoemulsions, cannabinoid colloidal dispersions, cannabinoid liquid mixtures, purified biosynthetic cannabinoids, distilled biosynthetic cannabinoids, biosynthetic cannabinoids, insect-derived cannabinoid glycosides, distilled insect-derived cannabinoid glycosides, purified insect-derived cannabinoid glycosides, beverages, softgels, topicals, cosmetics, foodstuffs, shaped foodstuffs, candies, gummies, chocolates, hydrocarbon extracted cannabinoids (derived from fresh-frozen *cannabis* and/or freeze dried *cannabis*), cannabinoid burger patties, cannabinoid meat replacements, cannabinoid insect meat replacements, cannabinoid foodstuffs, pet foods, and/or animal foods. In embodiments, the second product includes anything but a first product.

In embodiments a quality testing of the second product takes place before manifest. Waste from the second product can be used as initial inventory. Quality testing takes place of the second product to ensure that recalls may be instituted if necessary. In embodiments, the quality testing includes testing the second product prior to entering the stream of interstate commerce for: pH, chemicals, contaminants, bacteria, pathogens, yeast, mold, allergens, pesticides, metals, mycotoxins, toxins, quality, taste, appearance, texture, water content, and/or water activity.

In embodiments, the second product can be mixed with the first product and prepared for manifest. In embodiments, the first product can be mixed with the second product and prepared for manifest. In embodiments, the second product can be analyzed before being mixed with the first product. In embodiments, the first product can be analyzed before being mixed with the second product.

Fifth, a detailed transportation manifest is created prior to shipment the second product into the stream of commerce. In embodiments, the transportation manifest includes: origin of shipment, destination of shipment, detailed list of shipment contents shipper address, receiver address, date shipped, date received, and displaying the entire chain of custody. Sixth, the transporter name and license number is entered into the *cannabis*-related product traceability system and method. Seventh, the retailer's name and address is entered into the *cannabis*-related product traceability system. Eighth, the consumer's name and address is entered into the *cannabis*-related product traceability system.

In embodiments, the *cannabis*-related product traceability system provides a log to track insects and/or each batch of first end and/or second products. In embodiments, the *cannabis*-related product traceability system logs *cannabis* grown, or any step in between and including making the first product to making the second product in the FSS by used of a barcode or radio-frequency identification (RFID). In embodiments, the RFID uses electromagnetic fields to automatically identify and track tags attached to batches of cannabinoid-related products. Each *cannabis* growing assembly, plot of land, or acre of land, item of inventory, first product, and/or second product includes a tag that includes electronically-stored information such as: time and date the plants or seeds were planted, germinated, cloned, time and date the *cannabis* was harvested, *cannabis* plant nutrient and rooting solution composition and ingredients, growing medium moisture, growing chamber temperature and humidity, mass of each plants, yield of each plant, mass increase over time of each plant, species/genus of each plant, end-customer, quality assurance records, plant and/or clone water quality, etc. In embodiments, the *cannabis*-related product traceability system provides for an audit trail for state and federal laws, rules, and regulations and makes recalls possible.

In embodiments, *cannabis*-related product traceability system utilizes a blockchain platform to allow each node in the supply and distribution chain to ledger and in their block of data to transaction. In embodiments, *cannabis*-related product traceability system utilizes a blockchain platform to selectively trace *cannabis*-related first product and/or second products through their lifecycle.

In embodiments, a barcode or radio-frequency identification (RFID) is placed on the first product and/or second product. Preferably the RFID is preferable passive and NFC (near field communication). RFID tags contain an antenna and a memory chip that stores data. NFC technology operates at a relatively narrow range generally of inches and can also be set up for one- or two-way communications. A computing device which includes or smartphones which are NFC compatible act as an NFC writer or reader depending on the RFID tag and computing device software etc. Passive RFID tags have no power. The RFID's are activated by an electromagnetic signal sent from the RFID reader (as described above which may be a computing device such as a smartphone, tablet or a dedicated reader/writer). The signal doesn't travel as far as active RFID, so they're used for short read ranges. Passive RFID falls into one of three frequency ranges: Low frequency: 125-134.2 kHz; High frequency: 13.56 MHz; Ultra-high frequency: 856-960 MHz.

NFC is however based on RFID protocols. The devices run at passive RFID's high frequency. The NFC protocol can have two-way communication—unlike RFID's one-directional limitation—using one of two modes: card emulation and peer-to-peer (P2P). For example, a smartphone enabled with NFC can pass information back and forth to another NFC device. Contactless payment is an example of card emulation mode. NFC protocols are suited for some blockchain transaction.

The *cannabis*-related product traceability system described herein allows adherence and compliance and safety protocols for widespread commercialization of *cannabis*-related products. It also improves the lifecycle tracing and tracking of *cannabis*-related products, which are subject to national and international regulations where proof of quality to the end-customer is paramount. Blockchain technology may be integrated into production *cannabis*-related products which allows data to be distributed but not copied. In embodiments, each block in the blockchain has the Merkle root of its transactions and the hash of its previous block. The hash of Merkle root can be used as a definitive mechanism to verify the integrity of the block as even the slightest changes to any of the records in this tree will alter the value of the original Merkle Root.

In embodiments, each node in the blockchain network gets a copy of the blockchain and may add its ledger data to the chain but not alter prior entries. By utilizing the disclosed trace and track blockchain *cannabis*-related products from production to delivery or use by end user can be verified. This increased supply chain transparency provides data which may be used concerning content of products, testing, or safety of products, to reduce fraud and counterfeit products, and to complete compliance by manufacturers and distributors.

In embodiments, opt-in consumers having credentials to show their place on the blockchain can receive rewards for entering their blockchain data. All blockchain actions are complete via the computer or computing devices having processors which access a network. A significant advantage of this proposed blockchain-based workflow is in the increased traceability that it provides, since the physical goods are monitored from the beginning of the supply chain via the Digital ID validation series. Each identified quantity and/or quality of *cannabis*-related products represents an immutable timestamped record that may be recalled in case of dispute and litigation. Blockchain immutability and traceability are key functional attributes for improving efficiency in the supply chain process of tracking the change of ownership of the *cannabis*-related products. The blockchain must allow every participant on a supply chain network to track sourcing and origin of materials but also maintain immutable records of the production and storage of the *cannabis*-related products.

In embodiments, the *cannabis*-related product traceability system includes a quality analysis of the first product or the second product with an analyzer, wherein the analyzer is comprised of one or more analyzers selected from the group consisting of Fourier-transform infrared spectroscopy, gas chromatography, high-performance liquid chromatography, liquid chromatograph, liquid chromatography-mass spectrometry, mass spectrometry, and ultra-high performance liquid chromatography.

In embodiments, the *cannabis*-related product traceability system and method includes a quality analysis of the first product or the second product, wherein the quality analysis comprises determining a moisture content of the first product or the second product a moisture sensor. In embodiments, the moisture sensor is selected from one or more from the group consisting of a halogen moisture sensor, mass spectrometer, Fourier transform infrared spectroscopy, infrared spectroscopy, radio frequency (RF), a DC resistance circuit, frequency domain reflectometry (FDR), time domain reflectometry (TDR), time domain transmissometry (TDT), oven drying, gravimetric testing, forced air oven, vacuum oven, microwave, variable frequency microwave radiation, IR drying, toluene distillation, Karl Fischer titration, or any conceivable instantaneous contact or non-contact moisture analyzer. In embodiments, time-domain reflectometry or TDR is a measurement technique used to determine the characteristics of first product or the second product by observing reflected waveforms. In embodiments, time-domain transmissometry (TDT) is an analogous technique that measures the transmitted (rather than reflected) impulse of a *cannabis*-related product.

In embodiments, the *cannabis*-related product traceability system and method includes a quality analysis of the first product or the second product, wherein the quality analysis comprises determining a quality content of the first product or the second product with a quality sensor. In embodiments, the quality sensor includes one or more selected from the group consisting of a halogen moisture sensor, mass spectrometer, Fourier transform infrared spectroscopy, infrared spectroscopy, radio frequency (RF), a DC resistance circuit, frequency domain reflectometry (FDR), time domain reflectometry (TDR), time domain transmissometry (TDT), oven drying, gravimetric testing, forced air oven, vacuum oven, microwave, variable frequency microwave radiation, IR drying, toluene distillation, Karl Fischer titration, or an instantaneous contact or non-contact quality analyzer.

In embodiments, time-domain reflectometry or TDR is a measurement technique used to determine the quality characteristics of the first product or the second product by observing reflected waveforms. In embodiments, time-domain transmissometry (TDT) is an analogous technique that measures the transmitted (rather than reflected) impulse of the first product or the second product.

In embodiments, each and every system and/or method of the Farming Superstructure System (FSS) used to produce any *cannabis*-related product may be owned and/or operated by the same business entity. In embodiments, each and every system and/or method of the Farming Superstructure System used to produce any *cannabis*-related product may be owned and operated by the same business entity.

In embodiments, each and every system and/or method of the Farming Superstructure System (FSS) used to produce any *cannabis*-related product may be owned and/or operated by the separate business entities. In embodiments, each and every system and/or method of the Farming Superstructure System used to produce any *cannabis*-related product may be owned and operated by the separate business entities.

In embodiments, the business entity includes any organization, company, corporation, sole proprietorship, partnership, limited partnership, limited liability company, business corporation, non-profit, natural person, or anything otherwise engaged in or carrying on business, including but not limited to any past and present affiliates, subsidiaries, agents, employees, officers, directors, and all other persons acting on its behalf.

In embodiments, affiliates of the business entity include any person, organization, and/or additional business entity that controls, and/or is controlled by, and/or or is under common control of the business entity.

In embodiments, the business entity includes a limited partnership, limited liability partnership, limited liability limited partnership, limited liability company, professional limited liability company, sole proprietorship, a partnership, a limited liability company, a business corporation, a sole proprietorship, a partnership, a limited liability company, a business corporation, a company, a corporation, a professional corporation, a trust, and/or a fund.

In embodiments, the business entity includes any legally cognizable entity recognized today or any anytime in the future that may lawfully own, license or otherwise control property, including intellectual property, and/or operate a business.

In embodiments, the business entity includes any entity recognized today, and/or anytime in the future, and/or existing today or created anytime in the future.

In embodiments, the business entity includes a corporation, a company, a partnership, an association, a joint-stock company, a trust, a fund, and/or an organized group of persons, whether incorporated or not, and (in an official capacity) any receiver, trustee in bankruptcy, or similar official, and/or liquidating agent.

In embodiments, the business entity includes a corporation. In embodiments, the business entity does not include a corporation. In embodiments, the business entity includes a publicly traded company. In embodiments, the business entity includes a privately held company. In embodiments, the business entity includes a C corporation. In embodiments, the business entity includes a S corporation. In embodiments, the business entity includes a nonprofit organization.

In embodiments, the business entity includes one or more selected from the group consisting of a sole proprietorship, a partnership, a limited liability company, a business corporation, a sole proprietorship, a partnership, a limited liability company, a business corporation, and a conglomerate corporation.

In embodiments, the business entity includes one or more selected from the group consisting of a limited partnership, a limited liability partnership, a limited liability limited partnership, a limited liability company, a professional limited liability company, a company, a corporation, and a professional corporation.

In embodiment, the business entity and/or the affiliates of the business entity also own and/or operate the emulsification system, the colloid production system, the softgel production system, the mixing system, the shaping system, the cooking system, and/or the bioreactor, and any other system and/or module and/or process described in this specification.

In embodiments, the business entity includes an entity representing an association of people, whether natural, legal and/or a mixture of both, with a specific objective to produce the distilled cannabinoid and/or the crystallized cannabinoid and/or additional *cannabis*-related, food, animal food, cosmetic, medicinal, recreational, and/or pharmaceutical product.

Thus, specific systems and methods of a Farming Superstructure System (FSS) have been disclosed. It should be apparent, however, to those skilled in the art that many more modifications besides those already described are possible without departing from the inventive concepts herein. The inventive subject matter, therefore, is not to be restricted except in the spirit of the disclosure.

Thus, the applicant(s) should be understood to have support to claim and make a statement of invention to at least: i) each of the process devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) each system, method, and element shown or described as now applied to any specific field or devices mentioned, x) methods and apparatuses substantially as described hereinbefore and with reference to any of the accompanying examples, xi) the various combinations and permutations of each of the elements disclosed, xii) each potentially dependent claim or concept as a dependency on each and every one of the independent claims or concepts presented, and xiii) all inventions described herein.

With regard to claims whether now or later presented for examination, it should be understood that for practical reasons and so as to avoid great expansion of the examination burden, the applicant may at any time present only initial claims or perhaps only initial claims with only initial dependencies. Support should be understood to exist to the degree required under new matter laws—including but not limited to European Patent Convention Article 123(2) and United States Patent Law 35 USC 132 or other such laws— to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible.

Finally, any claims set forth at any time are hereby incorporated by reference as part of this description of the inventive technology, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Although the foregoing text sets forth a detailed description of numerous different embodiments of the disclosure, it should be understood that the scope of the disclosure is defined by the words of the claims set forth at the end of this patent. The detailed description is to be construed as exemplary only and does not describe every possible embodiment of the disclosure because describing every possible embodiment would be impractical, if not impossible. Numerous alternative embodiments could be implemented, using either current technology or technology developed after the filing date of this patent, which would still fall within the scope of the claims defining the disclosure.

Thus, many modifications and variations may be made in the techniques and structures described and illustrated herein without departing from the spirit and scope of the present disclosure. Accordingly, it should be understood that the methods and apparatus described herein are illustrative only and are not limiting upon the scope of the disclosure.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, a limited number of the exemplary methods and materials are described herein. It must be noted that as used herein and in the appended claims, the singular forms "a", "an", and "the" include plural referents unless the context clearly dictates otherwise.

The invention claimed is:

1. A beverage comprising a nanoemulsion including a cannabinoid and 7-hydroxymitragynine.

2. The beverage according to claim 1, comprising:
a serving size ranging from 0.1 to 2.5 fluid ounces.

3. The beverage according to claim 1, wherein:
said beverage comprises said 7-hydroxymitragynine in a concentration less than 1 weight percent per serving.

4. The beverage according to claim 1, comprising:
said beverage comprises said 7-hydroxymitragynine in a concentration ranging from 0.001 to 1 weight percent per serving.

5. The beverage according to claim 1, comprising:
one or more ingredients selected from the group consisting of glycerin and propylene glycol.

6. The beverage according to claim 1, comprising:
water.

7. The beverage according to claim 6, wherein:
said water comprises treated water, said treated water is treated in a water treatment system, said water treatment system includes one or more water treatment systems selected from the group consisting of a filter, a cation, an anion, a membrane, a filter, activated carbon, an adsorbent, an absorbent, an ultraviolet unit, an ozone unit, a microwave unit, and a distillation system.

8. The beverage according to claim 1, comprising:
a sweetener, said sweetener includes one or more sweeteners selected from the group consisting of a zero-calorie sweetener, honey, sugar, aspartame, acesulfame potassium, saccharin, sucralose, neotame, erythritol, *stevia, stevia* leaf extract, a sugar alcohol, and a polyol.

9. The beverage according to claim 1, comprising:
an acid, said acid includes one or more acids selected from the group consisting of acetic acid, ascorbic acid, benzoic acid, citric acid, fumaric acid, glacial acetic acid, gluconic acid, hydrochloric acid, lactic acid, malic acid, nitric acid, phosphoric acid, sorbic acid, sulfuric acid, and tartaric acid.

10. The beverage according to claim 1, comprising:
a flavoring, said flavoring includes one or more flavorings selected from the group consisting of basil, bergamot, black pepper, *cassia*, cedarwood, cinnamon, citronella, clary sage, clove, coffee, cypress, *eucalyptus*, evening primrose, fennel, fir needle, frankincense, *gardenia*, geranium, ginger, grapefruit, helichrysum, hop, hyssop, jasmine, juniper berry, lavender, lemon, lemongrass, mandarin, marjoram, *melaleuca*, melissa, myrrh, neroli, orange, oregano, palo santo, patchouli, peppermint, pine, chamomile, rose, rosemary, sandalwood, spikenard, tea tree, thyme, turmeric, vetiver, wintergreen, and ylang ylang.

11. The beverage according to claim 1, comprising:
an oil, said oil includes one or more oils selected from the group consisting of almond oil, an animal-based oil, apricot kernel oil, avocado oil, brazil nut oil, butter, canola oil, cashew oil, cocoa butter, coconut oil, corn oil, cottonseed oil, ethyl oleate, a fatty acid, fish oil, grapeseed oil, hazelnut oil, hemp oil, insect oil, isopropyl myristate, isopropyl palmitate, lard, lard oil, light mineral oil, macadamia nut oil, MCT oil, a medium chain triglyceride, mineral oil, mustard oil, myristyl alcohol, octyl dodecanol, olive oil, palm kernel oil, palm oil, peanut oil, persic oil, rapeseed oil, rice bran oil, rice oil, safflower oil, semi-refined sesame oil, semi-refined sunflower oil, sesame oil, soybean oil, squalane, tallow of beef, tallow of mutton, vegetable oil, and walnut oil.

12. The beverage according to claim 1, comprising:
an emulsifier.

13. The beverage according to claim 12, wherein:
said emulsifier comprises one or more emulsifiers selected from the group consisting of a surfactant, lecithin, polyethylene (40), stearate, polysorbate, polyoxyethylene sorbitan monooleate, polyoxyethylene (20) sorbitan monooleate, polysorbate 80, polysorbate 60, polysorbate 65, ammonium salts of phosphatidic acid, sucrose acetate isobutyrate, potassium pyrophosphate, sodium acid pyrophosphate, sodium pyrophosphate, potassium polymetaphosphate, sodium metaphosphate, insoluble or sodium polyphosphates, sodium polyphosphate, insoluble polyphosphate, glassy salts of fatty acid, mono- and di-glycerides of fatty acids, a monoglyceride of fatty acid, di-glyceride of fatty acid, acetic and fatty acid esters of glycerol, lactic and fatty acid ester of glycerol, citric and fatty acid ester of glycerol, diacetyltartaric and fatty acid esters of glycerol, mixed fatty acid esters of glycerol, sucrose ester of fatty acid, polyglycerol ester of fatty acid, polyglycerol ester of interesterified ricinoleic acid, propylene glycol monoester, propylene glycol diester, propylene glycol ester of fatty acid, propylene glycol ester, dioctyl sodium sulphosuccinate, sodium lactylate, sodium oleyl lactylate, sodium stearoyl lactylate, calcium lactylate, calcium oleyl lactylate, calcium stearoyl lactylate, sorbitan monostearate, maltodextrin, polyphosphates, formulated polyphosphates, and gum arabic.

14. The beverage according to claim 1, comprising:
propylene glycol, water, a sweetener, and an acid; wherein:
said sweetener includes one or more sweeteners selected from the group consisting of a zero-calorie sweetener, honey, sugar, aspartame, acesulfame potassium, saccharin, sucralose, neotame, erythritol, *stevia, stevia* leaf extract, a sugar alcohol, and a polyol;
said acid includes one or more acids selected from the group consisting of acetic acid, ascorbic acid, benzoic acid, citric acid, fumaric acid, glacial acetic acid, gluconic acid, hydrochloric acid, lactic acid, malic acid, nitric acid, phosphoric acid, sorbic acid, sulfuric acid, and tartaric acid.

15. The beverage according to claim 14, comprising:
a flavoring, said flavoring includes one or more flavorings selected from the group consisting of basil, bergamot, black pepper, *cassia*, cedarwood, cinnamon, citronella, clary sage, clove, coffee, cypress, *eucalyptus*, evening primrose, fennel, fir needle, frankincense, *gardenia*, geranium, ginger, grapefruit, helichrysum, hop, hyssop, jasmine, juniper berry, lavender, lemon, lemongrass, mandarin, marjoram, *melaleuca*, melissa, myrrh, neroli, orange, oregano, palo santo, patchouli, peppermint, pine, chamomile, rose, rosemary, sandalwood, spikenard, tea tree, thyme, turmeric, vetiver, wintergreen, and ylang ylang.

16. The beverage according to claim 1, comprising:
an ingredient, said ingredient includes one or more flavorings selected from the group consisting of ayahuasca, activated charcoal, an amphetamine, aspirin, butyrate, calcium, capsaicin, carnitine, carnosine, *cassia* cinnamon, chondroitin sulfate, chromium, coenzyme q-10, cranberry, creatine, curcumin, deprenyl, dimethyltryptamine, *echinacea*, fish oil, garlic, ginger, ginkgo, *ginseng*, gluconic acid, glucosamine, green tea, hoodia, inositol, lithium, lions mane mushroom, lutein, magnesium, a mineral, malate, melatonin, metformin, 3,4-methylenedioxy methamphetamine, milk thistle, n-acetylcysteine, niacin, niacinamide, nicotinamide riboside, omega-3 fatty acid, oxaloacetate, piracetam, psilocybin, pyruvate, resveratrol, *rhodiola*, saw palmetto, selenium, st. johns wort, a steroid alternative, a steroid, testosterone, theaflavins, turmeric, valerian, vitamins, vitamin B3, vitamin C, and zinc.

17. The beverage according to claim 1, comprising:
a calorie content ranging from 0 to 50 calories per serving and/or a carbohydrate content ranging from 0 to 20 grams per serving.

18. The beverage according to claim 1, comprising:
a serving size ranging from 2.5 to 16 fluid ounces.

19. The beverage according to claim 1, wherein:
said beverage comprises a carbonated beverage and includes carbon dioxide.

20. The beverage according to claim 1, wherein: said beverage comprises said cannabinoid and/or said 7-hydroxymitragynine including a droplet size of said cannabinoid and/or said 7-hydroxymitragynine ranging from 1 to 1,000 nanometers.

\* \* \* \* \*